US008754100B2

(12) United States Patent
Kitazawa et al.

(10) Patent No.: US 8,754,100 B2
(45) Date of Patent: Jun. 17, 2014

(54) NITROGEN-CONTAINING FUSED HETEROCYCLIC COMPOUNDS AND THEIR USE AS BETA AMYLOID PRODUCTION INHIBITORS

(75) Inventors: Noritaka Kitazawa, Tsukuba (JP); Daisuke Shinmyo, Tsukuba (JP); Koichi Ito, Tsukuba (JP); Nobuaki Sato, Tsukuba (JP); Daiju Hasegawa, Tsukuba (JP); Toshiyuki Uemura, Tsukuba (JP); Toru Watanabe, Tsukuba (JP)

(73) Assignee: EISAI R&D Management Co., Ltd., Tokyo (JP)

( * ) Notice: Subject to any disclaimer, the term of this patent is extended or adjusted under 35 U.S.C. 154(b) by 364 days.

(21) Appl. No.: 13/138,504

(22) PCT Filed: Feb. 24, 2010

(86) PCT No.: PCT/JP2010/053368

§ 371 (c)(1), (2), (4) Date: Nov. 16, 2011

(87) PCT Pub. No.: WO2010/098487

PCT Pub. Date: Sep. 2, 2010

(65) Prior Publication Data

US 2012/0053171 A1 Mar. 1, 2012

Related U.S. Application Data

(60) Provisional application No. 61/155,697, filed on Feb. 26, 2009.

(30) Foreign Application Priority Data

Feb. 26, 2009 (JP) ................................ 2009-043337

(51) Int. Cl.

| | |
|---|---|
| ***A01N 43/42*** | (2006.01) |
| ***A61K 31/44*** | (2006.01) |
| ***A01N 43/40*** | (2006.01) |
| ***C07D 471/02*** | (2006.01) |
| ***C07D 491/02*** | (2006.01) |
| ***C07D 498/02*** | (2006.01) |
| ***C07D 401/00*** | (2006.01) |

(52) U.S. Cl.

USPC ........... 514/300; 514/303; 514/338; 546/119; 546/121; 546/273.4

(58) Field of Classification Search

USPC ........ 546/119, 121, 273.4; 514/300, 303, 338

See application file for complete search history.

(56) References Cited

U.S. PATENT DOCUMENTS

| | | | | |
|---|---|---|---|---|
| 5,922,724 | A * | 7/1999 | Teuber et al. | 514/256 |
| 7,618,960 | B2 | 11/2009 | Kimura et al. | |
| 7,667,041 | B2 | 2/2010 | Kimura et al. | |
| 7,687,640 | B2 | 3/2010 | Kimura et al. | |
| 7,713,993 | B2 | 5/2010 | Kimura et al. | |
| 7,880,009 | B2 | 2/2011 | Kimura et al. | |
| 7,897,632 | B2 | 3/2011 | Kimura et al. | |
| 7,935,815 | B2 | 5/2011 | Kimura et al. | |
| 7,973,033 | B2 | 7/2011 | Kimura et al. | |
| 8,008,293 | B2 | 8/2011 | Kimura et al. | |
| 8,048,878 | B2 | 11/2011 | Kimura et al. | |
| 2011/0065360 | A1 | 3/2011 | Francis | |
| 2011/0065696 | A1 | 3/2011 | Kimura et al. | |
| 2011/0086860 | A1 | 4/2011 | Kimura et al. | |
| 2011/0275822 | A1 | 11/2011 | Minamisono et al. | |
| 2012/0135981 | A1 | 5/2012 | Wu et al. | |

FOREIGN PATENT DOCUMENTS

| | | | |
|---|---|---|---|
| EP | 1 992 618 | A1 | 11/2008 |
| EP | 2 181 992 | A1 | 5/2010 |
| JP | 2011-506335 | A | 3/2011 |
| JP | 2012-51806 | A | 3/2012 |
| JP | 5210152 | B2 | 6/2013 |
| UZ | 4 136 | C | 4/2010 |
| UZ | 4 225 | C | 9/2010 |
| WO | 9846605 | * | 10/1998 |
| WO | WO 2004/110350 | A2 | 12/2004 |

(Continued)

OTHER PUBLICATIONS

Communication Under Rule 71(3) EPC issued Dec. 12, 2012, in European Patent Application No. 08828870.9.

(Continued)

*Primary Examiner* — Niloofar Rahmani

(74) *Attorney, Agent, or Firm* — Birch, Stewart, Kolasch & Birch, LLP

(57) ABSTRACT

A compound represented by the formula [I]: or a pharmacologically acceptable salt or ester thereof, wherein Ring A represents a five-membered aromatic heterocyclic group or the like fused with a non-aromatic ring group, which may be substituted, Ring B represents a phenyl group or the like which may be substituted, X1 represents a single bond or the like, R1 and R2 each represent a C1-6 alkyl group or the like, m represents an integer of 0 to 3, and n represents an integer of 0 to 2, is effective as a therapeutic agent for a disease caused by Aβ.

[I]

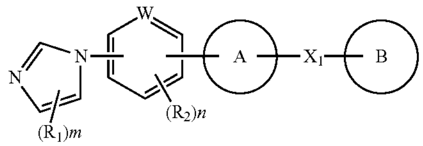

20 Claims, No Drawings

(56) References Cited

FOREIGN PATENT DOCUMENTS

| | | | |
|---|---|---|---|
| WO | WO 2007/102580 | A1 | 9/2007 |
| WO | WO 2009/073777 | A1 | 6/2009 |
| WO | WO 2010/025197 | A1 | 3/2010 |
| WO | WO 2010-097372 | A1 | 9/2010 |
| WO | WO 2010-097395 | A1 | 9/2010 |
| WO | WO 2010/098488 | A1 | 9/2010 |
| WO | WO 2010/098495 | A1 | 9/2010 |

OTHER PUBLICATIONS

Extended European Search Report issued Jan. 22, 2013, in European Patent Application No. 12191398.2.
Notification to Go through Formalities of Registration issued Dec. 28, 2012, in Chinese Patent Application No. 200580020584.8, with English translation.
Official Letter and Search Report issued Janaury 29, 2013, in Taiwan Patent Application No. 97132893, with English translation.
Response filed Feb. 13, 2013, in reply to the First Examination Report issued Oct. 17, 2012, in Australian Patent Application No. 2008292390.
Response filed Janaury 22, 2013. in reply to the Subsequent Substantive Examination Report issued Nov. 23, 2012. in Philippine Patent Application No. 1-2010-500161.
Response filed Jan. 14, 2013, in reply to the First Office Action issued in Chinese Patent Application No. 200880104785.X, with English translation.
Response filed Jan. 15, 2013, in reply to the Official Notice of Results of the Substantive Examination No. 38629/SHTT-SC2 issued Nov. 26, 2012, in Vietnamese Patent Application No. 1-2010-00393, with English translation.
Response filed Jan. 16, 2013, in reply to the Substantive Examination Adverse Report issued Dec. 31, 2012, in Malaysian Patent Application No. PI 20052354.
Substantive Examination Adverse Report issued Dec. 31, 2012, in Malaysian Patent Application No. PI 20052354.
Response filed Mar. 4, 2013, in reply to the Request According to Section 18 issued Nov. 13, 2012, in Israeli Patent Application No. 214780, with English translation.
Response filed Apr. 12, 2013, in reply to the Communication Under Rule 71(3) EPC issued Dec. 13, 2012, in European Patent Application No. 10708824.7.
First Office Action issued Feb. 5, 2013, in Chinese Patent Application No. 201080009393.2, with English translation.
Notice of Acceptance issued Mar. 25, 2013, in Australian Patent Application No. 2008292390.
Notice of the Result of Substantive Examination of a Patent Application issued Jun. 16, 2013, in GCC Patent Application No. 11619, with English translation.
Notification of Defects Prior to Allowance issued May 7, 2013, in Israeli Patent Application No. 203778, with English translation.
Notification of Reason for Rejection issued May 7, 2013, in Japanese Patent Application No. 2009-530168, with English Translation.
Notification to Grant Patent Right issued Jun. 6, 2013, in Chinese Patent Application No. 20088014785.X, with English translation.
Office Action issued Jun. 25, 2013, in Mexican Patent Application No. MX/a/2010/002098, with English translation.
Office Action issued May 23, 2013, in Vietnamese Patent Application No. 1-2010-00393, with English translation.
Reply filed Jun. 24, 2013, in response to the Notification of Reason for Rejection issued May 7, 2013, in Japanese Patent Application No. 2009-530168, with English translation.
Reply filed May 10, 2013, in response to the Substantive Examination Adverse Report issued Mar. 29, 2013, in Malaysian Patent Application No. PI 2010000422.
Response filed Apr. 26, 2013, in Taiwan Patent Application No. 97132893, with English Translation.
Substantive Examination Adverse Report issued Mar. 29, 2013, in Malaysian Patent Application No. PI 2010000422.
Substantive Examination Clear Report issued Jun. 14, 2013, in Malaysian Patent Application No. PI 20052354.
Reply filed Jun. 20, 2013, in Chinese Patent Application No. 201080009393.2, with English translation.
Reply filed Jul. 10, 2013, in response to the Office Action issued May 2, 2013, in Mexican Patent Application No. MX/a/2011/008501, with English translation.
Official Action issued Aug. 16, 2013, in Russian Patent Application No. 2011139132, with English translation.
Communication pursuant to Article 94(3) EPC issued Jul. 30, 2013, in European Patent Application No. 05743758.4.
Notice Before Allowance issued Aug. 5, 2013, in Israeli Patent Application No. 203778, with English translation.
Notification of Defects issued Aug. 12, 2013, in Israeli Patent Application No. 213973, with English translation.
Notification of the Second Office Action issued Jul. 15, 2013, in Chinese Patent Application No. 201080009393.2, with English translation.
Office Action issued Aug. 23, 2013, in U.S. Appl. No. 12/974,447.
Response filed Aug. 13, 2013, in reply to the Invitation Pursuant to Rules 70a(2) and 70(2) EPC issued in European Patent Application No. 12191398.2.
Response filed Aug. 29, 2013, in reply to the Office Action issued Jun. 25, 2013, in Mexican Patent Application No. MX/a/2010/002098, with English translation of claims.
Response filed Jul. 25, 2013, in reply to the Office Action issued May 7, 2013, in Israeli Patent Application No. 203778, with English translation.
Reply filed Nov. 14, 2013, in response to the Non-Final Office Action issued Aug. 23, 2013, in U.S. Appl. No. 12/974,447.
International Search Report, dated Jul. 30, 2010 in PCT/JP2010/053368.
Examiner's Report isued on Patent of Invention Application issued Jun. 15, 2012, in Chilean Patent Application No. 2098-2011, with English translation.
Response filed Sep. 6, 2012, in reply to Examiner's Report Issued on Patent of Invention Application issued Jun. 15, 2012, in Chilean Patent Application No. 2098-2011, with English translation.
Amendment Order issued Jul. 17, 2012, in Thai Patent Application No. 1101001732, with English translation.
Invitation to Respond to Written Opinion issued Dec. 18, 2012, in Singapore Patent Application No. 201105886-4.
Search Report issued Nov. 15, 2012, in Singapore Patent Application No. 201105886-4.
Written Opinion issued Nov. 15, 2012, in Singapore Patent Application No. 201105886-4.
Response filed Dec. 27, 2012 in reply to the Invitation to Respond to Written Opinion issued Dec. 18, 2012, in Singapore Patent Application No. 201105886-4.
Examination Report issued Dec. 7, 2012, in Pakistan Patent Application No. 143/2010.
Examination Report issued Dec. 7, 2012, in Pakistan Patent Application No. 657/2011.
Response filed Dec. 21 2012, in reply to the Office Action issued Jul. 17, 2012, in Thai Patent Application No. 1101001732, with English translation.
First Office Action issued Jan. 25, 2013, in Chinese Patent Application No. 2010600092889, with English translation.
Response filed Feb. 15, 2013, in reply to the Office Action issued Nov. 15, 2012, in Chilean Patent ApiNication No. 2098-2011, with English translation.
Request for Substantive Examination filed Jan. 25, 2013, in Indonesian Patent Application. No. W-00 2011 03066, with English translation.
Replaced Search Report, mailed Feb. 1, 2013, for Singapore Application No. 201105886-4.
Replaced Written Opinion, mailed Feb. 1, 2013, for Singapore Application No. 201105886-4.
Official Action issued May 2, 2013, in Mexican Patent Application No. MX/a/2011/008501, wiith English translation.
Invitation to Respond to Written Opinion issued May 23, 2013, in Singapore Patent Application No. 201105886-4.

(56) References Cited

OTHER PUBLICATIONS

Replaced Search Report issued May 3, 2013, in Singapore Patent Application No. 201105886-4.
Replaced Written Opinion issued May 3, 2013, in Singapore Patent Application No. 201105886-4.
Extended European Search Report issued Jun. 6, 2013, in European Patent Application No. 13162886.9.
Amendment filed May 24, 2013, in response to the Office Action issued Jan. 25, 2013, in Chinese Patent Application No. 2010800092889, with English translation.
Notification of Defects issued May 30, 2013, in Israeli Patent Application No. 214780, with English translation.
Reply filed Sep. 23, 2013, in response to the Office Action issued May 30, 2013, in Israeli Patent Application No. 214780. with English translation.
Second Office Action issued Sep. 26, 2013, in Chinese Patent Application No. 201080009286.9. with English translation.
Notice of Acceptance issued May 15, 2013. in New Zealand Patent Application No. 594776.
Response flied Oct. 15, 2013, in reply to the Official Action issued Aug. 16, 2013. in Russian Patent Apptication No. 2011139132, with English translation.
Search Report issued May 10, 2012, in Singapore Patent Application No. 201100985-9.
Written Opinion issued May 7, 2012, in Singapore Patent Application No. 201100985-9.
European Examination Report dated Sep. 28, 2012 issued in connection with corresponding European Application No. 09791956.7.
Amendment filed Dec. 7, 2011, in Singapore Patent Application No. 201105886-4.
Communication Pursuant to Rules 161(1) and 162 EPC issued Sep. 7, 2011, in European Patent Application No. 10708824.7
Examination Report issued Jul. 19, 2012, in New Zealand Patent Application No. 594776.
International Preliminary Report on Patentability and Written Opinion issued Sep. 9, 2012, in PCT International Application No. PCT/JP2010/053368.
International Search Report issued Jul. 30, 2010, in PCT International Application No. PCT/JP2010/053368.
Request for the Correction of Error in the Specification issued Dec. 13, 2011, in Singapore Patent Application No. 201105886-4.
Response filed Feb. 6, 2012, in reply to the Request for the Correction of Error in the Specification issued Dec. 13, 2011, in Singapore Patent Application No. 201105886-4.
Response filed Nov. 10, 2011, in reply to the Official Communication Pursuant to Rules 161(1) and 162 EPC issued in European Patent Application No. 10706824.7.
Supplemental Response filed Feb. 6, 2012, in reply to the Official Communication Pursuant to Rules 161(1) and 162 EPC issued in European Patent Application No. 10708824.7.
Communication Under Rule 71(3) EPC issued Dec. 13, 2012, in European Patent Application No. 10708824.7.
Examiner's Report Issued on Patent of Invention Application issued Nov. 15, 2012, in Chilean Patent Application No. 2098-2011, with English translation.
Notification Before Examining Israeli Patent Application No. 214760 issued Nov. 13, 2012, with English translation.
Communication Pursuant to Rules 161(1) and 162 EPC and Written Opinion issued Sep. 6, 2011, in European Patent Application No. 10708826.2.
Response filed Mar. 5, 2012, in reply to the Communication Pursuant to Rules 161(1) and 162 EPC and Written Opinion issued Sep. 6, 2011, in European Patent Application No. 10708826.2.
Amendment Under 37 CFR 1.111 filed Nov. 29, 2013, in response to the Office Action mailed May 29, 2013, in U.S. Appl. No. 13/143,130.
Decision on Grant issued Nov. 1, 2013, in Russian Patent Application No. 2011139132/04(058436), with English translation.
Response filed Dec. 2, 2013, in response to the Office Action issued Jul. 15, 2013, in Chinese Patent Application No. 201080009393.2, with English translation.
Response to Second Office Action filed Dec. 11, 2013, in Chinese Patent Application No. 201080009288.9, with English translation.
Notice of Allowance issued Dec. 13, 2013; in U.S. Appl. No. 12/974,447.
Reply filed Nov. 27, 2013, in response to the Office Action issued Jul. 30, 2013, in European Patent Application No. 05743758.4.
Response filed Dec. 8, 2013, in reply to the Office Action issued Aug. 12, 2013, in Israeli Patent Application No. 213973, with English translation.
Response filed Jan. 17, 2014, in reply to the Office Action issued Jul. 22, 2013, in European Patent Application No. 13 162 886.9.
Third Office Action issued Jan. 28, 2014, in Chinese Patent Application No. 201080009393.2, with English translation.
Communication Pursuant to Article 94(3) EPC issued Feb. 6, 2014, in European Patent Application No. 10 708 826.2.
Communication Pursuant to Article 94(3) EPC issued Mar. 28, 2014, in European Patent Application No. 13162886.9.
Office Action issued Apr. 8, 2014, in Japanese Patent Application No. 2011-536639, with English translation.
Response to Third Office Action filed Apr. 11, 2014, in Chinese Patent Application No. 201080009393.2, with English translation.
Berge et al., "Pharmaceutical Salts," Journal of Pharmaceutical Sciences (Jan. 1977), vol. 66. No. 1, pp. 1-19.
Kawaguchi et al., "Drug and crystal polymorphism," Journal of Human Environmental Engineering (Saikatsu Kogaku Kenkyu) (2002), vol. 4, No. 2, pp. 310-317, with partial English translation.
Office Action issued Apr. 11, 2014, in Japanese Patent Application No. 2011-514997, with English translation.

* cited by examiner

NITROGEN-CONTAINING FUSED HETEROCYCLIC COMPOUNDS AND THEIR USE AS BETA AMYLOID PRODUCTION INHIBITORS

This application is a National Phase of PCT/JP2010/053368 filed on Feb. 24, 2010, which claims priority under 35 USC 119(e) to U.S. Provisional Application No. 61/155,697 filed on Feb. 26, 2009 and under 35 USC 119(a) to Patent Application No. 2009-043337 filed in Japan, on Feb. 26, 2009, all of which are hereby expressly incorporated by reference into the present application.

TECHNICAL FIELD

The present invention relates to a pharmaceutical, more particularly, to a nitrogen-containing fused heterocyclic compound effective for the treatment of a neurodegenerative disease caused by amyloid-β (hereinafter referred to as Aβ) such as Alzheimer's disease or Down's syndrome and a medicine, in particular, a medicine for the treatment of a disease caused by Aβ comprising the compound as an active ingredient.

BACKGROUND ART

Alzheimer's disease is a disease characterized by degeneration and loss of neurons as well as formation of senile plaques and neurofibrillary degeneration. Currently, Alzheimer's disease is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as metabolites of amyloid precursor proteins (hereinafter referred to as APP) are highly involved in degeneration and loss of neurons and onset of symptoms of dementia (see NON-PATENT DOCUMENTS 1 and 2, for example). Main molecular species of Aβ-protein are Aβ40 consisting of 40 amino acids and Aβ42 with two amino acids added at the C-terminal. The Aβ40 and Aβ42 are known to have high aggregability (see NON-PATENT DOCUMENT 3, for example) and to be main components of senile plaques (see NON-PATENT DOCUMENTS 3, 4 and 5, for example). Further, it is known that the Aβ40 and Aβ42 are increased by mutation in APP and presenilin genes which is observed in familial Alzheimer's disease (see NON-PATENT DOCUMENTS 6, 7 and 8, for example). Accordingly, a compound that reduces the production of Aβ340 and Aβ342 is expected as a progression inhibitor or prophylactic agent for Alzheimer's disease.

Aβ is produced by cleaving APP by β-secretase and subsequently by γ-secretase. For this reason, attempts have been made to create γ-secretase and β-secretase inhibitors in order to reduce Aβ production. Many of these secretase inhibitors already known are, for example, peptides and peptide mimetics such as L-685,458 (see NON-PATENT DOCUMENT 9, for example), LY-411,575 (see NON-PATENT DOCUMENTS 10, 11 and 12, for example) and LY-450,139 (see NON-PATENT DOCUMENTS 13, 14 and 15). Nonpeptidic compounds are, for example, MRK-560 (see NON-PATENT DOCUMENTS 16 and 17) and compounds having a plurality of aromatic rings as disclosed in PATENT DOCUMENT 1 and 2. However, the compound represented by the formula (VI) as disclosed in page 17 of the specification of PATENT DOCUMENT 1 differs from the compound of the present invention in that the compound is limited to a compound having a 2-aminothiazolyl group as a main structure. And the compound represented by the formula (I) as disclosed in page 6 of the specification of PATENT DOCUMENT 2 differs from the compound of the present invention in that the compound is limited to a compound having an ethynylene, an ethenylene or methine linker described as $X_1$.

PRIOR ART DOCUMENTS

Patent Documents

PATENT DOCUMENT 1: WO 2004/110350
PATENT DOCUMENT 2: WO 2007/102580

NON-PATENT DOCUMENTS

NON-PATENT DOCUMENT 1: Klein W L, and seven others, Alzheimer's disease-affected brain: Presence of oligomeric Aβ ligands (ADDLs) suggests a molecular basis for reversible memory loss, Proceeding of the National Academy of Science USA, 2003, Sep., 2; 100 (18), p. 10417-10422.

NON-PATENT DOCUMENT 2: Nitsch R M, and sixteen others, Antibodies against β-amyloid slow cognitive decline in Alzheimer's disease, Neuron, 2003, May 22; 38, p. 547-554.

NON-PATENT DOCUMENT 3: Jarrett J T, and two others, The carboxy terminus of the 13 amyloid protein is critical for the seeding of amyloid formation: Implications for the pathogenesis of Alzheimers' disease, Biochemistry, 1993, 32 (18), p. 4693-4697.

NON-PATENT DOCUMENT 4: Glenner G G, and one other, Alzheimer's disease: initial report of the purification and characterization of a novel cerebrovascular amyloid protein, Biochemical and Biophysical Research Communications, 1984, May 16, 120 (3), p. 885-890.

NON-PATENT DOCUMENT 5: Masters C L, and five others, Amyloid plaque core protein in Alzheimer disease and Down syndrome, Proceeding of the National Academy of Science USA, 1985, June, 82 (12), p. 4245-4249.

NON-PATENT DOCUMENT 6: Gouras G K, and eleven others, Intraneuronal A042 accumulation in human brain, American Journal of Pathology, 2000, January, 156 (1), p. 15-20.

NON-PATENT DOCUMENT 7: Scheuner D, and twenty others, Secreted amyloid O-protein similar to that in the senile plaques of Alzheimer's disease is increased in vivo by the presenilin 1 and 2 and APP mutations linked to familial Alzheimer's disease, Nature Medicine, 1996, Aug., 2 (8), p. 864-870.

NON-PATENT DOCUMENT 8: Forman M S, and four others, Differential effects of the swedish mutant amyloid precursor protein on β-amyloid accumulation and secretion in neurons and normeuronal cells, The Journal of Biological Chemistry, 1997, Dec., 19, 272 (51), p. 32247-32253.

NON-PATENT DOCUMENT 9: Sheannan M S, and nine others, L-685, 458, an Aspartyl Protease Transition State Mimic, Is a Potent Inhibitor of Amyloid β-Protein Precursor γ-Secretase Activity, Biochemistry, 2000, Aug., 1, 39 (30), p. 8698-8704.

NON-PATENT DOCUMENT 10: Shearman M S, and six others, Catalytic Site-Directed γ-Secretase Complex Inhibitors Do Not Discriminate Pharmacologically between Notch S3 and β-APP Clevages, Biochemistry, 2003, Jim, 24, 42 (24), p. 7580-7586.

NON-PATENT DOCUMENT 11: Lanz T A, and three others, Studies of Aβ pharmacodynamics in the brain, cerebrospinal fluid, and plasma in young (plaque-free) Tg2576 mice using the γ-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-alaninamide (LY-411575), The Journal of Pharmacology and Experimental Therapeutics, 2004, April, 309 (1), p. 49-55.

NON-PATENT DOCUMENT 12: Wong G T, and twelve others, Chronic treatment with the γ-secretase inhibitor LY-411, 575 inhibits β-amyloid peptide production and alters lymphopoiesis and intestinal cell differentiation, The Journal of Biological Chemistry, 2004, Mar., 26, 279 (13), p. 12876-12882.

NON-PATENT DOCUMENT 13: Gitter B D, and ten others, Stereoselective inhibition of amyloid beta peptide secretion by LY450139, a novel functional gamma secretase inhibitor, Neurology of Aging 2004, 25, sup2, p. 571.

NON-PATENT DOCUMENT 14: Lanz T A, and eighteen others, Concentration-dependent modulation of amyloid-β in vivo and in vitro using the γ-secretase inhibitor, LY-450139, The Journal of Pharmacology and Experimantal Therapeutics, 2006, November, 319 (2) p. 924-933.

NON-PATENT DOCUMENT 15: Siemers E R, and thirteen others, Effects of a γ-secretase inhibitor in a randamized study of patients with Alzheimer disease, Neurology, 2006, 66, p. 602-604.

NON-PATENT DOCUMENT 16: Best JD, and nine others, In vivo characterization of Aβ (40) changes in brain and cerebrospinal fluid using the novel γ-secretase inhibitor N-[cis-4-[(4-chlorophenyl)sulfonyl]-4-(2,5-difluorophenyl)cyclohexyl]-1,1,1-trifluoromethanesulphonylamide (MK-560) in the rat, The Journal of Pharmacology and Experimental Therapeutics, 2006, May 317 (2) p. 786-790.

NON-PATENT DOCUMENT 17: Best JD, and thirteen others The novel γ-secretase inhibitor N-[cis-4-[(4-chlorophenyl)sulfonyl]-4-(2,5-difluorophenyl)cyclohexyl]-1,1,1-trifluoromethanesulphonylamide (MK-560) reduces amylid plaque deposition without evidence notch-related pathology in the Tg2576 mouse, The Journal of Pharmacology and Experimental Therapeutics, 2007, February, 320 (2) p. 552-558.

SUMMARY OF THE INVENTION

Problem to be Solved by the Invention

As described above, a compound that inhibits the production of Aβ from APP has been expected as a therapeutic or prophylactic agent for a disease caused by Aβ which is typified by Alzheimer's disease. However, a nonpeptidic compound having high efficacy which inhibits the production of Aβ has not yet been known. Accordingly, there is a need for a novel low-molecular-weight compound that inhibits the production of Aβ.

Means for Solving the Problem

As a result of extensive studies, the present inventors have found a nonpeptidic polycyclic compound that inhibits the production of Aβ from APP and thus found a therapeutic agent for a disease caused by Aβ which is typified by Alzheimer's disease. This finding has led to the accomplishment of the present invention.

Specifically, the present invention relates to the following 1) to 15):

1) A compound represented by the formula [I]:

[I]

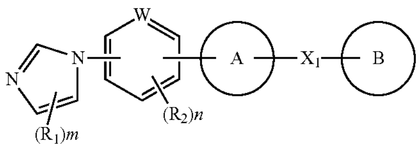

or a pharmacologically acceptable salt or ester thereof, wherein $R_1$ and $R_2$ are the same or different and each represent a substituent selected from the following Substituent Group a1;

m represents an integer of 0 to 3;

n represents an integer of 0 to 2;

W represents a nitrogen atom or a carbon atom;

Ring A represents a five-membered aromatic heterocyclic group fused with a 5- to 14-membered non-aromatic ring group, which contains two or more nitrogen atoms and may have 1 to 3 substituents selected from the following Substituent Group b1 (wherein the 5- to 14-membered non-aromatic ring group may have a crosslinked structure);

$X_1$ represents i) a single bond, ii) a C1-6 alkylene group, iii) a vinylene group which may have 1 to 2 C1-6 alkyl groups or iv) —$X_2$— (wherein $X_2$ represents —$NR_3$—, —$NR_3C(O)$—, —$C(O)NR_3$—, —O—, —S—, —S(O)— or —$S(O)_2$— and $R_3$ represents a hydrogen atom, a C1-6 alkyl group, a C3-6 cycloalkyl group, a C2-6 alkanoyl group or a C1-6 alkylsulfonyl group); and Ring B represents a monocyclic or fused cyclic aromatic ring group selected from the formulas [2] to [19]:

2

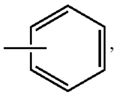

,

3

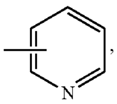

,

4

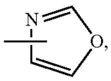

,

5

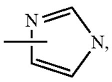

,

6

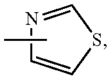

,

7

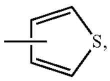

,

8

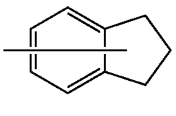

,

-continued

9

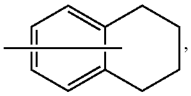

10

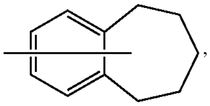

11

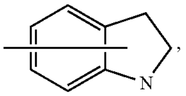

12

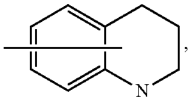

13

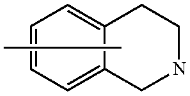

14

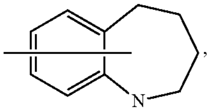

15

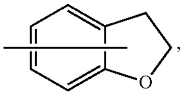

16

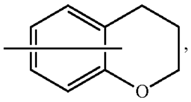

17

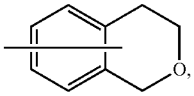

18

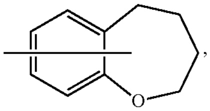

19

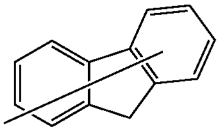

each of which may have 1 to 3 substituents selected from the following Substituent Group c1 [Substituent Group a1: a C1-6 alkyl group, a C3-8 cycloalkyl group, a C2-6 alkenyl group, a C1-6 alkoxy group, a C2-6 alkenyloxy group, a C3-8 cycloalkyloxy group, an amino group (wherein the amino group may have one C2-6 alkanoyl group or C1-6 alkylsulfonyl group or 1 to 2 C1-6 alkyl groups or C3-8 cycloalkyl groups), a cyano group, a formyl group, a halogen atom, a hydroxyl group and a nitro group;

Substituent Group b1: a C1-6 alkyl group (wherein the alkyl group may be substituted with 1 to 3 halogen atoms), a C2-6 alkenyl group, a C3-8 cycloalkyl group, a C6-14 aryl group, a C6-14 aryl-C1-6 alkyl group, a C1-6 alkoxy group, a C2-6 alkenyloxy group, a C3-8 cycloalkyloxy group, a C2-6 alkanoyl group, a C4-9 cycloalkylcarbonyl group, a C7-15 aroyl group, a C1-6 alkylsulfonyl group, a C2-6 alkenylsulfonyl group, a C3-8 cycloalkylsulfonyl group, a C6-14 arylsulfonyl group, a C1-6 alkylthio group, a C2-6 alkenylthio group, a C3-8 cycloalkylthio group, an aminosulfonyl group (wherein the aminosulfonyl group may have 1 to 2 C1-6 alkyl groups, C2-6 alkenyl groups or C3-8 cycloalkyl groups), an amino group (wherein the amino group may have one C2-6 alkanoyl group, C1-6 alkylsulfonyl group or C3-8 cycloalkylsulfonyl group or 1 to 2 C1-6 alkyl groups or C3-8 cycloalkyl groups), a cyano group, a formyl group, a halogen atom, a hydroxyl group, a nitro group, an oxo group, a 1-pyrrolidinyl group, a 1-piperidinyl group, a 1-homopiperidinyl group, an indolin-1-yl group, a 1,2,3,4-tetrahydroquinolin-1-yl group and a 4-morpholinyl group;

Substituent Group c1: i) an amino group (wherein the amino group may have one C2-6 alkanoyl group, C1-6 alkylsulfonyl group or C3-8 cycloalkylsulfonyl group or 1 to 2 C1-6 alkyl groups or C3-8 cycloalkyl groups), ii) a cyano group, iii) a halogen atom, iv) a hydroxyl group and v) v-i) a C1-6 alkyl group, v-ii) a C2-6 alkenyl group, v-iii) a C2-6 alkynyl group, v-iv) a C1-6 alkoxy group, v-v) a C1-6 alkylaminocarbonyl group, v-yl) a C1-6 alkylaminosulfonyl group, v-vii) a C1-6 alkylsulfonyl group, v-viii) a C1-6 alkylthio group, v-ix) a C2-6 alkanoyl group, v-x) a phenyl group, v-xi) a pyridyl group, v-xii) a pyridazinyl group, v-xiii) a pyrimidinyl group, v-xiv) a 1-pyrrolidinyl group, v-xv) a 1-piperidinyl group, v-xvi) a 1-homopiperidinyl group and v-xvii) a 4-morpholinyl group, each of which may have 1 to 3 substituents selected from the group consisting of a C1-6 alkyl group and a halogen atom];

2) The compound or pharmacologically acceptable salt or ester thereof according to 1) above, wherein Ring A is any one ring selected from the group consisting of the formulas [20] to [32]:

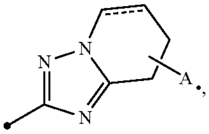

20

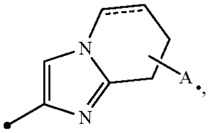

21

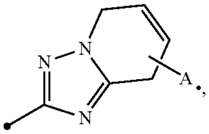

22

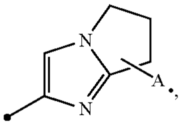

23

-continued

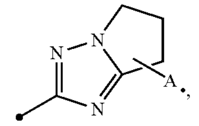
24

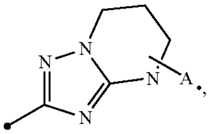
25

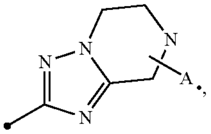
26

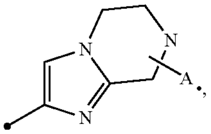
27

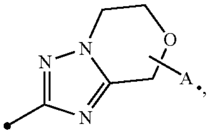
28

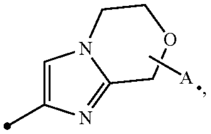
29

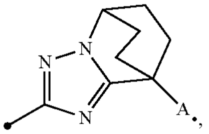
30

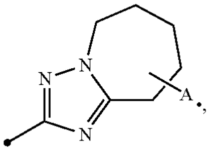
31

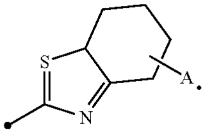
32 each of which may have 1 to 3 substituents selected from Substituent Group b1, wherein • represents a bonding site to the formula [33]:

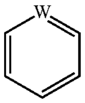
33

A• represents a bonding site to $X_1$, and

------- represents a single bond or a double bond;

3) The compound or pharmacologically acceptable salt or ester thereof according to 2) above, wherein Ring A is any one ring selected from the group consisting of the formulas [20], [21], [23], [24] and [26] to [29]:

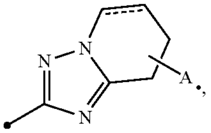
20

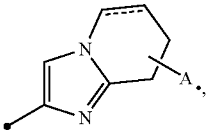
21

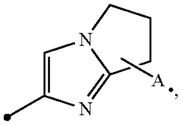
23

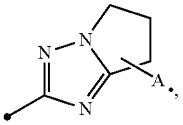
24

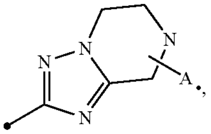
26

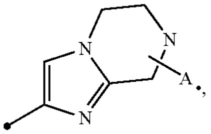
27

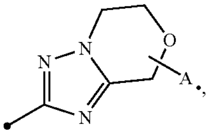
28

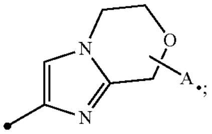
29

4) The compound or pharmacologically acceptable salt or ester thereof according to 2) above, wherein Ring A is any one ring selected from the group consisting of the formulas [20-1], [21-1], [23-1], [24-1] and [26-1] to [29-1]:

20-1

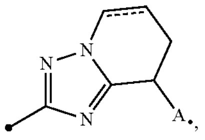

21-1

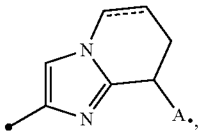

23-1

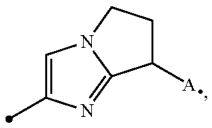

24-1

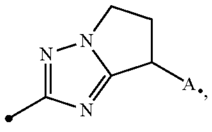

26-1

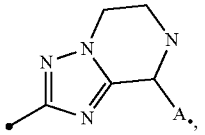

27-1

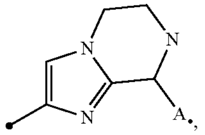

28-1

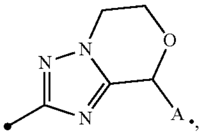

29-1

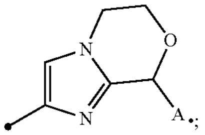

5) The compound or pharmacologically acceptable salt or ester thereof according to 1) above, wherein Ring B is a phenyl group, a pyridyl group, an oxazolyl group, an imidazolyl group, an thiazolyl group, a dihydrobenzofuranyl group or a thienyl group;

6) The compound or pharmacologically acceptable salt or ester thereof according to 1) above, wherein $X_1$ is i) a single bond or ii) a C1-6 alkylene group;

7) The compound or pharmacologically acceptable salt or ester thereof according to 1) above, wherein W is a carbon atom;

8) The compound or pharmacologically acceptable salt or ester thereof according to 1) above, wherein W is a nitrogen atom;

9) The compound or pharmacologically acceptable salt or ester thereof according to 1) above, wherein $R_1$ is a C1-6 alkyl group or a halogen atom and m is 1 to 2;

10) The compound or pharmacologically acceptable salt or ester thereof according to 1) above, wherein $R_2$ is a C1-6 alkoxy group and n is 1;

11) The compound or pharmacologically acceptable salt or ester thereof according to 1) above, wherein the substituent for Ring A is selected from the group consisting of: a C1-6 alkyl group (wherein the alkyl group may be substituted with 1 to 3 halogen atoms), a C3-8 cycloalkyl group, a C6-14 aryl group, a C6-14 aryl-C1-6 alkyl group, a C1-6 alkoxy group, a C3-8 cycloalkyloxy group, a C2-6 alkanoyl group, a C7-15 aroyl group, a C1-6 alkylsulfonyl group, a C3-8 cycloalkylsulfonyl group, a C6-14 arylsulfonyl group, a cyano group, a formyl group, a halogen atom, a hydroxyl group and an oxo group;

12) The compound or pharmacologically acceptable salt or ester thereof according to 1) above, wherein the substituent for Ring B is selected from the group consisting of: i) an amino group (wherein the amino group may have one C2-6 alkanoyl group, C1-6 alkylsulfonyl group or C3-8 cycloalkylsulfonyl group or 1 to 2 C1-6 alkyl groups or C3-8 cycloalkyl groups), ii) a cyano group, iii) a halogen atom, iv) a hydroxyl group and v) v)-i) a C1-6 alkyl group, v)-ii) a C1-6 alkoxy group, v)-iii) a C1-6 alkylthio group and v)-iv) a phenyl group, each of which may have 1 to 3 substituents selected from the group consisting of a C1-6 alkyl group and a halogen atom;

13) One compound selected from the group consisting of the following formulas [A-1] to [A-7]:

A-1

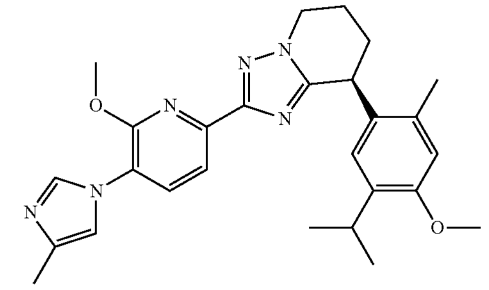

A-2

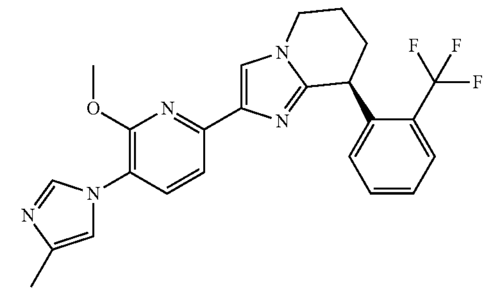

A-3

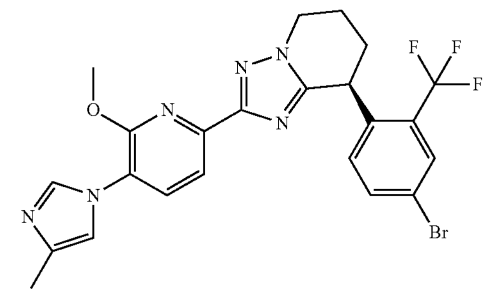

-continued

A-4

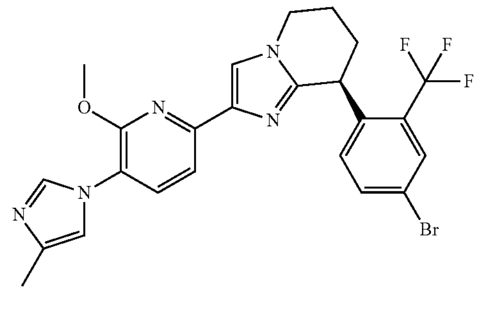

A-5

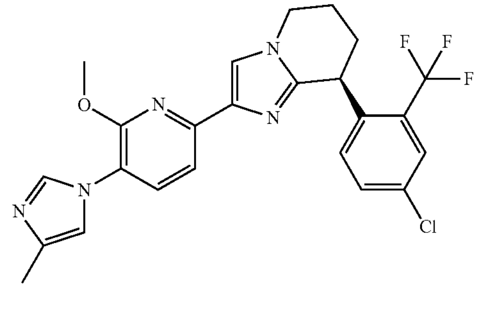

A-6

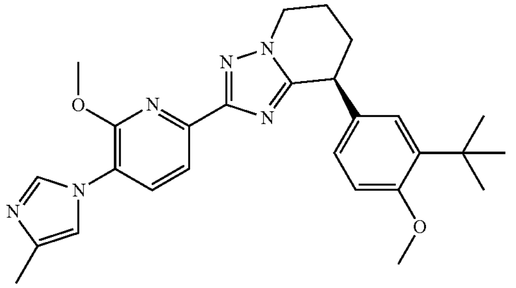

A-7

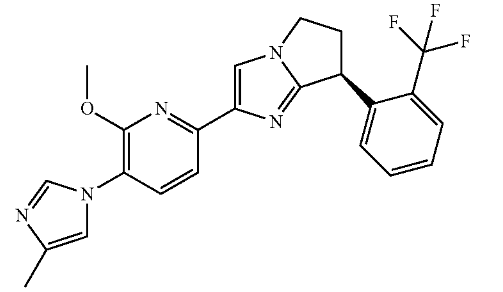

or a pharmacologically acceptable salt thereof.

14) A medicine comprising the compound or pharmacologically acceptable salt or ester thereof according to any one of 1) to 13) above as an active ingredient; and 15) The medicine according to 14) above for the treatment of a disease selected from Alzheimer's disease, dementia, Down's syndrome and amyloidosis.

MODE FOR CARRYING OUT THE INVENTION

The compound of the general formula (I) or pharmacologically acceptable salt thereof according to the present invention and the therapeutic agent for a disease caused by Aβ according to the present invention are novel inventions that have not yet been described in any documents.

The compound of the present invention can be converted to a chemical probe for capturing a target protein in a bioactive low-molecular compound. Specifically, the compound of the present invention can be converted to an affinity chromatography probe, a photoaffinity probe or the like by introducing a labeling group, a linker or the like into a moiety differing from a structural moiety essential for expression of activity of the compound by a technique described in J. Mass Spectrum. Soc. Jpn. Vol. 51, No. 5, 2003, p. 492-498 or WO 2007/139149, for example.

Examples of the labeling group, the linker or the like used for the chemical probe include groups shown in the following group consisting of (1) to (5):

(1) protein labeling groups such as photoaffinity labeling groups (such as a benzoyl group, a benzophenone group, an azido group, a carbonylazido group, a diaziridine group, an enone group, a diazo group and a nitro group) and chemical affinity groups (such as a ketone group substituted at the α-carbon atom with a halogen atom, a carbamoyl group, an ester group, an alkylthio group, Michael acceptors such as α,β-unsaturated ketones and esters, and an oxirane group), (2) cleavable linkers such as —S—S—, —O—Si—O—, monosaccharides (such as a glucose group and a galactose group) and disaccharides (such as lactose), and enzymatically cleavable oligopeptide linkers, (3) fishing tag groups such as biotin and 3-(4,4-difluoro-5,7-dimethyl-4H-3a,4a-diaza-4-bora-s-indacen-3-yl)propionyl, (4) detectable markers such as radioactive labeling groups such as $^{125}I$, $^{32}P$, $^{3}H$ and $^{14}C$; fluorescence labeling groups such as fluorescein, rhodamine, dansyl, umbelliferone, 7-nitrofurazanyl and 3-(4,4-difluoro-5,7-dimethyl-4H-3a,4a-diaza-4-bora-s-indacen-3-yl)propionyl; chemiluminescent groups such as luciferin and luminol; and heavy metal ions such as lanthanoid metal ions and radium ions, and (5) groups bound to solid-phase carriers such as glass beads, glass beds, microtiter plates, agarose beads, agarose beds, polystyrene beads, polystyrene beds, nylon beads and nylon beds.

When a probe is prepared by introducing a labeling group or the like selected from the group consisting of (1) to (5) above into the compound of the present invention in accordance with a method described in the above documents or the like, the probe can be used as a chemical probe for identification of labeled proteins useful for searching for novel drug targets, for example.

Meanings of symbols, terms and the like used in the present specification will be explained and the present invention will be described in detail below.

In the present specification, a structural formula of a compound may represent a certain isomer for convenience. However, the present invention includes all isomers and isomer mixtures such as geometric isomers which can be generated from the structure of a compound, optical isomers based on asymmetric carbon, stereoisomers and tautomers. The present invention is not limited to the description of a chemical formula for convenience and may include any one of the isomers or mixtures thereof. Accordingly, the compound of the present invention may have an asymmetric carbon atom in the molecule and exist as an optically active compound or racemate, and the present invention includes each of the optically active compound and the racemate without limitations. Although crystal polymorphs of the compound may be present, the compound is not limited thereto as well and may be present as a single crystal form or a mixture of single crystal forms. The compound may be an anhydride or hydrate.

The present invention also includes isotopically-labelled compounds, which are identical to the compounds of formula (I), except that one or more atoms are replaced by an atom having an atomic mass or mass number different from the atomic mass or mass number uusually found in nature. Examples of isotopes that can be incorporated into compounds of the invention include isotopes of hydrogen, carbon, nitrogen, oxygen, phosphorous, fluorine, iodine, and chlorine, such as $^{2}H$, $^{3}H$, $^{11}C$, $^{14}C$, $^{18}F$, $^{35}S$, $^{123}I$ and $^{125}I$.

Compounds of the present invention and pharmaceutically acceptable derivatives (e.g. salts) of said compounds that contain the aforementioned isotopes and/or other isotopes of other atoms are within the scope of the present invention. Isotopically-labelled compounds of the present invention, for example those into which radioactive isotopes such as $^{3}H$ and/or $^{14}C$ are incorporated, are useful in drug and/or substrate tissue distribution assays. $^{3}H$ and $^{14}C$ are considered useful due to their ease of preparation and detectability. $^{11}C$ and $^{18}F$ isotopes are considered useful in PET (positron emission tomography), and $^{125}I$ isotopes are considered useful in SPECT (single photon emission computerized tomography), all useful in brain imaging. Substitution with heavier isotopes such as 2H can afford certain therapeutic advantages resulting from greater metabolic stability, for example increased in vivo half-life or reduced dosage requirements and, hence, are considered useful in some circumstances. Isotopically labelled compounds of formula (I) of this invention can generally be prepared by carrying out the procedures disclosed in the Schemes and/or in the Examples below, by substituting a readily available isotopically labelled reagent for a non-isotopically labelled reagent.

The term "diseases attributable to An" includes a wide variety of conditions such as Alzheimer's disease (for example, refer to, Klein W L, and 7 others, Alzheimer's disease-affected brain: Presence of oligomeric Aβ ligands (ADDLs) suggests a molecular basis for reversible memory loss, Proceeding National Academy of Science USA, 2003, Sep. 2, 100 (18), p. 10417-10422; Nitsch R M, and 16 others, Antibodies against β-amyloid slow cognitive decline in Alzheimer's disease, Neuron, 2003, May 22, 38 (4), p. 547-554: Jarrett J T, and 2 others, The carboxy terminus of the P amyloid protein is critical for the seeding of amyloid formation: Implications for the pathogenesis of Alzheimer's disease, Biochemistry, 1993, May 11, 32 (18), p. 4693-4697; Glenner G G, and another, Alzheimer's disease; initial report of the purification and characterization of a novel cerebrovascular amyloid protein, Biochemical and biophysical research communications, 1984, May 16, 120 (3), p. 885-890; Masters C L, and 6 others, Amyloid plaque core protein in Alzheimer disease and Down syndrome, Proceeding National Academy of Science USA, 1985, June, 82 (12), p. 4245-4249; Gouras G K, and 11 others, Intraneuronal Aβ42 accumulation in human brain, American journal of pathology, 2000, January, 156 (1), p. 15-20; Scheuner D, and 20 others, Secreted amyloid β-protein similar to that in the senile plaques of Alzheimer's disease is increased in vivo by the presenilin 1 and 2 and APP mutations linked to familial Alzheimer's disease, Nature Medicine, 1996, Aug., 2 (8), p. 864-870; Forman M S, and 4 others, Differential effects of the Swedish mutant amyloid precursor protein on β-amyloid accumulation and secretion in neurons and normeuronal cells, The journal of biological chemistry, 1997, Dec. 19, 272 (51), p. 32247-32253), senile dementia (for example, refer to, Blass J P, Brain metabolism and brain disease: Is metabolic deficiency the proximate cause of Alzheimer dementia? Journal of Neuroscience Research, 2001, Dec. 1, 66 (5), p. 851-856), frontotemporal dementia (for example, refer to, Evin G, and 11 others, Alternative transcripts of presenilin-1 associated with frontotemporal dementia, Neuroreport, 2002, Apr. 16, 13 (5), p. 719-723), Pick disease (for example, refer to, Yasuhara O, and 3 others, Accumulation of amyloid precursor protein in brain lesions of patients with Pick disease, Neuroscience Letters, 1994, Apr. 25, 171 (1-2), p. 63-66), Down's syndrome (for example, refer to, Teller J K, and 10 others, Presence of soluble amyloid β-peptide precedes amyloid plaque formation in Down's syndrome, Nature Medicine, 1996, January, 2 (1), p. 93-95; Tokuda T, and 6 others, Plasma levels of amyloid p proteins Aβ1-40 and Aβ1-42 (43) are elevated in Down's syndrome, Annals of Neurology, 1997, February, 41 (2), p. 271-273), cerebrovascular angiopathy (for example, refer to, Hayashi Y, and 9 others, Evidence for presenilin-1 involvement in amyloid angiopathy in the Alzheimer's disease-affected brain, Brain Research, 1998, Apr. 13, 789 (2), p. 307-314; Barelli H, and 15 others, Characterization of new polyclonal antibodies specific for 40 and 42 amino acid-long amyloid peptides: their use to examine the cell biology of presenilins and the immunohistochemistry of sporadic Alzheimer's disease and cerebral amyloid angiopathy cases, Molecular Medicine, 1997, Oct., 3 (10), p. 695-707; Calhoun M E, and 10 others, Neuronal overexpression of mutant amyloid precursor protein results in prominent deposition of cerebrovascular amyloid, Proceeding National Academy of Science USA, 1999, Nov. 23, 96 (24), p. 14088-14093; Dermaut B, and 10 others, Cerebral amyloid angiopathy is a pathogenic lesion in Alzheimer's Disease due to a novel presenilin-1 mutation, Brain, 2001, December, 124 (12), p. 2383-2392), hereditary cerebral hemorrhage with amyloidosis (Dutch type) (for example, refer to, Cras P, and 9 others, Presenile Alzheimer dementia characterized by amyloid angiopathy and large amyloid core type senile plaques in the APP 692Ala→Gly mutation, Acta Neuropathologica (Berl), 1998, September, 96 (3), p. 253-260; Herzig M C, and 14 others, Aβ is targeted to the vasculature in a mouse model of hereditary cerebral hemorrhage with amyloidosis, Nature Neuroscience, 2004, Sep., 7 (9), p. 954-960; van Duinen S G, and 5 others, Hereditary cerebral hemorrhage with amyloidosis in patients of Dutch origin is related to Alzheimer disease, Proceeding National Academy of Science USA, 1987, August, 84 (16), p. 5991-5994; Levy E, and 8 others, Mutation of the Alzheimer's disease amyloid gene in hereditary cerebral hemorrhage, Dutch type, Science, 1990, Jun. 1, 248 (4959), p. 1124-1126), cognitive impairment (for example, refer to, Laws S M, and 7 others, Association between the presenilin-1 mutation Glu318Gly and complaints of memory impairment, Neurobiology of Aging, 2002, January-February, 23 (1), p. 55-58), memory disturbance/learning disturbance (for example, refer to, Vaucher E, and 5 others, Object recognition memory and cholinergic parameters in mice expressing human presenilin 1 transgenes, Experimental Neurology, 2002 June, 175 (2), p. 398-406; Morgan D, and 14 others, Aβ peptide vaccination prevents memory loss in an animal model of Alzheimer's disease, Nature, 2000 Dec. 21-28, 408 (6815), p. 982-985; Moran P M, and 3 others, Age-related learning deficits in transgenic mice expressing the 751-amino acid isoform of human f3-amyloid precursor protein, Proceeding National Academy of Science USA, 1995, Jun. 6, 92 (12), p. 5341-5345), amyloidosis, cerebral ischemia (for example, refer to, Laws S M, and 7 others, Association between the presenilin-1 mutation Glu318Gly and complaints of memory impairment, Neurobiology of Aging, 2002, January-February, 23 (1), p. 55-58; Koistinaho M, and 10 others, β-amyloid precursor protein transgenic mice that harbor diffuse Aβ deposits but do not form plaques show increased ischemic vulnerability: Role of inflammation, Proceeding National Academy of Science USA, 2002, Feb. 5, 99 (3), p. 1610-1615; Zhang F, and 4 others, Increased susceptibility to ischemic brain damage in transgenic mice overexpressing the amyloid precursor protein, The journal of neuroscience, 1997, Oct. 15, 17 (20), p. 7655-7661), cerebrovascular dementia (for example, refer to, Sadowski M, and 6 others, Links between the pathology of Alzheimer's disease and vascular dementia, Neurochemical Research, 2004, Jun., 29 (6), p. 1257-1266), ophthalmoplegia (for example, refer to, O'Riordan S, and 7 others, Presenilin-1 mutation (E280G), spastic paraparesis, and cranial MRI white-matter abnormalities, Neurology, 2002, Oct. 8, 59 (7), p. 1108-1110), multiple sclerosis (for example, refer to, Gehrmann J, and 4 others, Amyloid precursor protein (APP) expression in multiple sclerosis lesions, Glia, 1995, Oct., 15 (2), p. 141-51; Reynolds W F, and 6 others, Myeloperoxidase polymorphism is associated with gender specific risk for Alzheimer's disease, Experimental Neurology, 1999, January, 155 (1), p. 31-41), head injury, skull damage (for example, refer to, Smith D H, and 4 others, Protein accumulation in traumatic brain injury, NeuroMolecular Medicine, 2003, 4 (1-2), p. 59-72), apraxia (for example, refer to, Matsubara-Tsutsui M, and 7 others, Molecular evidence of presenilin 1 mutation in familial early onset dementia, American journal of Medical Genetics, 2002, Apr. 8, 114 (3), p. 292-298), prion disease, familial amyloid neuropathy, triplet repeat disease (for example, refer to, Kirkitadze M D, and 2 others, Paradigm shifts in Alzheimer's disease and other neurodegenerative disorders: the emerging role of oligomeric assemblies, Journal of Neuroscience Research, 2002, Sep. 1, 69 (5), p. 567-577; Evert B O, and 8 others, Inflammatory genes are upregulated in expanded ataxin-3-expressing cell lines and spinocerebellar ataxia type 3 brains, The Journal of Neuroscience, 2001, Aug. 1, 21 (15), p. 5389-5396; Mann D M, and another, Deposition of amyloid (A4) protein within the brains of persons with dementing disorders other than Alzheimer's disease and Down's syndrome, Neuroscience Letters, 1990, Feb. 5, 109 (1-2), p. 68-75), Parkinson's disease (for example, refer to, Primavera J, and 4 others, Brain accumulation of amyloid-β in Non-Alzheimer Neurodegeneration, Journal of Alzheimer's Disease, 1999, Oct., 1 (3), p. 183-193), Dementia with Lewy bodies (for example, refer to, Giasson B I, and 2 others, Interactions of amyloidogenic proteins. NeuroMolecular Medicine, 2003, 4 (1-2), p. 49-58; Masliah E, and 6 others, β-amyloid peptides enhance α-synuclein accumulation and neuronal deficits in a transgenic mouse model linking Alzheimer's disease and Parkinson's disease, Proceeding National Academy of Science USA, 2001, Oct. 9, 98 (21), p. 12245-12250; Barrachina M, and 6 others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46 (3), p. 253-260; Primavera J, and 4 others, Brain accumulation of amyloid-β in Non-Alzheimer Neurodegeneration, Journal of Alzheimer's Disease, 1999, Oct., 1 (3), p. 183-193), Parkinsonism-dementia complex (for example, refer to, Schmidt M L, and 6 others, Amyloid plaques in Guam amyotrophic lateral sclerosis/parkinsonism-dementia complex contain species of Aβ similar to those found in the amyloid plaques of Alzheimer's disease and pathological aging, Acta Neuropathologica (Berl), 1998, February, 95 (2), p. 117-122; Ito H, and 3 others, Demonstration of β amyloid protein-containing neurofibrillary tangles in parkinsonism-dementia complex on Guam, Neuropathology and applied neurobiology, 1991, Oct., 17 (5), p. 365-373), frontotemporal dementia and Parkinsonism linked to chromosome 17 (for example, refer to, Rosso S M, and 3 others, Coexistent tau andamyloid pathology in hereditary frontotemporal dementia with tau mutations, Annals of the New York academy of sciences, 2000, 920, p. 115-119), Dementia with argyrophilic grains (for example, refer to, Tolnay M, and 4 others, Low amyloid (Aβ) plaque load and relative predominance of diffuse plaques distinguish argyrophilic grain disease from Alzheimer's disease, Neuropathology and applied neurobiology, 1999, Aug., 25 (4), p. 295-305), Niemann-Pick disease (for example, refer to, Jin L W, and 3 others, Intracellular accumulation of amyloidogenic fragments of amyloid-β precursor protein in neurons with Niemann-Pick type C defects is associated with endosomal abnormalities, American Journal of Pathology, 2004, March, 164 (3), p. 975-985), amyotrophic lateral sclerosis (for example, refer to, Sasaki S, and another, Immunoreactivity of β-amyloid precursor protein in amyotrophic lateral sclerosis, Acta Neuropathologica (Berl), 1999, May, 97 (5), p. 463-468; Tamaoka A, and 4 others, Increased amyloid β protein in the skin of patients with amyotrophic lateral sclerosis, Journal of neurology, 2000, August, 247 (8), p. 633-635; Hamilton R L, and another, Alzheimer disease pathology in amyotrophic lateral sclerosis, Acta Neuropathologica, 2004, June, 107 (6), p. 515-522; Turner B J, and 6 others, Brain β-amyloidaccumulation in transgenic mice expressing mutant superoxide dismutase 1, Neurochemical Research, 2004, Dec., 29 (12), p. 2281-2286), hydrocephalus (for example, refer to, Weller R O, Pathology of cerebrospinal fluid and interstitial fluid of the CNS: Significance for Alzheimer's disease, prion disorders and multiple sclerosis, Journal of Neuropathology and Experimental Neurology, 1998, October, 57 (10), p. 885-894; Silverberg G D, and 4 others, Alzheimer's disease, normal-pressure hydrocephalus, and senescent changes in CSF circulatory physiology: a hypothesis, Lancet neurology, 2003, Aug., 2 (8), p. 506-511; Weller R O, and 3 others, Cerebral amyloid angiopathy: Accumulation of Aβ in interstitial fluid drainage pathways in Alzheimer's disease, Annals of the New York academy of sciences, 2000, April, 903, p. 110-117; Yow H Y, and another, A role for cerebrovascular disease in determining the pattern of β-amyloid deposition in Alzheimer's disease, Neurology and applied neurobiology, 2002, 28, p. 149; Weller R O, and 4 others, Cerebrovascular disease is a major factor in the failure of elimination of Aβ from the aging human brain, Annals of the New York academy of sciences, 2002, November, 977, p. 162-168), paraparesis (for example, refer to, O'Riordan S, and 7 others, Presenilin-1 mutation (E280G), spastic paraparesis, and cranial MRI white-matter abnormalities, Neurology, 2002, Oct. 8, 59 (7), p. 1108-1110; Matsubara-Tsutsui M, and 7 others, Molecular evidence of presenilin 1 mutation in familial early onset dementia, American journal of Medical Genetics, 2002, Apr. 8, 114 (3), p. 292-298; Smith M J, and 11 others, Variable phenotype of Alzheimer's disease with spastic paraparesis, Annals of Neurology, 2001, 49 (1), p. 125-129; Crook R, and 17 others, A variant of Alzheimer's disease with spastic pararesis and unusual plaques due to deletion of exon 9 of presenilin 1, Nature Medicine, 1998, April; 4 (4), p. 452-455), progressive supranuclear palsy (for example, refer to, Barrachina M, and 6 others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46 (3), p. 253-260; Primavera J, and 4 others, Brain accumulation of amyloid-β in Non-Alzheimer Neurodegeneration, Journal of Alzheimer's Disease, 1999, Oct., 1 (3), p. 183-193), cerebral hemorrhage (for example, refer to, Atwood C S, and 3 others, Cerebrovascular requirement for sealant, anti-coagulant and remodeling molecules that allow for the maintenance of vascular integrity and blood supply, Brain Research Reviews, 2003, September, 43 (1), p. 164-78; Lowenson J D, and 2 others, Protein aging: Extracellular amyloid formation and intracellular repair, Trends in cardiovascular medicine, 1994, 4 (1), p. 3-8), spasm (for example, refer to, Singleton A B, and 13 others, Pathology of early-onset Alzheimer's disease cases bearing the Thr113-114ins presenilin-1 mutation, Brain, 2000, December, 123 (Pt12), p. 2467-2474), mild cognitive impairment (for example, refer to, Gattaz W F, and 4 others, Platelet phospholipase A2 activity in Alzheimer's disease and mild cognitive impairment, Journal of Neural Transmission, 2004, May, 111 (5), p. 591-601; Assini A, and 14 others, Plasma levels of amyloid β-protein 42 are increased in women with mild cognitive impariment, Neurology, 2004, Sep. 14, 63 (5), p. 828-831), arteriosclerosis (for example, refer to, De Meyer GR, and 8 others, Platelet phagocytosis and processing of β-amyloid precursor protein as a mechanism of macrophage activation in atherosclerosis, Circulation Reserach, 2002, Jun. 14, 90 (11), p. 1197-1204).

The "Substituent Group a1", "Substituent Group b1" and "Substituent Group c1" have the following meanings in the compound represented by the formula (I) effective for the treatment or prevention of a disease caused by Aβ according to the present invention.

The "Substituent Group a1" refers to a group consisting of a C1-6 alkyl group, a C3-8 cycloalkyl group, a C2-6 alkenyl group, a C1-6 alkoxy group, a C2-6 alkenyloxy group, a C3-8 cycloalkyloxy group, an amino group (wherein the amino group may have one C2-6 alkanoyl group or C1-6 alkylsulfonyl group or 1 to 2 C1-6 alkyl groups or C3-8 cycloalkyl groups), a cyano group, a formyl group, a halogen atom, a hydroxyl group and a nitro group.

The "Substituent Group b1" refers to a group consisting of a C1-6 alkyl group (wherein the alkyl group may be substituted with 1 to 3 halogen atoms), a C2-6 alkenyl group, a C3-8 cycloalkyl group, a C6-14 aryl group, a C6-14 aryl-C1-6 alkyl group, a C1-6 alkoxy group, a C2-6 alkenyloxy group, a C3-8 cycloalkyloxy group, a C2-6 alkanoyl group, a C4-9 cycloalkylcarbonyl group, a C7-15 aroyl group, a C1-6 alkylsulfonyl group, a C2-6 alkenylsulfonyl group, a C3-8 cycloalkylsulfonyl group, a C6-14 arylsulfonyl group, a C1-6 alkylthio group, a C2-6 alkenylthio group, a C3-8 cycloalkylthio group, an aminosulfonyl group (wherein the aminosulfonyl group may have 1 to 2 C1-6 alkyl groups, C2-6 alkenyl groups or C3-8 cycloalkyl groups), an amino group (wherein the amino group may have one C2-6 alkanoyl group, C1-6 alkylsulfonyl group or C3-8 cycloalkylsulfonyl group or 1 to 2 C1-6 alkyl groups or C3-8 cycloalkyl groups), a cyano group, a formyl group, a halogen atom, a hydroxyl group, a nitro group, an oxo group, a 1-pyrrolidinyl group, a 1-piperidinyl group, a 1-homopiperidinyl group, an indolin-1-yl group, a 1,2,3,4-tetrahydroquinolin-1-yl group and a 4-morpholinyl group.

The "Substituent Group c1" refers to an amino group (wherein the amino group may have one C2-6 alkanoyl group, C1-6 alkylsulfonyl group or C3-8 cycloalkylsulfonyl group or 1 to 2 C1-6 alkyl groups or C3-8 cycloalkyl groups), ii) a cyano group, iii) a halogen atom, iv) a hydroxyl group and v) v-i) a C1-6 alkyl group, v-ii) a C2-6 alkenyl group, v-iii) a C2-6 alkynyl group, v-iv) a C1-6 alkoxy group, v-v) a C1-6 alkylthio group, v-yl) a C1-6 alkylaminocarbonyl group, v-vii) a C1-6 alkylsulfonyl group, v-viii) a C1-6 alkylaminosulfonyl group, v-ix) a C2-6 alkanoyl group, v-x) a phenyl group, v-xi) a pyridyl group, v-xii) a pyridazinyl group, v-xiii) a pyrimidinyl group, v-xiv) a 1-pyrrolidinyl group, v-xv) a 1-piperidinyl group, v-xvi) a 1-homopiperidinyl group and v-xvii) a 4-morpholinyl group, each of which may have 1 to 3 substituents selected from the group consisting of a C1-6 alkyl group and a halogen atom.

The "halogen atom" refers to a fluorine atom, a chlorine atom, a bromine atom, an iodine atom or the like and is preferably a fluorine atom, a chlorine atom or a bromine atom.

The "C1-6 alkyl group" refers to an alkyl group having 1 to 6 carbon atoms. Preferable examples of the group include linear or branched alkyl groups such as a methyl group, an ethyl group, an n-propyl group, an i-propyl group, an n-butyl group, an i-butyl group, a tert-butyl group, an n-pentyl group, an i-pentyl group, a neopentyl group, an n-hexyl group, a 1-methylpropyl group, an 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group and a 3-methylpentyl group.

The "C1-6 alkylene group" refers to an alkylene group having 1 to 6 carbon atoms. Preferable examples of the group include linear or branched alkylene groups such as a methylene group, an ethylene group, a methylmethylene group, a propylene group, a methylethylene group, an ethylmethylene group, a dimethylmethylene group, a butylene group, a methylpropylene group, an ethylethylene group, a dimethylethylene group, a propylmethylene group, a pentylene group and a hexylene group. Among these, a methylene group, an ethylene group, a methylmethylene group, a propylene group, a methylethylene group, an ethylmethylene group and a dimethylmethylene group are preferable, for example.

The "C3-8 cycloalkyl group" refers to a cyclic alkyl group having 3 to 8 carbon atoms. Preferable examples of the group include a cyclopropyl group, a cyclobutyl group, a cyclopentyl group, a cyclohexyl group, a cycloheptyl group and a cyclooctyl group.

The "C2-6 alkenyl group" refers to an alkenyl group having 2 to 6 carbon atoms. Preferable examples of the group include linear or branched alkenyl groups such as a vinyl group, an allyl group, a 1-propenyl group, an isopropenyl group, a 1-buten-1-yl group, a 1-buten-2-yl group, a 1-buten-3-yl group, a 2-buten-1-yl group and a 2-buten-2-yl group.

The "C2-6 alkynyl group" refers to an alkynyl group having 2 to 6 carbon atoms. Preferable examples of the group include linear or branched alkynyl groups such as an ethynyl group, a 1-propynyl group, a 2-propynyl group, a butynyl group, a pentynyl group and a hexynyl group.

The "C3-8 cycloalkyloxy group" refers to a cyclic alkyl group having 3 to 8 carbon atoms in which one hydrogen atom is replaced by an oxygen atom. Preferable examples of the group include a cyclopropoxy group, a cyclobutoxy group, a cyclopentoxy group, a cyclohexoxy group, a cycloheptyloxy group and a cyclooctyloxy group.

The "C3-8 cycloalkylthio group" refers to a cyclic alkyl group having 3 to 8 carbon atoms in which one hydrogen atom is replaced by a sulfur atom. Preferable examples of the group include a cyclopropylthio group, a cyclobutylthio group, a cyclopentylthio group, a cyclohexylthio group, a cycloheptylthio group and a cyclooctylthio group.

The "C1-6 alkoxy group" refers to an alkyl group having 1 to 6 carbon atoms in which a hydrogen atom is replaced by an oxygen atom. Preferable examples of the group include a methoxy group, an ethoxy group, an n-propoxy group, an i-propoxy group, an n-butoxy group, an i-butoxy group, a sec-butoxy group, a tert-butoxy group, an n-pentoxy group, an i-pentoxy group, a sec-pentoxy group, a tert-pentoxy group, an n-hexoxy group, an i-hexoxy group, a 1,2-dimethylpropoxy group, a 2-ethylpropoxy group, a 1-methyl-2-ethylpropoxy group, a 1-ethyl-2-methylpropoxy group, a 1,1,2-trimethylpropoxy group, a 1,1,2-trimethylpropoxy group, a 1,1-dimethylbutoxy group, a 2,2-dimethylbutoxy group, a 2-ethylbutoxy group, a 1,3-dimethylbutoxy group, a 2-methylpentoxy group, a 3-methylpentoxy group and a hexyloxy group.

The "C1-6 alkylthio group" refers to an alkyl group having 1 to 6 carbon atoms in which one hydrogen atom is replaced by a sulfur atom. Preferable examples of the group include a methylthio group, an ethylthio group, an n-propylthio group, an i-propylthio group, an n-butylthio group, an i-butylthio group, a tert-butylthio group, an n-pentylthio group, an i-pentylthio group, a neopentylthio group, an n-hexylthio group and a 1-methylpropylthio group.

The "C2-6 alkanoyl group" refers to an alkyl group having 1 to 6 carbon atoms in which one hydrogen atom is substituted with a carbonyl group. Preferable examples of the group include an acetyl group, a propionyl group and a butyryl group.

The "C1-6 alkylsulfonyl group" refers to an alkyl group having 1 to 6 carbon atoms in which one hydrogen atom is replaced by a sulfonyl group. Preferable examples of the group include a methanesulfonyl group and an ethanesulfonyl group.

The "C2-6 alkenyloxy group" refers to an alkenyl group having 2 to 6 carbon atoms in which one hydrogen atom is replaced by an oxygen atom. Preferable examples of the group include linear or branched alkenyloxy groups such as a vinyloxy group, an allyloxy group, a 1-propenyloxy group, an isopropenyloxy group, a 1-buten-1-yloxy group, a 1-buten-2-yloxy group, a 1-buten-3-yloxy group, a 2-buten-1-yloxy group and a 2-buten-2-yloxy group.

The "C2-6 alkenylthio group" refers to an alkenyl group having 2 to 6 carbon atoms in which one hydrogen atom is replaced by a sulfur atom. Preferable examples of the group include linear or branched alkenylsulfonyl groups such as a vinylthio group, an allylthio group, a 2-propenylthio group, a 1-buten-1-ylthio group, a 1-buten-2-ylthio group, a 1-buten-3-ylthio group, a 2-buten-1-ylthio group and a 2-buten-2-ylthio group.

The "C2-6 alkenylsulfonyl group" refers to an alkenyl group having 2 to 6 carbon atoms in which one hydrogen atom is replaced by a sulfonyl group. Preferable examples of the group include a vinylsulfonyl group, an allylsulfonyl group, a 2-propenylsulfonyl group, a 1-buten-1-ylsulfonyl group, a 1-buten-2-ylsulfonyl group and a 1-buten-3-ylsulfonyl group.

The "C3-8 cycloalkylsulfonyl group" refers to a cyclic alkyl group having 3 to 8 carbon atoms in which one hydrogen atom is replaced by a sulfonyl group. Preferable examples of the group include a cyclopropylsulfonyl group, a cyclobutylsulfonyl group, a cyclopentylsulfonyl group, a cyclohexylsulfonyl group, a cycloheptylsulfonyl group and a cyclooctylsulfonyl group.

The "C6-14 aryl group" refers to a monocyclic, bicyclic or tricyclic aromatic hydrocarbon ring group having 6 to 14 carbon atoms. Preferable examples of the group include 6- to 14-membered monocyclic, bicyclic or tricyclic aromatic hydrocarbon ring groups such as a phenyl group, an indenyl group, a naphthyl group, an azulenyl group, a heptalenyl group, a biphenyl group, a fluorenyl group, a phenalenyl group, a phenanthryl group and an anthryl group.

The "C7-15 aroyl group" refers to the aforementioned C6-14 aryl group in which one hydrogen atom is replaced by a carbonyl group. Preferable examples of the group include a benzoyl group, an indenecarbonyl group, a naphthoyl group, a biphenylcarbonyl group, a fluorenylcarbonyl group, a phenanthrylcarbonyl group and an anthrylcarbonyl group.

The "C6-14 aryl-C1-6 alkyl group" refers to the aforementioned C1-6 alkyl group in which one hydrogen atom is replaced by the aforementioned C6-14 aryl group. Preferable examples of the group include a benzyl group, a phenethyl group, a phenylpropyl group, a naphthylmethyl group and a biphenylmethyl group.

The "C6-14 arylsulfonyl group" refers to the aforementioned C6-14 aryl group in which one hydrogen atom is replaced by a sulfonyl group. Preferable examples of the group include a benzenesulfonyl group, a naphthalenesulfonyl group and a biphenylsulfonyl group.

The "C1-6 alkylaminocarbonyl group" refers to an alkyl group having 1 to 6 carbon atoms in which one hydrogen atom is replaced by an aminocarbonyl group. Preferable examples of the group include a methylaminocarbonyl group, an ethylaminocarbonyl group, a propylaminocarbonyl group, a butylaminocarbonyl group and a hexylaminocarbonyl group.

The "C1-6 alkylaminosulfonyl group" refers to an alkyl group having 1 to 6 carbon atoms in which one hydrogen atom is replaced by an aminosulfonyl group. Preferable examples of the group include a methylaminosulfonyl group, an ethylaminosulfonyl group, a propylaminosulfonyl group, a butylaminosulfonyl group and a hexylaminosulfonyl group.

When W is a nitrogen atom and $R^2$ is a hydroxyl group, the compound includes, for example, a tautomer represented by the formula:

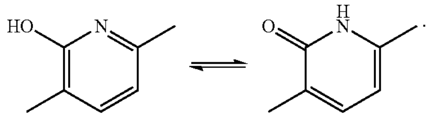

The "five-membered aromatic heterocyclic group fused with a 5- to 14-membered non-aromatic ring group, which contains one or more nitrogen atoms and may have 1 to 3 substituents selected from the following Substituent Group b1" in the definition of Ring A refers to a five-membered aromatic heterocycle containing one or more nitrogen atoms, such as pyrazole, imidazole, triazole, tetrazole, oxazole, thiazole, oxadiazole or thiadiazole, fused with a 5- to 14-membered non-aromatic ring such as a ring represented by the following formula:

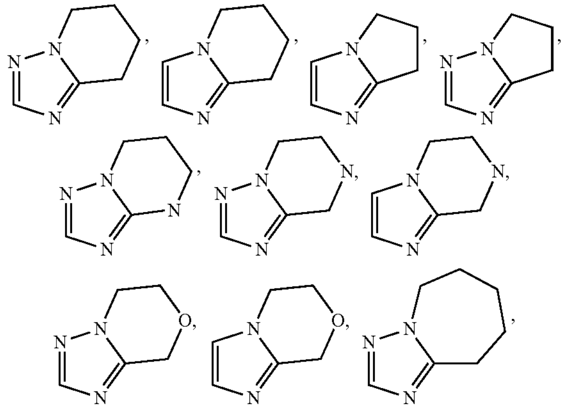

-continued

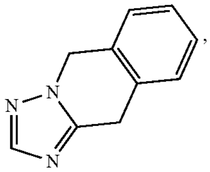

,

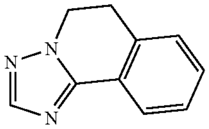

,

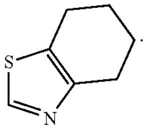

.

One to three substituents selected from Substituent Group b1 may exist at any substitutable position on the ring.

The sentence "the 5- to 14-membered non-aromatic ring group may have a crosslinked structure" in the definition of Ring A refers to the fact that two carbon atoms on the non-aromatic ring group together can form a crosslinked structure. For example, a ring having a crosslinked structure represented by the formula:

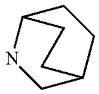

together with the aforementioned five-membered aromatic heterocyclic group such as the following triazolyl ring:

may form a fused ring represented by the following formula:

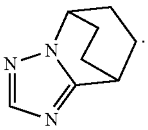 [SMILES: c1nc2n(n1)C1CCC2CC1 ; "."]

.

Ring A may be connected to $X_1$ at a substitutable position on the ring other than the five-membered aromatic heterocycle forming the fused ring. For example, when the connection between Ring A and $X_1$ is represented by the formula [34]:

34

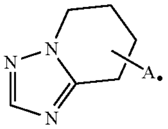

,

Ring A may be connected to $X_1$ at a substitutable position indicated by any one of the following formulas [34-1] to [34-4]:

34-1

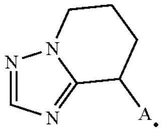

, 34-2

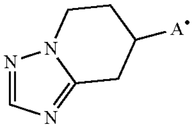

, 34-3

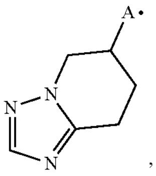

, 34-4

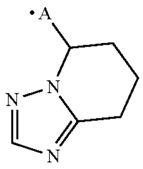

.

When the connection between Ring A and $X_1$ is represented by the formula [35]:

35

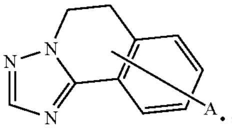

,

Ring A may be connected to $X_1$ at a substitutable position indicated by any one of the following formulas [35-1] to [35-6]:

35-1

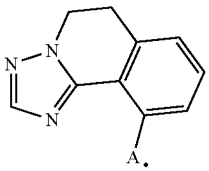

, 35-2

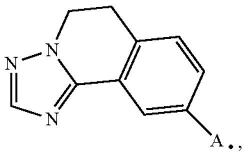

, 35-3

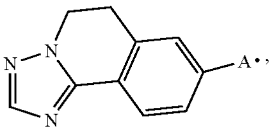

,

-continued 35-4

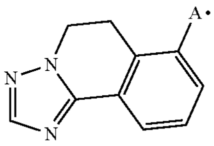

, 35-5

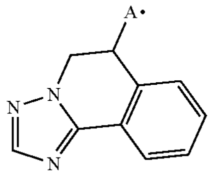

, 35-6

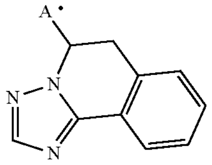

.

One to three substituents selected from Substituent Group c1 in the definition of Ring B may exist at any substitutable position on the ring. Ring B may be connected to $X_1$ at any substitutable position on the ring.

For example, when Ring B is represented by the formula [36]:

36

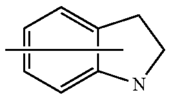

,

Ring B may be connected to $X_1$ at a substitutable position indicated by any one of the following formulas [36-1] to [36-7]:

36-1

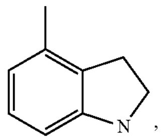

, 36-2

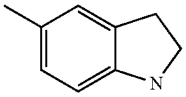

, 36-3

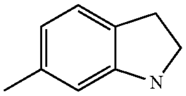

, 36-4

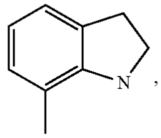

,

-continued 36-5

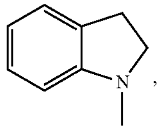

, 36-6

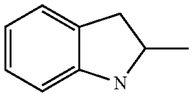

, 36-7

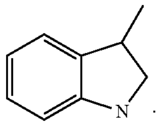

.

In the present invention, the "pharmacologically acceptable salt" is not particularly limited insofar as it is a pharmacologically acceptable salt formed with the compound of the general formula (I) which is a therapeutic agent for a disease caused by Aβ.

Preferable specific examples of the salt include hydrohalides (such as hydrofluorides, hydrochlorides, hydrobromides and hydroiodides), inorganic acid salts (such as sulfates, nitrates, perchlorates, phosphates, carbonates and bicarbonates), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

Next, the compound of the formula [I] according to the present invention will be described.

In the compound of the formula [I] or pharmacologically acceptable salt thereof, preferably, $R_1$ is a C1-6 alkyl group or a halogen atom and m is an integer of 1 to 2; particularly preferably, $R_1$ is a C1-6 alkyl group and m is an integer of 1 to 2; and most preferably, $R_1$ is a methyl group and m is 1.

In the compound of the formula [I] or pharmacologically acceptable salt thereof, preferably, $R_2$ is a halogen atom, a hydroxyl group or a C1-6 alkoxy group and n is an integer of 1 to 2; more preferably, $R_2$ is a C1-6 alkoxy group and n is an integer of 1 to 2; and particularly preferably, $R_2$ is a methoxy group and n is 1.

In the compound of the formula [I] or pharmacologically acceptable salt thereof, $X_1$ is preferably i) a single bond or ii) a C1-6 alkylene group.

In the compound of the formula [I] or pharmacologically acceptable salt thereof, Ring A is preferably represented by any one of the following formulas 20 to 32:

20

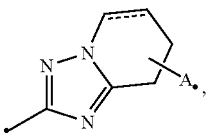

,

-continued
21
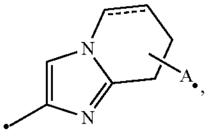
22
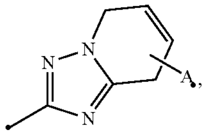
23
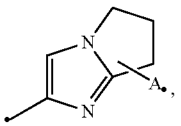
24
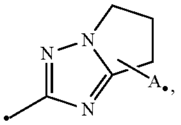
25
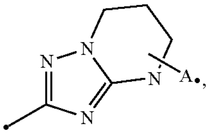
26
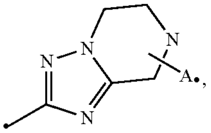
27
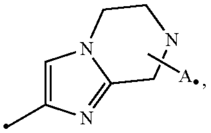
28
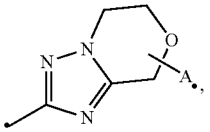
29
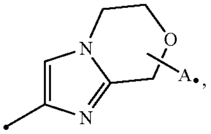
30
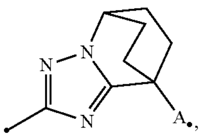
-continued
31
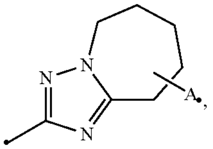
32
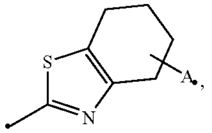
and is particularly preferably represented by any one of the following formulas:
20
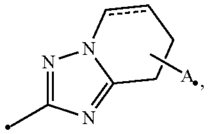
21
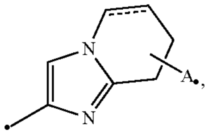
23
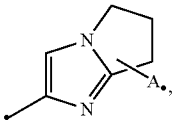
24
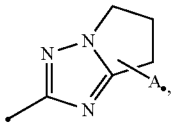
26
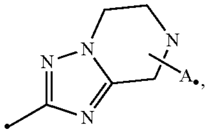
27
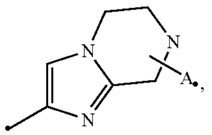
28
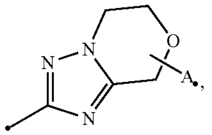

-continued

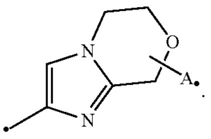

29

In the compound of the formula [I] or pharmacologically acceptable salt thereof, Ring B is preferably represented by any one of the formulas:

2

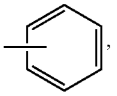

3

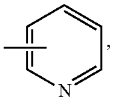

4

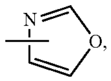

5

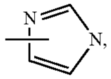

6

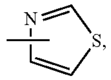

7

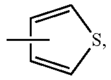

15

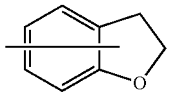

each of which may be substituted with 1 to 3 substituents selected from Substituent Group c1.

Substituent Group b1 is preferably a substituent group consisting of (1) a C1-6 alkyl group (wherein the alkyl group may be substituted with 1 to 3 halogen atoms), (2) a C3-8 cycloalkyl group, (3) a C6-14 aryl group, (4) a C6-14 aryl-C1-6 alkyl group, (5) a C1-6 alkoxy group, (6) a C3-8 cycloalkyloxy group, (7) a C2-6 alkanoyl group, (8) a C7-15 aroyl group, (9) a C1-6 alkylsulfonyl group, (10) a C3-8 cycloalkylsulfonyl group, (11) a C6-14 arylsulfonyl group, (12) a cyano group, (13) a formyl group, (14H) a halogen atom, (15) a hydroxyl group and (16) an oxo group.

Substituent Group c1 is preferably a substituent group consisting of (1) an amino group (wherein the amino group may have one C2-6 alkanoyl group, C1-6 alkylsulfonyl group or C3-8 cycloalkylsulfonyl group or 1 to 2 C1-6 alkyl groups or C3-8 cycloalkyl groups), (2) a cyano group, (3) a halogen atom, (4) a hydroxyl group and (5) (5)-1) a C1-6 alkyl group, (5)-2) a C1-6 alkoxy group, (5)-3) a C1-6 allylthio group and (5)-4) a phenyl group, each of which may have 1 to 3 substituents selected from the group consisting of a C1-6 alkyl group and a halogen atom.

At least one compound selected from the group consisting of the following formulas [A-1] to [A-7]:

A-1

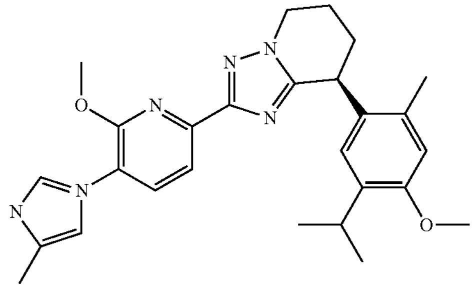

A-2

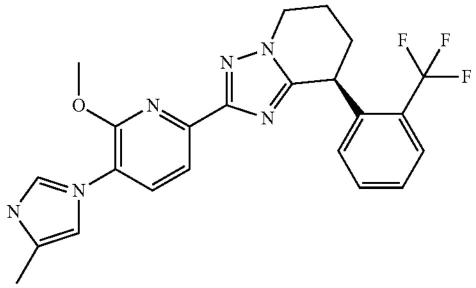

A-3

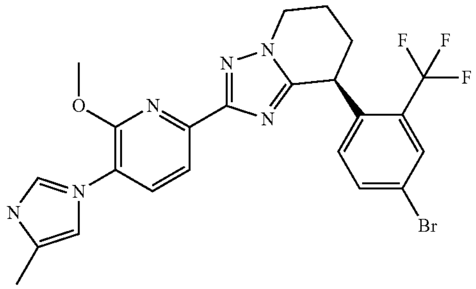

A-4

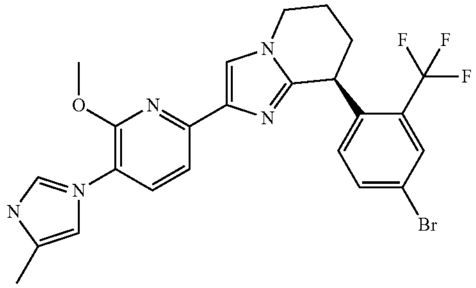

A-5

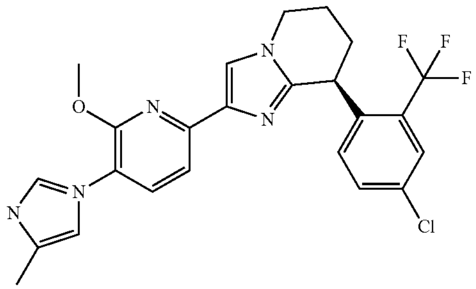

-continued

A-6

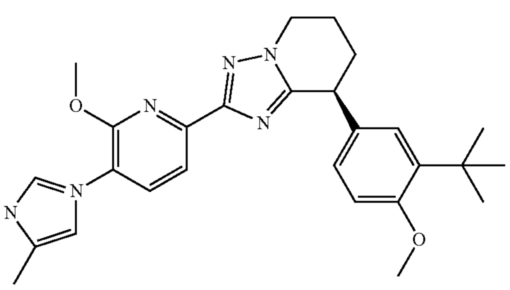

A-7

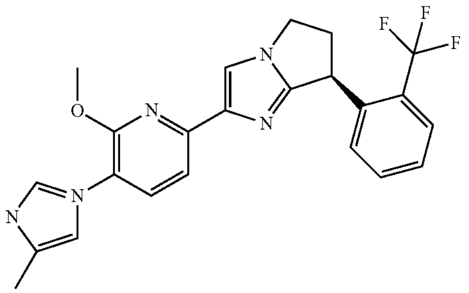

wherein $R_1$, $R_2$, m, n, W, Ring A, $X_1$ and Ring B are as defined above, is synthesized according to a method such as the following General Preparation Method 1 to General Preparation Method 8, for example. It is obvious that, in order to prepare the compound of the present invention conveniently, the method comprises a protection reaction step and a deprotection reaction step appropriately, using a protecting group known to a person skilled in the art which is suitably selected for each step (see T. Greene et al, "Protective Groups in Organic Synthesis", John Wiley & Sons, Inc, New York, 1981). It is obvious that, in order to prepare the compound of the present invention conveniently, the method comprises substituent conversion, substituent introduction and the like suitable for each step and known to a person skilled in the art. It is also obvious that, in order to prepare the compound of the present invention conveniently, all isomers and isomer mixtures such as geometric isomers which can be generated from the structure of the compound, optical isomers based on asymmetric carbon, stereoisomers, and tautomers can be prepared as a single compound by a technique known to a person skilled in the art which is suitable for each step such as fractional crystallization or column chromatography.

General Preparation Method 1

Typically used General Preparation Method 1 for the compound of the general formula (I) according to the present invention will be described below.

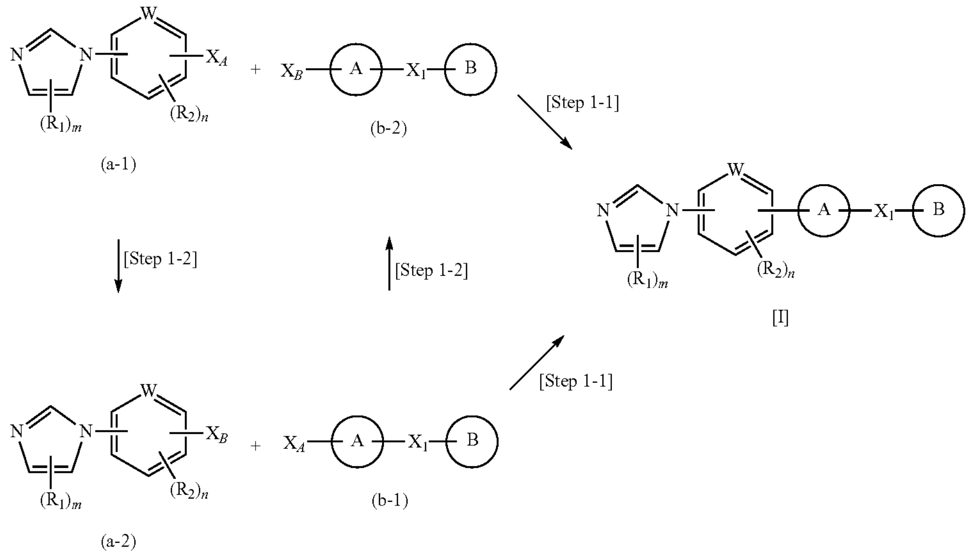

or a pharmacologically acceptable salt thereof is particularly suitable, for example, and is useful as a therapeutic agent for a disease caused by amyloid-β such as Alzheimer's disease, senile dementia, Down's syndrome or amyloidosis.

Methods for preparing the compound of the general formula (I) according to the present invention will be described below.

The compound represented by the general formula (I):

[I]

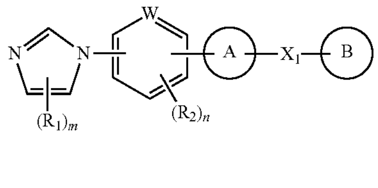

In the formula, $R_1$, $R_2$, m, n, W, Ring A, $X_1$ and Ring B are as defined above; $X_A$ represents a halogen atom such as a chlorine atom, a bromine atom or an iodine atom or a sulfonate group such as a methanesulfonate group, a p-toluenesulfonate group or a trifluoromethanesulfonate group; and $X_B$ represents a trialkylstannyl group, a boronic acid group or a boronate group such as a pinacol boronate group.

The above General Preparation Method 1 is a method for preparing the compound of the general formula [I] by subjecting to coupling reaction in Step 1-1a compound of the general formula (1) and a compound of the general formula (b-2) or a method for preparing the compound of the general formula [I] by subjecting to coupling reaction in Step 1-1a compound of the general formula (2) and a compound of the general formula (b-1) in which the substituents $X_A$ and $X_B$ are replaced by each other.

The coupling reaction in Step 1-1) varies according to the starting material and is not particularly limited insofar as the conditions are similar to those in this reaction. A method known to a person skilled in the art may be used for the reaction. Preferable examples of the method include Suzuki-Miyaura reaction (see A. Suzuki, "Chem. Rev.", 1995, vol. 95, p. 2457, for example) and Stille coupling reaction (see J. K. Stille, "Angew. Chem. Int. Ed. Engl.", 1986, vol. 25, p. 508, for example).

In Suzuki-Miyaura reaction, a halogen compound or trifluoromethanesulfonate compound of the general formula (1) is preferably coupled with 1.0 to 5.0 equivalents of a compound of the general formula (b-2) (wherein $X_B$ is preferably a boronic acid group, a boronate group such as a pinacol boronate group, an alkylboronalkenyl group or the like) with respect to the compound of the general formula (1) in the presence of 0.01 to 0.5 equivalent of a transition metal catalyst with respect to the compound of the general formula (1), for example. This reaction is preferably performed in the presence of a solvent from the viewpoint of handleability and stirring efficiency. The solvent used varies according to the starting material and the transition metal catalyst used, and is not particularly limited insofar as it does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water and a mixed solvent thereof. The reaction temperature must be a temperature that can complete the coupling reaction, and is preferably room temperature to 200° C. This reaction is performed preferably in an inert gas atmosphere, and more preferably in a nitrogen or argon atmosphere. Under preferable reaction conditions, the reaction is completed in 1 to 24 hours, and the progress of the reaction can be monitored by a known chromatography technique. The transition metal catalyst is preferably a known palladium complex, and more preferably a known palladium complex such as palladium (II) acetate, dichlorobis(triphenylphosphine)palladium (II), tetrakis(triphenylphosphine) palladium (0) or tris(dibenzylideneacetone)dipalladium (0). A phosphorus ligand (preferably triphenylphosphine, tri-o-tolylphosphine, tricyclohexylphosphine or tri-tert-butylphosphine, for example) may be appropriately added in order to make the reaction efficiently proceed. A quaternary ammonium salt, preferably tetrabutylammonium chloride or tetrabutylammonium bromide, for example, may also be appropriately added in order to make the reaction efficiently proceed. In this reaction, a preferable result may be achieved in the presence of a base. The base used at this time varies according to the starting material, the solvent used and the like, and is not particularly limited. Preferable examples of the base include sodium hydroxide, barium hydroxide, potassium fluoride, cesium fluoride, sodium carbonate, potassium carbonate, cesium carbonate and potassium phosphate. Under preferable reaction conditions, the reaction is completed in 1 to 24 hours, and the progress of the reaction can be monitored by a known chromatography technique.

In Stille coupling reaction, a halogen compound or trifluoromethanesulfonate group compound of the general formula (1) is preferably coupled with 1.0 to 5.0 equivalents of a compound of the general formula (b-2) (wherein $X_B$ is preferably a trialkylstaimyl group) with respect to the compound of the general formula (1) in the presence of 0.01 to 0.2 equivalent of a transition metal catalyst with respect to the compound of the general formula (1), for example. It is preferable to appropriately use in this reaction 0.1 to 5.0 equivalents of copper (I) halide or/and lithium chloride in order to make the reaction efficiently proceed. Preferable examples of the solvent used in this reaction include toluene, xylene, N,N-dimethylformamide, N,N-dimethylacetamide, 1-methyl-2-pyrrolidone and dimethyl sulfoxide. The reaction temperature must be a temperature that can complete the coupling reaction, and is preferably room temperature to 150° C. The preferable transition metal catalyst is a palladium complex, preferably a known palladium complex such as palladium (II) acetate, dichlorobis(triphenylphosphine)palladium (II), tetralds(triphenylphosphine)palladium (0) or tris(dibenzylideneacetone)dipalladium (0), for example, and more preferably palladium (II) acetate, tetrakis(triphenylphosphine)palladium (0) or tris(dibenzylideneacetone)dipalladium (0), for example. A phosphorus ligand (preferably triphenylphosphine, tri-o-tolylphosphine, 1,3-bis (diphenylphosphino)propane or tri-tert-butylphosphine, for example) may be appropriately added, for example, in order to make the reaction efficiently proceed. This reaction is performed preferably in an inert gas atmosphere, and more preferably in a nitrogen or argon atmosphere. Under preferable reaction conditions, the reaction is completed in 1 to 24 hours, and the progress of the reaction can be monitored by a known chromatography technique.

Step 1-2 is an example of a method for preparing a compound of the general formula (2) and a compound of the general formula (b-2) in which the substituents $X_A$ and $X_B$ are replaced by each other. This step varies according to the starting material and is not particularly limited insofar as the conditions are similar to those in this reaction. A method known to a person skilled in the art may be used for the reaction. It is possible to use methods similar to preparation methods such as Suzuki-Miyaura reaction (see A. Suzuki, "Chem. Rev.", 1995, vol. 95, p. 2457, for example) and Stille coupling reaction (see J. K. Stille, "Angew. Chem. Int. Ed. Engl.", 1986, vol. 25, p. 508, for example).

Preparation of Compound of General Formula (1)

The following formula shows an example of preparation of the compound of the general formula (1).

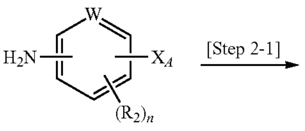

(a-3)

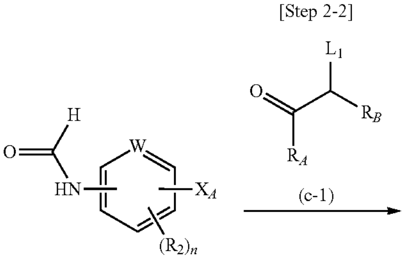

(a-5)

(c-1)

-continued

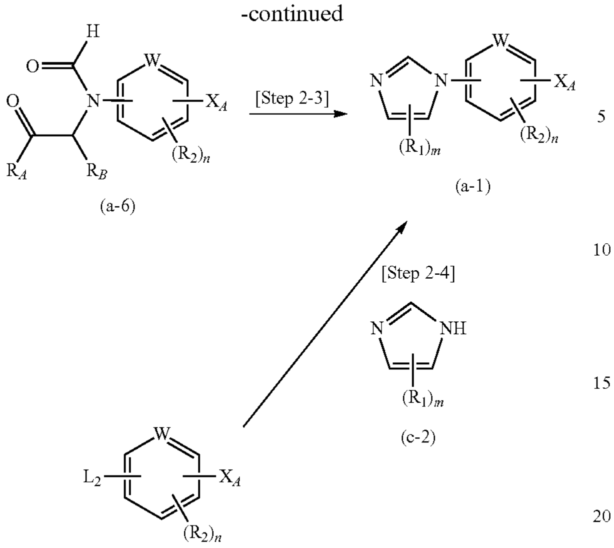

(a-6) (a-1) (c-2) (a-4)

In the formula, $R_1$, $R_2$, m, n, W and $X_A$ are as defined above; $R_A$ and $R_B$ are as defined for $R_1$ above; $L_1$ represents a halogen atom such as a chlorine atom, a bromine atom or an iodine atom or a sulfonate group such as a methanesulfonate group, a p-toluenesulfonate group or a trifluoromethanesulfonate group; and $L_2$ represents a halogen atom such as a fluorine atom, a chlorine atom, a bromine atom or an iodine atom, a sulfonate group such as a methanesulfonate group, a p-toluenesulfonate group or a trifluoromethanesulfonate group or a boronic acid group.

The compound of the general formula (1) can be prepared from an amine compound (3) as a starting material through formylation in Step 2-1, alkylation reaction in Step 2-2 and formation of an imidazole ring in Step 2-3, or can be prepared from a compound of the general formula (4) as a starting material by coupling reaction in Step 2-4.

Step 2-1 varies according to the starting material and is not particularly limited insofar as the conditions are similar to those in this reaction. A method known to a person skilled in the art may be used for the reaction. A method reported in many documents or the like (T. Greene et al, "Protective Groups in Organic Synthesis", John Wiley & Sons, Inc, New York, 1981, for example) may be used.

Step 2-2 varies according to the starting material and is not particularly limited insofar as the conditions are similar to those in this reaction. A method known to a person skilled in the art may be used for the reaction. Preferable examples of the method include a method of stirring a compound of the general formula (5) and 1.0 to 10.0 equivalents of a compound of the general formula (c-1) with respect to the compound of the general formula (5) in a solvent in the presence of 1.0 to 10.0 equivalents of a base with respect to the compound of the general formula (5). The base used varies according to the starting material and is not particularly limited. Preferable examples of the base include alkali metal hydrides (such as sodium hydride and lithium hydride), alkali metal salts (such as potassium carbonate, sodium carbonate and cesium carbonate) and metal alkoxides (such as sodium methoxide and potassium tert-butoxide). The solvent used varies according to the starting material, and is not particularly limited insofar as it does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as N,N-dimethylformamide and N-methylpyrrolidone; non-polar solvents such as toluene and benzene; and mixtures thereof. The reaction temperature must be a temperature that can complete the reaction without promoting formation of an undesirable by-product, and is preferably 0° C. to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

Step 2-3 varies according to the starting material and is not particularly limited insofar as the conditions are similar to those in this reaction. A method known to a person skilled in the art may be used for the reaction. A method reported in many documents or the like (such as described in The Chemistry of Heterocyclic Compounds. Imidazole and Derivatives, Part I, p. 33, Inters. Publish. 1953) may be used. Preferable examples of the method include a method for preparing the compound of the general formula (1) by forming an imidazole ring from a compound of the general formula (6) and ammonia, ammonium salt, formamide or the like as a nitrogen source. The solvent used is not particularly limited insofar as it does not inhibit the reaction and allows the starting material to be dissolved therein to a certain extent. Preferable examples of the solvent include non-polar solvents such as toluene and benzene; alcohol solvents such as methanol and ethanol; organic acids such as acetic acid or trifluoroacetic acid, sulfonic acids such as p-toluenesulfonic acid and trifluoromethanesulfonic acid; water; and mixtures thereof. Formamide may optionally be used as a nitrogen atom source and as a solvent. The reaction temperature must be a temperature that can complete the reaction without promoting formation of an undesirable by-product, and is preferably room temperature to 250° C., for example. The yield may be improved when the reaction is performed using a tight container. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The coupling reaction in Step 2-4 varies according to the starting material and is not particularly limited insofar as the conditions are similar to those in this reaction. A method known to a person skilled in the art may be used for the reaction. A method reported in many documents or the like (such as described in D. D. Davey et al, "J. Med. Chem.", 1991, vol. 34, p. 2671-2677) may be used. Examples of the method include a method of stirring a compound of the general formula (4) (wherein $L_2$ is preferably a halogen atom or the like) and 1.0 to 5.0 equivalents of an imidazole compound (c-2) with respect to the compound of the general formula (4) in a solvent in the presence or absence of 1.0 to 5.0 equivalents of a base with respect to the compound of the general formula (4). Preferable examples of the base used include sodium hydride, sodium hydroxide, potassium hydroxide, potassium carbonate, sodium carbonate, cesium carbonate, barium carbonate, pyridine, lutidine and triethylamine. The solvent used varies according to the starting material, and is not particularly limited insofar as it does not inhibit the reaction and allows the starting material to be dissolved therein to a certain extent. Preferable examples of the solvent include acetonitrile, tetrahydrofuran, dimethyl sulfoxide, N,N-dimethylformamide and N-methylpyrrolidone. The base may optionally be used as a solvent. The reaction temperature must be a temperature that can complete the reaction without promoting formation of an undesirable by-product, and is preferably room temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

Examples of the coupling reaction in Step 2-4 include a method of stirring a compound of the general formula (4) (wherein $L_2$ is preferably a boronic acid group or the like) in a solvent in the presence of a copper catalyst (such as described in J. P. Coltman et al, "Org. Letters.", 2000, vol. 2, p. 1233-1236). Preferable examples of the method include a method of stirring a compound of the general formula (4) and 0.1 to 10.0 equivalents of an imidazole compound (c-2) with respect to the compound of the general formula (4) in a solvent in the presence of 0.01 to 1.0 equivalent of a copper reagent such as copper, copper bromide or copper iodide with respect to the compound of the general formula (4). The copper reagent used varies according to the starting material and is not particularly limited. Preferable examples of the copper reagent include copper (I) halide, copper (II) acetate, copper (II) nitrate and hydroxo-bis[(N,N,N',N' tetramethylethylenediamine)copper (II)]chloride. The solvent used varies according to the starting material, the reagent and the like, and is not particularly limited insofar as it does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as ethyl acetate, N,N-dimethylformamide and N-methylpyrrolidone; non-polar solvents such as toluene, benzene and dichlorobenzene; and mixtures thereof. A base may be used depending on the starting material, the reagent and the like. Preferable examples of the base include organic bases such as triethylamine, pyridine and tetramethylethylenediamine; alkali metal salts such as potassium carbonate, sodium carbonate, potassium acetate, sodium acetate and cesium carbonate; and metal alkoxides such as sodium methoxide and potassium tert-butoxide. The reaction temperature must be a temperature that can complete the reaction without promoting formation of an undesirable by-product, and is preferably room temperature to 200° C., for example. Good results such as reduction in the reaction time and improvement of the yield can be achieved when the reaction is performed in an oxygen atmosphere or air stream. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The compound of the formula (3), the compound of the formula (4), the compound of the formula (c-1) and the compound of the formula (c-2) are known or commercially available compounds or are compounds that can be prepared from these compounds by a conventional method.

Preparation of Compound of General Formula (b-1)

The following formula shows an example of preparation of the compound of the general formula (b-1).

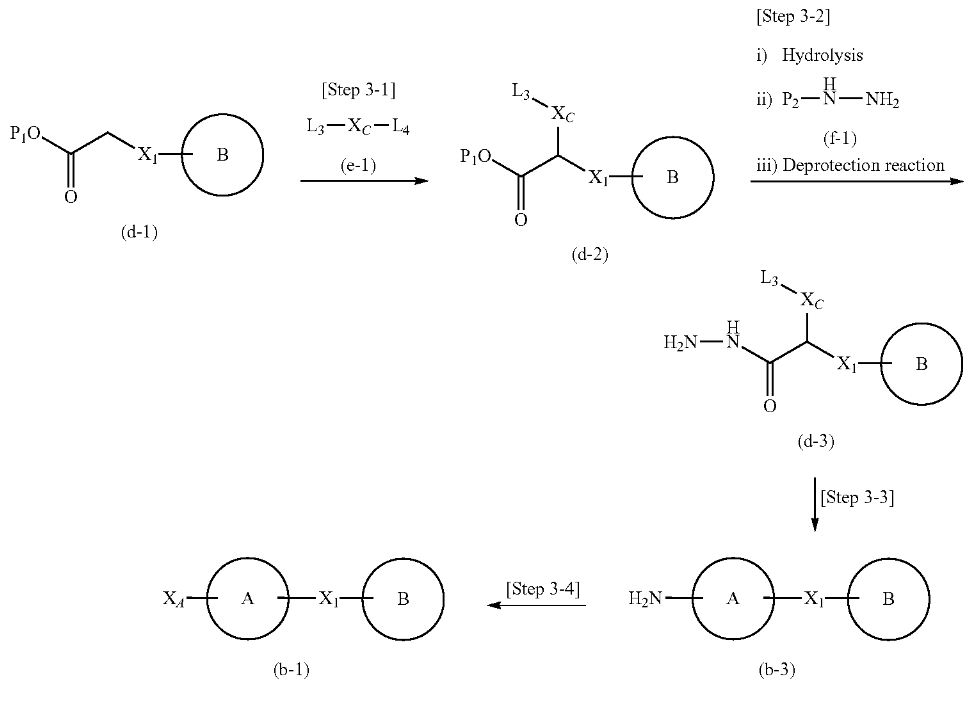

In the formula, $X_1$, $X_4$, Ring A and Ring B are as defined above; $L_3$ and $L_4$ are as defined for $L_1$ above; $X_C$ represents a C2-4 alkylene group, or a C2-3 alkylene group in which one methylene group is replaced by an oxygen atom or a nitrogen atom (wherein the nitrogen atom may have a substituent such as a C1-6 alkyl group or a benzyl group); $P_1$ represents a carboxyl-protecting group such as a methyl group, an ethyl group, a benzyl group, an allyl group, a triphenylmethyl group, a tert-butyl group or a tert-butyldimethylsilyl group, or a hydrogen atom; and $P_2$ represents a nitrogen-protecting group such as a tert-butoxycarbonyl group or a benzyloxycarbonyl group.

The compound of the general formula (b-1) can be prepared from a compound of the general formula (d-1) as a starting material through alkylation in Step 3-1, ester hydrolysis, hydrazidation and deprotection reaction in Step 3-2, formation of Ring A in Step 3-3 and Sandmeyer reaction in Step 3-4.

Step 3-1 varies according to the starting material and is not particularly limited insofar as the conditions are similar to those in this reaction. A method known to a person skilled in the art may be used for the reaction. Preferable examples of the method include a method of stirring a compound of the general formula (d-1) and 1.0 to 10.0 equivalents of a compound of the general formula (e-1) with respect to the compound of the general formula (d-1) in a solvent in the presence of 1.0 to 10.0 equivalents of a base with respect to the compound of the general formula (d-1). The base used varies according to the starting material and is not particularly limited. Preferable examples of the base include alkali metal hydrides (such as sodium hydride and lithium hydride), alkali metal salts (such as potassium carbonate, sodium carbonate and cesium carbonate), metal alkoxides (such as sodium methoxide and potassium tert-butoxide) and organometallic bases (such as butyllithium, lithium diisopropylamide and lithium bistrimethylsilylamide). The solvent used varies according to the starting material, and is not particularly limited insofar as it does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as N,N-dimethylformamide and N-methylpyrrolidone; non-polar solvents such as toluene and benzene; and mixtures thereof. The reaction temperature must be a temperature that can complete the reaction without promoting formation of an undesirable by-product, and is preferably −100° C. to 100° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The ester hydrolysis reaction as the first stage of Step 3-2 varies according to the starting material and is not particularly limited insofar as the conditions are similar to those in this reaction. A deprotection reaction known to a person skilled in the art may be used for the reaction. A method reported in many documents or the like (see T. Greene et al, "Protective Groups in Organic Synthesis", John Wiley & Sons, Inc, New York, 1981, for example) may be used. The hydrazidation reaction as the second stage varies according to the starting material and is not particularly limited insofar as the conditions are similar to those in this reaction. An amidation reaction known to a person skilled in the art may be used for the reaction. A method reported in many documents or the like (such as described in The Chemical Society of Japan (ed.), Jikken Kagaku Koza (Courses in Experimental Chemistry), 4th edition (vol. 22) Yuki Gosei (Organic Synthesis) [IV], Maruzen Co., Ltd, November 1992, p. 137-144) may be used. The deprotection reaction as the third stage varies according to the starting material and is not particularly limited insofar as the conditions are similar to those in this reaction. A deprotection reaction known to a person skilled in the art may be used for the reaction. A method reported in many documents or the like (see T. Greene et al, "Protective Groups in Organic Synthesis", John Wiley & Sons, Inc, New York, 1981, for example) may be used.

The Ring A formation reaction in Step 3-3 varies according to the starting material and is not particularly limited insofar as the conditions are similar to those in this reaction. A method known to a person skilled in the art may be used for the reaction. Preferable examples of the method include a method of heating a compound of the general formula (d-3) and 1.0 to 10.0 equivalents of aminoguanidine, isothiourea, cyanamide or the like with respect to the compound of the general formula (d-3) in a solvent under basic or acidic conditions. The base or acid used varies according to the starting material and is not particularly limited. Examples of the base or acid include bases such as alkali metal hydrides (such as sodium hydride and lithium hydride), alkali metal salts (such as potassium carbonate, sodium carbonate and cesium carbonate), metal alkoxides (such as sodium methoxide and potassium tert-butoxide) and organic bases (such as triethylamine, pyridine and 1,8-diazabicyclo[5.4.0]undec-7-ene); and acids such as hydrochloric acid, sulfuric acid, p-toluenesulfonic acid and camphorsulfonic acid. The solvent used varies according to the starting material, and is not particularly limited insofar as the solvent does not inhibit the reaction and allows the starting material to be dissolved therein to a certain extent. Preferable examples of the solvent include alcohol solvents such as methanol, ethanol and tert-butanol; ether solvents such as tetrahydrofuran, 1,4-dioxane and diethyl ether; halogenated solvents such as methylene chloride, 1,2-dichloroethane and chloroform; polar solvents such as acetonitrile, N,N-dimethylformamide and N-methylpyrrolidone; non-polar solvents such as xylene, toluene and benzene; and mixtures thereof. The reaction temperature must be a temperature that can complete the reaction without promoting formation of an undesirable by-product, and is preferably −100° C. to 100° C., for example. Under preferable reaction conditions, the reaction is completed in 1 to 48 hours, and the progress of the reaction can be monitored by a known chromatography technique. An undesirable by-product can be removed by a technique known to a person skilled in the art such as a conventional chromatography technique, extraction or/and crystallization.

The Sandmeyer reaction in Step 3-4 varies according to the starting material and is not particularly limited insofar as the conditions are similar to those in this reaction. A method known to a person skilled in the art may be used for the reaction. A method reported in many documents or the like (such as described in The Chemical Society of Japan (ed.), Jikken Kagaku Koza (Courses in Experimental Chemistry), 4th edition (vol. 19) Yuki Gosei (Organic Synthesis) [I], Maruzen Co., Ltd, November 1992, p. 450-453) may be used.

The compound of the formula (d-1), the compound of the formula (e-1) and the compound of the formula (f-1) are known or commercially available compounds or are compounds that can be prepared from these compounds by a conventional method.

General Preparation Method 2

Typically used General Preparation Method 2 for the compound of the general formula [I] according to the present invention will be described below.

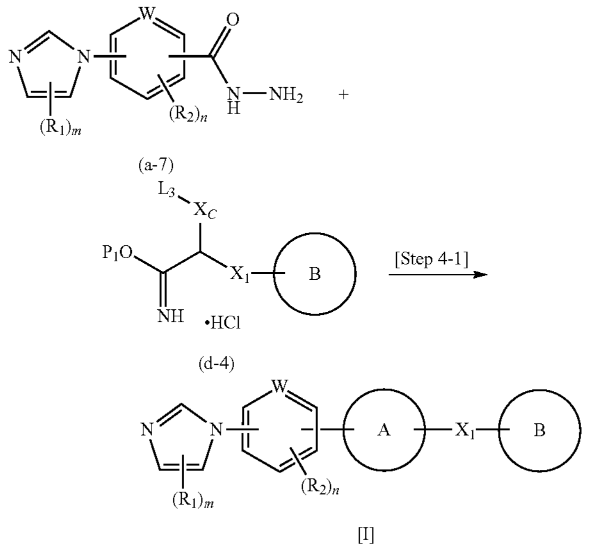

(a-7)

(d-4)

[I]

In the formula, $R_1$, $R_2$, $X_1$, $X_C$, $P_1$, $L_3$, m, n, W, Ring A and Ring B are as defined above.

The above General Preparation Method 2 shows an example of a method for preparing the compound of the general formula [I] by subjecting a compound of the general formula (7) and a compound of the general formula (d-4) to cyclization reaction in Step 4-1.

The Ring A formation reaction in Step 4-1 varies according to the starting material and is not particularly limited insofar as the conditions are similar to those in this reaction. A method known to a person skilled in the art may be used for the reaction. Preferable examples of the method include a method of stirring a compound of the general formula (7) and 1.0 to 5.0 equivalents of a compound of the general formula (d-4) with respect to the compound of the general formula (7) in a solvent in the presence of 1.0 to 10.0 equivalents of a base with respect to the compound of the general formula (7). This reaction is preferably performed in the presence of a solvent from the viewpoint of handleability and stirring efficiency. The solvent used varies according to the starting material, and is not particularly limited insofar as it does not inhibit the reaction and allows the starting material to be dissolved therein to a certain extent. Preferable examples of the solvent include alcohol solvents such as methanol, ethanol and tert-butanol; ether solvents such as tetrahydrofuran, 1,4-dioxane and diethyl ether; halogenated solvents such as methylene chloride, 1,2-dichloroethane and chloroform; polar solvents such as acetonitrile, propionitrile, N,N-dimethylformamide and N-methylpyrrolidone; non-polar solvents such as toluene and benzene; and mixtures thereof. The base used varies according to the starting material and is not particularly limited. Preferable examples of the base include alkali metal hydrides (such as sodium hydride and lithium hydride), alkali metal salts (such as potassium carbonate, sodium carbonate and cesium carbonate), metal alkoxides (such as sodium methoxide and potassium tert-butoxide) and organic bases (such as triethylamine, N,N-diisopropylethylamine, 1,8-diazabicyclo[5.4.0]undec-7-ene and imidazole). The reaction temperature must be a temperature that can complete the reaction without promoting formation of an undesirable by-product, and is preferably room temperature to 200° C., for example. Under preferable reaction conditions, the reaction is completed in 1 to 7 days, and the progress of the reaction can be monitored by a known chromatography technique. An undesirable by-product can be removed by a technique known to a person skilled in the art such as a conventional chromatography technique, extraction or/and crystallization.

Preparation of Compound of General Formula (7)

The following formula shows an example of preparation of the compound of the general formula (7).

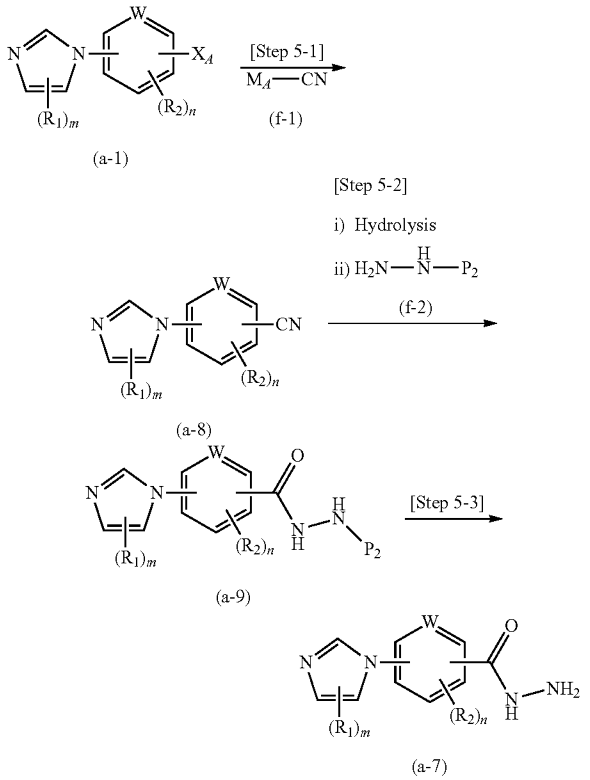

(a-1) (f-1) (f-2) (a-8) (a-9) (a-7)

In the formula, $R_1$, $R_2$, m, n, $X_A$, W, and $P_2$ are as defined above; and $M_A$ represents a metal such as zinc or copper.

The compound of the general formula (7) can be prepared from a compound of the general formula (1) as a starting material through coupling reaction in Step 5-1, hydrolysis reaction and hydrazidation in Step 5-2 and deprotection reaction in Step 5-3.

The coupling reaction in Step 5-1 varies according to the starting material and is not particularly limited insofar as the conditions are similar to those in this reaction. A method known to a person skilled in the art may be used for the reaction. A halogen compound or trifluoromethanesulfonate compound of the general formula (1) is preferably coupled with 1.0 to 5.0 equivalents of a metal cyanide such as zinc (II) cyanide represented by the general formula (f-1) with respect to the compound of the general formula (1) in the presence of 0.01 to 0.2 equivalent of a transition metal catalyst with respect to the compound of the general formula (1), for example. This reaction is preferably performed in the presence of a solvent from the viewpoint of handleability and stirring efficiency. The solvent used varies according to the starting material and the transition metal catalyst used, and is not particularly limited insofar as it does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C. This reaction is performed preferably in an inert gas atmosphere, and more preferably in a nitrogen or argon atmosphere. The transition metal catalyst is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). It is also preferable to appropriately add a phosphorus ligand (preferably triphenylphosphine, tri-o-tolylphosphine, tri-tert-butylphosphine or 2-(di-tert-butylphosphino)biphenyl, for example) in order to make the reaction efficiently proceed. A preferable result may be achieved in the presence of a base. The base used is not particularly limited insofar as it is used in a coupling reaction similar to this reaction. Preferable examples of the base include triethylamine, N,N-diisopropylethylamine, N,N-dicyclohexylmethylamine and tetrabutylammonium chloride. Under preferable reaction conditions, the reaction is completed in 1 to 24 hours, and the progress of the reaction can be monitored by a known chromatography technique.

The hydrolysis reaction as the first stage of Step 5-2 varies according to the starting material and is not particularly limited insofar as the conditions are similar to those in this reaction. A method known to a person skilled in the art may be used for the reaction. A method reported in many documents (such as described in The Chemical Society of Japan (ed.), Jikken Kagaku Koza (Courses in Experimental Chemistry), 4th edition (vol. 22) Yuki Gosei (Organic Synthesis) [IV], Maruzen Co., Ltd, November 1992, p. 12-13) may be used. The hydrazidation reaction as the second stage varies according to the starting material and is not particularly limited insofar as the conditions are similar to those in this reaction. An amidation reaction known to a person skilled in the art may be used for the reaction. A method reported in many documents or the like (such as described in The Chemical Society of Japan (ed.), Jikken Kagaku Koza (Courses in Experimental Chemistry), 4th edition (vol. 22) Yuki Gosei (Organic Synthesis) [IV], Maruzen Co., Ltd, November 1992, p. 137-144) may be used.

The deprotection reaction in Step 5-3 varies according to the starting material and is not particularly limited insofar as the conditions are similar to those in this reaction. A deprotection reaction known to a person skilled in the art may be used for the reaction. A method reported in many documents or the like (see T. Greene et al, "Protective Groups in Organic Synthesis", John Wiley & Sons, Inc, New York, 1981, for example) may be used.

The compound of the formula (f-2) is a known or commercially available compound or is a compound that can be prepared from such a compound by a conventional method. Preparation of Compound of General Formula (d-4)

The following formula shows an example of preparation of the compound of the general formula (d-4).

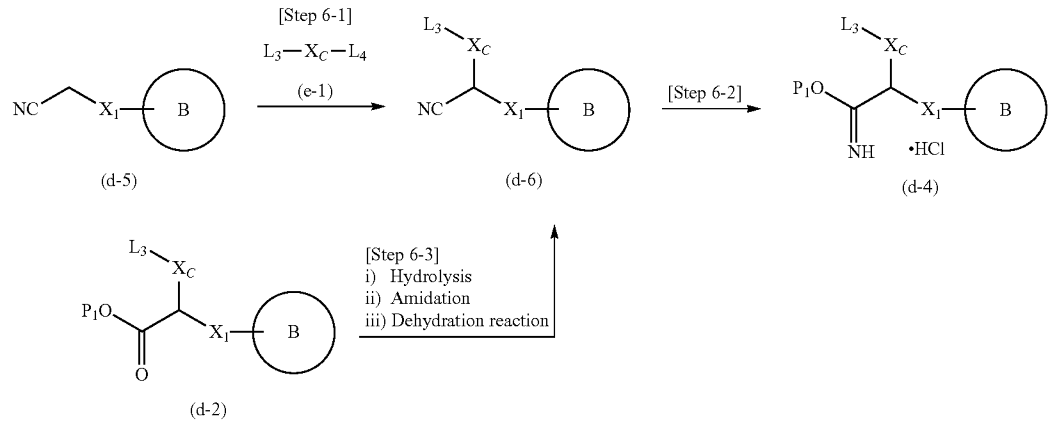

In the formula, $X_1$, $X_C$, Ring B, $P_1$, $L_3$ and $L_4$ are as defined above.

The compound of the general formula (d-4) can be prepared from a compound of the general formula (d-5) as a starting material through alkylation reaction in Step 6-1 and imidation in Step 6-2.

A compound of the general formula (d-6) can also be prepared from a compound of the general formula (d-2) as a starting material through hydrolysis reaction, amidation and dehydration reaction in Step 6-3.

Step 6-1 is performed by the same method as in the aforementioned Step 3-1 and can prepare a compound of the general formula (d-6) from a compound of the general formula (d-5).

Step 6-2 varies according to the starting material and is not particularly limited insofar as the conditions are similar to those in this reaction. A method known to a person skilled in the art may be used for the reaction. Preferable examples of the method include a method of stirring the compound of the general formula (d-6) in an alcohol solvent in the presence of 5.0 to 100.0 equivalents of an acid with respect to the compound of the general formula (d-6). The acid used varies according to the starting material and is not particularly limited. Preferable examples of the acid include hydrogen chloride gas and acetyl chloride. The solvent used varies according to the starting material, and is not particularly limited insofar as it does not inhibit the reaction and allows the starting material to be dissolved therein to a certain extent. Preferable examples of the solvent include alcoholic solvents such as methanol, ethanol and tert-butanol. Preferable examples of the solvent also include halogenated solvents such as a methylene chloride, 1,2-dichloroethane and chloroform; polar solvents such as N,N-dimethylformamide and N-methylpyrrolidone; non-polar solvents such as toluene and benzene; and mixed solvents thereof. The reaction temperature must be a temperature that can complete the reaction without promoting formation of an undesirable by-product, and is preferably 0° C. to 100° C., for example. Under preferable reaction conditions, the reaction is completed in 1 to 7 days, and the progress of the reaction can be monitored by a known chromatography technique. An undesirable by-product can be removed by a technique known to a person skilled in the art such as a conventional chromatography technique, extraction or/and crystallization.

The ester hydrolysis as the first stage of Step 6-3 is performed by the same method as in the aforementioned Step 3-2. The amidation reaction as the second stage is not particularly limited insofar as the conditions are similar to those in this reaction. An amidation reaction known to a person skilled in the art may be used for the reaction. A method reported in many documents or the like (such as described in The Chemical Society of Japan (ed.), Jikken Kagaku Koza (Courses in Experimental Chemistry), 4th edition (vol. 22) Yuki Gosei (Organic Synthesis) [IV], Maruzen Co., Ltd, November 1992, p. 137-144) may be used. The dehydration reaction from amide to nitrile as the third stage varies according to the starting material and is not particularly limited insofar as the conditions are similar to those in this reaction. A dehydration reaction known to a person skilled in the art may be used for the reaction. A method reported in many documents or the like (such as described in The Chemical Society of Japan (ed.), Jikken Kagaku Koza (Courses in Experimental Chemistry), 4th edition (vol. 20) Yuki Gosei (Organic Synthesis) [IV], Maruzen Co., Ltd, November 1992, p. 449-450) may be used.

The compound of the formula (d-2) and the compound of the formula (d-5) are known or commercially available compounds or are compounds that can be prepared from these compounds by a conventional method.

General Preparation Method 3

Typically used General Preparation Method 3 for the compound of the general formula (I) according to the present invention will be described below.

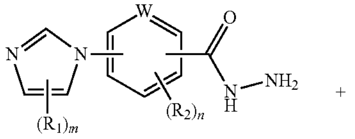

(a-7)

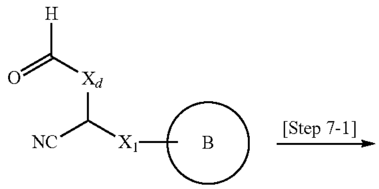

(d-7)

-continued

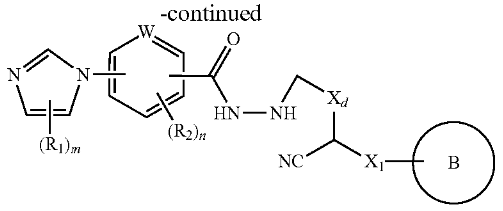

(a-10)

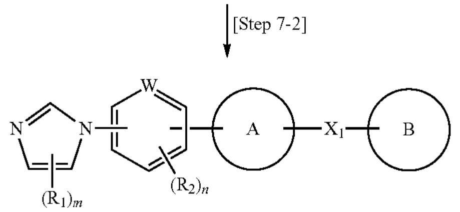

[I]

In the formula, $R_1$, $R_2$, m, n, W, Ring A, $X_1$ and Ring B are as defined above; and $X_d$ represents a C1-3 alkylene group, or a C1-2 alkylene group in which one methylene group is replaced by an oxygen atom or a nitrogen atom (wherein the nitrogen atom may have a substituent such as a C1-6 alkyl group or a benzyl group).

The above General Preparation Method 3 shows an example of a method for preparing the compound [I] by condensing a hydrazide compound (a-7) and an aldehyde compound (d-7) in Step 7-1 and then performing intramolecular cyclization in Step 7-2.

Although a compound (a-10) may be prepared by alkylation of a hydrazide compound (a-7) and a compound (d-6), it is difficult to control the positions and number of alkylated sites. The compound (a-10) is preferably prepared by condensation of a hydrazide compound (a-7) with an aldehyde compound (d-7).

The condensation reaction in Step 7-1 varies according to the material and is not particularly limited insofar as the conditions are similar to those in this reaction. A method known to a person skilled in the art may be used for the reaction. Preferable examples of the method include a method using a boron hydride reagent and a method of reductive alkylation using catalytic reduction.

In the method using a boron hydride reagent, it is preferable to react a hydrazide compound (a-7) and 1.0 to 1.5 equivalents of an aldehyde compound (d-7) with respect to the compound (a-7) with 1.0 to 4.0 equivalents of sodium triacetoxyhydroborate with respect to the compound (a-7) in an ether solvent such as tetrahydrofuran or dioxane, a halogenated solvent such as dichloromethane or a mixed solvent thereof in the presence of 2.0 to 6.0 equivalents of acetic acid with respect to the compound (a-7), for example. The reaction temperature is preferably 0° C. to room temperature.

It is also preferable to react a hydrazide compound (a-7) and 1.0 to 1.5 equivalents of an aldehyde compound (d-7) with respect to the compound (a-7) with 1.0 to 4.0 equivalents of sodium cyanotrihydroborate with respect to the compound (7) in an alcohol solvent such as methanol or ethanol, an ether solvent such as tetrahydrofuran or dioxane or a mixed solvent thereof, for example. An acid catalyst such as acetic acid may be added as necessary. The reaction temperature is preferably 0° C. to room temperature.

It is also preferable to use a method of subjecting a hydrazide compound (a-7) and an aldehyde compound (d-7) to dehydration reaction in the presence of an acid such as acetic acid or p-toluenesulfonic acid to form an imine and then reducing the imine with a boron hydride reagent.

In the reductive alkylation using catalytic reduction, it is preferable to catalytically reduce a hydrazide compound (a-7) and 1.0 to 1.5 equivalents of an aldehyde compound (d-7) with respect to the compound (a-7) in an alcohol solvent such as methanol or ethanol, an ether solvent such as tetrahydrofuran or dioxane or a mixed solvent thereof in the presence of a catalyst such as platinum oxide or palladium-carbon in a hydrogen atmosphere at 1 to 4 atm, for example. An acid catalyst such as acetic acid or hydrochloric acid may be added as necessary.

It is also preferable to use a method of subjecting a hydrazide compound (a-7) and an aldehyde compound (d-7) to dehydration reaction in the presence of an acid such as acetic acid or p-toluenesulfonic acid to form an imine and then reductively alkylating the imine using catalytic reduction.

Step 7-2 is intramolecular cyclization reaction and is an example of forming at one time a triazole ring fused with a non-aromatic ring group, for example. This reaction varies according to the material and is not particularly limited insofar as the conditions are similar to those in this reaction. A method known to a person skilled in the art may be used for the reaction. The reaction solvent is not particularly limited insofar as it does not inhibit the reaction. Examples of the solvent include aromatic hydrocarbon solvents such as an acetic acid solvent, toluene and xylene; ether solvents such as tetrahydrofuran and dioxane; alcohol solvents such as methanol and ethanol; and mixed solvents thereof. An acids such as acetic acid, p-toluenesulfonic acid or hydrochloric acid may be added as necessary. The reaction temperature must be a temperature that can complete the reaction without promoting formation of an undesirable by-product, and is preferably room temperature to solvent reflux temperature, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

Preparation of Compound of General Formula (d-7)

The following formula shows an example of preparation of the compound of the general formula (d-7).

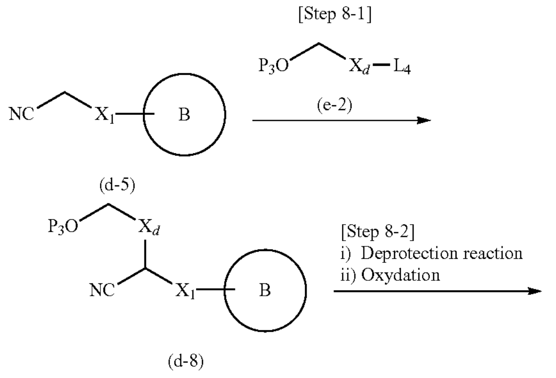

-continued

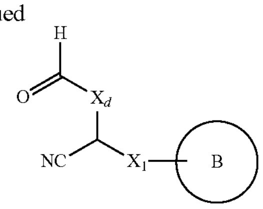

(d-7)

In the formula, $X_1$, $L_4$, $X_d$ and Ring B are as defined above; and $P_3$ represents an alcohol-protecting group such as a tert-butyldimethylsilyl group or a benzyl group.

The aldehyde compound (d-7) can be prepared from a nitrile compound (d-5) as a starting material through alkylation reaction in Step 8-1 and deprotection reaction and alcohol oxidation reaction in Step 8-2.

Step 8-1 is performed by the same method as in the aforementioned Step 3-1 and can prepare a compound of the general formula (d-8) from a compound of the general formula (d-5). The alcohol-protecting group $P_3$ in the compound of the general formula (e-2) is not particularly limited insofar as the protecting group is stable under reaction conditions and can be easily removed. Preferable examples thereof include a tert-butyldimethylsilyl group and a benzyl group. The compound (e-2) is commercially available or may be easily synthesized by protecting an alcohol compound by a method known to a person skilled in the art (see T. Greene et al, "Protective Groups in Organic Synthesis", John Wiley & Sons, Inc, New York, 1981, for example).

The deprotection reaction as the first stage of Step 8-2 is not particularly limited insofar as the conditions are similar to those in this reaction. A deprotection reaction known to a person skilled in the art may be used for the reaction. A method reported in many documents or the like (see T. Greene et al, "Protective Groups in Organic Synthesis", John Wiley & Sons, Inc, New York, 1981, for example) may be used. For example, when the protecting group is a tert-butyldimethylsilyl group, it is preferable to use an acid such as hydrochloric acid, trifluoroacetic acid, formic acid or acetic acid, or use tetra-n-butylammonium fluoride or the like. When the protecting group is a benzyl group, catalytic hydrogenolysis is preferable. The reaction of oxidation to aldehyde as the second stage varies according to the starting material and is not particularly limited insofar as the conditions are similar to those in this reaction. An oxidation reaction known to a person skilled in the art may be used for the reaction. A method reported in many documents or the like (such as described in The Chemical Society of Japan (ed.), Jikken Kagaku Koza (Courses in Experimental Chemistry), 4th edition (vol. 21) Yuki Gosei (Organic Synthesis) [IV], Maruzen Co., Ltd, November 1992, p. 2-23) may be used. Preferable examples of the method include pyridinium chlorochromate oxidation, Swem oxidation, Pfitzner-Moffatt oxidation and Dess-Martin oxidation.

Preparation of Compound of General Formula (d-8)

The following formula shows an example of preparation of the compound of the general formula (d-8).

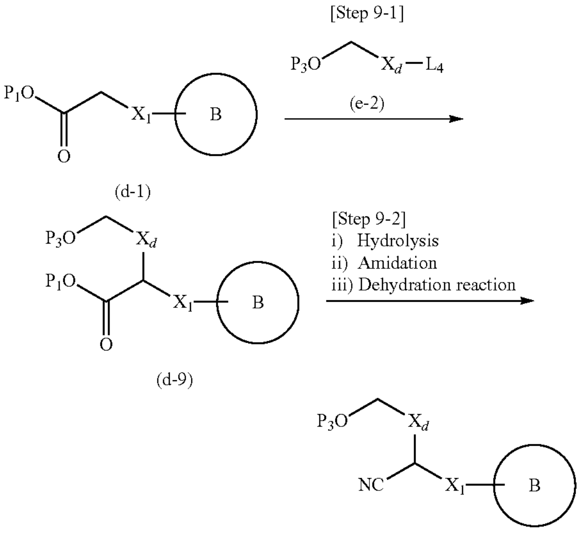

(d-1)

(d-9)

(d-8)

In the formula, $X_1$, $X_d$, $L_4$, $P_1$, $P_3$ and Ring B are as defined above.

The nitrile compound (d-8) can be prepared from a compound (d-1) as a starting material through alkylation in Step 9-1 and ester hydrolysis, amidation and dehydration reaction in Step 9-2.

Step 9-1 is performed by the same method as in the aforementioned Step 3-1 and can prepare a compound (d-9) from a compound (d-1).

Step 9-2 is performed by the same method as in the aforementioned Step 6-3 and can prepare the nitrile compound (d-8) from the compound (d-9).

General Preparation Method 4

Typically used General Preparation Method 4 for the compound of the general formula (I) according to the present invention will be described below.

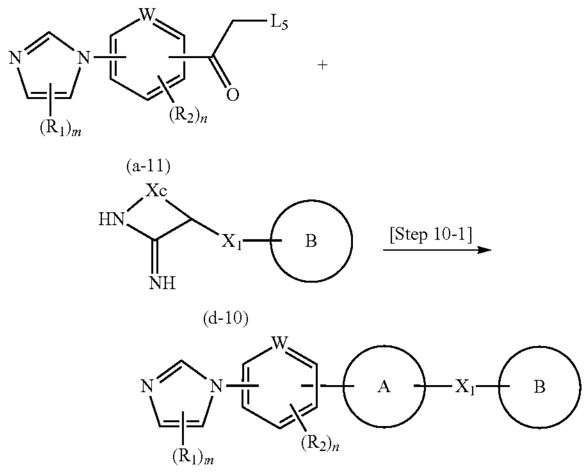

(a-11)

(d-10)

[I]

In the formula, $R_1$, $R_2$, m, n, W, $X_c$, Ring A, $X_1$ and Ring B are as defined above; and $L_5$ represents a halogen atom such as chlorine, bromine or iodine.

The above General Preparation Method 4 shows an example of a method for preparing the compound [1] by reacting a compound of the general formula (11) with a cyclic amidine compound (d-10).

Step 10-1 is an example of forming an imidazole ring fused with a non-aromatic ring group, for example, by alkylation and subsequent dehydration reaction of a cyclic amidine compound (d-10). Alkylation proceeds regioselectively, so that a single Ring A is formed (as described in L. Langlois et al., "J. Htrocyclic Chem.", 1982, vol. 19, p. 193-200). Preferable examples of the method include a method of reacting a compound (a-11) with 1.0 to 2.0 equivalents of a compound (d-10) with respect to the compound (a-11) in a solvent. The solvent is not particularly limited insofar as it does not inhibit the reaction. Examples of the solvent include ether solvents such as tetrahydrofuran and dioxane; alcohol solvents such as methanol and ethanol; water; and mixed solvents thereof. The reaction temperature must be a temperature that can complete the reaction without promoting formation of an undesirable by-product, and is preferably room temperature to solvent reflux temperature, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

Preparation of Compound of General Formula (11)

The following formula shows an example of preparation of the compound of the general formula (11).

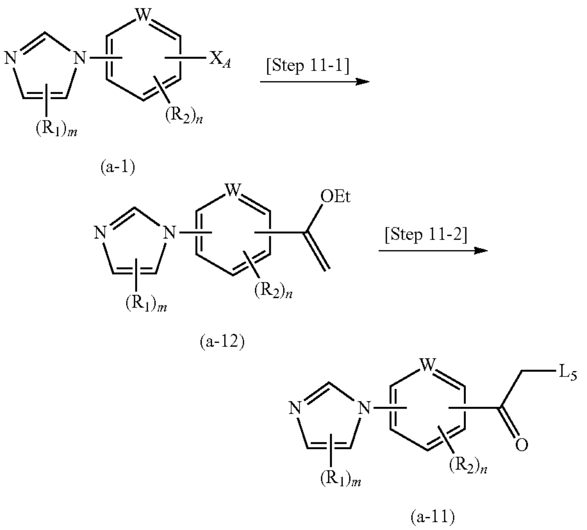

(a-1)

(a-12)

(a-11)

In the formula, $R_1$, $R_2$, m, n, W, $X_a$ and $L_5$ are as defined above.

The compound of the general formula (a-11) can be prepared from a compound (a-1) as a starting material through coupling reaction in Step 11-1 and halogenation in Step 11-2.

The coupling reaction in Step 11-1 varies according to the starting material and is not particularly limited insofar as the conditions are similar to those in this reaction. A method known to a person skilled in the art may be used for the reaction. Preferable examples of the method include a method of reacting a compound (1) with 1.0 to 1.2 equivalents of tributyl(1-ethoxyvinyl)tin with respect to the compound (1) in a solvent in the presence of a palladium catalyst. The palladium catalyst is preferably 0.02 to 0.1 equivalent of bis(triphenylphosphine)palladium (II) chloride with respect to the compound (1), for example. The solvent used varies according to the starting material, the reagent and the like, and is not particularly limited insofar as it does not inhibit the reaction and allows the starting material to be dissolved therein to a certain extent. Preferable examples of the solvent include non-polar solvents such as toluene and xylene; ether solvents such as tetrahydrofuran and dioxane; polar solvents such as N,N-dimethylformamide; and mixtures thereof. The reaction temperature is preferably room temperature to solvent reflux temperature.

Step 11-2 is a step of converting a vinyl ether compound (a-12) to an α-haloketone compound (a-11). This reaction varies according to the starting material and are not particularly limited insofar as the conditions are similar to those in this reaction. A method known to a person skilled in the art may be used for the reaction. For example, a method using bromine, iodine, N-bromosuccinimide or the like is preferable.

In the method using N-bromosuccinimide, it is preferable to react a vinyl ether compound (a-12) with 1.0 to 1.1 equivalents of N-bromosuccinimide with respect to the compound (a-12) in an ether solvent such as tetrahydrofuran or dioxane, a halogenated solvent such as dichloromethane, an alcohol solvent such as methanol or ethanol, a mixed solvent thereof, or a mixed solvent of these solvents and water, for example. The reaction temperature is preferably 0° C. to room temperature. The compound (a-11) may be either taken out as a salt or prepared before use and used as is by a method known to a person skilled in the art.

Preparation of Compound of General Formula (d-10)

The following formula shows an example of preparation of the compound of the general formula (d-10).

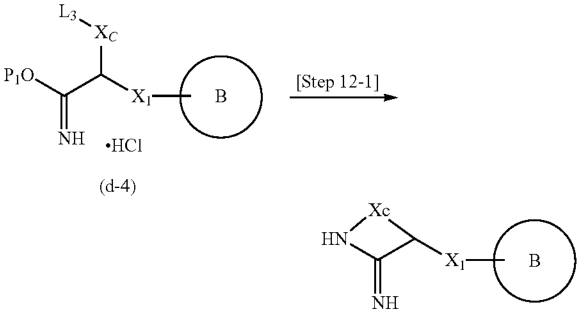

(d-4)

(d-10)

In the formula, $P_1$, $L_3$, $X_c$, $X_1$ and Ring B are as defined above.

The cyclic amidine compound (d-10) can be prepared from a compound (d-4) as a starting material through amidination and subsequent cyclization reaction in Step 12-1.

The cyclic amidine formation in Step 12-1 is not particularly limited insofar as the conditions are similar to those in this reaction. Examples thereof include a method of stirring an imidate compound (d-4) in a saturated ammonia-alcohol solution. The reaction temperature is preferably room temperature. The progress of the reaction can be monitored by LC-MS.

General Preparation Method 5

Typically used General Preparation Method 5 for the compound of the general formula (I) according to the present invention will be described below.

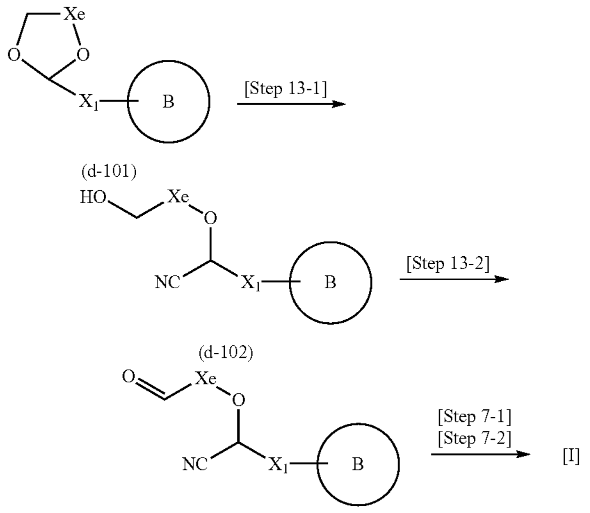

(d-101)

(d-102)

(d-103)

In the formula, $X_1$ and Ring B are as defined above; and $X_e$ represents a C1-2 alkylene group.

The above General Preparation Method 5 shows a general method for preparing the compound of the general formula (I) having an oxygen atom at the β-position of $X_1$.

The compound of the general formula (I) can be prepared by making an acetal compound (d-101) as a starting material undergo cyanohydrination following acetal cleavage in Step 13-1 and oxidation reaction in Step 13-2 and subjecting the resulting compound of the general formula (d-103) to the reactions in Steps 7-1 and 7-2 of the aforementioned General Preparation Method 3.

The cyanohydrination following acetal cleavage in Step 13-1 varies according to the starting material and is not particularly limited insofar as the conditions are similar to those in this reaction. A method known to a person skilled in the art may be used for the reaction. A method reported in many documents or the like (such as described in Synthesis, p. 498, 1983; Tetrahedron Lett, vol. 31, p. 5343, 1990) may be used. Preferably, an acetal compound (d-101) is reacted with 1.0 to 2.0 equivalents of trimethylsilyl cyanide with respect to the compound (d-101) in a solvent or without a solvent in the presence of 0.01 to 0.5 equivalent of a Lewis acid with respect to the compound (d-101) under anhydrous conditions, for example. Examples of the Lewis acid used include zinc (II) iodide, titanium tetrachloride, tin tetrachloride, iron (III) chloride, zinc (II) chloride and zinc (II) bromide. The solvent used varies according to the starting material, and is not particularly limited insofar as the solvent does not inhibit the reaction and allows the starting material to be dissolved therein to a certain extent. Preferable examples of the solvent include halogenated solvents such as methylene chloride, 1,2-dichloroethane and chloroform; polar solvents such as N,N-dimethylformamide, nitromethane and N-methylpyrrolidone; non-polar solvents such as toluene and benzene; ether solvents such as tetrahydrofuran, 1,4-dioxane and diethyl ether; and mixtures thereof. The reaction temperature must be a temperature that can complete the reaction without promoting formation of an undesirable by-product, and is preferably 0° C. to solvent reflux temperature, for example. The product in the reaction solution is a trimethyl silyl ether of alcohol, and is converted to an alcohol by post-treatment with water.

Step 13-2 is performed by the same method as in the oxidation reaction as the second stage of the aforementioned Step 8-2 and can prepare a compound of the general formula (d-103) from an alcohol compound (d-102).

The compound of the general formula (I) can be prepared by subjecting the aldehyde compound (d-103) to the reactions in Steps 7-1 and 7-2 of the aforementioned General Preparation Method 3.

The compound (d-101) is a known or commercially available compound or is a compound that can be prepared from such a compound by a conventional method.

General Preparation Method 6

Typically used General Preparation Method 6 for the compound of the general formula (I) according to the present invention will be described below.

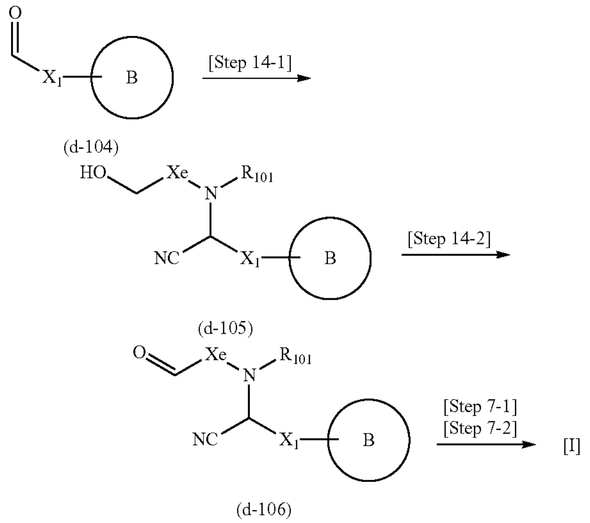

In the formula, $X_1$ and Ring B are as defined above; $R_{101}$ represents a substituent for nitrogen (such as a methyl group, an isopropyl group, a phenyl group or a benzyl group); and $X_e$ represents a C1-2 alkylene group.

The above General Preparation Method 6 shows a general method for preparing the compound of the general formula (I) having a nitrogen atom at the β-position of $X_1$.

General Preparation Method 6 is an example of a method for preparing the compound of the general formula (I) by making an aldehyde compound (d-104) as a starting material undergo aminonitrile formation in Step 14-1 and oxidation reaction in Step 14-2 and subjecting the resulting compound of the general formula (d-106) to the reactions in Steps 7-1 and 7-2 of the aforementioned General Preparation Method 3.

The aminonitrile formation in Step 14-1 varies according to the starting material and is not particularly limited insofar as the conditions are similar to those in this reaction. A method known to a person skilled in the art may be used for the reaction. A method reported in many documents or the like (such as described in Tetrahedron Lett, vol. 48, p. 8001, 2007; Synthesis, p. 109, 1983) may be used.

Step 14-2 is performed by the same method as in the oxidation reaction as the second stage of the aforementioned Step 8-2 and can prepare a compound of the general formula (d-106) from an alcohol compound (d-105).

The compound [I] can be prepared by subjecting the aldehyde compound (d-106) to the reactions in Steps 7-1 and 7-2 of the aforementioned General Preparation Method 3.

The compound (d-104) is a known or commercially available compound or is a compound that can be prepared from such a compound by a conventional method.

General Preparation Method 7

Typically used General Preparation Method 7 for the compound of the general formula (I) according to the present invention will be described below.

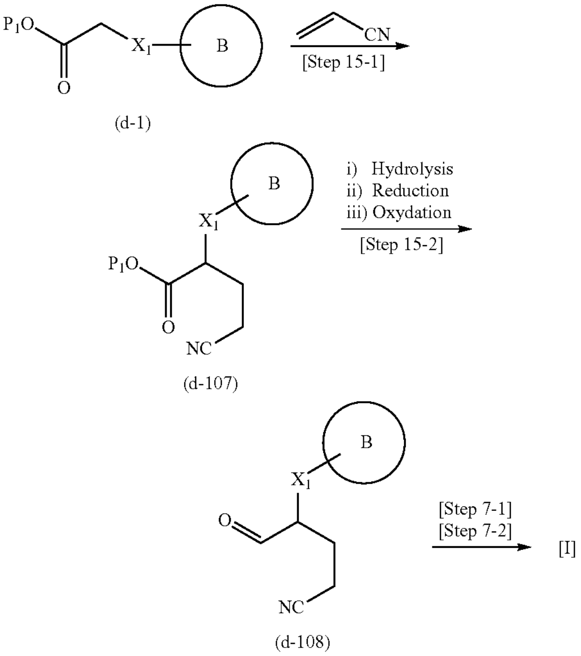

In the formula, $X_1$, $P_1$ and Ring B are as defined above.

The above General Preparation Method 7 shows an example of a general method for preparing the compound of the general formula (I) having a bonding position of $X_1$ differing from that of the compound of the general formula (I) derived from the compound of the general formula (d-7).

General Preparation Method 7 is an example of a method for preparing the compound of the general formula (I) by making an ester compound (d-1) as a starting material undergo Michael addition reaction in Step 15-1 and conversion from ester to aldehyde in Step 15-2 and subjecting the resulting compound of the general formula (d-108) to the reactions in Steps 7-1 and 7-2 of the aforementioned General Preparation Method 3.

The Michael addition reaction in Step 15-1 varies according to the starting material and is not particularly limited insofar as the conditions are similar to those in this reaction. A method known to a person skilled in the art may be used for the reaction. A method reported in many documents or the like (such as described in "Modern Synthetic Reactions House 2nd edition" (W. A. Benjamin, Inc, California, 1972) p. 595-623; J. Med. Chem, vol. 36, p. 2416, 1993) may be used.

The conversion from ester to aldehyde in Step 15-2 is achieved by hydrolysis of ester, reduction of carboxylic acid to alcohol and oxidation of alcohol to aldehyde. The ester hydrolysis as the first stage is performed by the same method as in the first stage of the aforementioned Step 3-2. The reduction as the second stage is not particularly limited insofar as the conditions are similar to those in this reaction. A reduction reaction known to a person skilled in the art may be used for the reaction. A method reported in many documents or the like (such as described in The Chemical Society of Japan (ed.), Jikken Kagaku Koza (Courses in Experimental Chemistry), 4th edition (vol. 20) Yuki Gosei (Organic Synthesis) [IV], Maruzen Co., Ltd, November 1992, p. 10-14) may be used; borane reduction is preferable. The oxidation as the third stage is performed by the same method as in the oxidation as the second stage of the aforementioned Step 8-2 and can prepare a compound of the general formula (d-108) from an ester compound (d-107).

The compound [I] can be prepared by subjecting the aldehyde compound (d-108) to the reactions in Steps 7-1 and 7-2 of the aforementioned General Preparation Method 3.

General Preparation Method 8

Typically used General Preparation Method 8 for the compound of the general formula (I) according to the present invention will be described below.

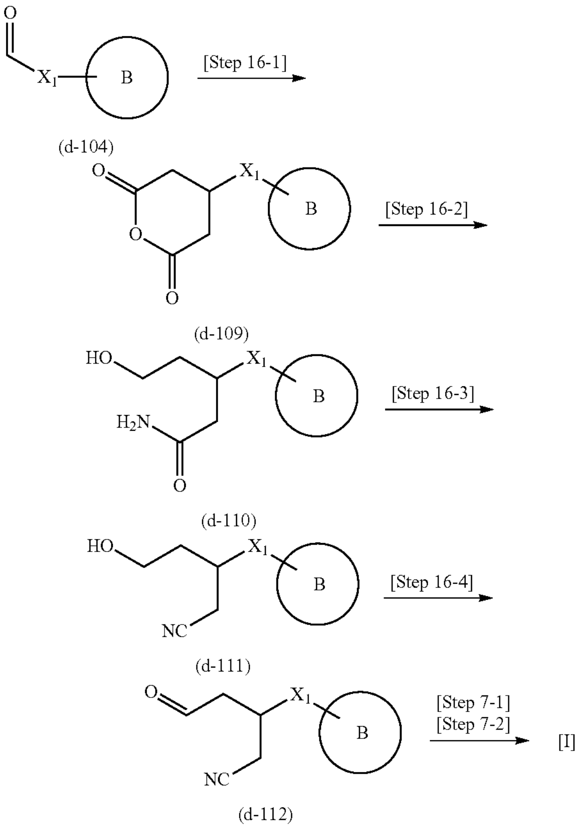

(d-104) (d-109) (d-110) (d-111) (d-112)

In the formula, $X_1$, $P_1$ and Ring B are as defined above.

The above General Preparation Method 8 shows an example of a general method for preparing the compound of the general formula (I) having a bonding position of $X_1$ differing from that of the compound of the general formula (I) derived from the compound of the general formula (d-7).

General Preparation Method 8 is an example of a method for preparing the compound of the general formula (I) by making an aldehyde compound (d-104) as a starting material undergo conversion to glutaric anhydride in Step 16-1, conversion to amidoalcohol in Step 16-2, reaction of dehydration of amide in Step 16-3 and reaction of oxidation to aldehyde in Step 16-4 and subjecting the resulting compound of the general formula (d-112) to the reactions in Steps 7-1 and 7-2 of the aforementioned General Preparation Method 3.

The conversion to glutaric anhydride in Step 16-1 varies according to the starting material and is not particularly limited insofar as the conditions are similar to those in this reaction. A method known to a person skilled in the art may be used for the reaction. A method reported in many documents or the like (such as described in Tetrahedron Asymmetry, vol. 16, p. 2475, 2005) may be used.

Step 16-2 includes cleavage of glutaric anhydride with ammonia and subsequent reaction of reducing carboxylic acid to alcohol. The cleavage of glutaric anhydride with ammonia as the first stage varies according to the starting material and is not particularly limited insofar as the conditions are similar to those in this reaction. A method known to a person skilled in the art may be used for the reaction. A method reported in many documents or the like (such as described in J. Med. Chem, vol. 34, p. 1162, 1991) may be used. The reduction as the second stage is performed by the same method as in the reduction reaction as the second stage of the aforementioned Step 15-2.

Step 16-3 includes protection of alcohol, reaction of dehydration of amide to nitrile and reaction of deprotection of alcohol. The alcohol protection as the first stage varies according to the starting material and is not particularly limited insofar as the conditions are similar to those in this reaction. A method known to a person skilled in the art may be used for the reaction. A method reported in many documents or the like (T. Greene et al, "Protective Groups in Organic Synthesis", John Wiley & Sons, Inc, New York, 1981, for example) may be used. The protecting group is preferably a tert-butyldiphenylsilyl group in order to ensure stability of the protecting group against the subsequent step. The dehydration reaction as the second stage is performed by the same method as in the dehydration reaction as the third stage of the aforementioned Step 6-3. The deprotection reaction as the third stage varies according to the starting material and is not particularly limited insofar as the conditions are similar to those in this reaction. A deprotection reaction known to a person skilled in the art may be used for the reaction. A method reported in many documents or the like (T. Greene et al, "Protective Groups in Organic Synthesis", John Wiley & Sons, Inc, New York, 1981, for example) may be used.

The oxidation in Step 16-4 is performed by the same method as in the oxidation reaction as the second stage of the aforementioned Step 8-2 and can prepare a compound of the general formula (d-112) from an alcohol compound (d-1H).

The compound [I] can be prepared by subjecting the aldehyde compound (d-112) to the reactions in Steps 7-1 and 7-2 of the aforementioned General Preparation Method 3.

As described above in detail, the compound of the general formula (I) can be prepared according to General Preparation Methods 1 to 8 for the compound of the present invention, and can also be prepared by another method well known to a person skilled in the art. The examples described later will provide reference to these Preparation Methods, and the compound of the general formula (I) can be easily prepared by a method itself known to a person skilled in the art based on these examples.

The compound of the general formula (I) or pharmacologically acceptable salt thereof according to the present invention is effective for the treatment of a disease caused by Aβ and is excellent in terms of pharmacokinetics, toxicity, stability, absorption and the like.

A therapeutic agent for a disease caused by Aβ comprising the compound of the formula (I) or pharmacologically acceptable salt or ester thereof according to the present invention as an active ingredient can be prepared by a conventional method. Preferable examples of the dosage form include tablets, powders, fine granules, granules, coated tablets, capsules, syrups, troches, inhalants, suppositories, injections, ointments, ophthalmic solutions, ophthalmic ointments, nasal drops, ear drops, cataplasms and lotions. The agent can be prepared by using ingredients typically used such as an excipient, a binder, a lubricant, a colorant and a corrective, and ingredients used where necessary such as a stabilizer, an emulsifier, an absorbefacient, a surfactant, a pH adjuster, a preservative and an antioxidant, and can be prepared by blending ingredients generally used as materials for a pharmaceutical preparation. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerin fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerin, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrant used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder.

For example, an oral preparation is prepared by adding an active ingredient compound or a salt thereof or a hydrate of the compound or salt, an excipient, and, where necessary, a binder, a disintegrant, a lubricant, a colorant and a corrective, for example, and then forming the mixture into powder, fine granules, granules, tablets, coated tablets or capsules, for example, by a conventional method. It is obvious that tablets or granules may be appropriately coated, for example, sugar coated, where necessary. A syrup or an injection preparation is prepared by adding a pH adjuster, a solubilizer and an isotonizing agent, for example, and a solubilizing agent, a stabilizer and the like where necessary by a conventional method. An external preparation may be prepared by any conventional method without specific limitations. As a base material, any of various materials usually used for a pharmaceutical, a quasi drug, a cosmetic or the like can be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like may be added where necessary. Further, an ingredient having a differentiation inducing effect such as a blood flow enhancer, a bactericide, an antiphlogistic, a cell activator, vitamin, amino acid, a humectant or a keratolytic agent may be blended where necessary.

The dose of the therapeutic agent according to the present invention varies according to the degree of symptoms, age, sex, body weight, mode of administration, type of salt and specific type of disease, for example. Typically, the compound of the formula (I) or pharmacologically acceptable salt thereof is orally administered to an adult at about 30 μg to 10 g, preferably 100 μg to 5 g, and more preferably 100 μg to 100 mg per day, or is administered to an adult by injection at about 30 μg to 1 g, preferably 100 μg to 500 mg, and more preferably 100 μg to 30 mg per day, in a single dose or several divided doses, respectively.

To treat a disease caused by amyloid-β such as Alzheimer's disease, senile dementia, Down's syndrome or amyloidosis, the compound of the formula (I) or pharmacologically acceptable salt thereof according to the present invention may be used in combination with compounds having the following mechanisms.

For example, such compounds include cholinesterase inhibitors (e.g., donepezil, huperzine A, tacrine, rivastigmine, galantamine); AMPA receptor antagonists (e.g., 1,2-dihydropyridine compounds such as 3-(2-cyanophenyl)-5-(2-pyridyl)-1-phenyl-1,2-dihydropyridin-2-one); NMDA receptor antagonists (e.g., memantine); acetylcholine releasing stimulants (e.g., pramiracetam; aniracetam); calcium channel agonists (e.g., nefiracetam); free radical scavengers (e.g., EGb 761); platelet activating factor antagonists (e.g., EGb 761); platelet aggregation antagonists (e.g., EGb 761, triflusal); insulin sensitizers (e.g., rosiglitazone); peroxisome proliferator-activated receptor agonists (e.g., rosiglitazone); peroxisome proliferator-activated receptor gamma agonists (e.g., rosiglitazone); monoamine oxidase B inhibitors (e.g., rasagiline, selegiline, procaine); carnitine acetyltransferase stimulants (e.g., levacecamine); NSAIDs (e.g., triflusal, cyclooxygenase-2 inhibitors, such as celecoxib); nerve growth factor agonists (e.g., xaliproden, FPF 1070); beta-amyloid inhibitors (e.g., tarenflurbil, tramiprosate, leuprorelin-D); immunomodulators (e.g., tarenflurbil, immune globulin, icosapentethyl ester); NF-kappa B inhibitors (e.g., tarenflurbil); thyrotropin releasing hormone (e.g., taltirelin); dopamine D2 receptor antagonists (e.g., risperidone); serotonin 2 receptor antagonists (e.g., risperidone); muscarinic M1 receptor agonists (e.g., cevimeline); alpha 1 adrenoceptor agonists (e.g., modafinil); serotonin 3 receptor antagonists (e.g., alosetron); dopamine D2 receptor agonists (e.g., aripiprazole); dopamine D2 receptor antagonists (e.g., aripiprazole); serotonin 1A receptor agonists (e.g., aripiprazole); serotonin 2A receptor antagonists (e.g., aripiprazole); glucocorticoid antagonists (e.g., mifepristone); progesterone antagonists (e.g., mifepristone); HMG-CoA reductase inhibitors (e.g., atorvastatin, simvastatin); adenosine uptake inhibitors (e.g., propentofylline); phosphodiesterase inhibitors (e.g., propentofylline); acetylcholine receptor agonists (e.g., choline alfoscerate); membrane permeability enhancers (e.g., choline alfoscerate); cannabinoid 1 receptor antagonists (e.g., rimonabant); cannabinoid receptor agonists (e.g., dronabinol); angiogenesis inhibitors (e.g., paclitaxel); immunosuppressants (e.g., paclitaxel); tubulin antagonists (e.g., paclitaxel); thromboxane A synthase inhibitors (e.g., triflusal); antioxidants (e.g., idebenone); alpha adrenoreceptor antagonists (e.g., nicergoline); estrogen antagonists (e.g., conjugated estrogens, trilostane); 3-beta hydroxysteroid dehydrogenase inhibitors (e.g., trilostane); signal transduction pathway inhibitors (e.g., trilostane); melatonin receptor agonists (e.g., ramelteon); immunostimulants (e.g., immune globulin, icosapentethyl ester, procaine); HIV entry inhibitors (e.g., procaine); sodium channel antagonists (e.g., procaine); microtubule inhibitor (e.g., CPH 82); glycine NMDA agonists (e.g., cycloserine); adenosine A1 receptor antagonists (e.g., KW 3902); ATPase stimulants (e.g., triacetyluridine); mitochondrial function enhancers (e.g., triacetyluridine); growth hormone releasing factor agonists (e.g., tesamorelin); butylcholine esterase inhibitor (e.g., bisnorcymserine); alpha adrenergic receptor antagonists (e.g., nicergoline); NO synthase type II inhibitors (e.g., arundic acid); chelating agents (e.g., PBT 2); amyloid fibrillogenesis inhibitors (e.g., TTP488, PF 4494700); serotonin 4 receptor agonists (e.g., PRX 03140); serotonin 6 receptor antagonists (e.g., SB 742457); benzodiazepine receptor inverse agonists (e.g., radequinil); Ca channel antagonists (e.g., safinamide); nicotinic receptor agonists (e.g., ispronicline); and BACE inhibitor (e.g., CTS 21166).

Further, the above compounds include, for example, donepezil, huperzine A, tacrine, rivastigmine, galantamine, pramiracetam, aniracetam, nefiracetam, EGb 761, rosiglitazone, rasagiline, levacecamine, celecoxib, 3-(2-cyanophenyl)-5-(2-pyridyl)-1-phenyl-1,2-dihydropyridin-2-one, talampanel, becampanel, memantine, xaliproden, tarenflurbil, tramiprosate, leuprorelin-D, taltirelin, risperidone, cevimeline, modafinil, alosetron, aripiprazole, mifepristone, atorvastatin, propentofylline, choline alfoscerate, FPF 1070 (CAS Number 143637-01-8), rimonabant, dronabinol, docosahexaenoic acid, paclitaxel, triflusal, idebenone, nicergoline, conjugated estrogens, trilostane, simvastatin, selegiline, ramelteon, immune globulin, icosapentethyl ester, procaine, CPH 82, cycloserine, KW 3902 (CAS Number 136199-02-5), triacetyluridine, estrogen dementia therapeutics (e.g., MIGENIX, Vancouver, Canada), tesamorelin, bisnorcymserine, nicergoline, arundic acid, PBT 2, TTP488, PF 4494700, PRX 03140, SB 742457, radequinil, safinamide, ispronicline, CTS 21166, Bapineuzumab, NP 031112, (2S, 3aS,7aS)-1{[(R,R)-2-Phenylcyclopropyl]carbonyl}-2-[(thiazolidin-3-yl)carbonyl]octahydro-1H-indole, citalopram, venlafaxine, levprorelin, prasterone, peptide T (CAS Number 53-43-0), besipiridine, lexipafant, stacofylline, SGS 742 (CAS Number 123690-78-8), T 588 (CAS Number 142935-03-3), nerispiridine, dexanabinol, sabcomeline, GTS 21 (CAS Number 156223-05-1), CX 516 (CAS Number 154235-83-3), ABT 089 (CAS Number 161417-03-4), anapsos, tesofensine, SIB 1553A (i.e., 4-[[2-(1-methyl-2-pyrrolidinyl)ethyl]thio]phenol), ladostigil, radequinil, GPI 1485, ispronicline, arundic acid, MEM 1003 (i.e., 3-Isopropyl 5-(2-methoxyl) 4-(2-chloro-3-cyanophenyl)-2,6-dimethylpyridine-3,5-dicarboxylate), V 3381 (i.e., 2-(2,3-Dihydro-1H-inden-3-ylamino)acetamide hydrochloride), farampator, paliroden, prasterone-paladin, urocortin, DP b99 (i.e., 2,2'-(Ethylenedioxy)bis(2,1-phenylene)bis[N-[2-[2-(octyloxy) ethoxy]-2-oxoethyl]imino]bis(acetic acid)), capserod, DU 125530, bapineuzumab, AL 108 (i.e., L-Asparaginyl-L-alanyl-L-prolyl-L-valyl-L-seryl-L-isoleucyl-L-prolyl-L-glutamine), DAS 431, DEBIO 9902, DAR 100, mitoquinone, IPL 455903 (i.e., 5(S)-[3-(Cyclopentyloxy)-4-methoxyphenyl]-3(S)-(3-methylbenzyl)piperidin-2-one), E2CDS, PYM 50028, PBT 2, lecozotan, SB 742457, CX 717, AVE 1625 (i.e., 1-(bis(4-chlorophenyl)methyl)-3-((3,5-difluorophenyl) (methylsulfonyl)methylene)azetidine), LY 450139 (i.e., N2-[2(s)-Hydroxy-3-methylbutyryl]-N1-[3-methyl-2-oxo-2,3,4,5-tetrahydro-1H-3-benzazepin-1(S)-yl]-L-alaninamide), EM 1421 (i.e., 4,4'-[(2R,3S)-2,3-Dimethylbutane-1,4-diyl] bis(1,2-dimethoxybenzene), SRN 001, TTP 488, PRX 03140, dimebolin, glycine-proline-glutamate, C105, AL 208, MEM 3454, AC 1202, L 830982, LY 451395 (i.e., (R)—N-[2-[4'-(methylsulfonamidomethyl)biphenyl-4-yl]propyl] propane-2-sulfonamide), MK 0249, LY 2062430, diethylnorspermine, neboglamine, S 18986, SA 4503 (CAS Number 165377-44-6), GRI 1, S 17092 (i.e., (2S,3aS,7aS)-1{[(R,R)-2-Phenylcyclopropyl]carbonyl}-2-[(thiazolidin-3-yl)carbonyl]octahydro-1H-indole), SL 251188, EUK 189, R 1450, 6,6-dimethyl-3-(2-hydroxyethyl)thio-1-(thiazol-2-yl)-6,7-dihydro-2-benzothiophen-4(5H)-one, CERE 110, dexefaroxan, CAD 106, HF 0220, HF 0420, EHT 0202, VP 025, MEM 1414, BGC 201259 (i.e., N,N-Dimethylcarbamic acid, 4-[1(S)-(methylamino)-3-(4-nitrophenoxy)propyl]phenyl ester), EN 100, ABT 834, ABT 239 (i.e., 4-[2-[2-[(2R)-2-Methylpyrrolidinyl]ethyl]-benzofuran-5-yl]benzonitrile), SGS 518, R 1500, C 9138, SSR 180711, alfatradiol, R 1577, T 817MA (i.e., 1-[3-[2-(1-Benzothien-5-yl)ethoxy]propyl] azetidin-3-olmaleate), CNP 1061 (i.e., 4-Methyl-5-(2-nitrooxyethyl)thiazole), KTX 0101 (i.e., sodium beta-hydroxybutyrate), GSK 189254 (i.e., 643-Cyclobutyl-2,3,4,5-tetrahydro-1H-benzo[d]azepin-7-yloxy]-N-methylnicotinamide), AZD 1080, ACC 001, PRX 07034, midazolam, R-phenserine, AZD 103 (CAS Number 488-59-5), SN 522, NGX 267 (CAS Number 503431-81-0), N-PEP-12, RN 1219, FGLL, AVE 8112, EVT 101, NP 031112, MK 0752, MK 0952, LX 6171, PAZ 417, AV 965, PF 3084014, SYN 114, GSI 953, SAM 315, SAM 531, D-serine, leteprinim potassium, BR 16A (CAS Number 149175-77-9), RPR 107393 (CAS Number 190841-57-7), NXD 2858, REN 1654, CDD 0102, NC 1900 (CAS Number 132925-74-7), ciclosporin, NCX 2216 (i.e., (E)-4-(Nitrooxy)butyl 3-[4-[2-(2-fluorobiphenyl-4-yl)propanoyloxy]-3-methoxyphenyl] acrylate), NXD 3109, NXD 1191, ZSET 845 (i.e., 3,3-diphenylimidazo[1,2-a]pyridin-2-(3H)-one), ET 002, NT 13, RO 638695 (i.e., [1,6-(1,6-dioxohexyl)]dipynolidine-(2R)-carboxylic acid), bisnorcymserine, BA 1016, XD 4241, EUK 207 (i.e., (SP-5-13)-(acetato-KO) [13,16,19,22-tetraoxa-3,6-diazatricyclo [21.3.18,12]octacosa-1(27),2,6,8,10,12(28),23,25-octaene-27,28-diolato(2-)-κN3,κN6,κO27,κO28] manganese), LG 617 inhibitors, ZSET 1446, PAN 811, F 14413 (i.e., 2-[5-fluoro-2(S)-methoxy-2,3-dihydro-1,4-benzodioxin-2-yl]-4,5-dihydro-1H-imidazole), FP 7832 (i.e., N-[2-(5-methoxy-1-nitroso-1H-indol-3-yl)ethyl]acetamide), ARA 014418 (i.e., N-(4-methoxybenzyl)-N'-(5-nitro-1,3-thiazol-2-yl)urea), AZD 3102, KP 544 (i.e., 2-amino-5-(4-chlorophenylethynyl)-4-(4-trans-hydroxycyclohexylamino)pyrimidine), DP 155, 5-chloro-N-[3-[2-(dimethylamino)ethyl]-1H-indol-5-yl]naphthalene-2-sulfonamide, TAK 070, huperzine, N-[2-(3,5-dimethyladamant-1-yl)ethyl]acetamidine hydrochloride, 6-[4-[(dimethylamino)methyl]-5-ethyl-2-methoxyphenyl] pyridin-2-amine, 4,6-diphenyl-3-(4-(pyrimidin-2-yl)piperazin-1-yl)pyridazine, N-[(1S,2R)-3-(3,5-difluorophenyl)-1-hydroxy-1-[(5S,6R)-5-methyl-6-(neopentyloxy)morpholin-3-yl]propan-2-yl]acetamide hydrochloride, N-[(1R,2S)-3-(3,5-difluorophenyl)-1-hydroxy-1-[(2R,4R)-4-phenoxypyrrolidin-2-yl]propan-2-yl]-3-[(R)-2-(methoxymethyl)pyrrolidine-1-carbonyl]-5-methylbenzamide, R 1589, midafotel, phenserine, coluracetam, physostigmine, cipralisant, nitroflurbiprofen, PPI 1019 (i.e., (3α,5β,7α,12α)-trihydroxycholan-24-oyl-L-leucyl-L-valyl-L-phenylalanyl-L-phenylalanyl-L-alanine), dapsone, MDL 100453 (CAS Number 129938-34-7), NS 377, midaxifylline, propofol phosphate, metrifonate, ceronapril, tenilsetam, sufoxazine, seglitide, ebiratide, nebracetam, milacemide, iododoxorubicin, SM 10888 (CAS Number 129297-21-8), U 80816 (CAS Number 138554-11-7), YM 954 (CAS Number 132041-85-1), SUT 8701 (CAS Number 123577-73-1), apovincamine, FR 121196 (CAS Number 133920-65-7), LY 274614 (CAS Number 136109-04-1), CL 275838 (CAS Number 115931-65-2), igmesine, K 7259 (CAS Number 133667-88-6), vinconate, itasetron, CL 287663 (CAS Number 125109-98-0), WAY 100289 (CAS Number 136013-69-9), SR 46559A (CAS Number 137733-33-6), GYKI 46903 (CAS Number 142999-59-5), L 670548 (CAS Number 121564-89-4), Y 29794 (CAS Number 129184-48-1), AF 125 (CAS Number 7631-86-9), KFM 19 (CAS Number 133058-72-7), ST 796 (i.e., (S)-3-[3-(trifluoromethyl)benzoyl)amino]hexahydroazepin-2-one), RU 33965 (CAS Number 122321-05-5), SDZ 210086 (i.e., (−)-1',2(S)-Dimethylspiro[1,3-d]oxane-4,4'-piperidine]), L 689660 (CAS Number 144860-79-7), L 689560 (CAS Number 139051-78-8), ST 618 (i.e., 1-(6,7-Dimethoxy-1,2,3,4-tetrahydro-2-naphthyl)-4-hydroxy pyrrolidin-2-one), U 74500A (CAS Number 110101-65-0), GEA 857 (CAS Number 120493-42-7), BIBN 99 (CAS Number 145301-48-0), DX 9366, ONO 1603 (CAS Number 114668-76-7), MDL 102234 (CAS Number 137766-81-5), P 9939 (CAS Number 157971-37-4), PD 140532 (CAS Number 157971-39-6), azetirelin, MR 16728 (CAS Number 147614-21-9), dabelotine, MDL 102503 (i.e., 8-[1(R)-methyl-2-phenylethyl]-1,3-dipropyl-7H-xanthine), PD 141606 (i.e., (±)-(Z)-3-(3-Phenyl-2-propynyloxyimino)-1-azabicyclo[2.2.1]heptane), SNK 882 (CAS Number 152221-12-0), L 696986 (CAS Number 141553-45-9), tazomeline, LY 235959 (CAS Number 137433-06-8), 2-(2-thiooxopyrrolidin-1-yl)acetamide, AK 30 NGF, ABT 418 (CAS Number 147402-53-7), itameline, HUP 13, sibopirdine, KST 5452 (CAS Number 157998-88-4), TJ 54, U 92798 (i.e., 7-[4-[Bis(4-fluorophenyl)methyl] perhydro-1,4-diazepin-1-ylmethyl]-4-isopropyl-2-methoxy-2,4,6-cycloheptatrien-1-one), U 92032 (CAS Number 142223-92-5), 3-(sulfamoyloxy)estra-1,3,5(10)-trien-17-one, P 11012 (CAS Number 164723-36-8), A 82695 (CAS Number 147388-86-1), FR 76659 (CAS Number 116904-25-7), apaxifylline, CX 417, 7 MEOTA (CAS Number 5778-80-3), BU 4514N (CAS Number 151013-39-7), pregnenolone, mexidol, ST 857 (CAS Number 154755-63-2), RU 49041 (CAS Number 123828-80-8), RU 35929 (CAS Number 111711-47-8), P 878184, P 128 (CAS Number 157716-52-4), eurystatin A, eurystatin B, LK 12, NBI 108, NBI 107, NBI 117, L 705106, bacoside A+B, clausenamide, SM 21 (CAS Number 155156-22-2), alaptide, RS 17017 (i.e., 1-(4-Amino-5-chloro-2-methoxyphenyl)-5-(1-piperidinyl)-1-pentanone hydrochloride), AF 150(S) (i.e., (S)-1-Methyl-piperidine-4-spiro-(2'-methylthiazoline)D, RO 153505 (CAS Number 78771-13-8), PV 113 (i.e., 1,2,3,4-Tetrahydropyrrole-[1,2-a]-pyrazine), arisugacin, A 98284 (i.e., 2(R)-(3-Methylxazol-5-yl)quinuclidine), AP 5 (CAS Number 136941-85-0), BD 1054, SDZ NDD 094 (i.e., bis-(2-(2-methylimidazol-1-yl]methyl)-pyridine-tris(hydrogen-fumarate), AZ 36041 (CAS Number 173324-76-0), quilostigmine, A 84543 (i.e., 3-[1-Methylpyrrolidin-2-(S)-ylmethoxy]pyridine fumarate), BTG 4247 (i.e., (2-2-Chloroethoxy[4-(dimethylamino)phenyl]phosphoryl]-acetohydrazine), CGP 50068 (CAS Number 158647-49-5), cerebrocrast, desferri-nordanoxamine, isolichenan, MHP 133 (i.e., 3-(N,N-dimethylcarbamoyloxy)-1-methyl-2-(4-phenyl-semicarbazonomethyl)pyridium chloride), FR 152558 (CAS Number 151098-08-7), GVS 111 (CAS Number 157115-85-0), P 11149 (CAS Number 164724-79-2), PDC 008004, KST 2818 (CAS Number 158623-26-8), KST 5410 (CAS Number 158623-27-9), RU 52583 (CAS Number 123829-33-4), PD 151832 (CAS Number 149929-39-5), UCL 1199 (i.e., 4-[2-[(5-Nitropyridin-2-ylsulfanyl)ethyl]-1H-imidazole), isovanihuperzine A, SIB 1765F (CAS Number 179120-52-6), JWS USC 751× (i.e., 3-[[4-[(5-dimethylaminoethyl)-2-furanyl]methyl]thio]ethyl] amino]-4-nitropyridazine), GR 175737 (i.e., 3-(4-Chlorobenzyl)-5-[2-(1H-imidazol-4-ypethyl]-1,2,4-oxadiazole), KS 505A (CAS Number 131774-53-3), ZTTA 1 (i.e., N-benzyloxycarbonyl-thiopropyl-thiopropynal-dimethylacetal), AGN 190837 (CAS Number 136527-40-7), P 10358 (188240-59-7), WAY 131256 (CAS Number 174001-71-9), DBO 83 (i.e., 3-(6-chloropyrazin-3-yl)-diazabicyclo [3.2.1] octane dihydrochloride monohydrate), FUB 181 (CAS Number 152029-80-6), RJR 2557, WSU 2088, LVV-haemorphin-7, M 40 (i.e., galanin[1-12]-Pro3-(Ala-Leu)$_2$-Ala-NH$_2$), SIB 1757, SKF 74652 (i.e., [5-chloro-2-(4-methoxy phenyl)-3-benzofuranyl][4-[3-(dimethylamino)-propoxy]phenyl] methanone), CGP 71982, SCH 57790 (i.e., 4-cyclohexyl-alpha-[4-[[4-methoxyphenyl]sulfinyl]phenyl]-1-piperazineacetonitrile), Putrescine-D-YiAbetal1, DU 14 (i.e., p-O-(sulfamoyl)-N-tetradecanoyl tyramine), CLZ 4, SL 340026, PPRT 424, ciproxifan, UR 1827 (i.e., 2-(1-benzylpiperidin-4-yl)-1-[4-(5-methylpyrimidin-4-ylamino)phenyl]-1-ethanone), caproctamine, TGS 20 (i.e., L-pyroglutamil-D-alanine amide), PG 9 (i.e., alpha-tropanyl 2-[(4-bromo) phenyl]propionate), TEI 3356 (i.e., (16S)-15-Deoxy-16-hydroxy-16-methyl-9-(O)-methano-DELTA6(9alpha)-prostaglandin I1), LY 392098 (i.e., Thiophene, 3-[(2-methylethyl-2)sulphonylaminopropyl-2]phenyl-4-yl-), PG 1000, DM 232, NEPP 11 (i.e., 12-iso-15-Deoxy-18-(4-methyl)phenyl-13,14-dihydro-delta7-prostaglandinA1 methyl ester), VA 100 (i.e., (2,3-Dihydro-2-[[(4-fluorobenzoyl) amino]ethyl]-1-methyl-5-phenyl-1H-1,4-benzodiazepine), VA 101 (i.e., (2,3-dihydro-2-[[(2-thienylcarbonyl)amino] ethyl]-1-methyl-5-phenyl-1H-1,4-benzodiazepine), NC 111585 (i.e., (3S)-1,3-Bis-[3-[(3-azabicyclo[2.2.2]octanyl)-1,2,5-thiadiazol-4-yloxy]-1-propyn-1-yl]benzene, 2L-(+)-tartrate), IN 201, imoproxifan, kanokodiol, picroside I, picroside II, DM 235 (i.e., 1-(4-Benzoylpiperazin-1-yl)propan-1-one), monoclonal antibody 10D5, JLK2, JLK 6, JLK 7, DAPT (i.e., N-[N-(3,5-difluorophenacetyl)-L-alanyl]-S-phenylglycine t-butyl ester), huperine X, SGS 111 (i.e., (S)-ethyl 2-[1-(2-phenylacetyl)pyrrolidine-2-carboxamido]acetate), NP 7557, C 9136, C 7617, R 1485, rofecoxib, velnacrine, montirelin, lazabemide, ORG 2766 (CAS Number 50913-82-1), sabeluzole, adafenoxate, CAS Number 9061-61-4, ipidacrine, bemesetron, idazoxan, linopirdine, selfotel, suritozole, milameline, xanomeline, TJ 960, fasoracetam, eptastigmine, ensaculin, zanapezil, posatirelin, zacopride, RS 86 (CAS Number 3576-73-6), ORG 5667 (CAS Number 37552-33-3), RX 77368 (CAS Number 76820-40-1), BMS 181168 (CAS Number 123259-91-6), BY 1949 (CAS Number 90158-59-1), AWD 5239 (CAS Number 109002-93-9), YM 796 (171252-79-2), aloracetam, CI-933 (CAS Number 91829-95-7), ST 793 (CAS Number 99306-37-3), cebaracetam, zifrosilone, talsaclidine, alvameline, JTP 2942 (148152-77-6), OPC 14117 (CAS Number 103233-65-4), elziverine, AP 521 (i.e., N-(1,3-Benzodioxol-5-ylmethyl)-1,2,3,4-tetrahydro[1]benzothieno[2,3-c]pyridine-3(R)-carboxamide hydrochloride), S 8510 (CAS Number 151466-23-8), JTP 4819 (CAS Number 162203-65-8), icopezil, SC 110, FK 960 (CAS Number 133920-70-4), DMP 543 (CAS Number 160588-45-4), ganstigmine, CI 1017 (i.e., (R)-(−) -(Z)-1-Azabicyclo [2.2.1]heptan-3-one, O-(3-(3'-methoxyphenyl)-2-propionyl)-oxime maleate), T 82 (i.e., 2-[2-(1-Benzylpiperidin-4-yl)ethyl]-2,3-dihydro-9-methoxy-1H-pyrrolo[3,4-b]quinolin-1-one hemifumarate), NGD 971, vaccine of Aspartyl-alanyl-glutamyl-phenylalanyl-arginyl-histidyl-aspartyl-seryl-glycyl-tyrosyl-glutamyl-valyl-histidyl-leucyl-valyl-phenylalanyl-phenylalanyl-alanyl-glutamyl-aspartyl-valylglycyl-seryl-asparaginyl-lysyl-glycyl-alanyl-isoleucyl-isoleucyl-glycyl-leucyl-methionyl-valyl-glycyl-glycyl-valyl-valyl-isoleucyl-alanine, PBT 1 (CAS Number 130-26-7), TCH 346, FK 962 (i.e., N-(1-acetylpiperidin-4-yl)-4-fluorobenzamide), voxergolide, KW 6055 (CAS Number 63233-46-5), thiopilocarpine, ZK 93426 (CAS Number 89592-45-0), SDZ NVI 085 (CAS Number 104195-17-7), CI 1002 (CAS Number 149028-28-4), Z 321 (CAS Number 130849-58-0), mirisetron, CHF 2060 (i.e., N-Heptylcarbamic acid 2,4a,9-trimethyl-2,3,4,4a,9,9a-hexahydro-1,2-oxazino [6,5-b]indol-6-yl ester-L-tartrate), gedocarnil, terbequinil, HOE 065 (CAS Number 123060-44-6), SL 650102, GR 253035, ALE 26015, SB 271046 (i.e., 5-Chloro-N-(4-methoxy-3-piperazin-1-yl-phenyl)-3-methyl-2-benzothiophenesulfonamide), iAbeta5, SCH 211803 (i.e., Piperidine, 1-[1-(3-methyl-2-aminophenyl)carbonylpiperidin-4-yl]-4-[(3-chlorophenyl)sulphonylphenyl-4]methyl-), EVT 301, alpha-Linolenic acid/linoleic acid, Kamikihi-To, siagoside, FG 7142 (CAS Number 78538-74-6), RU 47067 (CAS Number 111711-92-3), RU 35963 (CAS Number 139886-03-6), FG 7080 (CAS Number 100332-18-1), E 2030 (CAS Number 142007-70-3), transforming growth factor beta-1, A 72055 (i.e., 2',1-Dimethylspiro[piperidine-4,5'oxazolidine]-3'-carboxaldehyde), NS 626, dimiracetam, GT 3001, GT 2501, GT 2342, GT 2016 (CAS Number 152241-24-2), ORG 20091 (CAS Number 141545-50-8), BCE 001 (CAS Number 95678-81-2), CGP 35348 (CAS Number 123690-79-9), WAY 100635 (CAS Number 146714-97-8), E 4804 (CAS Number 162559-34-4), LIGA 20 (CAS Number 126586-85-4), NG 121 (i.e., 2-[4,8-Dimethyl-3(E),7(E)-monoadienyl]-3,5-dihydroxy-2-methyl-3,4,7,9-tetrahydro-2H-fluoro[3,4-h]-1-benzopyran-7-one), MF 247 (i.e., N-[10-(Diethylamino)decyl]carbamic acid (3aS,8aR)-1,3a,8-trimethyl-1,2,3,3a,8,8a-hexahydropyrrolo[2,3-b]indol-5-yl ester), JTP 3399 (i.e., N-Benzyl-2(S)-[2(S)-(phenoxyacetyl)pyrrolidin-1-ylcarbonyl]pyrrolidine-1-carboxamide), KF 17329, thioperamide, F 3796 (i.e., 1-[2-(1-Benzylpiperidin-4-yl)ethyl]-3-[3,4-(methylene-dioxy)benzoyl]thiourea), GT 4001, GT 4002, FPL 14995 (CAS Number 123319-03-9), RU 34332 (CAS Number 137157-58-5), SR 96777A (CAS Number 115767-94-7), SIB T1980, NS 649 (CAS Number 146828-02-6), PD 142505 (CAS Number 149929-08-8), GYM 52466 (CAS Number 102771-26-6), RO 246173 (CAS Number 159723-57-6), SCH 50911 (CAS Number 160415-07-6), Z 4105 (CAS Number 119737-52-9), RS 67333 (CAS Number 168986-60-5), NS 1546, ZM 241385 (CAS Number 139180-30-6), RO 249975 (i.e., [1S,3S(2'S),5R]-3-(1-Benzyl-5-oxopynolidin-2-ylmethyl)-5-(1H-imidazol-5-ylmethyl)cyclohexane-1-acetamide), AF 185 (i.e., 8-Methyl-3-(2-propynyl)-1,3,8-triazaspiro[4,5]decane-2,4-dione), CEP 427, CX 423, CX 438, CX 480, CDP-ethanolamine, GT 4003, GT 4011, GT 5011, MS 430 (CAS Number 122113-44-4), MBF 379 (i.e., [3,3-Bis(hydroxymethyl)-8-hydroxy-3,4-dihydro-2H-1,4-benzoxazin-5-yl][3',5'-dihydroxy-4'-(2-oxo-2-phenylethoxy)phenyl]methanone), NGD 187 (CAS Number 163565-48-8), DUP 856, MR 3066, MF 8615 (i.e., 5-Amino-6-chloro-4-hydroxy-3,4-dihydro-1H-thiopyrano-[3,4-b]quinolinone), himbacine, ABS 300, RJR 2403 (CAS Number 538-79-4), MF 268 (CAS Number 174721-00-7), RO 465934 (i.e., N,N-Dimethylcarbamic acid 3-(2-cyclohexyl)-2,3,3a,4,5,9b-hexahydro-1H-benzo[e]indol-6-yl ester), NS 393, RGH 2716 (CAS Number 134069-68-4), WIN 678702 (12,12-Bis(3-furyl)-6,11-dihydro-6,11-ethanobenzo[b]quinolizinium chloride), RS 66252 (i.e., 1-Butyl-2-[(2'-(2H-tetrazol-5-yl)-biphenyl-4-yl)methyl]-1H-indole-3-carboxylic acid), AIT 034 (CAS Number 138117-48-3), NG 012 (CAS Number 131774-53-3), PD 142012 (CAS Number 5778-84-7), GT 4054, GT 4077, GT 4035, P 26 (CAS Number 152191-74-7), RGH 5279 (i.e., (−)-(13aR, 13b5)-13a-Ethyl-2,3,5,6,13a,13b-hexahydro-1H-indolo[3,2,1-de]pyrido[3,2,1-ij][1,5]naphthyridine-12-carboxylic acid 2-acetoxyethyl ester), AIT 083, CeNeS, estradiol (i.e., 1,3,5(10)-Estratriene-3,17beta-diol), WAY 132983 ((3R,4R)-3-(3-hexasulfanylpyrazin-2-yloxy)-1-azabicyclo[2.2.1]heptane hydrochloride), ABS 205, ABS 401, SX 3507 (i.e., 3-(3-Propyl-1,2,4-oxadiazol-5-yl)quinoxaline-2(1H)-one), ARR 17779 (i.e., (−)-Spiro[1-azabicyclo[2.2.2]octaene-3,5-oxazolidine]-2-one), XE 991 (i.e., 10,10-bis(4-Pyridylmethyl) anthracen-10(9H)-one), phenethylnorcymserine, RO 657199, RJR 1781 (i.e., R(+)-2-(3-pyridyl)-1-azabicyclo [2.2.2.]octane), RJR 1782 (i.e., S(−)-2-(3-pyridyl)-1-azabicyclo[2.2.2.]octane), gilatide, tolserine, TC 2559 (i.e., (E)-N-Methyl-4-[3-(5-ethoxypyridin)yl]-3-buten-1-amine), ER 127528 (i.e., 1-(3-Fluorobenzyl)-4-[(2-fluoro-5,6-dimethoxy-1-indanone-2-yl)methyl]piperidine hydrochloride), thiatolserine, targacept, axonyx, cymserine, thiacymserine, monoclonal antibody 266, Apan-CH, DP 103, SPI 339 (i.e., 4-[3-(4-Oxo-4,5,6,7-tetrahydroindol-1-yl)propionylamino]benzoic acid ethyl ester), S 37245 (i.e., 4-(1,4-Benzodioxan-5-yl)-1-[3(S)-hydroxy-5-nitro-indan-2-yl]-piperazine), LLG 88, AZD 2858, trometamol, AN 240, NG 002 (i.e., 5-Hydroxy-5-(2-hydroxy-1-methylethyl)-4-methoxyfuran-2(5H)-one), UCB 29427 (i.e., 2-Cyclopropyl-4-(cyclopropylamino)-6-(morpholino)-1,3,5-triazine), TRH-SR, RO 401641 (CAS Number 122199-02-4), MPV 1743AIII (CAS Number 150586-64-4), IDRA 21 (CAS Number 22503-72-6), CEP 431, ACPD (CAS Number 67684-64-4), CT 3577 (i.e., 3,7-Dimethyl-1-[11-(3,4,5-trimethoxybenzylamino)-11-oxoundecyl]xanthine), CT 2583, NXD 9062, Desferrinordanoxamine, DP b99, PBT 1, T 817MA, Alfatradiol (CAS No. 57-91-0), AL 108, SL 650102, RS 67333 (CAS No. 168986-60-5), RS 17017, SGS 518, SYN 114, SB 271046, RO 657199, PRX 07034, Suritozole (CAS No. 110623-33-19), Terbequinil (CAS No. 113079-82-6), FG 7142 (CAS No. 78538-74-6). RU 34332 (CAS No. 137157-58-5), SX 3507, RO 153505 (CAS No. 78771-13-8), RU 33965 (CAS No. 122321-05-5), S 8510 (CAS No. 151466-23-8), Sabeluzole (CAS No. 104383-17-7), Cerebrocrast (CAS No. 118790-71-9), NS 626, NS 649 (CAS No. 146828-02-6), U 92032 (CAS No. 142223-92-5), MEM 1003, U 92798, RGH 2716 (CAS No. 134069-68-4), Safinamide (CAS No. 133865-89-1), AZD 0328, MEM 63908, ABT 418 (CAS No. 147402-53-7), ARR 17779, RJR 2403 (CAS No. 538-79-4), TC 2559, A 82695 (CAS No. 147388-86-1), A 84543, A 98284, DBO 83, RJR 2557, SIB 1765F (CAS No. 179120-52-6), GTS 21 (CAS No. 156223-05-1), MEM 3454, SIB 1553A, EVP 6124, SSR 180711, ABT 089 (CAS No. 161417-03-4), ABT 107, ABT 560, TC 5619, TAK 070, N-[(1S,2R)-3-(3,5-Difluorophenyl)-1-hydroxy-1-[(5S,6R)-5-methyl-6-(neopentyloxy)morpholin-3-yl]propan-2-yl]acetamide hydrochloride, 6-Fluoro-5-(2-fluoro-5-methylphenyl)-3,4-dihydropyridine, 2-Amino-6-[2-(3'-methoxybiphenyl-3-yl)ethyl]-3,6-dimethyl-5,6-hydroxypyrimidin-4(3H)-one, AZD 1080, ARA 014418, XD 4241, Z 321 (CAS No. 130849-58-0), ONO 1603 (CAS No. 114668-76-7), JTP 3399, Eurystatin A (CAS No. 137563-63-4), Eurystatin B (CAS No. 137563-64-5), P 128 (CAS No. 157716-52-4), Y 29794(CAS No. 129184-48-1), ZTTA 1, JTP 4819 (CAS No. 162203-65-8), Monoclonal antibody 266, duloxetine, escitalopram oxalate, fluoxetine, fluvoxamine maleate, paroxetine, sertraline, dapoxetine, desvenlafaxine, sibutramine, nefazodone, milnacipran, desipramine, duloxetine, and bicifadine.

The present invention will now be described in detail with reference to examples; however, the examples are provided only for illustration purposes. The prophylactic or therapeutic agent for a disease caused by Aβ according to the present invention is not limited to the following specific examples in any cases. A person skilled in the art can fully implement the present invention by making various modifications to not only the following reference examples and examples but also the claims of the present specification, and such modifications are within the scope of the claims of the present specification.

When example compounds have stereoisomers, the names of compounds with optical rotation may not necessarily correspond to the structural formulas sequentially in the following examples, if the absolute configuration is not determined.

The following abbreviations are used in the following examples.

DMF: N,N-Dimethylformamide

THF: Tetrahydrofuran

EDC: 1-Ethyl-3-(3-dimethylaminopropyl)carbodiimide hydrochloride

HOBT: 1-Hydroxybenzotriazole

IPEA: Diisopropylethylamine

TEA: Triethylamine

BOPCl: Bis(2-oxo-3-oxazolidinyl)phosphonic chloride

Chromatography was performed using BW-300 manufactured by Fuji Silysia Chemical Ltd. as a carrier unless otherwise specified.

The preparative columns used for analysis and preparative separation of chiral compounds, CHIRALPAK AD-H, CHIRALPAK™ IA, CHIRALPAK™ IB, CHIRALCEL™ OJ-H and CHIRALCEL™ OD-H, were all manufactured by Daicel Chemical Industries, Ltd.

EXAMPLES

Examples 1 and 2

Synthesis of (+)-8-(5-isopropyl-4-methoxy-2-methylphenyl)-2-[6-methoxy-5-(4-methylimidazol-1-yl)pyridin-2-yl]-5,6,7,8-tetrahydro[1,2,4]triazolo[1,5-a]pyridine and (−)-8-(5-isopropyl-4-methoxy-2-methylphenyl)-2-[6-methoxy-5-(4-methylimidazol-1-yl)pyridin-2-yl]-5,6,7,8-tetrahydro[1,2,4]triazolo[1,5-a]pyridine

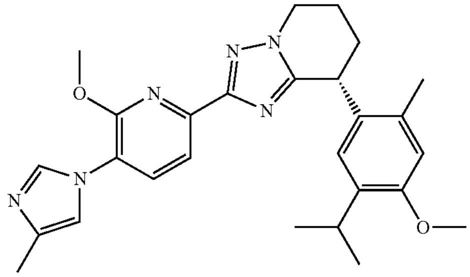

-continued

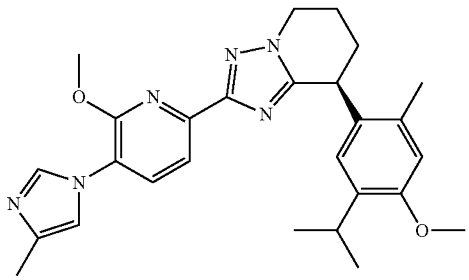

2-Methoxy-3-(4-methylimidazol-1-yl)-6-tributylstannylpyridine obtained in Preparation Example 1-2 (315 mg), 2-bromo-8-(5-isopropyl-4-methoxy-2-methylphenyl)-5,6,7,8-tetrahydro[1,2,4]triazolo[1,5-a]pyridine obtained in Preparation Example 2-1 (120 mg), 1,3-bis(diphenylphosphino)propane (54 mg) and Copper (I) oxide (94 mg) were suspended in N-methyl-2-pyrrolidinone (5 mL). Palladium (II) acetate (15 mg) was added and the mixture was heated with stirring at 120° C. in a nitrogen atmosphere for three hours. After leaving to cool, ethyl acetate and water were added. The reaction solution was filtered through celite and the organic layer was separated. The resulting organic layer was washed with brine and then dried over anhydrous sodium sulfate. The drying agent was separated by filtration, and then the organic layer was concentrated under reduced pressure. The residue was purified by NH silica gel column chromatography to obtain a racemate of the title compound (103 mg). The resulting racemate was separated by CHIRALPAK™ IA (2 cm×25 cm; mobile phase:hexane:ethanol=5:5) to obtain the title optically active compound with positive optical rotation (41 mg, >99% ee) and the title optically active compound with negative optical rotation (40 mg, 99% ee).

The property values of the title optically active compound with positive optical rotation are as follows.

ESI-MS; m/z 237 [½M$^+$+H], 473 [M$^+$+H].

$^1$H-NMR ($CDCl_3$) δ (ppm): 1.06 (d, J=6.8 Hz, 3H), 1.10 (d, J=6.8 Hz, 3H), 1.90-2.38 (m, 4H), 2.30 (s, 3H), 2.34 (s, 3H), 3.19 (qq, J=6.8, 6.8 Hz, 1H), 3.81 (s, 3H), 4.17 (s, 3H), 4.39-4.53 (m, 3H), 6.59 (s, 1H), 6.68 (s, 1H), 7.00 (s, 1H), 7.57 (d, J=8.0 Hz, 1H), 7.79 (d, J=8.0 Hz, 1H), 7.80-7.82 (m, 1H).

The property values of the title optically active compound with negative optical rotation are as follows.

ESI-MS; m/z 237 [½M$^+$+H], 473 [M$^+$+H].

$^1$H-NMR ($CDCl_3$) δ (ppm): 1.06 (d, J=6.8 Hz, 3H), 1.10 (d, J=6.8 Hz, 3H), 1.90-2.38 (m, 4H), 2.30 (s, 3H), 2.34 (s, 3H), 3.19 (qq, J=6.8, 6.8 Hz, 1H), 3.81 (s, 3H), 4.17 (s, 3H), 4.39-4.53 (m, 3H), 6.59 (s, 1H), 6.68 (s, 1H), 7.00 (s, 1H), 7.57 (d, J=8.0 Hz, 1H), 7.79 (d, J=8.0 Hz, 1H), 7.81 (m, 1H).

Examples 3 and 4

Synthesis of (+)-2-[6-methoxy-5-(4-methylimidazol-1-yl)pyridin-2-yl]-8-(2-trifluoromethoxyphenyl)-5,6,7,8-tetrahydro[1,2,4]triazolo[1,5-a]pyridine and (−)-2-[6-methoxy-5-(4-methylimidazol-1-yl)pyridin-2-yl]-8-(2-trifluoromethoxyphenyl)-5,6,7,8-tetrahydro[1,2,4]triazolo[1,5-a]pyridine

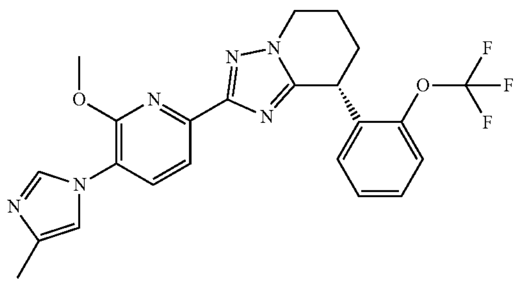

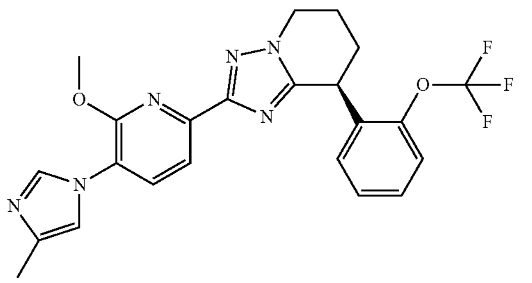

A racemate of the title compound (43 mg) was obtained according to the method of Examples 1 and 2 from 2-bromo-8-(2-trifluoromethoxyphenyl)-5,6,7,8-tetrahydro[1,2,4]triazolo[1,5-a]pyridine obtained in Preparation Example 2-2 (120 mg) in place of 2-bromo-8-(5-isopropyl-4-methoxy-2-methylphenyl)-5,6,7,8-tetrahydro[1,2,4]triazolo[1,5-a]pyridine. The resulting racemate was separated by CHIRALPAK™ AD-H (2 cm×25 cm, mobile phase:ethanol, flow rate: 10 mL/min) to obtain the title compound with a retention time of 11.6 minutes and positive optical rotation (8 mg) and the title compound with a retention time of 14.5 minutes and negative optical rotation (6.8 mg).

The property values of the title optically active compound with a retention time of 11.6 minutes are as follows.

$^1$H-NMR ($CDCl_3$) δ (ppm): 2.00-2.26 (m, 3H), 2.29 (s, 3H), 2.34-2.42 (m, 1H), 4.16 (s, 3H), 4.40 (dd, J=5.5, 5.5 Hz, 2H), 4.70 (dd, J=7.0, 5.9 Hz, 1H), 6.95 (d, J=7.4 Hz, 1H), 6.98-7.01 (m, 1H), 7.17-7.23 (m, 1H), 7.29-7.36 (m, 2H), 7.57 (d, J=7.8 Hz, 1H), 7.76 (d, J=7.8 Hz, 1H), 7.80-7.84 (m, 1H).

The property values of the title optically active compound with a retention time of 14.5 minutes are as follows.

$^1$H-NMR ($CDCl_3$) δ (ppm): 2.00-2.26 (m, 3H), 2.29 (s, 3H), 2.34-2.42 (m, 1H), 4.16 (s, 3H), 4.40 (dd, J=5.5, 5.5 Hz, 2H), 4.70 (dd, J=7.0, 5.9 Hz, 1H), 6.95 (d, J=7.4 Hz, 1H), 6.98-7.01 (m, 1H), 7.17-7.23 (m, 1H), 7.29-7.36 (m, 2H), 7.57 (d, J=7.8 Hz, 1H), 7.76 (d, J=7.8 Hz, 1H), 7.80-7.84 (m, 1H).

Examples 5 and 6

Synthesis of (+)-2-[6-methoxy-5-(4-methylimidazol-1-yl)pyridin-2-yl]-8-(3-trifluoromethylphenyl)-5,6,7,8-tetrahydro[1,2,4]triazolo[1,5-a]pyridine and (−)-2-[6-methoxy-5-(4-methylimidazol-1-yl)pyridin-2-yl]-8-(3-trifluoromethylphenyl)-5,6,7,8-tetrahydro[1,2,4]triazolo[1,5-a]pyridine

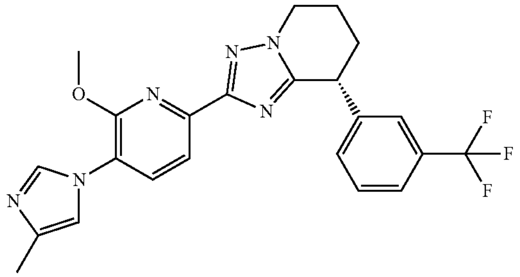

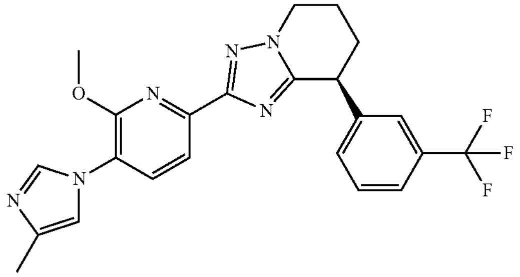

A racemate of the title compound (125 mg) was obtained according to the method of Examples 1 and 2 from 2-methoxy-3-(4-methylimidazol-1-yl)-6-tributylstannylpyridine obtained in Preparation Example 1-2 (415 mg) and from 2-bromo-8-(3-trifluoromethylphenyl)-5,6,7,8-tetrahydro[1,2,4]triazolo[1,5-a]pyridine obtained in Preparation Example 2-4 (150 mg) in place of 2-bromo-8-(5-isopropyl-4-methoxy-2-methylphenyl)-5,6,7,8-tetrahydro[1,2,4]triazolo[1,5-a]pyridine. The resulting racemate was separated by CHIRALPAK™ IB (2 cm×25 cm; mobile phase:hexane:ethanol=5:5) to obtain the title optically active compound with positive optical rotation (51 mg, >99% ee) and the title optically active compound with negative optical rotation (51 mg, >99% ee).

The property values of the title optically active compound with positive optical rotation are as follows.

ESI-MS; m/z 228 [½$M^+$+H], 455 [$M^+$+H].

$^1$H-NMR ($CDCl_3$) δ (ppm): 2.05-2.28 (m, 3H), 2.30 (s, 3H), 2.39-2.48 (m, 1H), 4.16 (s, 3H), 4.39-4.51 (m, 3H), 7.00 (m, 1H), 7.32 (d, J=6.8 Hz, 1H), 7.44-7.49 (m, 2H), 7.55 (d, J=7.6 Hz, 1H), 7.59 (d, J=7.6 Hz, 1H), 7.77 (d, J=7.6 Hz, 1H), 7.82-7.83 (m, 1H).

The property values of the title optically active compound with negative optical rotation are as follows.

ESI-MS; m/z 228 [½$M^+$+H], 455 [$M^+$+H].

$^1$H-NMR ($CDCl_3$) δ (ppm): 2.05-2.28 (m, 3H), 2.30 (s, 3H), 2.39-2.48 (m, 1H), 4.16 (s, 3H), 4.39-4.51 (m, 3H), 7.00

(m, 1H), 7.32 (d, J=6.8 Hz, 1H), 7.44-7.49 (m, 2H), 7.55 (d, J=7.6 Hz, 1H), 7.59 (d, J=7.6 Hz, 1H), 7.77 (d, J=7.6 Hz, 1H), 7.82-7.83 (m, 1H).

Examples 7 and 8

Synthesis of (−)-2-[5-methoxy-6-(4-methylimidazol-1-yl)pyridin-3-yl]-8-(2-trifluoromethylphenyl)-5,6,7,8-tetrahydro[1,2,4]triazolo[1,5-a]pyridine and (+)-2-[5-methoxy-6-(4-methylimidazol-1-yl)pyridin-3-yl]-8-(2-trifluoromethylphenyl)-5,6,7,8-tetrahydro[1,2,4]triazolo[1,5-a]pyridine

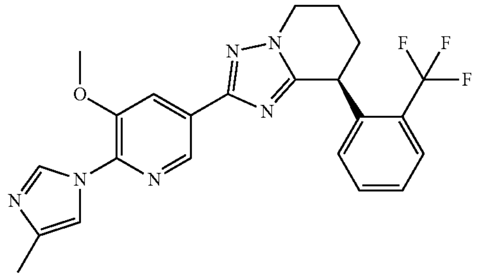

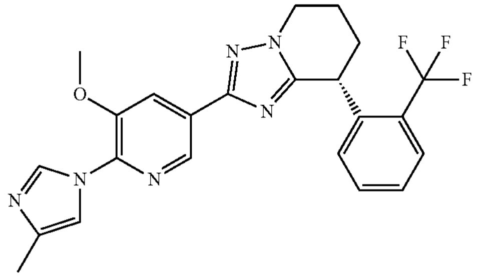

A racemate of the title compound was obtained according to the method of Examples 1 and 2 from a solution of 3-methoxy-2-(4-methyl-1H-imidazol-1-yl)-5-tributylstarmylpyridine obtained in Preparation Example 1-3 (100 mg) in N,N-dimethylformamide (2 mL) and from 2-bromo-8-(2-trifluoromethylphenyl)-5,6,7,8-tetrahydro[1,2,4]triazolo[1,5-a]pyridine obtained in Preparation Example 2-2 (60 mg) in place of 2-bromo-8-(5-isopropyl-4-methoxy-2-methylphenyl)-5,6,7,8-tetrahydro[1,2,4]triazolo[1,5-a]pyridine. The resulting racemate was separated by CHIRALCEL™ AD-H (2 cm×25 cm; mobile phase:ethanol) to obtain the title optically active compound with a retention time of 11 minutes and negative optical rotation (13.5 mg, >99% ee) and the title optically active compound with a retention time of 17 minutes and positive optical rotation (29.9 mg, >99% ee).

The property values of the title compound with negative optical rotation are as follows.

ESI-MS; m/z 455 [$M^+$+H].

$^1$H-NMR ($CDCl_3$) δ (ppm): 1.94-2.04 (m, 1H), 2.10-2.36 (m, 2H), 2.29 (s, 3H), 2.45-2.53 (m, 1H), 3.99 (s, 3H), 4.32-4.45 (m, 2H), 4.73 (dd, J=8.0, 6.0 Hz, 1H), 7.01 (d, J=7.6 Hz, 1H), 7.41 (t, J=7.6 Hz, 1H), 7.49 (t, J=7.6 Hz, 1H), 7.55 (brs, 1H), 7.75 (d, J=7.6 Hz, 1H), 7.95 (d, J=2.0 Hz, 1H), 8.37 (brs, 1H), 8.70 (d, J=2.0 Hz, 1H).

The property values of the title compound with positive optical rotation are as follows.

ESI-MS; m/z 455 [$M^+$+H].

$^1$H-NMR ($CDCl_3$) δ (ppm): 1.94-2.04 (m, 1H), 2.10-2.36 (m, 2H), 2.29 (s, 3H), 2.45-2.53 (m, 1H), 3.99 (s, 3H), 4.32-4.45 (m, 2H), 4.73 (dd, J=8.0, 6.0 Hz, 1H), 7.01 (d, J=7.6 Hz, 1H), 7.41 (t, J=7.6 Hz, 1H), 7.49 (t, J=7.6 Hz, 1H), 7.55 (brs, 1H), 7.75 (d, J=7.6 Hz, 1H), 7.95 (d, J=2.0 Hz, 1H), 8.37 (brs, 1H), 8.70 (d, J=2.0 Hz, 1H).

Examples 9 and 10

Synthesis of (+)-2-[6-methoxy-5-(4-methylimidazol-1-yl)pyridin-2-yl]-8-(2-trifluoromethylbenzyl)-5,6,7,8-tetrahydro[1,2,4]triazolo[1,5-a]pyridine and (−)-2-[6-methoxy-5-(4-methylimidazol-1-yl)pyridin-2-yl]-8-(2-trifluoromethylbenzyl)-5,6,7,8-tetrahydro[1,2,4]triazolo[1,5-a]pyricline

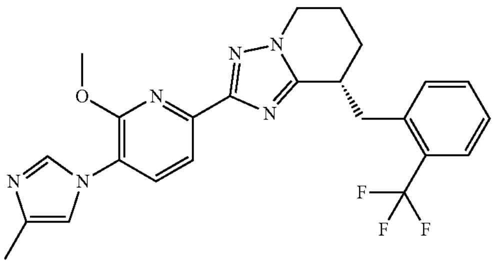

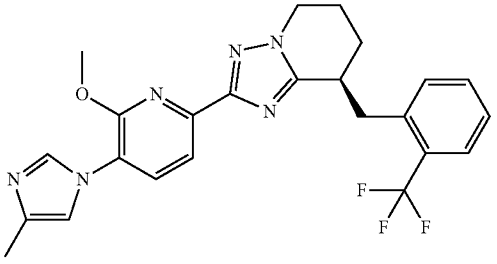

A racemate of the title compound (223 mg) was obtained according to the method of Examples 1 and 2 from 2-methoxy-3-(4-methylimidazol-1-yl)-6-tributylstannylpyridine obtained in Preparation Example 1-2 (377 mg) and from 2-bromo-8-(2-trifluoromethylbenzyl)-5,6,7,8-tetrahydro[1,2,4]triazolo[1,5-a]pyridine obtained in Preparation Example 2-7 (237 mg) in place of 2-bromo-8-(5-isopropyl-4-methoxy-2-methylphenyl)-5,6,7,8-tetrahydro[1,2,4]triazolo[1,5-a]pyridine. The resulting racemate was separated by CHIRALPAK™ AD-H (2 cm×25 cm; mobile phase:hexane: ethanol=5:5) to obtain the title optically active compound with positive optical rotation (74 mg, >99% ee) and the title optically active compound with negative optical rotation (74 mg, 99% ee).

The property values of the title optically active compound with positive optical rotation are as follows.

ESI-MS; m/z 235 [½$M^+$+H], 469 [$M^+$+H].

$^1$H-NMR ($CDCl_3$) δ (ppm): 1.58-1.70 (m, 1H), 1.89-2.03 (m, 2H), 2.15-2.23 (m, 1H), 2.31 (s, 3H), 3.00-3.10 (m, 1H), 3.36-3.44 (m, 1H), 3.83 (dd, J=14.6, 4.6 Hz, 1H), 4.18 (s, 3H), 4.19-4.27 (m, 1H), 4.30-4.38 (m, 1H), 7.03 (s, 1H), 7.37 (dd, J=7.6, 7.2 Hz, 1H), 7.46-7.55 (m, 2H), 7.64 (d, J=7.6 Hz, 1H), 7.69 (d, J=8.0 Hz, 1H), 7.82-7.86 (m, 2H).

The property values of the title optically active compound with negative optical rotation are as follows.

ESI-MS; m/z 235 [½$M^+$+H], 469 [$M^+$+H].

$^1$H-NMR ($CDCl_3$) δ (ppm): 1.58-1.70 (m, 1H), 1.89-2.03 (m, 2H), 2.15-2.23 (m, 1H), 2.31 (s, 3H), 3.00-3.10 (m, 1H), 3.36-3.44 (m, 1H), 3.83 (dd, J=14.6, 4.6 Hz, 1H), 4.18 (s, 3H), 4.19-4.27 (m, 1H), 4.30-4.38 (m, 1H), 7.03 (s, 1H), 7.37 (dd, J=7.6, 7.2 Hz, 1H), 7.46-7.55 (m, 2H), 7.64 (d, J=7.6 Hz, 1H), 7.69 (d, J=8.0 Hz, 1H), 7.82-7.86 (m, 2H).

Examples 11 and 12

Synthesis of (+)-2-[6-methoxy-5-(4-methylimidazol-1-yl)pyridin-2-yl]-4-(4-trifluoromethylphenyl)-4,5,6,7-tetrahydrobenzothiazole and (−)-2-[6-methoxy-5-(4-methylimidazol-1-yl)pyridin-2-yl]-4-(4-trifluoromethylphenyl)-4,5,6,7-tetrahydrobenzothiazole

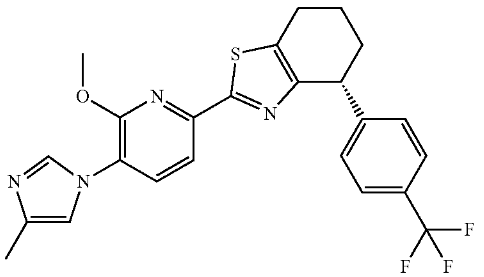

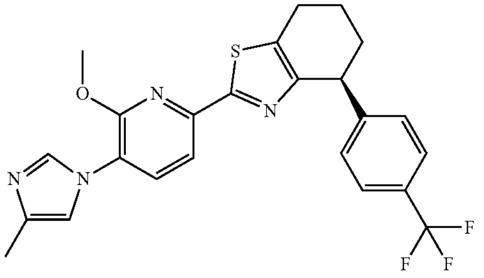

A racemate of the title compound (79 mg) was obtained according to the method of Examples 1 and 2 from 2-methoxy-3-(4-methylimidazol-1-yl)-6-tributylstannylpyridine obtained in Preparation Example 1-2 (198 mg) and from 2-bromo-4-(4-trifluoromethylphenyl)-4,5,6,7-tetrahydrobenzothiazole obtained in Preparation Example 2-8 (150 mg) in place of 2-bromo-8-(5-isopropyl-4-methoxy-2-methylphenyl)-5,6,7,8-tetrahydro[1,2,4]triazolo[1,5-a]pyridine. The resulting racemate was separated by CHIRALPAK™ IB (2 cm×25 cm; mobile phase:hexane:ethanol=9:1) to obtain the title optically active compound with positive optical rotation (27 mg, >99% ee) and the title optically active compound with negative optical rotation (28 mg, >99% ee).

The property values of the title optically active compound with positive optical rotation are as follows.

ESI-MS; m/z 471 [$M^+$+H].

$^1$H-NMR ($CDCl_3$) δ (ppm): 1.85-2.00 (m, 3H), 2.25-2.33 (m, 4H), 2.89-3.04 (m, 2H), 4.10 (s, 3H), 4.36 (t, J=5.6 Hz, 1H), 6.97 (d, J=1.2 Hz, 1H), 7.22 (d, J=7.6 Hz, 2H), 7.51-7.56 (m, 3H), 7.68 (d, J=8.0 Hz, 1H), 7.81 (d, J=1.2 Hz, 1H).

The property values of the title optically active compound with negative optical rotation are as follows.

ESI-MS; m/z 471 [$M^+$+H].

$^1$H-NMR ($CDCl_3$) δ (ppm): 1.85-2.00 (m, 3H), 2.25-2.33 (m, 4H), 2.89-3.04 (m, 2H), 4.10 (s, 3H), 4.36 (t, J=5.6 Hz, 1H), 6.97 (d, J=1.2 Hz, 1H), 7.22 (d, J=7.6 Hz, 2H), 7.51-7.56 (m, 3H), 7.68 (d, J=8.0 Hz, 1H), 7.81 (d, J=1.2 Hz, 1H).

Examples 13 and 14

Synthesis of (+)-2-[6-methoxy-5-(4-methylimidazol-1-yl)pyridin-2-yl]-8-(4-fluoro-2-trifluoromethylphenyl)-5,6,7,8-tetrahydro[1,2,4]triazolo[1,5-a]pyridine and (−)-2-[6-methoxy-5-(4-methylimidazol-1-yl)pyridin-2-yl]-8-(4-fluoro-2-trifluoromethylphenyl)-5,6,7,8-tetrahydro[1,2,4]triazolo[1,5-a]pyridine

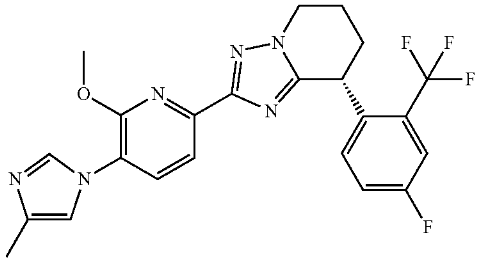

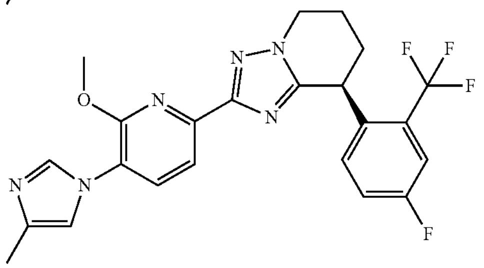

A racemate of the title compound (66 mg) was obtained according to the method of Examples 1 and 2 from 2-bromo-8-(4-fluoro-2-trifluoromethylphenyl)-5,6,7,8-tetrahydro[1,2,4]triazolo[1,5-a]pyridine obtained in Preparation Example 2-5 (250 mg) in place of 2-bromo-8-(5-isopropyl-4-methoxy-2-methylphenyl)-5,6,7,8-tetrahydro[1,2,4]triazolo[1,5-a]pyricline. The resulting racemate was separated by CHIRALPAK™ IB (2 cm×25 cm, mobile phase:ethanol:hexane=3:7, flow rate: 15 mL/min) to obtain the title compound with a retention time of 16 minutes and positive optical rotation (12.6 mg) and the title compound with a retention time of 18.7 minutes and negative optical rotation (15.1 mg).

The property values of the title optically active compound with a retention time of 16 minutes are as follows.

$^1$H-NMR ($CDCl_3$) δ (ppm): 1.88-2.00 (m, 1H), 2.10-2.23 (m, 1H), 2.23-2.34 (m, 1H), 2.29 (s, 3H), 2.42-2.52 (m, 1H), 4.15 (s, 3H), 4.30-4.50 (m, 2H), 4.70 (dd, J=8.2, 6.2 Hz, 1H), 6.96-7.01 (m, 2H), 7.14-7.20 (m, 1H), 7.42-7.47 (m, 1H), 7.56 (d, J=8.2 Hz, 1H), 7.73 (d, J=8.2 Hz, 1H), 7.80-7.84 (m, 1H).

The property values of the title optically active compound with a retention time of 18.7 minutes are as follows.

$^1$H-NMR ($CDCl_3$) δ (ppm): 1.88-2.00 (m, 1H), 2.10-2.23 (m, 1H), 2.23-2.34 (m, 1H), 2.29 (s, 3H), 2.42-2.52 (m, 1H), 4.15 (s, 3H), 4.30-4.50 (m, 2H), 4.70 (dd, J=8.2, 6.2 Hz, 1H), 6.96-7.01 (m, 2H), 7.14-7.20 (m, 1H), 7.42-7.47 (m, 1H), 7.56 (d, J=8.2 Hz, 1H), 7.73 (d, J=8.2 Hz, 1H), 7.80-7.84 (m, 1H).

Examples 15 and 16

Synthesis of (+)-2-[6-methoxy-5-(4-methylimidazol-1-yl)pyridin-2-yl]-7-(3-trifluoromethylphenyl)-5,6,7,8-tetrahydro[1,2,4]triazolo[1,5-a]nridine and (−)-2-[6-methoxy-5-(4-methylimidazol-1-yl)pyridin-2-yl]-7-(3-trifluoromethylphenyl)-5,6,7,8-tetrahydro[1,2,4]triazolo[1,5-a]pyridine

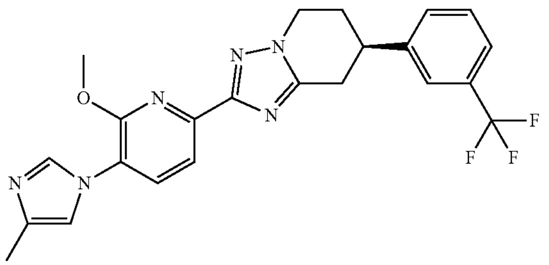

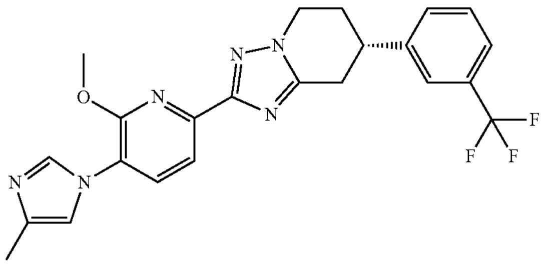

A racemate of the title compound (25 mg) was obtained according to the method of Examples 1 and 2 from 2-methoxy-3-(4-methylimidazol-1-yl)-6-tributylstannylpyridine obtained in Preparation Example 1-2 (190 mg) and from 2-bromo-7-(3-trifluoromethylphenyl)-5,6,7,8-tetrahydro[1,2,4]triazolo[1,5-a]pyridine obtained in Preparation Example 2-10 (115 mg) in place of 2-bromo-8-(5-isopropyl-4-methoxy-2-methylphenyl)-5,6,7,8-tetrahydro[1,2,4]triazolo[1,5-a]pyridine. The resulting racemate was separated by CHIRALPAK™ IB (2 cm×25 cm, mobile phase:ethanol:hexane=3:7, flow rate: 15 mL/min) to obtain the title compound with a retention time of 27 minutes and positive optical rotation (2.0 mg) and the title compound with a retention time of 38.5 minutes and negative optical rotation (1.2 mg).

The property values of the title optically active compound with a retention time of 27 minutes are as follows.

$^1$H-NMR ($CDCl_3$) δ (ppm): 2.31 (s, 3H), 2.33-2.49 (m, 2H), 3.11 (dd, J=16.0, 9.4 Hz, 1H), 3.33-3.47 (m, 2H), 4.18 (s, 3H), 4.28-4.37 (m, 1H), 4.46 (ddd, J=8.6, 5.1, 3.1 Hz, 1H), 7.02-7.04 (m, 1H), 7.44-7.61 (m, 4H), 7.64 (d, J=7.8 Hz, 1H), 7.83 (d, J=7.8 Hz, 1H), 7.85 (d, J=1.2 Hz, 1H).

The property values of the title optically active compound with a retention time of 38.5 minutes are as follows.

$^1$H-NMR ($CDCl_3$) δ (ppm): 2.31 (s, 3H), 2.33-2.49 (m, 2H), 3.11 (dd, J=16.0, 9.4 Hz, 1H), 3.33-3.47 (m, 2H), 4.18 (s, 3H), 4.28-4.37 (m, 1H), 4.46 (ddd, J=8.6, 5.1, 3.1 Hz, 1H), 7.02-7.04 (m, 1H), 7.44-7.61 (m, 4H), 7.64 (d, J=7.8 Hz, 1H), 7.83 (d, J=7.8 Hz, 1H), 7.85 (d, J=1.2 Hz, 1H).

Examples 17 and 18

Synthesis of (+)-2-[6-methoxy-5-(4-methylimidazol-1-yl)pyridin-2-yl]-8-(5-fluoro-2-trifluoromethylphenyl)-5,6,7,8-tetrahydro[1,2,4]triazolo[1,5-a]pyridine and (−)-2-[6-methoxy-5-(4-methylimidazol-1-yl)pyridin-2-yl]-8-(5-fluoro-2-trifluoromethylphenyl)-5,6,7,8-tetrahydro[1,2,4]triazolo[1,5-a]pyridine

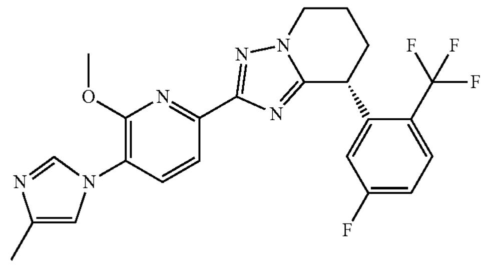

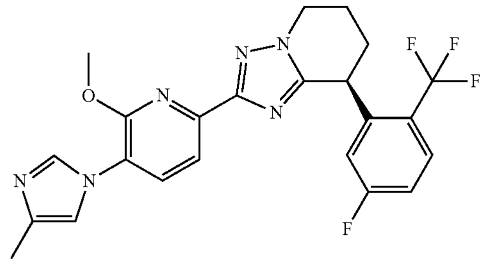

A racemate of the title compound (10.2 mg) was obtained according to the method of Examples 1 and 2 from 2-bromo-8-(5-fluoro-2-trifluoromethylphenyl)-5,6,7,8-tetrahydro[1,2,4]triazolo[1,5-a]pyridine obtained in Preparation Example 2-6 (250 mg) in place of 2-bromo-8-(5-isopropyl-4-methoxy-2-methylphenyl)-5,6,7,8-tetrahydro[1,2,4]triazolo[1,5-a]pyridine. The resulting racemate was separated by CHIRALPAK™ IA (2 cm×25 cm, mobile phase:ethanol:hexane=3:7, flow rate: 15 mL/min) to obtain the title compound with a retention time of 12.5 minutes and positive optical rotation (2.1 mg) and the title compound with a retention time of 22 minutes and negative optical rotation (1.41 mg).

The property values of the title optically active compound with a retention time of 12.5 minutes are as follows.

$^1$H-NMR ($CDCl_3$) δ (ppm): 1.90-2.01 (m, 1H), 2.10-2.23 (m, 1H), 2.23-2.35 (m, 1H), 2.29 (s, 3H), 2.43-2.53 (m, 1H), 4.16 (s, 3H), 4.38-4.50 (m, 2H), 4.75 (dd, J=7.4, 6.6 Hz, 1H), 6.67-6.71 (m, 1H), 6.98-7.01 (m, 1H), 7.05-7.11 (m, 1H), 7.57 (d, J=7.8 Hz, 1H), 7.71-7.76 (m, 1H), 7.74 (d, J=7.8 Hz, 1H), 7.79-7.82 (m, 1H).

The property values of the title optically active compound with a retention time of 22 minutes are as follows.

$^1$H-NMR ($CDCl_3$) δ (ppm): 1.90-2.01 (m, 1H), 2.10-2.23 (m, 1H), 2.23-2.35 (m, 1H), 2.29 (s, 3H), 2.43-2.53 (m, 1H), 4.16 (s, 3H), 4.38-4.50 (m, 2H), 4.75 (dd, J=7.4, 6.6 Hz, 1H), 6.67-6.71 (m, 1H), 6.98-7.01 (m, 1H), 7.05-7.11 (m, 1H), 7.57 (d, J=7.8 Hz, 1H), 7.71-7.76 (m, 1H), 7.74 (d, J=7.8 Hz, 1H), 7.79-7.82 (m, 1H).

Examples 19 and 20

Synthesis of (+)-(7,8-anti)-2-[6-methoxy-5-(4-methylimidazol-1-yl)pyridin-2-yl]-8-methyl-7-(4-trifluoromethylphenyl)-5,6,7,8-tetrahydro[1,2,4]triazolo[1,5-a]pyridine and (−)-(7,8-anti)-2-[6-methoxy-5-(4-methylimidazol-1-yl)pyridin-2-yl]-8-methyl-7-(4-trifluoromethylphenyl)-5,6,7,8-tetrahydro[1,2,4]triazolo[1,5-a]pyridine

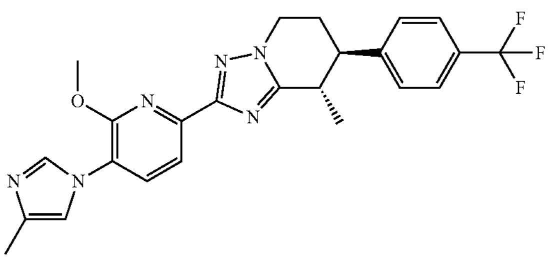

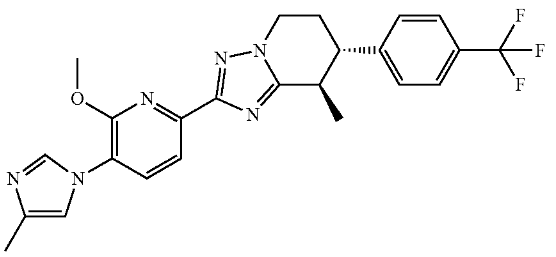

A racemate of the title compound (80 mg) was obtained according to the method of Examples 1 and 2 from 2-bromo-8-methyl-7-(4-trifluoromethylphenyl)-5,6,7,8-tetrahydro[1,2,4]triazolo[1,5-a]pyridine obtained in Preparation Example 2-11 in place of 2-bromo-8-(5-isopropyl-4-methoxy-2-methylphenyl)-5,6,7,8-tetrahydro[1,2,4]triazolo[1,5-a]pyridine. The resulting racemate was separated by CHIRALCEL™ OD-H (2 cm×25 cm, mobile phase:ethanol:hexane=2:8, flow rate: 15 mL/min) to obtain the title compound with a retention time of 28.0 minutes and negative optical rotation (4.8 mg) and the title compound with a retention time of 37.2 minutes and positive optical rotation (6.1 mg).

The property values of the title optically active compound with a retention time of 28.0 minutes are as follows.

$^1$H-NMR ($CDCl_3$) δ (ppm): 1.39 (d, J=7.0 Hz, 3H), 2.31 (s, 3H), 2.31-2.45 (m, 2H), 2.91 (ddd, J=11.3, 11.3, 3.1 Hz, 1H), 3.18-3.29 (m, 1H), 4.18 (s, 3H), 4.32 (ddd, J=11.7, 11.7, 3.9 Hz, 1H), 4.45-4.51 (m, 1H), 6.91-6.93 (m, 1H), 7.39 (d, J=7.8 Hz, 2H), 7.63 (d, J=7.8 Hz, 1H), 7.63-7.68 (m, 2H), 7.84 (d, J=7.8 Hz, 1H), 7.85 (d, J=1.2 Hz, 1H).

The property values of the title optically active compound with a retention time of 37.2 minutes are as follows.

$^1$H-NMR ($CDCl_3$) δ (ppm): 1.39 (d, J=7.0 Hz, 3H), 2.31 (s, 3H), 2.31-2.45 (m, 2H), 2.91 (ddd, J=11.3, 11.3, 3.1 Hz, 1H), 3.18-3.29 (m, 1H), 4.18 (s, 3H), 4.32 (ddd, J=11.7, 11.7, 3.9 Hz, 1H), 4.45-4.51 (m, 1H), 6.91-6.93 (m, 1H), 7.39 (d, J=7.8 Hz, 2H), 7.63 (d, J=7.8 Hz, 1H), 7.63-7.68 (m, 2H), 7.84 (d, J=7.8 Hz, 1H), 7.85 (d, J=1.2 Hz, 1H).

Examples 21 and 22

Synthesis of (+)-2-[3-methoxy-4-(4-methyl-1H-imidazol-1-yl)phenyl]8-(2-trifluoromethylphenyl)-5,6,7,8-tetrahydro[1,2,4]triazolo[1,5-a]pyridine and (−)-2-[3-methoxy-4-(4-methyl-1H-imidazol-1-yl)phenyl]8-(2-trifluoromethylphenyl)-5,6,7,8-tetrahydro[1,2,4]triazolo[1,5-a]pyridine

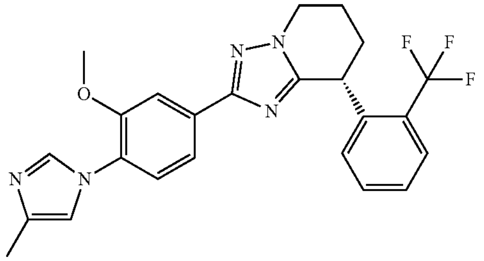

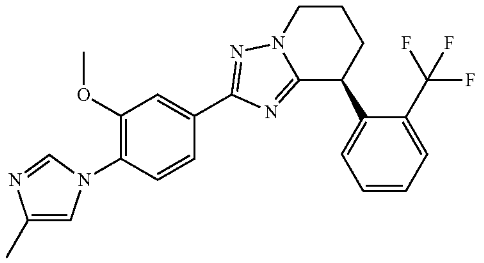

A racemate of the title compound was obtained according to the method of Examples 1 and 2 from 1-(2-methoxy-4-tributylstannylphenyl)-4-methyl-1H-imidazole obtained in Preparation Example 1-4 (276 mg) and from 2-bromo-8-(2-trifluoromethylphenyl)-5,6,7,8-tetrahydro[1,2,4]triazolo[1,5-a]pyridine obtained in Preparation Example 2-3 (100 mg) in place of 2-bromo-8-(5-isopropyl-4-methoxy-2-methylphenyl)-5,6,7,8-tetrahydro[1,2,4]triazolo[1,5-a]pyridine. The resulting racemate was separated by CHIRALPAK™ IA (2 cm×25 cm; mobile phase:hexane:ethanol=80:20) to obtain the title optically active compound with a retention time of 5.8 minutes and positive optical rotation (35.6 mg, >99% ee) and the title optically active compound with a retention time of 7.2 minutes and negative optical rotation (40.6 mg, >99% ee).

The property values of the title compound with positive optical rotation are as follows.

ESI-MS; m/z 454 [$M^+$+H].

$^1$H-NMR ($CDCl_3$) δ (ppm): 1.93-2.01 (m, 1H), 2.10-2.20 (m, 1H), 2.24-2.30 (m, 1H), 2.29 (d, J=1.2 Hz, 3H), 2.43-2.51 (m, 1H), 3.90 (s, 3H), 4.36-4.39 (m, 2H), 4.74 (dd, J=6.4 Hz, 8.0 Hz, 1H), 6.94 (t, J=1.2 Hz, 1H), 7.00 (d, J=7.6 Hz, 1H), 7.25 (d, J=8.8 Hz, 1H), 7.39 (t, J=7.6 Hz, 1H), 7.47 (t, J=7.6 Hz, 1H), 7.69 (dd, J=1.6 Hz, 8.8 Hz, 1H), 7.70 (d, J=1.6 Hz, 1H), 7.72 (d, J=1.2 Hz, 1H), 7.73 (d, J=7.6 Hz, 1H).

The property values of the title compound with negative optical rotation are as follows.

ESI-MS; m/z 454 [$M^+$+H].

$^1$H-NMR ($CDCl_3$) δ (ppm): 1.93-2.01 (m, 1H), 2.10-2.20 (m, 1H), 2.24-2.30 (m, 1H), 2.29 (d, J=1.2 Hz, 3H), 2.43-2.51 (m, 1H), 3.90 (s, 3H), 4.36-4.39 (m, 2H), 4.74 (dd, J=6.4 Hz, 8.0 Hz, 1H), 6.94 (t, J=1.2 Hz, 1H), 7.00 (d, J=7.6 Hz, 1H), 7.25 (d, J=8.8 Hz, 1H), 7.39 (t, J=7.6 Hz, 1H), 7.47 (t, J=7.6

Hz, 1H), 7.69 (dd, J=1.6 Hz, 8.8 Hz, 1H), 7.70 (d, J=1.6 Hz, 1H), 7.72 (d, J=1.2 Hz, 1H), 7.73 (d, J=7.6 Hz, 1H).

Examples 23 and 24

Synthesis of (+)-2-[6-methoxy-5-(4-methyl-1H-imidazol-1-yl)pyridin-2-yl]5-(3-trifluoromethylphenyl)-5,6,7,8-tetrahydro[1,2,4]triazolo[1,5-a]pyridine and (−)-2-[6-methoxy-5-(4-methyl-1H-imidazol-1-yl)pyridin-2-yl]5-(3-trifluoromethylphenyl)-5,6,7,8-tetrahydro[1,2,4]triazolo[1,5-a]pyridine

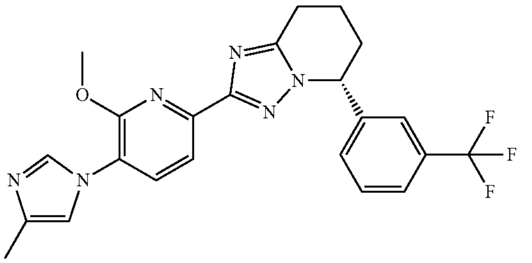

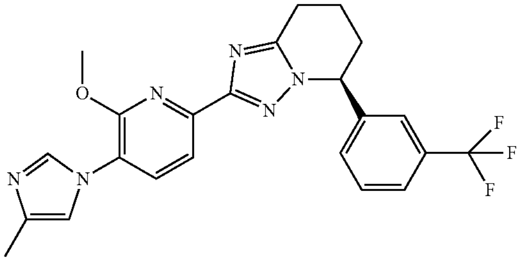

A racemate of the title compound (38.7 mg) was obtained according to the method of Examples 1 and 2 from 2-methoxy-3-(4-methylimidazol-1-yl)-6-tributylstannylpyridine obtained in Preparation Example 1-2 (62.2 mg) and from 2-bromo-5-(3-trifluoromethylphenyl)-5,6,7,8-tetrahydro[1,2,4]triazolo[1,5-a]pyridine obtained in Preparation Example 2-12 (32 mg) in place of 2-bromo-8-(5-isopropyl-4-methoxy-2-methylphenyl)-5,6,7,8-tetrahydro[1,2,4]triazolo[1,5-a]pyridine. The resulting racemate was separated by CHIRALPAK™ IA (2 cm×25 cm; mobile phase:hexane:ethanol=60:40) to obtain the title optically active compound with a retention time of 3.8 minutes and positive optical rotation (13.4 mg, >99% ee) and the title optically active compound with a retention time of 6.3 minutes and negative optical rotation (10.4 mg, >99% ee).

The property values of the title compound with positive optical rotation are as follows.

ESI-MS; m/z 455 [$M^+$+H].

$^1$H-NMR ($CDCl_3$) δ (ppm): 1.94-2.00 (m, 2H), 2.16-2.23 (m, 1H), 2.29 (d, J=1.2 Hz, 3H), 2.46-2.55 (m, 1H), 3.07-3.24 (m, 2H), 4.13 (s, 3H), 5.66 (t, J=5.2 Hz, 1H), 7.00 (t, J=1.2 Hz, 1H), 7.14 (d, J=7.6 Hz, 1H), 7.36 (s, 1H), 7.48 (t, J=7.6 Hz, 1H), 7.58 (d, J=7.6 Hz, 2H), 7.75 (d, J=7.6 Hz, 1H), 7.81 (d, J=1.2 Hz, 1H).

The property values of the title compound with negative optical rotation are as follows.

ESI-MS; m/z 455 [$M^+$+H].

$^1$H-NMR ($CDCl_3$) δ (ppm): 1.94-2.00 (m, 2H), 2.16-2.23 (m, 1H), 2.29 (d, J=1.2 Hz, 3H), 2.46-2.55 (m, 1H), 3.07-3.24 (m, 2H), 4.13 (s, 3H), 5.66 (t, J=5.2 Hz, 1H), 7.00 (t, J=1.2 Hz, 1H), 7.14 (d, J=7.6 Hz, 1H), 7.36 (s, 1H), 7.48 (t, J=7.6 Hz, 1H), 7.58 (d, J=7.6 Hz, 2H), 7.75 (d, J=7.6 Hz, 1H), 7.81 (d, J=1.2 Hz, 1H).

Example 25

Synthesis of 4-[6-methoxy-5-(4-methyl-1H-imidazol-1-yl)pyridin-2-yl]-7-(4-trifluoromethylphenyl)2,3,5-triaza-tricyclo[5.2.2.0*2,6*]undeca-3,5-diene

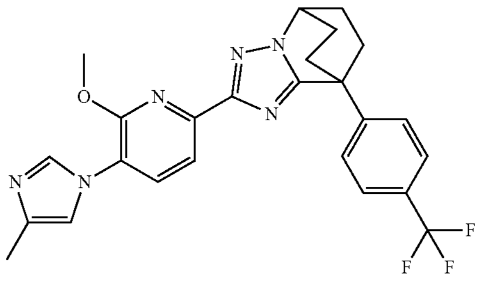 [SMILES: COc1nc(-c2nc3n(n2)C2CCC3(c3ccc(C(F)(F)F)cc3)CC2)ccc1-n1cnc(C)c1]

The title compound (0.35 mg) was obtained according to the method of Examples 1 and 2 from 2-methoxy-3-(4-methylimidazol-1-yl)-6-tributylstannylpyridine obtained in Preparation Example 1-2 (10.8 mg) and from 4-bromo-7-(4-trifluoromethylphenyl)-2,3,5-triaza-tricyclo[5.2.2.0*2,6*]undeca-3,5-diene obtained in Preparation Example 2-13 (2.8 mg) in place of 2-bromo-8-(5-isopropyl-4-methoxy-2-methylphenyl)-5,6,7,8-tetrahydro[1,2,4]triazolo[1,5-a]pyridine. The property values of the compound are as follows.

ESI-MS; m/z 481 [$M^+$+H].

$^1$H-NMR ($CDCl_3$) δ (ppm): 2.03-2.17 (m, 6H), 2.30 (s, 3H), 2.30-2.35 (m, 2H), 4.17 (s, 3H), 5.13 (s, 1H), 7.01 (s, 1H), 7.59 (d, J=8.0 Hz, 1H), 7.73 (d, J=8.4 Hz, 2H), 7.80-7.87 (m, 4H).

Examples 26, 27, 28 and 29

Synthesis of (+)-(6,8-syn)-6-methoxy-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (−)-(6,8-syn)-6-methoxy-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (+)-(6,8-anti)-6-methoxy-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (−)-(6,8-anti)-6-methoxy-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine

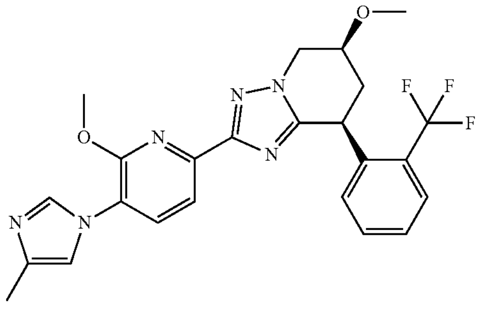

-continued

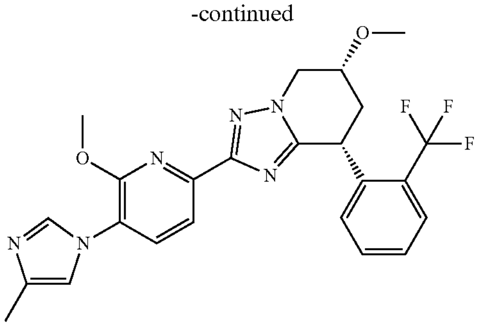

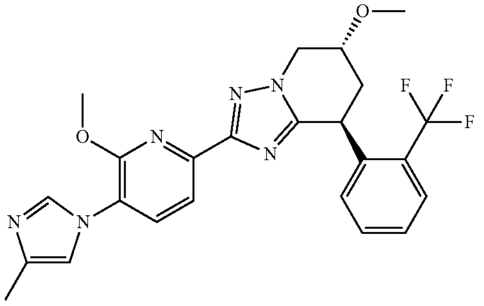

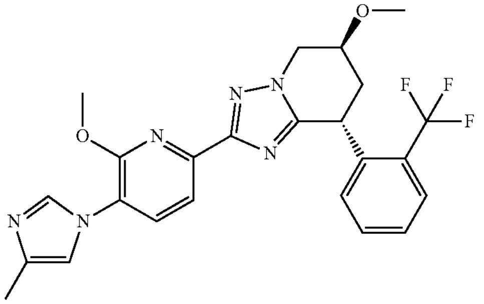

Synthesis of 2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridin-6-ol The title compound (910 mg) was obtained as a yellow solid according to the method of Examples 1 and 2 from 2-methoxy-3-(4-methylimidazol-1-yl)-6-tributylstannylpyridine obtained in Preparation Example 1-2 (1.31 g) and from 2-bromo-8-(2-trifluoromethylphenyl)-5,6,7,8-tetrahydro[1,2,4]triazolo[1,5-a]pyridin-6-ol obtained in Preparation Example 2-9 (900 mg) in place of 2-bromo-8-(5-isopropyl-4-methoxy-2-methylphenyl)-5,6,7,8-tetrahydro[1,2,4]triazolo[1,5-a]pyridine.

ESI-MS; m/z 471 [$M^+$+H].

Synthesis of (+)-(6,8-syn)-6-methoxy-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (−)-(6,8-syn)-6-methoxy-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (−)-(6,8-anti)-6-methoxy-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (+)-(6,8-anti)-6-methoxy-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine 2-[6-Methoxy-5-(4-methylimidazol-1-yl)pyridin-2-yl]-8-(2-trifluoromethylphenyl)-5,6,7,8-tetrahydro[1,2,4]triazolo[1,5-a]pyridin-6-ol (100 mg) was dissolved in tetrahydrofuran (2 mL), and then sodium hydride (21.3 mg) and methyl iodide (19.9 μL) were added at 0° C. After stirring at room temperature for 24 hours, the reaction solution was partitioned with a saturated sodium bicarbonate solution and ethyl acetate. The organic layer was washed with brine, dried over magnesium sulfate and then concentrated under reduced pressure. The racemic anti-compound purified by silica gel column chromatography (mobile phase:ethyl acetate/heptane=0 to 100%) (16.9 mg) was separated by CHIRALPAK™ IA (2 cm×25 cm, mobile phase:ethanol:hexane=4:6, flow rate: 13 mL/min) to obtain the title optically active compound with a retention time of 13.5 minutes and positive optical rotation (3.3 mg) and the title optically active compound with a retention time of 19.5 minutes and negative optical rotation (5.4 mg). On the other hand, the racemic syn-compound (25.9 mg) was separated by CHIRALPAK™ IB (2 cm×25 cm, mobile phase:ethanol:hexane=2:8, flow rate: 15 mL/min) to obtain the title optically active compound with a retention time of 22.6 minutes and positive optical rotation (2.5 mg) and the title optically active compound with a retention time of 38.5 minutes and negative optical rotation (1.4 mg).

The property values of the title optically active compound obtained from the anti-compound with a retention time of 13.5 minutes are as follows.

$^1$H-NMR ($CDCl_3$) δ (ppm): 1.95 (dd, J=13.5, 11.3 Hz, 1H), 2.29 (s, 3H), 2.72-2.80 (m, 1H), 3.47 (s, 3H), 4.03-4.09 (m, 1H), 4.15 (s, 3H), 4.43 (dd, J=14.1, 3.2 Hz, 1H), 4.64 (dd, J=14.1, 1.5 Hz, 1H), 4.84 (dd, J=11.3, 4.9 Hz, 1H) 6.96-6.99 (m, 1H), 7.11 (d, J=7.8 Hz, 1H), 7.38-7.45 (m, 1H), 7.46-7.51 (m, 1H), 7.54 (d, J=7.8 Hz, 1H), 7.71 (d, J=7.8 Hz, 1H), 7.74 (d, J=7.8 Hz, 1H), 7.81 (d, J=1.2 Hz, 1H).

The property values of the title optically active compound obtained from the anti-compound with a retention time of 19.5 minutes are as follows. $^1$H-NMR ($CDCl_3$) δ (ppm): 1.95 (dd, J=13.5, 11.3 Hz, 1H), 2.29 (s, 3H), 2.72-2.80 (m, 1H), 3.47 (s, 3H), 4.03-4.09 (m, 1H), 4.15 (s, 3H), 4.43 (dd, J=14.1, 3.2 Hz, 1H), 4.64 (dd, J=14.1, 1.5 Hz, 1H), 4.84 (dd, J=11.3, 4.9 Hz, 1H) 6.96-6.99 (m, 1H), 7.11 (d, J=7.8 Hz, 1H), 7.38-7.45 (m, 1H), 7.46-7.51 (m, 1H), 7.54 (d, J=7.8 Hz, 1H), 7.71 (d, J=7.8 Hz, 1H), 7.74 (d, J=7.8 Hz, 1H), 7.81 (d, J=1.2 Hz, 1H).

The property values of the title optically active compound obtained from the syn-compound with a retention time of 22.6 minutes are as follows.

$^1$H-NMR ($CDCl_3$) δ (ppm): 2.02 (ddd, J=12.9, 9.8, 9.8 Hz, 1H), 2.29 (s, 3H), 2.69-2.78 (m, 1H), 3.41 (s, 3H), 3.96-4.04 (m, 1H), 4.21 (s, 3H), 4.24 (dd, J=12.9, 8.6 Hz, 1H), 4.68-4.76 (m, 2H), 6.97-6.99 (m, 1H), 7.12 (d, J=7.8 Hz, 1H), 7.37-7.43 (m, 1H), 7.45-7.51 (m, 1H), 7.55 (d, J=7.8 Hz, 1H), 7.72 (d, J=7.8 Hz, 1H), 7.73 (d, J=7.8 Hz, 1H), 7.81 (d, J=1.7 Hz, 1H).

The property values of the title optically active compound obtained from the syn-compound with a retention time of 38.5 minutes are as follows.

$^1$H-NMR ($CDCl_3$) δ (ppm): 2.02 (ddd, J=12.9, 9.8, 9.8 Hz, 1H), 2.29 (s, 3H), 2.69-2.78 (m, 1H), 3.41 (s, 3H), 3.96-4.04 (m, 1H), 4.21 (s, 3H), 4.24 (dd, J=12.9, 8.6 Hz, 1H), 4.68-4.76 (m, 2H), 6.97-6.99 (m, 1H), 7.12 (d, J=7.8 Hz, 1H), 7.37-7.43 (m, 1H), 7.45-7.51 (m, 1H), 7.55 (d, J=7.8 Hz, 1H), 7.72 (d, J=7.8 Hz, 1H), 7.73 (d, J=7.8 Hz, 1H), 7.81 (d, J=1.7 Hz, 1H).

The compounds of Examples 30 to 41 were obtained by the same method as in Examples 1 and 2 (Table 1).

TABLE 1
| Production Ex No. | Structural formula |
|---|---|
| Example 30 | 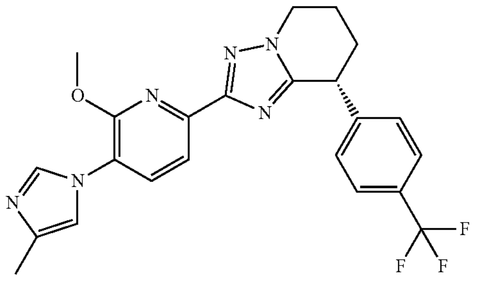 [SMILES: COc1nc(-c2nc3n(n2)CCC[C@@H]3c2ccc(C(F)(F)F)cc2)ccc1-n1cnc(C)c1] |
| Example 31 | 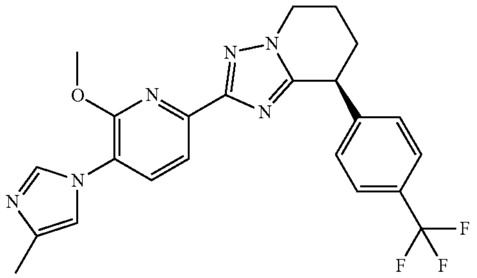 [SMILES: COc1nc(-c2nc3n(n2)CCC[C@H]3c2ccc(C(F)(F)F)cc2)ccc1-n1cnc(C)c1] |
| Example 32 | 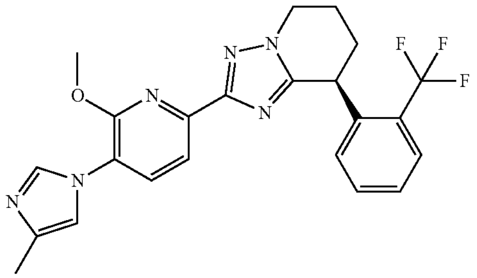 [SMILES: COc1nc(-c2nc3n(n2)CCC[C@H]3c2ccccc2C(F)(F)F)ccc1-n1cnc(C)c1] |
| Example 33 | 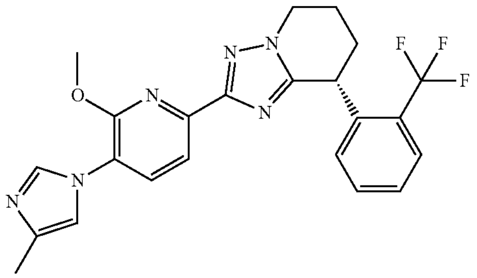 [SMILES: COc1nc(-c2nc3n(n2)CCO[C@@H]3c2ccccc2C(F)(F)F)ccc1-n1cnc(C)c1] |
| Example 34 | 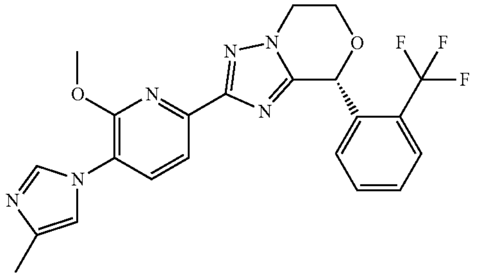 |
TABLE 1-continued
| Production Ex No. | Structural formula |
|---|---|
| Example 35 | 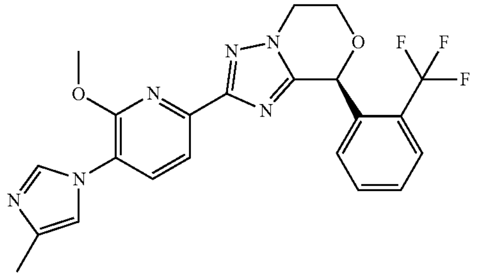 |
| Example 36 | 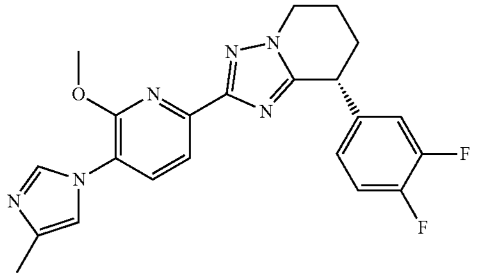 [SMILES: COc1nc(-c2nc3n(n2)CCC[C@@H]3c2ccc(F)c(F)c2)ccc1-n1cnc(C)c1] |
| Example 37 | 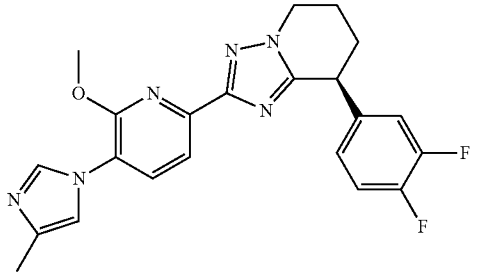 [SMILES: COc1nc(-c2nc3n(n2)CCC[C@H]3c2ccc(F)c(F)c2)ccc1-n1cnc(C)c1] |
| Example 38 | 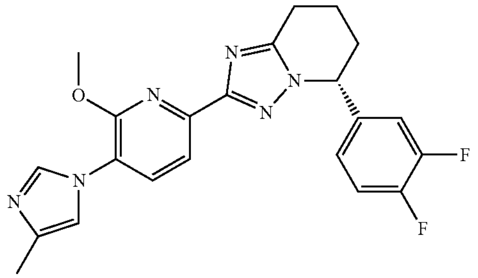 [SMILES: COc1nc(-c2nc3n(n2)[C@@H](c2ccc(F)c(F)c2)CCC3)ccc1-n1cnc(C)c1] |
| Example 39 | 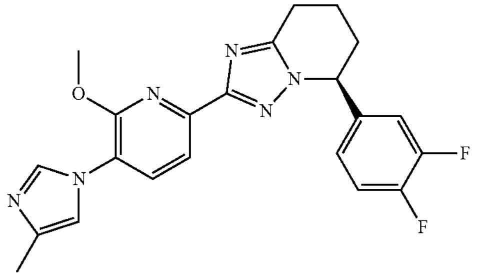 [SMILES: COc1nc(-c2nc3n(n2)[C@H](c2ccc(F)c(F)c2)CCC3)ccc1-n1cnc(C)c1] |

TABLE 1-continued

| Production Ex No. | Structural formula |
|---|---|
| Example 40 | 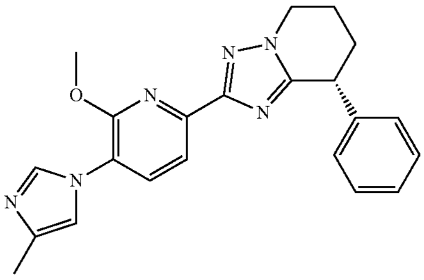 [SMILES: COc1nc(-c2nc3n(n2)CCC[C@@H]3c2ccccc2)ccc1-n1cnc(C)c1] |
| Example 41 | 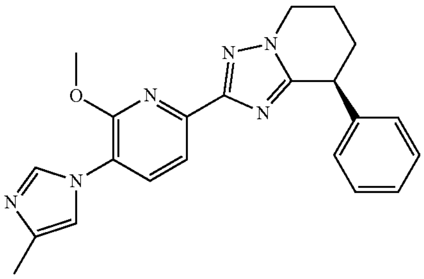 [SMILES: COc1nc(-c2nc3n(n2)CCC[C@H]3c2ccccc2)ccc1-n1cnc(C)c1] |

Examples 42 and 43

Synthesis of −8-4-bromo-2-trifluoromethylphenyl-2-[6-methoxy-5-(4-methylimidazol-1-yl)pyridin-2-yl]-5,6,7,8-tetrahydro[1,2,4]triazolo[1,5-a]pyridine and (+)-8-(4-bromo-2-trifluoromethylphenyl)-2,6-methoxy-5-(4-methylimidazol-1-yl)pyridin-2-yl]-5,6,7,8-tetrahydro[1,2,4]triazolo[1,5-a]pyridine

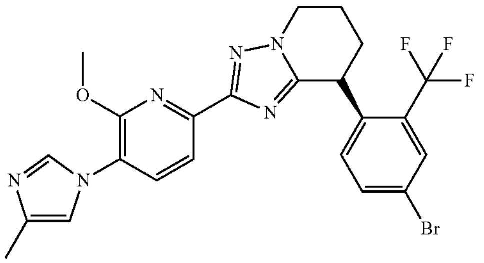

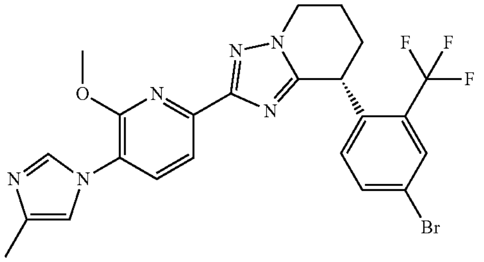

Ethyl 2-(4-bromo-2-trifluoromethylphenyl)-5-chloropentanimidate hydrochloride obtained in Preparation Example 3-1 (100 mg) was added to a suspension of 6-methoxy-5-(4-methylimidazol-1-yl)pyridine-2-carboxylic acid hydrazide hydrochloride obtained in Preparation Example 1-6 (50 mg) and imidazole (83 mg) in N,N-dimethylformamide (1 mL), and the mixture was stirred at room temperature for three hours. Ethanol (1 mL) was added to the reaction solution, followed by stirring at room temperature for five days. Then, the reaction solution was stirred at 70° C. for two hours. The reaction solution was left to cool to room temperature. Then, ethyl acetate, water and 2 N hydrochloric acid (0.3 mL) were added and the organic layer was separated. The resulting organic layer was sequentially washed with water and brine, dried over anhydrous magnesium sulfate and then concentrated under reduced pressure. The resulting residue was purified by silica gel column chromatography (carrier: Chromatorex™ NH; elution solvent:ethyl acetate:heptane=1:3→1:1→1:0) to obtain a racemate of the title compound. The resulting racemate was separated by CHIRALPAK™ AD-H (2 cm×25 cm; mobile phase:ethanol) to obtain the title optically active compound with a retention time of 18 minutes and negative optical rotation (31.3 mg, >99% ee) and the title optically active compound with a retention time of 29 minutes and positive optical rotation (29.9 mg, >98% ee).

The property values of the title compound with negative optical rotation are as follows.

ESI-MS; m/z 535 [$M^+$+H].

$^1$H-NMR ($CDCl_3$) δ (ppm): 1.87-1.98 (m, 1H), 2.10-2.35 (m, 2H), 2.30 (s, 3H), 2.42-2.53 (m, 1H), 4.15 (s, 3H), 4.35-4.51 (m, 2H), 4.69 (dd, J=8.4, 6.0 Hz, 1H), 6.88 (d, J=8.4 Hz, 1H), 6.99 (brs, 1H), 7.56 (d, J=8.0 Hz, 1H), 7.59 (dd, J=8.4, 2.0 Hz, 1H), 7.72 (d, J=8.0 Hz, 1H), 7.81 (d, J=1.6 Hz, 1H), 7.87 (d, J=2.0 Hz, 1H).

The property values of the title compound with positive optical rotation are as follows.

ESI-MS; tniz 533 [$M^+$+H].

$^1$H-NMR ($CDCl_3$) δ (ppm): 1.87-1.98 (m, 1H), 2.10-2.35 (m, 2H), 2.30 (s, 3H), 2.42-2.53 (m, 1H), 4.15 (s, 3H), 4.35-4.51 (m, 2H), 4.69 (dd, J=8.4, 6.0 Hz, 1H), 6.88 (d, J=8.4 Hz, 1H), 6.99 (brs, 1H), 7.56 (d, J=8.0 Hz, 1H), 7.59 (dd, J=8.4, 2.0 Hz, 1H), 7.72 (d, J=8.0 Hz, 1H), 7.81 (d, J=1.6 Hz, 1H), 7.87 (d, J=2.0 Hz, 1H).

Examples 44 and 45

Synthesis of (+)-2-[6-methoxy-5-(4-methylimidazol-1-yl)pyridin-2-yl]-7-(2-trifluoromethylphenyl)-6,7-dihydro-5H-pyrrolo[1,2-b][1,2,4]triazole and (−)-2-[6-methoxy-5-(4-methylitnidazol-1-yl)pyridin-2-yl]-7-(2-trifluoromethylphenyl)-6,7-dihydro-5H-pyrrolo[1,2-b][1,2,4]triazole

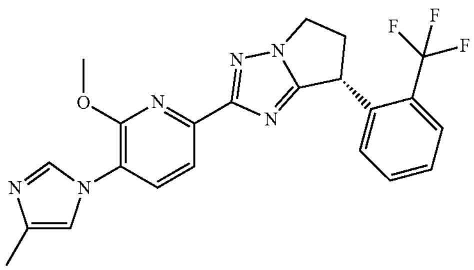

-continued

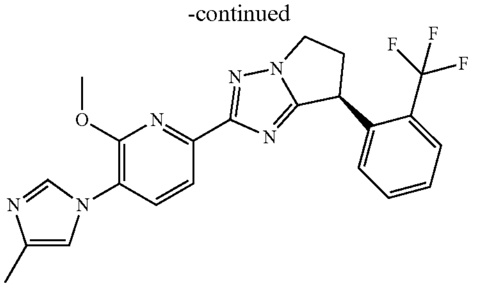

A racemate of the title compound (81 mg) was obtained according to the method of Examples 42 and 43 from 6-methoxy-5-(4-methylimidazol-1-yl)pyridine-2-carboxylic acid hydrazide hydrochloride obtained in Preparation Example 1-6 (250 mg) and from ethyl 4-chloro-2-(2-trifluoromethylphenyl)butylimidate hydrochloride obtained in Preparation Example 3-14 (367 mg) in place of ethyl 2-(4-bromo-2-trifluoromethylphenyl)-5-chloropentanimidate hydrochloride. The resulting racemate was separated by CHIRALPAK™ IB (2 cm×25 cm; mobile phase:hexane:ethanol=7:3) to obtain the title optically active compound with positive optical rotation (10 mg, >99% ee) and the title optically active compound with negative optical rotation (10 mg, >99% ee).

The property values of the title optically active compound with positive optical rotation are as follows.

ESI-MS; m/z 441 [$M^+$+H].

$^1$H-NMR ($CDCl_3$) δ (ppm): 2.32 (s, 3H), 2.67-2.78 (m, 1H), 3.34-3.43 (m, 1H), 4.10 (s, 3H), 4.46-4.54 (m, 1H), 4.64-4.72 (m, 1H), 4.97 (dd, J=8.4, 8.0 Hz, 1H), 7.03 (d, J=1.2 Hz, 1H), 7.24 (d, J=8.0 Hz, 1H), 7.41 (dd, J=8.0, 7.6 Hz, 1H), 7.52 (dd, J=7.6, 6.8 Hz, 1H), 7.71-7.75 (m, 2H), 7.87 (d, J=1.2 Hz, 1H), 8.08 (d, J=8.0 Hz, 1H).

The property values of the title optically active compound with negative optical rotation are as follows.

ESI-MS; m/z 441 [$M^+$+H].

$^1$H-NMR ($CDCl_3$) δ (ppm): 2.32 (s, 3H), 2.67-2.78 (m, 1H), 3.34-3.43 (m, 1H), 4.10 (s, 3H), 4.46-4.54 (m, 1H), 4.64-4.72 (m, 1H), 4.97 (dd, J=8.4, 8.0 Hz, 1H), 7.03 (d, J=1.2 Hz, 1H), 7.24 (d, J=8.0 Hz, 1H), 7.41 (dd, J=8.0, 7.6 Hz, 1H), 7.52 (dd, J=7.6, 6.8 Hz, 1H), 7.71-7.75 (m, 2H), 7.87 (d, J=1.2 Hz, 1H), 8.08 (d, J=8.0 Hz, 1H).

Examples 46 and 47

Synthesis of (+)-8-(biphenyl-4-yl)-2-[6-methoxy-5-(4-methylimidazol-1-yl)pyridin-2-yl]-5,6,7,8-tetrahydro[1,2,4]triazolo[1,5-a]pyridine and (−)-8-(biphenyl-4-yl)-2-[6-methoxy-5-(4-methylimidazol-1-yl)pyridin-2-yl]-5,6,7,8-tetrahydro[1,2,4]triazolo[1,5-a]pyridine

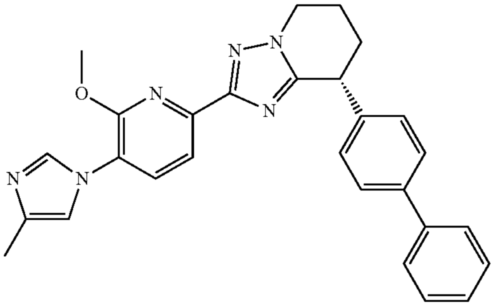

-continued

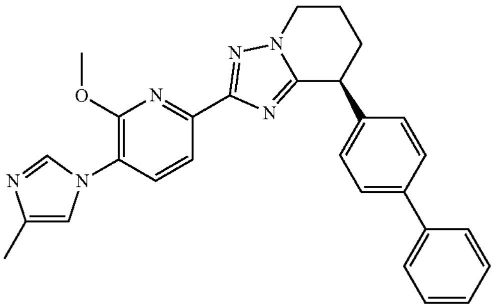

A racemate of the title compound was obtained according to the method of Examples 42 and 43 from the imidate hydrochloride obtained in Preparation Example 3-5 in place of ethyl 2-(4-bromo-2-trifluoromethylphenyl)-5-chloropentanimidate hydrochloride. The resulting racemate was separated by CHIRALPAK™ IA (2 cm×25 cm; mobile phase: 50% ethanol-hexane) to obtain the title optically active compound with a retention time of 13 minutes and positive optical rotation (21.9 mg, >99% ee) and the title optically active compound with a retention time of 20 minutes and negative optical rotation (20.9 mg, >98% ee).

The property values of the title compound with positive optical rotation are as follows.

ESI-MS; m/z 463 [$M^+$+H].

$^1$H-NMR ($CDCl_3$) δ (ppm): 2.05-2.33 (m, 3H), 2.30 (s, 3H), 2.35-2.46 (m, 1H), 4.17 (s, 3H), 4.35-4.51 (m, 3H), 7.00 (brs, 1H), 7.20 (d, J=8.0 Hz, 2H), 7.34 (t, J=8.0 Hz, 1H), 7.43 (t, J=8.0 Hz, 2H), 7.54-7.61 (m, 5H), 7.79-7.85 (m, 2H).

The property values of the title compound with negative optical rotation are as follows.

ESI-MS; m/z 463 [$M^+$+H].

$^1$H-NMR ($CDCl_3$) δ (ppm): 2.05-2.33 (m, 3H), 2.30 (s, 3H), 2.35-2.46 (m, 1H), 4.17 (s, 3H), 4.35-4.51 (m, 3H), 7.00 (brs, 1H), 7.20 (d, J=8.0 Hz, 2H), 7.34 (t, J=8.0 Hz, 1H), 7.43 (t, J=8.0 Hz, 2H), 7.54-7.61 (m, 5H), 7.79-7.85 (m, 2H).

Examples 48 and 49

Synthesis of (−)-8-(biphenyl-2-yl)-2-[6-methoxy-5-(4-methylimidazol-1-yl)pyridin-2-yl]-5,6,7,8-tetrahydro[1,2,4]triazolo[1,5-a]pyridine and (+)-8-(biphenyl-2-yl)-2-[6-methoxy-5-(4-methylimidazol-1-yl)pyridin-2-yl]-5,6,7,8-tetrahydro[1,2,4]triazolo[1,5-a]pyridine

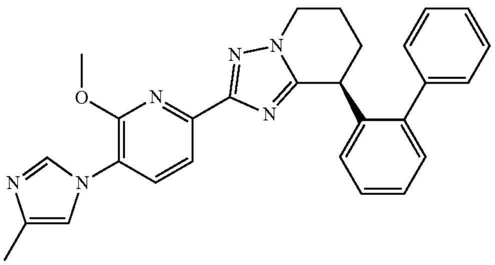

-continued

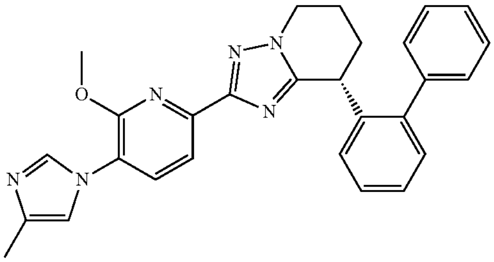

-continued

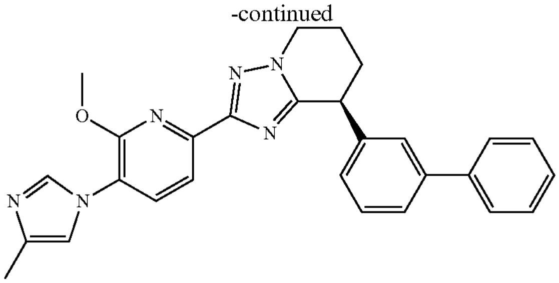

A racemate of the title compound was obtained according to the method of Examples 42 and 43 from the imidate hydrochloride obtained in Preparation Example 3-6 in place of ethyl 2-(4-bromo-2-trifluoromethylphenyl)-5-chloropentanimidate hydrochloride. The resulting racemate was separated by CHIRALPAK™ IA (2 cm×25 cm; mobile phase: 50% ethanol-hexane) to obtain the title optically active compound with a retention time of 9 minutes and negative optical rotation (12.6 mg, >99% ee) and the title optically active compound with a retention time of 12 minutes and positive optical rotation (11.8 mg, >98% ee).

The property values of the title compound with negative optical rotation are as follows.

ESI-MS; m/z 463 [$M^+$+H].

$^1$H-NMR ($CDCl_3$) δ (ppm): 1.83-1.97 (m, 2H), 2.04-2.21 (m, 2H), 2.30 (s, 3H), 4.16 (s, 3H), 4.25-4.40 (m, 2H), 4.48-4.56 (m, 1H), 6.95 (d, J=7.2 Hz, 1H), 7.00 (brs, 1H), 7.20-7.50 (m, 8H), 7.58 (d, J=8.0 Hz, 1H), 7.80 (d, J=8.0 Hz, 1H), 7.82 (brs, 1H).

The property values of the title compound with positive optical rotation are as follows.

ESI-MS; m/z 463 [$M^+$+H].

$^1$H-NMR ($CDCl_3$) δ (ppm): 1.83-1.97 (m, 2H), 2.04-2.21 (m, 2H), 2.30 (s, 3H), 4.16 (s, 3H), 4.25-4.40 (m, 2H), 4.48-4.56 (m, 1H), 6.95 (d, J=7.2 Hz, 1H), 7.00 (brs, 1H), 7.20-7.50 (m, 8H), 7.58 (d, J=8.0 Hz, 1H), 7.80 (d, J=8.0 Hz, 1H), 7.82 (brs, 1H).

Examples 50 and 51

Synthesis of (+)-8-(biphenyl-3-yl)-2-[6-methoxy-5-(4-methylimidazol-1-yl)pyridin-2-yl]-5,6,7,8-tetrahydro[1,2,4]triazolo[1,5-a]pyridine and (−)-8-(biphenyl-3-yl)-2-[6-methoxy-5-(4-methylimidazol-1-yl)pyridin-2-yl]-5,6,7,8-tetrahydro[1,2,4]triazolo[1,5-a]pyridine

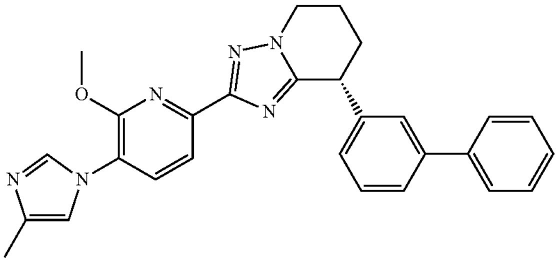

A racemate of the title compound was obtained according to the method of Examples 42 and 43 from the imidate hydrochloride obtained in Preparation Example 3-7 in place of ethyl 2-(4-bromo-2-trifluoromethylphenyl)-5-chloropentanimidate hydrochloride. The resulting racemate was separated by CHIRALPAK™ IA (2 cm×25 cm; mobile phase: 50% ethanol-hexane) to obtain the title optically active compound with a retention time of 9 minutes and positive optical rotation (40.9 mg, >99% ee) and the title optically active compound with a retention time of 19 minutes and negative optical rotation (39.8 mg, >99% ee).

The property values of the title compound with positive optical rotation are as follows.

ESI-MS; m/z 463 [$M^+$+H].

$^1$H-NMR ($CDCl_3$) δ (ppm): 2.05-2.34 (m, 3H), 2.30 (d, J=1.2 Hz, 3H), 2.37-2.47 (m, 1H), 4.17 (s, 3H), 4.35-4.55 (m, 3H), 7.00 (t, J=1.2 Hz, 1H), 7.09 (d, J=8.0 Hz, 1H), 7.31-7.37 (m, 2H), 7.37-7.44 (m, 3H), 7.48-7.56 (m, 3H), 7.58 (d, J=8.0 Hz, 1H), 7.81 (d, J=8.0 Hz, 1H), 7.82 (d, J=1.2 Hz, 1H).

The property values of the title compound with negative optical rotation are as follows.

ESI-MS; m/z 463 [$M^+$+H].

$^1$H-NMR ($CDCl_3$) δ (ppm): 2.05-2.34 (m, 3H), 2.30 (d, J=1.2 Hz, 3H), 2.37-2.47 (m, 1H), 4.17 (s, 3H), 4.35-4.55 (m, 3H), 7.00 (t, J=1.2 Hz, 1H), 7.09 (d, J=8.0 Hz, 1H), 7.31-7.37 (m, 2H), 7.37-7.44 (m, 3H), 7.48-7.56 (m, 3H), 7.58 (d, J=8.0 Hz, 1H), 7.81 (d, J=8.0 Hz, 1H), 7.82 (d, J=1.2 Hz, 1H).

Examples 52 and 53

Synthesis of (+)-2-[6-methoxy-5-(4-methylimidazol-1-yl)pyridin-2-yl]-8-(4-fluorophenyl)-5,6,7,8-tetrahydro[1,2,4]triazolo[1,5-a]pyridine and (−)-2-[6-methoxy-5-(4-methylimidazol-1-yl)pyridin-2-yl]-8-(4-fluorophenyl)-5,6,7,8-tetrahydro[1,2,4]triazolo[1,5-a]pyridine

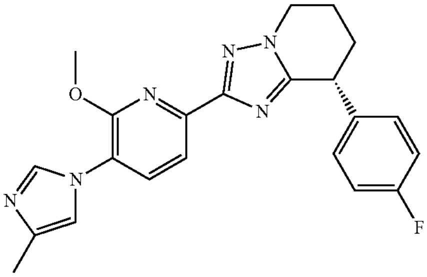

-continued

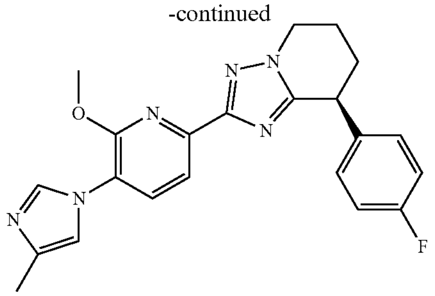

A racemate of the title compound was obtained according to the method of Examples 42 and 43 from the imidate hydrochloride obtained in Preparation Example 3-15 in place of ethyl 2-(4-bromo-2-trifluoromethylphenyl)-5-chloropentanimidate hydrochloride. The resulting racemate was separated by CHIRALPAK™ IB (2 cm×25 cm; mobile phase:hexane: ethanol=5:5) to obtain the title optically active compound with positive optical rotation (74 mg, >99% ee) and the title optically active compound with negative optical rotation (75 mg, >99% ee).

The property values of the title optically active compound with positive optical rotation are as follows.

ESI-MS; m/z 405 $[M^+ +H]$.

$^1$H-NMR ($CDCl_3$) δ (ppm): 2.03-2.26 (m, 3H), 2.30 (s, 3H), 2.33-2.40 (m, 1H), 4.16 (s, 3H), 4.34-4.45 (m, 3H), 7.00-7.06 (m, 3H), 7.08-7.13 (m, 2H), 7.59 (d, J=8.0 Hz, 1H), 7.78 (d, J=8.0 Hz, 1H), 8.82 (d, J=1.2 Hz, 1H).

The property values of the title optically active compound with negative optical rotation are as follows.

ESI-MS; m/z 405 $[M^+ +H]$.

$^1$H-NMR ($CDCl_3$) δ (ppm): 2.03-2.26 (m, 3H), 2.30 (s, 3H), 2.33-2.40 (m, 1H), 4.16 (s, 3H), 4.34-4.45 (m, 3H), 7.00-7.06 (m, 3H), 7.08-7.13 (m, 2H), 7.59 (d, J=8.0 Hz, 1H), 7.78 (d, J=8.0 Hz, 1H), 8.82 (d, J=1.2 Hz, 1H).

Examples 54 and 55

Synthesis of (+)-2-[6-methoxy-5-(4-methylimidazol-1-yl)pyridin-2-yl]-8-4-methoxyphenyl)-5,6,7,8-tetrahydro[1,2,4]triazolo[1,5-a]pyridine and (−)-2-[6-methoxy-5-(4-methylimidazol-1-yl)pyridin-2-yl]-8-(4-methoxyphenyl)-5,6,7,8-tetrahydro[1,2,4]triazolo[1,5-a]pyridine

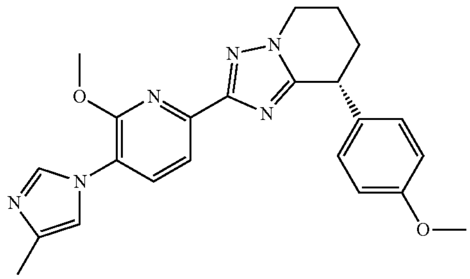

-continued

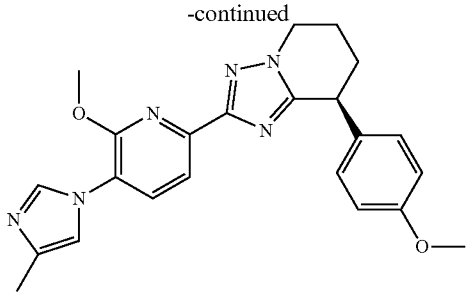

A racemate of the title compound was obtained according to the method of Examples 42 and 43 from the imidate hydrochloride obtained in Preparation Example 3-16 in place of ethyl 2-(4-bromo-2-trifluoromethylphenyl)-5-chloropentanimidate hydrochloride. The resulting racemate was separated by CHIRALPAK™ IB (2 cm×25 cm; mobile phase:hexane: ethanol=5:5) to obtain the title optically active compound with positive optical rotation (64 mg, >99% ee) and the title optically active compound with negative optical rotation (55 mg, >99% ee).

The property values of the title optically active compound with positive optical rotation are as follows.

ESI-MS; m/z 417 $[M^+ +H]$.

$^1$H-NMR ($CDCl_3$) δ (ppm): 2.03-2.12 (m, 2H), 2.15-2.26 (m, 1H), 2.30 (s, 3H), 2.30-2.38 (m, 1H), 3.79 (s, 3H), 4.16 (s, 3H), 4.33-4.45 (m, 3H), 6.84-6.89 (m, 2H), 6.99-7.08 (m, 3H), 7.58 (d, J=8.0 Hz, 1H), 7.79 (d, J=8.0 Hz, 1H), 7.82 (d, J=0.8 Hz, 1H).

The property values of the title optically active compound with negative optical rotation are as follows.

EST-MS; m/z 417 $[M^+ +H]$.

$^1$H-NMR ($CDCl_3$) δ (ppm): 2.03-2.12 (m, 2H), 2.15-2.26 (m, 1H), 2.30 (s, 3H), 2.30-2.38 (m, 1H), 3.79 (s, 3H), 4.16 (s, 3H), 4.33-4.45 (m, 3H), 6.84-6.89 (m, 2H), 6.99-7.08 (m, 3H), 7.58 (d, J=8.0 Hz, 1H), 7.79 (d, J=8.0 Hz, 1H), 7.82 (d, J=0.8 Hz, 1H).

Examples 56 and 57

Synthesis of (+)-8-(5-tert-butyl-2-methoxyphenyl)-2-[6-methoxy-5-(4-methylimidazol-1-yl)pyridin-2-yl]-5,6,7,8-tetrahydro[1,2,4]triazolo[1,5-a]pyridine and (−)-8-5-tert-butyl-2-methoxyphenyl)-2-[6-methoxy-5-(4-methylimidazol-1-yl)pyridin-2-yl]-5,6,7,8-tetrahydro[1,2,4]triazolo[1,5-a]pyridine

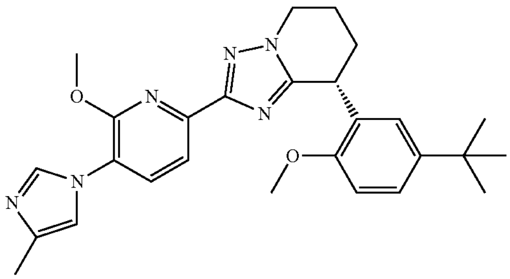

-continued

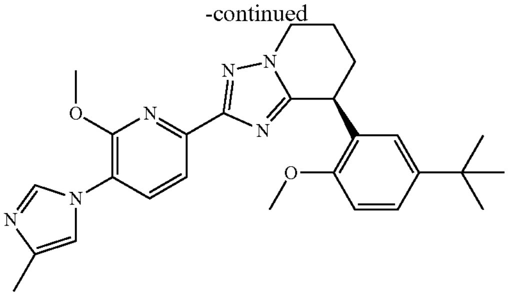

A racemate of the title compound was obtained according to the method of Examples 42 and 43 from the imidate hydrochloride obtained in Preparation Example 3-3 in place of ethyl 2-(4-bromo-2-trifluoromethylphenyl)-5-chloropentanimidate hydrochloride. The resulting racemate was separated by CHIRALPAK™ AD-H (2 cm×25 cm; mobile phase: 25% ethanol-hexane) to obtain the title optically active compound with a retention time of 10 minutes and positive optical rotation (41.8 mg, >99% ee) and the title optically active compound with a retention time of 17 minutes and negative optical rotation (33.5 mg, >99% ee).

The property values of the title compound with positive optical rotation are as follows.

ESI-MS; m/z 473 [$M^+$+H].

$^1$H-NMR ($CDCl_3$) δ (ppm): 1.23 (s, 9H), 2.00-2.35 (m, 4H), 2.30 (d, J=1.2 Hz, 3H), 3.75 (s, 3H), 4.17 (s, 3H), 4.39 (t, J=5.6 Hz, 2H), 4.62 (t, J=6.4 Hz, 1H), 6.83 (d, J=8.4 Hz, 1H), 6.91 (d, J=2.4 Hz, 1H), 6.99 (t, J=1.2 Hz, 1H), 7.23-7.29 (m, 1H), 7.57 (d, J=8.0 Hz, 1H), 7.78 (d, J=8.0 Hz, 1H), 7.81 (d, J=1.2 Hz, 1H).

The property values of the title compound with negative optical rotation are as follows.

ESI-MS; m/z 473 [$M^+$+H].

$^1$H-NMR ($CDCl_3$) δ (ppm): 1.23 (s, 9H), 2.00-2.35 (m, 4H), 2.30 (d, J=1.2 Hz, 3H), 3.75 (s, 3H), 4.17 (s, 3H), 4.39 (t, J=5.6 Hz, 2H), 4.62 (t, J=6.4 Hz, 1H), 6.83 (d, J=8.4 Hz, 1H), 6.91 (d, J=2.4 Hz, 1H), 6.99 (t, J=1.2 Hz, 1H), 7.23-7.29 (m, 1H), 7.57 (d, J=8.0 Hz, 1H), 7.78 (d, J=8.0 Hz, 1H), 7.81 (d, J=1.2 Hz, 1H).

Examples 58 and 59

Synthesis of (+)-8-(3-tert-butyl-4-methoxyphenyl)-2-[6-methoxy-5-(4-methylimidazol-1-yl)pyridin-2-yl]-5,6,7,8-tetrahydro[1,2,4]triazolo[1,5-a]pyridine and (−)-8-3-tert-butyl-4-methoxyphenyl)-2-[6-methoxy-5-(4-methylimidazol-1-yl)pyridin-2-yl]-5,6,7,8-tetrahydro[1,2,4]triazolo[1,5-a]pyridine

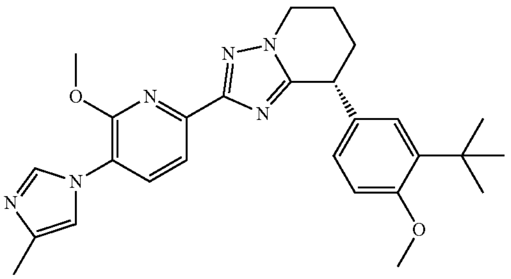

-continued

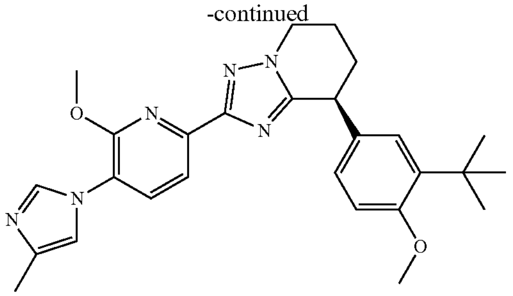

A racemate of the title compound was obtained according to the method of Examples 42 and 43 from the imidate hydrochloride obtained in Preparation Example 3-8 in place of ethyl 2-(4-bromo-2-trifluoromethylphenyl)-5-chloropentanimidate hydrochloride. The resulting racemate was separated by CHIRALPAK™ AD-H (2 cm×25 cm; mobile phase: 30% ethanol-hexane) to obtain the title optically active compound with a retention time of 11 minutes and positive optical rotation (43.5 mg, >99% ee) and the title optically active compound with a retention time of 18 minutes and negative optical rotation (42.8 mg, >99% ee).

The property values of the title compound with positive optical rotation are as follows.

ESI-MS; m/z 473 [$M^+$+H].

$^1$H-NMR ($CDCl_3$) δ (ppm): 1.35 (s, 9H), 2.00-2.40 (m, 4H), 2.30 (s, 3H), 3.81 (s, 3H), 4.17 (s, 3H), 4.30-4.46 (m, 3H), 6.79 (d, J=8.4 Hz, 1H), 6.82 (dd, J=8.4, 2.4 Hz, 1H), 7.00 (brs, 1H), 7.13 (J=2.4 Hz, 1H), 7.58 (d, J=8.0 Hz, 1H), 7.81 (d, J=8.0 Hz, 1H), 7.82 (s, 1H).

The property values of the title compound with negative optical rotation are as follows.

ESI-MS; m/z 473 [$M^+$+H].

$^1$H-NMR ($CDCl_3$) δ (ppm): 1.35 (s, 9H), 2.00-2.40 (m, 4H), 2.30 (s, 3H), 3.81 (s, 3H), 4.17 (s, 3H), 4.30-4.46 (m, 3H), 6.79 (d, J=8.4 Hz, 1H), 6.82 (dd, J=8.4, 2.4 Hz, 1H), 7.00 (brs, 1H), 7.13 (J=2.4 Hz, 1H), 7.58 (d, J=8.0 Hz, 1H), 7.81 (d, J=8.0 Hz, 1H), 7.82 (s, 1H).

Examples 60 and 61

Synthesis of (+)-8-(3,3-dimethyl-2,3-dihydrobenzofuran-5-yl)-2-[6-methoxy-5-(4-methylimidazol-1-yl)pyridin-2-yl]-5,6,7,8-tetrahydro[1,2,4]triazolo[1,5-a]pyridine and (−)-8-(3,3-dimethyl-2,3-dihydrobenzofuran-5-yl)-2-[6-methoxy-5-(4-methylimidazol-1-yl)pyridin-2-yl]-5,6,7,8-tetrahydro[1,2,4]triazolo[1,5-a]pyridine

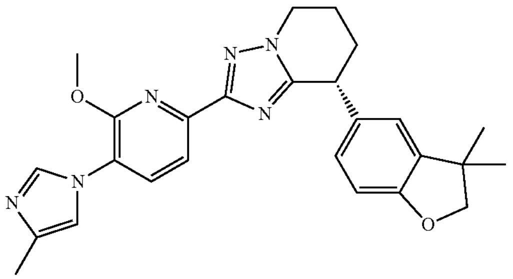

-continued

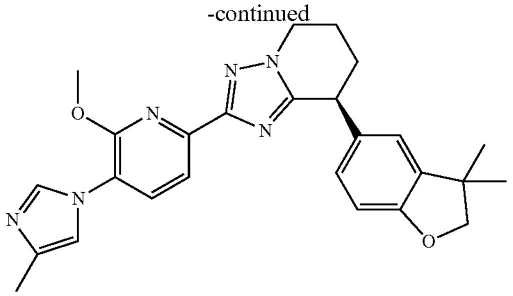

A racemate of the title compound was obtained according to the method of Examples 42 and 43 from the imidate hydrochloride obtained in Preparation Example 3-2 in place of ethyl 2-(4-bromo-2-trifluoromethylphenyl)-5-chloropentanimidate hydrochloride. The resulting racemate was separated by CHIRALPAK™ AD-H (2 cm×25 cm; mobile phase: 50% ethanol-hexane) to obtain the title optically active compound with a retention time of 10 minutes and positive optical rotation (54.0 mg, >99% ee) and the title optically active compound with a retention time of 18 minutes and negative optical rotation (47.4 mg, >99% ee).

The property values of the title compound with positive optical rotation are as follows.

ESI-MS; m/z 457 [$M^+$+H].

$^1$H-NMR ($CDCl_3$) δ (ppm): 1.30 (s, 3H), 1.32 (s, 3H), 2.00-2.13 (m, 2H), 2.16-2.40 (m, 2H), 2.30 (s, 3H), 4.16 (s, 3H), 4.23 (s, 2H), 4.30-4.47 (m, 3H), 6.72 (d, J=8.0 Hz, 1H), 6.83 (dd, J=8.0, 1.6 Hz, 1H), 6.87 (d, J=1.6 Hz, 1H), 7.00 (brs, 1H), 7.58 (d, J=8.0 Hz, 1H), 7.80 (d, J=8.0 Hz, 1H), 7.82 (s, 1H).

The property values of the title compound with negative optical rotation are as follows.

ESI-MS; m/z 457 [$M^+$+H].

$^1$H-NMR ($CDCl_3$) δ (ppm): 1.30 (s, 3H), 1.32 (s, 3H), 2.00-2.13 (m, 2H), 2.16-2.40 (m, 2H), 2.30 (s, 3H), 4.16 (s, 3H), 4.23 (s, 2H), 4.30-4.47 (m, 3H), 6.72 (d, J=8.0 Hz, 1H), 6.83 (dd, J 8.0, 1.6 Hz, 1H), 6.87 (d, J=1.6 Hz, 1H), 7.00 (brs, 1H), 7.58 (d, J=8.0 Hz, 1H), 7.80 (d, J=8.0 Hz, 1H), 7.82 (s, 1H).

Examples 62 and 63

Synthesis of (−)-8-(3-tert-butyl-2-methoxyphenyl)-2-[6-methoxy-5-(4-methylimidazol-1-yl)pyridin-2-yl]-5,6,7,8-tetrahydro[1,2,4]triazolo[1,5-a]pyridine and (+)-8-(3-tert-butyl-2-methoxyphenyl)-2-[6-methoxy-5-(4-methylimidazol-1-yl)pyridin-2-yl]-5,6,7,8-tetrahydro[1,2,4]triazolo[1,5-a]pyridine

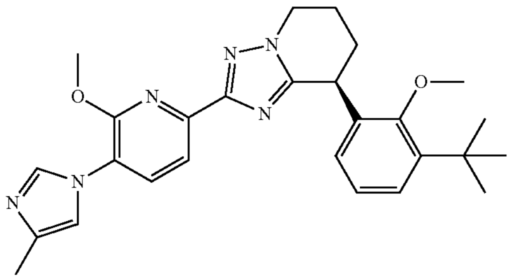

-continued

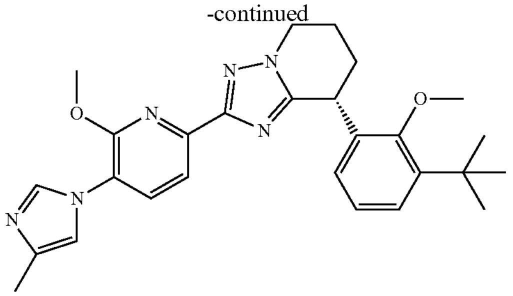

A racemate of the title compound was obtained according to the method of Examples 42 and 43 from the imidate hydrochloride obtained in Preparation Example 3-9 in place of ethyl 2-(4-bromo-2-trifluoromethylphenyl)-5-chloropentanimidate hydrochloride. The resulting racemate was separated by CHIRALPAK™ IB (2 cm×25 cm; mobile phase: 10% ethanol-hexane) to obtain the title optically active compound with a retention time of 23 minutes and negative optical rotation (48.5 mg, >99% ee) and the title optically active compound with a retention time of 38 minutes and positive optical rotation (53.8 mg, >99% ee).

The property values of the title compound with negative optical rotation are as follows.

ESI-MS; m/z 473 [$M^+$+H].

$^1$H-NMR ($CDCl_3$) δ (ppm): 1.44 (s, 9H), 1.98-2.16 (m, 2H), 2.18-2.40 (m, 2H), 2.30 (d, J=1.2 Hz, 3H), 3.98 (s, 3H), 4.16 (s, 3H), 4.36-4.46 (m, 2H), 4.73 (t, J=6.8 Hz, 1H), 6.71 (dd, J=8.0, 1.6 Hz, 1H), 6.96 (t, J=8.0, 1H), 6.99 (brs, 1H), 7.25-7.29 (m, 1H), 7.56 (d, J=7.6 Hz, 1H), 7.76 (d, J=7.6 Hz, 1H), 7.81 (d, J=1.2 Hz, 1H).

The property values of the title compound with positive optical rotation are as follows.

ESI-MS; m/z 473 [$M^+$+H].

$^1$H-NMR ($CDCl_3$) δ (ppm): 1.44 (s, 9H), 1.98-2.16 (m, 2H), 2.18-2.40 (m, 2H), 2.30 (d, J=1.2 Hz, 3H), 3.98 (s, 3H), 4.16 (s, 3H), 4.36-4.46 (m, 2H), 4.73 (t, J=5.6 Hz, 1H), 6.71 (dd, J=8.0, 1.6 Hz, 1H), 6.96 (t, J=8.0, 1H), 6.99 (brs, 1H), 7.25-7.29 (m, 1H), 7.56 (d, J=7.6 Hz, 1H), 7.76 (d, J=7.6 Hz, 1H), 7.81 (d, J=1.2 Hz, 1H).

Examples 64 and 65

Synthesis of (+)-8-(3-bromophenyl)-2-[6-methoxy-5-(4-methyl-1H-imidazol-1-yl)pyridin-2-yl]-5,6-dihydro-8H-[1,2,4]triazolo[1,5-c][1,4]oxazine and (−)-8-(3-bromophenyl)-2-[6-methoxy-5-(4-methyl-1H-imidazol-1-yl)pyridin-2-yl]-5,6-dihydro-8H-[1,2,4]triazolo[1,5-c][1,4]oxazine

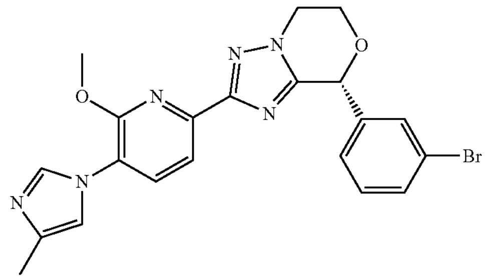

-continued

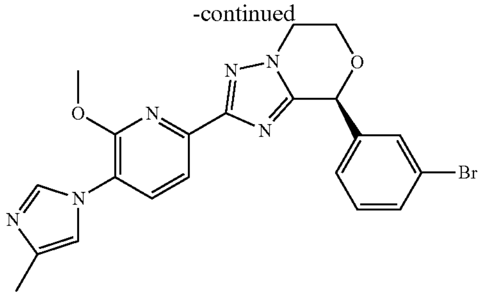

A racemate of the title compound was obtained according to the method of Examples 42 and 43 from the imidate hydrochloride obtained in Preparation Example 3-17 in place of ethyl 2-(4-bromo-2-trifluoromethylphenyl)-5-chloropentanimidate hydrochloride. This was separated by CHIRALPAK™ IB (2 cm×25 cm, mobile phase:hexane:ethanol=8:2, flow rate: 15 mL/min) to obtain the title optically active compound with a retention time of 5.27 minutes resulting from analysis by CHIRALPAK™ TB (Lot. IB00CD-LG026, hexane:ethanol=8:2, 1.0 mL/min) and positive optical rotation and the title optically active compound with a retention time of 7.98 minutes resulting from the same analysis and negative optical rotation, respectively.

The property values of the title optically active compound with positive optical rotation are as follows.

$^1$H-NMR ($CDCl_3$) δ (ppm): 2.31 (s, 3H), 4.11-4.21 (m, 1H), 4.17 (s, 3H), 4.31 (dt, J=4.8, 12.4 Hz, 1H), 4.34-4.51 (m, 2H), 5.98 (s, 1H), 7.01 (t, J=0.8 Hz, 1H), 7.29 (t, J=8.0 Hz, 1H), 7.45-7.47 (m, 1H), 7.51-7.54 (m, 1H), 7.62 (d, J=8.0 Hz, 1H), 7.67 (d, J=1.6 Hz, 1H), 7.82 (d, J=8.0 Hz, 1H), 7.84 (d, J=1.6 Hz, 1H).

The property values of the title optically active compound with negative optical rotation are as follows.

$^1$H-NMR ($CDCl_3$) δ (ppm): 2.31 (s, 3H), 4.11-4.21 (m, 1H), 4.17 (s, 3H), 4.31 (dt, J=4.8, 12.4 Hz, 1H), 4.34-4.51 (m, 2H), 5.98 (s, 1H), 7.01 (t, J=0.8 Hz, 1H), 7.29 (t, J=8.0 Hz, 1H), 7.45-7.47 (m, 1H), 7.51-7.54 (m, 1H), 7.62 (d, J=8.0 Hz, 1H), 7.67 (d, J=1.6 Hz, 1H), 7.82 (d, J=8.0 Hz, 1H), 7.84 (d, J=1.6 Hz, 1H).

Examples 66 and 67

Synthesis of (+)-2-[6-methoxy-5-4-methyl-1H-imidazol-1-yl)pyridin-2-yl]-8-3-nitrophenyl)-5,6-dihydro-8H-[1,2,4]triazolo[1,5-c][1,4]oxazine and (−)-2-[6-methoxy-5-(4-methyl-1H-imidazol-1-yl)pyridin-2-yl]-8-(3-nitrophenyl)-5,6-dihydro-8H-[1,2,4]triazolo[1,5-c][1,4]oxazine

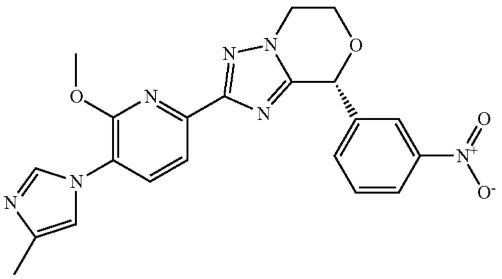

-continued

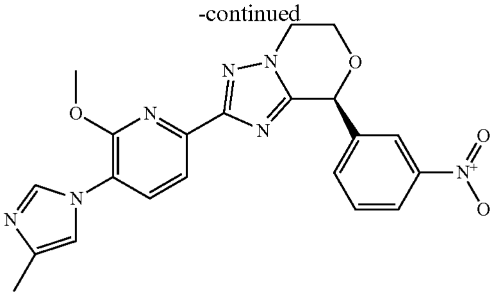

A racemate of the title compound was obtained according to the method of Examples 42 and 43 from the imidate hydrochloride obtained in Preparation Example 3-18 in place of ethyl 2-(4-bromo-2-trifluoromethylphenyl)-5-chloropentanimidate hydrochloride. This was separated by CHIRALPAK™ IB manufactured by Daicel Chemical Industries, Ltd. (2 cm×25 cm, mobile phase:hexane:ethanol=8:2, flow rate: 15 mL/min) to obtain the title optically active compound with a retention time of 10.6 minutes resulting from analysis by CHIRALPAK™ IB (Lot. IB00CD-FD026, hexane:ethanol=7:3, 1.0 mL/min) and positive optical rotation and the title optically active compound with a retention time of 15.0 minutes resulting from the same analysis and negative optical rotation, respectively.

The property values of the title optically active compound with positive optical rotation are as follows.

$^1$H-NMR ($CDCl_3$) δ (ppm): 2.31 (s, 3H), 4.16 (s, 3H), 4.25 (ddd, J=4.4, 8.0, 12.4 Hz, 1H), 4.40 (dt, J=4.0, 12.4 Hz, 1H), 4.45-4.56 (m, 2H), 6.08 (s, 1H), 7.01 (t, J=0.8 Hz, 1H), 7.62 (t, J=7.6 Hz, 1H), 7.62 (d, J=8.0 Hz, 1H), 7.80 (d, J=7.6 Hz, 1H), 7.84 (d, J=1.2 Hz, 1H), 7.94-7.96 (m, 1H), 8.25-8.27 (m, 1H), 8.48 (m, 1H).

The property values of the title optically active compound with negative optical rotation are as follows.

$^1$H-NMR ($CDCl_3$) δ (ppm): 2.31 (s, 3H), 4.16 (s, 3H), 4.25 (ddd, J=4.4, 8.0, 12.4 Hz, 1H), 4.40 (dt, J=4.0, 12.4 Hz, 1H), 4.45-4.56 (m, 2H), 6.08 (s, 1H), 7.01 (t, J=0.8 Hz, 1H), 7.62 (t, J=7.6 Hz, 1H), 7.62 (d, J=8.0 Hz, 1H), 7.80 (d, J=7.6 Hz, 1H), 7.84 (d, J=1.2 Hz, 1H), 7.94-7.96 (m, 1H), 8.25-8.27 (m, 1H), 8.48 (m, 1H).

Examples 68 and 69

Synthesis of (+)-2-[6-methoxy-5-(4-methylimidazol-1-yl)pyridin-2-yl]-8-(3-bromo-4-methoxyphenyl)-5,6,7,8-tetrahydro[1,2,4]triazolo[1,5-a]pyridine and (−)-2-[6-methoxoxy-5-(4-methylimidazol-1-yl)pyridin-2-yl]-8-(3-bromo-4-methoxyphenyl)-5,6,7,8-tetrahydro[1,2,4]triazolo[1,5-a]pyridine

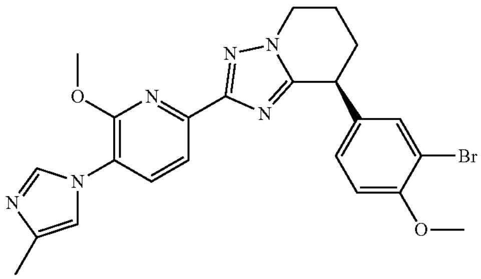

-continued

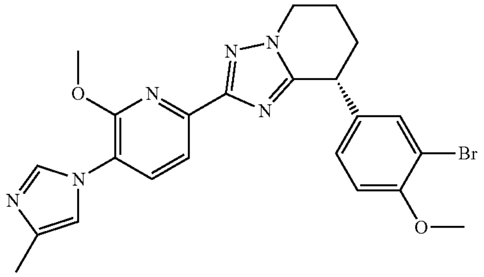

A racemate of the title compound was obtained according to the method of Examples 42 and 43 from the imidate hydrochloride obtained in Preparation Example 3-4 in place of ethyl 2-(4-bromo-2-trifluoromethylphenyl)-5-chloropentanimidate hydrochloride. The resulting racemate was separated by CHIRALPAK™ IB (2 cm×25 cm, mobile phase:ethanol: hexane=3:7, flow rate: 15 mL/min) to obtain the title compound with a retention time of 37.5 minutes and positive optical rotation (3.52 mg) and the title compound with a retention time of 44 minutes and negative optical rotation (2.53 mg).

The property values of the title optically active compound with a retention time of 37.5 minutes are as follows.

$^1$H-NMR ($CDCl_3$) δ (ppm): 2.12-2.17 (m, 2H), 2.28-2.29 (m, 1H), 2.31-2.41 (m, 1H), 2.41 (s, 3H), 3.89 (s, 3H), 4.19 (s, 3H), 4.32-4.42 (m, 3H), 6.86 (d, J=8.6 Hz, 1H), 7.03-7.08 (m, 2H), 7.33 (d, J=1.9 Hz, 1H), 7.65 (d, J=7.8 Hz, 1H), 7.87 (d, J=7.8 Hz, 1H), 8.25 (d, J=1.2 Hz, 1H).

The property values of the title optically active compound with a retention time of 44 minutes are as follows.

$^1$H-NMR ($CDCl_3$) δ (ppm): 2.12-2.17 (m, 2H), 2.28-2.29 (m, 1H), 2.31-2.41 (m, 1H), 2.41 (s, 3H), 3.89 (s, 3H), 4.19 (s, 3H), 4.32-4.42 (m, 3H), 6.86 (d, J=8.6 Hz, 1H), 7.03-7.08 (m, 2H), 7.33 (d, J=1.9 Hz, 1H), 7.65 (d, J=7.8 Hz, 1H), 7.87 (d, J=7.8 Hz, 1H), 8.25 (d, J=1.2 Hz, 1H).

Examples 70 and 71

(+)-8-(6-Bromopyridin-2-yl)-2-[6-methoxy-5-(4-methyl-1H-imidazol-1-yl)pyridin-2-yl]-5,6,7,8-tetrahydro[1,2,4]triazolo[1,5-a]pyridine and (−)-8-(6-bromopyridin-2-yl)-2-[6-methoxy-5-(4-methyl-1H-imidazol-1-yl)pyridin-2-yl]-5,6,7,8-tetrahydro[1,2,4]triazolo[1,5-a]pyridine

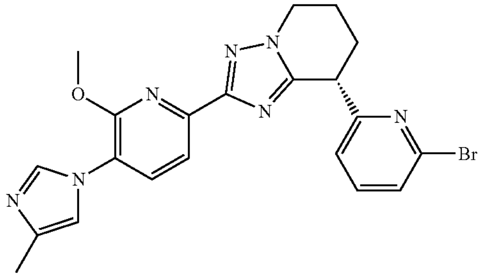

-continued

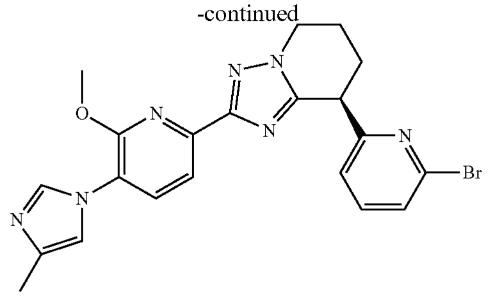

A racemate of the title compound was obtained according to the method of Examples 42 and 43 from the imidate hydrochloride obtained in Preparation Example 3-10 in place of ethyl 2-(4-bromo-2-trifluoromethylphenyl)-5-chloropentanimidate hydrochloride. The resulting racemate (37.2 mg) was separated by CHIRALPAK™ IA manufactured by Daicel Chemical Industries, Ltd. (2 cm×25 cm; mobile phase:hexane:ethanol=50:50) to obtain the title optically active compound with a retention time of 5.1 minutes and positive optical rotation (11 mg, >99% ee) and the title optically active compound with a retention time of 8.9 minutes and negative optical rotation (9.1 mg, >99% ee).

The property values of the title compound with positive optical rotation are as follows.

ESI-MS; m/z 466 [$M^+$+H].

$^1$H-NMR ($CDCl_3$) δ (ppm): 2.08-2.27 (m, 2H), 2.30 (d, J=1.2 Hz, 3H), 2.38-2.43 (m, 2H), 4.16 (s, 3H), 4.31-4.45 (m, 2H), 4.54 (t, J=6.4 Hz, 1H), 7.00 (t, J=1.2 Hz, 1H), 7.14 (dd, J=0.8 Hz, 8.0 Hz, 1H), 7.39 (dd, J=0.8 Hz, 8.0 Hz, 1H), 7.50 (t, J=8.0 Hz, 1H), 7.60 (d, J=7.6 Hz, 1H), 7.78 (d, J=7.6 Hz, 1H), 7.82 (d, J=1.2 Hz, 1H).

The property values of the title compound with negative optical rotation are as follows.

ESI-MS; m/z 466 [$M^+$+H].

$^1$H-NMR ($CDCl_3$) δ (ppm): 2.08-2.27 (m, 2H), 2.30 (d, J=1.2 Hz, 3H), 2.38-2.43 (m, 2H), 4.16 (s, 3H), 4.31-4.45 (m, 2H), 4.54 (t, J=6.4 Hz, 1H), 7.00 (t, J=1.2 Hz, 1H), 7.14 (dd, J=0.8 Hz, 8.0 Hz, 1H), 7.39 (dd, J=0.8 Hz, 8.0 Hz, 1H), 7.50 (t, J=8.0 Hz, 1H), 7.60 (d, J=7.6 Hz, 1H), 7.78 (d, J=7.6 Hz, 1H), 7.82 (d, J=1.2 Hz, 1H).

Example 72

Synthesis of 2-[6-methoxy-5-(4-methylimidazol-1-yl)pyridin-2-yl]-8-2-trifluoromethphenyl)-7,8-dihydro-6H-[1,2,4]triazolo[1,5-a]pyridin-5-one

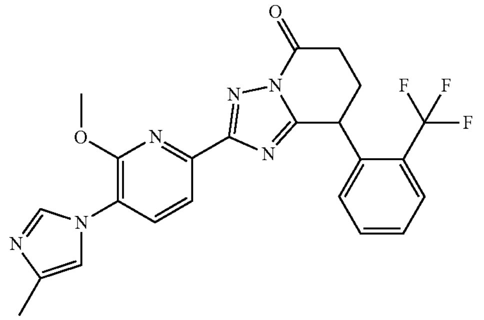 [SMILES: COc1nc(-c2nc3n(n2)C(=O)CCC3c2ccccc2C(F)(F)F)ccc1-n1cnc(C)c1]

Synthesis of ethyl 4-[5-[6-methoxy-5-(4-methylimidazol-1-yl)pyridin-2-yl]-2H-[1,2,4]triazol-3-yl]-4-(2-trifluoromethylphenyl)butyrate The title compound (370 mg) was obtained according to Examples 42 and 43 from ethyl 4-ethoxycarbonimidoyl-4-(2-trifluoromethylphenyl)butyrate hydrochloride obtained in Preparation Example 3-19 (244 mg). The resulting compound was used directly for the next step as a crude product.

Synthesis of 4-[5-[6-methoxy-5-(4-methyl-imidazol-1-yl)-pyridin-2-yl]-2H-[1,2,4]-triazol-3-yl]-4-(2-trifluoromethylphenyl)-butyric acid Ethyl 4-[5-[6-methoxy-5-(4-methyl-imidazol-1-yl)-pyridin-2-yl]-2H-[1,2,4]-triazol-3-yl]-4-(2-trifluoromethylphenyl)-butyrate (370 mg) was dissolved in tetrahydrofuran (1 ml). Water (1 ml) and 5 N sodium hydroxide (1 ml) were added and the reaction was initiated. After three hours, the reaction solution was partitioned with diethyl ether and water. The resulting aqueous layer was neutralized with 5 N hydrochloric acid and extracted with methylene chloride twice. Concentration under reduced pressure gave an orange oil (208 mg) which was used for the next step.

ESI-MS; m/z 487 [$M^+$+H].

Synthesis of 2-[6-methoxy-5-(4-methylimidazol-1-yl)pyridin-2-yl]-8-(2-trifluoromethylphenyl)-7,8-dihydro-6H-[1,2,4]triazolo[1,5-a]pyridin-5-one 4-[5-[6-Methoxy-5-(4-methyl-imidazol-1-yl)-pyridin-2-yl]-2H-[1,2,4]-triazol-3-yl]-4-(2-trifluoromethylphenyl)-butyric acid (208 mg) was dissolved in tetrahydrofuran (4.3 ml). Diisopropylethylamine (220 ul), 1-hydroxybenzotriazole (86.8 mg) and benzotriazol-1-yloxytris(pyrrolidino)phosphonium hexafluorophosphate (334 mg) were added at room temperature and the reaction was initiated. After 19 hours, the reaction was terminated with water, followed by dilution with ethyl acetate. The organic layer was washed with saturated ammonium chloride and brine and dried over magnesium sulfate. Concentration under reduced pressure gave an oil. The oil was purified by silica gel column chromatography (mobile phase:ethyl acetate/heptane=0 to 100%) to obtain the title compound (128 mg) as an orange solid.

$^1$H-NMR ($CDCl_3$) δ (ppm): 2.17 (s, 3H), 2.18-2.34 (m, 2H), 2.89-2.97 (m, 1H), 3.23-3.34 (m, 1H), 4.09 (s, 3H), 4.87 (dd, J=11.8, 5.5 Hz, 1H), 7.31-7.35 (m, 1H), 7.40-7.48 (m, 1H), 7.53-7.59 (m, 1H), 7.66-7.75 (m, 2H), 7.82 (d, J=7.8 Hz, 1H), 7.93 (d, J=7.8 Hz, 1H), 7.97-8.01 (m, 1H).

The compounds of Examples 74 to 83 were obtained by the same method as in Examples 42 and 43 (Table 2).

TABLE 2

| Example No. | Structural formula |
| --- | --- |
| Example 74 | 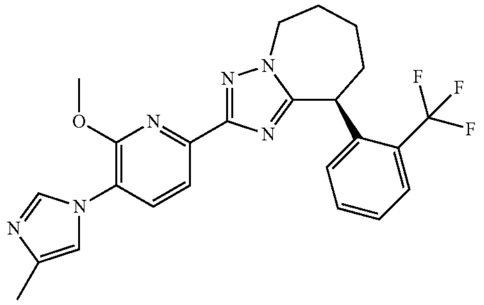 [SMILES: COc1nc(-c2nc3n(n2)CCCC[C@H]3c2ccccc2C(F)(F)F)ccc1-n1cnc(C)c1] |
| Example 75 | 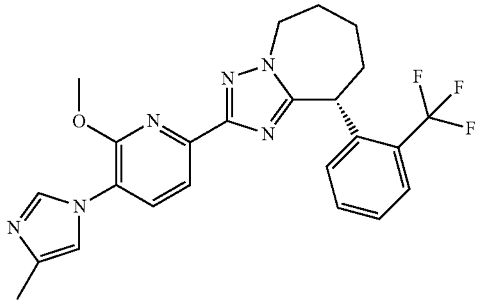 [SMILES: COc1nc(-c2nc3n(n2)CCCC[C@@H]3c2ccccc2C(F)(F)F)ccc1-n1cnc(C)c1] |
| Example 76 | 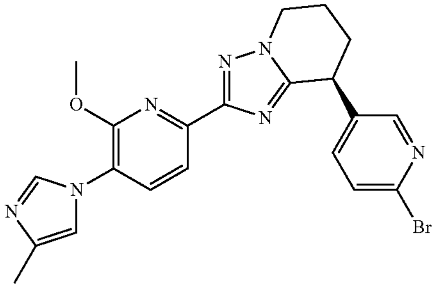 [SMILES: COc1nc(-c2nc3n(n2)CCC[C@H]3c2ccc(Br)nc2)ccc1-n1cnc(C)c1] |
| Example 77 | 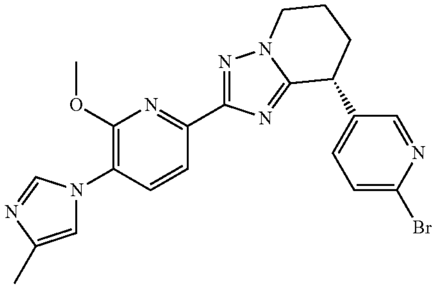 [SMILES: COc1nc(-c2nc3n(n2)CCC[C@@H]3c2ccc(Br)nc2)ccc1-n1cnc(C)c1] |
| Example 78 | 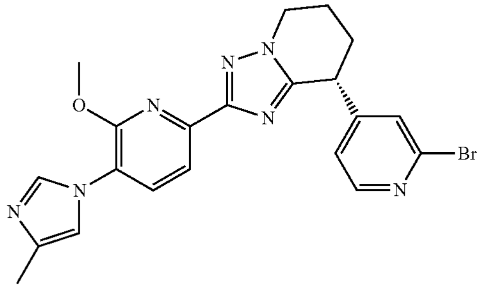 [SMILES: COc1nc(-c2nc3n(n2)CCC[C@@H]3c2ccnc(Br)c2)ccc1-n1cnc(C)c1] |

TABLE 2-continued

| Example No. | Structural formula |
|---|---|
| Example 79 | 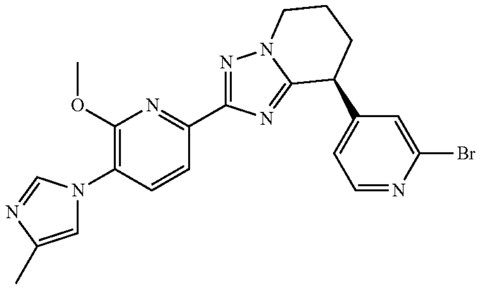 [SMILES: COc1nc(-c2nc3n(n2)CCC[C@H]3c2ccnc(Br)c2)ccc1-n1cnc(C)c1] |
| Example 80 | 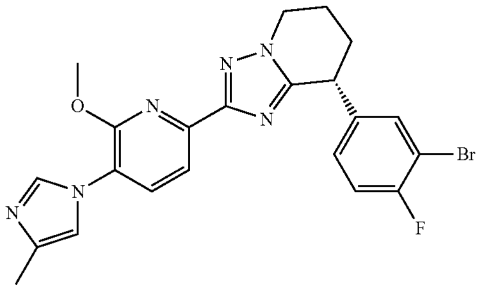 [SMILES: COc1nc(-c2nc3n(n2)CCC[C@@H]3c2ccc(F)c(Br)c2)ccc1-n1cnc(C)c1] |
| Example 81 | 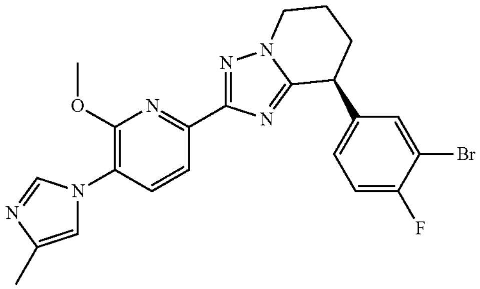 |
| Example 82 | 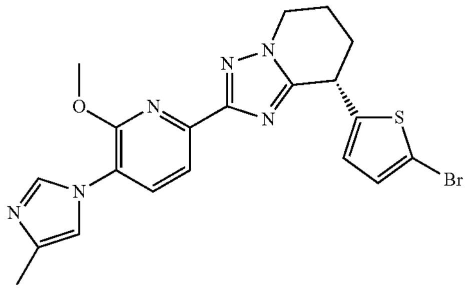 [SMILES: COc1nc(-c2nc3n(n2)CCC[C@@H]3c2ccc(Br)s2)ccc1-n1cnc(C)c1] |
| Example 83 | 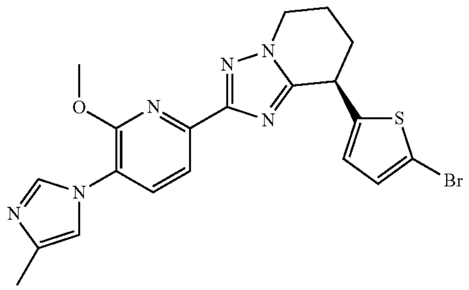 [SMILES: COc1nc(-c2nc3n(n2)CCC[C@H]3c2ccc(Br)s2)ccc1-n1cnc(C)c1] |

Examples 84 and 85

Synthesis of (+)-7-benzyl-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine and (−)-7-benzyl-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine

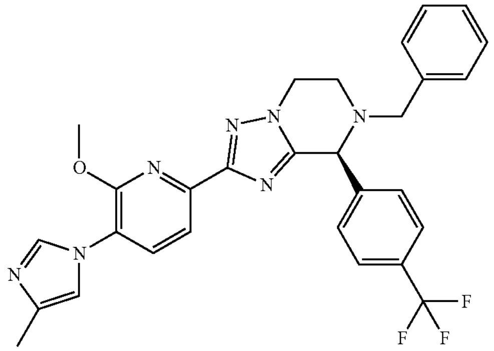

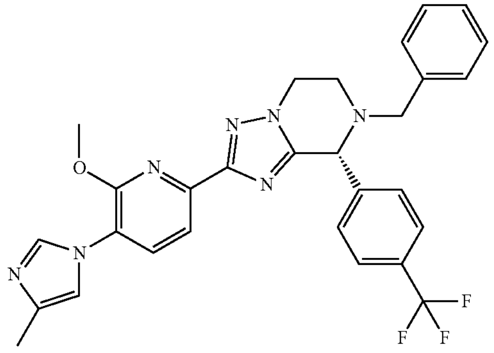

Synthesis of [benzyl-(2-oxoethyl)amino]-(4-trifluoromethylphenyl)acetonitrile

Dimethyl sulfoxide (689 μL) was slowly added dropwise to a solution of oxalyl chloride (584 μL) in dichloromethane (15 mL) at −78° C. After stirring at the same temperature for 10 minutes, a solution of [benzyl-(2-hydroxyethypamino]-(4-trifluoromethylphenyl)acetonitrile obtained in Preparation Example 4-1 (1.08 g) in dichloromethane (5 mL) was added to the reaction solution, and the mixture was stirred at the same temperature for 10 minutes. Triethylamine (1.8 mL) was added to the reaction solution, and the mixture was stirred at the same temperature for 10 minutes and then at 0° C. for 20 minutes. The reaction solution was partitioned with a saturated sodium bicarbonate solution and ethyl acetate. The resulting organic layer was washed with brine, and dried over anhydrous magnesium sulfate and then concentrated under reduced pressure. The resulting residue was purified by silica gel column chromatography (elution solvent:heptane:ethyl acetate=9:1→8:1) to obtain 959 mg of the title compound. The property values of the compound are as follows.

$^1$H-NMR ($CDCl_3$) δ (ppm): 3.37-3.47 (m, 2H), 3.62 (d, J=13.2 Hz, 1H), 3.91 (d, J=12.8 Hz, 1H), 5.08 (s, 1H), 7.30-7.43 (m, 5H), 7.69 (d, J=8.0 Hz, 1H), 7.76 (d, J=8.0 Hz, 1H) 9.52 (m, 1H).

Synthesis of 6-methoxy-5-(4-methyl-1H-imidazol-1-yl)pyridine-2-carboxylic acid N'-(2-{benzyl-[cyano-(4-trifluoromethylphenyl)methyl]amino}ethyl)hydrazide 6-Methoxy-5-(4-methylimidazol-1-yl)pyridine-2-carboxylic acid hydrazide hydrochloride obtained in Preparation Example 1-6 (852 mg), methanol (10 mL) and acetic acid (1 mL) were sequentially added to a solution of [benzyl-(2-oxoethypamino]-(4-trifluoromethylphenyl)acetonitrile (950 mg) in dichloromethane (50 mL), and the mixture was stirred at room temperature for five minutes. Sodium cyanoborohydride (359 mg) was added to the reaction solution, followed by stirring at room temperature for 16 hours. The reaction solution was partitioned with a saturated sodium bicarbonate solution and ethyl acetate. The organic layer was dried over anhydrous magnesium sulfate, allowed to pass through a silica pad and then concentrated under reduced pressure. The resulting residue was purified by silica gel column chromatography (elution solvent:ethyl acetate:methanol=1:0→9:1) to obtain 1.31 g of the title compound. The property values of the compound are as follows.

$^1$H-NMR ($CDCl_3$) δ (ppm): 2.30 (s, 3H), 2.74-2.96 (m, 3H), 3.03-3.35 (m, 1H), 3.45 (d, J=13.2 Hz, 1H), 4.02 (s, 3H), 4.07 (d, J=12.8 Hz, 1H), 5.01 (m, 1H), 5.23 (s, 1H), 7.01 (t, J=1.2 Hz, 1H), 7.30-7.32 (m, 1H), 7.35-7.39 (m, 2H), 7.44 (m, 2H), 7.68 (d, J=8.4 Hz, 2H), 7.70 (d, J=7.6 Hz, 1H), 7.79 (d, J=8.4 Hz, 2H), 7.86 (s, 1H), 7.87 (d, J=8.0 Hz, 1H), 8.86 (d, J=7.2 Hz, 1H).

Synthesis of (±)-7-benzyl-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine and (−)-7-benzyl-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine Acetic acid (1.37 mL) was added to a solution of 6-methoxy-5-(4-methyl-1H-imidazol-1-yl)pyridine-2-carboxylic acid N'-(2-{benzyl-[cyano-(4-trifluoromethylphenyl)methyl]amino}ethyl)hydrazide (1.3 g) in toluene (13.7 mL), and the mixture was stirred at 80° C. for two days. The reaction solution was concentrated and partitioned with a saturated sodium bicarbonate solution and ethyl acetate. The organic layer was dried over anhydrous magnesium sulfate, allowed to pass through a silica pad and then concentrated under reduced pressure. The resulting residue was recrystallized from heptane-ethyl acetate to obtain 308 mg of a racemate of the title compound. The resulting racemate of the title compound (30 mg) was separated by CHIRALPAK™ IB (2 cm×25 cm, mobile phase:hexane:ethanol=7:3, flow rate: 15 mL/min) to obtain the title optically active compound with a retention time of 13.0 minutes resulting from analysis by CHIRALPAK™ IB manufactured by Daicel Chemical Industries, Ltd. (Lot. IB00CD-LG026, hexane:ethanol=7:3, 1.0 mL/min) (8.6 mg) and the title optically active compound with a retention time of 14.9 minutes resulting from the same analysis (7.4 mg), respectively.

The property values of the title optically active compound with a retention time of 13.0 minutes under the analysis conditions are as follows.

ESI-MS; m/z 546 [$M^+$+H].

$^1$H-NMR ($CDCl_3$) δ (ppm): 2.29 (s, 3H), 2.93 (m, 1H), 3.36 (dt, J=4.4, 8.4 Hz, 1H), 3.49 (d, J=13.6 Hz, 1H), 3.87 (d, J=13.2 Hz, 1H), 4.14 (s, 3H), 4.33-4.44 (m, 2H), 4.97 (s, 1H), 6.99 (s, 1H), 7.29-7.38 (m, 5H), 7.57 (d, J=7.6 Hz, 1H), 7.63 (d, J=8.0 Hz, 2H), 7.67 (d, J=8.4 Hz, 2H), 7.73 (d, J=7.6 Hz, 1H), 7.83 (s, 1H).

The property values of the title optically active compound with a retention time of 14.9 minutes under the analysis conditions are as follows.

ESI-MS; m/z 546 [$M^+$+H].

$^1$H-NMR ($CDCl_3$) δ (ppm): 2.29 (s, 3H), 2.93 (m, 1H), 3.36 (dt, J=4.4, 8.4 Hz, 1H), 3.49 (d, J=13.6 Hz, 1H), 3.87 (d, J=13.2 Hz, 1H), 4.14 (s, 3H), 4.33-4.44 (m, 2H), 4.97 (s, 1H), 6.99 (s, 1H), 7.29-7.38 (m, 5H), 7.57 (d, J=7.6 Hz, 1H), 7.63 (d, J=8.0 Hz, 2H), 7.67 (d, J=8.4 Hz, 2H), 7.73 (d, J=7.6 Hz, 1H), 7.83 (d, J=1.2 Hz, 1H).

Examples 86 and 87

Synthesis of (+)-2-[6-methoxy-5-(4-methyl-1H-imidazol-1-yl)pyridin-2-yl]-7-phenyl-8-(4-trifluoromethylphenyl)-5,6,7,8-tetrahydro[1,2,4]triazolo[1,5-a]pyrazine and (−)-2-[6-methoxy-5-(4-methyl-1H-imidazol-1-yl)pyridin-2-yl]-7-phenyl-8-(4-trifluoromethylphenyl)-5,6,7,8-tetrahydro[1,2,4]triazolo[1,5-a]pyrazine

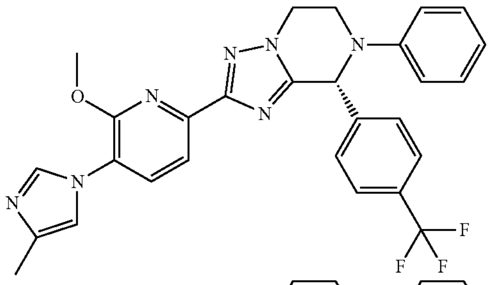

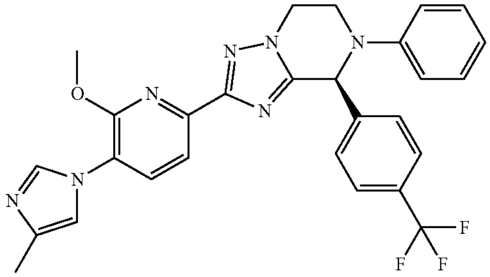

A racemate of the title compound (48 mg) was obtained according to the method of Examples 84 and 85 from [(2-hydroxyethyl)phenylamino]-(4-trifluoromethylphenyl)acetonitrile obtained in Preparation Example 4-2 in place of [benzyl-(2-oxoethyl)amino]-(4-trifluoromethylphenyl)acetonitrile. This was separated by CHIRALPAK™ IB manufactured by Daicel Chemical Industries, Ltd. (2 cm×25 cm, mobile phase:hexane:ethanol=8:2, flow rate: 15 mL/min) to obtain the title optically active compound with a retention time of 8.78 minutes resulting from analysis by CHIRALPAK™ IB (Lot. IB00CD-FD026, hexane:ethanol=8:2, 1.0 mL/min) and negative optical rotation (14 mg, >99% ee) and the title optically active compound with a retention time of 11.27 minutes resulting from the same analysis and positive optical rotation (14 mg, >99% ee).

The property values of the title optically active compound with negative optical rotation are as follows.

ESI-MS; m/z 532 [$M^+$+H].

$^1$H-NMR ($CDCl_3$) δ (ppm): 2.31 (s, 3H), 3.69-3.76 (m, 1H), 4.01-4.05 (m, 1H), 4.17 (s, 3H), 4.33-4.38 (m, 1H), 4.42-4.49 (m, 1H), 6.21 (s, 1H), 6.95-7.03 (m, 4H), 7.28-7.33 (m, 2H), 7.57-7.62 (m, 4H), 7.65 (d, J=7.6 Hz, 1H), 7.86 (d, J=1.2 Hz, 1H), 7.88 (d, J=8.0 Hz, 1H).

The property values of the title optically active compound with positive optical rotation are as follows.

ESI-MS; m/z 532 [$M^+$+H].

$^1$H-NMR ($CDCl_3$) δ (ppm): 2.31 (s, 3H), 3.69-3.76 (m, 1H), 4.01-4.05 (m, 1H), 4.17 (s, 3H), 4.33-4.38 (m, 1H), 4.42-4.49 (m, 1H), 6.21 (s, 1H), 6.95-7.03 (m, 4H), 7.28-7.33 (m, 2H), 7.57-7.62 (m, 4H), 7.65 (d, J=7.6 Hz, 1H), 7.86 (d, J=1.2 Hz, 1H), 7.88 (d, J=8.0 Hz, 1H).

Examples 88 and 89

Synthesis of (+)-2-[6-methoxy-5-(4-methyl-1H-imidazol-1-yl)pyridin-2-yl]-8-methyl-8-phenyl-5,6,7,8-tetrahydro[1,2,4]triazolo[1,5-a]pyridine and (−)-2-[6-methoxy-5-(4-methyl-1H-imidazol-1-yl)pyridin-2-yl]-8-methyl-8-phenyl-5,6,7,8-tetrahydro[1,2,4]triazolo[1,5-a]pyridine

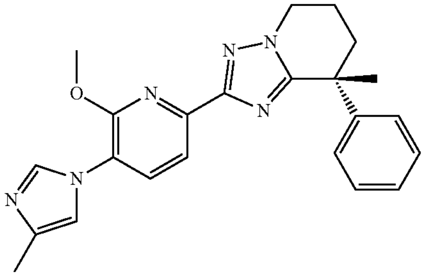

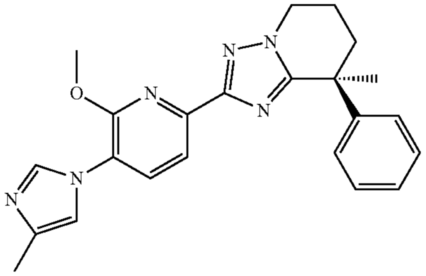

A racemate of the title compound was obtained according to Examples 84 and 85 from 5-hydroxy-2-methyl-2-phenylpentanenitrile (CAS #745054-73-3) as a starting material in place of [benzyl-(2-oxoethyl)amino]-(4-trifluoromethylphenyl)acetonitrile. This was separated by CHIRALCEL™ IB manufactured by Daicel Chemical Industries, Ltd. (2 cm×25 cm, mobile phase:hexane:ethanol=8:2, flow rate: 15 mL/min) to obtain the title optically active compound with a retention time of 5.4 minutes resulting from analysis by CHIRALPAK™ IB manufactured by Daicel Chemical Industries, Ltd. (Lot. IB00CD-LG026, hexane:ethanol=8:2, 1.0 mL/min) and negative optical rotation and the title optically active compound with a retention time of 7.1 minutes resulting from the same analysis and positive optical rotation, respectively.

The property values of the title optically active compound with negative optical rotation are as follows.

$^1$H-NMR ($CDCl_3$) δ (ppm): 1.87 (s, 3H), 1.89-2.11 (m, 3H), 2.31 (s, 3H), 2.41 (m, 1H), 4.18 (s, 3H), 4.24 (m, 1H), 4.40 (m, 1H), 7.02 (m, 1H), 7.09-7.12 (m, 2H), 7.20-7.24 (m, 1H), 7.27-7.31 (m, 2H), 7.62 (d, J=7.6 Hz, 1H), 7.84 (d, J=1.2 Hz, 1H), 7.89 (d, J=8.0 Hz, 1H).

The property values of the title optically active compound with positive optical rotation are as follows.

$^1$H-NMR ($CDCl_3$) δ (ppm): 1.87 (s, 3H), 1.89-2.11 (m, 3H), 2.31 (s, 3H), 2.41 (m, 1H), 4.18 (s, 3H), 4.24 (m, 1H), 4.40 (m, 1H), 7.02 (m, 1H), 7.09-7.12 (m, 2H), 7.20-7.24 (m, 1H), 7.27-7.31 (m, 2H), 7.62 (d, J=7.6 Hz, 1H), 7.84 (d, J=1.2 Hz, 1H), 7.89 (d, J=8.0 Hz, 1H).

Examples 90 and 91

Synthesis of (+)-2-[6-methoxy-5-(4-methylimidazol-1-yl)pyridin-2-yl]-6-(2-trifluoromethylphenyl)-5,6,7,8-tetrahydro[1,2,4]triazolo[1,5-a]pyridine and (−)-2-[6-methoxy-5-(4-methylimidazol-1-yl)pyridin-2-yl]-6-(2-trifluoromethylphenyl)-5,6,7,8-tetrahydro[1,2,4]triazolo[1,5-a]pyridine

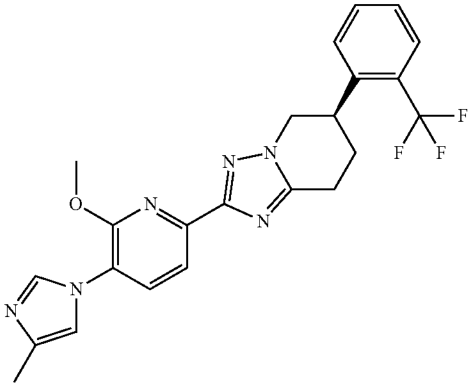

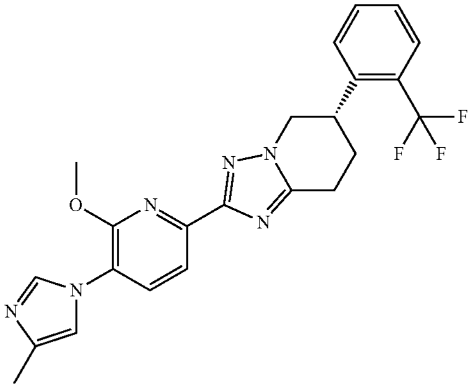

A racemate of the title compound (186 mg) was obtained according to Examples 84 and 85 from 5-hydroxy-4-(2-trifluoromethylphenyl)pentanenitrile obtained in Preparation Example 4-3 in place of [benzyl-(2-oxoethyl)amino]-(4-trifluoromethylphenyl)acetonitrile. The resulting racemate was separated by CHIRALPAK™ IB manufactured by Daicel Chemical Industries, Ltd. (2 cm×25 cm, mobile phase:ethanol:hexane=3:7, flow rate: 15 mL/min) to obtain the title compound with a retention time of 13.0 minutes and positive optical rotation (42 mg) and the title compound with a retention time of 22.5 minutes and negative optical rotation (49.7 mg).

The property values of the title optically active compound with a retention time of 13.0 minutes are as follows.

$^1$H-NMR ($CDCl_3$) δ (ppm): 2.20-2.34 (m, 2H), 2.31 (s, 3H), 3.09 (ddd, J=15.2, 13.0, 6.2 Hz, 1H), 3.30 (ddd, J=15.2, 5.1, 2.7 Hz, 1H), 3.72-3.82 (m, 1H), 4.17 (s, 3H), 4.23 (dd, J=11.7, 11.7 Hz, 1H), 4.60 (dd, J=15.2, 5.1 Hz, 1H), 7.02-7.04 (m, 1H), 7.43-7.52 (m, 2H), 7.60-7.65 (m, 1H), 7.64 (d, J=7.8 Hz, 1H), 7.75 (d, J=7.8 Hz, 1H), 7.83 (d, J=7.8 Hz, 1H), 7.85 (d, J=1.2 Hz, 1H).

The property values of the title optically active compound with a retention time of 22.5 minutes are as follows.

$^1$H-NMR ($CDCl_3$) δ (ppm): 2.20-2.34 (m, 2H), 2.31 (s, 3H), 3.09 (ddd, J=15.2, 13.0, 6.2 Hz, 1H), 3.30 (ddd, J=15.2, 5.1, 2.7 Hz, 1H), 3.72-3.82 (m, 1H), 4.17 (s, 3H), 4.23 (dd, J=11.7, 11.7 Hz, 1H), 4.60 (dd, J=15.2, 5.1 Hz, 1H), 7.02-7.04 (m, 1H), 7.43-7.52 (m, 2H), 7.60-7.65 (m, 1H), 7.64 (d, J=7.8 Hz, 1H), 7.75 (d, J=7.8 Hz, 1H), 7.83 (d, J=7.8 Hz, 1H), 7.85 (d, J=1.2 Hz, 1H).

Examples 92 and 93

Synthesis of (+)-2-[6-methoxy-5-(4-methylimidazol-1-yl)pyridin-2-yl]-7-(4-trifluoromethylphenyl)-5,6,7,8-tetrahydro[1,2,4]triazolo[1,5-a]pyridine and (−)-2-[6-methoxy-5-(4-methylimidazol-1-yl)pyridin-2-yl]-7-(4-trifluoromethylphenyl)-5,6,7,8-tetrahydro[1,2,4]triazolo[1,5-a]pyridine

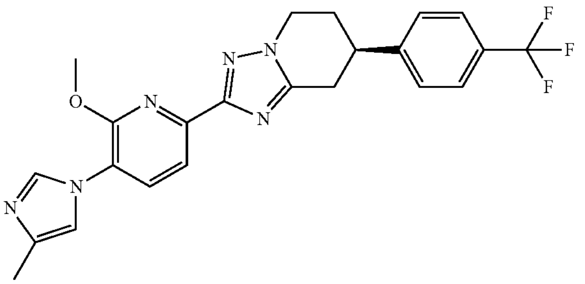

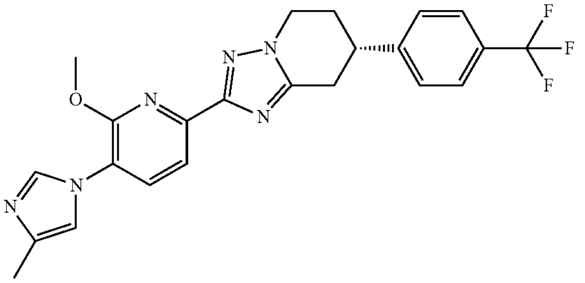

A racemate of the title compound (184.1 mg) was obtained according to Examples 84 and 85 from 5-hydroxy-3-(4-trifluoromethylphenyl)pentanenitrile obtained in Preparation Example 4-4 in place of [benzyl-(2-oxoethyl)amino]-(4-trifluoromethylphenyl)acetonitrile. The resulting racemate was separated by CHIRALPAK™ IB manufactured by Daicel Chemical Industries, Ltd. (2 cm×25 cm, mobile phase:ethanol:hexane=5:5, flow rate: 13 mL/min) to obtain the title compound with a retention time of 16.5 minutes and positive optical rotation (43.0 mg) and the title compound with a retention time of 23.0 minutes and negative optical rotation (44.0 mg).

The property values of the title optically active compound with a retention time of 16.5 minutes are as follows.

$^1$H-NMR ($CDCl_3$) δ (ppm): 2.31 (s, 3H), 2.33-2.49 (m, 2H), 3.11 (dd, J=16.7, 9.4 Hz, 1H), 3.34-3.47 (m, 2H), 4.18 (s, 3H), 4.28-4.37 (m, 1H), 4.39-4.47 (m, 1H), 7.01-7.05 (m, 1H), 7.40 (d, J=8.2 Hz, 2H), 7.62-7.68 (m, 3H), 7.83 (d, J=7.8 Hz, 1H), 7.84-7.87 (m, 11.1).

The property values of the title optically active compound with a retention time of 23.0 minutes are as follows.

$^1$H-NMR ($CDCl_3$) δ (ppm): 2.31 (s, 3H), 2.33-2.49 (m, 2H), 3.11 (dd, J=16.7, 9.4 Hz, 1H), 3.34-3.47 (m, 2H), 4.18 (s, 3H), 4.28-4.37 (m, 1H), 4.39-4.47 (m, 1H), 7.01-7.05 (m, 1H), 7.40 (d, J=8.2 Hz, 2H), 7.62-7.68 (m, 3H), 7.83 (d, J=7.8 Hz, 1H), 7.84-7.87 (m, 1H).

Examples 94 and 95

Synthesis of (+)-2-[6-methoxy-5-(4-methylimidazol-1-yl)pyridin-2-yl]-7-(2-trifluoromethylphenyl)-5,6,7,8-tetrahydro[1,2,4]triazolo[1,5-a]pyridine and (−)-2-[6-methoxy-5-(4-methylimidazol-1-yl)pyridin-2-yl]-7-(2-trifluoromethylphenyl)-5,6,7,8-tetrahydro[1,2,4]triazolo[1,5-a]pyridine

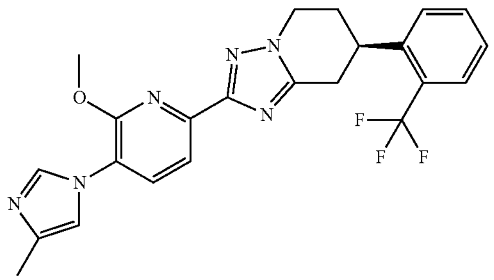

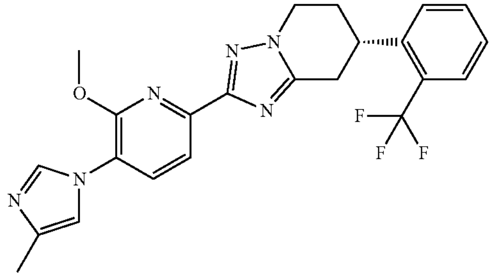

A racemate of the title compound (222 mg) was obtained according to the method of Examples 84 and 85 from 5-hydroxy-3-(2-trifluoromethylphenyl)pentanenitrile obtained in Preparation Example 4-5 in place of [benzyl-(2-oxoethyl)amino]-(4-trifluoromethylphenyl)acetonitrile. The resulting racemate was separated by CHIRALCEL™ OD-H (2 cm×25 cm, mobile phase:ethanol:hexane=2:8, flow rate: 15 mL/min) to obtain the title compound with a retention time of 22.5 minutes and positive optical rotation (25.1 mg) and the title compound with a retention time of 49.5 minutes and negative optical rotation (35.8 mg).

The property values of the title optically active compound with a retention time of 22.5 minutes are as follows.

$^1$H-NMR ($CDCl_3$) δ (ppm): 2.30 (s, 3H), 2.31-2.42 (m, 2H), 3.08 (dd, J=17.1, 11.7 Hz, 1H), 3.41 (dd, J=17.1, 5.1 Hz, 1H), 3.62-3.73 (m, 1H), 4.18 (s, 3H), 4.27-4.37 (m, 1H), 4.52 (ddd, J=13.3, 5.1, 2.3 Hz, 1H), 6.92-6.94 (m, 1H), 7.40-7.45 (m, 1H), 7.48 (d, J=7.8 Hz, 1H), 7.60 (d, J=7.8 Hz, 1H), 7.64 (d, J=7.8 Hz, 1H), 7.73 (d, J=7.8 Hz, 1H), 7.82 (d, J=7.8 Hz, 1H), 7.86 (d, J=1.0 Hz, 1H).

The property values of the title optically active compound with a retention time of 49.5 minutes are as follows.

$^1$H-NMR ($CDCl_3$) δ (ppm): 2.30 (s, 3H), 2.31-2.42 (m, 2H), 3.08 (dd, J=17.1, 11.7 Hz, 1H), 3.41 (dd, J=17.1, 5.1 Hz, 1H), 3.62-3.73 (m, 1H), 4.18 (s, 3H), 4.27-4.37 (m, 1H), 4.52 (ddd, J=13.3, 5.1, 2.3 Hz, 1H), 6.92-6.94 (m, 1H), 7.40-7.45

(m, 1H), 7.48 (d, J=7.8 Hz, 1H), 7.60 (d, J=7.8 Hz, 1H), 7.64 (d, J=7.8 Hz, 1H), 7.73 (d, J=7.8 Hz, 1H), 7.82 (d, J=7.8 Hz, 1H), 7.86 (d, J=1.0 Hz, 1H).

Examples 96 and 97

Synthesis of (+)-2-[6-methoxy-5-(4-methylimidazol-1-yl)pyridin-2-yl]-8-(2-fluoro-4-trifluoromethylphenyl)-5,6,7,8-tetrahydro[1,2,4]triazolo[1,5-a]pyridine and (−)-2-[6-methoxy-5-(4-methylimidazol-1-yl)pyridin-2-yl]-8-(2-fluoro-4-trifluoromethylphenyl)-5,6,7,8-tetrahydro[1,2,4]triazolo[1,5-a]pyridine

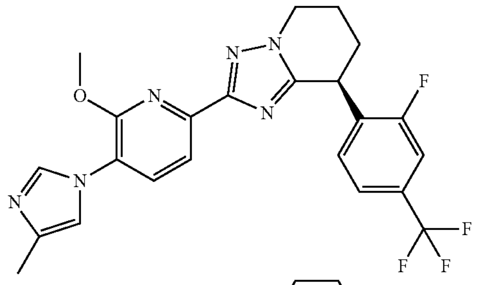

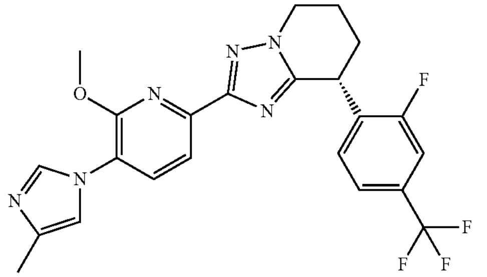

A racemate of the title compound (52.7 mg) was obtained according to the method of Examples 84 and 85 from 2-(2-fluoro-4-trifluoromethylphenyl)-5-hydroxypentanenitrile obtained in Preparation Example 4-6 in place of [benzyl-(2-oxoethyl)amino]-(4-trifluoromethylphenyl)acetonitrile. The resulting racemate was separated by CHIRALPAK™ IB (2 cm×25 cm, mobile phase:ethanol:hexane=2:8, flow rate: 15 mL/min) to obtain the title compound with a retention time of 48 minutes and positive optical rotation (1.81 mg) and the title compound with a retention time of 56.5 minutes and negative optical rotation (2.15 mg).

The property values of the title optically active compound with a retention time of 48 minutes are as follows.

$^1$H-NMR ($CDCl_3$) δ (ppm): 2.04-2.25 (m, 3H), 2.30 (s, 3H), 2.38-2.48 (m, 1H), 4.16 (s, 3H), 4.42 (dd, J=7.4, 5.5 Hz, 2H), 4.69 (dd, J=7.0, 7.0 Hz, 1H), 6.98-7.01 (m, 1H), 7.08-7.14 (m, 1H), 7.37 (d, J=9.0 Hz, 1H), 7.59 (d, J=7.8 Hz, 1H), 7.76 (d, J=7.8 Hz, 1H), 7.83 (d, J=1.2 Hz, 1H).

The property values of the title optically active compound with a retention time of 56.5 minutes are as follows.

$^1$H-NMR ($CDCl_3$) δ (ppm): 2.04-2.25 (m, 3H), 2.30 (s, 3H), 2.38-2.48 (m, 1H), 4.16 (s, 3H), 4.42 (dd, J=7.4, 5.5 Hz, 2H), 4.69 (dd, J=7.0, 7.0 Hz, 1H), 6.98-7.01 (m, 1H), 7.08-7.14 (m, 1H), 7.37 (d, J=9.0 Hz, 1H), 7.59 (d, J=7.8 Hz, 1H), 7.76 (d, J=7.8 Hz, 1H), 7.83 (d, J=1.2 Hz, 1H).

The compounds of Examples 98 to 99 were obtained by the same method as in Examples 84 and 85 (Table 3).

TABLE 3

| Example No. | Structural formula |
|---|---|
| Example 98 | 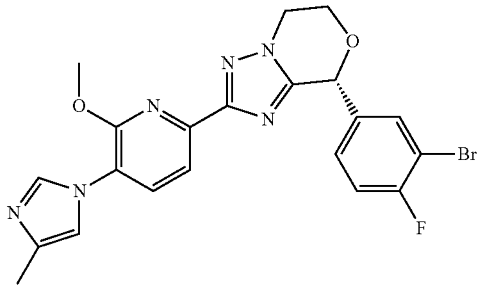 [SMILES: COc1nc(-c2nc3n(n2)CCO[C@@H]3c2ccc(F)c(Br)c2)ccc1-n1cnc(C)c1] |
| Example 99 | 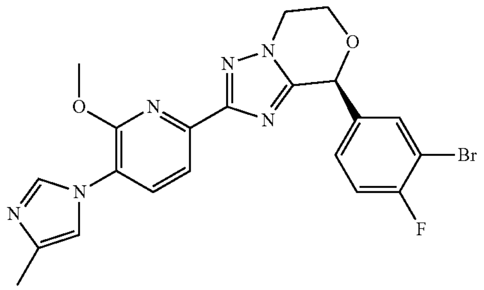 [SMILES: COc1nc(-c2nc3n(n2)CCO[C@H]3c2ccc(F)c(Br)c2)ccc1-n1cnc(C)c1] |

Examples 100 and 101

Synthesis of (−)-8-(4-bromo-2-trifluoromethylphenyl)-2-[6-methoxy-5-(4-methylimidazol-1-yl)pyridin-2-yl]-5,6,7,8-tetrahydroimidazo[1,2-a]pyridine and (+)-8-(4-bromo-2-trifluoromethylphenyl)-2-[6-methoxy-5-(4-methylimidazol-1-yl)pyridin-2-yl]-5,6,7,8-tetrahydroimidazo[1,2-a]pyridine

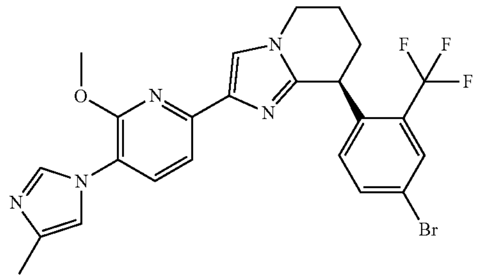

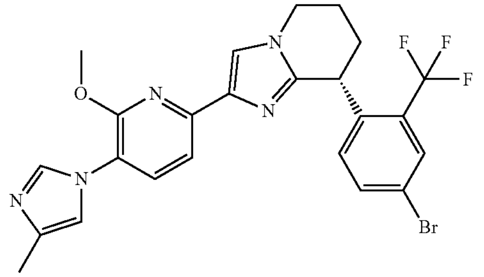

Synthesis of 3-(4-bromo-2-trifluoromethylphenyl)piperidine-2-ylideneamine

A saturated ammonia-ethanol solution (2.5 mL) was added to ethyl 2-(4-bromo-2-trifluoromethylphenyl)-5-chloropentanimidate hydrochloride obtained in Preparation Example 3-1 (500 mg), and the mixture was stirred at room temperature for eight days. The insoluble matter was removed by filtration and then the filtrate was concentrated under reduced pressure. Methylene chloride and a 1 N sodium hydroxide solution were added to the resulting residue, and the organic layer was separated. The aqueous layer was reextracted with methylene chloride. The combined organic layers were dried over anhydrous potassium carbonate and concentrated under reduced pressure to obtain 320 mg of the title compound. The property values of the compound are as follows.

ESI-MS; ink 321 [$M^{+}$+H].

$^{1}$H-NMR (DMSO-$D_6$) δ (ppm): 1.42-1.65 (m, 3H), 1.95-2.05 (m, 1H), 3.35-3.45 (m, 2H), 3.68 (d, J=6.8 Hz, 1H), 5.55 (brs, 2H), 7.32 (d, J=8.4 Hz, 1H), 7.85-7.92 (m, 2H).

Synthesis of (+8-(4-bromo-2-trifluoromethylphenyl)-2-[6-methoxy-5-(4-methylimidazol-1-yl)pyridin-2-yl]-5,6,7,8-tetrahydroimidazo[1,2-a]pyridine and (+)-8-(4-bromo-2-trifluoromethylphenyl)-2-[6-methoxy-5-(4-methylimidazol-1-yl)pyridin-2-yl]-5,6,7,8-tetrahydroimidazo[1,2-a]pyridine N-bromosuccinimide (98 mg) was added to a solution of 6-(1-ethoxyvinyl)-2-methoxy-3-(4-methylimidazol-1-yl)pyridine obtained in Preparation Example 1-7 (130 mg) in Tetrahydrofuran (5 mL)-water (0.2 mL), followed by stirring at room temperature for 15 minutes. A solution of 3-(4-bromo-2-trifluoromethylphenyl)piperidin-2-ylideneamine (318 mg) in ethanol (2 mL) was added to the reaction solution, followed by stirring at room temperature for two hours and 15 minutes. Then, the reaction solution was heated under reflux for one hour and 30 minutes. The reaction solution was left to cool to room temperature. Ethyl acetate, water and a saturated sodium bicarbonate solution were added to the reaction solution, and the organic layer was separated. The resulting organic layer was sequentially washed with half-saturated brine and brine, dried over anhydrous magnesium sulfate and then concentrated under reduced pressure. The resulting residue was purified by silica gel column chromatography (carrier: Chromatorex™ NH; elution solvent:ethyl acetate:heptane=1:9→1:1) to obtain a racemate of the title compound.

The resulting racemate was separated by CHIRALCEL™ OD-H (2 cm×25 cm; mobile phase: 20% isopropanol-hexane) to obtain the title optically active compound with a retention time of 14 minutes and negative optical rotation (36.1 mg, >99% ee) and the title optically active compound with a retention time of 20 minutes and positive optical rotation (36.3 mg, >97% ee).

The property values of the title compound with negative optical rotation are as follows.

ESI-MS; m/z 534 [$M^{+}$+H].

$^{1}$H-NMR ($CDCl_3$) δ (ppm): 1.82-1.94 (m, 1H), 2.00-2.22 (m, 2H), 2.29 (s, 3H), 2.35-2.45 (m, 1H), 4.03 (s, 3H), 4.17 (dd, J=6.8, 5.6 Hz, 2H), 4.65 (dd, J=8.4, 6.0 Hz, 1H), 6.92 (d, J=8.4 Hz, 1H), 6.93 (s, 1H), 7.46 (d, J=8.0 Hz, 1H), 7.50 (d, J=8.0 Hz, 1H), 7.54 (s, 1H), 7.55 (dd, J=8.4, 2.0 Hz, 1H), 7.74 (d, J=1.2 Hz, 1H), 7.84 (d, J=2.0 Hz, 1H).

The property values of the title compound with positive optical rotation are as follows.

ESI-MS; m/z 534 [$M^{+}$+H].

$^{1}$H-NMR ($CDCl_3$) δ (ppm): 1.82-1.94 (m, 1H), 2.00-2.22 (m, 2H), 2.29 (s, 3H), 2.35-2.45 (m, 1H), 4.03 (s, 3H), 4.17 (dd, J=6.8, 5.6 Hz, 2H), 4.65 (dd, J=8.4, 6.0 Hz, 1H), 6.92 (d, J=8.4 Hz, 1H), 6.93 (s, 1H), 7.46 (d, J=8.0 Hz, 1H), 7.50 (d, J=8.0 Hz, 1H), 7.54 (s, 1H), 7.55 (dd, J=8.4, 2.0 Hz, 1H), 7.74 (d, J=1.2 Hz, 1H), 7.84 (d, J=2.0 Hz, 1H).

Examples 102 and 103

Synthesis of (−)-2-[6-methoxy-5-(4-methylimidazol-1-yl)pyridin-2-yl]-8-(2-trifluoromethylphenyl)-5,6,7,8-tetrahydroimidazo[1,2-a]pyridine and (+)-2-[6-methoxy-5-(4-methylimidazol-1-yl)pyridin-2-yl]-8-(2-trifluoromethylphenyl)-5,6,7,8-tetrahydroimidazo[1,2-a]pyridine

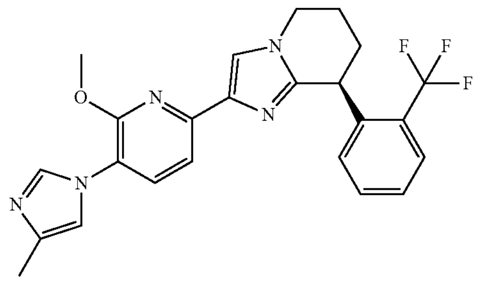

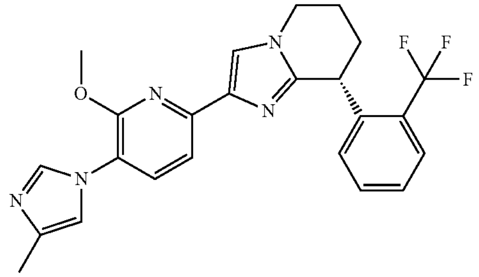

A racemate of the title compound was obtained according to the method of Examples 100 and 101 from ethyl 2-(2-trifluoromethylphenyl)-5-chloropentanimidate hydrochloride obtained in Preparation Example 3-12. The resulting racemate was separated by CHIRALCEL™ OD-H (2 cm×25 cm; mobile phase: 30% isopropanol-hexane) to obtain the title optically active compound with a retention time of 10 minutes and negative optical rotation (12.2 mg, >99% ee) and the title optically active compound with a retention time of 22 minutes and positive optical rotation (11.8 mg, >97% ee).

The property values of the title compound with negative optical rotation are as follows.

ESI-MS; m/z 454 [$M^{+}$+H].

$^{1}$H-NMR ($CDCl_3$) δ (ppm): 1.85-2.23 (m, 3H), 2.28 (s, 3H), 2.35-2.45 (m, 1H), 4.04 (s, 3H), 4.10-4.25 (m, 2H), 4.73 (t, J=6.8 Hz, 1H), 6.92 (brs, 1H), 7.01 (d, J=7.6 Hz, 1H), 7.35 (t, J=7.6 Hz, 1H), 7.43 (t, J=7.6 Hz, 1H), 7.45 (d, J=8.0 Hz, 1H), 7.51 (d, J=8.0 Hz, 1H), 7.55 (s, 1H), 7.71 (d, J=7.6 Hz, 1H), 7.74 (brs, 1H).

The property values of the title compound with positive optical rotation are as follows.

ESI-MS; m/z 454 [$M^{+}$+H].

$^{1}$H-NMR ($CDCl_3$) δ (ppm): 1.85-2.23 (m, 3H), 2.28 (s, 3H), 2.35-2.45 (m, 1H), 4.04 (s, 3H), 4.10-4.25 (m, 2H), 4.73 (t, J=6.8 Hz, 1H), 6.92 (brs, 1H), 7.01 (d, J=7.6 Hz, 1H), 7.35 (t, J=7.6 Hz, 1H), 7.43 (t, J=7.6 Hz, 1H), 7.45 (d, J=8.0 Hz, 1H), 7.51 (d, J=8.0 Hz, 1H), 7.55 (s, 1H), 7.71 (d, J=7.6 Hz, 1H), 7.74 (brs, 1H).

Examples 104 and 105

Synthesis of (−)-2-[6-methoxy-5-(4-methylimidazol-1-yl)pyridin-2-yl]-7-(2-trifluoromethylphenyl)-6,7-dihydro-5H-pyrrolo[1,2-a]imidazole and (+)-2-[6-methoxy-5-4-methylimidazol-1-yl)pyridin-2-yl]-7-(2-trifluoromethylphenyl)-6,7-dihydro-5H-pyrrolo[1,2-a]imidazole

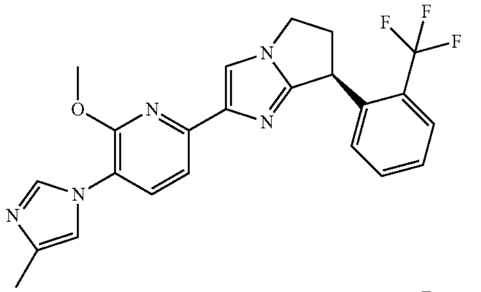

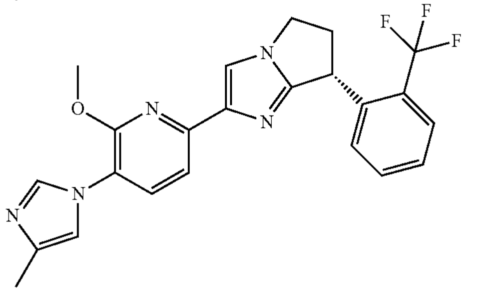

A racemate of the title compound was obtained according to the method of Examples 100 and 101 from ethyl 4-chloro-2-(2-trifluoromethylphenyl)butylimidate hydrochloride obtained in Preparation Example 3-14 in place of ethyl 2-(4-bromo-2-trifluoromethylphenyl)-5-chloropentanimidate hydrochloride. The resulting racemate was purified by CHIRALPAK™ IB (2 cm×25 cm; mobile phase: 30% isopropanol-hexane) and then separated by CHIRALCEL™ OD-H) (2 cm×25 cm; mobile phase: 30% isopropanol-hexane) to obtain the title optically active compound with a retention time of 10 minutes and negative optical rotation (2.43 mg, >99% ee) and the title optically active compound with a retention time of 16 minutes and positive optical rotation (2.00 mg, >99% ee).

The property values of the title compound with positive optical rotation are as follows.

ESI-MS; m/z 440 $[M^+ + H]$.

$^1$H-NMR ($CDCl_3$) δ (ppm): 2.29 (d, J=1.2 Hz, 3H), 2.40-2.52 (m, 1H), 3.17-3.28 (m, 1H), 4.06 (s, 3H), 4.07-4.21 (m, 2H), 4.82 (dd, J=6.0, 8.4 Hz, 1H), 6.96 (brs, 1H), 7.05 (d, J=7.6 Hz, 1H), 7.37 (t, J=7.6 Hz, 1H), 7.47 (t, J=7.6 Hz, 1H), 7.51 (d, J=8.0 Hz, 1H), 7.59 (d, J=8.0 Hz, 1H), 7.68 (s, 1H), 7.71 (d, J=7.6 Hz, 1H), 7.76 (d, J=1.6 Hz, 1H).

The property values of the title compound with negative optical rotation are as follows.

ESI-MS; m/z 440 $[M^+ + H]$.

$^1$H-NMR ($CDCl_3$) δ (ppm): 2.29 (d, J=1.2 Hz, 3H), 2.40-2.52 (m, 1H), 3.17-3.28 (m, 1H), 4.06 (s, 3H), 4.07-4.21 (m, 2H), 4.82 (dd, J=6.0, 8.4 Hz, 1H), 6.96 (brs, 1H), 7.05 (d, J=7.6 Hz, 1H), 7.37 (t, J=7.6 Hz, 1H), 7.47 (t, J=7.6 Hz, 1H), 7.51 (d, J=8.0 Hz, 1H), 7.59 (d, J=8.0 Hz, 1H), 7.68 (s, 1H), 7.71 (d, J=7.6 Hz, 1H), 7.76 (d, J=1.6 Hz, 1H).

Examples 106 and 107

Synthesis of (−)-8-(4-fluoro-2-trifluoromethylphenyl)-2-[6-methoxy-5-(4-methylimidazol-1-yl)pyridin-2-yl]-5,6,7,8-tetrahydroimidazo[1,2-a]pyridine and (+)-8-(4-fluoro-2-trifluoromethylphenyl)-2-[6-methoxy-5-(4-methylimidazol-1-yl)pyridin-2-yl]-5,6,7,8-tetrahydroimidazo[1,2-a]pyridine

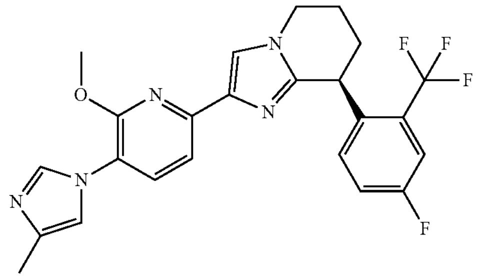

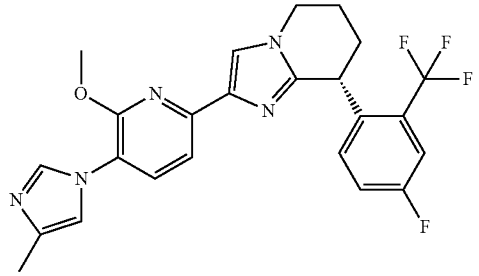

A racemate of the title compound was obtained according to the method of Examples 100 and 101 from ethyl 2-(4-fluoro-2-trifluoromethylphenyl)-5-chloropentanimidate hydrochloride obtained in Preparation Example 3-13 in place of ethyl 2-(4-bromo-2-trifluoromethylphenyl)-5-chloropentanimidate hydrochloride. The resulting racemate was separated by CHIRALPAK™ IA (2 cm×25 cm; mobile phase: 30% isopropanol-hexane) to obtain the title optically active compound with a retention time of 11 minutes and negative optical rotation (14.8 mg, >99% ee) and the title optically active compound with a retention time of 21 minutes and positive optical rotation (22.7 mg, >98% ee).

The property values of the title compound with negative optical rotation are as follows.

ESI-MS; m/z 472 $[M^+ + H]$.

$^1$H-NMR ($CDCl_3$) δ (ppm): 1.84-1.94 (m, 1H), 1.98-2.22 (m, 2H), 2.28 (s, 3H), 2.35-2.46 (m, 1H), 4.03 (s, 3H), 4.17 (dd, J=7.2, 4.8 Hz, 2H), 4.67 (dd, J=8.0, 6.0 Hz, 1H), 6.93 (brs, 1H), 7.02 (dd, J=8.4, 5.6 Hz, 1H), 7.14 (td, J=8.4, 2.4 Hz, 1H), 7.41 (dd, J=8.8, 2.4 Hz, 1H), 7.46 (d, J=8.0 Hz, 1H), 7.50 (d, J=8.0 Hz, 1H), 7.54 (s, 1H), 7.74 (d, J=1.2 Hz, 1H).

The property values of the title compound with positive optical rotation are as follows.

ESI-MS; m/z 472 $[M^+ + H]$.

$^1$H-NMR ($CDCl_3$) δ (ppm): 1.84-1.94 (m, 1H), 1.98-2.22 (m, 2H), 2.28 (s, 3H), 2.35-2.46 (m, 1H), 4.03 (s, 3H), 4.17 (dd, J=7.2, 4.8 Hz, 2H), 4.67 (dd, J=8.0, 6.0 Hz, 1H), 6.93 (brs, 1H), 7.02 (dd, J=8.4, 5.6 Hz, 1H), 7.14 (td, J=8.4, 2.4 Hz, 1H), 7.41 (dd, J=8.8, 2.4 Hz, 1H), 7.46 (d, J=8.0 Hz, 1H), 7.50 (d, J=8.0 Hz, 1H), 7.54 (s, 1H), 7.74 (d, J=1.2 Hz, 1H).

Examples 108 and 109

Synthesis of (−)-8-(4-chloro-2-trifluoromethylphenyl)-2-[6-methoxy-5-(4-methylimidazol-1-yl)pyridin-2-yl]-5,6,7,8-tetrahydroimidazo[1,2-a]pyridine and (+)-8-(4-chloro-2-trifluoromethylphenyl)-2-[6-methoxy-5-(4-methylimidazol-1-yl)pyridin-2-yl]-5,6,7,8-tetrahydroimidazo[1,2-a]pyridine

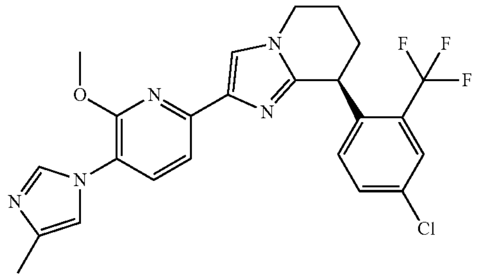

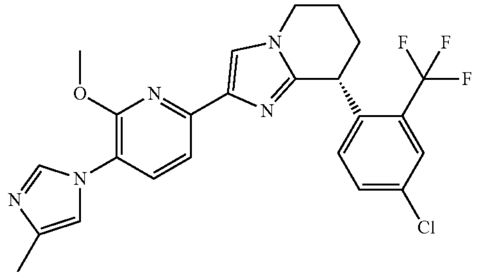

A racemate of the title compound was obtained according to the method of Examples 100 and 101 from ethyl 2-(4-chloro-2-trifluoromethylphenyl)-5-chloropentanimidate hydrochloride obtained in Preparation Example 3-20 in place of ethyl 2-(4-bromo-2-trifluoromethylphenyl)-5-chloropentanimidate hydrochloride. The resulting racemate was separated by CHIRALPAK™ IA (2 cm×25 cm; mobile phase: 40% isopropanol-hexane) to obtain the title optically active compound with a retention time of 12 minutes and negative optical rotation (43.0 mg, >99% ee) and the title optically active compound with a retention time of 22 minutes and positive optical rotation (41.2 mg, >98% ee).

The property values of the title compound with negative optical rotation are as follows.

ESI-MS; m/z 488 [$M^+$+H].

$^1$H-NMR ($CDCl_3$) δ (ppm): 1.82-1.95 (m, 1H), 2.00-2.22 (m, 2H), 2.29 (s, 3H), 2.35-2.45 (m, 1H), 4.03 (s, 3H), 4.17 (dd, J=6.8, 5.2 Hz, 2H), 4.67 (dd, J=8.0, 6.0 Hz, 1H), 6.93 (brs, 1H), 6.98 (d, J=8.4 Hz, 1H), 7.40 (dd, J=8.4, 2.4 Hz, 1H), 7.46 (d, J=8.0 Hz, 1H), 7.49 (d, J=8.0 Hz, 1H), 7.54 (s, 1H), 7.69 (d, J=2.4 Hz, 1H), 7.74 (d, J=1.2 Hz, 1H).

The property values of the title compound with positive optical rotation are as follows.

ESI-MS; m/z 488 [$M^+$+H].

$^1$H-NMR ($CDCl_3$) δ (ppm): 1.82-1.95 (m, 1H), 2.00-2.22 (m, 2H), 2.29 (s, 3H), 2.35-2.45 (m, 1H), 4.03 (s, 3H), 4.17 (dd, J=6.8, 5.2 Hz, 2H), 4.67 (dd, J=8.0, 6.0 Hz, 1H), 6.93 (brs, 1H), 6.98 (d, J=8.4 Hz, 1H), 7.40 (dd, J=8.4, 2.4 Hz, 1H), 7.46 (d, J=8.0 Hz, 1H), 7.49 (d, J=8.0 Hz, 1H), 7.54 (s, 1H), 7.69 (d, J=2.4 Hz, 1H), 7.74 (d, J=1.2 Hz, 1H).

Examples 110 and 111

Synthesis of (+1-8-(5-tert-butyl-2-methoxyphenyl)-2-[6-methoxy-5-(4-methylimidazol-1-yl)pyridin-2-yl]-5,6,7,8-tetrahydroimidazo[1,2-a]pyridine and (−)-8-(5-tert-butyl-2-methoxyphenyl)-2-[6-methoxy-5-(4-methylimidazol-1-yl)pyridin-2-yl]-5,6,7,8-tetrahydroimidazo[1,2-a]pyridine

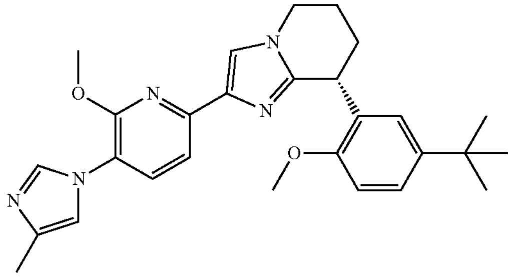

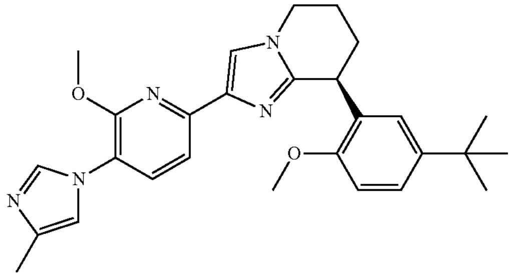

A racemate of the title compound was obtained according to the method of Examples 100 and 101 from ethyl 2-(5-tert-butyl-2-methoxyphenyl)-5-chloropentanimidate hydrochloride obtained in Preparation Example 3-3 in place of ethyl 2-(4-bromo-2-trifluoromethylphenyl)-5-chloropentanimidate hydrochloride. The resulting racemate was separated by CHIRALPAK™ IA (2 cm×25 cm; mobile phase: 15% isopropanol-hexane) to obtain the title optically active compound with a retention time of 14 minutes and positive optical rotation and the title optically active compound with a retention time of 26 minutes and negative optical rotation.

The respective optically active compounds were purified by CHIRALPAK™ IA (2 cm×25 cm; mobile phase: 15% ethanol-hexane) to obtain the title optically active compound with positive optical rotation (14.5 mg, >99% ee) and the title optically active compound with negative optical rotation (14.5 mg, >99% ee).

The property values of the title compound with positive optical rotation are as follows.

ESI-MS; m/z 472 [$M^+$+H].

$^1$H-NMR ($CDCl_3$) δ (ppm): 1.21 (s, 9H), 1.90-2.35 (m, 4H), 2.29 (s, 3H), 3.78 (s, 3H), 4.00-4.20 (m, 2H), 4.05 (s, 3H), 4.63 (t, J=6.0 Hz, 1H), 6.81 (d, J=8.4 Hz, 1H), 6.86 (d, J=2.4 Hz, 1H), 6.94 (s, 1H), 7.22 (dd, J=8.4, 2.4 Hz, 1H), 7.47 (d, J=8.0 Hz, 1H), 7.54 (d, J=8.0 Hz, 1H), 7.55 (s, 1H), 7.74 (s, 1H).

The property values of the title compound with negative optical rotation are as follows.

ESI-MS; m/z 472 [$M^+$+H].

$^1$H-NMR ($CDCl_3$) δ (ppm): 1.21 (s, 9H), 1.90-2.35 (m, 4H), 2.29 (s, 3H), 3.78 (s, 3H), 4.00-4.20 (m, 2H), 4.05 (s, 3H), 4.63 (t, J=6.0 Hz, 1H), 6.81 (d, J=8.4 Hz, 1H), 6.86 (d, J=2.4 Hz, 1H), 6.94 (s, 1H), 7.22 (dd, J=8.4, 2.4 Hz, 1H), 7.47 (d, J=8.0 Hz, 1H), 7.54 (d, J=8.0 Hz, 1H), 7.55 (s, 1H), 7.74 (s, 1H).

Examples 112 and 113

Synthesis of (−)-8-(3-tert-butyl-4-methoxyphenyl)-2-[6-methoxy-5-(4-methylimidazol-1-yl)pyridin-2-yl]-5,6,7,8-tetrahydroimidazo[1,2-a]pyridine and (+)-8-(3-tert-butyl-4-methoxyphenyl)-2-[6-methoxy-5-(4-methlimidazol-1-yl)pyridin-2-yl]-5,6,7,8-tetrahydroimidazo[1,2-a]pyridine

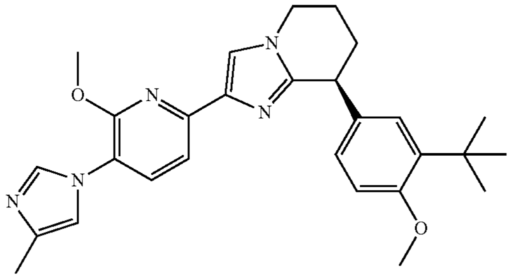

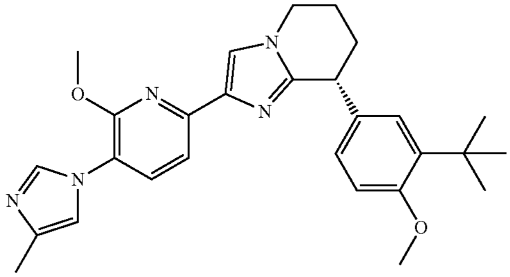

A racemate of the title compound was obtained according to the method of Examples 100 and 101 from the imidate hydrochloride obtained in Preparation Example 3-8 in place of ethyl 2-(4-bromo-2-trifluoromethylphenyl)-5-chloropentanimidate hydrochloride. The resulting racemate was roughly purified by CHIRALPAK™ IB (2 cm×25 cm; mobile phase: 20% ethanol-hexane). Then, the racemate was separated by CHIRALPAK™ IB (2 cm×25 cm; mobile phase: 10% ethanol-hexane) to obtain the title optically active compound with a retention time of 16 minutes and negative optical rotation and the title optically active compound with a retention time of 18 minutes and positive optical rotation (22.7 mg, >99% ee).

The title optically active compound with negative optical rotation was purified again by CHIRALPAK™ IA (2 cm×25 cm; mobile phase: 25% isopropanol-hexane) to obtain the title optically active compound with negative optical rotation (18.5 mg, >99% ee).

The property values of the title compound with negative optical rotation are as follows.

ESI-MS; m/z 472 $[M^{+}+H]$.

$^{1}$H-NMR ($CDCl_3$) δ (ppm): 1.35 (s, 9H), 1.90-2.15 (m, 3H), 2.25-2.35 (m, 1H), 2.29 (d, J=1.2 Hz, 3H), 3.80 (s, 3H), 4.03-4.20 (m, 2H), 4.04 (s, 3H), 4.33 (t, J=5.6 Hz, 1H), 6.77 (d, J=8.4 Hz, 1H), 6.80 (dd, J=8.4, 2.4 Hz, 1H), 6.94 (t, J=1.2 Hz, 1H), 7.13 (d, J=2.4 Hz, 1H), 7.48 (d, J=8.0 Hz, 1H), 7.54 (s, 1H), 7.58 (d, J=8.0 Hz, 1H), 7.74 (d, J=1.2 Hz, 1H).

The property values of the title compound with positive optical rotation are as follows.

ESI-MS; m/z 472 $[M^{+}+H]$.

$^{1}$H-NMR ($CDCl_3$) δ (ppm): 1.35 (s, 9H), 1.90-2.15 (m, 3H), 2.25-2.35 (m, 1H), 2.29 (d, J=1.2 Hz, 3H), 3.80 (s, 3H), 4.03-4.20 (m, 2H), 4.04 (s, 3H), 4.33 (t, J=5.6 Hz, 1H), 6.77 (d, J=8.4 Hz, 1H), 6.80 (dd, J=8.4, 2.4 Hz, 1H), 6.94 (t, J=1.2 Hz, 1H), 7.13 (d, J=2.4 Hz, 1H), 7.48 (d, J=8.0 Hz, 1H), 7.54 (s, 1H), 7.58 (d, J=8.0 Hz, 1H), 7.74 (d, J=1.2 Hz, 1H).

Examples 114 and 115

Synthesis of (−)-8-(3,3-dimethyl-2,3-dihydrobenzofuran-5-yl)-2-[6-methoxy-5-(4-methylimidazol-1-yl)pyridin-2-yl]-5,6,7,8-tetrahydroimidazo[1,2-a]pyridine and (+)-8-(3,3-dimethyl-2,3-dihydrobenzofuran-5-yl)-2-[6-methoxy-5-(4-methylimidazol-1-yl)pyridin-2-yl]-5,6,7,8-tetrahydroimidazo[1,2-a]pyridine

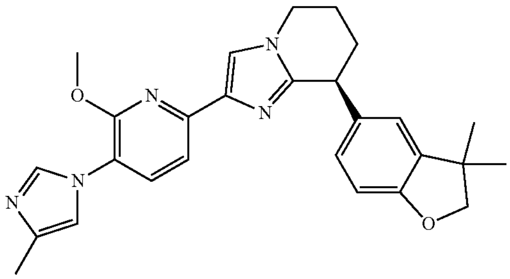

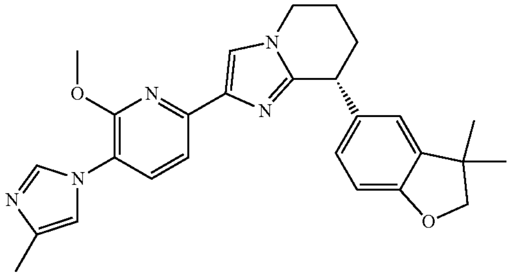

A racemate of the title compound was obtained according to the method of Examples 100 and 101 from the imidate hydrochloride obtained in Preparation Example 3-2 in place of ethyl 2-(4-bromo-2-trifluoromethylphenyl)-5-chloropentanimidate hydrochloride. The resulting racemate was separated by CHIRALCEL™ OD-11 (2 cm×25 cm; mobile phase: 25% isopropyl alcohol-hexane) to obtain the title optically active compound with a retention time of 10 minutes and negative optical rotation and the title optically active compound with a retention time of 16 minutes and positive optical rotation (22.5 mg, >99% ee).

The title optically active compound with negative optical rotation was purified again by CHIRALPAK™ IA (2 cm×25 cm; mobile phase: 30% ethanol-hexane) to obtain the title optically active compound with negative optical rotation (19.8 mg, >99% ee).

The property values of the title compound with negative optical rotation are as follows.

ESI-MS; m/z 456 $[M^{+}+H]$.

$^{1}$H-NMR ($CDCl_3$) δ (ppm): 1.31 (s, 6H), 1.90-2.16 (m, 3H), 2.25-2.36 (m, 1H), 2.29 (s, 3H), 4.04 (s, 3H), 4.05-4.21 (m, 2H), 4.22 (s, 2H), 4.34 (t, J=6.0 Hz, 1H), 6.69 (d, J=8.4 Hz, 1H), 6.88 (dd, J=8.4, 1.6 Hz, 1H), 6.91 (d, J=1.6 Hz, 1H), 6.94 (brs, 1H), 7.49 (d, J=8.0 Hz, 1H), 7.55 (s, 1H), 7.57 (d, J=8.0 Hz, 1H), 7.75 (brs, 1H).

The property values of the title compound with positive optical rotation are as follows.

ESI-MS; m/z 456 $[M^{+}+H]$.

$^{1}$H-NMR ($CDCl_3$) δ (ppm): 1.31 (s, 6H), 1.90-2.16 (m, 3H), 2.25-2.36 (m, 1H), 2.29 (s, 3H), 4.04 (s, 3H), 4.05-4.21 (m, 2H), 4.22 (s, 2H), 4.34 (t, J=6.0 Hz, 1H), 6.69 (d, J=8.4 Hz, 1H), 6.88 (dd, J=8.4, 1.6 Hz, 1H), 6.91 (d, J=1.6 Hz, 1H), 6.94 (brs, 1H), 7.49 (d, J=8.0 Hz, 1H), 7.55 (s, 1H), 7.57 (d, J=8.0 Hz, 1H), 7.75 (brs, 1H).

Examples 116 and 117

Synthesis of (+)-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine and (−)-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine

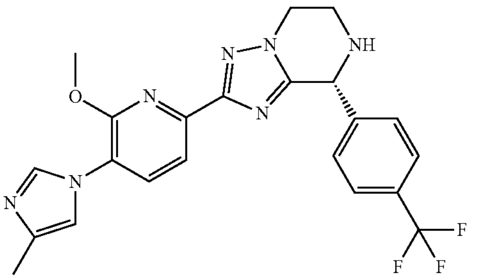

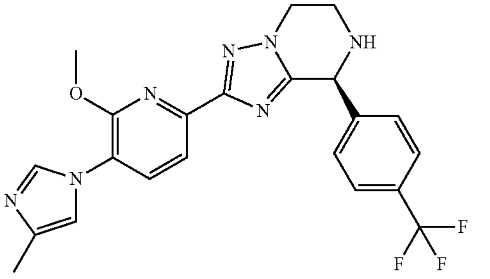

Acetic acid (1 mL) and 20% palladium hydroxide-carbon (400 mg) were added to a solution of 7-benzyl-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine obtained in Examples 84 and 85 (411 mg) in methanol (40 mL), and the mixture was stirred at room temperature in a hydrogen atmosphere for two days. After the reaction atmosphere was replaced with nitrogen, ethyl acetate was added to the reaction solution. The mixture was filtered through celite and concentrated under reduced pressure. The resulting residue was purified by silica gel column chromatography (carrier: Chromatorex™ NH, elution solvent: ethyl acetate) to obtain 290 mg of a racemate of the title compound. The resulting racemate of the title compound (36 mg) was separated by CHIRALPAK™ IA (2 cm×25 cm, mobile phase:hexane:ethanol=1:1, flow rate: 15 mL/min) to obtain the title optically active compound with a retention time of 8.5 minutes resulting from analysis by CHIRALPAK™ IA (Lot. IA00CE-FA020, hexane:ethanol=1:1, 1.0 mL/min) and positive optical rotation (10 mg, >99% ee) and the title optically active compound with a retention time of 16.0 minutes resulting from the same analysis and negative optical rotation (11 mg, >99% ee).

The property values of the title optically active compound with positive optical rotation are as follows.

ESI-MS; m/z 456 $[M^{+}+H]$.

$^{1}$H-NMR ($CDCl_3$) δ (ppm): 2.30 (s, 3H), 3.36-3.49 (m, 2H), 4.16 (s, 3H), 4.34-4.46 (m, 2H), 5.42 (s, 1H), 7.00 (s, 1H), 7.58-7.66 (m, 5H), 7.78 (d, J=7.6 Hz, 1H), 7.83 (s, 1H).

The property values of the title optically active compound with negative optical rotation are as follows.

ESI-MS; m/z 456 $[M^{+}+H]$.

$^{1}$H-NMR ($CDCl_3$) δ (ppm): 2.30 (s, 3H), 3.36-3.49 (m, 2H), 4.16 (s, 3H), 4.34-4.46 (m, 2H), 5.42 (s, 1H), 7.00 (t, J=1.2 Hz, 1H), 7.58-7.66 (m, 5H), 7.78 (d, J=7.6 Hz, 1H), 7.83 (d, J=1.6 Hz, 1H).

Examples 118 and 119

Synthesis of (+)-2-[6-methoxy-5-(4-methyl-1H-imidazol-1-yl)pyridin-2-yl]-7-methyl-8-(4-trifluoromethylphenyl)-5,6,7,8-tetrahydro[1,2,4]triazolo[1,5-a]pyrazine and (−)-2-[6-methoxy-5-(4-methyl-1H-imidazol-1-yl)pyridin-2-0]-7-methyl-8-(4-trifluoromethylphenyl)-5,6,7,8-tetrahydro[1,2,4]triazolo[1,5-a]pyrazine

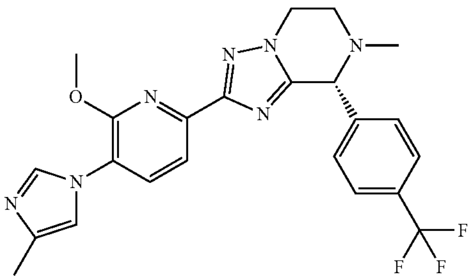

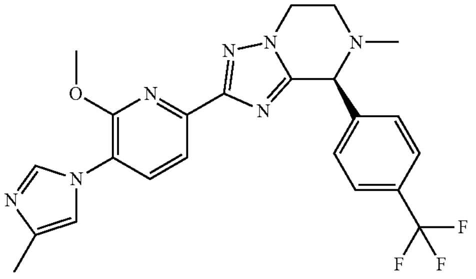

A 37% formaldehyde solution (2 mL) was added to a solution of 2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine obtained in Examples 116 and 117 (54 mg) in formic acid (2 mL), and the mixture was stirred with heating under reflux for 3.5 hours. The reaction solution was neutralized with a saturated sodium bicarbonate solution at 0° C. and partitioned with ethyl acetate. The organic layer was dried over anhydrous magnesium sulfate and then concentrated under reduced pressure. The resulting residue was purified by silica gel column chromatography (carrier: Chromatorex™ NH, elution solvent: heptane acetate:ethyl acetate=1:1→0:1) to obtain 24 mg of a racemate of the title compound. The resulting racemate of the title compound was separated by CHIRALPAK™ IA (2 cm×25 cm, mobile phase:hexane:ethanol=6:4, flow rate: 15 mL/min) to obtain the title optically active compound with a retention time of 6.6 minutes resulting from analysis by CHIRALPAK™ IA (Lot. IA00CE-FA020, hexane:ethanol=1:1, 1.0 mL/min) and positive optical rotation (6.5 mg, >99% ee) and the title optically active compound with a retention time of 15.2 minutes resulting from the same analysis and negative optical rotation (7.5 mg, >99% ee).

The property values of the title optically active compound with positive optical rotation are as follows.

ESI-MS; m/z 470 $[M^{+}+H]$.

$^{1}$H-NMR ($CDCl_3$) δ (ppm): 2.29 (s, 3H), 2.38 (s, 3H), 3.03 (ddd, J=4.4, 9.6, 12.8 Hz, 1H), 3.34 (ddd, J=2.8, 4.4, 12.4 Hz, 1H), 4.14 (s, 3H), 4.41-4.54 (m, 2H), 4.59 (s, 1H), 6.98 (t, J=1.2, 1H), 7.53 (d, J=9.2 Hz, 2H), 7.55 (d, J=8.0 Hz, 1H), 7.65 (d, J=8.4 Hz, 2H), 7.70 (d, J=8.0 Hz, 1H), 7.81 (d, J=1.2 Hz, 1H).

The property values of the title optically active compound with negative optical rotation are as follows.

ESI-MS; m/z 470 $[M^{+}+H]$.

$^{1}$H-NMR ($CDCl_3$) δ (ppm): 2.29 (s, 3H), 2.38 (s, 3H), 3.03 (ddd, J=4.4, 9.6, 12.8 Hz, 1H), 3.34 (ddd, J=2.8, 4.4, 12.4 Hz, 1H), 4.14 (s, 3H), 4.41-4.54 (m, 2H), 4.59 (s, 1H), 6.98 (t, J=1.2, 1H), 7.53 (d, J=9.2 Hz, 2H), 7.55 (d, J=8.0 Hz, 1H), 7.65 (d, J=8.4 Hz, 2H), 7.70 (d, J=8.0 Hz, 1H), 7.81 (d, J=1.2 Hz, 1H).

Examples 120 and 121

Synthesis of (+)-1-[2-[6-methoxy-5-(4-methyl-1H-imidazol-1-yl)pyridin-2-yl]-8-(4-trifluoromethylphenyl)-5,6-dihydro-8H-[1,2,4]triazolo[1,5-a]pyrazin-7-yl]ethanone and (−1-[2-[6-methoxy-5-(4-methyl-1H-imidazol-1-yl)pyridin-2-yl]-8-(4-trifluoromethylphenyl)-5,6-dihydro-8H-[1,2,4]triazolo[1,5-a]pyrazin-7-yl]ethanone

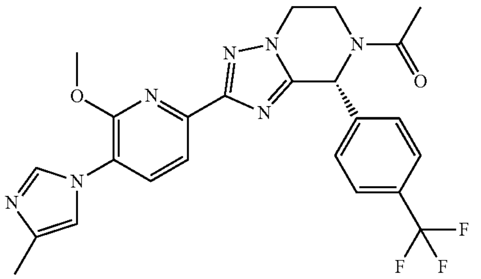

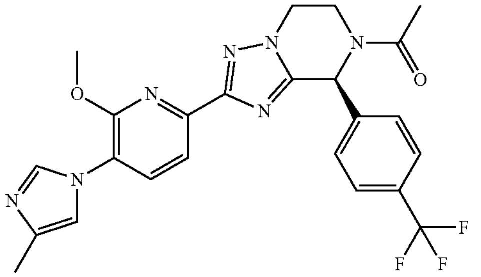

Pyridine (31.3 μL) and acetic anhydride (14.5 μL) were added to a solution of 2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine obtained in Examples 116 and 117 (35 mg) in dichloromethane (1 mL) at 0° C., and the mixture was stirred at room temperature for 1.5 hours. Water was added to the reaction solution, followed by extraction with chloroform. The organic layer was concentrated under reduced pressure. The resulting residue was purified by silica gel column chromatography (carrier: Chromatorex™ NH; elution solvent: ethyl acetate:methanol=1:0→9:1) to obtain a racemate of the title compound. The resulting racemate of the title compound was separated by CHIRALPAK™ IB (2 cm×25 cm, mobile phase:hexane:ethanol=65:35, flow rate: 15 mL/min) to obtain the title optically active compound with a retention time of 6.95 minutes resulting from analysis by CHIRALPAK™ IB (Lot. IB00CD-FD025, hexane:ethanol=8:2, 1.0 mL/min) and positive optical rotation (6.3 mg, >99% ee) and the title optically active compound with a retention time of 8.25 minutes resulting from the same analysis and negative optical rotation (7.4 mg, >99% ee).

The property values of the title optically active compound with positive optical rotation are as follows.

ESI-MS; m/z 498 $[M^{+}+H]$.

$^{1}$H-NMR ($CD_3OD$) δ (ppm): 2.25 (s, 3H), 2.33 (s, 3H), 3.74-3.81 (m, 1H), 4.13 (s, 3H), 4.37-4.51 (m, 3H), 7.16 (s, 1H), 7.22 (s, 1H), 7.60 (d, J=8.0 Hz, 2H), 7.71 (d, J=8.4 Hz, 2H), 7.85 (d, J=8.0 Hz, 1H), 7.89 (d, J=8.0 Hz, 1H), 7.98 (d, J=1.6 Hz, 1H).

The property values of the title optically active compound with negative optical rotation are as follows.

ESI-MS; m/z 498 $[M^{+}+H]$.

$^{1}$H-NMR ($CD_3OD$) δ (ppm): 2.25 (s, 3H), 2.33 (s, 3H), 3.74-3.81 (m, 1H), 4.13 (s, 3H), 4.37-4.51 (m, 3H), 7.16 (s, 1H), 7.22 (s, 1H), 7.60 (d, J=8.0 Hz, 2H), 7.71 (d, J=8.4 Hz, 2H), 7.85 (d, J=8.0 Hz, 1H), 7.89 (d, J=8.0 Hz, 1H), 7.98 (d, J=1.6 Hz, 1H).

Examples 122 and 123

Synthesis of (+)-[2-[6-methoxy-5-(4-methyl-1H-imidazol-1-yl)pyridin-2-yl]-8-(4-trifluoromethylphenyl)-5,6-dihydro-8H-[1,2,4]triazolo[1,5-a]pyrazin-7-yl]phenylmethanone and (−)-[2-[6-methoxy-5-(4-methyl-1H-imidazol-1-yl)pyridin-2-yl]-8-(4-trifluoromethylphenyl)-5,6-dihydro-8H-[1,2,4]triazolo[1,5-a]pyrazin-7-yl]phenylmethanone

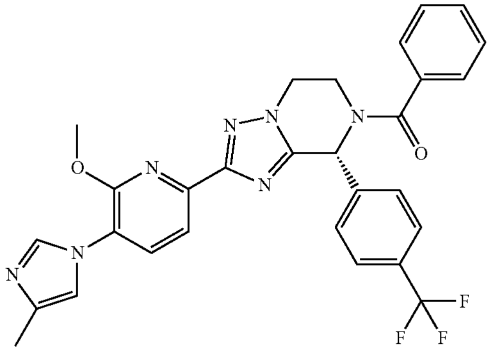

-continued

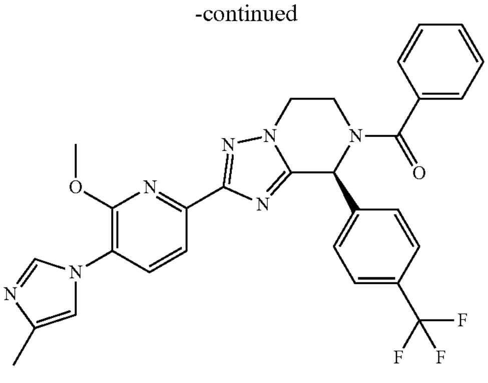

A racemate of the title compound was obtained according to the method of Examples 120 and 121 from 2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine obtained in Examples 116 and 117. The resulting racemate of the title compound was separated by CHIRALPAK™ IA (2 cm×25 cm, mobile phase:ethanol, flow rate: 15 mL/min) to obtain the title optically active compound with a retention time of 7.5 minutes resulting from analysis by CHIRALPAK™ IA (Lot. IA00CE-FA020, ethanol, 1.0 mL/min) and negative optical rotation (6.5 mg, >99% ee) and the title optically active compound with a retention time of 14.4 minutes resulting from the same analysis and positive optical rotation (10.9 mg, >99% ee).

The property values of the title optically active compound with negative optical rotation are as follows.

ESI-MS; m/z 560 $[M^{+}+H]$.

$^{1}$H-NMR ($CDCl_3$) δ (ppm): 2.31 (s, 3H), 3.53-3.65 (m, 2H), 4.17 (s, 3H), 4.40-4.42 (m, 2H), 7.03 (s, 1H), 7.46-7.23 (m, 6H), 7.64-7.68 (m, 5H), 7.85-7.86 (m, 2H).

The property values of the title optically active compound with positive optical rotation are as follows.

ESI-MS; m/z 560 $[M^{+}+H]$.

$^{1}$H-NMR ($CDCl_3$) δ (ppm): 2.31 (s, 3H), 3.53-3.65 (m, 2H), 4.17 (s, 3H), 4.40-4.42 (m, 2H), 7.03 (s, 1H), 7.46-7.23 (m, 6H), 7.64-7.68 (m, 5H), 7.85-7.86 (m, 2H).

Examples 124 and 125

Synthesis of (+)-7-methanesulfonyl-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine and (−)-7-methanesulfonyl-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine

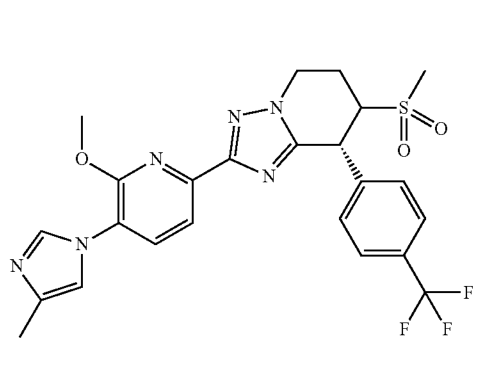

-continued

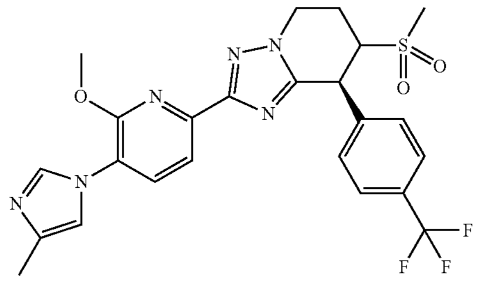

A racemate of the title compound was obtained according to the method of Examples 120 and 121 from 2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine obtained in Examples 116 and 117. The resulting racemate of the title compound was separated by CHIRALPAK™ IB (2 cm×25 cm, mobile phase:hexane:ethanol=65:35, flow rate: 15 mL/min) to obtain the title optically active compound with a retention time of 7.95 minutes resulting from analysis by CHIRALPAK™ IB (Lot. IB00CD-FD025, hexane:ethanol=8:2, 1.0 mL/min) and positive optical rotation (16 mg, >99% ee) and the title optically active compound with a retention time of 8.99 minutes resulting from the same analysis and negative optical rotation (14.8 mg, >99% ee).

The property values of the title optically active compound with positive optical rotation are as follows.

ESI-MS; m/z 534 $[M^{+}+H]$.

$^{1}$H-NMR ($CDCl_3$) δ (ppm): 2.31 (s, 3H), 2.91 (s, 3H), 3.59 (ddd, J=5.2, 11.2, 14.8 Hz, 1H), 4.17 (s, 3H), 4.25-4.30 (m, 1H), 4.45-4.52 (m, 2H), 6.52 (s, 1H), 7.03 (t, J=1.2 Hz, 1H), 7.56 (d, J=8.4 Hz, 2H), 7.65 (d, J=8.0 Hz, 1H), 7.67 (d, J=8.4 Hz, 2H), 7.85 (d, J=8.0 Hz, 1H), 7.87 (d, J=1.2 Hz, 1H).

The property values of the title optically active compound with negative optical rotation are as follows.

ESI-MS; m/z 534 $[M^{+}+H]$.

$^{1}$H-NMR ($CDCl_3$) δ (ppm): 2.31 (s, 3H), 2.91 (s, 3H), 3.59 (ddd, J=5.2, 11.2, 14.8 Hz, 1H), 4.17 (s, 3H), 4.25-4.30 (m, 1H), 4.45-4.52 (m, 2H), 6.52 (s, 1H), 7.03 (t, J=1.2 Hz, 1H), 7.56 (d, J=8.4 Hz, 2H), 7.65 (d, J=8.0 Hz, 1H), 7.67 (d, J=8.4 Hz, 2H), 7.85 (d, J=8.0 Hz, 1H), 7.87 (d, J=1.2 Hz, 1H).

Examples 126 and 127

Synthesis of (+)-7-benzenesulfonyl-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine and (−)-7-benzenesulfonyl-2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine

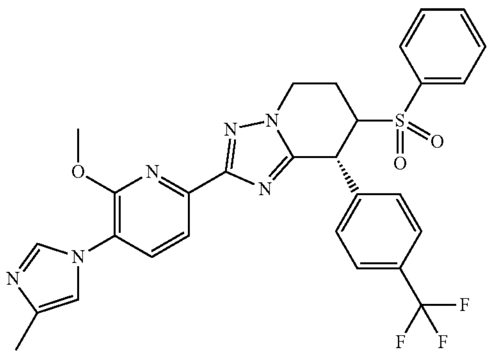

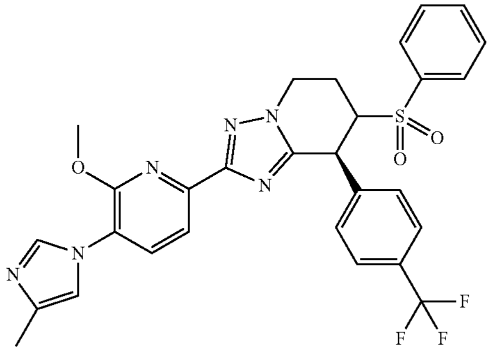

A racemate of the title compound was obtained according to the method of Examples 120 and 121 from 2-[6-methoxy-5-(4-methyl-1H-imidazol-1-yl)pyridin-2-yl]-8-(4-trifluoromethylphenyl)-5,6,7,8-tetrahydro[1,2,4]triazolo[1,5-a]pyrazine obtained in Examples 116 and 117. The resulting racemate of the title compound was separated by CHIRALPAK™ IA (2 cm×25 cm, mobile phase:hexane:ethanol=6:4, flow rate: 15 mL/min) to obtain the title optically active compound with a retention time of 9.5 minutes resulting from analysis by CHIRALPAK™ IA (Lot. IA00CE-FA020, hexane:ethanol=1:1, 1.0 mL/min) (11.4 mg, >99% ee) and the title optically active compound with a retention time of 12.9 minutes resulting from the same analysis (16.6 mg, >99% ee).

The property values of the title optically active compound with a retention time of 9.5 minutes under the analysis conditions are as follows.

ESI-MS; m/z 596 [M$^+$+H].

$^1$H-NMR ($CDCl_3$) δ (ppm): 2.31 (s, 3H), 3.52 (ddd, J=4.4, 12.0, 15.2 Hz, 1H), 3.98 (dt, J=5.2, 12.8 Hz, 1H), 4.15 (s, 3H), 4.21 (dd, J=4.0, 131.2 Hz, 1H), 4.30 (dd, J=5.2, 15.2 Hz, 1H), 6.62 (s, 1H), 7.02 (t, J=1.2 Hz, 1H), 7.45-7.49 (m, 4H), 7.57-7.62 (m, 3H), 7.64 (d, J=8.0 Hz, 1H), 7.82-7.86 (m, 4H).

The property values of the title optically active compound with a retention time of 12.9 minutes under the analysis conditions are as follows.

ESI-MS; m/z 596 [M$^+$+H].

$^1$H-NMR ($CDCl_3$) δ (ppm): 2.31 (s, 3H), 3.52 (ddd, J=4.4, 12.0, 15.2 Hz, 1H), 3.98 (dt, J=5.2, 12.8 Hz, 1H), 4.15 (s, 3H), 4.21 (dd, J=4.0, 131.2 Hz, 1H), 4.30 (dd, J=5.2, 15.2 Hz, 1H), 6.62 (s, 1H), 7.02 (t, J=1.2 Hz, 1H), 7.45-7.49 (m, 4H), 7.57-7.62 (m, 3H), 7.64 (d, J=8.0 Hz, 1H), 7.82-7.86 (m, 4H).

Examples 128, 129, 130, 131, 132 and 133

Synthesis of (+)-(6,8-syn)-6-fluoro-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (−)-(6,8-syn)-6-fluoro-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (+)-2-[6-methoxy-5-(4-methylimidazol-1-yl)pyridin-2-yl]-8-(2-trifluoromethylphenyl)-7,8-dihydro[1,2,4]triazolo[1,5-a]pyridine and (−)-2-[6-methoxy-5-(4-methylimidazol-1-yl)pyridin-2-yl]-8-(2-trifluoromethylphenyl)-7,8-dihydro[1,2,4]triazolo[1,5-a]pyridine and (+)-2-[6-methoxy-5-(4-methylimidazol-1-yl)pyridin-2-yl]-8-(2-trifluoromethylphenyl)-5,8-dihydro[1,2,4]triazolo[1,5-a]pyridine and (−)-2-[6-methoxy-5-(4-methylimidazol-1-yl)pyridin-2-yl]-8-(2-trifluoromethylphenyl)-5,8-dihydro[1,2,4]triazolo[1,5-a]pyridine

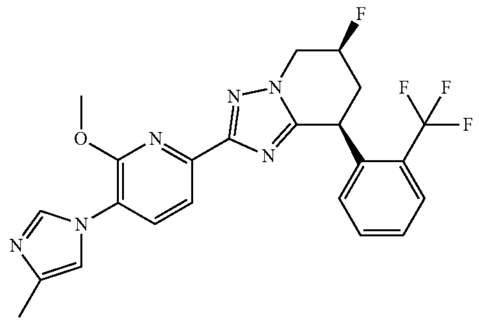

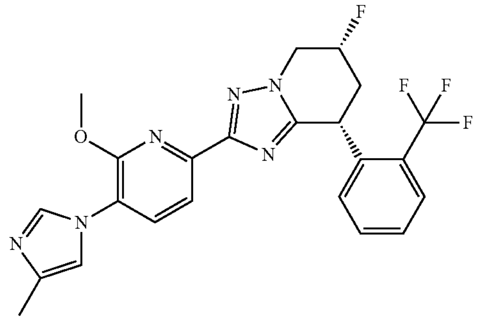

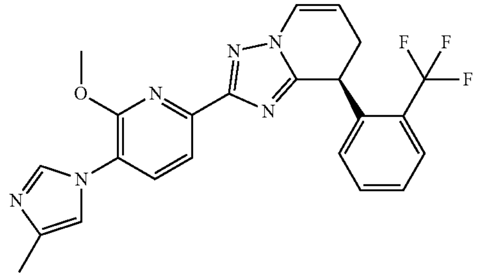

-continued

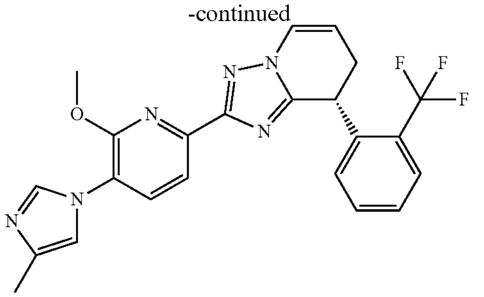

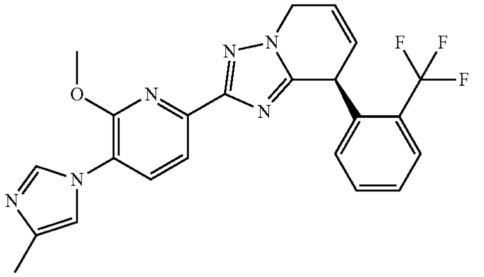

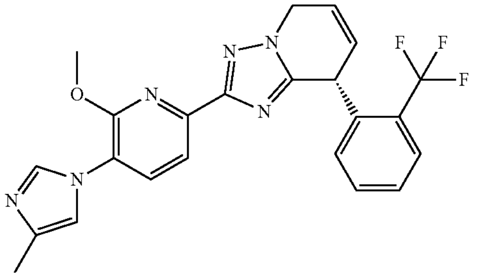

2-[6-Methoxy-5-(4-methylimidazol-1-yl)pyridin-2-yl]-8-(2-trifluoromethylphenyl)-5,6,7,8-tetrahydro[1,2,4]triazolo[1,5-a]pyridin-6-ol obtained in Example 26 (100 mg) was dissolved in methylene chloride (1 mL), and [bis(2-methoxyethyl)amino]sulfur trifluoride (78.5 μL) was added at room temperature. After stirring for 24 hours, the reaction solution was partitioned with a saturated sodium bicarbonate solution and ethyl acetate. The organic layer was washed with brine, dried over magnesium sulfate and then concentrated under reduced pressure. Purification by silica gel column chromatography (mobile phase:ethyl acetate/heptane=0 to 100%) gave a mixture of a fluorinated compound and two olefin compounds (48.7 mg). The mixture was separated by CHIRALPAK™ AD-H (2 cm×25 cm, mobile phase:ethanol:hexane=3:7, flow rate: 15 mL/min) to obtain a 7,8-dihydro compound with a retention time of 11.8 minutes and positive optical rotation (1.6 mg) and a 7,8-dihydro compound with a retention time of 14.1 minutes and negative optical rotation (1.7 mg), and a fluorinated compound with a retention time of 23.0 minutes and positive optical rotation (2.7 mg) and a fluorinated compound with a retention time of 26.3 minutes and negative optical rotation (3.9 mg). At this time, the 5,8-dihydro compound was recovered as a racemate with a retention time of 15.5 minutes. The racemate was separated by CHIRALPAK™ IA (2 cm×25 cm, mobile phase:ethanol:hexane=4:6, flow rate: 13 mL/min) to obtain a 5,8-dihydro compound with a retention time of 13.4 minutes and positive optical rotation (3.3 mg) and a 5,8-dihydro compound with a retention time of 16.1 minutes and negative optical rotation (2.3 mg).

The property values of the title optically active compound obtained from the fluorinated compound with a retention time of 23.0 minutes are as follows.

$^1$H-NMR ($CDCl_3$) δ (ppm): 2.29 (s, 3H), 2.52 (ddd, J=14.8, 14.8, 7.4 Hz, 1H), 2.64-2.80 (m, 1H), 4.15 (s, 3H), 4.59-4.75 (m, 2H), 4.91 (dd, J=7.0, 7.0 Hz, 1H), 5.25-5.43 (m, 1H), 6.98-7.00 (m, 1H), 7.03 (d, J=6.6 Hz, 1H), 7.37-7.42 (m, 1H), 7.43-7.48 (m, 1H), 7.57 (d, J=7.8 Hz, 1H), 7.73 (d, J=6.6 Hz, 1H), 7.75 (d, J=7.8 Hz, 1H), 7.83 (d, J=1.2 Hz, 1H).

The property values of the title optically active compound obtained from the fluorinated compound with a retention time of 26.3 minutes are as follows.

$^1$H-NMR ($CDCl_3$) δ (ppm): 2.29 (s, 3H), 2.52 (ddd, J=14.8, 14.8, 7.4 Hz, 1H), 2.64-2.80 (m, 1H), 4.15 (s, 3H), 4.59-4.75 (m, 2H), 4.91 (dd, J=7.0, 7.0 Hz, 1H), 5.25-5.43 (m, 1H), 6.98-7.00 (m, 1H), 7.03 (d, J=6.6 Hz, 1H), 7.37-7.42 (m, 1H), 7.43-7.48 (m, 1H), 7.57 (d, J=7.8 Hz, 1H), 7.73 (d, J=6.6 Hz, 1H), 7.75 (d, J=7.8 Hz, 1H), 7.83 (d, J=1.2 Hz, 1H).

The property values of the title optically active compound obtained from the 7,8-dihydro compound with a retention time of 11.8 minutes are as follows.

$^1$H-NMR ($CDCl_3$) δ (ppm): 2.29 (s, 3H), 2.59-2.69 (m, 1H), 2.95-3.05 (m, 1H), 4.16 (s, 3H), 4.95 (dd, J=9.0, 9.0 Hz, 1H), 5.72 (ddd, J=7.8, 3.9, 3.9 Hz, 1H), 6.90-7.05 (m, 1H), 7.26-7.35 (m, 2H), 7.40-7.45 (m, 1H), 7.49-7.56 (m, 1H), 7.58 (d, J=8.2 Hz, 1H), 7.74 (d, J=6.6 Hz, 1H), 7.78 (d, J=8.2 Hz, 1H), 7.83 (d, J=1.2 Hz, 1H).

The property values of the title optically active compound obtained from the 7,8-dihydro compound with a retention time of 14.1 minutes are as follows.

$^1$H-NMR ($CDCl_3$) δ (ppm): 2.29 (s, 3H), 2.59-2.69 (m, 1H), 2.95-3.05 (m, 1H), 4.16 (s, 3H), 4.95 (dd, J=9.0, 9.0 Hz, 1H), 5.72 (ddd, J=7.8, 3.9, 3.9 Hz, 1H), 6.90-7.05 (m, 1H), 7.26-7.35 (m, 2H), 7.40-7.45 (m, 1H), 7.49-7.56 (m, 1H), 7.58 (d, J=8.2 Hz, 1H), 7.74 (d, J=6.6 Hz, 1H), 7.78 (d, J=8.2 Hz, 1H), 7.83 (d, J=1.2 Hz, 1H).

The property values of the title optically active compound obtained from the 5,8-dihydro compound with a retention time of 13.4 minutes are as follows.

$^1$H-NMR ($CDCl_3$) δ (ppm): 2.29 (s, 3H), 4.16 (s, 3H), 5.00 (dd, J=17.5, 6.6 Hz, 1H), 5.10 (dd, J=17.5, 4.7 Hz, 1H), 5.35-5.41 (m, 1H), 6.06 (s, 2H), 6.91 (d, J=7.4 Hz, 1H), 6.97-7.05 (m, 1H), 7.34-7.46 (m, 2H), 7.57 (d, J=7.8 Hz, 1H), 7.73 (d, J=7.4 Hz, 1H), 7.78 (d, J=7.8 Hz, 1H), 7.83 (d, J=1.2 Hz, 1H).

The property values of the title optically active compound obtained from the 5,8-dihydro compound with a retention time of 16.1 minutes are as follows.

$^1$H-NMR ($CDCl_3$) δ (ppm): 2.29 (s, 3H), 4.16 (s, 3H), 5.00 (dd, J=17.5, 6.6 Hz, 1H), 5.10 (dd, J=17.5, 4.7 Hz, 1H), 5.35-5.41 (m, 1H), 6.06 (s, 2H), 6.91 (d, J=7.4 Hz, 1H), 6.97-7.05 (m, 1H), 7.34-7.46 (m, 2H), 7.57 (d, J=7.8 Hz, 1H), 7.73 (d, J=7.4 Hz, 1H), 7.78 (d, J=7.8 Hz, 1H), 7.83 (d, J=1.2 Hz, 1H).

Examples 134 and 135

Synthesis of (+)-6,6-difluoro-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (−)-6,6-difluoro-2,6-methoxy-5-(4-methylimidazol-1-yl)pyridin-2-yl]-8-(2-trifluoromethylphenyl)-5,6,7,8-tetrahydro[1,2,4]triazolo[1,5-a]pyridine

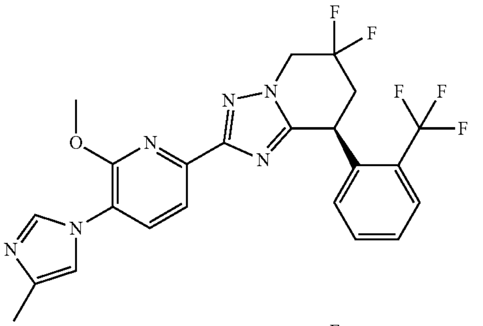

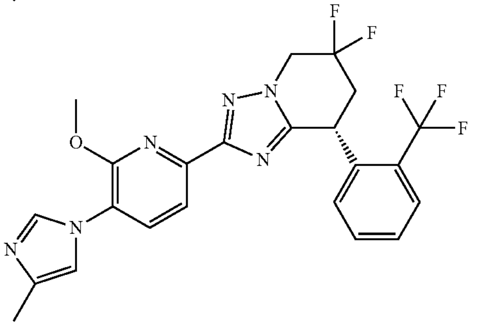

Synthesis of 2-[6-methoxy-5-(4-methylimidazol-1-yl)pyridin-2-yl]-8-(2-trifluoromethylphenyl)-7,8-dihydro-[1,2,4]triazolo[1,5-a]pyridin-6-one 2-[6-Methoxy-5-(4-methylimidazol-1-yl)pyridin-2-yl]-8-(2-trifluoromethylphenyl)-5,6,7,8-tetrahydro[1,2,4]triazolo[1,5-a]pyridin-6-ol obtained in Example 26 (125 mg) was dissolved in methylene chloride (3 mL), and Dess-Martin reagent (226 mg) was added at room temperature. After stirring for 30 minutes, the reaction solution was partitioned with a saturated sodium bicarbonate solution and ethyl acetate. The organic layer was washed with brine, dried over magnesium sulfate and then concentrated under reduced pressure. The resulting crude product was purified by silica gel column chromatography (mobile phase:ethyl acetate/heptane=0 to 100%→methanol/ethyl acetate=10%) to obtain the title compound (28 mg).

ESI-MS; m/z 469 [$M^+$+H].

Synthesis of (±)-6,6-difluoro-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (−)-6,6-difluoro-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine A racemate of the title compound was obtained according to the method of Examples 128, 129, 130, 131, 132 and 133 from 2-[6-methoxy-5-(4-methylimidazol-1-yl)pyridin-2-yl]-8-(2-trifluoromethylphenyl)-7,8-dihydro[1,2,4]triazolo[1,5-a]pyridin-6-one (20.6 mg). The resulting racemate (2.5 mg) was separated by CHIRALPAK™ IA (2 cm×25 cm, mobile phase:ethanol:hexane=3:7, flow rate: 15 mL/min) to obtain the title compound with a retention time of 22.5 minutes and positive optical rotation (1.4 mg) and the title compound with a retention time of 28.5 minutes and negative optical rotation (0.7 mg). The property values of the title optically active compound with a retention time of 22.5 minutes are as follows.

$^1$H-NMR ($CDCl_3$) δ (ppm): 2.19-2.38 (m, 1H), 2.30 (s, 3H), 2.54-2.68 (m, 1H), 2.74-2.85 (m, 2H), 4.15 (s, 3H), 4.81 (dd, J=7.8, 6.6 Hz, 1H), 6.99-7.06 (m, 1H), 7.25 (d, J=7.8 Hz, 1H), 7.43-7.48 (m, 1H), 7.49-7.55 (m, 1H), 7.57 (d, J=8.2 Hz, 1H), 7.77 (d, J=7.8 Hz, 1H), 7.79 (d, J=8.2 Hz, 1H), 7.84 (d, J=1.2 Hz, 1H).

The property values of the title optically active compound with a retention time of 28.5 minutes are as follows.

$^1$H-NMR ($CDCl_3$) δ (ppm): 2.19-2.38 (m, 1H), 2.30 (s, 3H), 2.54-2.68 (m, 1H), 2.74-2.85 (m, 2H), 4.15 (s, 3H), 4.81 (dd, J=7.8, 6.6 Hz, 1H), 6.99-7.06 (m, 1H), 7.25 (d, J=7.8 Hz, 1H), 7.43-7.48 (m, 1H), 7.49-7.55 (m, 1H), 7.57 (d, J=8.2 Hz, 1H), 7.77 (d, J=7.8 Hz, 1H), 7.79 (d, J=8.2 Hz, 1H), 7.84 (d, J=1.2 Hz, 1H).

Examples 136 and 137

Synthesis of (+)-5,5-difluoro-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine and (−)-5,5-difluoro-2-[6-methoxy-5-(4-methylimidazol-1-yl)pyridin-2-yl]-8-(2-trifluoromethylphenyl)-5,6,7,8-tetrahydro[1,2,4]triazolo[1,5-a]pyridine

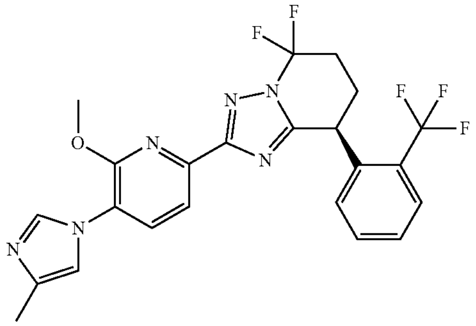

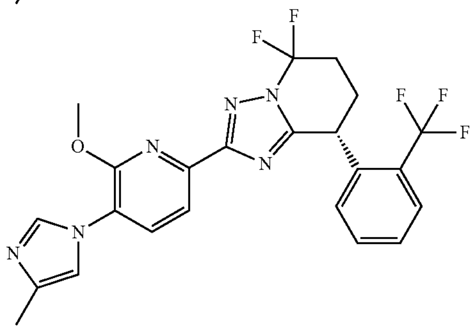

A racemate of the title compound (15 mg) was obtained according to the method of Examples 134 and 135 from 2-[6-methoxy-5-(4-methylimidazol-1-yl)pyridin-2-yl]-8-(2- trifluoromethylphenyl)-7,8-dihydro-6H-[1,2,4]triazolo[1,5-a]pyridin-5-one obtained in Example 72 (100 mg). The resulting racemate was separated by CHIRALPAK™ IB (2 cm×25 cm, mobile phase:ethanol:hexane=2:8, flow rate: 15 mL/min) to obtain the title compound with a retention time of 24.6 minutes and positive optical rotation (1.4 mg) and the title compound with a retention time of 28.5 minutes and negative optical rotation (1.6 mg).

The property values of the title optically active compound with a retention time of 24.6 minutes are as follows.

$^1$H-NMR ($CDCl_3$) δ (ppm): 2.22-2.28 (m, 1H), 2.30 (s, 3H), 2.52-2.67 (m, 2H), 2.74-2.85 (m, 1H), 4.15 (s, 3H), 4.23 (dd, J=11.7, 11.7 Hz, 1H), 4.82 (dd, J=7.8, 6.6 Hz, 1H), 6.95-7.01 (m, 1H), 7.05 (d, J=7.8 Hz, 1H), 7.43-7.48 (m, 1H), 7.49-7.54 (m, 1H), 7.58 (d, J=7.8 Hz, 1H), 7.77 (d, J=7.8 Hz, 1H), 7.79 (d, J=7.8 Hz, 1H), 7.84 (d, J=1.2 Hz, 1H).

The property values of the title optically active compound with a retention time of 28.5 minutes are as follows.

$^1$H-NMR ($CDCl_3$) δ (ppm): 2.22-2.28 (m, 1H), 2.30 (s, 3H), 2.52-2.67 (m, 2H), 2.74-2.85 (m, 1H), 4.15 (s, 3H), 4.23 (dd, J=11.7, 11.7 Hz, 1H), 4.82 (dd, J=7.8, 6.6 Hz, 1H), 6.95-7.01 (m, 1H), 7.05 (d, J=7.8 Hz, 1H), 7.43-7.48 (m, 1H), 7.49-7.54 (m, 1H), 7.58 (d, J=7.8 Hz, 1H), 7.77 (d, J=7.8 Hz, 1H), 7.79 (d, J=7.8 Hz, 1H), 7.84 (d, J=1.2 Hz, 1H).

Examples 138, 139, 140 and 141

Synthesis of (+)-(7,8-syn)-2-[6-methoxy-5-(4-methylimidazol-1-yl)pyridin-2-yl]-8-fluoro-7-(4-trifluoromethylphenyl)-5,6,7,8-tetrahydro[1,2,4]triazolo[1,5-a]pyridine and (−)-(7,8-syn)-2-[6-methoxy-5-(4-methylimidazol-1-yl)pyridin-2-yl]-8-fluoro-7-(4-trifluoromethylphenyl)-5,6,7,8-tetrahydro[1,2,4]triazolo[1,5-a]pyridine and (+)-(7,8-anti)-2-[6-methoxy-5-(4-methylimidazol-1-yl)pyridin-2-yl]-8-fluoro-7-(4-trifluoromethylphenyl)-5,6,7,8-tetrahydro[1,2,4]triazolo[1,5-a]pyridine and (−)-(7,8-anti)-2-[6-methoxy-5-(4-methylimidazol-1-yl)pyridin-2-yl]-8-fluoro-7-(4-trifluoromethylphenyl)-5,6,7,8-tetrahydro[1,2,4]triazolo[1,5-a]pyridine

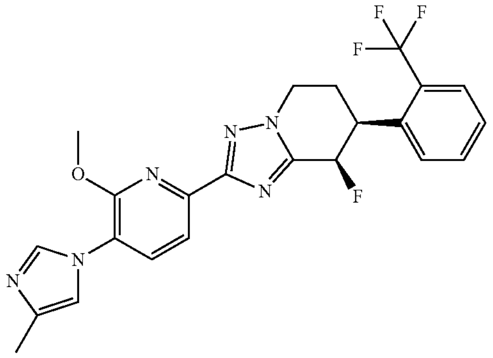

-continued

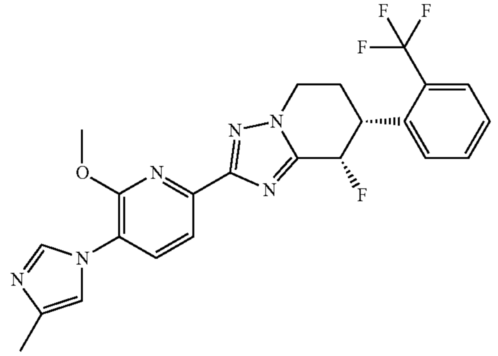

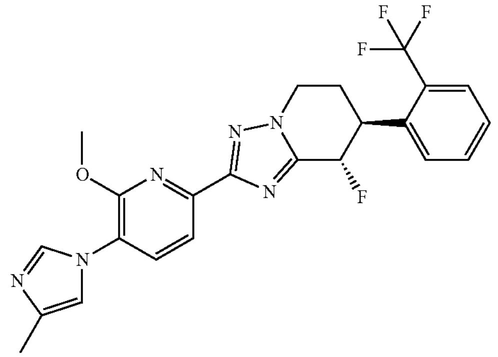

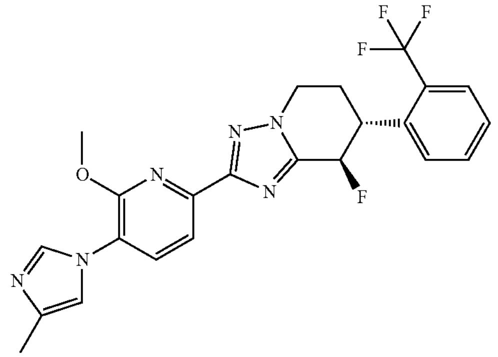

A solution of 2-[6-methoxy-5-(4-methylimidazol-1-yl)pyridin-2-yl]-7-(2-trifluoromethylphenyl)-5,6,7,8-tetrahydro[1,2,4]triazolo[1,5-a]pyridine obtained in Examples 94 and 95 (50 mg) in tetrahydrofuran (1 mL) was added at 0° C. to a lithium diisopropylamine solution prepared from n-butyllithium (93.1 μL) and diisopropylamine (35 μL) in tetrahydrofuran (1 mL). After stirring at the same temperature for 30 minutes, N-fluoro-N'-chloromethyltriethylenediamine bis (tetrafluoroborate) (90.2 mg) was added. After stirring 0° C. for 50 minutes, the reaction temperature was raised to room temperature. After further 50 minutes, the reaction solution was partitioned with water and ethyl acetate. The organic layer was washed with brine and then dried over magnesium sulfate. The oil obtained by removal under reduced pressure was dissolved in methylene chloride (1.1 mL), followed by addition of [bis(2-methoxyethyl)amino]sulfur trifluoride (40.6 μL). The by-product hydroxide was converted to a fluorinated compound.

The racemic syn-compound purified by silica gel column chromatography (mobile phase:ethyl acetate/heptane=0 to 100%) (10.6 mg) was separated by CHIRALPAK™ AD-H (2 cm×25 cm, mobile phase:ethanol:hexane=2:8, flow rate: 15 mL/min) to obtain the title optically active compound with a retention time of 33.0 minutes and negative optical rotation (1.1 mg) and the title optically active compound with a retention time of 46.0 minutes and positive optical rotation (0.6 mg). On the other hand, the racemic anti-compound (7.1 mg) was separated by CHIRALPAK™ IA (2 cm×25 cm, mobile phase:ethanol:hexane=2:8, flow rate: 15 mL/min) to obtain the title optically active compound with a retention time of 42.5 minutes and positive optical rotation (0.68 mg) and the title optically active compound with a retention time of 61.0 minutes and negative optical rotation (0.44 mg). The property values of the title optically active compound obtained from the syn-compound with a retention time of 33.0 minutes are as follows.

$^1$H-NMR ($CDCl_3$) δ (ppm): 2.20-2.30 (m, 1H), 2.31 (s, 3H), 2.95-3.05 (m, 1H), 3.65-3.80 (m, 1H), 4.19 (s, 3H), 4.30-4.40 (m, 1H), 4.65-4.72 (m, 1H), 5.75 (dd, J=49.2, 5.5 Hz, 1H), 6.92-6.94 (m, 1H), 7.46-7.51 (m, 1H), 61-7.71 (m, 2H), 7.66 (d, J=7.8 Hz, 1H), 7.76 (d, J=7.8 Hz, 1H), 7.84-7.87 (m, 1H), 7.87 (d, J=7.8 Hz, 1H).

The property values of the title optically active compound obtained from the syn-compound with a retention time of 46.0 minutes are as follows.

$^1$H-NMR ($CDCl_3$) δ (ppm): 2.20-2.30 (m, 1H), 2.31 (s, 3H), 2.95-3.05 (m, 1H), 3.65-3.80 (m, 1H), 4.19 (s, 3H), 4.30-4.40 (m, 1H), 4.65-4.72 (m, 1H), 5.75 (dd, J=49.2, 5.5 Hz, 1H), 6.92-6.94 (m, 1H), 7.46-7.51 (m, 1H), 61-7.71 (m, 2H), 7.66 (d, J=7.8 Hz, 1H), 7.76 (d, J=7.8 Hz, 1H), 7.84-7.87 (m, 1H), 7.87 (d, J=7.8 Hz, 1H).

The property values of the title optically active compound obtained from the anti-compound with a retention time of 42.5 minutes are as follows.

$^1$H-NMR ($CDCl_3$) δ (ppm): 2.25-2.40 (m, 1H), 2.31 (s, 3H), 2.49-2.59 (m, 1H), 3.96-4.08 (m, 1H), 4.19 (s, 3H), 4.30-4.45 (m, 2H), 5.95 (dd, J=50.0, 7.0 Hz, 1H), 7.03-7.05 (m, 1H), 7.20-7.23 (m, 1H), 7.44-7.49 (m, 1H), 7.56-7.61 (m, 1H), 7.66 (d, J=7.8 Hz, 1H), 7.78 (d, J=7.8 Hz, 1H), 7.86-7.88 (m, 1H), 7.92 (d, J=7.8 Hz, 1H).

The property values of the title optically active compound obtained from the anti-compound with a retention time of 61.0 minutes are as follows.

$^1$H-NMR ($CDCl_3$) δ (ppm): 2.25-2.40 (m, 1H), 2.31 (s, 3H), 2.49-2.59 (m, 1H), 3.96-4.08 (m, 1H), 4.19 (s, 3H), 4.30-4.45 (m, 2H), 5.95 (dd, J=50.0, 7.0 Hz, 1H), 7.03-7.05 (m, 1H), 7.20-7.23 (m, 1H), 7.44-7.49 (m, 1H), 7.56-7.61 (m, 1H), 7.66 (d, J=7.8 Hz, 1H), 7.78 (d, J=7.8 Hz, 1H), 7.86-7.88 (m, 1H), 7.92 (d, J=7.8 Hz, 1H).

Examples 142 and 143

Synthesis of (+)-2-[6-methoxy-5-(4-methylimidazol-1-yl)pyridin-2-yl]-8-(4-methoxy-3-pyrimidin-2-ylphenyl)-5,6,7,8-tetrahydro[1,2,4]triazolo[1,5-a]pyridine and (−)-2-[6-methoxy-5-(4-methylimidazol-1-yl)pyridin-2-yl]-8-(4-methoxy-3-pyrimidin-2-ylphenyl)-5,6,7,8-tetrahydro[1,2,4]triazolo[1,5-a]pyridine

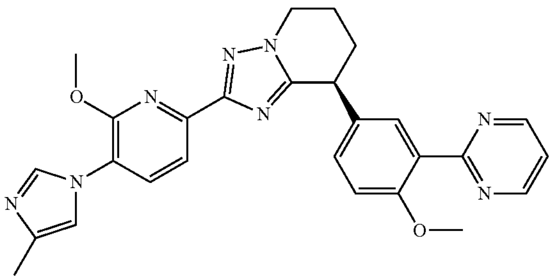

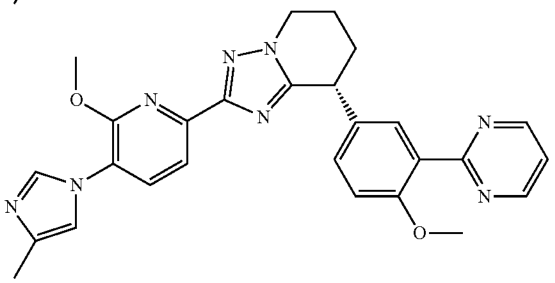

2-[6-Methoxy-5-(4-methylimidazol-1-yl)pyridin-2-yl]-8-(3-bromo-4-methoxyphenyl)-5,6,7,8-tetrahydro[1,2,4]triazolo[1,5-a]pyridine obtained in Examples 68 and 69 (61 mg) was dissolved in N-methylpyrrolidone (1.5 mL). Palladium acetate (5.52 mg), 1,3-bis(diphenylphosphino)propane (20.3 mg), 2-tributylstannylpyrimidine (45.4 mg) and cuprous oxide (26.4 mg) were added and the reaction was initiated at 120° C. After 19 hours, the reaction solution was partitioned with ethyl acetate and water. The organic layer was washed with aqueous ammonia (twice) and brine. Concentration under reduced pressure gave an oil. The oil was purified by silica gel column chromatography (mobile phase:ethyl acetate/heptane=0 to 100%→methanol/ethyl acetate=10%) to obtain a racemate of the title compound (33 mg). The resulting racemate was separated by CHIRALPAK™ IA (2 cm×25 cm, mobile phase:ethanol:hexane=8:2, flow rate: 10 mL/min) to obtain the title compound with a retention time of 38 minutes and positive optical rotation (8.2 mg) and the title compound with a retention time of 57.6 minutes and negative optical rotation (7.8 mg).

The property values of the title optically active compound with a retention time of 38 minutes are as follows.

$^1$H-NMR ($CDCl_3$) δ (ppm): 2.02-2.28 (m, 3H), 2.30 (s, 3H), 2.34-2.43 (m, 1H), 3.87 (s, 3H), 4.16 (s, 3H), 4.34-4.46 (m, 3H), 6.96-7.13 (m, 2H), 7.16-7.25 (m, 2H), 7.55 (d, J=2.3 Hz, 1H), 7.58 (d, J=7.8 Hz, 1H), 7.80 (d, J=7.8 Hz, 1H), 7.82 (d, J=2.3 Hz, 1H), 8.84 (d, J=5.0 Hz, 2H).

The property values of the title optically active compound with a retention time of 57.6 minutes are as follows.

$^1$H-NMR ($CDCl_3$) δ (ppm): 2.02-2.28 (m, 3H), 2.30 (s, 3H), 2.34-2.43 (m, 1H), 3.87 (s, 3H), 4.16 (s, 3H), 4.34-4.46 (m, 3H), 6.96-7.13 (m, 2H), 7.16-7.25 (m, 2H), 7.55 (d, J=2.3

Hz, 1H), 7.58 (d, J=7.8 Hz, 1H), 7.80 (d, J=7.8 Hz, 1H), 7.82 (d, J=2.3 Hz, 1H), 8.84 (d, J=5.0 Hz, 2H).

Examples 144 and 145

Synthesis of (+)-2-[6-methoxy-5-(4-methylimidazol-1-yl)pyridin-2-yl]-8-(4-methoxy-3-pyridazin-3-ylphenyl)-5,6,7,8-tetrahydro[1,2,4]triazolo[1,5-a]pyridine and (−)-2-[6-methoxy-5-(4-methylimidazol-1-yl)pyridin-2-yl]-8-(4-methoxy-3-pyridazin-3-ylphenyl)-5,6,7,8-tetrahydro[1,2,4]triazolo[1,5-a]pyridine

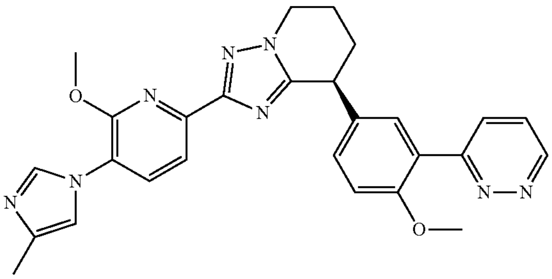

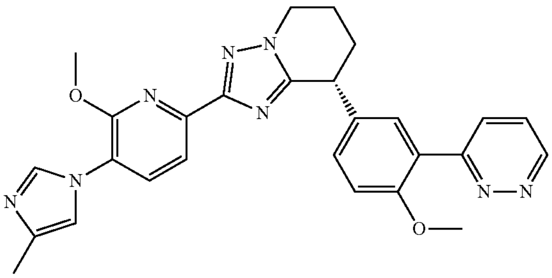

A racemate of the title compound (37.7 mg) was obtained according to the method of Examples 142 and 143 from 2-[6-methoxy-5-(4-methylimidazol-1-yl)pyridin-2-yl]-8-(3-bromo-4-methoxyphenyl)-5,6,7,8-tetrahydro[1,2,4]triazolo[1,5-a]pyridine obtained in Examples 68 and 69. The resulting racemate was separated by CHIRALPAK™ IA (2 cm×25 cm, mobile phase:ethanol:hexane=9:1, flow rate: 10 mL/min) to obtain the title compound with a retention time of 20.5 minutes and positive optical rotation (7.4 mg) and the title compound with a retention time of 65.5 minutes and negative optical rotation (9.9 mg).

The property values of the title optically active compound with a retention time of 20.5 minutes are as follows.

$^1$H-NMR ($CDCl_3$) δ (ppm): 2.04-2.28 (m, 3H), 2.30 (s, 3H), 2.37-2.45 (m, 1H), 3.85 (s, 3H), 4.16 (s, 3H), 4.37-4.45 (m, 3H), 6.88-6.93 (m, 2H), 7.17-7.24 (m, 2H), 7.59 (d, J=8.2 Hz, 1H), 7.62 (dd, J=5.2, 2.2 Hz, 1H), 7.78 (d, J=8.2 Hz, 1H), 7.82 (d, J=1.2 Hz, 1H), 9.17 (dd, J=5.2, 1.2 Hz, 1H), 9.37 (dd, J=1.3, 1.2 Hz, 1H).

The property values of the title optically active compound with a retention time of 65.5 minutes are as follows.

$^1$H-NMR ($CDCl_3$) δ (ppm): 2.04-2.28 (m, 3H), 2.30 (s, 3H), 2.37-2.45 (m, 1H), 3.85 (s, 3H), 4.16 (s, 3H), 4.37-4.45 (m, 3H), 6.88-6.93 (m, 2H), 7.17-7.24 (m, 2H), 7.59 (d, J=8.2 Hz, 1H), 7.62 (dd, J=5.2, 2.2 Hz, 1H), 7.78 (d, J=8.2 Hz, 1H), 7.82 (d, J=1.2 Hz, 1H), 9.17 (dd, J=5.2, 1.2 Hz, 1H), 9.37 (dd, J=1.3, 1.2 Hz, 1H).

Examples 146 and 147

Synthesis of (+)-2-[6-methoxy-5-4-methylimidazol-1-yl)pyridin-2-yl]-8-4-fluoro-3-pyrimidin-2-ylphenyl)-5,6,7,8-tetrahydro[1,2,4]triazolo[1,5-a]pyridine and (−)-2-[6-methoxy-5-(4-methylimidazol-1-yl)pyridin-2-yl]-8-(4-fluoro-3-pyrimidin-2-ylphenyl)-5,6,7,8-tetrahydro[1,2,4]triazolo[1,5-a]pyridine

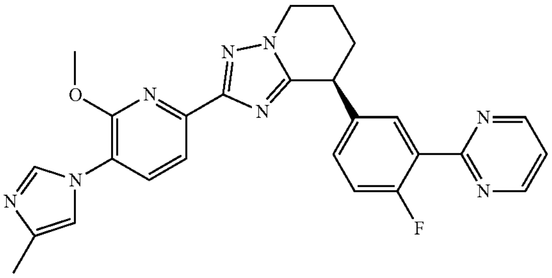

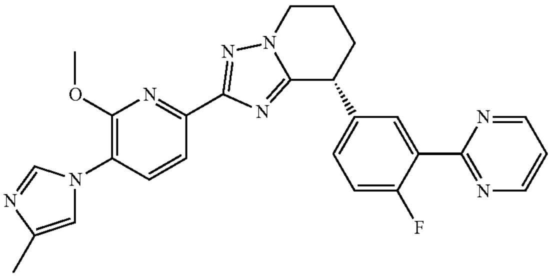

A racemate of the title compound (32 mg) was obtained according to the method of Examples 142 and 143 from 2-[6-methoxy-5-(4-methylimidazol-1-yl)pyridin-2-yl]-8-(3-bromo-4-fluorophenyl)-5,6,7,8-tetrahydro[1,2,4]triazolo[1,5-a]pyridine obtained in Examples 80 and 81 (70 mg). The resulting racemate was separated by CHIRALPAK™ IA (2 cm×25 cm, mobile phase:ethanol:hexane=75:25, flow rate: 10 mL/min) to obtain the title compound with a retention time of 25 minutes and positive optical rotation (3.8 mg) and the title compound with a retention time of 34.5 minutes and negative optical rotation (3 mg). The property values of the title optically active compound with a retention time of 25 minutes are as follows.

$^1$H-NMR ($CDCl_3$) δ (ppm): 2.10-2.18 (m, 2H), 2.20-2.25 (m, 1H), 2.30 (s, 3H), 2.37-2.48 (m, 1H), 4.16 (s, 3H), 4.42 (dd, J=11.7, 6.2 Hz, 2H), 4.48 (dd, J=6.6, 6.6 Hz, 1H), 6.91-6.98 (m, 1H), 7.15-7.26 (m, 3H), 7.58 (d, J=7.8 Hz, 1H), 7.78 (d, J=7.8 Hz, 1H), 7.82 (d, J=1.2 Hz, 1H), 7.91 (dd, J=7.0, 1.2 Hz, 1H), 8.85 (d, J=5.1 Hz, 2H).

The property values of the title optically active compound with a retention time of 34.5 minutes are as follows.

$^1$H-NMR ($CDCl_3$) δ (ppm): 2.10-2.18 (m, 2H), 2.20-2.25 (m, 1H), 2.30 (s, 3H), 2.37-2.48 (m, 1H), 4.16 (s, 3H), 4.42 (dd, J=11.7, 6.2 Hz, 2H), 4.48 (dd, J=6.6, 6.6 Hz, 1H), 6.91-6.98 (m, 1H), 7.15-7.26 (m, 3H), 7.58 (d, J=7.8 Hz, 1H), 7.78 (d, 0.1=7.8 Hz, 1H), 7.82 (d, J=1.2 Hz, 1H), 7.91 (dd, J=7.0, 1.2 Hz, 1H), 8.85 (d, J=5.1 Hz, 2H).

Examples 148 and 149

Synthesis of (+)-2-[6-methoxy-5-(4-methyl-1H-imidazol-1-yl)pyridin-2-yl]-8-(3-pyrazin-2-ylphenyl)-5,6-dihydro-8H-[1,2,4]triazolo[1,5-c][1,4oxazine and (−)-2-[6-methoxy-5-4-methyl-1H-imidazol-1-yl) pyridin-2-yl]-8-(3-pyrazin-2-ylphenyl)-5,6-dihydro-8H-1,2,4]triazolo[1,5-c][1,4]oxazine

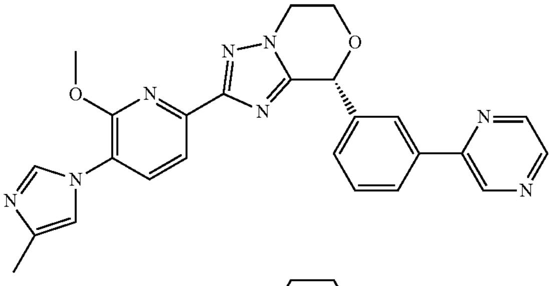

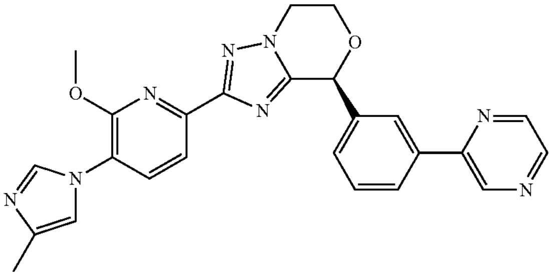

A racemate of the title compound was obtained according to the method of Examples 142 and 143 from 8-(3-bromophenyl)-2-[6-methoxy-5-(4-methyl-1H-imidazol-1-yl)pyridin-2-yl]-5,6-dihydro-8H-[1,2,4]triazolo[1,5-c][1,4]oxazine obtained in Examples 64 and 65 (40 mg). The resulting racemate of the title compound was separated by CHIRALCEL™ IB (2 cm×25 cm, mobile phase:hexane:ethanol=1:1, flow rate: 15 mL/min) to obtain the title optically active compound with a retention time of 14.16 minutes resulting from analysis by CHIRALPAK™ IB (Lot. IB00CD-FD026, hexane:ethanol=7:3, 1.0 mL/min) and positive optical rotation (1.6 mg, >99% ee) and the title optically active compound with a retention time of 18.25 minutes resulting from the same analysis and negative optical rotation (3.5 mg, >99% ee).

The property values of the title optically active compound with positive optical rotation are as follows.

$^1$H-NMR ($CDCl_3$) δ (ppm): 2.30 (s, 3H), 4.17 (s, 3H), 4.18-4.25 (m, 1H), 4.38 (dt, J=4.4, 12.0 Hz, 1H), 4.41-4.56 (m, 2H), 6.11 (s, 1H), 7.00 (d, J=2.4 Hz, 1H), 7.56-7.63 (m, 3H), 7.81-7.84 (m, 2H), 8.05 (dt, J=1.6, 7.6 Hz, 1H), 8.19 (t, J=2.0 Hz, 1H), 8.53 (d, J=2.4 Hz, 1H), 8.64 (dd, J=1.6, 3.6 Hz, 1H), 9.04 (d, J=1.2 Hz, 1H).

The property values of the title optically active compound with negative optical rotation are as follows.

$^1$H-NMR ($CDCl_3$) δ (ppm): 2.30 (s, 3H), 4.17 (s, 3H), 4.18-4.25 (m, 1H), 4.38 (dt, J=4.4, 12.0 Hz, 1H), 4.41-4.56 (m, 2H), 6.11 (s, 1H), 7.00 (d, J=2.4 Hz, 1H), 7.56-7.63 (m, 3H), 7.81-7.84 (m, 2H), 8.05 (dt, J=1.6, 7.6 Hz, 1H), 8.19 (t, J=2.0 Hz, 1H), 8.53 (d, J=2.4 Hz, 1H), 8.64 (dd, J=1.6, 3.6 Hz, 1H), 9.04 (d, J=1.2 Hz, 1H).

Examples 150 and 151

Synthesis of (+)-2-[6-methoxy-5-4-methylimidazol-1-yl)pyridin-2-yl]-8-4-methoxy-3-(1-methyl-1H-pyrazol-4-yl)phenyl)-5,6,7,8-tetrahydro[1,2,4]triazolo[1,5-a]pyridine and (+)-2-[6-methoxy-5-(4-methylimidazol-1-yl)pyridin-2-yl]-8-(4-methoxy-3-(1-methyl-1H-pyrazol-4-yl)phenyl)-5,6,7,8-tetrahydro[1,2,4]triazolo[1,5-a]pyridine

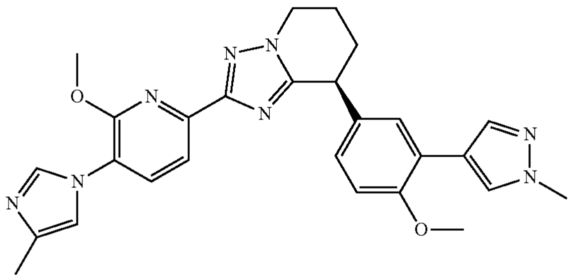

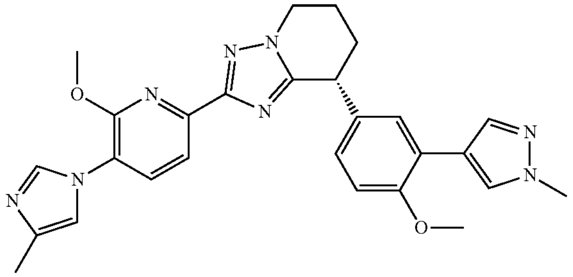

2-[6-Methoxy-5-(4-methylimidazol-1-yl)pyridin-2-yl]-8-(3-bromo-4-methoxyphenyl)-5,6,7,8-tetrahydro[1,2,4]triazolo[1,5-a]pyridine obtained in Examples 68 and 69 (100 mg) was dissolved in toluene (3 mL) and methanol (600 μL). A 2 M sodium carbonate solution (101 μL), 1-methyl-4-(4,4,5,5-tetramethyl-1,3,2-dioxaborolan-2-yl)-1H-pyrazole (63 mg) and tetralcistriphenylphosphine palladium (23.4 mg) were added and the mixture was stirred under microwave irradiation at 120° C. for three hours. The reaction solution was partitioned with ethyl acetate and water. Then, the organic layer was washed with water and brine and dried over magnesium sulfate. Concentration under reduced pressure gave an oil. The oil was purified by silica gel column chromatography (mobile phase:ethyl acetate/heptane=0 to 100%→methanol/ethyl acetate=20%) to obtain a racemate of the title compound (50.6 mg). The resulting racemate was separated by CHIRALPAK™ IB (2 cm×25 cm, mobile phase: ethanol:hexane=5:5, flow rate: 12 mL/min) to obtain the title compound with a retention time of 29.5 minutes and positive optical rotation (13.2 mg) and the title compound with a retention time of 39.0 minutes and negative optical rotation (11.6 mg). The property values of the title optically active compound with a retention time of 29.5 minutes are as follows.

$^1$H-NMR ($CDCl_3$) δ (ppm): 2.04-2.16 (m, 2H), 2.18-2.27 (m, 1H), 2.30 (s, 3H), 2.34-2.43 (m, 1H), 3.89 (s, 3H), 3.93 (s, 3H), 4.17 (s, 3H), 4.33-4.47 (m, 3H), 6.87-6.94 (m, 2H), 6.99-7.01 (m, 1H), 7.31 (d, J=2.0 Hz, 1H), 7.58 (d, J=7.8 Hz, 1H), 7.80 (d, J=7.8 Hz, 1H), 7.81-7.83 (m, 3H).

The property values of the title optically active compound with a retention time of 39.0 minutes are as follows.

$^1$H-NMR ($CDCl_3$) δ (ppm): 2.04-2.16 (m, 2H), 2.18-2.27 (m, 1H), 2.30 (s, 3H), 2.34-2.43 (m, 1H), 3.89 (s, 3H), 3.93 (s, 3H), 4.17 (s, 3H), 4.33-4.47 (m, 3H), 6.87-6.94 (m, 2H), 6.99-7.01 (m, 1H), 7.31 (d, J=2.0 Hz, 1H), 7.58 (d, J=7.8 Hz, 1H), 7.80 (d, J=7.8 Hz, 1H), 7.81-7.83 (m, 3H).

Examples 152 and 153

Synthesis of (+)-2-[6-methoxy-5-(4-methylimidazol-1-yl)pyridin-2-yl]-8-(4-methoxy-3-pyridin-3-ylphenyl)-5,6,7,8-tetrahydro[1,2,4]triazolo[1,5-a]pyridine and (−)-2-[6-methoxy-5-(4-methylimidazol-1-yl)pyridin-2-yl]-8-(4-methoxy-3-pyridin-3-ylphenyl)-5,6,7,8-tetrahydro[1,2,4]triazolo[1,5-a]pyridine

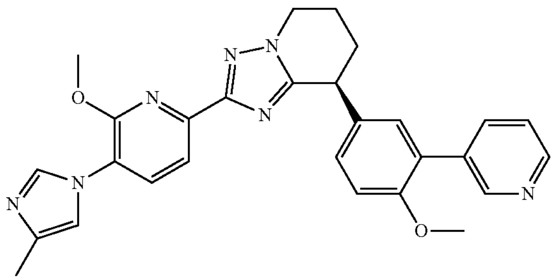

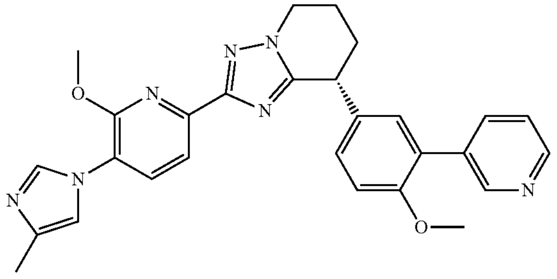

A racemate of the title compound (56 mg) was obtained according to the method of Examples 150 and 151 from 2-[6-methoxy-5-(4-methylimidazol-1-yl)pyridin-2-yl]-8-(3-bromo-4-methoxyphenyl)-5,6,7,8-tetrahydro[1,2,4]triazolo[1,5-a]pyridine obtained in Examples 68 and 69 (100 mg). The resulting racemate was separated by CHIRALPAK™ IB (2 cm×25 cm, mobile phase:ethanol:hexane=3:7, flow rate: 15 mL/min) to obtain the title compound with a retention time of 41.5 minutes and positive optical rotation (17.5 mg) and the title compound with a retention time of 53.5 minutes and negative optical rotation (18 mg).

The property values of the title optically active compound with a retention time of 41.5 minutes are as follows.

$^1$H-NMR ($CDCl_3$) δ (ppm): 2.06-2.16 (m, 2H), 2.19-2.28 (m, 1H), 2.30 (s, 3H), 2.35-2.44 (m, 1H), 3.81 (s, 3H), 3.99 (s, 3H), 4.16 (s, 3H), 4.34-4.47 (m, 3H), 6.95 (d, J=9.4 Hz, 1H), 6.95-7.05 (m, 1H), 7.09-7.14 (m, 2H), 7.31 (dd, J=7.8, 5.7 Hz, 1H), 7.59 (d, J=7.8 Hz, 1H), 7.78-7.84 (m, 3H), 7.87 (d, J=2.0 Hz, 1H), 8.54 (dd, J=5.7, 2.0 Hz, 1H).

The property values of the title optically active compound with a retention time of 53.5 minutes are as follows.

$^1$H-NMR ($CDCl_3$) δ (ppm): 2.06-2.16 (m, 2H), 2.19-2.28 (m, 1H), 2.30 (s, 3H), 2.35-2.44 (m, 1H), 3.81 (s, 3H), 3.99 (s, 3H), 4.16 (s, 3H), 4.34-4.47 (m, 3H), 6.95 (d, J=9.4 Hz, 1H), 6.95-7.05 (m, 1H), 7.09-7.14 (m, 2H), 7.31 (dd, J=7.8, 5.7 Hz, 1H), 7.59 (d, J=7.8 Hz, 1H), 7.78-7.84 (m, 3H), 7.87 (d, J=2.0 Hz, 1H), 8.54 (dd, J=5.7, 2.0 Hz, 1H).

Examples 154 and 155

Synthesis of (+)-8-[3-(6-chloropyridin-3-yl)-4-methoxyphenyl]-2-[6-methoxy-5-(4-methylimidazol-1-yl)pyridin-2-yl-5,6,7,8-tetrahydro[1,2,4]triazolo[1,5-a]pyridine and (−)-8-[3-(6-chloropyridin-3-yl)-4-methoxyphenyl]-2-[6-methoxy-5-(4-methylimidazol-1-yl)pyridin-2-yl-5,6,7,8-tetrahydro[1,2,4]triazolo[1,5-a]pyridine

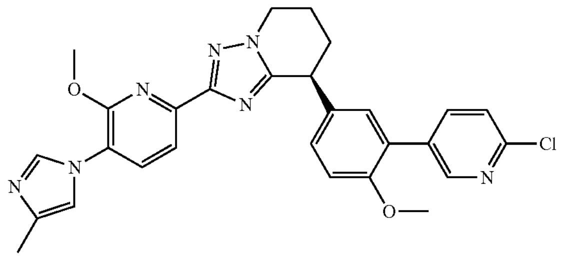

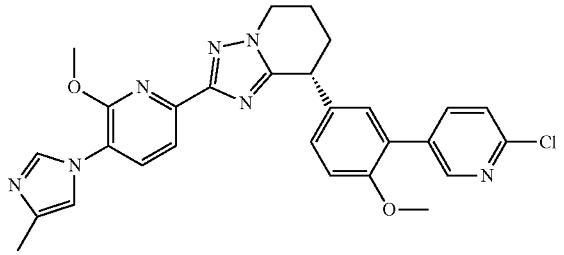

A racemate of the title compound (90.3 mg) was obtained according to the method of Examples 150 and 151 from 2-[6-methoxy-5-(4-methylimidazol-1-yl)pyridin-2-yl]-8-(3-bromo-4-methoxyphenyl)-5,6,7,8-tetrahydro[1,2,4]triazolo[1,5-a]pyridine obtained in Examples 68 and 69 (100 mg). The resulting racemate was separated by CHIRALPAK™ IB (2 cm×25 cm, mobile phase:ethanol:hexane=2:8, flow rate: 15 mL/min) to obtain the title compound with a retention time of 42 minutes and positive optical rotation (22 mg) and the title compound with a retention time of 58.5 minutes and negative optical rotation (20 mg).

The property values of the title optically active compound with a retention time of 42 minutes are as follows.

$^1$H-NMR ($CDCl_3$) δ (ppm): 2.04-2.17 (m, 2H), 2.18-2.28 (m, 1H), 2.30 (s, 3H), 2.35-2.45 (m, 1H), 3.81 (s, 3H), 3.99 (s, 3H), 4.16 (s, 3H), 4.34-4.47 (m, 3H), 6.95 (d, J=8.2 Hz, 1H), 6.98-7.03 (m, 1H), 7.07-7.16 (m, 2H), 7.34 (d, J=8.2 Hz, 1H), 7.59 (d, J=8.2 Hz, 1H), 7.75-7.85 (m, 3H), 8.49 (d, J=2.0 Hz, 1H).

The property values of the title optically active compound with a retention time of 58.5 minutes are as follows.

$^1$H-NMR ($CDCl_3$) δ (ppm): 2.04-2.17 (m, 2H), 2.18-2.28 (m, 1H), 2.30 (s, 3H), 2.35-2.45 (m, 1H), 3.81 (s, 3H), 3.99 (s, 3H), 4.16 (s, 3H), 4.34-4.47 (m, 3H), 6.95 (d, J=8.2 Hz, 1H), 6.98-7.03 (m, 1H), 7.07-7.16 (m, 2H), 7.34 (d, J=8.2 Hz, 1H), 7.59 (d, J=8.2 Hz, 1H), 7.75-7.85 (m, 3H), 8.49 (d, J=2.0 Hz, 1H).

Example 156

Synthesis of (+)-8-biphenyl-3-yl-2-[6-methoxy-5-(4-methyl-1H-imidazol-1-yl)pyridin-2-yl]-5,6-dihydro-8H-[1,2,4]triazolo[1,5-c][1,4]oxazine

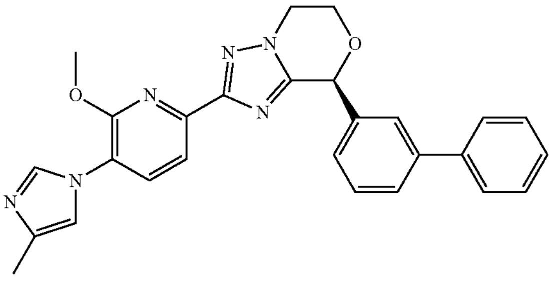 [SMILES: COc1nc(-c2nc3n(n2)CCO[C@H]3c2cccc(-c3ccccc3)c2)ccc1-n1cnc(C)c1]

The title compound (22 mg) was obtained according to the method of Examples 150 and 151 from (+)-8-(3-bromophenyl)-2-[6-methoxy-5-(4-methyl-1H-imidazol-1-yl)pyridin-2-yl]-5,6-dihydro-8H-[1,2,4]triazolo[1,5-c][1,4]oxazine obtained in Example 64 (42.6 mg). The property values of the compound are as follows.

$^1$H-NMR ($CDCl_3$) δ (ppm): 2.30 (s, 3H), 4.17 (s, 3H), 4.18-4.22 (m, 1H), 4.36 (dt, J=4.4, 12.4 Hz, 1H), 4.44-4.52 (m, 2H), 6.08 (s, 1H), 7.01 (t, J=1.2 Hz, 1H), 7.35 (tt, J=2.0, 7.2 Hz, 1H), 7.41-7.50 (m, 4H), 7.57-7.63 (m, 4H), 7.70 (t, J=1.6 Hz, 1H), 7.82 (d, J=9.2 Hz, 1H), 7.83 (s, 1H).

Example 157

Synthesis of (−)-8-biphenyl-3-yl-2-[6-methoxy-5-(4-methyl-1H-imidazol-1-yl)pyridin-2-yl]-5,6-dihydro-8H-[1,2,4]triazolo[1,5-c][1,4]oxazine

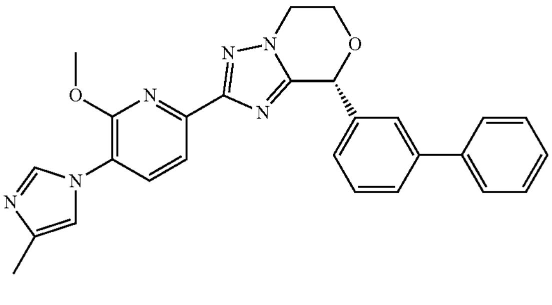 [SMILES: COc1nc(-c2nc3n(n2)CCO[C@@H]3c2cccc(-c3ccccc3)c2)ccc1-n1cnc(C)c1]

The title compound (17 mg) was obtained according to the method of Examples 150 and 151 from (−)-8-(3-bromophenyl)-2-[6-methoxy-5-(4-methyl-1H-imidazol-1-yl)pyridin-2-yl]-5,6-dihydro-8H-[1,2,4]triazolo[1,5-c][1,4]oxazine obtained in Example 65 (22.7 mg). The property values of the compound are as follows.

$^1$H-NMR ($CDCl_3$) δ (ppm): 2.30 (s, 3H), 4.17 (s, 3H), 4.18-4.22 (m, 1H), 4.36 (dt, J=4.4, 12.4 Hz, 1H), 4.44-4.52 (m, 2H), 6.08 (s, 1H), 7.01 (t, J=1.2 Hz, 1H), 7.35 (tt, J=2.0, 7.2 Hz, 1H), 7.41-7.50 (m, 4H), 7.57-7.63 (m, 4H), 7.70 (t, J=1.6 Hz, 1H), 7.82 (d, J=9.2 Hz, 1H), 7.83 (s, 1H).

Examples 158 and 159

(+)-2-[6-Methoxy-5-(4-methyl-1H-imidazol-1-yl)pyridin-2-yl]-8-(6-phenylpyridin-2-yl)-5,6,7,8-tetrahydro[1,2,4]triazolo[1,5-a]pyridine and (−)-2-[6-methoxy-5-(4-methyl-1H-imidazol-1-yl)pyridin-2-yl]-8-(6-phenylpyridin-2-yl)-5,6,7,8-tetrahydro[1,2,4]triazolo[1,5-a]pyridine

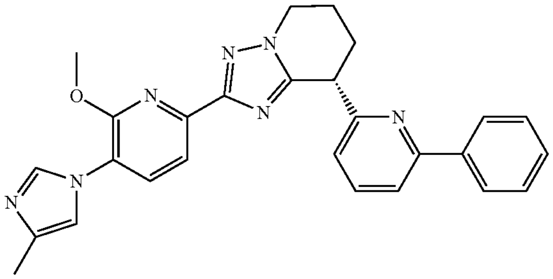

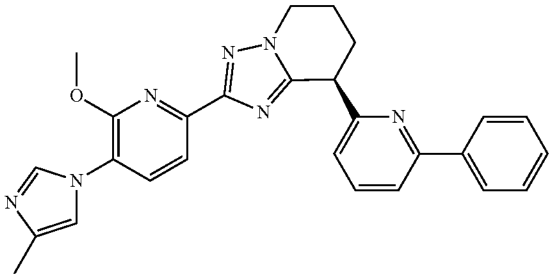

A racemate of the title compound (19 mg) was obtained according to the method of Examples 150 and 151 from 8-(6-bromopyridin-2-yl)-2-[6-methoxy-5-(4-methyl-1H-imidazol-1-yl)pyridin-2-yl]-5,6,7,8-tetrahydro[1,2,4]triazolo[1,5-a]pyridine obtained in Examples 70 and 71 (41.7 mg). The resulting racemate was separated by CHIRALPAK™ IA (2 cm×25 cm; mobile phase:hexane:ethanol=50:50) to obtain the title optically active compound with a retention time of 4.9 minutes and positive optical rotation (7.1 mg, >99% ee) and the title optically active compound with a retention time of 7.6 minutes and negative optical rotation (6.3 mg, >99% ee).

The property values of the title compound with positive optical rotation are as follows.

ESI-MS; m/z 464 [M$^+$+H]. 1H-NMR ($CDCl_3$) δ (ppm): 2.09-2.14 (m, 1H), 2.30 (d, J=1.2 Hz, 3H), 2.31-2.53 (m, 2H), 2.54-2.59 (m, 1H), 4.17 (s, 3H), 4.34-4.39 (m, 1H), 4.44-4.50 (m, 1H), 4.65 (t, J=6.0 Hz, 1H), 7.00 (t, J=1.2 Hz, 1H), 7.14 (dd, J=0.8 Hz, 7.6 Hz, 1H), 7.38-7.47 (m, 3H), 7.58 (d, J=8.0 Hz, 1H), 7.63 (dd, J=0.8 Hz, 7.6 Hz, 1H), 7.71 (t, J=7.6 Hz, 1H), 7.81 (d, J=8.0 Hz, 1H), 7.82 (d, J=1.2 Hz, 1H), 7.96-7.98 (m, 2H).

The property values of the title compound with negative optical rotation are as follows.

ESI-MS; m/z 464 [M$^+$+H]. 1H-NMR ($CDCl_3$) δ (ppm): 2.09-2.14 (m, 1H), 2.30 (d, J=1.2 Hz, 3H), 2.31-2.53 (m, 2H), 2.54-2.59 (m, 1H), 4.17 (s, 3H), 4.34-4.39 (m, 1H), 4.44-4.50 (m, 1H), 4.65 (t, J=6.0 Hz, 1H), 7.00 (t, J=1.2 Hz, 1H), 7.14 (dd, J=0.8 Hz, 7.6 Hz, 1H), 7.38-7.47 (m, 3H), 7.58 (d, J=8.0 Hz, 1H), 7.63 (dd, J=0.8 Hz, 7.6 Hz, 1H), 7.71 (t, J=7.6 Hz, 1H), 7.81 (d, J=8.0 Hz, 1H), 7.82 (d, J=1.2 Hz, 1H), 7.96-7.98 (m, 2H).

Examples 160 and 161

Synthesis of (+)-2-[6-methoxy-5-(4-methylimidazol-1-yl)pyridin-2-yl]-8-(3-methanesulfonyl-4-methoxyphenyl)-5,6,7,8-tetrahydro[1,2,4]triazolo[1,5-a]pyridine and (−)-2-[6-methoxy-5-(4-methylimidazol-1-yl)pyridin-2-yl]-8-(3-methanesulfonyl-4-methoxyphenyl)-5,6,7,8-tetrahydro[1,2,4]triazolo[1,5-a]pyridine

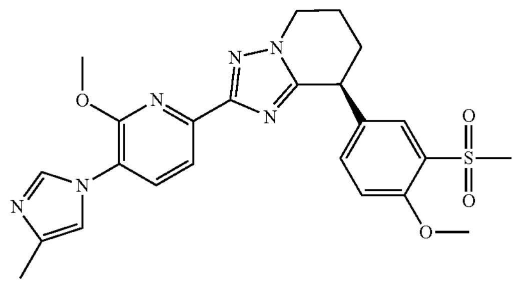

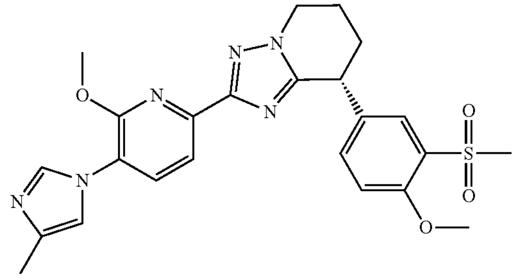

2-[6-Methoxy-5-(4-methylimidazol-1-yl)pyridin-2-yl]-8-(3-bromo-4-methoxyphenyl)-5,6,7,8-tetrahydro[1,2,4]friazolo[1,5-a]pyricline obtained in Examples 68 and 69 (100 mg) was dissolved in dimethyl sulfoxide (2 mL). Sodium methanesulfinate (165 mg), L-proline (18.6 mg), sodium hydroxide (12.8 mg) and copper iodide (30.8 mg) were added. The reaction was initiated under microwave irradiation at 140° C. After three hours, the reaction solution was partitioned with ethyl acetate and water. Then, the organic layer was washed with water and brine and dried over magnesium sulfate. Concentration under reduced pressure gave an oil. The oil was purified by silica gel column chromatography (mobile phase:ethyl acetate/heptane=0 to 100%→methanol/ethyl acetate=15%) to obtain a racemate of the title compound (58.9 mg). The resulting racemate was separated by CHIRALCEL™ OJ-H (2 cm×25 cm, mobile phase:ethanol:hexane=5:5, flow rate: 12 mL/min) to obtain the title compound with a retention time of 16.0 minutes and positive optical rotation (19 mg) and the title compound with a retention time of 22.0 minutes and negative optical rotation (16.5 mg).

The property values of the title optically active compound with a retention time of 16.0 minutes are as follows.

$^1$H-NMR ($CDCl_3$) δ (ppm): 2.03-2.18 (m, 2H), 2.18-2.28 (m, 1H), 2.30 (s, 3H), 2.35-2.44 (m, 1H), 3.24 (s, 3H), 3.99 (s, 3H), 4.16 (s, 3H), 4.36-4.45 (m, 3H), 6.89-6.92 (m, 1H), 6.92 (d, J=9.0 Hz, 1H), 7.34-7.38 (m, 1H), 7.59 (d, J=9.0 Hz, 1H), 7.75 (d, J=9.0 Hz, 1H), 7.81-7.85 (m, 1H), 7.87 (d, J=2.3 Hz, 1H).

The property values of the title optically active compound with a retention time of 22.0 minutes are as follows.

$^1$H-NMR ($CDCl_3$) δ (ppm): 2.03-2.18 (m, 2H), 2.18-2.28 (m, 1H), 2.30 (s, 3H), 2.35-2.44 (m, 1H), 3.24 (s, 3H), 3.99 (s, 3H), 4.16 (s, 3H), 4.36-4.45 (m, 3H), 6.89-6.92 (m, 1H), 6.92 (d, J=9.0 Hz, 1H), 7.34-7.38 (m, 1H), 7.59 (d, J=9.0 Hz, 1H), 7.75 (d, J=9.0 Hz, 1H), 7.81-7.85 (m, 1H), 7.87 (d, J=2.3 Hz, 1H).

Example 162

2-[6-Methoxy-5-(4-methyl-1H-imidazol-1-yl)pyridin-2-yl]-5,6,7,8-tetrahydro[1,2,4]triazolo[1,5-a]pyridine-8-carboxylic acid phenylamide

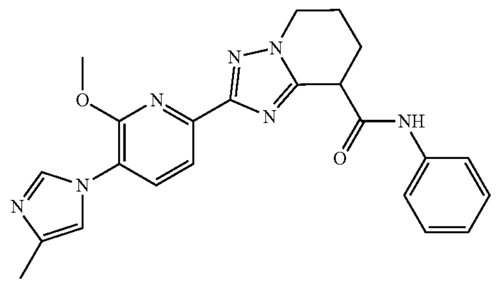 [SMILES: COc1nc(-c2nc3n(n2)CCCC3C(=O)Nc2ccccc2)ccc1-n1cnc(C)c1]

2-[6-Methoxy-5-(4-methyl-1H-imidazol-1-yl)pyridin-2-yl]-5,6,7,8-tetrahydro[1,2,4]triazolo[1,5-a]pyridine-8-carboxylic acid obtained in Preparation Example 5-1 (25 mg) was dissolved in N,N-dimethylformamide (0.5 mL). Aniline (7.2 mg), 1-ethyl-3-(dimethylaminopropyl)carbodiimide hydrochloride (40.6 mg), 1-hydroxybenzotriazole (28.6 mg) and N,N-diisopropylethylamine (75.7 μL) were sequentially added and the mixture was stirred at room temperature for five hours. Ethyl acetate and water were added to the reaction solution, and the organic layer and the aqueous layer were separated. The aqueous layer was further extracted with ethyl acetate. The resulting organic layers were combined, sprayed with nitrogen gas and concentrated. The residue was purified by NH silica gel column chromatography to obtain the title compound (14.1 mg). The compound was further separated by CHIRALPAK™ IA (2 cm×25 cm; mobile phase:hexane:ethanol=50:50) to obtain the title compound with a retention time of 7.6 minutes (4.5 mg). The property values of the compound are as follows.

ESI-MS; m/z 430 [$M^+$+H]. 1H-NMR ($CDCl_3$) δ (ppm): 2.14-2.34 (m, 2H), 2.32 (d, J=1.2 Hz, 3H), 2.38-2.54 (m, 2H), 4.05 (t, J=6.4 Hz, 1H), 4.19 (s, 3H), 4.27-4.37 (m, 2H), 7.04 (t, J=1.2 Hz, 1H), 7.12 (tt, J=0.8 Hz, 7.6 Hz, 1H), 7.33 (dt, J=0.8 Hz, 7.6 Hz, 2H), 7.58 (dd, J=0.8 Hz, 7.6 Hz, 2H), 7.69 (d, J=8.0 Hz, 1H), 7.85 (d, J=8.0 Hz, 1H), 7.86 (d, J=1.2 Hz, 1H), 10.20 (s, 1H).

The compounds of Examples 163 to 170 were obtained by the same method as in Example 162 (Table 4).

TABLE 4
| Example No. | Structural formula |
|---|---|
| Example 163 | 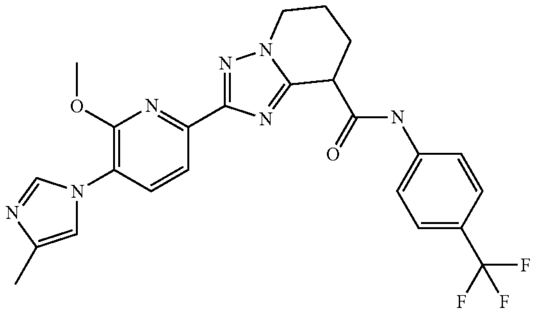 [SMILES: COc1nc(-c2nc3n(n2)CCCC3C(=O)Nc2ccc(C(F)(F)F)cc2)ccc1-n1cnc(C)c1] |
| Example 164 | 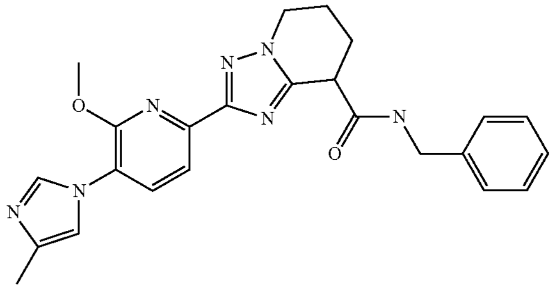 [SMILES: COc1nc(-c2nc3n(n2)CCCC3C(=O)NCc2ccccc2)ccc1-n1cnc(C)c1] |
| Example 165 | 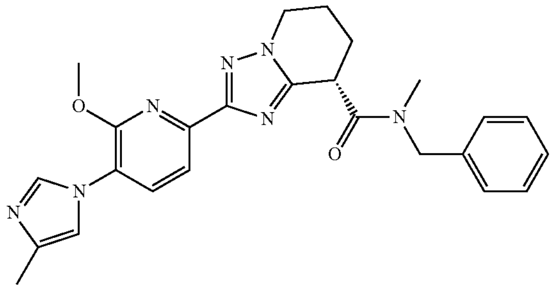 [SMILES: COc1nc(-c2nc3n(n2)CCC[C@@H]3C(=O)N(C)Cc2ccccc2)ccc1-n1cnc(C)c1] |
| Example 166 | 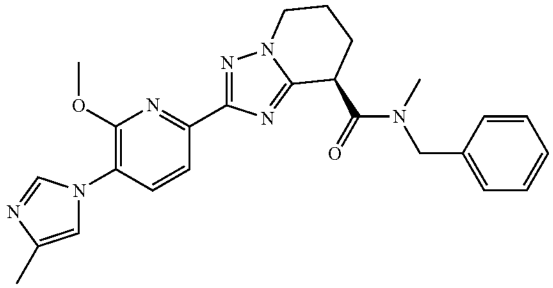 [SMILES: COc1nc(-c2nc3n(n2)CCC[C@H]3C(=O)N(C)Cc2ccccc2)ccc1-n1cnc(C)c1] |
| Example 167 | 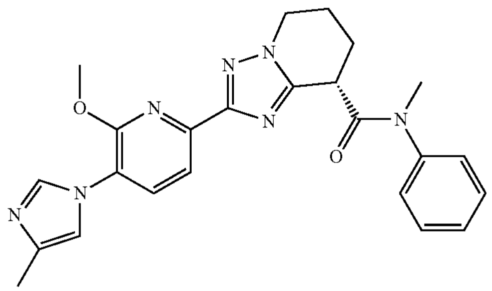 [SMILES: COc1nc(-c2nc3n(n2)CCC[C@@H]3C(=O)N(C)c2ccccc2)ccc1-n1cnc(C)c1] |

TABLE 4-continued

| Example No. | Structural formula |
|---|---|
| Example 168 | 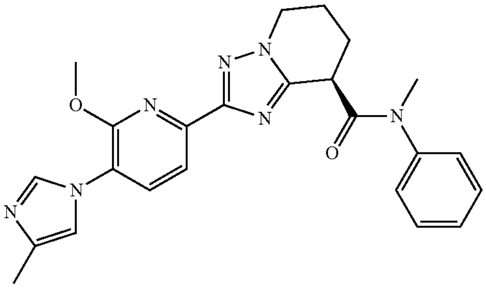 [SMILES: COc1nc(-c2nc3n(n2)CCC[C@H]3C(=O)N(C)c2ccccc2)ccc1-n1cnc(C)c1] |
| Example 169 | 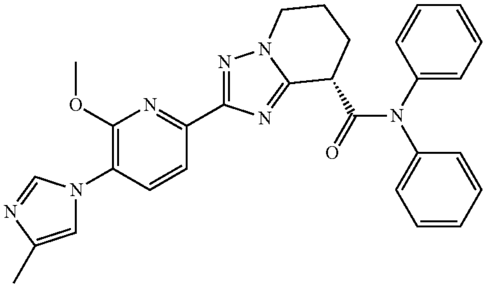 [SMILES: COc1nc(-c2nc3n(n2)CCC[C@@H]3C(=O)N(c2ccccc2)c2ccccc2)ccc1-n1cnc(C)c1] |
| Example 170 | 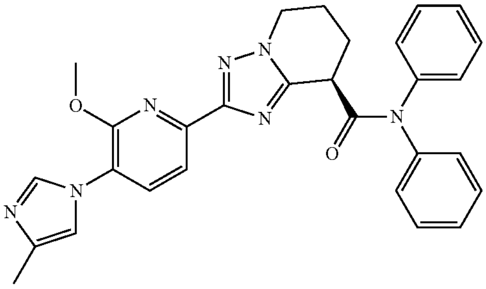 [SMILES: COc1nc(-c2nc3n(n2)CCC[C@H]3C(=O)N(c2ccccc2)c2ccccc2)ccc1-n1cnc(C)c1] |

Examples 171 and 172

Synthesis of (+)-2-[6-methoxy-5-4-methyl-1H-imidazol-1-yl)pyridin-2-yl]-8-(5-phenyl-1H-imidazol-2-yl)-5,6,7,8-tetrahydro[1,2,4]triazolo[1,5-a]pyridine and (−)-2-[6-methoxy-5-(4-methyl-1H-imidazol-1-yl)pyridin-2-yl]-8-(5-phenyl-1H-imidazol-2-yl]-5,6,7,8-tetrahydro[1,2,4]triazolo[1,5-a]pyridine

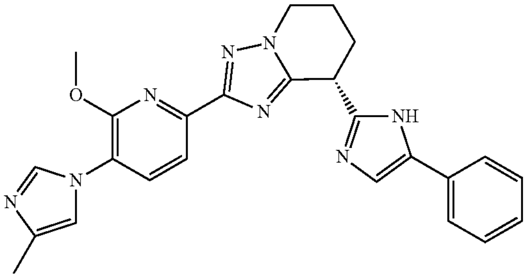

-continued

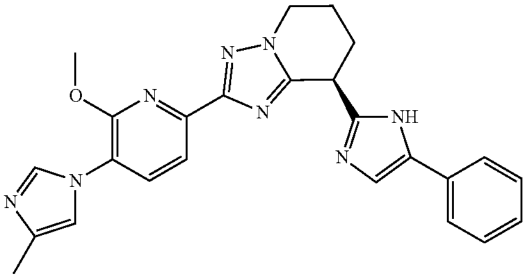

Synthesis of 2-[6-methoxy-5-(4-methyl-1H-imidazol-1-yl)pyridin-2-yl]-5,6,7,8-tetrahydro[1,2,4]triazolo[1,5-a]pyridine-8-carboxylic acid (2-oxo-2-phenylethyl)amide The title compound (25.6 mg) was obtained according to the method of Example 162 from 2-[6-methoxy-5-(4-methyl-1H-imidazol-1-yl)pyridin-2-yl]-5,6,7,8-tetrahydro[1,2,4]triazolo[1,5-a]pyridine-8-carboxylic acid obtained in Preparation Example 5-1 (33.2 mg) and α-aminoacetophenone hydrochloride (173 mg). The property values of the compound are as follows.

$^1$H-NMR ($CDCl_3$) δ (ppm): 2.12-2.45 (m, 4H), 2.32 (d, J=1.2 Hz, 3H), 3.97 (t, J=6.4 Hz, 1H), 4.22 (s, 3H), 4.25-4.36 (m, 2H), 4.79 (dd, J=4.0 Hz, 19.6 Hz, 1H), 4.87 (dd, J=4.0 Hz, 19.6 Hz, 1H), 7.04 (t, J=1.2 Hz, 1H), 7.51 (dt, J=1.2 Hz, 7.6 Hz, 2H), 7.63 (tt, J=1.2 Hz, 7.6 Hz, 1H), 7.71 (d, J=8.0 Hz, 1H), 7.86 (d, J=1.2 Hz, 1H), 7.99 (dd, J=1.2 Hz, 7.6 Hz, 2H), 8.05 (d, J=8.0 Hz, 1H), 9.07 (t, J=4.0 Hz, 1H).

Synthesis of (+)-2-[6-methoxy-5-(4-methyl-1H-imidazol-1-yl)pyridin-2-yl]-8-(5-phenyl-1H-imidazol-2-yl)-5,6,7,8-tetrahydro[1,2,4]triazolo[1,5-a]pyridine and (−)-2-[6-methoxy-5-(4-methyl-1H-imidazol-1-yl)pyridin-2-yl]-8-(5-phenyl-1H-imidazol-2-yl)-5,6,7,8-tetrahydro[1,2,4]triazolo[1,5-a]pyridine 2-[6-Methoxy-5-(4-methyl-1H-imidazol-1-yl)pyridin-2-yl]-5,6,7,8-tetrahydro[1,2,4]triazolo[1,5-a]pyridine-8-carboxylic acid (2-oxo-2-phenylethyl)amide (25 mg) was dissolved in glacial acetic acid (0.5 mL). Ammonium acetate (20.4 mg) was added and the mixture was stirred with heating under reflux for eight hours. The reaction solution was ice-cooled. Then, ethyl acetate, water and concentrated aqueous ammonia (1 mL) were added and the organic layer was separated. The resulting organic layer was sequentially washed with a saturated sodium bicarbonate solution and brine and dried over anhydrous sodium sulfate. The drying agent was separated by filtration and then the organic layer was concentrated under reduced pressure. The residue was purified by NH silica gel column chromatography to obtain a racemate of the title compound (16.8 mg). The resulting racemate was separated by CHIRALPAK™ IA (2 cm×25 cm; mobile phase:hexane:ethanol=50:50) to obtain the title optically active compound with a retention time of 4.2 minutes and positive optical rotation (6.3 mg, >99% ee) and the title optically active compound with a retention time of 6.1 minutes and negative optical rotation (6.9 mg, >99% ee).

The property values of the title compound with positive optical rotation are as follows.

ESI-MS; m/z 453 [$M^+$+H]. 1H-NMR ($CDCl_3$) δ (ppm): 2.22-2.76 (m, 4H), 2.31 (s, 3H), 4.11 (s, 3H), 4.25-4.44 (m, 2H), 4.49 (t, J=6.0 Hz, 1H), 7.01 (s, 1H), 7.01-7.39 (m, 5H), 7.63-7.65 (m, 1H), 7.74 (brs, 1H), 7.84 (brs, 2H), 11.09 (brs, 1H).

The property values of the title compound with negative optical rotation are as follows.

ESI-MS; m/z 453 [$M^+$+H]. 1H-NMR ($CDCl_3$) δ (ppm): 2.22-2.76 (m, 4H), 2.31 (s, 3H), 4.11 (s, 3H), 4.25-4.44 (m, 2H), 4.49 (t, J=6.0 Hz, 1H), 7.01 (s, 1H), 7.01-7.39 (m, 5H), 7.63-7.65 (m, 1H), 7.74 (brs, 1H), 7.84 (brs, 2H), 11.09 (brs, 1H).

Example 173

Synthesis of 2-[6-methoxy-5-(4-methyl-1H-imidazol-1-yl)pyridin-2-yl]-8-(5-phenyloxazol-2-yl)-5,6,7,8-tetrahydro[1,2,4]triazolo[1,5-a]pyridine

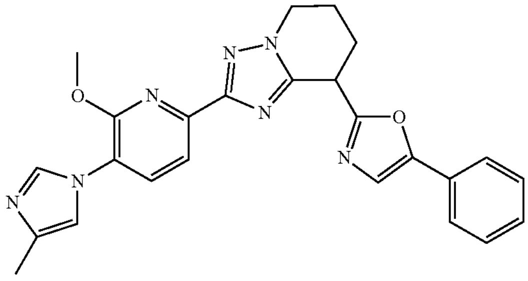 [SMILES: COc1nc(-c2nc3n(n2)CCCC3c2ncc(-c3ccccc3)o2)ccc1-n1cnc(C)c1]

2-[6-Methoxy-5-(4-methyl-1H-imidazol-1-yl)pyridin-2-yl]-5,6,7,8-tetrahydro[1,2,4]triazolo[1,5-a]pyridine-8-carboxylic acid (2-oxo-2-phenylethyl)amide obtained in Example 172 (35.7 mg) was suspended in toluene (0.5 mL). Oxalyl chloride (20.4 mg) was added and the mixture was stirred with heating under reflux for two hours. Toluene (3 mL) and phosphoryl chloride (60 μL) were added, followed by further stirring for two hours and 30 minutes. The reaction solution was ice-cooled. Then, chloroform and a saturated sodium bicarbonate solution were added and the organic layer was separated. The resulting organic layer was concentrated under reduced pressure. The residue was purified by NH silica gel column chromatography to obtain the title compound (4.4 mg). The compound was further purified by CHIRALPAK™ IA (2 cm×25 cm; mobile phase:hexane: ethanol=50:50) to obtain the title compound (1.2 mg, racemate). The property values of the compound are as follows.

ESI-MS; m/z 454 [$M^+$+H]. 1H-NMR ($CDCl_3$) δ (ppm): 2.18-2.24 (m, 1H), 2.30 (d, J=1.2 Hz, 3H), 2.40-2.55 (m, 3H), 4.16 (s, 3H), 4.32-4.38 (m, 1H), 4.44-4.50 (m, 1H), 4.75 (t, J=5.6 Hz, 1H), 7.00 (t, J=1.2 Hz, 1H), 7.29 (s, 1H), 7.33 (tt, J=1.2 Hz, 7.6 Hz, 1H), 7.41 (dt, J=1.2 Hz, 7.6 Hz, 2H), 7.59 (d, J=8.0 Hz, 1H), 7.62 (dd, J=1.2 Hz, 7.6 Hz, 2H), 7.81 (d, J=8.0 Hz, 1H), 7.83 (d, J=1.2 Hz, 1H).

Example 174

Synthesis of 2-[6-methoxy-5-(4-methyl-1H-imidazol-1-yl)pyridin-2-yl]-8-(5-phenylthiazol-2-yl)-5,6,7,8-tetrahydro[1,2,4]triazolo[1,5-a]pyridine

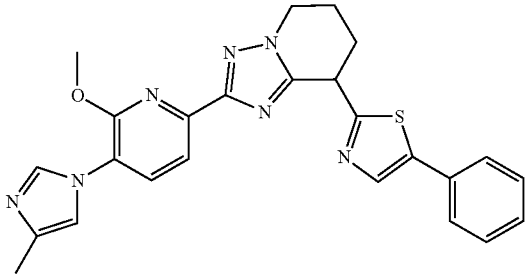 [SMILES: COc1nc(-c2nc3n(n2)CCCC3c2ncc(-c3ccccc3)s2)ccc1-n1cnc(C)c1]

2-[6-Methoxy-5-(4-methyl-1H-imidazol-1-yl)pyridin-2-yl]-5,6,7,8-tetrahydro[1,2,4]triazolo[1,5-a]pyridine-8-carboxylic acid (2-oxo-2-phenylethyl)amide obtained in Example 172 (26.6 mg) was dissolved in THF (1 mL). Lawesson reagent (45.6 mg) was added and the mixture was stirred with heating under reflux for 11 hours. The reaction solution was ice-cooled. Then, chloroform and a saturated sodium bicarbonate solution were added and the organic layer was separated. The resulting organic layer was dried over anhydrous sodium sulfate. The drying agent was separated by filtration and then the organic layer was concentrated under reduced pressure. The residue was purified by NH silica gel column chromatography to obtain the title compound (2.8 mg). The compound was further purified by CHIRALCEL™ IB (2 cm×25 cm; mobile phase:hexane:ethanol=30:70) to obtain the title compound (1.5 mg, racemate). The property values of the compound are as follows.

ESI-MS; m/z 470 [$M^+$+H]. 1H-NMR ($CDCl_3$) δ (ppm): 2.19-2.22 (m, 1H), 2.31 (s, 3H), 2.34-2.38 (m, 1H), 2.51-2.59 (m, 2H), 4.17 (s, 3H), 4.33-4.45 (m, 2H), 4.81 (t, J=6.0 Hz, 1H), 7.01 (s, 1H), 7.32 (tt, J=1.2 Hz, 7.6 Hz, 1H), 7.39 (dt, J=1.2 Hz, 7.6 Hz, 2H), 7.52 (dd, J=1.2 Hz, 7.6 Hz, 2H), 7.62 (d, J=8.0 Hz, 1H), 7.83 (d, J=1.2 Hz, 1H).7.86 (d, J=8.0 Hz, 1H), 7.89 (s, 1H).

Examples 175 and 176 (+)-2-[6-Methoxy-5-(4-methyl-1H-imidazol-1-yl)pyridin-2-yl]-8-pyridin-2-yl-5,6,7,8-tetrahydro[1,2,4]triazolo[1,5-a]pyridine and (+2-[6-methoxy-5-(4-methyl-1H-imidazol-1-yl)pyridin-2-yl]-8-pyridin-2-yl-5,6,7,8-tetrahydro[1,2,4]triazolo[1,5-a]pyridine

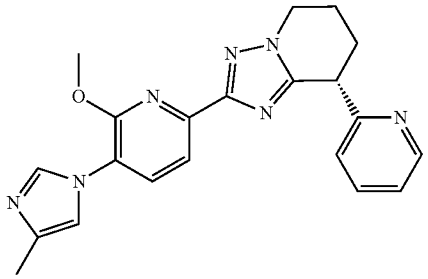

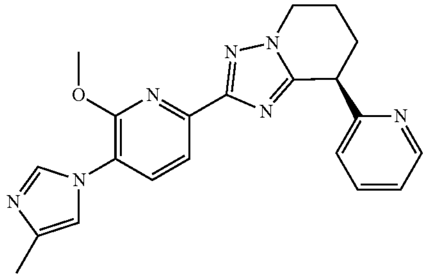

8-(6-bromopyridin-2-yl)-2-[6-methoxy-5-(4-methyl-1H-imidazol-1-yl)pyridin-2-yl]-5,6,7,8-tetrahydro[1,2,4]triazolo[1,5-a]pyridine obtained in Examples 70 and 71 (35 mg) was dissolved in ethanol (2 mL). 10% palladium-carbon (10 mg) was added and the mixture was stirred in a hydrogen atmosphere at 1 atm at room temperature for seven hours. Palladium-carbon was removed by filtration through celite, followed by concentration under reduced pressure. The residue was purified by NH silica gel column chromatography to obtain a racemate of the title compound (16.6 mg). The resulting racemate (16.6 mg) was separated by CHIRALPAK™ AD-H (2 cm×25 cm; mobile phase:ethanol) to obtain the title optically active compound with a retention time of 4.3 minutes and positive optical rotation (7.3 mg, 70% ee) and the title optically active compound with a retention time of 7.7 minutes and negative optical rotation (5.2 mg, 94% ee).

The property values of the title compound with positive optical rotation are as follows.

ESI-MS; m/z 388 [$M^+$+H]. 1H-NMR ($CDCl_3$) δ (ppm): 2.08-2.28 (m, 2H), 2.30 (d, J=1.2 Hz, 3H), 2.34-2.45 (m, 2H), 4.16 (s, 3H), 4.32-4.46 (m, 2H), 4.57 (t, J=6.0 Hz, 1H), 7.00 (t, J=1.2 Hz, 1H), 7.17-7.21 (m, 2H), 7.58 (d, J=7.6 Hz, 1H), 7.65 (dt, J=2.0 Hz, 8.0 Hz, 1H), 7.78 (d, J=7.6 Hz, 1H), 7.82 (d, J=1.2 Hz, 1H), 8.57-8.58 (m, 1H).

The property values of the title compound with negative optical rotation are as follows.

ESI-MS; m/z 388 [$M^+$+H]. 1H-NMR ($CDCl_3$) δ (ppm): 2.08-2.28 (m, 2H), 2.30 (d, J=1.2 Hz, 3H), 2.34-2.45 (m, 2H), 4.16 (s, 3H), 4.32-4.46 (m, 2H), 4.57 (t, J=6.0 Hz, 1H), 7.00 (t, J=1.2 Hz, 1H), 7.17-7.21 (m, 2H), 7.58 (d, J=7.6 Hz, 1H), 7.65 (dt, J=2.0 Hz, 8.0 Hz, 1H), 7.78 (d, J=7.6 Hz, 1H), 7.82 (d, J=1.2 Hz, 1H), 8.57-8.58 (m, 1H).

The compounds of Examples 177 to 180 were obtained by the same method as in Examples 175 and 176 (Table 5).

TABLE 5

| Example No. | Structural formula |
|---|---|
| Example 177 | 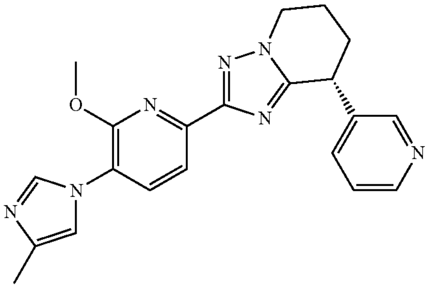 [SMILES: COc1nc(-c2nc3n(n2)CCC[C@@H]3c2cccnc2)ccc1-n1cnc(C)c1] |
| Example 178 | 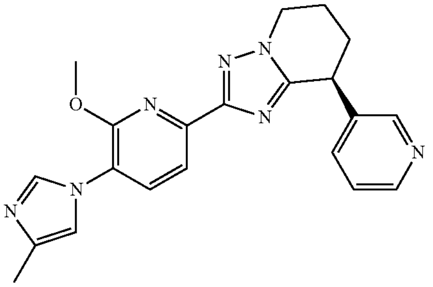 [SMILES: COc1nc(-c2nc3n(n2)CCC[C@H]3c2cccnc2)ccc1-n1cnc(C)c1] |
| Example 179 | 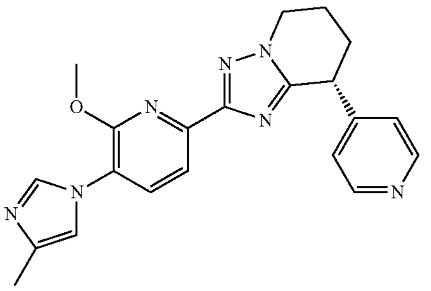 [SMILES: COc1nc(-c2nc3n(n2)CCC[C@@H]3c2ccncc2)ccc1-n1cnc(C)c1] |

TABLE 5-continued

| Example No. | Structural formula |
|---|---|
| Example 180 | 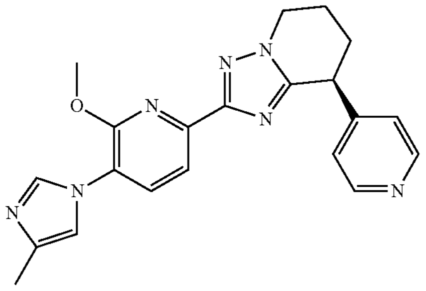 [SMILES: COc1nc(-c2nc3n(n2)CCC[C@H]3c2ccncc2)ccc1-n1cnc(C)c1] |

Example 181

Synthesis of 2-[6-methoxy-5-(4-methyl-1H-imidazol-1-yl)pyridin-2-yl]-9-(2-trifluoromethylphenyl)-6,7,8,9-tetrahydro-5H-[1,2,4]triazolo[1,5-a]azepin-9-ol

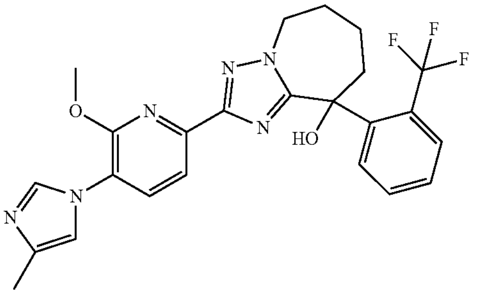 [SMILES: COc1nc(-c2nc3n(n2)CCCCC3(O)c2ccccc2C(F)(F)F)ccc1-n1cnc(C)c1]

Sodium hydride (60%) was added to a solution of 2-[6-methoxy-5-(4-methyl-1H-imidazol-1-yl)pyridin-2-yl]-9-(2-trifluoromethylphenyl)-6,7,8,9-tetrahydro-5H-[1,2,4]triazolo[1,5-a]azepine obtained in Examples 74 and 75 (83 mg) in DMF (5 mL) with stirring under ice-cooling until bubbling was stopped. Thereafter, the mixture was stirred at room temperature in an oxygen atmosphere. After four days, ice water, chloroform and a saturated sodium thiosulfate solution were added to the reaction solution, and the organic layer was separated. The organic layer was dried over anhydrous magnesium sulfate and then concentrated under reduced pressure. The residue was diluted with toluene and concentrated under reduced pressure. The residue was diluted again with toluene and concentrated under reduced pressure. The precipitated solid was collected by filtration, washed with chloroform and then air-dried to obtain 36.8 mg of the title compound. The property values of the compound are as follows.

$^1$H-NMR ($CDCl_3$) δ (ppm): 1.78-1.82 (m, 1H), 1.90-2.04 (m, 1H), 2.08-2.30 (m, 3H), 2.28 (s, 3H), 2.55-2.64 (m, 1H), 4.10 (s, 3H), 4.45-4.61 (m, 2H), 4.93 (brs, 1H), 6.93 (s, 1H), 7.41 (d, J=8.0 Hz, 1H), 7.43-7.54 (m, 3H), 7.60 (d, J=8.0 Hz, 1H), 7.64 (s, 1H), 7.79 (d, J=7.6 Hz, 1H).

Example 182

Synthesis of 2-[6-methoxy-5-(4-methyl-1H-imidazol-1-yl)pyridin-2-yl]-9-(2-trifluoromethylphenyl)-6,7-dihydro-5H-[1,2,4]triazolo[1,5-a]azepine

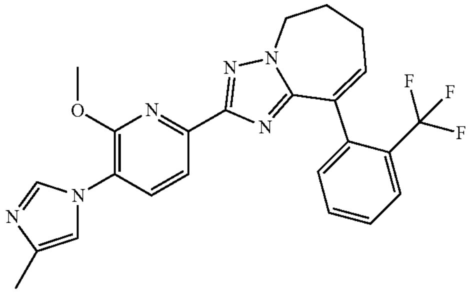 [SMILES: COc1nc(-c2nc3n(n2)CCCC=C3c2ccccc2C(F)(F)F)ccc1-n1cnc(C)c1]

A mixture of 2-[6-methoxy-5-(4-methyl-1H-imidazol-1-yl)pyridin-2-yl]-9-(2-trifluoromethylphenyl)-6,7,8,9-tetrahydro-5H-[1,2,4]triazolo[1,5-a]azepin-9-ol obtained in Example 181 (49 mg), p-toluenesulfonic acid (76 mg) and toluene (7 mL) was heated under reflux for two hours. Ethyl acetate and saturated sodium bicarbonate were added to the reaction solution, and the organic layer was separated. The organic layer was dried over anhydrous magnesium sulfate and then concentrated under reduced pressure. The solid was removed by filtration. The mother liquor was concentrated under reduced pressure, and then the residue was purified by silica gel column chromatography (chloroform-methanol system) to obtain 3.46 mg of the title compound as an oil. The property values of the compound are as follows.

$^1$H-NMR ($CDCl_3$) δ (ppm): 2.20-2.31 (m, 2H), 2.29 (s, 3H), 2.73-2.77 (m, 2H), 4.12 (s, 3H), 4.58-4.61 (m, 2H), 6.25 (dd, J=5.2, 5.2 Hz, 1H), 6.96 (s, 1H), 7.44-7.50 (m, 2H), 7.49 (d, J=7.2 Hz, 1H), 7.59 (t, J=7.2 Hz, 1H), 7.61 (d, J=7.2 Hz, 1H), 7.69 (d, J=7.2 Hz, 1H), 7.78 (s, 1H).

Examples 183 and 184

Synthesis of (+)-2-[6-methoxy-5-(4-methylimidazol-1-yl)pyridin-2-yl]-4-(2-trifluoromethylphenyl)-4,5,6,7-tetrahydropyrazolo[1,5-a]pyridine and (−)-2-[6-methoxy-5-4-methylimidazol-1-yl)pyridin-2-yl]-4-2-trifluoromethylphenyl)-4,5,6,7-tetrahydropyrazolo[1,5-a]pyridine

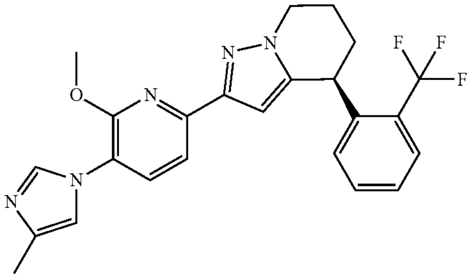

-continued

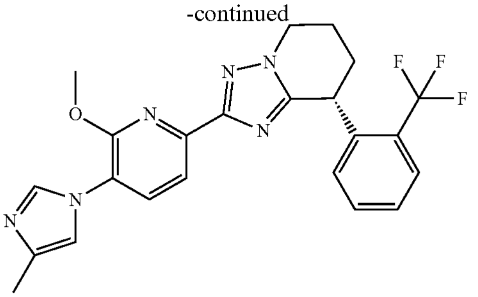

Synthesis of 5-chloro-2-(2-trifluoromethylphenyl)valeric acid chloride

5-Chloro-2-(2-trifluoromethylphenyl)valeric acid obtained in Preparation Example 2-3 (500 mg) was dissolved in tetrahydrofuran (9 mL). Dimethylformamide (0.1 ml) and oxalyl chloride (184 μL) were added at 0° C. and the reaction was initiated at room temperature. After 1.5 hours, concentration under reduced pressure gave an oil (532 mg), which was used directly for the next reaction as a crude product.

Synthesis of 7-chloro-1-[6-methoxy-5-(4-methylimidazol-1-yl)pyridin-2-yl]-4-(2-trifluoromethylphenyl) heptane-1,3-dione A solution of 1-[6-methoxy-5-(4-methylimidazol-1-yl)pyridin-2-yl]ethanone obtained in Preparation Example 1-8 (412 mg) in tetrahydrofuran (10 ml) was added at −30° C. to a lithium diisopropylamine solution prepared from n-butyllithium (1.4 mL) and diisopropylamine (528 μL) in tetrahydrofuran (30 mL). After stirring at the same temperature for 30 minutes, 5-chloro-2-(2-trifluoromethylphenyl)valeric acid chloride (532 mg) was added and the mixture was stirred for 1.5 hours. After further stirring at room temperature for 30 minutes, the reaction was terminated with water, followed by dilution with ethyl acetate. The organic layer was washed with brine and dried over magnesium sulfate. The oil after concentration under reduced pressure was purified by silica gel chromatography (mobile phase:ethyl acetate/heptane=0 to 100%) to obtain the title compound (90 mg).

ESI-MS; m/z 494 [$M^+$+H].

Synthesis of (+)-2-[6-methoxy-5-(4-methylimidazol-1-yl)pyridin-2-yl]-4-(2-trifluoromethylphenyl)-4,5,6,7-tetrahydropyrazolo[1,5-a]pyridine and (−)-2-[6-methoxy-5-4-methylimidazol-1-yl)pyridin-2-yl]-4-(2-trifluoromethylphenyl)-4,5,6,7-tetrahydropyrazolo [1,5-a]pyridine 7-Chloro-1-[6-methoxy-5-(4-methylimidazol-1-yl)pyridin-2-yl]-4-(2-trifluoromethylphenyl)heptane-1,3-dione (90 mg) was dissolved in ethanol (2 mL), and hydrazine monohydrate (26.5 μL) was added at room temperature. After 1.5 hours, the mixture was heated under reflux. Further, ethanol (1 mL) and hydrazine monohydrate (13.3 μL) were added 3.5 hours after the heating. After heating under reflux for 18 hours, the reaction solution was partitioned with ethyl acetate and water. The organic layer was washed with brine and dried over magnesium sulfate. Concentration under reduced pressure gave an oil. The oil was purified by silica gel column chromatography (mobile phase:ethyl acetate/heptane=0 to 100%) to obtain a racemate of the title compound (31.2 mg).

The resulting racemate was separated by CHIRALPAK™ AD-H (2 cm×25 cm, mobile phase:ethanol:hexane=3:7, flow rate: 13 mL/min) to obtain the title compound with a retention time of 23.5 minutes and positive optical rotation (9.0 mg) and the title compound with a retention time of 34.2 minutes and negative optical rotation (8.2 mg).

The property values of the title optically active compound with a retention time of 23.5 minutes are as follows.

$^1$H-NMR ($CDCl_3$) δ (ppm): 1.89-1.95 (m, 1H), 2.05-2.40 (m, 3H), 2.29 (s, 3H), 3.99 (s, 3H), 4.25 (ddd, J=12.9, 10.9, 5.1 Hz, 1H), 4.42 (ddd, J=12.9, 9.3, 5.4 Hz, 1H), 4.59 (dd, J=10.2, 5.5 Hz, 1H), 6.28 (s, 1H), 6.95-6.97 (m, 1H), 7.27-7.30 (m, 1H), 7.36-7.41 (m, 1H), 7.48-7.50 (m, 1H), 7.54 (d, J=7.8 Hz, 1H), 7.60 (d, J=7.8 Hz, 1H), 7.72 (d, J=7.8 Hz, 1H), 7.77 (d, J=1.2 Hz, 1H).

The property values of the title optically active compound with a retention time of 34.2 minutes are as follows.

$^1$H-NMR ($CDCl_3$) δ (ppm): 1.89-1.95 (m, 1H), 2.05-2.40 (m, 3H), 2.29 (s, 3H), 3.99 (s, 3H), 4.25 (ddd, J=12.9, 10.9, 5.1 Hz, 1H), 4.42 (ddd, J=12.9, 9.3, 5.4 Hz, 1H), 4.59 (dd, J=10.2, 5.5 Hz, 1H), 6.28 (s, 1H), 6.95-6.97 (m, 1H), 7.27-7.30 (m, 1H), 7.36-7.41 (m, 1H), 7.48-7.50 (m, 1H), 7.54 (d, J=7.8 Hz, 1H), 7.60 (d, J=7.8 Hz, 1H), 7.72 (d, J=7.8 Hz, 1H), 7.77 (d, J=1.2 Hz, 1H).

Example 185

Synthesis of 2-[6-methoxy-5-(4-methyl-1H-imidazol-1-yl)pyridin-2-yl]-4-(2-trifluoromethylphenyl)-4,5,6,7-tetrahydro[1,2,4]triazolo[1,5-a]pyrimidine

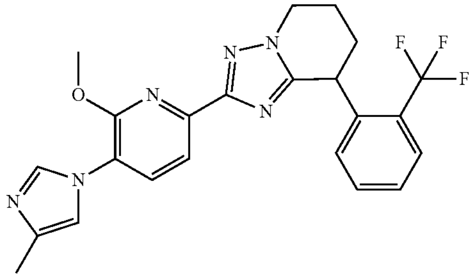 [SMILES: COc1nc(-c2nc3n(n2)CCCC3c2ccccc2C(F)(F)F)ccc1-n1cnc(C)c1]

Synthesis of phenyl (2-trifluoromethylphenyl)carbamate

2-Aminobenzotrifluoride (5 mL) and pyridine (6.44 mL) were dissolved in tetrahydrofuran (100 mL), and phenyl chloroformate (5.5 mL) was added dropwise under ice-cooling. After dropwise addition of the reagent, the mixture was brought back to room temperature and stirred for 4.5 hours. Water was added to the reaction solution and the mixture was concentrated under reduced pressure, followed by extraction with ethyl acetate. The resulting organic layer was washed with 2 N hydrochloric acid and brine and then dried over anhydrous sodium sulfate. The drying agent was separated by filtration, and then the organic layer was concentrated under reduced pressure. The residue was purified by silica gel column chromatography to obtain the title compound (12.1 g). The property values of the compound are as follows.

ESI-MS; m/z 282 [$M^+$+H].

Synthesis of (2-trifluoromethylphenyl)carbamic acid hydrazide

Phenyl (2-trifluoromethylphenyl)carbamate (12.1 g) was dissolved in ethanol (150 mL). Hydrazine monohydrate (16.7 mL) was added and the mixture was heated under reflux for 2.25 hours. The reaction solution was concentrated under reduced pressure and the residue was purified by silica gel column chromatography to obtain the title compound (7.5 g).

The property values of the compound are as follows.

$^1$H-NMR ($CDCl_3$) δ (ppm): 3.90 (brs, 2H), 6.29 (brs, 1H), 7.13 (dd, J=7.6, 6.4 Hz, 1H), 7.52 (dd, J=8.4, 6.4 Hz, 1H), 7.58 (d, J=7.6 Hz, 1H), 8.28 (d, J=8.4 Hz, 1H), 8.87 (brs, 1H).

Synthesis of {5-[6-methoxy-5-(4-methyl-1H-imidazol-1-yl)pyridin-2-yl]-[1,3,4]oxazol-2-yl}-(2-trifluoromethylphenyl)amine

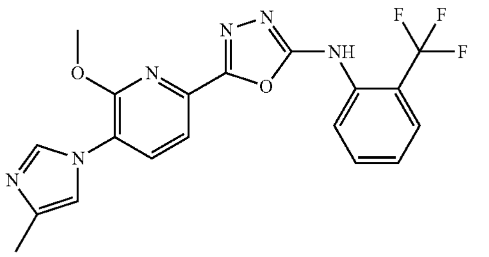 [SMILES: COc1nc(-c2nnc(Nc3ccccc3C(F)(F)F)o2)ccc1-n1cnc(C)c1]

6-Methoxy-5-(4-methyl-1H-imidazol-1-yl)pyridine-2-carboxylic acid obtained in Preparation Example 1-5 (581 mg), (2-trifluoromethylphenyl)carbamic acid hydrazide (230 mg) and N,N-diisopropylethylamine (914 μL) were dissolved in dichloromethane (10 mL), followed by addition of bis(2-oxo-3-oxazolidinyl)phosphinic acid chloride (321 mg). After addition of the reagent, the mixture was stirred at room temperature overnight. A sodium bicarbonate solution and a 5% methanol/ethyl acetate mixed solvent were added to the reaction solution, and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain a condensate (349 mg).

Phosphorus oxychloride (30 mL) was added to the condensate (2.06 g), and the mixture was heated with stirring at 120° C. for 1.6 hours. After leaving to cool, the reaction solution was concentrated under reduced pressure. A sodium hydroxide solution and a 10% methanol/chloroform mixed solvent were added and the organic layer was separated. The resulting organic layer was washed with 2 N hydrochloric acid and brine and then dried over anhydrous sodium sulfate. The drying agent was separated by filtration and then the organic layer was concentrated under reduced pressure. The resulting residual solid was washed with tert-butyl methyl ether to obtain the title compound (754 mg). The property values of the compound are as follows.

ESI-MS; m/z 417 [$M^+$+H].

Synthesis of 3-chloropropyl)-{5-[6-methoxy-5-(4-methyl-1H-imidazol-1-yl)pyridin-2-yl][1,3,4]oxazol-2-yl}-(2-trifluoromethylphenyl)amine {5-[6-Methoxy-5-(4-methyl-1H-imidazol-1-yl)pyridin-2-yl]-[1,3,4]oxazol-2-yl}-(2-trifluoromethylphenyl)amine (657 mg) and 1-chloro-3-iodopropane (1.66 mL) were dissolved in N,N-dimethylformamide (15 mL), and 60% sodium hydride (172 mg) was added under ice-cooling. After addition of the reagent, the mixture was brought back to room temperature and stirred for two hours. Water and ethyl acetate were added to the reaction solution, and the organic layer was separated. The resulting organic layer was washed with brine and then dried over anhydrous sodium sulfate. The drying agent was separated by filtration, and then the organic layer was concentrated under reduced pressure. The residue was purified by NH silica gel column chromatography to obtain the title compound (216 mg). The property values of the compound are as follows.

ESI-MS; m/z 493 [$M^+$+H].

Synthesis of 2-[6-methoxy-5-(4-methyl-1H-imidazol-1-yl)pyridin-2-yl]-4-(2-trifluoromethylphenyl)-4,5,6,7-tetrahydro[1,2,4]triazolo[1,5-a]pyrimidine (3-Chloropropyl)-{5-[6-methoxy-5-(4-methyl-1H-imidazol-1-yl)pyridin-2-yl]-[1,3,4]oxazol-2-yl}-(2-trifluoromethylphenyl)amine (239 mg) and ammonium acetate dried under reduced pressure (1.12 g) were suspended in acetic acid (10 mL). The suspension was heated with stirring at 180° C. for two hours using a microwave reactor. The reaction solution was concentrated under reduced pressure. A sodium bicarbonate solution and ethyl acetate were added and the organic layer was separated. The resulting organic layer was washed with brine and then dried over anhydrous sodium sulfate. The drying agent was separated by filtration and then the organic layer was concentrated under reduced pressure. The residue was purified by NH silica gel column chromatography and further purified again by CHIRALPAK™ IB (2 cm×25 cm; mobile phase:hexane:ethanol=4:6) to obtain the title compound (30 mg). The property values of the compound are as follows.

ESI-MS; m/z 456 [$M^+$+H].

$^1$H-NMR ($CDCl_3$) δ (ppm): 2.28 (s, 3H), 2.30-2.50 (m, 2H), 3.64-3.74 (m, 2H), 4.12 (s, 3H), 4.30-7.41 (m, 2H), 6.94-6.98 (m, 1H), 7.47-7.54 (m, 3H), 7.59 (d, J=7.6 Hz, 1H), 7.67 (ddd, J=7.6, 7.6, 1.2 Hz, 1H), 7.76-7.82 (m, 2H).

Preparation Example 1-1

Synthesis of 6-bromo-2-methoxy-3-(4-methyl-1H-imidazol-1-yl)pyridine

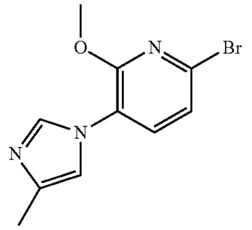

Synthesis of N-(6-bromo-2-methoxypyridin-3-yl)formamide

Acetic anhydride (203 mL) was added dropwise to formic acid (204 mL) under ice-cooling, and the mixture was stirred at the same temperature for 25 minutes. 6-Bromo-2-methoxypyridine-3-amine powder (CAS #89466-18-2, 146 g) was put into the reaction mixture over 10 minutes, and then the reaction solution was stirred at the same temperature for 30 minutes. The water bath was removed. tert-Butyl methyl ether (300 mL) and n-heptane (500 mL) were sequentially added dropwise to the reaction solution, and then the reaction solution was stirred for 30 minutes. The precipitated powder was collected by filtration. The resulting powder was crushed with a mortar, washed with tert-butyl methyl ether and then dried under reduced pressure to obtain 137.4 g of the title compound.

Then, the combined filtrate and washing solution were concentrated under reduced pressure. The residue was triturated with tert-butyl methyl ether and dried under reduced pressure to obtain 21.9 g of the title compound. The property values of the compound are as follows.

$^1$H-NMR ($CDCl_3$) δ (ppm): 4.03 (s, 3H), 7.08 (d, J=8.0 Hz, 1H), 7.61 (brs, 1H), 8.47-8.51 (m, 2H).

Synthesis of N-(6-bromo-2-methoxypyridin-3-yl)-N-(2-oxopropyl)formamide

Chloroacetone (82 mL) was added dropwise to a suspension of N-(6-bromo-2-methoxypyridin-3-yl)formamide (159.3 g), cesium carbonate (359 g) and potassium iodide (11.4 g) in N,N-dimethylformamide (800 mL) over seven minutes. Then, the reaction solution was stirred at room temperature for one hour and 20 minutes.

The reaction solution was concentrated under reduced pressure. Ethyl acetate and water were added to the resulting residue, and the organic layer was separated. The resulting organic layer was washed with brine, dried over anhydrous magnesium sulfate and then concentrated under reduced pressure to obtain 215.2 g of the title compound. The property values of the compound are as follows.

$^1$H-NMR ($CDCl_3$) δ (ppm): 2.17 (s, 3H), 4.00 (s, 3H), 4.47 (s, 2H), 7.13 (d, J=7.6 Hz, 1H), 7.48 (d, J=7.6 Hz, 1H), 8.22 (s, 1H).

Synthesis of 6-bromo-2-methoxy-3-(4-methyl-1H-imidazol-1-yl)pyridine

A suspension of ammonium acetate (267 g) and N-(6-bromo-2-methoxypyridin-3-yl)-N-(2-oxopropyl)formamide (199 g) in glacial acetic acid (400 mL) was stirred at 130° C. for one hour and 10 minutes. The reaction solution was brought back to room temperature. Ethyl acetate and ice water were added to the reaction solution, and the mixture was ice-cooled. Then, concentrated aqueous ammonia (500 mL) was added dropwise and then the organic layer was separated. The resulting organic layer was sequentially washed with water and brine and dried over anhydrous magnesium sulfate. Then, the organic layer was purified by short silica gel column chromatography (carrier: Wakogel™ C-200 manufactured by Wako Pure Chemical Industries, Ltd.; elution solvent: ethyl acetate). The eluted fraction was concentrated. The resulting residue was triturated with ethyl acetate and tert-butyl methyl ether and dried under reduced pressure to obtain 107.7 g of the title compound.

Then, the trituration mother liquor was concentrated. The resulting residue was purified by silica gel column chromatography (carrier: Wakogel™ C-200; elution solvent:toluene-ethyl acetate system). The target fraction was concentrated. The resulting residue was triturated with tert-butyl methyl ether and dried under reduced pressure to obtain 12.9 g of the title compound.

The property values of the compound are as follows.

ESI-MS; m/z 268 [$M^+$+H].

$^1$H-NMR ($CDCl_3$) δ (ppm): 2.29 (d, J=0.8 Hz, 3H), 4.03 (s, 3H), 6.92 (dd, J=1.2, 0.8 Hz, 1H), 7.16 (d, J=8.0 Hz, 1H), 7.40 (d, J=8.0 Hz, 1H), 7.73 (d, J=1.2 Hz, 1H).

Preparation Example 1-2

Synthesis of 2-methoxy-3-(4-methyl-1H-imidazol-1-yl)-6-tributylstannylpyridine

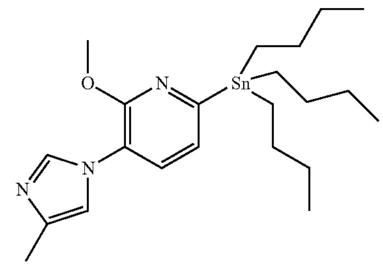 [SMILES: CCC[CH2][Sn]([CH2]CCC)([CH2]CCC)[c]1ccc(-n2cnc(C)c2)c(OC)n1]

6-Bromo-2-methoxy-3-(4-methyl-1H-imidazol-1-yl)pyridine (10 g) and hexa-n-butylditin (31.8 mL) were dissolved in toluene (300 mL). Tetrakis(triphenylphosphine)palladium (2.2 g) was added and the mixture was heated under reflux in a nitrogen atmosphere for four hours. After leaving to cool, the insoluble matter was removed from the reaction solution by filtration through celite, followed by concentration under reduced pressure. The resulting residue was purified by NH silica gel column chromatography and then by silica gel column chromatography to obtain the title compound (5.4 g). The property values of the compound are as follows.

$^1$H-NMR ($CDCl_3$) δ (ppm): 0.90 (t, J=7.2 Hz, 9H), 1.03-1.22 (m, 6H), 1.30-1.40 (m, 6H), 1.49-1.70 (m, 6H), 2.29 (s, 3H), 4.01 (s, 3H), 6.96 (s, 1H), 7.10 (d, J=7.2 Hz, 1H), 7.63 (d, J=7.2 Hz, 1H), 7.75-7.77 (m, 1H).

Preparation Example 1-3

Synthesis of 3-methoxy-2-(4-methyl-1H-imidazol-1-yl)-5-tributylstannylpyridine

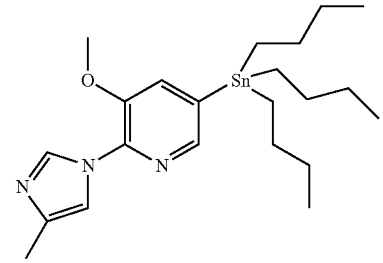 [SMILES: CCC[CH2][Sn]([CH2]CCC)([CH2]CCC)[c]1cnc(-n2cnc(C)c2)c(OC)c1]

Synthesis of N-(5-bromo-3-methoxypyridin-2-yl)formamide

Iron (67.3 g) and ammonium chloride (129 g) were added to a solution of 5-bromo-3-methoxy-2-nitropyridine (56.0 g, CAS #152684-26-9) in ethanol (500 mL) and water (200 mL). The reaction solution was stirred at 80 to 90° C. for one hour and then left to cool to room temperature. The reaction solution was filtered through celite and washed with ethanol. Then, the filtrate was concentrated under reduced pressure. The residue was diluted with ethyl acetate and water, and the organic layer was separated. The resulting organic layer was washed with brine, dried over anhydrous magnesium sulfate and then concentrated under reduced pressure. The residue was diluted with THF (84 mL). The THF solution was added dropwise to a mixed solution of formic acid (78.1 mL) and acetic anhydride (78.3 mL) at room temperature. Then, the reaction solution was stirred for one hour. Ice water (500 mL) was added to the reaction solution, and the precipitated crystals were collected by filtration. The crystals were washed with water and then air-dried. The crystals were recrystallized from toluene to obtain 34.1 g of the title compound. The property values of the compound are as follows.

ESI-MS; m/z 231 [$M^+$+H].

Synthesis of N-(5-bromo-3-methoxypyridin-2-yl)-N-(2-oxopropyl)formamide

Cesium carbonate (96 g), potassium iodide (2.45 g) and chloroacetone (23.5 mL) were added to a solution of N-(5-chloro-3-methoxypyridin-2-yl)formamide (34.1 g) in DMF (200 mL), and the mixture was stirred at 80° C. for 45 minutes. Ice water and ethyl acetate were added to the reaction solution, and the organic layer was separated. The organic layer was washed with brine and then dried over anhydrous magnesium sulfate and concentrated under reduced pressure to obtain 52.8 g of the crude title compound. The property values of the compound are as follows.

ESI-MS; m/z 287 [$M^+$+H].

Synthesis of 5-bromo-3-methoxy-2-(4-methyl-1H-imidazol-1-yl)pyridine

A mixture of the crude N-(5-bromo-3-methoxypyridin-2-yl)-N-(2-oxopropyl)formamide (26.4 g), acetic acid (52.8 mL) and ammonium acetate (35.5 g) was stirred at 130° C. for one hour. The reaction solution was left to cool to room temperature and concentrated under reduced pressure. The residue diluted with ice water, ethyl acetate and aqueous ammonia, and the organic layer was separated. The organic layer was washed with brine and then dried over anhydrous magnesium sulfate and concentrated under reduced pressure. The residue was purified by silica gel column chromatography (elution solvent:heptane-ethyl acetate system) to obtain 5.69 g of the title compound. The property values of the compound are as follows.

ESI-MS; ink 268 [$M^+$+H].

$^1$H-NMR ($CDCl_3$) δ (ppm): 2.29 (s, 3H), 3.97 (s, 3H), 7.48 (brs, 1H), 7.49 (d, J=2.0 Hz, 1H), 8.12 (d, J=2.0 Hz, 1H), 8.30 (brs, 1H).

Synthesis of 3-methoxy-2-(4-methyl-1H-imidazol-1-yl)-5-tributylstannylpyridine

Hexa-n-butylditin (2.07 mL) and tetrakis(triphenylphosphine)palladium (0) (319 mg) were added to a suspension of 5-bromo-3-methoxy-2-(4-methyl-1H-imidazol-1-yl)pyridine (740 mg) in xylene (11 mL), and the mixture was stirred at 155° C. for two hours and 30 minutes. The reaction solution was purified by silica gel column chromatography (carrier: Wakogel C-200; elution solvent:heptane:ethyl acetate=3:1) to obtain 325 mg of the title compound. The property values of the compound are as follows.

$^1$H-NMR ($CDCl_3$) δ (ppm): 0.90 (t, J=7.2 Hz, 9H), 1.13 (t, J=7.2 Hz, 6H), 1.30-1.40 (m, 6H), 1.50-1.60 (m, 6H), 2.30 (d, J=1.2 Hz, 3H), 3.95 (s, 3H), 7.38 (d, J=1.2 Hz, 1H), 7.52 (t, J=1.2 Hz, 1H), 8.03 (d, J=1.2 Hz, 1H), 8.33 (d, J=1.2 Hz, 1H).

Preparation Example 1-4

Synthesis of 1-(2-methoxy-4-tributylstannylphenyl)-4-methyl-1H-imidazole

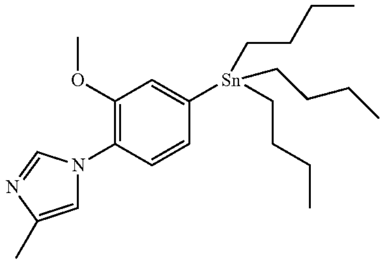 [SMILES: CCC[CH2][Sn]([CH2]CCC)([CH2]CCC)[c]1ccc(-n2cnc(C)c2)c(OC)c1]

1-(4-bromo-2-methoxy-phenyl)-4-methyl-1H-imidazole (CAS No. 870838-56-5, 900 mg) and hexa-n-butylditin (3.91 g) were dissolved in toluene (20 mL). Tetrakistriphenylphosphine palladium (195 mg) was added and the mixture was stirred with heating under reflux for seven hours and 20 minutes. After leaving to cool, the insoluble matter was removed by filtration through celite, followed by concentration under reduced pressure. The residue was purified by NH silica gel column chromatography to obtain the title compound (893 mg). The property values of the compound are as follows.

$^1$H—NNIR($CDCl_3$) δ (ppm): 0.90 (t, J=7.2 Hz, 9H), 1.09-1.11 (m, 6H), 1.32-1.40 (m, 6H), 1.53-1.59 (m, 6H), 2.30 (d, J=1.2 Hz, 3H), 3.85 (s, 3H), 6.92 (t, J=1.2 Hz, 1H), 7.09 (dd, J=1.2 Hz, 7.6 Hz, 1H), 7.10 (d, J=1.2 Hz, 1H), 7.21 (d, J=7.6 Hz, 1H), 7.69 (d, J=1.2 Hz, 1H).

Preparation Example 1-5

Synthesis of 6-methoxy-5-(4-methyl-1H-imidazol-1-yl)pyridine-2-carboxylic acid

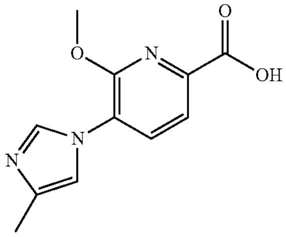 [SMILES: COc1nc(C(=O)O)ccc1-n1cnc(C)c1]

Synthesis of 6-methoxy-5-(4-methyl-1H-imidazol-1-yl)pyridine-2-carbonitrile

6-Bromo-2-methoxy-3-(4-methyl-1H-imidazol-1-yl)pyridine obtained in Preparation Example 1-1) (50 g) and zinc (II) cyanide (35 g) were suspended in N-methylpyrrolidone (400 mL). Tetrakis(triphenylphosphine)palladium (0) (8.5 g) was added and the mixture was stirred at 100° C. for one hour and 10 minutes. The reaction solution was added dropwise to a solution of ice water (1.5 L) and concentrated aqueous ammonia (150 mL) mixed by stirring. The precipitated powder was filtered. The resulting powder was washed with water and then air-dried overnight to obtain 56.5 g of the title compound. The property values of the compound are as follows.

$^{1}$H-NMR ($CDCl_3$) δ (ppm): 2.30 (s, 3H), 4.09 (s, 3H), 7.02 (brs, 1H), 7.44 (d, J=8.0 Hz, 1H), 7.64 (d, J=8.0 Hz, 1H), 7.90 (brs, 1H).

Synthesis of 6-methoxy-5-(4-methyl-1H-imidazol-1-yl)pyridine-2-carboxylic acid

Lithium hydroxide powder (13 g) was added to a suspension of 6-methoxy-5-(4-methyl-1H-imidazol-1-yl)pyridine-2-carbonitrile (52.4 g) in water (464 mL), and the mixture was heated under reflux for three hours. The reaction solution was left to cool to room temperature. The reaction solution was filtered through celite, and the celite was washed with water (100 mL×4). Concentrated hydrochloric acid was added to the filtrate under ice-cooling to adjust the pH to 4 to 5. The precipitated powder was collected by filtration. The resulting powder was washed with water and then air-dried for three days to obtain 51.9 g of the title compound. The property values of the compound are as follows.

$^{1}$H-NMR (DMSO-$D_6$) δ (ppm): 2.17 (s, 3H), 4.01 (s, 3H), 7.33 (brs, 1H), 7.76 (d, J=7.6 Hz, 1H), 7.99 (d, J=7.6 Hz, 1H), 8.02 (brs, 1H).

Preparation Example 1-6

Synthesis of 6-methoxy-5-(4-methyl-1H-imidazol-1-yl)pyridine-2-carboxylic acid hydrazide and 6-methoxy-5-4-methyl-1H-imidazol-1-yl)pyridine-2-carboxylic acid hydrazide hydrochloride

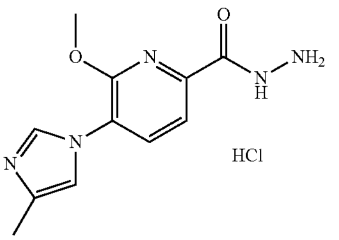 [SMILES: COc1nc(C(=O)NN)ccc1-n1cnc(C)c1 ; Cl]

Synthesis of benzyl N'-[6-methoxy-5-(4-methyl-1H-imidazol-1-yl)pyridine-2-carbonyl]hydrazinecarboxylate Benzyl carbazate (27.8 g), 1-hydroxybenztriazole (24.8 g) and 1-ethyl-3-(dimethylaminopropyl)carbodiimide hydrochloride (35.4 g) were sequentially added to a solution of 6-methoxy-5-(4-methyl-1H-imidazol-1-yl)pyridine-2-carboxylic acid obtained in Preparation Example 1-5 (51.9 g) and IPEA (44 mL) in N,N-dimethylformamide (184 mL), and the mixture was stirred at room temperature for six hours and 30 minutes. Ethyl acetate, ice water and a saturated sodium bicarbonate solution were added to the reaction solution, and the organic layer was separated. The resulting organic layer was dried over anhydrous magnesium sulfate and then filtered through an NH silica gel pad. The resulting filtrate was concentrated under reduced pressure. Ethyl acetate was added to the resulting residue, and the powder was collected by filtration. The resulting powder was air-dried to obtain 28.4 g of the title compound.

Further, the aqueous layer already extracted was reextracted with ethyl acetate. The resulting organic layer was washed with brine, dried over anhydrous magnesium sulfate and then filtered through an NH silica gel pad. The resulting filtrate was concentrated under reduced pressure. Ethyl acetate was added to the resulting residue, and the powder was collected by filtration. The resulting powder was air-dried to obtain 9.15 g of the title compound. The property values of the compound are as follows.

$^{1}$H-NMR ($CDCl_3$) δ (ppm): 2.31 (d, J=1.2 Hz, 3H), 4.08 (s, 3H), 5.23 (s, 2H), 6.87 (brs, 1H), 7.01 (t, J=1.2 Hz, 1H), 7.32-7.45 (m, 5H), 7.71 (d, J=8.0 Hz, 1H), 7.87 (d, J=1.2 Hz, 1H), 7.91 (d, J=8.0 Hz, 1H), 9.17 (brs, 1H).

Synthesis of 6-methoxy-5-(4-methyl-1,1-imidazol-1-yl)pyridine-2-carboxylic acid hydrazide and 6-methoxy-5-(4-methyl-1H-imidazol-1-yl)pyridine-2-carboxylic acid hydrazide hydrochloride 10% palladium-carbon (50% wet, 2.84 g) was added to a solution of benzyl N'-[6-methoxy-5-(4-methyl-1H-imidazol-1-yl)pyridine-2-carbonyl]hydrazinecarboxylate (28.4 g) in methanol (300 mL). The mixture was hydrogenated at an intermediate pressure (2 to 3 atm) for five hours. Chloroform (600 mL) was added to the reaction solution, and then the palladium-carbon was removed by filtration through celite. The filtrate was concentrated under reduced pressure to obtain 19.5 mg of a free form of the title compound. The property values of the compound are as follows.

$^{1}$H-NMR ($CDCl_3$) δ (ppm): 2.30 (d, J=1.2 Hz, 3H), 4.06 (s, 3H), 4.10 (s, 1H), 4.11 (s, 1H), 7.01 (t, J=1.2 Hz, 1H), 7.70 (d, J=8.0 Hz, 1H), 7.86 (d, J=1.2 Hz, 1H), 7.89 (d, J=8.0 Hz, 1H), 8.69 (brs, 1H).

A hydrochloride of the title compound was obtained by the same operation, provided that the hydrogenation reaction was performed in a chloroform-methanol mixed solvent. The property values of the compound are as follows.

$^{1}$H-NMR ($CDCl_3$) δ (ppm): 2.31 (d, J=1.2 Hz, 3H), 4.06 (s, 3H), 7.01 (t, J=1.2 Hz, 1H), 7.71 (d, J=7.6 Hz, 1H), 7.88 (d, J=1.2 Hz, 1H), 7.89 (d, J=7.6 Hz, 1H), 8.69 (brs, 1H).

Preparation Example 1-7

Synthesis of 6-(1-ethoxyvinyl)-2-methoxy-3-(4-methyl-1H-imidazol-1-yl)pyridine

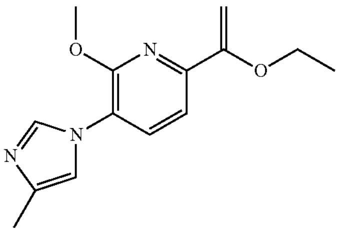 [SMILES: C=C(OCC)c1ccc(-n2cnc(C)c2)c(OC)n1]

1-Ethoxyvinyltri-n-butyltin (3.7 mL) was added to a suspension of 6-bromo-2-methoxy-3-(4-methyl-1H-imidazol-1-yl)pyridine obtained in Preparation Example 1-1) (2.66 g) and bis(triphenylphosphine)palladium (II) chloride (350 mg) in dioxane (25 mL), and the mixture was stirred at 100° C. for five hours and 45 minutes. The reaction solution was left to cool to room temperature and then concentrated under reduced pressure. The resulting residue was purified by silica gel column chromatography (carrier: Wakogel™ C-200; elution solvent:heptane:ethyl acetate=1:0→9:1→3:1→1:1). The target fraction was concentrated. The resulting powder was triturated with diethyl ether-n-hexane and dried under reduced pressure to obtain 1.57 g of the title compound. Then, the trituration mother liquor was concentrated to obtain 858 mg of the title compound. The property values of the compound are as follows.

$^1$H-NMR ($CDCl_3$) δ (ppm): 1.45 (t, J=7.2 Hz, 3H), 2.30 (s, 3H), 3.98 (q, J=7.2 Hz, 2H), 4.04 (s, 3H), 4.38 (d, J=1.6 Hz, 1H), 5.48 (d, J=1.6 Hz, 1H), 6.97 (s, 1H), 7.38 (d, J=8.0 Hz, 1H), 7.52 (d, J=8.0 Hz, 1H), 7.78 (s, 1H).

Preparation Example 1-8

Synthesis of 1-[6-methoxy-5-(4-methyl-1H-imidazol-1-yl)pyridin-2-yl]ethanone

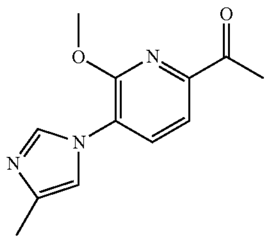 [SMILES: COc1nc(C(C)=O)ccc1-n1cnc(C)c1]

6-Bromo-2-methoxy-3-(4-methyl-1H-imidazol-1-yl)pyridine obtained in Preparation Example 1-1) (2.5 g) was dissolved in N-methylpyrrolidone (93 mL). Palladium acetate (418 mg), 1,3-bis(diphenylphosphino)propane (1.54 g), 1-ethoxyvinyltri-N-butyltin (3.15 mL) and cuprous oxide (2 g) were added, followed by stirring at 120° C. After 16 hours, the reaction solution was partitioned with water and ethyl acetate. The organic layer was washed with aqueous ammonia (twice) and brine. After drying over magnesium sulfate, concentration under reduced pressure gave an oil. The oil was dissolved in methylene chloride (20 mL), followed by addition of trifluoroacetic acid (20 mL). After stirring for one hour, concentration under reduced pressure gave an oil which was partitioned with water and methylene chloride. The organic layer was washed with 1 N sodium hydroxide, water (four times) and brine and dried over magnesium sulfate. The oil after concentration under reduced pressure was purified by silica gel chromatography (mobile phase:ethyl acetate/heptane=0 to 100%) to obtain the title compound (1 g) as a yellow solid.

ESI-MS; m/z 232 [$M^+$+H].

Preparation Example 2-1

Synthesis of 2-bromo-8-(5-isopropyl-4-methoxy-2-methylphenyl)-5,6,7,8-tetrahydro[1,2,4]triazolo[1,5-a]pyridine

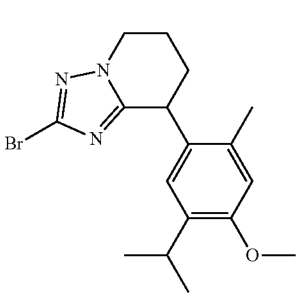 [SMILES: COc1cc(C)c(C2CCCn3nc(Br)nc32)cc1C(C)C]

Synthesis of methyl (5-isopropyl-4-methoxy-2-methylphenyl)acetate (5-Isopropyl-4-methoxy-2-methylphenyl)acetic acid (CAS No. 81354-65-6, 5.5 g) was dissolved in methanol (50 mL), and thionyl chloride (3.5 mL) was added dropwise under ice-cooling. After dropwise addition of the reagent, the mixture was brought back to room temperature and stirred for two hours. The reaction solution was concentrated under reduced pressure. A saturated sodium bicarbonate solution and tert-butyl methyl ether were added and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (5.0 g). The property values of the compound are as follows.

$^1$H-NMR ($CDCl_3$) δ (ppm): 1.19 (d, J=7.2 Hz, 3H), 1.19 (d, J=7.2 Hz, 3H), 2.28 (s, 3H), 3.25 (qq, J=7.2, 7.2 Hz, 1H), 3.58 (s, 2H), 3.68 (s, 3H), 3.80 (s, 3H), 6.66 (s, 1H), 7.00 (s, 1H).

Synthesis of methyl 5-chloro-2-(5-isopropyl-4-methoxy-2-methylphenyl)pentanoate

60% sodium hydride (928 mg) was suspended in anhydrous N,N-dimethylformamide (50 mL). A solution of methyl (5-isopropyl-4-methoxy-2-methylphenyl)acetate (5 g) in anhydrous N,N-dimethylformamide (30 mL) was added in a nitrogen atmosphere, so that the internal temperature was maintained at 4 to 6° C. After stirring at the same temperature for five minutes, 1-chloro-3-iodopropane (4.5 mL) was added so that the internal temperature was maintained at 4 to 6° C. After addition of the reagent, the mixture was brought back to room temperature and stirred for four hours. Ethyl acetate was added to the reaction solution, followed by washing with water. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (7.7 g). The property values of the compound are as follows.

$^1$H-NMR ($CDCl_3$) δ (ppm): 1.17 (d, J=7.2 Hz, 3H), 1.19 (d, J=7.2 Hz, 3H), 1.64-1.97 (m, 3H), 2.14-2.25 (m, 1H), 2.35 (s, 3H), 3.24 (qq, J=7.2, 7.2 Hz, 1H), 3.48-3.56 (m, 2H), 3.64 (s, 3H), 3.77 (t, 7.6 Hz, 1H), 3.08 (s, 3H), 6.64 (s, 1H), 7.08 (s, 1H).

Synthesis of tert-butyl N'-[5-chloro-2-(5-isopropyl-4-methoxy-2-methylphenyl)pentanoyl]hydrazinecarboxylate Methyl 5-chloro-2-(5-isopropyl-4-methoxy-2-methylphenyl)pentanoate (7.7 g) was dissolved in a mixed solvent of methanol (25 mL) and tetrahydrofuran (25 mL). A 5 N sodium hydroxide solution (22 mL) was added and the mixture was stirred at room temperature for four hours. The reaction solution was concentrated under reduced pressure and water was added, followed by washing with heptane. The aqueous layer was made acidic with 5 N hydrochloric acid, followed by extraction with tert-butyl methyl ether. The resulting organic layer was washed with brine and then dried over anhydrous sodium sulfate. The drying agent was separated by filtration and the organic layer was concentrated under reduced pressure to obtain 5-chloro-2-(5-isopropyl-4-methoxy-2-methylphenyl)pentanoic acid (6.2 g).

5-Chloro-2-(5-isopropyl-4-methoxy-2-methylphenyl)pentanoic acid (6.2 g), tert-butyl carbazate (4.1 g) and N,N-diisopropylethylamine (10.8 mL) were dissolved in dichloromethane (120 mL). Bis(2-oxo-3-oxazolidinyl)phosphinic acid chloride (7.9 g) was added under ice-cooling. After addition of the reagent, the mixture was brought back to room temperature and stirred overnight. The reaction solution was concentrated under reduced pressure. A sodium bicarbonate solution and tert-butyl methyl ether were added and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (6.1 g). The property values of the compound are as follows.

ESI-MS; m/z 435 $[M^{+}+Na]$.

Synthesis of 5-chloro-2-(5-isopropyl-4-methoxy-2-methylphenyl)pentanoic acid hydrazide tert-Butyl N'-[5-chloro-2-(5-isopropyl-4-methoxy-2-methylphenyl)pentanoyl]hydrazinecarboxylate (6.1 g) was dissolved in ethyl acetate (50 mL). A 4 N hydrochloric acid-ethyl acetate solution (50 mL) was added and the mixture was stirred at room temperature for 3.5 hours. The reaction solution was made alkaline with a 5 N sodium hydroxide solution under ice-cooling, and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (4.4 g). The property values of the compound are as follows.

ESI-MS; m/z 313 $[M^{4}.+H]$.

$^{1}$H-NMR ($CDCl_3$) δ (ppm): 1.186 (d, J=6.8 Hz, 3H), 1.190 (d, J=7.2 Hz, 3H), 1.61-1.85 (m, 2H), 1.93-2.04 (m, 1H), 2.26-2.88 (m, 1H), 2.27 (s, 3H), 3.25 (qq, J=7.2, 6.8 Hz, 1H), 3.48-3.59 (m, 3H), 3.75-3.89 (m, 5H), 6.49 (brs, 1H), 6.65 (s, 1H), 7.08 (s, 1H).

Synthesis of 8-(5-isopropyl-4-methoxy-2-methylphenyl)-5,6,7,8-tetrahydro-[1,2,4]triazolo[1,5-a]pyridin-2-ylamine 5-Chloro-2-(5-isopropyl-4-methoxy-2-methylphenyl)pentanoic acid hydrazide (4.4 g) and cyanamide (3.6 g) were dissolved in ethanol (150 mL). p-Toluenesulfonic acid monohydrate (4 g) was added and the mixture was heated under reflux at 80° C. for two hours. After cooling to room temperature, triethylamine (9.8 mL) was added and the mixture was further heated under reflux at 80° C. for three days. The reaction solution was concentrated under reduced pressure. A sodium bicarbonate solution and ethyl acetate were added and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (2.4 g). The property values of the compound are as follows.

ESI-MS; m/z 301 $[M^{+}+H]$.

$^{1}$H-NMR ($CDCl_3$) δ (ppm): 1.12 (d, J=6.8 Hz, 3H), 1.14 (d, J=6.8 Hz, 3H), 1.86-2.26 (m, 4H), 2.27 (s, 3H), 3.19 (qq, J=6.8, 6.8 Hz 1H), 3.79 (s, 3H), 4.02 (brs, 2H), 4.06-4.12 (m, 2H), 4.19-4.24 (m, 1H), 6.64 (s, 1H), 6.69 (s, 1H).

Synthesis of 2-bromo-8-(5-isopropyl-4-methoxy-2-methylphenyl)-5,6,7,8-tetrahydro[1,2,4]triazolo[1,5-a]pyridine 8-(5-Isopropyl-4-methoxy-2-methylphenyl)-5,6,7,8-tetrahydro[1,2,4]triazolo[1,5-a]pyridin-2-ylamine (1.5 g) and copper (II) bromide (1.7 g) were dissolved in acetonitrile (50 mL). Isoamyl nitrite (1 mL) was added and the mixture was heated with stirring at 70° C. for 45 minutes. Ethyl acetate was added to the reaction solution, followed by washing with aqueous ammonia. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (1.4 g). The property values of the compound are as follows.

ESI-MS; m/z 364 $[M^{+}+H]$.

$^{1}$H-NMR ($CDCl_3$) δ (ppm): 1.11 (d, J=7.2 Hz, 3H), 1.12 (d, J=7.2 Hz, 3H), 1.90-2.30 (m, 4H), 2.26 (s, 3H), 3.19 (qq, J=7.2, 7.2 Hz, 1H), 3.80 (s, 3H), 4.24-4.29 (m, 2H), 4.30-4.36 (m, 1H), 6.59 (s, 1H), 6.65 (s, 1H).

The compounds of Preparation Examples 2-2 to 2-6 were obtained by the same method as in Example 2-1 (Table 6).

TABLE 6

| Production Ex No. | Structural formula | $^{1}$H-NMR or ESI mass |
|---|---|---|
| 2-2 | 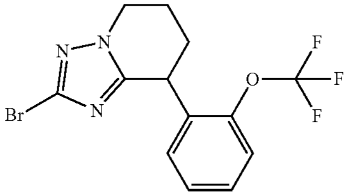 [SMILES: FC(F)(F)Oc1ccccc1C1CCCn2nc(Br)nc21] | ESI-MS: m/z 364$[M^{+} + H]$. |
| 2-3 | 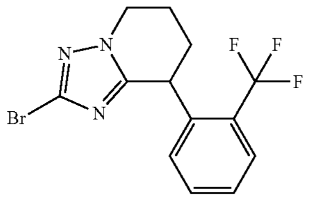 [SMILES: FC(F)(F)c1ccccc1C1CCCn2nc(Br)nc21] | ESI-MS: m/z 346, 348$[M^{+} + H]$. $^{1}$H-NMR ($CDCl_3$) δ (ppm): 1.86-1.96 (m, 1H), 2.06-2.20 (m, 1H), 2.21-2.30 (m, 1H), 2.40-2.49 (m, 1H), 4.22-4.36 (m, 2H), 4.61 (d, J = 9.2, 6.0 Hz, 1H), 6.99 (d, J - 8.0 Hz, 1H), 7.38 (dd, J = 8.0, 7.2 Hz, 1H), 7.49 (dd, J = 8.0, 7.2 Hz, 1H), 7.69 (d, J = 8.0 Hz, 1H). |

TABLE 6-continued

| Production Ex No. | Structural formula | $^1$H-NMR or ESI mass |
|---|---|---|
| 2-4 | 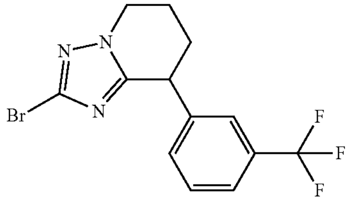 [SMILES: FC(F)(F)c1cccc(C2CCCn3nc(Br)nc32)c1] | ESI-MS: m/z 346, 348[$M^+$ + H]. |
| 2-5 | 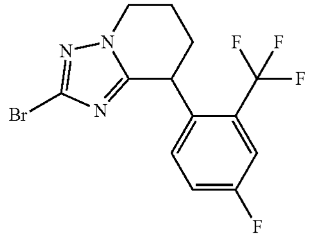 [SMILES: Fc1ccc(C2CCCn3nc(Br)nc32)c(C(F)(F)F)c1] | ESI-MS: m/z 364[$M^+$ + H]. |
| 2-6 | 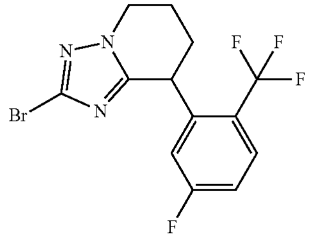 [SMILES: Fc1ccc(C(F)(F)F)c(C2CCCn3nc(Br)nc32)c1] | ESI-MS: m/z 364[$M^+$ + H]. |

Preparation Example 2-7

Synthesis of 2-bromo-8-(2-trifluoromethylbenzyl)-5,6,7,8-tetrahydro[1,2,4]triazolo[1,5-a]pyridine

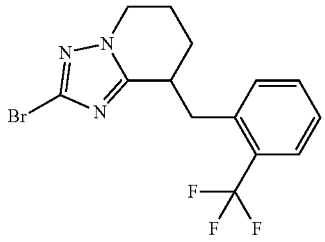 [SMILES: FC(F)(F)c1ccccc1CC1CCCn2nc(Br)nc21]

Synthesis of ethyl 5-chloro-2-[1-(2-trifluoromethylphenyl)methylidene]pentanoate 2-(Trifluoromethyl)benzaldehyde (1 g) and ethyl 5-chloro-2-(diethoxyphosphoryl)pentanoate (CAS No. 870843-20-2, 2.1 g) were dissolved in a mixed solvent of tetrahydrofuran (30 mL) and ethanol (10 mL). Lithium hydroxide (412 mg) was added and the mixture was stirred at room temperature overnight. Water was added to the reaction solution, followed by extraction with ethyl acetate. The resulting organic layer was washed with brine and then dried over anhydrous sodium sulfate. The drying agent was separated by filtration, and then the organic layer was concentrated under reduced pressure. The residue was purified by silica gel column chromatography to obtain a geometric isomer mixture of the title compound (1.4 g).

Synthesis of 1-amino-3-(2-trifluoromethylbenzyl)piperidin-2-one

The geometric isomer mixture of ethyl 5-chloro-2-[1-(2-trifluoromethylphenyl)methylidene]pentanoate (1.4 g) was dissolved in ethanol (30 mL) and catalytically hydrogenated for two hours using a 10% palladium-carbon cartridge in the H-Cube™ (manufactured by THALES Nanotechnology Inc.) system. The reaction solution was concentrated under reduced pressure to reduce the amount of the catalyst to about half. Hydrazine monohydrate (4.4 mL) was added and the mixture was heated under reflux for 12 hours. The reaction solution was concentrated under reduced pressure and water was added, followed by extraction with ethyl acetate. The resulting organic layer was washed with brine and then dried over anhydrous sodium sulfate. The drying agent was separated by filtration, and then the organic layer was concentrated under reduced pressure. The residue was purified by NH silica gel column chromatography to obtain the title compound (916 mg). The property values of the compound are as follows.

ESI-MS; m/z 273 [$M^+$+H].

$^1$H-NMR ($CDCl_3$) δ (ppm): 1.43-1.53 (m, 1H), 1.65-1.80 (m, 2H), 1.88-1.98 (m, 1H), 2.67-2.76 (m, 1H), 2.80-2.89 (m, 1H), 3.45-3.55 (m, 2H), 3.65 (dd, J=14.6, 4.2 Hz, 1H), 4.53 (brs, 2H), 7.31 (dd, J=8.0, 7.2 Hz, 1H), 7.40 (d, J=8.0 Hz, 1H), 7.48 (dd, J=7.6, 7.2 Hz, 1H), 7.64 (d, J=7.6 Hz, 1H).

Synthesis of 8-(2-trifluoromethylbenzyl)-5,6,7,8-tetrahydro[1,2,4]triazolo[1,5-a]pyridin-2-ylamine 1-Amino-3-(2-trifluoromethylbenzyl)piperidin-2-one (916 mg) and cyanamide (849 mg) were dissolved in ethanol (15 mL). p-Toluenesulfonic acid monohydrate (961 mg) was added and the mixture was heated under reflux at 80° C. for 3.5 hours. After cooling to room temperature, triethylamine (2.3 mL) was added and the mixture was further heated under reflux at 80° C. for four days. A sodium bicarbonate solution and ethyl acetate were added to the reaction solution, and the organic layer was separated. The resulting organic layer was washed with brine and then dried over anhydrous sodium sulfate. The drying agent was separated by filtration and then the organic layer was concentrated under reduced pressure. The resulting solid was washed with ethyl acetate to obtain the title compound (244 mg). The property values of the compound are as follows.

ESI-MS; m/z 297 [$M^+$+H].

$^1$H-NMR ($CDCl_3$) δ (ppm): 1.48-1.60 (m, 1H), 1.75-1.94 (m, 2H), 2.04-2.13 (m, 1H), 2.92 (ddd, J=14.4, 10.8, 1.2 Hz, 1H), 3.13-3.22 (m, 1H), 3.67 (dd, J=14.6, 4.2 Hz, 1H), 3.88-4.12 (m, 4H), 7.34 (dd, J=7.6, 7.2 Hz, 1H), 7.41 (d, J=7.6 Hz, 1H), 7.51 (dd, J=8.0, 7.2 Hz, 1H), 7.67 (d, J=8.0 Hz, 1H).

2-Bromo-8-(2-trifluoromethylbenzyl)-5,6,7,8-tetrahydro[1,2,4]triazolo[1,5-a]pyridine The title compound was obtained by the same method as in Preparation Example 2-1 from 8-(2-trifluoromethylbenzyl)-5,6,7,8-tetrahydro[1,2,4]triazolo[1,5-a]pyridin-2-ylamine.

ESI-MS; m/z 360, 362 [$M^+$+H].

Preparation Example 2-8

Synthesis of 2-bromo-4-(4-trifluoromethylphenyl)-4,5,6,7-tetrahydrobenzothiazole

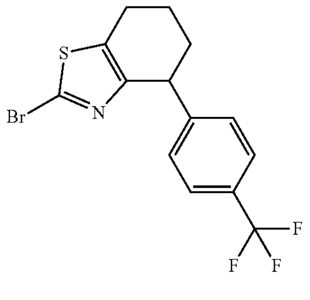 [SMILES: FC(F)(F)c1ccc(C2CCCc3sc(Br)nc32)cc1]

Synthesis of 2-(4-trifluoromethylphenyl)cyclohexanone

1-Bromo-4-trifluoromethylbenzene (5 mL), cyclohexanone (7.4 mL) and potassium tert-butoxide (8 g) were suspended in tetrahydrofuran (100 mL). Tris(dibenzylieneacetone)dipalladium (1.3 g) and 2-dicyclohexylphosphino-2'-(N,N-dimethylamino)biphenyl (843 mg) were added and the mixture was heated with stirring at 70° C. in a nitrogen atmosphere for 1.5 hours. After leaving to cool, tert-butyl methyl ether was added, followed by filtration through celite. The resulting organic layer was concentrated under reduced pressure. The residue was purified by silica gel column chromatography three times. The resulting solid was washed with heptane to obtain the title compound (2.1 g). The property values of the compound are as follows.

ESI-MS; m/z 243 [$M^+$+H].

$^1$H-NMR ($CDCl_3$) δ (ppm): 1.80-1.93 (m, 2H), 1.96-2.08 (m, 2H), 2.16-2.24 (m, 1H), 2.26-2.34 (m, 1H), 2.44-2.60 (m, 2H), 3.65-3.77 (m, 1H), 7.25 (d, J=8.0 Hz, 2H), 7.59 (d, J=8.0 Hz, 2H).

Synthesis of 4-(4-trifluoromethylphenyl)-4,5,6,7-tetrahydrobenzothiazol-2-ylamine 2-(4-Trifluoromethylphenyl)cyclohexanone (1.2 g) was dissolved in chloroform (20 mL). A solution of bromine in tetrahydrofuran prepared at 0.3 M (20 mL) was added dropwise while maintaining the internal temperature at 5° C. or less. Thereafter, the mixture was brought back to room temperature and stirred for three hours. A sodium bicarbonate solution and chloroform were added to the reaction solution, and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain a diastereomer mixture of 2-bromo-6-(4-trifluoromethylphenyl)cyclohexanone (1.2 g).

The diastereomer mixture of 2-bromo-6-(4-trifluoromethylphenyl)cyclohexanone (500 mg) was dissolved in ethanol (10 mL). Thiourea (130 mg) was added and the mixture was stirred at room temperature overnight. A sodium bicarbonate solution and ethyl acetate were added to the reaction solution, and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (394 mg).

The property values of the compound are as follows.

ESI-MS; m/z 243 [M++H].

$^1$H-NMR ($CDCl_3$) δ (ppm): 1.74-1.88 (m, 3H), 2.13-2.22 (m, 1H), 2.62-2.77 (m, 2H), 4.00-4.05 (m, 1H), 4.72 (brs, 2H), 7.22 (d, J=8.4 Hz, 2H), 7.53 (d, J=8.4 Hz, 2H).

Synthesis of 2-bromo-4-(4-trifluoromethylphenyl)-4,5,6,7-tetrahydrobenzothiazole The title compound was obtained by the same method as in Preparation Example 2-1 from 4-(4-trifluoromethylphenyl)-4,5,6,7-tetrahydrobenzothiazol-2-ylamine. The property values of the compound are as follows.

ESI-MS; m/z 364 [M++H].

$^1$H-NMR ($CDCl_3$) δ (ppm): 1.78-1.93 (m, 3H), 2.18-2.28 (m, 1H), 2.75-2.90 (m, 2H), 4.23-4.28 (m, 1H), 7.17 (d, J=8.2 Hz, 2H), 7.54 (d, J=8.2 Hz, 2H).

Preparation Example 2-9

Synthesis of 2-bromo-8-(2-trifluoromethylphenyl)-5,6,7,8-tetrahydro[1,2,4]triazolo[1,5-a]pyridin-6-ol

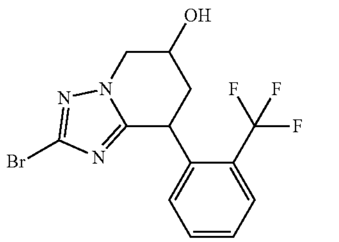 [SMILES: OC1CC(c2ccccc2C(F)(F)F)c2nc(Br)nn2C1]

Synthesis of methyl 3-oxiranyl-2-(2-trifluoromethylphenyl)propionate

Methyl (2-trifluoromethylphenyl)acetate (5.0 g) was dissolved in tetrahydrofuran (10 mL), and the solution was added at −78° C. to a solution containing potassium bistrimethylsilylamide (50 mL) in tetrahydrofuran (190 mL). After stirring for 30 minutes, epibromohydrin (1.96 mL) was added at the same temperature. After further 10 minutes, a boron trifluoride-diethyl ether complex (3.16 mL) was added. After stirring at −78° C. for one hour, the reaction was terminated with a saturated sodium bicarbonate aqueous solution. The organic layer diluted with ethyl acetate was washed with a saturated sodium bicarbonate aqueous solution and brine and dried over magnesium sulfate. Concentration under reduced pressure gave a residue which was dissolved in methanol (50 mL) and methylene chloride (50 mL) and treated with potassium carbonate (15.8 g). After one hour, potassium carbonate was precipitated by adding methylene chloride (200 mL) and removed by filtration through celite. The resulting solution was washed with saturated ammonium chloride aqueous solution and brine and dried over magnesium sulfate. Concentration under reduced pressure gave a crude product. The crude product was purified by silica gel column chromatography (mobile phase:ethyl acetate/heptane=0 to 30%) to obtain a diastereomer mixture (2.61 g).

Synthesis of 1-amino-5-hydroxy-3-(2-trifluoromethylphenyl)piperidin-2-one

Methyl 3-oxiranyl-2-(2-trifluoromethylphenyl)propionate (2.61 g) was dissolved in ethanol (20 mL). Hydrazine monohydrate (2.3 mL) was added at room temperature, and the mixture was reacted for 24 hours. Concentration under reduced pressure gave an oil which was partitioned with methylene chloride and water. The aqueous layer was extracted with methylene chloride four times. After drying over magnesium sulfate, concentration under reduced pressure gave the title compound (1.8 g) as a pale yellow solid.

ESI-MS; m/z 275 [$M^+$+H].

Synthesis of 2-bromo-8-(2-trifluoromethylphenyl)-5,6,7,8-tetrahydro-[1,2,4]triazolo[1,5-a]pyridin-6-ol The title compound was obtained as a white solid by the same method as in Preparation Example 2-7 from 1-amino-5-hydroxy-3-(2-trifluoromethylphenyl)piperidin-2-one.

ESI-MS; m/z 362 [$M^+$+H].

Preparation Example 2-10

Synthesis of 2-bromo-7-(3-trifluoromethylphenyl)-5,6,7,8-tetrahydro[1,2,4]triazolo[1,5-a]pyridine

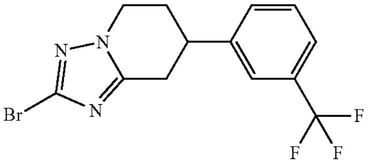 [SMILES: FC(F)(F)c1cccc(C2CCn3nc(Br)nc3C2)c1]

Synthesis of 4-(3-trifluoromethylphenyl)tetrahydropyran-2-one (Acetylacetonato)bis(ethylene)rhodium (I) (180 mg) was dissolved in 1,4-dioxane (144 mL). Racemic BINAP (2,2'-bis(diphenylphosphino)-1,1'-binaphthalene) (867 mg) was added at room temperature, followed by stirring for 30 minutes. Subsequently, water (14.4 mL) and 3-(trifluoromethyl)phenylboronic acid (5.29 g) were added, followed by stirring for 10 minutes. Then, 5,6-dihydro-2H-pyran-2-one (2 mL) was added and the mixture was reacted at 100° C. for 12 hours. The reaction solution was partitioned with ethyl acetate and water. Then, the organic layer was washed with a saturated sodium bicarbonate solution and dried over magnesium sulfate. Concentration under reduced pressure gave an oil. The oil was purified by silica gel column chromatography (mobile phase:ethyl acetate/heptane=0 to 60%) to obtain the title compound (2.5 g).

ESI-MS; m/z 245 [$M^+$+H].

Synthesis of 5-hydroxy-3-(3-trifluoromethylphenyl)pentanoic acid hydrazide 4-(3-Trifluoromethylphenyl)tetrahydropyran-2-one (2.5 g) was dissolved in ethanol (10 mL), and hydrazine monohydrate (4.96 mL) was added at room temperature. The mixture was stirred at 80° C. for 4.5 hours and then concentrated under reduced pressure. The resulting oil was partitioned with methylene chloride and water. The aqueous layer was extracted with methylene chloride five times. After drying over magnesium sulfate, concentration under reduced pressure and purification by silica gel column chromatography (amino silica gel, mobile phase:ethyl acetate/heptane=0 to 50%→methanol/ethyl acetate=10%) gave the title compound (1.55 g).

ESI-MS; m/z 277 [$M^+$+H].

Synthesis of tert-butyl N'-[5-hydroxy-3-(3-trifluoromethylphenyl)pentanoyl]hydrazinecarboxylate 5-Hydroxy-3-(3-trifluoromethylphenyl)pentanoic acid hydrazide (1.55 g) was dissolved in tetrahydrofuran (26 mL), and di-tert-butyl dicarbonate (1.35 g) was added at room temperature. After stirring for 15 hours, the reaction solution was diluted with ethyl acetate and washed with a saturated sodium bicarbonate solution and brine. After drying over magnesium sulfate, concentration under reduced pressure gave the title compound (2.0 g). The resulting compound was used directly for the next reaction as a crude product.

Synthesis of tert-butyl N'-[5-bromo-3-(3-trifluoromethylphenyl)pentanoyl]hydrazinecarboxylate tert-Butyl N'-[5-hydroxy-3-(3-trifluoromethylphenyl)pentanoyl]hydrazinecarboxylate (2.0 g) was dissolved in methylene chloride (53 mL). Pyridine (1.29 mL), carbon tetrabromide (2.64 g) and triphenylphosphine (2.1 g) were added at room temperature, followed by stirring for 30 minutes. The reaction solution was partitioned with water and ethyl acetate. Then, the organic layer was washed with saturated ammonium chloride aqueous solution and a saturated sodium bicarbonate aqueous solution and dried over magnesium sulfate. Concentration under reduced pressure gave an oil. The oil was purified by silica gel column chromatography (mobile phase:ethyl acetate/heptane=0 to 50%) to obtain the title compound (1.6 g).

Synthesis of 5-bromo-3-(3-trifluoromethylphenyl)pentanoic acid hydrazide tert-Butyl N'-[5-bromo-3-(3-trifluoromethylphenyl)pentanoyl]hydrazinecarboxylate (1.6 g) was dissolved in methylene chloride (8 mL), and trifluoroacetic acid (10 mL) was added at 0° C. The mixture was stirred at room temperature for two hours and then concentrated under reduced pressure. The resulting oil was diluted with ethyl acetate, and then washed with 1 N sodium hydroxide aqueous solution and brine and dried over magnesium sulfate. The oil after concentration under reduced pressure (990 mg) was used directly for the next reaction as a crude product.

Synthesis of 2-bromo-7-(3-trifluoromethylphenyl)-5,6,7,8-tetrahydro[1,2,4]triazolo[1,5-a]pyridine The title compound was obtained by the same method as in Preparation Example 2-1 from 5-bromo-3-(3-trifluoromethylphenyl)pentanoic acid hydrazide.

ESI-MS; m/z 348 [$M^+$+H].

Preparation Example 2-11

Synthesis of 2-bromo-8-methyl-7-(4-trifluoromethylphenyl)-5,6,7,8-tetrahydro[1,2,4]triazolo[1,5-a]pyridine

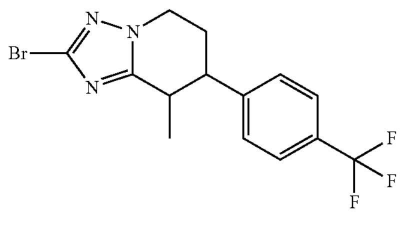 [SMILES: CC1c2nc(Br)nn2CCC1c1ccc(C(F)(F)F)cc1]

Synthesis of 3-methyl-4-(4-trifluoromethylphenyl)tetrahydropyran-2-one 4-(4-Trifluoromethylphenyl)tetrahydropyran-2-one (995 mg) derived by the same method as in Preparation Example 2-10 from 4-(trifluoromethyl)phenylboronic acid (5.29 g) and 5,6-dihydro-2H-pyran-2-one was dissolved in tetrahydrofuran (10 mL). The solution was added dropwise at −78° C. to a lithium diisopropylamide solution previously prepared from n-butyllithium (3.91 mL) and diisopropylamine (1.46 mL) in tetrahydrofuran (30 mL). After stirring at the same temperature for 30 minutes, iodomethane (760 μL) and hexamethylphosphoramide (1.77 mL) were added and stirring was continued. After stirring for 30 minutes, the reaction solution was gradually heated to room temperature over three hours and 20 minutes. The reaction was terminated with saturated ammonium chloride aqueous solution. The organic layer was washed with brine and then dried over magnesium sulfate. Removal under reduced pressure gave an oil. The oil was purified by silica gel column chromatography (mobile phase:ethyl acetate/heptane=0 to 50%) to obtain the title compound (500 mg).

ESI-MS; m/z 259 [$M^+$+IT].

Synthesis of 2-bromo-8-methyl-7-(4-trifluoromethylphenyl)-5,6,7,8-tetrahydro[1,2,4]triazolo[1,5-a]pyridine The title compound was obtained by the same method as in Preparation Example 2-10 from 3-methyl-4-(4-trifluoromethylphenyl)tetrahydropyran-2-one.

Preparation Example 2-12

Synthesis of 2-bromo-5-(3-trifluoromethylphenyl)5,6,7,8-tetrahydro[1,2,4]triazolo[1,5-a]pyridine

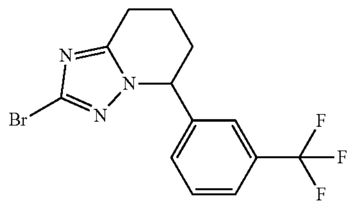 [SMILES: FC(F)(F)c1cccc(C2CCCc3nc(Br)nn32)c1]

Synthesis of ethyl 5-(N'-tert-butoxycarbonylhydrazino)-5-(3-trifluoromethylphenyl)pentanoate Ethyl 5-oxo-5-(3-trifluoromethylphenyl)pentanoate (CAS No. 898777-75-8, 330 mg) and tert-butyl carbazate (227 mg) were dissolved in a mixed solvent of THF (6 mL) and acetic acid (3 mL). After stirring at room temperature for 25 minutes, sodium cyanoborohydride (108 mg) was added. After further one hour and 30 minutes, sodium cyanoborohydride (108 mg) was added and the mixture was stirred at room temperature for one hour. A saturated sodium bicarbonate solution and diethyl ether were added to the reaction solution, and the organic layer was separated. The resulting organic layer was washed with a saturated sodium bicarbonate solution and then dried over anhydrous sodium sulfate. The drying agent was separated by filtration and then the organic layer was concentrated under reduced pressure. The residue was purified by silica gel column chromatography to obtain the title compound (324 mg). The property values of the compound are as follows.

$^1$H-NMR ($CDCl_3$) δ (ppm): 1.22 (t, J=7.2 Hz, 3H), 1.43 (s, 9H), 1.47-1.84 (m, 4H), 2.27 (t, J=6.8 Hz, 2H), 4.09 (q, J=7.2 Hz, 2H), 4.14 (t, J=7.2 Hz, 1H), 4.25 (brs, 1H), 5.88 (brs, 1H), 7.43-7.62 (m, 4H).

Synthesis of tert-butyl [2-oxo-6-(3-trifluoromethylphenyl)piperidin-1-yl]carbamate Ethyl 5-(N'-tert-butoxycarbonylhydrazino)-5-(3-trifluoromethylphenyl)pentanoate (323 mg) was dissolved in methanol (7 mL). A 1 N sodium hydroxide solution (5 mL) was added and the mixture was stirred at room temperature for two hours and 30 minutes. 1 N hydrochloric acid (5 mL) and ethyl acetate were added to the reaction solution, and the organic layer was separated and dried over anhydrous sodium sulfate. The drying agent was separated by filtration and then the organic layer was concentrated under reduced pressure. The residue was dissolved in dimethylformamide (8 mL). 1-Ethyl-3-(dimethylaminopropyl)carbodiimide hydrochloride (317 mg) and 1-hydroxybenzotriazole (223 mg) were added and the mixture was stirred at room temperature for 13 hours. 1-Ethyl-3-(dimethylaminopropyl)carbodiimide hydrochloride (317 mg) was added to the reaction solution, and the mixture was further stirred for one hour. Diethyl ether and water were added to the reaction solution, and the organic layer was separated. The resulting organic layer was washed with brine and then dried over anhydrous sodium sulfate. The drying agent was separated by filtration and then the organic layer was concentrated under reduced pressure. The residue was purified by silica gel column chromatography to obtain the title compound (214 mg). The property values of the compound are as follows.

$^1$H-NMR ($CDCl_3$) δ (ppm): 1.43 (s, 9H), 1.86-1.94 (m, 3H), 2.26-2.39 (m, 1H), 2.59-2.69 (m, 2H), 4.99 (brs, 1H), 6.39 (brs, 1H), 7.39 (d, J=7.6 Hz, 1H), 7.44 (s, 1H), 7.50 (t, J=7.6 Hz, 1H), 7.57 (d, J=7.6 Hz, 1H).

Synthesis of 1-amino-6-(3-trifluoromethylphenyl)piperidin-2-one tert-Butyl [2-oxo-6-(3-trifluoromethylphenyl)piperidin-1-yl]carbamate (210 mg) was dissolved in chloroform (4 mL), followed by addition of trifluoroacetic acid (2 mL). After stirring at room temperature for four hours, concentration under reduced pressure gave the title compound (119 mg). The property values of the compound are as follows.

$^1$H-NMR ($CDCl_3$) δ (ppm): 1.72-1.92 (m, 3H), 2.23-2.59 (m, 1H), 2.59 (dt, J=2.4 Hz, 6.4 Hz, 2H), 4.36 (s, 2H), 4.79 (t, J=6.4 Hz, 1H), 7.37 (d, J=7.6 Hz, 1H), 7.44 (s, 1H), 7.52 (t, J=7.6 Hz, 1H), 7.58 (d, J=7.6 Hz, 1H).

Synthesis of 2-bromo-5-(3-trifluoromethylphenyl)-5,6,7,8-tetrahydro[1,2,4]triazolo[1,5-a]pyridine The title compound was obtained according to the method of Preparation Example 2-7 from 1-amino-6-(3-trifluoromethylphenyl)piperidin-2-one. The property values of the compound are as follows.

$^1$H-NMR ($CDCl_3$) δ (ppm): 1.89-2.04 (m, 2H), 2.07-2.15 (m, 1H), 2.41-2.49 (m, 1H), 3.03 (dt, J=3.2 Hz, 6.8 Hz, 2H), 5.46 (t, J=6.0 Hz, 1H), 7.14 (d, J=7.6 Hz, 1H), 7.33 (s, 1H), 7.49 (t, J=7.6 Hz, 1H), 7.59 (d, J=7.6 Hz, 1H).

Preparation Example 2-13

Synthesis of 4-bromo-7-(4-trifluoromethylphenyl)-2,3,5-triaza-tricyclo[5.2.2.0*2,6*]undeca-3,5-diene

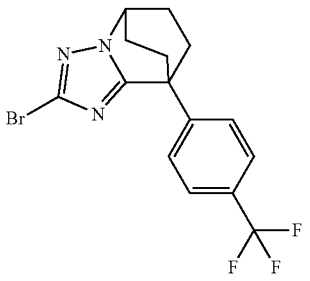 [SMILES: FC(F)(F)c1ccc(C23CCC(CC2)n2nc(Br)nc23)cc1]

Synthesis of dimethyl 4-hydroxy-1-(4-trifluoromethylphenyl)-3-cyclohexene-1,3-dicarboxylate Methyl (4-trifluorophenyl)acetate (CAS No. 135325-18-7, 1 g) and methyl acrylate (789 mg) were dissolved in THF (13 mL). Potassium tert-Butoxide (617 mg) was added and the mixture was stirred at room temperature for 14 hours and 30 minutes. Water was added to the reaction solution, followed by stirring at 85° C. for five hours and 30 minutes. After leaving to cool, ethyl acetate was added to the reaction solution, followed by neutralization with 1 N hydrochloric acid. The organic layer was separated, washed with brine and then dried over anhydrous sodium sulfate. The drying agent was separated by filtration and then the organic layer was concentrated under reduced pressure. The residue was purified by silica gel column chromatography to obtain the title compound (1.13 g). The property values of the compound are as follows.

$^1$H-NMR ($CDCl_3$) δ (ppm): 2.13-2.60 (m, 4H), 2.75 (d, J=16.4 Hz, 1H), 3.08 (d, J=16.4 Hz, 1H), 3.66 (s, 3H), 3.82 (s, 3H), 7.47 (d, J=8.8 Hz, 2H), 7.60 (d, J=8.8 Hz, 2H), 12.11 (s, 1H).

Synthesis of methyl 4-oxo-1-(4-trifluoromethylphenyl)cyclohexanecarboxylate

Dimethyl 4-hydroxy-1-(4-trifluoromethylphenyl)-3-cyclohexene-1,3-dicarboxylate (1.13 g) was dissolved in a mixed solvent of THF (3 mL) and methanol (3 mL). A 1 N potassium hydroxide solution (1.89 mL) was added and the mixture was stirred at 100° C. for eight hours. After leaving to cool, ethyl acetate and water were added to the reaction solution, followed by neutralization with 1 N hydrochloric acid. The organic layer was separated, washed with brine and then dried over anhydrous sodium sulfate. The drying agent was separated by filtration and then the organic layer was concentrated under reduced pressure. The residue was purified by silica gel column chromatography to obtain the title compound (272 mg). The property values of the compound are as follows.

$^1$H-NMR ($CDCl_3$) δ (ppm): 2.21-2.28 (m, 2H), 2.41-2.47 (m, 2H), 2.52-2.60 (m, 2H), 2.77-2.83 (m, 2H), 3.74 (s, 3H), 7.54 (d, J=8.4 Hz, 2H), 7.64 (d, J=8.4 Hz, 2H).

Synthesis of methyl 4-(N'-tert-butoxycarbonylhydrazino)-1-(4-trifluoromethylphenyl)cyclohexanecarboxylate Methyl 4-oxo-1-(4-trifluoromethylphenyl)cyclohexanecarboxylate (100 mg) and tert-butyl carbazate (66 mg) were dissolved in a mixed solvent of THF (6 mL) and acetic acid (3 mL). After stirring at room temperature for 50 minutes, sodium cyanoborohydride (31.4 mg) was added. After further two hours, sodium cyanoborohydride (31.4 mg) was added and the mixture was stirred at room temperature for one hour. Diethyl ether and a saturated sodium bicarbonate solution were added to the reaction solution, and the organic layer was separated. The resulting organic layer was washed with a saturated sodium bicarbonate solution and then dried over anhydrous sodium sulfate. The drying agent was separated by filtration and then the organic layer was concentrated under reduced pressure. The residue was purified by silica gel column chromatography to obtain the title compound (74.5 mg). The property values of the compound are as follows.

$^1$H-NMR ($CDCl_3$) δ (ppm): 1.28-1.36 (m, 2H), 1.47 (s, 9H), 1.60-1.66 (m, 2H), 1.94-1.96 (m, 2H), 2.66-2.69 (m, 2H), 2.87 (brs, 1H), 3.66 (s, 3H), 4.05 (brs, 1H), 6.08 (brs, 1H), 7.48 (d, J=8.4 Hz, 2H), 7.57 (d, J=8.4 Hz, 2H).

Synthesis of tert-butyl[3-oxo-4-(4-trifluoromethylphenyl)-2-aza-bicyclo[2,2,2]oct-2-yl]carbamate Methyl 4-(N'-tert-butoxycarbonylhydrazino)-1-(4-trifluoromethylphenyl)cyclohexanecarboxylate (74.5 mg) was dissolved in methanol (1.5 mL), followed by addition of a 1 N sodium hydroxide solution (1 mL) The mixture was stirred at room temperature for 15 hours and then stirred with heating under reflux for 11 hours and 30 minutes. After leaving to cool, diethyl ether was added to the reaction solution, followed by neutralization with 1 N hydrochloric acid. The organic layer was separated and then washed with brine. The resulting organic layer was dried over anhydrous sodium sulfate. The drying agent was separated by filtration and then the organic layer was concentrated under reduced pressure. The residue was purified by silica gel column chromatography to obtain the title compound (35.7 mg). The property values of the compound are as follows.

$^1$H-NMR ($CDCl_3$) δ (ppm): 1.48 (s, 9H), 1.80-1.85 (m, 2H), 2.02-2.11 (m, 2H), 2.22-2.32 (m, 4H), 3.90 (s, 1H), 6.77 (brs, 1H), 7.48 (d, J=8.4 Hz, 2H), 7.60 (d, J=8.4 Hz, 2H).

Synthesis of 4-bromo-7-(4-trifluoromethylphenyl)-2,3,5-triaza-tricyclo [5.2.2.0*2,6*]undeca-3,5-diene The title compound was obtained according to the method of Preparation Example 2-12 from tert-butyl [3-oxo-4-(4-trifluoromethylphenyl)-2-aza-bicyclo[2,2,2]oct-2-yl]carbamate. The property values of the compound are as follows.

$^1$H-NMR ($CDCl_3$) δ (ppm): 1.93-2.12 (m, 6H), 2.24-2.30 (m, 2H), 4.97 (tt, J=1.6 Hz, 3.2 Hz, 1H), 7.69 (d, J=8.8 Hz, 2H), 7.72 (d, J=8.8 Hz, 2H).

Preparation Example 3-1

Synthesis of ethyl 2-(4-bromo-2-trifluoromethylphenyl)-5-chloropentanimidate hydrochloride

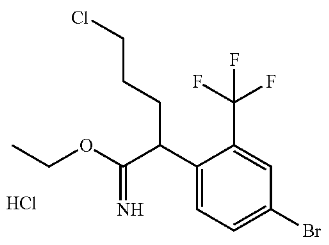 [SMILES: CCOC(=N)C(CCCCl)c1ccc(Br)cc1C(F)(F)F ; Cl]

Synthesis of 4-bromo-1-bromomethyl-2-trifluoromethylbenzene

N-Bromosuccinimide (2.6 g) and 2,2'-azobis(isobutyronitrile) (35 mg) were added to a solution of 5-bromo-2-methylbenzotrifluoride (CAS #86845-27-4, 3.5 g) in carbon tetrachloride (35 mL), and the mixture was heated under reflux for five hours. The reaction solution was ice-cooled and then the insoluble matter was removed by filtration. The filtrate was concentrated under reduced pressure. The resulting residue was purified by silica gel column chromatography (carrier: Wakogel C-200; elution solvent: heptane) to obtain 3.86 g of the title compound. The property values of the compound are as follows.

$^1$H-NMR ($CDCl_3$) δ (ppm): 4.58 (s, 2H), 7.47 (d, J=8.4 Hz, 1H), 7.69 (dd, J=8.4, 2.0 Hz, 1H), 7.79 (d, J=2.0 Hz, 1H).

Synthesis of (4-bromo-2-trifluoromethylphenyl)acetonitrile

Potassium cyanide (630 mg) was added to an emulsion of 4-bromo-1-bromomethyl-2-trifluoromethylbenzene (3.86 g) in ethanol (15 mL)-water (5 mL), and the mixture was stirred at 70° C. for three hours and 15 minutes. Water and ethyl acetate were added to the reaction solution, and the organic layer was separated. The resulting organic layer was washed with brine, dried over anhydrous magnesium sulfate and then concentrated under reduced pressure. The resulting residue was purified by silica gel column chromatography (carrier: Wakogel C-200; elution solvent:heptane:ethyl acetate=9:1) to obtain 2.28 g of the title compound. The property values of the compound are as follows.

$^1$H-NMR ($CDCl_3$) δ (ppm): 3.91 (s, 2H), 7.57 (d, J=8.4 Hz, 1H), 7.76 (dd, J=8.4, 2.0 Hz, 1H), 7.85 (d, J=2.0 Hz, 1H).

Synthesis of 2-(4-bromo-2-trifluoromethylphenyl)-5-chloropentanenitrile

A solution of (4-bromo-2-trifluoromethylphenyl)acetonitrile (2.28 g) in tetrahydrofuran (6 mL) was added to a suspension of sodium hydride (containing 60% in mineral oil, 362 mg) in tetrahydrofuran (12 mL) under ice-cooling. The mixture was stirred at the same temperature for 20 minutes. 1-Chloro-3-iodopropane (0.94 mL) was added dropwise to the reaction solution, and then the reaction solution was stirred at room temperature for 40 minutes. Ice water and heptane were added to the reaction solution, and the organic layer was separated. The resulting organic layer was washed with brine, dried over anhydrous magnesium sulfate and then concentrated under reduced pressure. The resulting residue was purified by silica gel column chromatography (carrier: Wakogel™ C-200; elution solvent:heptane:ethyl acetate=49:1→19:1) to obtain 2.67 g of the title compound. The property values of the compound are as follows.

$^1$H-NMR ($CDCl_3$) δ (ppm): 1.88-2.17 (m, 4H), 3.58 (t, J=6.0 Hz, 2H), 4.13 (t, J=7.2 Hz, 1H), 7.59 (d, J=8.4 Hz, 1H), 7.78 (dd, J=8.4, 2.0 Hz, 1H), 7.84 (d, J=2.0 Hz, 1H).

Synthesis of ethyl 2-(4-bromo-2-trifluoromethylphenyl)-5-chloropentanimidate hydrochloride A solution of 2-(4-bromo-2-trifluoromethylphenyl)-5-chloropentanenitrile (2.67 g) in ethanol (7.5 mL) was bubbled with hydrogen chloride gas under ice-cooling for 15 minutes. The reaction solution was stirred at room temperature for one day. The reaction solution was concentrated under reduced pressure. Diethyl ether was added to the residue, and the resulting powder was collected by filtration. The product collected by filtration was dried under reduced pressure to obtain 2.96 g of the title compound. The property values of the compound are as follows.

ESI-MS; m/z 388 [$M^+$+H-HCl].

$^1$H-NMR (DMSO-$D_6$) δ (ppm): 1.27 (t, J=7.2 Hz, 3H), 1.49-1.75 (m, 2H), 2.10-2.35 (m, 2H), 3.64 (t, J=6.4 Hz, 2H), 4.26 (t, J=7.6 Hz, 1H), 4.34-4.50 (m, 2H), 7.73 (d, J=8.4 Hz, 1H), 7.97 (d, J=2.0 Hz, 1H), 8.02 (dd, J=8.4, 2.0 Hz, 1H), 11.69 (brs, 1H).

Preparation Example 3-2

Synthesis of ethyl 5-chloro-2-(3,3-dimethyl-2,3-dihydrobenzofuran-5-yl)pentanimidate hydrochloride

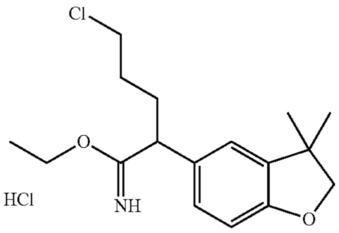 [SMILES: CCOC(=N)C(CCCCl)c1ccc2c(c1)C(C)(C)CO2 ; Cl]

Synthesis of 3,3,5-trimethyl-2,3-dihydrobenzofuran

3-Chloro-2-methylpropene (9.7 mL) was added dropwise to a mixed solution of p-cresol (CAS #106-44-5, 10.8 g) and concentrated sulfuric acid (2.5 g), and the mixture was stirred at room temperature for one hour and 20 minutes. The reaction solution was ice-cooled and a 5 N sodium hydroxide aqueous solution (20 mL) was added, followed by stirring at 90° C. for 45 minutes. A 5 N sodium hydroxide aqueous solution (10 mL) was added to the reaction solution, and the mixture was stirred at 90° C. for two hours and 45 minutes. The reaction solution was left to cool to room temperature. tert-Butyl methyl ether was added to the reaction solution, and the organic layer was separated. The resulting organic layer was sequentially washed with water (three times) and brine, dried over anhydrous magnesium sulfate and then concentrated under reduced pressure. The resulting residue was purified by silica gel column chromatography (carrier: Merck silica gel 60 (230-400 mesh); elution solvent:heptane:ethyl acetate=1:0→49:1). The target fraction was concentrated and the resulting residue was purified again by silica gel column chromatography (carrier: Chromatorex™ NH; elution solvent: heptane). The target fraction was concentrated and the resulting residue was distilled under reduced pressure to obtain 1.87 g of the target compound (bp. 102° C./20 mmHg). The property values of the compound are as follows.

$^1$H-NMR ($CDCl_3$) δ (ppm): 1.33 (s, 6H), 2.30 (s, 3H), 4.20 (s, 2H), 6.68 (d, J=7.6 Hz, 1H), 6.88-6.95 (m, 2H).

Synthesis of ethyl 5-chloro-2-(3,3-dimethyl-2,3-dihydrobenzofuran-5-yl)pentanimidate hydrochloride The title compound was obtained according to the method of Preparation Example 3-1 from 3,3,5-trimethyl-2,3-dihydrobenzofuran. The property values of the compound are as follows.

ESI-MS; m/z 310 [$M^+$+H-HCl].

Preparation Example 3-3

Synthesis of ethyl 2-(5-tert-butyl-2-methoxyphenyl)-5-chloropentanimidate hydrochloride

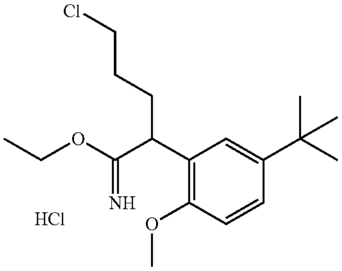 [SMILES: CCOC(=N)C(CCCCl)c1cc(C(C)(C)C)ccc1OC ; Cl]

Synthesis of 4-tert-butyl-1-methoxy-2-methylbenzene

Potassium carbonate (8.4 g) and methyl iodide (2.9 mL) were added to a solution of 4-tert-butyl-2-methylphenol (CAS #98-27-1, 5.0 g) in N,N-dimethylformamide (25 mL), and the mixture was stirred at room temperature for three days. Ice water and hexane were added to the reaction solution, and the organic layer was separated. The resulting organic layer was sequentially washed with water and brine, dried over anhydrous magnesium sulfate and then concentrated under reduced pressure to obtain 5.16 g of the title compound. The property values of the compound are as follows.

$^1$H-NMR ($CDCl_3$) δ (ppm): 1.30 (s, 9H), 2.22 (s, 3H), 3.81 (s, 3H), 6.76 (d, J=9.2 Hz, 1H), 7.15-7.19 (m, 2H).

Synthesis of 2-bromomethyl-4-tert-butyl-1-methoxybenzene

N-Bromosuccinimide (5.66 g) and 2,2'-azobis(isobutyronitrile) (71 mg) were added to a solution of 4-tert-butyl-1-methoxy-2-methylbenzene (5.16 g) in carbon tetrachloride (25 mL), and the mixture was heated under reflux for 1.5 hours. The reaction solution was ice-cooled and then the insoluble matter was removed by filtration. The filtrate was concentrated under reduced pressure to obtain 7.78 g of the title compound. The property values of the compound are as follows.

$^1$H-NMR ($CDCl_3$) δ (ppm): 1.30 (s, 9H), 3.88 (s, 3H), 4.58 (s, 2H), 6.81 (d, J=8.4 Hz, 1H), 7.31 (dd, J=8.4, 2.4 Hz, 1H), 7.34 (d, J=2.4 Hz, 1H).

Synthesis of (5-tert-butyl-2-methoxyphenyl)acetonitrile

Potassium cyanide (2.96 g) was added to a solution of 2-bromomethyl-4-tert-butyl-1-methoxybenzene (7.78 g) in dimethyl sulfoxide (50 mL), and the mixture was stirred at room temperature for 16 hours. Ice and tert-butyl methyl ether were added to the reaction solution, and the organic layer was separated. The aqueous layer was reextracted with tert-butyl methyl ether. The combined organic layers were sequentially washed with water (twice) and brine, dried over anhydrous magnesium sulfate and then concentrated under reduced pressure. The resulting residue was purified by silica gel column chromatography (carrier: Chromatorex™ NH; elution solvent: heptane→ethyl acetate:heptane=1:49). The target fraction was concentrated. The resulting residue was triturated with hexane to obtain 1.90 g of the title compound. The trituration mother liquor was concentrated. Then, the resulting residue was triturated with hexane to obtain 0.47 g of the title compound. The property values of the compound are as follows.

$^1$H-NMR ($CDCl_3$) δ (ppm): 1.31 (s, 9H), 3.68 (s, 2H), 3.85 (s, 3H), 6.82 (d, J=8.4 Hz, 1H), 7.32 (dd, J=8.4, 2.4 Hz, 1H), 7.36 (d, J=2.4 Hz, 1H).

Synthesis of 2-(5-tert-butyl-2-methoxyphenyl)-5-chloropentanenitrile

A solution of n-butyllithium in hexane (2.69 M, 3.0 mL) was added to a solution of N,N-diisopropylamine (1.2 mL) in THF (15 mL) under ice-cooling, and the mixture was stirred at the same temperature for 10 minutes. The solution was cooled to −78° C. and a solution of (5-tert-butyl-2-methoxyphenyl)acetonitrile (1.5 g) in THF (6.5 mL) was added dropwise. The solution was stirred at −30° C. for 25 minutes and then cooled again to −78° C. 1-Chloro-3-iodopropane (1.2 mL) was added dropwise to the solution, and then the reaction solution was gradually heated to room temperature. After ice-cooling the reaction solution, a solution of lithium hexamethyldisilazide in tetrahydrofuran (1.0 M, 4.4 mL) was added to the reaction solution. Then, a lithium diisopropylamide solution prepared from N,N-diisopropylamine (0.6 mL) and a solution of n-butyllithium in hexane (2.69 M, 1.5 mL) was added to the reaction solution. A saturated ammonium chloride aqueous solution was added to the reaction solution. Then, ethyl acetate and water were added and the organic layer was separated. The resulting organic layer was sequentially washed with 1 N hydrochloric acid, water, a saturated sodium bicarbonate aqueous solution and brine, dried over anhydrous magnesium sulfate and then concentrated under reduced pressure. The resulting residue was purified by silica gel column chromatography (carrier: Merck silica gel 60 (230-400 mesh); elution solvent:heptane:ethyl acetate=1:49) to obtain 864 mg of a 1:7 mixture of (5-tert-butyl-2-methoxyphenyl)acetonitrile and the title compound. The property values of the title compound are as follows.

$^1$H-NMR ($CDCl_3$) δ (ppm): 1.31 (s, 1.86-2.12 (m, 4H), 3.54-3.60 (m, 2H), 3.84 (s, 3H), 4.18-4.24 (m, 1H), 6.83 (d, J=8.4 Hz, 1H), 7.31 (dd, J=8.4, 2.4 Hz, 1H), 7.40 (d, J=2.4 Hz, 1H).

Synthesis of ethyl 2-(5-tert-butyl-2-methoxyphenyl)-5-chloropentanimidate hydrochloride and ethyl 2-(5-tert-butyl-2-methoxyphenyl)acetimidate hydrochloride A solution of the 1:7 mixture of (5-tert-butyl-2-methoxyphenyl)acetonitrile and 2-(5-tert-butyl-2-methoxyphenyl)-5-chloropentanenitrile (864 mg) in ethanol (8 mL) was bubbled with hydrogen chloride gas under ice-cooling for 15 minutes. The reaction solution was stirred at room temperature for one day. The reaction solution was concentrated under reduced pressure to obtain a mixture of the title compound.

The property values of ethyl 2-(5-tert-butyl-2-methoxyphenyl)-5-chloropentanimidate hydrochloride are as follows.

ESI-MS; m/z 326 [$M^+$+H-HCl].

The property values of ethyl 2-(5-tert-butyl-2-methoxyphenyl)acetimidate hydrochloride are as follows.

ESI-MS; m/z 250 [$M^+$+H-HCl].

Preparation Example 3-4

Synthesis of ethyl 2-(3-bromo-4-methoxyphenyl)-5-chloropentanimidate hydrochloride

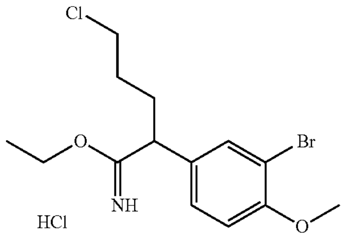 [SMILES: CCOC(=N)C(CCCCl)c1ccc(OC)c(Br)c1 ; Cl]

The title compound (3.62 g) was obtained as a white solid from 3-bromo-4-methoxyphenylacetonitrile (3.0 g) according to the method of Example 3-1.

ESI-MS; m/z 350 [$M^+$+H-HCl].

The compounds of Preparation Examples 3-5 to 3-13 were obtained below by the same method as in Example 3-1 (Table 7).

TABLE 7

| Production Ex No. | Structural formula |
|---|---|
| 3-5 | 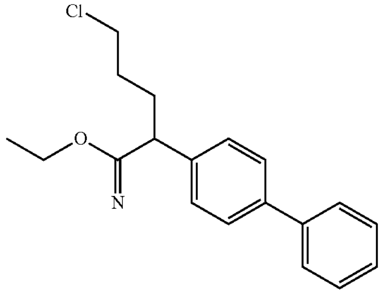 [SMILES: CCOC(=N)C(CCCCl)c1ccc(-c2ccccc2)cc1] |

TABLE 7-continued

| Production Ex No. | Structural formula |
|---|---|
| 3-6 | 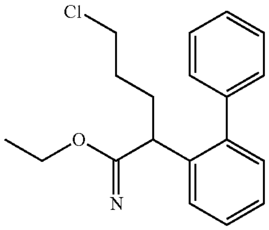 [SMILES: CCOC(=N)C(CCCCl)c1ccccc1-c1ccccc1] |
| 3-7 | 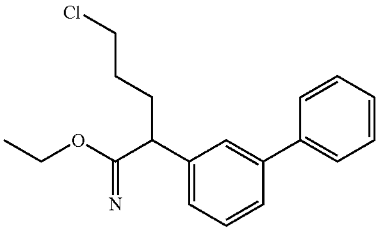 [SMILES: CCOC(=N)C(CCCCl)c1cccc(-c2ccccc2)c1] |
| 3-8 | 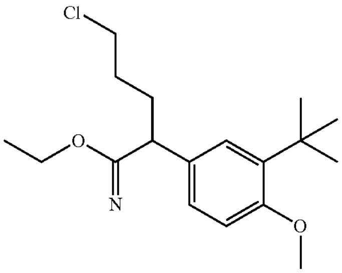 [SMILES: CCOC(=N)C(CCCCl)c1ccc(OC)c(C(C)(C)C)c1] |
| 3-9 | 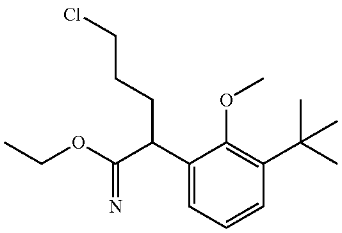 [SMILES: CCOC(=N)C(CCCCl)c1cccc(C(C)(C)C)c1OC] |
| 3-10 | 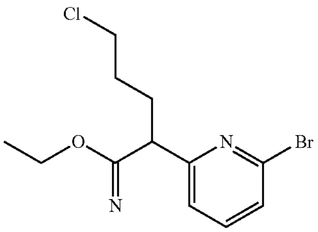 [SMILES: CCOC(=N)C(CCCCl)c1cccc(Br)n1] |
| 3-11 | 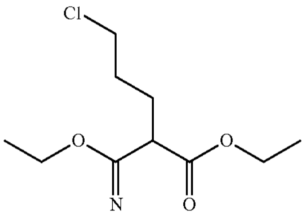 |

TABLE 7-continued

| Production Ex No. | Structural formula |
|---|---|
| 3-12 | 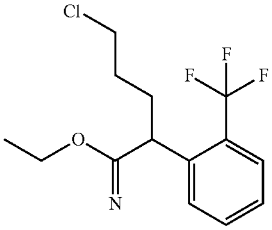 [SMILES: CCOC(=N)C(CCCCl)c1ccccc1C(F)(F)F] |
| 3-13 | 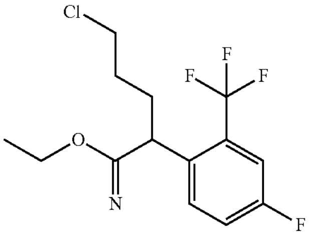 [SMILES: CCOC(=N)C(CCCCl)c1ccc(F)cc1C(F)(F)F] |

Preparation Example 3-14

Synthesis of ethyl 4-chloro-2-(2-trifluoromethylphenyl)butanimidate hydrochloride

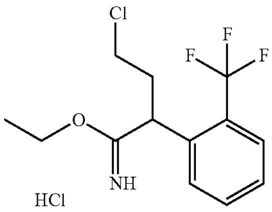 [SMILES: CCOC(=N)C(CCCl)c1ccccc1C(F)(F)F ; Cl]

Synthesis of 4-(tert-butyldimethylsilyloxy)-2-(2-trifluoromethylphenyl)butyronitrile (2-Trifluoromethylphenyl)acetonitrile (3 g) and tetrabutylammonium bisulfate (550 mg) were suspended in toluene (30 mL), and a 50% sodium hydroxide aqueous solution (15 mL) was added dropwise under ice-cooling. After stirring for 10 minutes, (2-bromoethoxy)-tert-butyldimethylsilane (5.2 mL) was added at the same temperature. The mixture was brought back to room temperature and stirred overnight. Water was added to the reaction solution, followed by extraction with tert-butyl methyl ether. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (5 g). The property values of the compound are as follows.

ESI-MS; m/z 344 $[M^{+}+H]$.

$^{1}H$-NMR ($CDCl_3$) δ (ppm): 0.08 (s, 3H), 0.11 (s, 3H), 0.92 (s, 9H), 1.98-2.14 (m, 2H), 3.80-3.95 (m, 2H), 4.52 (dd, J=10.2, 6.2 Hz, 1H), 7.42-7.48 (m, 1H), 7.59-7.65 (m, 1H), 7.68-7.74 (m, 2H).

Synthesis of 4-hydroxy-2-(2-trifluoromethylphenyl)butyronitrile 4-(tert-Butyldimethylsilyloxy)-2-(2-trifluoromethylphenyl)butyronitrile (5 g) was dissolved in tetrahydrofuran (70 mL). Tetrabutylammonium fluoride (1 M solution in tetrahydrofuran) (18 mL) was added and the mixture was stirred at room temperature for 4.5 hours. The reaction solution was concentrated under reduced pressure and the residue was purified by silica gel column chromatography to obtain the title compound (3.1 g). The property values of the compound are as follows.

$^1$H-NMR ($CDCl_3$) δ (ppm): 2.11-2.19 (m, 2H), 3.86-3.97 (m, 2H), 4.49 (dd, J=8.6, 7.0 Hz, 1H), 7.45-7.51 (m, 1H), 7.62-7.68 (m, 1H), 7.69-7.76 (m, 2H).

Synthesis of 4-chloro-2-(2-trifluoromethylphenyl)butyronitrile

4-Hydroxy-2-(2-trifluoromethylphenyl) butyronitrile (2.6 g) was dissolved in pyridine (10 mL). Thionyl chloride (2.1 mL) was carefully added and the mixture was heated with stirring at 60° C. for four hours. Water was added to the reaction solution, followed by extraction with ethyl acetate. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (1.3 g). The property values of the compound are as follows.

$^1$H-NMR ($CDCl_3$) δ (ppm): 2.27-2.44 (m, 2H), 3.72-3.79 (m, 2H), 4.53 (dd, J=9.8, 5.0 Hz, 1H), 7.46-7.53 (m, 1H), 7.62-7.66 (m, 1H), 7.70-7.76 (m, 2H).

Synthesis of ethyl 4-chloro-2-(2-trifluoromethylphenyl)butanimidate hydrochloride The title compound (1.3 g) was obtained by the same method as in Preparation Example 3-1 from 4-chloro-2-(2-trifluoromethylphenyl) butyronitrile (1.5 g). The property values of the compound are as follows.

ESI-MS; m/z 294 [$M^+$+H-HCl].

$^1$H-NMR ($CDCl_3$) δ (ppm): 1.41 (t, J=7.0 Hz, 3H), 2.56-2.66 (m, 1H), 3.03-3.14 (m, 1H), 3.56-3.68 (m, 2H), 4.59-4.75 (m, 3H), 7.50 (dd, J=7.6, 7.6 Hz, 1H), 7.68 (dd, J=7.6, 7.6 Hz, 1H), 7.74 (d, J=7.6 Hz, 1H), 7.93 (d, J=7.6 Hz, 1H).

The compounds of Preparation Examples 3-15 to 3-16 were obtained by the same method as in Example 3-14 (Table 8).

TABLE 8

| Production Ex No. | Structural formula |
|---|---|
| 3-15 | 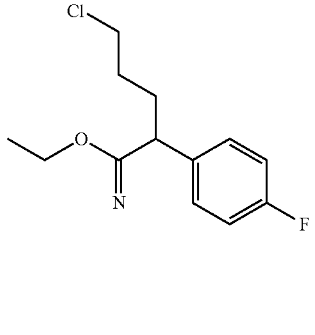 [SMILES: CCOC(=N)C(CCCCl)c1ccc(F)cc1] |

TABLE 8-continued

| Production Ex No. | Structural formula |
|---|---|
| 3-16 | 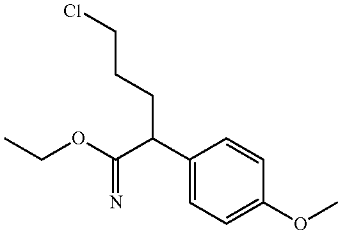 [SMILES: CCOC(=N)C(CCCCl)c1ccc(OC)cc1] |

Preparation Example 3-17

Synthesis of ethyl 2-(3-bromophenyl)-2-(2-chloroethoxy)acetimidate hydrochloride

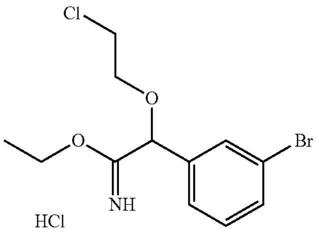 [SMILES: CCOC(=N)C(OCCCl)c1cccc(Br)c1 ; Cl]

Synthesis of (3-bromophenyl)-(2-hydroxyethoxy)acetonitrile

Zinc iodide (50.6 mg) was added to a mixture of 2-(3-bromophenyl)-1,3-dioxolane (3 mL) and trimethylsilyl cyanide (2.49 mL), followed by stirring at room temperature for 1.5 hours. A saturated sodium bicarbonate aqueous solution was added to the reaction solution, followed by extraction with diethyl ether. The organic layer was dried over anhydrous magnesium sulfate and concentrated under reduced pressure. Then, the resulting residue was purified by silica gel column chromatography (elution solvent:heptane:ethyl acetate=7:3→1:1) to obtain 3.93 g of the title compound. The property values of the compound are as follows.

$^1$H-NMR ($CDCl_3$) δ (ppm): 1.83 (br, 1H), 3.73-3.78 (m, 1H), 3.84-3.90 (m, 3H), 5.33 (s, 1H), 7.35 (t, J=7.6 Hz, 1H), 7.44-7.47 (m, 1H), 7.56-7.59 (m, 1H), 7.67 (dt, J=0.4, 1.2 Hz, 1H).

Synthesis of (3-bromophenyl)-(2-chloroethoxy)acetonitrile

Thionyl chloride (1.23 mL) was added dropwise to a solution of (3-bromophenyl)-(2-hydroxyethoxy)acetonitrile (3.62 g) in pyridine (12.1 mL) at 50° C., and the mixture was stirred at 60° C. for two hours. Water was added to the reaction solution, followed by extraction with ethyl acetate. The organic layer was washed with water. The organic layer was dried over anhydrous magnesium sulfate and concentrated under reduced pressure. Then, the resulting residue was purified by silica gel column chromatography (elution solvent:

heptane:ethyl acetate=9:1→8:2) to obtain 3.21 g of the title compound. The property values of the compound are as follows.

$^1$H-NMR ($CDCl_3$) δ (ppm): 3.70-3.73 (m, 2H), 3.87 (ddd, J=5.2, 6.4, 10.4 Hz, 1H), 4.01 (ddd, J=5.6, 5.6, 10.0 Hz, 1H), 5.36 (s, 1H), 7.33 (t, J=7.6 Hz, 1H), 7.45-7.48 (m, 1H), 7.57-7.59 (m, 1H), 7.67 (dt, J=0.4, 1.6 Hz, 1H).

Synthesis of ethyl 2-(3-bromophenyl)-2-(2-chloroethoxy)acetimidate hydrochloride The title compound (2.71 g) was obtained by the same method as in Preparation Example 3-1 from (3-bromophenyl)-(2-chloroethoxy)acetonitrile (3.21 g). The property values of the compound are as follows.

$^1$H-NMR (DMSO-$D_6$) δ (ppm): 1.24 (t, J=7.2 Hz, 3H), 3.76-3.90 (m, 4H), 4.41-4.43 (m, $21^{-1}$), 5.50 (s, 1H), 7.40-7.47 (m, 2H), 7.63-7.68 (m, 2H).

The compound of Preparation Example 3-18 were obtained by the same method as in Example 3-17 (Table 9).

TABLE 9

| Production Ex No. | Structural formula |
|---|---|
| 3-18 | 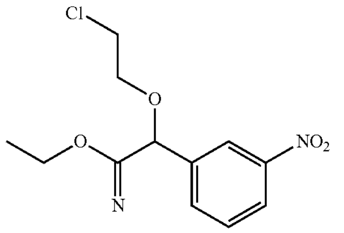 [SMILES: CCOC(=N)C(OCCCl)c1cccc([N+](=O)[O-])c1] |

Preparation Example 3-19

Synthesis of ethyl 4-ethoxycarbonimidoyl-4-(2-trifluoromethylphenyl)butanoate

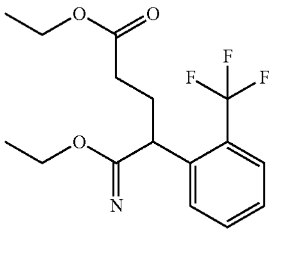 [SMILES: CCOC(=N)C(CCC(=O)OCC)c1ccccc1C(F)(F)F]

Synthesis of methyl 4-cyano-4-(2-trifluoromethylphenyl)butanoate 2-(Trifluoromethyl)phenylacetonitrile (2.0 g) was dissolved in tetrahydrofuran (50 mL). Potassium tert-butoxide (60.6 mg), 18-crown-6 (2.85 g) and methyl acrylate (973 μL) were added at 0° C. and the mixture was stirred at the same temperature for 40 minutes. The reaction was terminated with saturated ammonium chloride, followed by dilution with ethyl acetate. The organic layer was washed with brine and dried over magnesium sulfate. Concentration under reduced pressure gave an oil. The oil was purified by silica gel column chromatography (mobile phase:ethyl acetate/heptane=0 to 30%) to obtain the title compound (2.2 g).

$^1$H-NMR ($CDCl_3$) δ (ppm): 2.25 (dd, J=14.9, 7.4 Hz, 2H), 2.51-2.65 (m, 2H), 3.70 (s, 3H), 4.31 (t, J=7.8 Hz, 1H), 7.46-7.51 (m, 1H), 7.65-7.67 (m, 1H), 7.69-7.73 (m, 2H).

Synthesis of ethyl 4-ethoxycarbonimidoyl-4-(2-trifluoromethylphenyl)butanoate hydrochloride Methyl 4-cyano-4-(2-trifluoromethylphenyl)butanoate (200 mg) was dissolved in ethanol (1.03 mL), and acetyl chloride (838 μl) was added at 0° C. The mixture was heated to room temperature and the reaction was initiated. After stirring for 24 hours, concentration under reduced pressure gave a crude product of the title compound as an oil (300 mg).

ESI-MS; m/z 332 [$M^+$+H-HCl].

Preparation Example 3-20

Synthesis of ethyl 2-(4-chloro-2-trifluoromethylphenyl)-5-chloropentanimidate hydrochloride

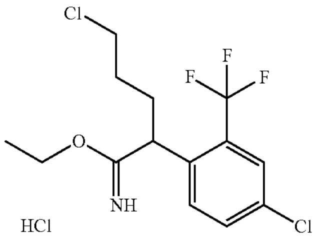 [SMILES: CCOC(=N)C(CCCCl)c1ccc(Cl)cc1C(F)(F)F ; Cl]

Synthesis of methyl (4-chloro-2-trifluoromethylphenyl)acetate

Thionyl chloride (9.5 mL) was added dropwise to a solution of 4-chloro-2-(trifluoromethyl)phenylacetic acid (CAS #601513-31-9, 10.5 g) in methanol (50 mL) under ice-cooling. Then, the reaction solution was heated under reflux for three hours. The reaction solution was concentrated under reduced pressure. A saturated sodium bicarbonate solution and ethyl acetate were added to the resulting residue, and the organic layer was separated. The resulting organic layer was sequentially washed with a saturated sodium bicarbonate solution and brine, dried over anhydrous magnesium sulfate and then concentrated under reduced pressure to obtain 10.96 g of the title compound. $^1$H-NMR ($CDCl_3$) δ (ppm): 3.71 (s, 3H), 3.80 (s, 2H), 7.35 (d, J=8.4 Hz, 1H), 7.50 (dd, J=8.4, 2.0 Hz, 1H), 7.65 (d, J=2.0 Hz, 1H).

Synthesis of methyl 5-chloro-2-(4-chloro-2-trifluoromethylphenyl)pentanoate

A solution of methyl (4-chloro-2-trifluoromethylphenyl) acetate (5.5 g) and 3-chloro-1-iodopropane (4.6 mL) in tetrahydrofuran (15 mL) was added dropwise to a suspension of sodium hydride (containing 60% in mineral oil, 955 mg) in tetrahydrofuran (50 mL) under ice-cooling. The reaction solution was stirred at the same temperature for 10 minutes and then at room temperature for three hours and 20 minutes. Ice water and ethyl acetate were added to the reaction solution, and the organic layer was separated. The aqueous layer was reextracted with ethyl acetate. The combined organic layers were washed with brine and dried over anhydrous magnesium sulfate, followed by concentration under reduced pressure. The resulting residue was purified by silica gel column chromatography (carrier: Wakogel™ C-200; elution solvent:heptane:ethyl acetate=19:1) to obtain 5.30 g of the title compound. The property values of the compound are as follows.

$^1$H-NMR ($CDCl_3$) δ (ppm): 1.59-1.71 (m, 1H), 1.76-1.96 (m, 2H), 2.17-2.28 (m, 1H), 3.51 (t, J=6.4 Hz, 2H), 3.68 (s, 3H), 3.99 (t, J=7.2 Hz, 1H), 7.52 (dd, J=8.4, 2.0 Hz, 1H), 7.55 (d, J=8.4 Hz, 1H), 7.65 (d, J=2.0 Hz, 1H).

Synthesis of 5-chloro-2-(4-chloro-2-trifluoromethylphenyl)pentanoic acid

A 5 N sodium hydroxide aqueous solution (13 mL) was added to a mixed solution of methyl 5-chloro-2-(4-chloro-2-trifluoromethylphenyl)pentanoate (5.3 g) in tetrahydrofuran (15 mL)-methanol (15 mL), and the mixture was stirred at room temperature for two hours and 10 minutes. After adding ice water to the reaction solution, the organic solvent was evaporated from the reaction solution under reduced pressure. The resulting aqueous layer was washed with heptane. The aqueous layer was made acidic with 5 N hydrochloric acid under ice-cooling, followed by extraction with ethyl acetate twice. The combined ethyl acetate layers were washed with brine, dried over anhydrous magnesium sulfate and then concentrated under reduced pressure to obtain 4.75 g of the title compound.

$^1$H-NMR ($CDCl_3$) δ (ppm): 1.59-1.71 (m, 1H), 1.79-2.01 (m, 2H), 2.19-2.30 (m, 1H), 3.51 (t, J=6.4 Hz, 2H), 4.03 (t, J=7.6 Hz, 1H), 7.54 (brs, 2H), 7.67 (brs, 1H).

Synthesis of 5-chloro-2-(4-chloro-2-trifluoromethylphenyl)pentanoic acid amide Ammonium chloride (3.23 g), 1-hydroxybenzotriazole (2.45 g), IPEA (13.7 mL) and benzotriazol-1-yloxytris(pyrrolidino)phosphonimn hexafluorophosphate (9.43 g) were sequentially added to a solution of 5-chloro-2-(4-chloro-2-trifluoromethylphenyl)pentanoic acid (4.75 g) in N,N-dimethylformamide (45 mL). The mixture was stirred at room temperature overnight. Ice water and tert-butyl methyl ether were added to the reaction solution, and the organic layer was separated. The aqueous layer was reextracted with tert-butyl methyl ether. The combined organic layers were sequentially washed with 1 N hydrochloric acid, water, a saturated sodium bicarbonate aqueous solution and brine, dried over anhydrous magnesium sulfate and then concentrated under reduced pressure. The resulting residue was purified by silica gel column chromatography (carrier: Wakogel™ C-200; elution solvent:heptane:ethyl acetate=4:1→3:1) to obtain 3.89 g of the title compound. The property values of the compound are as follows.

$^1$H-NMR ($CDCl_3$) δ (ppm): 1.60-1.67 (m, 1H), 1.80-1.97 (m, 2H), 2.20-2.31 (m, 1H), 3.45-3.56 (m, 2H), 3.77 (t, J=7.2 Hz, 1H), 5.30 (brs, 1H), 5.41 (brs, 1H), 7.54 (dd, J=8.4, 2.0 Hz, 1H), 7.66 (d, J=2.0 Hz, 1H), 7.69 (d, J=8.4 Hz, 1H).

Synthesis of 5-chloro-2-(4-chloro-2-trifluoromethylphenyl)pentanenitrile

Methyl dichlorophosphate (1.9 mL) was added dropwise at 20° C. or less to an ice-cooled solution of 5-chloro-2-(4-chloro-2-trifluoromethylphenyl)pentanoic acid amide (3.0 g) and 1,8-diazabicyclo[5,4,0]undec-7-ene (6.4 mL) in methylene chloride (30 mL). After completion of the dropwise addition, the reaction solution was stirred at room temperature for one hour and 25 minutes. A saturated sodium bicarbonate aqueous solution was added to the reaction solution. After stirring for five minutes, the organic layer was separated. The aqueous layer was reextracted with methylene chloride. The combined organic layers were sequentially washed with 1 N hydrochloric acid, water, a saturated sodium bicarbonate aqueous solution and brine, dried over anhydrous magnesium sulfate and then concentrated under reduced pressure. The resulting residue was purified by silica gel column chromatography (carrier: Wakogel C-200; elution solvent:heptane: ethyl acetate=49:1→19:1) to obtain 2.25 g of the title compound.

The property values of the compound are as follows.

$^1$H-NMR ($CDCl_3$) δ (ppm): 1.89-2.18 (m, 4H), 3.58 (t, J=6.0 Hz, 2H), 4.15 (dd, J=8.0, 6.4 Hz, 1H), 7.63 (dd, J=8.4, 2.0 Hz, 1H), 7.66 (d, J=8.4 Hz, 1H), 7.70 (d, J=2.0 Hz, 1H).

Synthesis of ethyl 2-(4-chloro-2-trifluoromethylphenyl)-5-chloropentanimidate hydrochloride The title compound was obtained by the same method as in Preparation Example 3-1 from 5-chloro-2-(4-chloro-2-trifluoromethylphenyl)pentanenitrile.

ESI-MS; m/z 342 [$M^+$+H-HCl].

Preparation Example 4-1

Synthesis of [benzyl(2-hydroxyethyl)amino]-(4-trifluoromethylphenyl)acetonitrile

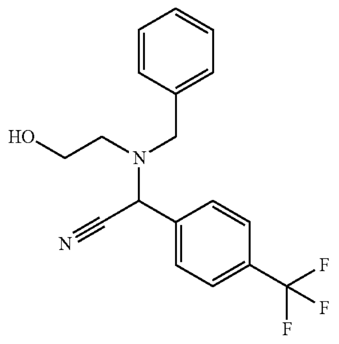 [SMILES: N#CC(c1ccc(C(F)(F)F)cc1)N(CCO)Cc1ccccc1]

4-(Trifluoromethyl)benzaldehyde (CAS #455-19-6, 2 g) and methanol (1 mL) were added to a solution of sodium bisulfite (1.33 g) in water (40 mL) at room temperature, and the mixture was stirred at room temperature for 10 minutes. Sodium cyanide (1.33 g) was added to the reaction solution, and the mixture was stirred at the same temperature for 40 minutes. N-Benzylethanolamine (1.83 g) and methanol (3 mL) were added to the reaction solution, and the mixture was stirred at the same temperature for 16 hours. The reaction solution was partitioned with ethyl acetate. The organic layer was dried over anhydrous magnesium sulfate and then concentrated under reduced pressure. The resulting residue was purified by silica gel column chromatography (elution solvent:heptane:ethyl acetate=9:1→1:1) to obtain 1.79 g of the title compound. The property values of the compound are as follows.

$^1$H-NMR ($CDCl_3$) δ (ppm): 1.66 (brs, 1H), 2.70-2.81 (m, 2H), 3.55 (d, J=13.6 Hz, 1H), 3.58-3.61 (m, 1H), 3.75-3.82 (m, 1H), 4.02 (d, J=13.2 Hz, 1H), 5.06 (s, 1H), 7.30-7.40 (m, 5H), 7.64-7.71 (m, 4H).

Preparation Example 4-2

Synthesis of [(2-hydroxyethyl)phenylamino]-(4-trifluoromethylphenyl)acetonitrile

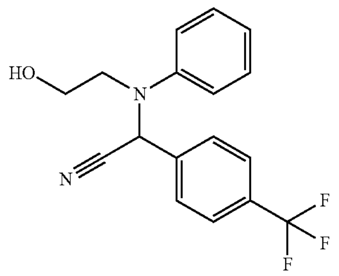 [SMILES: N#CC(c1ccc(C(F)(F)F)cc1)N(CCO)c1ccccc1]

Trimethylsilyl cyanide (723 μL) was added to a mixture of 4-(trifluoromethyl)benzaldehyde (CAS #455-19-6, 1 g), N-phenylethanolamine (870 mg) and sulfamic acid (28 mg), and the mixture was stirred at room temperature for 20 hours. The reaction solution was partitioned with water and chloroform. The organic layer was dried over anhydrous magnesium sulfate. The organic layer was concentrated under reduced pressure. The resulting residue was purified by silica gel column chromatography (elution solvent:heptane:ethyl acetate=9:1→1:1) to obtain 775 mg of the title compound. The property values of the compound are as follows.

$^1$H-NMR ($CDCl_3$) δ (ppm): 1.59 (brs, 1H), 3.30 (ddd, J=5.6, 7.2, 12.4 Hz, 1H), 3.53 (ddd, J=4.8, 7.2, 7.2 Hz, 1H), 3.64-3.69 (m, 2H), 5.70 (s, 1H), 7.01-7.06 (m, 3H), 7.31-7.35 (m, 2H), 7.69-7.72 (m, 4H).

Preparation Example 4-3

Synthesis of 5-hydroxy-4-(2-trifluoromethylphenyl) pentanenitrile

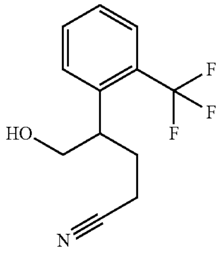 [SMILES: N#CCCC(CO)c1ccccc1C(F)(F)F]

Synthesis of tert-butyl (2-trifluoromethylphenyl)acetate (2-Trifluoromethyl)phenylacetic acid (10.5 g) was dissolved in tetrahydrofuran (150 mL), and tert-butyl 2,2,2-trichloroacetimidate (18.4 mL) and a boron trifluoride-diethyl ether complex (323 μL) were added at 0° C. After stirring at room temperature for 22 hours, the reaction was terminated with a saturated sodium bicarbonate aqueous solution, followed by dilution with ethyl acetate. The organic layer was washed with a saturated sodium bicarbonate aqueous solution and brine and dried over magnesium sulfate. Concentration under reduced pressure gave a white solid. The solid was simply purified by an amino silica gel pad (mobile phase:ethyl acetate:heptane=1:15) to obtain the title compound (13.0 g). Synthesis of tert-butyl 4-cyano-2-(2-trifluoromethylphenyl)butanoate tert-Butyl (2-trifluoromethylphenyl)acetate (12.9 g) was dissolved in toluene (129 mL). Benzyltrimethylammonium hydroxide (782 μL) was added at room temperature, followed by stirring for 10 minutes. Thereafter, acrylonitrile (6.49 mL) was added at 0° C. and the reaction was initiated. After stirring at room temperature for 12 hours, the reaction was terminated with 2 N hydrochloric acid, followed by dilution with diethyl ether. The organic layer was washed with water (twice) and brine and dried over magnesium sulfate. Concentration under reduced pressure gave a yellow oil (17 g), which was used directly for the next reaction as a crude product.

Synthesis of 4-cyano-2-(2-trifluoromethylphenyl)butanoic acid tert-Butyl 4-cyano-2-(2-trifluoromethylphenyl)butanoate (7.2 g) was dissolved in methylene chloride (40 mL). Trifluoroacetic acid (50 mL) was added at 0° C. and the reaction was initiated. After stirring at room temperature for one hour, concentration under reduced pressure gave an oil. The resulting oil was dissolved in diethyl ether, washed with water (three times) and brine and dried over magnesium sulfate. Concentration under reduced pressure gave a yellow oil. The oil was dissolved again in diethyl ether and partitioned between diethyl ether and 5 N sodium hydroxide (15 mL). The resulting aqueous layer was made acidic with 5 N hydrochloric acid (16 mL) and extracted with methylene chloride twice to obtain the title compound (6.76 g) as a colorless transparent oil.

Synthesis of 5-hydroxy-4-(2-trifluoromethylphenyl) pentanenitrile

Thionyl chloride (8.25 mL) was added to 4-cyano-2-(2-trifluoromethylphenyl)butanoic acid (2.9 g), and the mixture was heated under reflux. After one hour, concentration under reduced pressure gave an oil. The oil was dissolved in tetrahydrofuran (50 mL) and ethanol (20 mL), and sodium borohydride (855 mg) was added at 0° C. After stirring at room temperature for one hour, the reaction was terminated with water, followed by dilution with ethyl acetate. The organic layer was washed with 1 N hydrochloric acid, a saturated sodium bicarbonate aqueous solution and brine and dried over magnesium sulfate. Concentration under reduced pressure gave a pale yellow oil. The oil was purified by silica gel column chromatography (mobile phase:ethyl acetate/heptane=0 to 50%) to obtain the title compound (2.14 g).

ESI-MS; m/z 244 [$M^+$+H].

Preparation Example 4-4

Synthesis of 5-hydroxy-3-(4-trifluoromethylphenyl) pentanenitrile

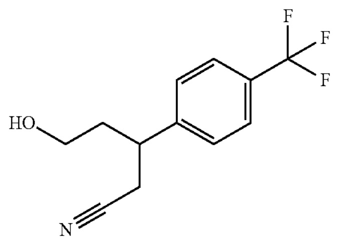 [SMILES: N#CCC(CCO)c1ccc(C(F)(F)F)cc1]

Synthesis of 5-hydroxy-3-(4-trifluoromethylphenyl)pentanoic acid amide

Saturated ammonia/methanol (10 mL) was added to 4-(3-trifluoromethylphenyl)tetrahydropyran-2-one obtained according to the method of Preparation Example 2-10 (1.0 g), and the mixture was stirred at 60° C. for 23 hours. To complete the reaction, saturated ammonia/methanol (5 mL) was further added and stirring was continued at the same temperature. After 24 hours, concentration under reduced pressure and purification by silica gel column chromatography (mobile phase:ethyl acetate/heptane=0 to 100%) gave the title compound (850 mg).

ESI-MS; m/z 262 [$M^+$+H].

Synthesis of 5-(tert-butyldiphenylsilanyloxy)-3-(4-trifluoromethylphenyl)pentanoic acid amide 5-Hydroxy-3-(4-trifluoromethylphenyl)pentanoic acid amide (350 mg) was dissolved in dimethylformamide (13 mL), and imidazole (365 mg) and tert-butyldiphenylsilyl chloride (697 μL) were added at room temperature. After stirring for one hour, the reaction solution was partitioned with ethyl acetate and water. The organic layer was washed with water (twice), 1 N hydrochloric acid and brine. After drying over magnesium sulfate, concentration under reduced pressure and purification by silica gel column chromatography (mobile phase:ethyl acetate/heptane=0 to 90%) gave the title compound (680 mg).

ESI-MS; m/z 500 [$M^+$+H].

Synthesis of 5-(tert-butyldiphenylsilanyloxy)-3-(4-trifluoromethylphenyl)-pentanenitrile 5-(tert-Butyldiphenylsilanyloxy)-3-(4-trifluoromethylphenyl)pentanoic acid amide (640 mg) was dissolved in methylene chloride (13 mL), and 1,8-diazabicyclo[5,4,0]undec-7-ene (862 μL) and methyl dichlorophosphate (301 μL) were added at 0° C. After stirring at room temperature for 1.5 hours, the reaction was terminated with a saturated sodium bicarbonate aqueous solution. The organic layer was washed with brine and then dried over magnesium sulfate. Concentration under reduced pressure gave an oil. The oil was allowed to pass through a silica gel pad (mobile phase:ethyl acetate:heptane=1:2) to obtain the title compound (600 mg).

Synthesis of 5-hydroxy-3-(4-trifluoromethylphenyl) pentanenitrile 5-(tert-Butyldiphenylsilanylsilanylsilanyloxy)-3-(4-trifluoromethylphenyl)pentanenitrile (600 mg) was dissolved in tetrahydrofuran (6 mL), and tetrabutylammonium fluoride (1.5 mL) was added at room temperature. After two hours, the mixture was partitioned with water and ethyl acetate. The organic layer was washed with brine and then dried over magnesium sulfate. Concentration under reduced pressure gave an oil. The oil was purified by silica gel column chromatography (mobile phase:ethyl acetate/heptane=70%) to obtain the title compound (306 mg).

ESI-MS; m/z 244 [$M^+$+H].

Preparation Example 4-5

Synthesis of 5-hydroxy-3-(2-trifluoromethylphenyl) pentanenitrile

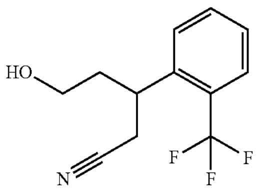 [SMILES: N#CCC(CCO)c1ccccc1C(F)(F)F]

Synthesis of 3-(2-trifluoromethylphenyl)pentanedioic acid

Piperidine (1.0 mL) was added to 2-trifluoromethylbenzaldehyde (5.0 g) and ethyl acetoacetate (7.27 mL) at 0° C. Then, the mixture was brought to room temperature and stirred for four days. Ethanol (50 mL) was added to the resulting reaction mixture, which was stirred with refluxing for five hours. Concentration under reduced pressure gave an oil. The resulting oil was simply purified by silica gel column chromatography (mobile phase:ethyl acetate/heptane=0 to 40%). Although the oil (7.81 g) contained a large amount of impurities, the oil was dissolved in ethanol (18.5 mL) and water (24.9 mL) to use the oil directly for the next reaction. Potassium hydroxide (32.7 g) was added and the reaction was initiated by heating under reflux. After 1.5 hours, the reaction mixture was partitioned with water and diethyl ether. The resulting aqueous layer was neutralized with concentrated hydrochloric acid (20 mL). Following extraction with methylene chloride twice, drying over magnesium sulfate and concentration under reduced pressure gave a yellow solid. The resulting crude product was recrystallized from ethyl acetate (30 mL) and heptane (65 mL) to obtain the title compound (1.2 g) as a white powder.

ESI-MS; m/z 277 [$M^+$+H].

Synthesis of 4-(2-trifluoromethylphenyl)dihydropyrane-2,6-dione 3-(2-Trifluoromethylphenyl)pentanedioic acid (1.2 g) was dissolved in acetic anhydride (12 mL), and the mixture was stirred at 110° C. for two hours. The oil after concentration under reduced pressure was dissolved in ethyl acetate and washed with a saturated sodium bicarbonate solution and brine. After drying over magnesium sulfate, concentration under reduced pressure gave an orange solid. The solid was recrystallized from ethyl acetate (10 mL) and heptane (70 mL) to obtain the title compound (636 mg) as a white powder.

$^1$H-NMR ($CDCl_3$) δ (ppm): 2.19-2.35 (m, 2H), 2.91 (ddd, J=18.3, 12.5, 6.2 Hz, 1H), 3.10 (ddd, J=18.3, 4.3, 2.7 Hz, 1H), 4.2 (dd, J=12.0, 5.9 Hz, 1H), 7.35 (d, J=7.8 Hz, 1H), 7.45 (m, 1H), 7.60-7.65 (m, 1H), 7.75 (d, J=7.8 Hz, 1H).

Synthesis of 4-carbamoyl-3-(2-trifluoromethylphenyl)butanoic acid

Saturated ammonia/methanol (10 mL) was added to 4-(2-trifluoromethylphenyl)dihydropyrane-2,6-dione (636 mg), and the mixture was stirred at room temperature for 15 hours. Concentration under reduced pressure gave a crude product (716 mg) which was used for the next reaction without purification.

Synthesis of 5-hydroxy-3-(2-trifluoromethylphenyl)pentanoic acid amide

4-Carbamoyl-3-(2-trifluoromethylphenyl)butanoic acid (646 mg) was dissolved in methylene chloride (32 mL), and a diborane-tetrahydrofuran solution (7.12 mL) was added at 0° C. After stirring at room temperature for two hours, the reaction solution was cooled to 0° C. The reaction was terminated with 1 N hydrochloric acid, followed by dilution with ethyl acetate. The organic layer was washed with 1 N sodium hydroxide and brine and dried over magnesium sulfate. Concentration under reduced pressure gave a crude product (388 mg) which was used for the next reaction without purification.

Synthesis of 5-hydroxy-3-(2-trifluoromethylphenyl) pentanenitrile

The title compound was obtained according to the method of Preparation Example 4-4 from 5-hydroxy-3-(2-trifluoromethylphenyl)pentanoic acid amide.

Preparation Example 4-6

Synthesis of 2-(2-fluoro-4-trifluoromethylphenyl)-5-hydroxypentanenitrile

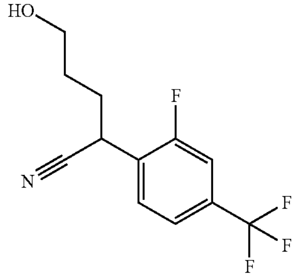 [SMILES: N#CC(CCCO)c1ccc(C(F)(F)F)cc1F]

The title compound (1.3 g) was obtained according to the method of Example 4-1 from 2-fluoro-4-(trifluoromethyl) phenylacetonitrile (2 g).

$^1$H-NMR ($CDCl_3$) δ (ppm): 1.70-1.84 (m, 2H), 1.98-2.14 (m, 2H), 3.66-3.78 (m, 2H), 4.25 (t, J=6.8 Hz, 1H), 7.35 (d, J=9.8 Hz, 1H), 7.49 (d, J=9.8 Hz, 1H), 7.61-7.66 (m, 1H).

Preparation Example 5-1

Synthesis of 2-[6-methoxy-5-(4-methyl-1H-imidazol-1-yl)pyridin-2-yl]-5,6,7,8-tetrahydro[1,2,4]triazolo[1,5-a]pyridine-8-carboxylic acid

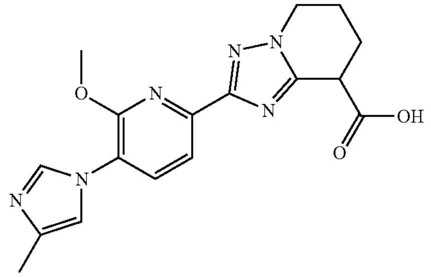 [SMILES: COc1nc(-c2nc3n(n2)CCCC3C(=O)O)ccc1-n1cnc(C)c1]

Synthesis of ethyl 2-[6-methoxy-5-(4-methyl-1H-imidazol-1-yl)pyridin-2-yl]-5,6,7,8-tetrahydro[1,2,4]triazolo[1,5-a]pyridine-8-carboxylate The title compound (695 mg) was obtained according to the method of Examples 42 and 43 from the imidate hydrochloride obtained in Preparation Example 3-11 in place of ethyl 2-(4-bromo-2-trifluoromethylphenyl)-5-chloropentanimidate hydrochloride. The property values of the compound are as follows.

$^1$H-NMR ($CDCl_3$) δ (ppm): 1.30 (t, J=7.2 Hz, 3H), 2.10-2.40 (m, 4H), 2.30 (s, 3H), 4.11 (t, J=6.0 Hz, 1H), 4.16 (s, 3H), 4.20-4.39 (m, 4H), 7.01 (s, 1H), 7.62 (d, J=8.0 Hz, 1H), 7.82 (d, J=8.0 Hz, 1H), 7.83 (s, 1H).

Synthesis of 2-[6-methoxy-5-(4-methyl-1H-imidazol-1-yl)pyridin-2-yl]-5,6,7,8-tetrahydro[1,2,4]triazolo[1,5-a]pyridine-8-carboxylic acid Ethyl 2-[6-methoxy-5-(4-methyl-1H-imidazol-1-yl)pyridin-2-yl]-5,6,7,8-tetrahydro[1,2,4]triazolo[1,5-a]pyridine-8-carboxylate (331 mg) was dissolved in a mixed solvent of THF (5 mL) and methanol (5 mL) A 5 N sodium hydroxide aqueous solution (693 μL) was added and the mixture was stirred at room temperature for two days. The reaction solution was neutralized with 5 N hydrochloric acid (693 μl), and then concentrated under reduced pressure to remove the organic solvent. Methanol (2 mL) was added to the residue, and the precipitated salt was separated by filtration. Thereafter, the filtrate was concentrated under reduced pressure to obtain the title compound.

ESI-MS; m/z 355 [$M^+$+H].

Preparation Example 1-9

Synthesis of 3-methoxy-4-(4-methylimidazol-1-yl)benzoic acid hydrazide

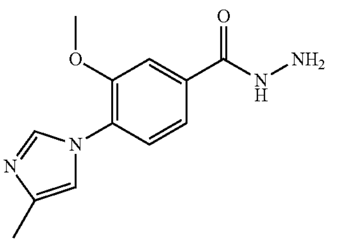 [SMILES: COc1cc(C(=O)NN)ccc1-n1cnc(C)c1]

Synthesis of benzyl N'-[3-methoxy-4-(4-methylimidazol-1-yl)benzoyl]hydrazinecarboxylate IPEA (1.05 mL) and 1-ethyl-3-(dimethylaminopropyl)carbodiimide hydrochloride (1.16 g) were sequentially added to a solution of 3-methoxy-4-(4-methylimidazol-1-yl)benzoic acid (CAS#937026-26-1, 933 mg), benzyl carbazate (737 mg) and HOBT (817 mg) in DMF (15 mL), and the mixture was stirred at room temperature overnight. Ethyl acetate, ice water and a saturated sodium bicarbonate solution were added to the reaction solution, and the organic layer was separated. The resulting organic layer was sequentially washed with water and brine. The combined aqueous layer was extracted with ethyl acetate. The combined organic layer was dried over anhydrous magnesium sulfate and then concentrated under reduced pressure. Ethyl acetate and NH silica gel were added to the resulting residue and then the mixture was concentrated under reduced pressure.

The resulting residue was purified by silica gel column chromatography (carrier: Chromatorex™ NH; elution solvent: ethyl acetate:heptane=1:1→10:1→10% methanol in ethyl acetate). The target fraction was concentrated. The resulting powder was triturated with ethyl acetate and tert-butyl methyl ether to obtain 1.30 g of the title compound. The property values of the compound are as follows.

$^1$H-NMR (DMSO-$D_6$) δ (ppm): 2.16 (s, 3H), 3.90 (s, 3H), 5.14 (s, 2H), 7.22 (s, 1H), 7.25-7.45 (m, 5H), 7.52 (d, J=8.0 Hz, 1H), 7.56 (d, J=8.0 Hz, 1H), 7.67 (s, 1H), 7.88 (s, 1H), 9.43 (brs, 1H), 10.46 (brs, 1H).

Synthesis of 3-methoxy-4-(4-methylimidazol-1-yl)benzoic acid hydrazide

To a solution of benzyl N'-[3-methoxy-4-(4-methylimidazol-1-yl)benzoyl]hydrazinecarboxylate (1.25 g) in methanol (60 mL) was added 20% palladium hydroxide-carbon (50% wet, 250 mg) and the mixture was hydrogenated at an intermediate pressure (3.8 atm) for two hours and 30 minutes. The palladium-carbon was removed by filtration through celite. The filtrate was concentrated under reduced pressure to obtain 826 mg of the title compound. The property values of the compound are as follows.

ESI-MS; m/z 247 [$M^+$+H].

$^1$H-NMR (DMSO-$D_6$) δ (ppm): 2.16 (d, J=1.2 Hz, 3H), 3.89 (s, 3H), 4.55 (brs, 2H), 7.20 (s, 1H), 7.46 (d, J=8.0 Hz, 1H), 7.52 (dd, J=8.0, 1.6 Hz, 1H), 7.64 (d, J=1.6 Hz, 1H), 7.84 (d, J=1.2 Hz, 1H), 9.90 (brs, 1H).

Preparation Example 1-10

Synthesis of 1-[4-(1-ethoxyvinyl)-2-methoxyphenyl]-4-methyl-1H-imidazol

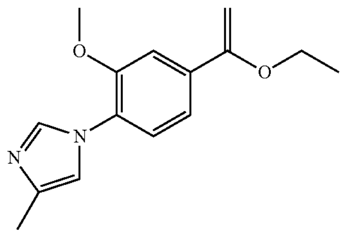

According to the method of Preparation Example 1-7, 575 mg of the title compound was obtained from 1-(4-bromo-2-methoxyphenyl)-4-methyl-1H-imidazol (CAS #87038-56-5, 1.5 g). The property values of the compound are as follows.

$^1$H-NMR ($CDCl_3$) δ (ppm): 1.45 (t, J=7.2 Hz, 3H), 2.49 (s, 3H), 3.95 (q, J=7.2 Hz, 2H), 3.96 (s, 3H), 4.27 (d, J=2.8 Hz, 1H), 4.70 (d, J=2.8 Hz, 1H), 7.33 (d, J=1.6 Hz, 1H), 7.34 (dd, J=8.8, 1.6 Hz, 1H), 7.73 (d, J=8.8 Hz, 1H), 8.65 (s, 1H).

Preparation Example 1-11

Synthesis of 6-bromo-3-imidazol-1-yl-2-methoxypyridine

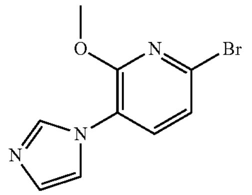

According to the method of Preparation Example 1-1, 257 mg of the title compound was obtained from N-(6-bromo-2-methoxypyridine-3-yl)formamide ESI-MS; m/z 254 [$M^+$+H].

Preparation Example 1-12

Synthesis of 6-bromo-2-methoxy-3-(2-methyl-1H-imidazol-1-yl)pyridine

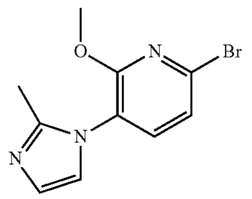

Synthesis of 6-bromo-2-methoxypyridyl-3-boronic acid

To an ice-cold solution of diisopropylamine (777 μL) in THF (20 mL) was added n-butyllithium (2.6M hexane solution) and the mixture was stirred at same temperature for 10 minutes. The solution was cooled to −78° C. then 2-Bromo-6-methoxypyridine (CAS#40473-07-2, 799 mg) and triisopropyl borate (1.27 ml) were added dropwise. The reaction temperature was raised to room temperature and stirred for an hour. To the reaction mixture was added an ammonium chloride solution, and the mixture was extracted with ethyl acetate. The organic layer was washed with brine and dried over anhydrous sodium sulfate. The drying agent was separated by filtration and then the organic layer was concentrated under reduced pressure. The residual crystal was collected by filtration and washed with diethyl ether to obtain the title compound (545 mg).

Synthesis of 6-bromo-2-methoxy-3-(2-methyl-1H-imidazol-1-yl)pyridine

To a solution of 6-bromo-2-methoxypyridyl-3-boronic acid (1 g) and 2-methyl-1H-imidazol (354 mg) in dichloromethane (20 mL) was added di-μ-hydroxo-bis[(N,N,N',N'-tetramethylethylenediamine)copper (II)]chloride (300 mg). The reaction mixture was stirred in an oxygen atmosphere at room temperature for 3 days. The mixture was filtered through celite and the filtrate was concentrated under reduced pressure. The resulting residue was purified by silica gel column chromatography to obtain the title compound (311 mg).

The compounds of Preparation Example 1-13 to Preparation Example 1-15 were obtained according to the methods of Preparation Example 1-7. (Table 11)

TABLE 11

| Preparation Example No. | Structural formula |
|---|---|
| 1-13 | 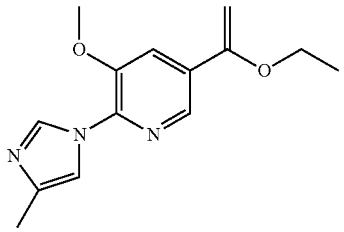 [SMILES: C=C(OCC)c1cnc(-n2cnc(C)c2)c(OC)c1] |
| 1-14 | 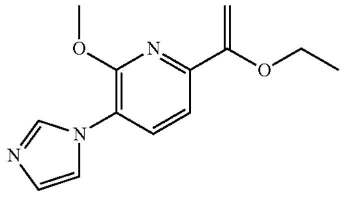 [SMILES: C=C(OCC)c1ccc(-n2ccnc2)c(OC)n1] |
| 1-15 | 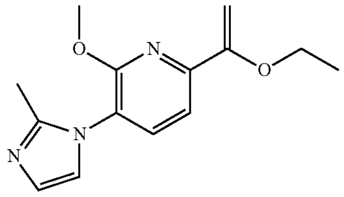 [SMILES: C=C(OCC)c1ccc(-n2ccnc2C)c(OC)n1] |

Preparation Example 3-21

Synthesis of 2-[2-bromo-5-(cyano-dimethyl-methyl)phenyl-5-chloropentanimidic acid ethyl ester hydrochloride

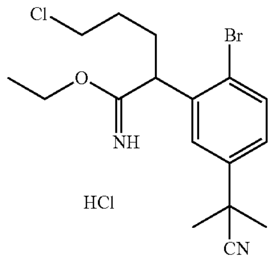 [SMILES: CCOC(=N)C(CCCCl)c1cc(C(C)(C)C#N)ccc1Br ; Cl]

Synthesis of 2-(4-bromo-3-methylphenyl)-2-methylpropionitrile

To an ice-cold suspension of sodium hydride (60% in oil, 524 mg) in THF (5 ml) and N-methylpyrrolidone (5 ml) was added the solution of (4-bromo-3-methylphenyl)acetonitrile (CAS #215800-25-2, 1.1 g) and iodomethane (1 ml) in THF (3 ml) and N-methylpyrrolidone 3 ml). After stirring for 40 minutes at room temperature, water and tert-butyl methyl ether was added. The organic layer was separated and the aqueous layer was extracted with tert-butyl methyl ether. The combined organic layer was washed with water (twice) and brine. After drying over anhydrous magnesium sulfate, the drying agent was separated by filtration and then the organic layer was concentrated under reduced pressure. The residue was purified by silica gel column chromatography (carrier: Wakogel™ C-200; elution solvent:heptane:ethyl acetate=19:1) to obtain the title compound (1.06 g). The property values of the compound are as follows.

$^1$H-NMR ($CDCl_3$) δ (ppm): 1.71 (s, 6H), 2.43 (s, 3H), 7.14 (dd, J=8.4, 2.4 Hz, 1H), 7.34 (d, J=2.4 Hz, 1H), 7.53 (d, J=8.4 Hz, 1H).

Synthesis of 2-(4-bromo-3-cyanomethyl-phenyl)-2-methylpropionitrile

N-bromosuccinimide (1.04 g) and 2,2'-azobis(isobutylnitrile) (30 mg) were added to the carbon tetrachloride solution (7 ml) of 2-(4-bromo-3-methylphenyl)-2-methylpropionitrile (1.26 g) and then the solution was refluxed with heating for an hour. The solution was cooled on ice, then after removing the insoluble substances by filtration, the filtrate was concentrated under reduced pressure. The obtained residue was dissolved in ethanol (10 ml) and water (1 ml) and a solution of potassium cyanide (0.41 g) was added to the solution. The reaction mixture was stirring overnight at room temperature. To the reaction mixture was added the ice-cold water and ethyl acetate, and the organic layer was separated. The obtained organic layer was sequentially washed with water (twice) and brine. After drying over anhydrous magnesium sulfate, the organic layer was concentrated under reduced pressure. The residue was purified by silica gel column chromatography (carrier; Wakogel™ C-200; elution solvent; heptane:ethyl acetate, 19:1→5:1) to obtain the title compound. (917 mg) The property values of the obtained compound are as follows; $^1$H-NMR ($CDCl_3$) δ (ppm): 1.74 (s, 6H), 3.87 (s, 2H), 7.38 (dd, J=8.4, 2.4 Hz, 1H), 7.57 (d, J=2.4 Hz, 1H), 7.64 (d, J=8.4 Hz, 1H).

Synthesis of 2-[2-bromo-5-(cyano-dimethyl-methyl)phenyl]-5-chloropentanitrile Under ice-cold condition, to the mixture solution of 2-(4-bromo-3-cyanomethyl-phenyl)-2-methylpropionitrile in THF (5 ml) and DMF (5 ml) was added sodium hydride (60% in oil, 144 mg), and the reaction mixture was stirred for 10 minutes under the same temperature. To the reaction mixture was added 1-bromo-3-chloropropane (0.44 ml) and the mixture was stirred for 25 minutes under the same temperature. The ice-cold water and tert-butyl methyl ether was added to the reaction mixture and then the organic layer was separated. The water layer was re-extracted by the tert-butyl methyl ether. The combined organic layer was washed with brine and dried over anhydrous magnesium sulfate.

After concentration, the obtained residue was purified by silica gel column chromatography (carrier: Wakogel™ C-200, elution solvent:heptane:ethyl acetate, 19:1→5:1) to obtain the title compound (941 mg). The property values of the obtained compound are as follows; $^{1}$H-NMR ($CDCl_3$) δ (ppm): 1.75 (s, 6H), 1.87-2.18 (m, 4H), 3.61 (t, J=6.0 Hz, 2H), 4.31-4.36 (M, 1H), 7.38 (dd, J=8.4, 2.4 Hz, 1H), 7.60 (d, J=2.4 Hz, 1H), 7.63 (d, J=8.4 Hz, 1H).

Synthesis of ethyl 2-[2-bromo-5-(cyano-dimethyl-methyl)phenyl]-5-chloropentanimidate hydrochloride

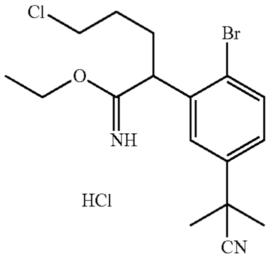 [SMILES: CCOC(=N)C(CCCCl)c1cc(C(C)(C)C#N)ccc1Br ; Cl]

Under the ice-cold condition, a solution of 2-[2-bromo-5-(cyano-dimethyl-phenyl)]-5-chloropentanenitrile (100 mg) in ethanol (4 ml) was bubbled with hydrogen chloride gas for 10 minutes. After the reaction solution was stirred at room temperature for 2 hours, the solution was concentrated under reduced pressure. Tert-butyl methyl ether was added to the residue and the solution was concentrated under reduced pressure to obtain the title compound (124 mg). The property value of the obtained compound is as follows; ESI-MS; m/z 387 [$M^{+}$+H-HCl].

The compounds of Preparation Example 3-22 to Preparation Example 3-32 were obtained according to the methods described in Preparation Example 3-21.

TABLE 12

| Preparation Example | Structural formula |
|---|---|
| 3-22 | 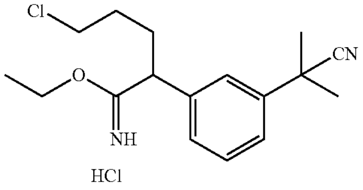 [SMILES: CCOC(=N)C(CCCCl)c1cccc(C(C)(C)C#N)c1 ; Cl] |
| 3-23 | 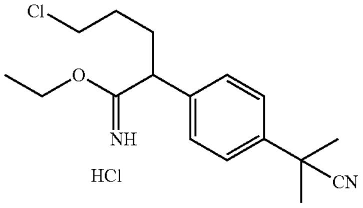 [SMILES: CCOC(=N)C(CCCCl)c1ccc(C(C)(C)C#N)cc1 ; Cl] |
| 3-24 | 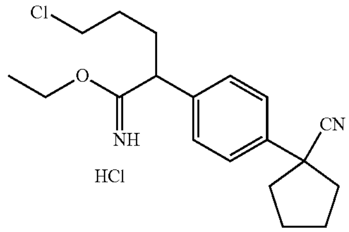 [SMILES: CCOC(=N)C(CCCCl)c1ccc(C2(C#N)CCCC2)cc1 ; Cl] |
| 3-25 | 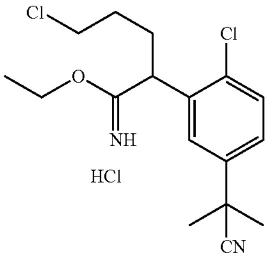 [SMILES: CCOC(=N)C(CCCCl)c1cc(C(C)(C)C#N)ccc1Cl ; Cl] |
| 3-26 | 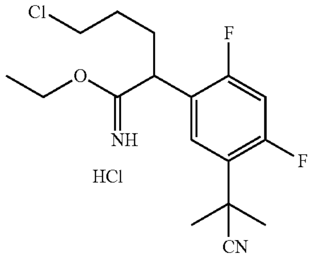 |
| 3-27 | 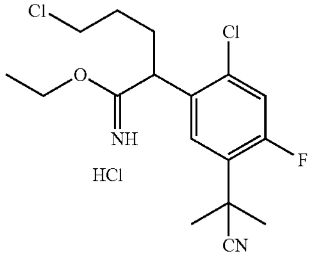 [SMILES: CCOC(=N)C(CCCCl)c1cc(C(C)(C)C#N)c(F)cc1F ; Cl] |

TABLE 12-continued

| Preparation Example | Structural formula |
|---|---|
| 3-28 | 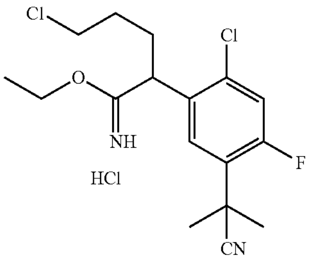 |
| 3-29 | 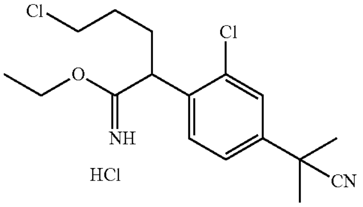 [SMILES: CCOC(=N)C(CCCCl)c1ccc(C(C)(C)C#N)cc1Cl ; Cl] |
| 3-30 | 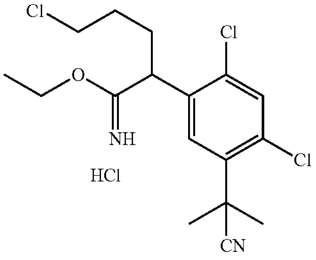 [SMILES: CCOC(=N)C(CCCCl)c1cc(C(C)(C)C#N)c(Cl)cc1Cl ; Cl] |
| 3-31 | 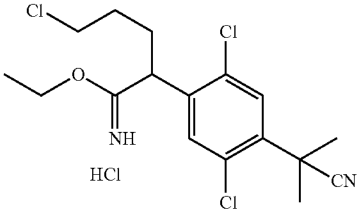 [SMILES: CCOC(=N)C(CCCCl)c1cc(Cl)c(C(C)(C)C#N)cc1Cl ; Cl] |
| 3-32 | 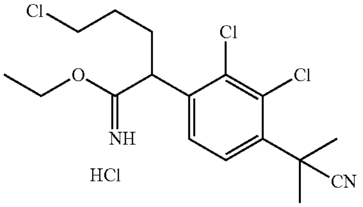 [SMILES: CCOC(=N)C(CCCCl)c1ccc(C(C)(C)C#N)c(Cl)c1Cl ; Cl] |

The compounds of Preparation Example 3-33 to Preparation Example 3-37 were obtained according to the methods described in Preparation Example 3-3.

TABLE 13

| Preparation Example | Structural formula |
|---|---|
| 3-33 | 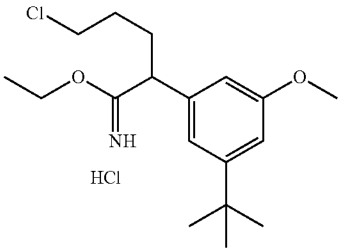 [SMILES: CCOC(=N)C(CCCCl)c1cc(OC)cc(C(C)(C)C)c1 ; Cl] |
| 3-34 | 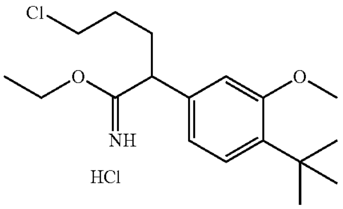 [SMILES: CCOC(=N)C(CCCCl)c1ccc(C(C)(C)C)c(OC)c1 ; Cl] |
| 3-35 | 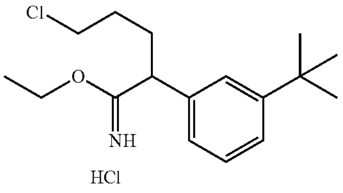 [SMILES: CCOC(=N)C(CCCCl)c1cccc(C(C)(C)C)c1 ; Cl] |
| 3-36 | 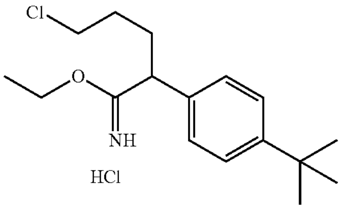 |
| 3-37 | 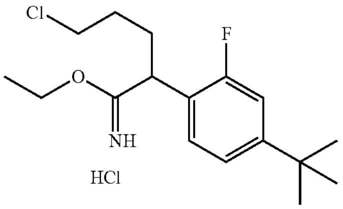 [SMILES: CCOC(=N)C(CCCCl)c1ccc(C(C)(C)C)cc1F ; Cl] |

The compounds of Preparation Example 3-38 to Preparation Example 3-45 were obtained according to the methods described in Preparation Example 3-1.

TABLE 14

| Preparation Example | Structural formula |
|---|---|
| 3-38 | 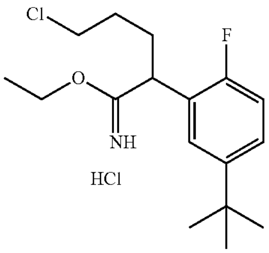 [SMILES: CCOC(=N)C(CCCCl)c1cc(C(C)(C)C)ccc1F ; Cl] |

TABLE 14-continued

| Preparation Example | Structural formula |
|---|---|
| 3-39 | 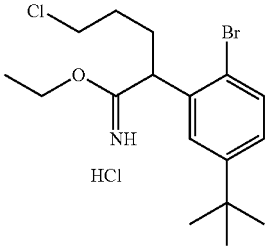 [SMILES: CCOC(=N)C(CCCCl)c1cc(C(C)(C)C)ccc1Br ; Cl] |
| 3-40 | 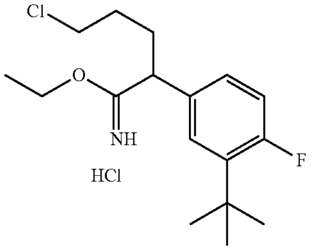 [SMILES: CCOC(=N)C(CCCCl)c1ccc(F)c(C(C)(C)C)c1 ; Cl] |
| 3-41 | 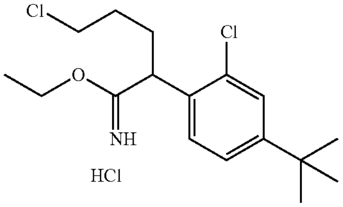 [SMILES: CCOC(=N)C(CCCCl)c1ccc(C(C)(C)C)cc1Cl ; Cl] |
| 3-42 | 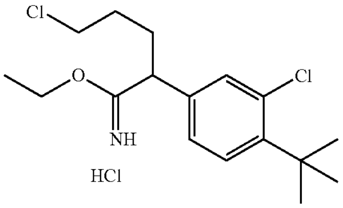 [SMILES: CCOC(=N)C(CCCCl)c1ccc(C(C)(C)C)c(Cl)c1 ; Cl] |
| 3-43 | 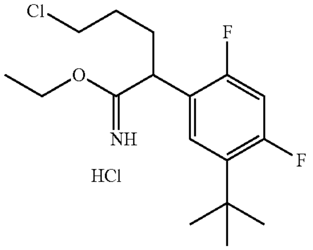 [SMILES: CCOC(=N)C(CCCCl)c1cc(C(C)(C)C)c(F)cc1F ; Cl] |
| 3-44 | 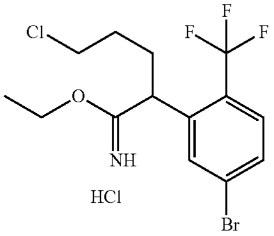 [SMILES: CCOC(=N)C(CCCCl)c1cc(Br)ccc1C(F)(F)F ; Cl] |
| 3-45 | 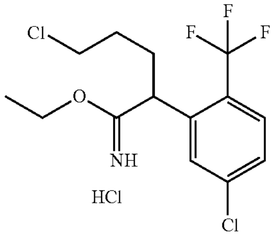 [SMILES: CCOC(=N)C(CCCCl)c1cc(Cl)ccc1C(F)(F)F ; Cl] |

Preparation Example of the Compound 3-46

Synthesis of 1-[2,4-dichloro-5-(4-chloro-1-cyanobutyl)phenyl]cyclopropanecarbonitrite

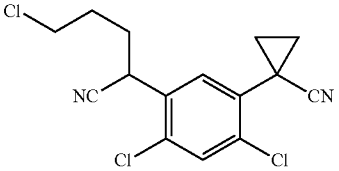 [SMILES: N#CC(CCCCl)c1cc(C2(C#N)CC2)c(Cl)cc1Cl]

Synthesis of (2,4-dichloro-5-methylphenyl)acetonitrile

To a solution of 1,5-dichloro-2-chloromethyl-4-methylbenzene (CAS #101349-87-5, 5.22 g) in dimethyl sulfoxide (20 ml) was added potassium cyanide (1.36 g) and the reaction solution was stirred at room temperature for 6 hours. Potassium cyanide (0.68 g) was added to the reaction solution and the solution was further stirred at room temperature overnight. To the reaction solution were added ice-cold water and tert-butyl methyl ether and the organic layer was separated. The water layer was re-extracted by the tert-butyl methyl ether. The combined organic layer was sequentially washed with water (twice) and brine. After drying over anhydrous magnesium sulfate, the organic layer was concentrated under reduced pressure. The obtained residue was purified by silica gel column chromatography (carrier: Walcogel™ C-200; elution solvent:heptane:ethyl acetate 49:1→19:1) to obtain the title compound (1.88 g). The property values of the obtained compound are as follows; $^{1}$H-NMR ($CDCl_3$) δ (ppm): 2.38 (s, 3H), 3.78 (s, 2H), 7.38 (s, 1H), 7.43 (s, 1H).

Synthesis of 1-(2,4-dichloro-5-methylphenyl)cyclopropanecarbonitrile

To a mixture of (2,4-dichloro-5-methylphenyl)acetonitrile (385 mg) and 1,2-dibromoethane (1.0 g) were added benzyltriethylammonium-chloride (44 mg) and a 50% solution of sodium hydroxide (0.8 ml) and the mixture was stirred overnight at room temperature. Ice-cold water and tert-butyl methyl ether were added to the reaction mixture and the organic layer was separated. The obtained organic layer was sequentially washed with water (twice) and brine. After drying over anhydrous magnesium sulfate, the organic layer was concentrated under reduced pressure. The obtained residue was purified by silica column chromatography (carrier:

Wakogel™ C-200; elution solvent:heptane:ethyl acetate 49:1→19:1) to obtain the title compound (317 mg). The property values of the obtained compound are as follows; $^1$H-NMR ($CDCl_3$) δ (ppm): 1.32 (dd, J=7.6, 5.2 Hz, 2H), 1.72 (dd, J=7.6, 5.2 Hz, 2H), 2.34 (s, 3H), 7.20 (s, 1H), 7.43 (s, 1H).

Synthesis of 1-[2,4-dichloro-5-(4-chloro-1-cyanobutyl)phenyl]cyclopropane-carbonitrile Similar to the methods of Preparation Example 3-21, the title compound (113 mg) was obtained from 1-(2,4-dichloro-5-methylphenyl)cyclopropanecarbonitrile (317 mg). The property values of the obtained compound are as follows; $^1$H-NMR ($CDCl_3$) δ (ppm): 1.30-1.34 (m, 1H), 1.40-1.45 (m, 1H), 1.77-1.85 (m, 2H), 1.93-2.15 (m, 4H), 3.61 (t, J=5.6 Hz, 2H), 4.23-4.29 (m, 1H), 7.54 (s, 1H).

Preparation Example 3-47

Synthesis of ethyl 5-chloro-2-[2-methoxy-5-(2,2,2-trifluoro-1,1-dimethylethyl)phenyl]pentanimidate

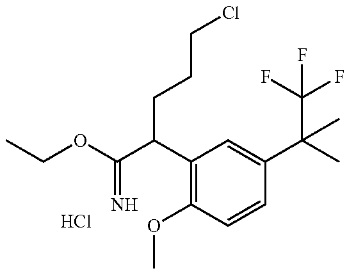 [SMILES: CCOC(=N)C(CCCCl)c1cc(C(C)(C)C(F)(F)F)ccc1OC ; Cl]

Synthesis of 1-(4-methoxy-3-methylphenybethanone

To a solution of 4-hydroxy-3-methylacetophenone (CAS #876-02-8, 5 g) in DMF (30 ml) were added potassium carbonate (9.21 g) and iodomethane (6.14 g). The reaction solution was stirred at room temperature for 3 days. Water and heptane were added to the reaction mixture and the organic layer was separated. The obtained organic layer was washed with brine and was dried over anhydrous magnesium sulfate. After filtration for removing the drying agent, the organic layer was concentrated under reduced pressure. The residue was dissolved in a solution of heptane and ethyl acetate mixture (heptane:ethyl acetate, 3:1), and the solution was passed through silica gel column chromatography. The solution was concentrated under the reduced pressure to obtain the title compound (5.7 g). The property values of the compound are as follows; $^1$H-NMR ($CDCl_3$) δ (ppm): 2.25 (s, 3H), 2.55 (s, 3H), 3.90 (s, 3H), 6.85 (d, J=8.4 Hz, 1H), 7.78 (d, J=2.0 Hz, 1H), 7.83 (dd, J=8.4, 2.0 Hz, 1H).

Synthesis of trimethyl-[2,2,2-trifluoro-1-(4-methoxy-3-methylphenyl)-1-methylethoxy]silane To an ice-cold solution of 1-(4-methoxy-3-methylphenyl) ethanone (1 g) in DMF (6 ml) were added lithium acetate (20.1 mg) and (trifluoromethyl)trimethylsilane (1.04 g). Under the same temperature, the solution was stirred for 1.5 hours and then stirred for 3.5 hours at room temperature. Water and heptane were added to the reaction solution and the organic layer was separated. The obtained organic layer was washed with brine and dried over anhydrous magnesium sulfate. After removing the drying agent, the organic layer was concentrated under reduced pressure. The residue was purified by silica gel column chromatography (elution solvent: heptane heptane:ethyl acetate 7:3) to obtain the title compound (711 mg). The property values of the obtained compound are as follows; $^1$H-NMR ($CDCl_3$) δ (ppm): 0.13 (s, 3H), 1.79 (s, 3H), 2.23 (s, 3H), 3.84 (s, 3H), 6.80 (d, J=8.8 Hz, 1H), 7.27 (d, J=2.4 Hz, 1H), 7.32 (dd, J=8.8, 2.4 Hz, 1H)

Synthesis of 1,1,1-trifluoro-2-(4-methoxy-3-methylphenyl)-propane-2-ol

Trimethyl-[2,2,2-trifluoro-1-(4-methoxy-3-methylphenyl)-1-methylethoxy]silane (711 mg) was dissolved in THF (20 ml) and 1N HCl solution (20 ml) was added. After stirring at room temperature for 6 days, water and ethyl acetate were added to the reaction mixture and the organic layer was separated. The obtained organic layer was washed with brine and dried over anhydrous magnesium sulfate. After removing the drying agent, the organic layer was concentrated under reduced pressure. The residue was purified by silica gel column chromatography (elution solvent: heptane→heptane: ethyl acetate 7:3) to obtain the title compound (442 mg). The property values of the obtained compound are as follows; $^1$H-NMR ($CDCl_3$) δ (ppm): 1.76 (s, 3H), 2.24 (s, 3H), 3.84 (s, 3H), 6.83 (d, J=8.4 Hz, 1H), 7.34-7.37 (m, 2H).

Synthesis of 1-methoxy-2-methyl-4-(2,2,2-trifluoro-1,1-dimethylethyl)benzene

To an ice-cold solution of 1,1,1-trifluoro-2-(4-methoxy-3-methylphenyl)-propane-2-ol (440 mg) in dichloromethane (20 ml) were added titanium tetrachloride (357 mg). Under the same temperature, it was stirred for 2 hours. Ice-cold water and dichloromethane were added to the organic layer and the organic layer was separated. The obtained organic layer was washed with saturated sodium bicarbonate solution and dried over anhydrous potassium carbonate. After removing the drying agent, the organic layer was concentrated under reduced pressure. After the residue was dissolved in dichloro methane (15 ml), it was cooled at −70° C. and titanium tetrachloride (302 mg) and dimethylzinc (1M, n-hexane solution, 3.18 ml) was added. The mixture was brought back to room temperature and stirred for 3 hours. Ice-cold water and dichloromethane were added to the solution and the organic layer was separated. The obtained organic layer was washed with saturated sodium bicaronate solution and then dried over anhydrous magnesium sulfate. After removing the drying agent, the organic layer was concentrated under reduced pressure.

The residue was purified by silica gel column chromatography (elution solvent: heptane→heptane:ethyl acetate 9:1) to obtain the title compound (203 mg). The property values of the obtained compound are as follows; $^1$H-NMR ($CDCl_3$) δ (ppm): 1.54 (s, 6H), 2.23 (s, 3H), 3.83 (s, 3H), 6.80 (d, J=8.4 Hz, 1H), 7.25-7.29 (m, 2H).

Synthesis of ethyl 5-chloro-2-[2-methoxy-5-(2,2,2-trifluoro-1-methoxy-1-methylethyl)phenyl]pentanimidate hydrochloride According to the method of Preparation Example 3-1, the titled compound was obtained from 1-methoxy-2-methyl-4-(2,2,2-trifluoro-1,1-dimethylethyl)benzene.

Preparation Example 3-48

Synthesis of ethyl 5-chloro-2-[2-methoxy-5-(2,2,2-trifluoro-1-methoxy-1-methylethyl)phenyl]pentanimidate hydrochloride

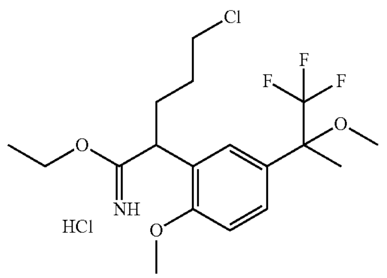 [SMILES: CCOC(=N)C(CCCCl)c1cc(C(C)(OC)C(F)(F)F)ccc1OC ; Cl]

Synthesis of 1-methoxy-2-methyl-4-(2,2,2-trifluoro-1-methoxy-1-methylethyl)benzene To a solution of 1,1,1-trifluoro-2-(4-methoxy-3-methylphenyl)-propane-2-ol (1 g) in DMF (20 ml) were added sodium hydride (60% in mineral oil, 205 mg) and iodomethane (727 mg). After stirring for 5 hours at room temperature, the reaction mixture was ice cooled, then water and ethyl acetate were added to the reaction mixture. The organic layer was separated and washed with brine, and dried over anhydrous magnesium sulfate. After removing the drying agent, the organic layer was concentrated under reduced pressure.

The residue was purified by silica gel column chromatography (elution solvent: heptane→heptane:ethyl acetate 9:1) to obtain the title compound (747 mg). The property values of the obtained compound are as follows; $^1$H-NMR ($CDCl_3$) δ (ppm): 1.74 (s, 3H), 2.24 (s, 3H), 3.21 (s, 3H), 3.85 (s, 3H), 6.83 (d, J=8.4 Hz, 1H), 7.25-7.30 (m, 2H).

Synthesis of ethyl 5-chloro-2-[2-methoxy-5-(2,2,2-trifluoro-1-methoxy-1-methylethyl)phenyl]pentanimidate hydrochloride According to the method of Preparation Example 3-1, the title compound was obtained from 1-methoxy-2-methyl-4-(2,2,2-trifluoro-1-methoxy-1-methylethyl)benzene.

Preparation Example 6-1

Synthesis of (2-fluoro-5-piperidin-1-ylphenyl)methanol

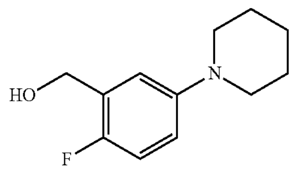 [SMILES: OCc1cc(N2CCCCC2)ccc1F]

Synthesis of methyl 2-fluoro-5-nitro benzoate

To an ice-cold solution of 2-fluoro-5-nitro benzoic acid (3 g) in methanol (30 ml) was added thionyl chloride (2.32 ml) dropwise. After stirring overnight at room temperature, the reaction mixture was concentrated under reduced pressure. Ethyl acetate and sodium bicarbonate aqueous solution were added to the residue and the organic layer was separated. The obtained organic layer was washed with brine and then dried over anhydrous sodium sulfate. After removing the drying agent, the organic layer was concentrated under reduced pressure to obtain the title compound (3.28 g).

Synthesis of methyl 5-amino-2-fluoro benzoate

To a solution of methyl 2-fluoro-5-nitro benzoate (2 g) in methanol (80 ml) was added nickel dichloride (II) 6 hydrate (475 mg), and the reaction mixture was cooled to −30° C. Under the same temperature, sodium borohydride (1.13 g) was added portionwise. The solution was warmed up to −20° C. and stirred for 20 minutes, then potassium carbonate aqueous solution was added. After removing the insoluble substance by celite filtration, the filtrate was concentrated under the reduced pressure to remove methanol. The obtained residue was extracted with ethyl acetate. The extract was washed with brine and dried over anhydrous sodium sulfate. After removing the drying agent by filtration, the organic layer was concentrated under reduced pressure. The residue was purified by silica gel column chromatography to obtain the title compound (1.5 g).

Synthesis of methyl 2-fluoro-5-(piperidin-1-yl)benzoate

Methyl 5-amino-2-fluoro benzoate (1.5 g), 1,5-dibromopentane (5.93 ml) and IPEA (7.66 ml) were dissolved in toluene (30 ml) and the mixture was stirred at 100° C. for 15 hours. After cooling, ethyl acetate was added to the solution and the organic layer was separated. The organic layer was washed with water, brine and dried with anhydrous sodium sulfate. After removing the drying agent by filtration, the organic layer was concentrated under reduced pressure. The residue was purified by silica gel column chromatography to obtain the title compound (2.12 g). The property value of the obtained compound is as follows; ESI-MS; m/z 238 [$M^+$+H].

Synthesis of (2-fluoro-5-piperidin-1-yl)phenyl methanol

Methyl 2-fluoro-5-(piperidine-1-yl)benzoate (2.12 g) was added dropwise to a suspension of lithium aluminum hydride (372 mg) in THF (30 ml) under ice-cooling. After the completion of addition, the mixture was warmed to room temperature and stirred for 1 hour. Water (372 ml), 5N aqueous sodium hydroxide solution (372 ml) and water (1.12 ml) was sequentially added to the mixture under ice-cooling. The precipitate was removed by filtration through Celite and the filtrate was concentrated under reduced pressure to obtain the title compound (1.88 g).

ESI-MS; m/z 210[$M^{+}$+H].

The compounds of Preparation Example 6-2 to Preparation Example 6-10 were obtained according to the method of Preparation Example 6-1 (Table 15).

TABLE 15

| Preparation Example No. | Structural formula |
|---|---|
| 6-2 | 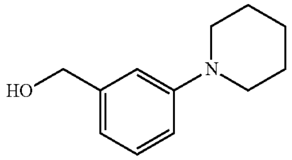 [SMILES: OCc1cccc(N2CCCCC2)c1] |
| 6-3 | 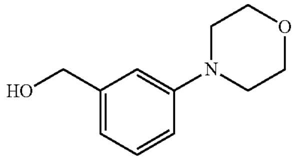 [SMILES: OCc1cccc(N2CCOCC2)c1] |
| 6-4 | 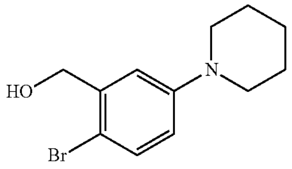 [SMILES: OCc1cc(N2CCCCC2)ccc1Br] |
| 6-5 | 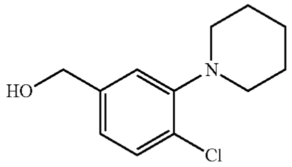 [SMILES: OCc1ccc(Cl)c(N2CCCCC2)c1] |
| 6-6 | 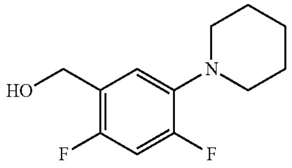 [SMILES: OCc1cc(N2CCCCC2)c(F)cc1F] |
| 6-7 | 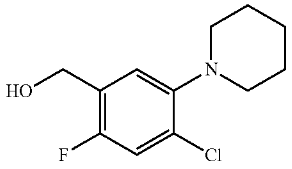 [SMILES: OCc1cc(N2CCCCC2)c(Cl)cc1F] |
| 6-8 | 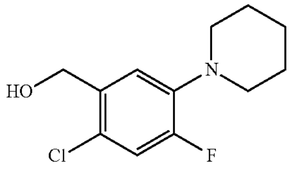 [SMILES: OCc1cc(N2CCCCC2)c(F)cc1Cl] |

TABLE 15-continued

| Preparation Example No. | Structural formula |
|---|---|
| 6-9 | 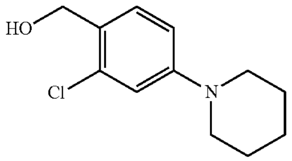 |
| 6-10 | 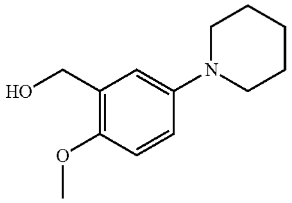 [SMILES: COc1ccc(N2CCCCC2)cc1CO] |

Preparation Example 6-11

Synthesis of (1-pyrrolidin-1-yl)phenyl methanol

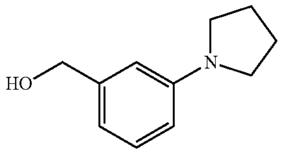 [SMILES: OCc1cccc(N2CCCC2)c1]

Synthesis of 1-[3-(tert-butyldimethylsilyloxymethyl)phenyl]pyrrolidine

Tris(dibenzylideneacetone)dipalladium (152 mg) was added to a suspension of (3-Bromobenzyloxy)-tert-butyldimethylsilane (1.00 g) obtained in Preparation Example 7-2, pyrrolidine (416 μl), BINAP (310 mg) and sodium tert-butoxide (348 mg) in toluene (20 ml) under a nitrogen atmosphere. The mixture was heated at 80° C. with stirring for 3 hours and then cooled to room temperature. The mixture was diluted with ethyl acetate, filtered through Celite and concentrated under reduced pressure. The residue was purified by silica gel column chromatography to obtain the title compound (913 mg).

ESI-MS; m/z 292 [$M^{+}$+H].

Synthesis of (3-pyrrolidin-1-yl)phenyl methanol

Tetrabutylammonium fluoride (1.0 M solution in THF, 3.8 ml) was added to a solution of 1-[3-(tert-butyldimethylsilyloxymethyl)phenyl]pyrrolidine in THF (20 ml) and the mixture was stirred at room temperature for 3.5 hours. The reaction mixture was concentrated under reduced pressure and the residue was purified by silica gel column chromatography to obtain the title compound (557 mg).

ESI-MS; m/z 178 [$M^{+}$+H].

The compounds of Preparation Examples 6-12 to 6-16 were obtained according to the method of Preparation Example 6-11 (Table 16).

TABLE 16

| Preparation Example No. | Structural formula |
|---|---|
| 6-12 | 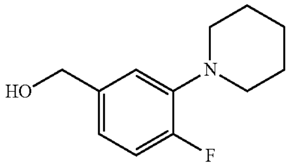 |
| 6-13 | 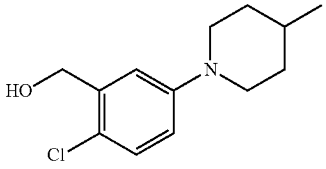 [SMILES: CC1CCN(c2ccc(Cl)c(CO)c2)CC1] |
| 6-14 | 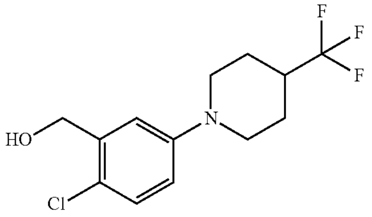 [SMILES: OCc1cc(N2CCC(C(F)(F)F)CC2)ccc1Cl] |
| 6-15 | 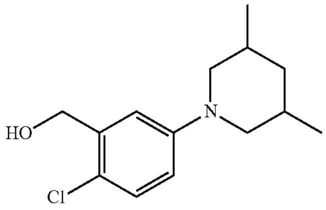 [SMILES: CC1CC(C)CN(c2ccc(Cl)c(CO)c2)C1] |
| 6-16 | 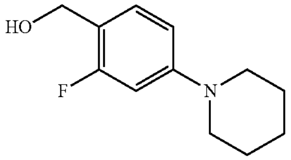 [SMILES: OCc1ccc(N2CCCCC2)cc1F] |

Preparation Example 6-17

Synthesis of [5-(4,4-difluoronineridin-1-yl)-2-fluorophenyl]methanol

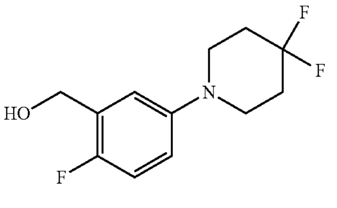 [SMILES: OCc1cc(N2CCC(F)(F)CC2)ccc1F]

Synthesis of 1-benzyl-1-methyl-4-oxopiperidinium iodide

Iodomethane (20.2 ml) was added to a solution of 1-benzyl-4-piperidone (50 ml) in acetone (300 ml) and the mixture was stirred at room temperature overnight. The deposited crystals were collected and washed with acetone to obtain a title compound (77.1 g).

Synthesis of methyl 2-fluoro-5-(4-oxopiperidin-1-yl)benzoate

Potassium carbonate (149 mg) and 1-benzyl-1-methyl-4-oxopiperidinium iodide (2.87 g) were sequentially added to a solution of methyl 5-amino-2-fluorobenzoate (1.22 g) obtained in Preparation Example 6-1 in a mixed solvent of ethanol 10 ml) and water (5 ml). The reaction mixture was refluxed for 2.5 hours. The mixture was diluted with water and extracted with ethyl acetate. The organic layer was washed with brine and dried over anhydrous sodium sulfate. The filtrate was concentrated under reduced pressure and the residue was purified by silica gel column chromatography to obtain the title compound (1.22 g).

ESI-MS; m/z 252 $[M^{+}+H]$.

Synthesis of methyl 5-(4,4-difluoropiperidin-1-yl)-2-fluorobenzoate

Diethylaminosulfur trifluoride (1.72 ml) was added to a solution of methyl 2-fluoro-5-(4-oxopiperidin-1-yl)benzoate (1.22 g) in dichloromethane (20 ml). The reaction mixture was stirred at room temperature for 1.5 hours. An aqueous saturated solution of sodium bicarbonate was added to the reaction mixture and the mixture was extracted with ethyl acetate. The organic layer was washed with brine and dried over anhydrous sodium sulfate. The filtrate was concentrated under reduced pressure and the residue was purified by silica gel column chromatography to obtain the title compound (878 mg).

ESI-MS; m/z 274 $[M^{+}+H]$.

Synthesis of [5-(4,4-difluoropiperidin-1-yl)-2-fluorophenyl]methanol

According to the method of Preparation Example 6-1, a title compound (761 mg) was obtained from methyl 5-(4,4-difluoropiperidin-1-yl)-2-fluorobenzoate (878 mg).

ESI-MS; m/z 246 $[M^{+}+H]$.

The compounds of Preparation Examples 6-18 and 6-19 were obtained according to the method of Preparation Example 6-17 (Table 17).

TABLE 17

| Preparation Example No. | Structural formula |
|---|---|
| 6-018 | 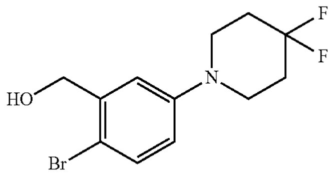 [SMILES: OCc1cc(N2CCC(F)(F)CC2)ccc1Br] |
| 6-019 | 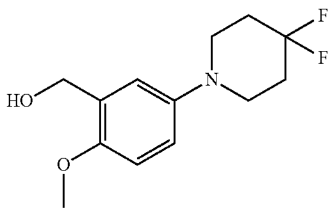 [SMILES: COc1ccc(N2CCC(F)(F)CC2)cc1CO] |

Preparation Example 6-20

Synthesis of [(3-bromo-4-piperidin-1-yl)phenyl]methanol

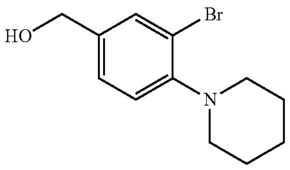 [SMILES: OCc1ccc(N2CCCCC2)c(Br)c1]

Synthesis of methyl 4-fluoro-3-nitrobenzoate

According to the method of Preparation Example 6-1, a title compound (2.19 g) was obtained from 4-fluoro-3-nitrobenzoic acid (2.00 g).

Synthesis of methyl 3-nitro-4-(piperidine-1-yl)benzoate

Piperidine (1.24 ml) was added to a solution of methyl 4-fluoro-3-nitrobenzoate (1.00 g) in DMF (20 ml) and the mixture was stirred at room temperature for 1 hour. The reaction mixture was diluted with ethyl acetate, sequentially washed with water and brine, and dried over anhydrous sodium sulfate. The filtrate was concentrated under reduced pressure and the residue was purified by silica gel column chromatography to obtain the title compound (1.50 g).

ESI-MS; m/z 265 [$M^+$+H].

Synthesis of methyl 3-amino-4-(piperidin-1-yl)benzoate

Using 10% palladium carbon cartridge, a solution of methyl 3-nitro-4-(piperidin-1-yl)benzoate (3.07 g) in methanol (50 ml) was pumped through the H-Cube™ reactor (ThalesNano Inc.). After all the reaction mixture had passed through the H-Cube™ reactor, the reaction mixture was concentrated under reduced pressure. The residue was purified by NH-silica gel column chromatography to obtain a title compound (2.32 g).

ESI-MS; m/z 235 [$M^+$+H].

Synthesis of methyl 3-bromo-4-(piperidin-1-yl)benzoate

Isoamyl nitrite (439 μl) was added to the mixture of methyl 3-amino-4-(piperidin-1-yl)benzoate (500 mg) and copper (II) bromide (714 mg) in acetonitrile (25 ml). The reaction mixture was stirred at 70° C. for 30 minutes. The mixture was diluted with ethyl acetate, sequentially washed with ammonium solution and brine, and then dried over anhydrous sodium sulfate. The filtrate was concentrated under reduced pressure and the residue was purified by silica gel column chromatography to obtain the title compound (158 mg).

Synthesis of (3-bromo-4-piperidin-1-yl)phenyl methanol

According to the method of Preparation Example 6-1, a title compound (488 mg) was obtained from methyl 3-bromo-4-(piperidin-1-yl)benzoate (546 mg).

The compounds of Preparation Example 6-21 and Preparation Example 6-22 were obtained according to the method of Preparation Example 6-20 (Table 18).

TABLE 18

| Preparation Example No. | Structural formula |
|---|---|
| 6-21 | 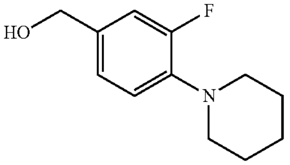 [SMILES: OCc1ccc(N2CCCCC2)c(F)c1] |
| 6-22 | 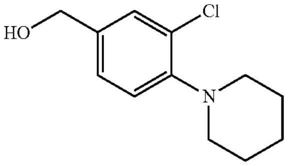 [SMILES: OCc1ccc(N2CCCCC2)c(Cl)c1] |

Preparation Example 6-23

Synthesis of {2-chloro-4-[cyclopropylmethyl (2,2,2-trifluoroethyl)amino]phenyl}methanol

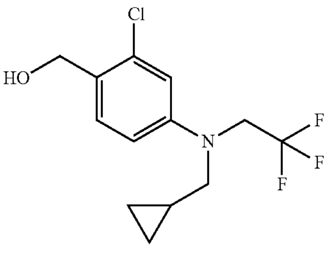 [SMILES: OCc1ccc(N(CC2CC2)CC(F)(F)F)cc1Cl]

Synthesis of methyl 2-chloro-4-fluorobenzoate

According to the method of Preparation Example 6-1, a title compound (4.37 g) was obtained from 2-chloro-4-fluorobenzoic acid (4.00 g).

Synthesis of methyl 2-chloro-4-(cyclopropylmethylamino)benzoate

Cyclopropylmethylamine (1.51 g) and potassium carbonate (1.46 g) were added to a solution of methyl 2-chloro-4-fluorobenzoate (1.00 g). The reaction mixture was stirred at room temperature for 6 hours and then heated with stirring at 100° C. for 6 hours under a microwave reactor. The reaction mixture was diluted with water and extracted with ethyl acetate. The organic layer was washed with brine and dried over anhydrous sodium sulfate. The filtrate was concentrated under reduced pressure and the residue was purified by silica gel column chromatography to obtain the title compound (1.23 g).

ESI-MS; m/z 240 [$M^+$+H].

Synthesis of methyl 2-chloro-4-[cyclopropylmethyl (2,2,2-trifluoroacetyl)amino]benzoate Trifluoroacetic anhydride (1.18 ml) was added to a solution of methyl 2-chloro-4-(cyclopropylmethylamino)benzoate (1.00 g) and pyridine (686 μl) in dichloromethane (40 ml). The reaction mixture was stirred at room temperature for 1 hour. The mixture was concentrated under reduced pressure and the residue was purified by silica gel column chromatography to obtain the title compound (1.42 g).

Synthesis of {2-chloro-4-[cyclopropylmethyl(2,2,2-trifluoroethyl)amino]phenyl}methanol Borane-THF complex (1.0M solution in THF, 13.7 ml) was added under ice-cooling to a solution of methyl 2-chloro-4-[cyclopropylmethyl(2,2,2-trifluoroacetyl)amino]benzoate (500 mg) in dichloromethane (10 ml). The reaction mixture was then refluxed overnight. After cooling to room temperature, the mixture was diluted with water and extracted with ethyl acetate. The organic layer was washed with brine and dried over anhydrous sodium sulfate.

The filtrate was concentrated under reduced pressure and the residue was purified by silica gel column chromatography to obtain the title compound (257 mg).

ESI-MS; m/z 294 $[M^{+}+H]$.

The compound of Preparation Example 6-24 was obtained according to the method of Preparation Example 6-23 (Table 19).

TABLE 19

| Preparation Example No. | Structural formula |
|---|---|
| 6-24 | 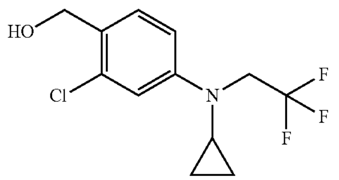 [SMILES: OCc1ccc(N(CC(F)(F)F)C2CC2)cc1Cl] |

Preparation Example 6-25

Synthesis of [5-(1-fluorocyclopropyl)-2-methoxyphenyl]methanol

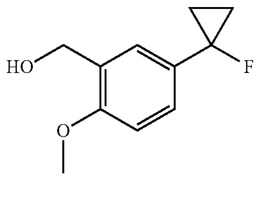

Synthesis of 1-(3-bromo-4-methoxyphenyl)cyclopropanol

Ethylmagnesium bromide (3M solution in diethyl ether, 54.4 ml) was added at room temperature to a solution of methyl 3-bromo-4-methoxybenzoate (CAS No. 35450-37-4, 10 g) and titanium (IV) isopropoxide (23.9 ml) in THF (100 ml). The reaction mixture was stirred at room temperature overnight. Ethyl acetate and water were added to the reaction mixture and the precipitate was removed through Celite. The organic layer was separated, washed with brine and dried over anhydrous magnesium sulfate. The filtrate was concentrated under reduced pressure and the residue was purified by silica gel column chromatography to obtain the title compound (7.77 g).

Synthesis of [1-(3-bromo-4-methoxyphenyl)cyclopropyloxy]trimethylsilane

Trimethylsilyl chloride (6.54 ml) was added to a solution of 1-(3-bromo-4-methoxyphenyl)cyclopropanol (5.0 g) and triethylamine (8.61 ml) in THF (100 ml). The reaction mixture was stirred at room temperature for 3 days. The reaction mixture was diluted with water and extracted with ethyl acetate. The organic layer was washed with brine and dried over anhydrous magnesium sulfate. The filtrate was concentrated under reduced pressure and the residue was purified by silica gel column chromatography to obtain the title compound (3.84 g).

Synthesis of 2-bromo-4-(1-fluorocyclopropyl)-1-methoxybenzene

Diethylaminosulfur trifluoride (2.4 ml) was added to a solution of [1-(3-bromo-4-methoxyphenyl)cyclopropyloxy]trimethylsilane (3.84 g) in dichloromethane (68 ml). The reaction mixture was stirred at room temperature for 2.5 hours. The reaction mixture was diluted with water and extracted with ethyl acetate. The organic layer was washed with brine and dried over anhydrous magnesium sulfate. The filtrate was concentrated under reduced pressure and the residue was purified by silica gel column chromatography to obtain the title compound (1.88 g).

Synthesis of 5-(1-fluorocyclopropyl)-2-methoxybenzaldehyde n-Butyllithium (2.7M solution in hexane, 3.42 ml) was added at −78° C. to a solution of 2-bromo-4-(1-fluorocyclopropyl)-1-methoxybenzene (1.88 g) in THF (62 ml), followed by addition of a solution of DMF (650 μl) in THF. After the reaction mixture was stirred at −78° C. for 30 minutes, a saturated aqueous solution of sodium bicarbonate was added to the reaction mixture and extracted with ethyl acetate. The organic layer was washed with brine and dried over anhydrous magnesium sulfate. The filtrate was concentrated under reduced pressure and the residue was purified by silica gel column chromatography to obtain the title compound (1.00 g).

Synthesis of [5-(1-fluorocyclopropyl)-2-methoxyphenyl]methanol

Sodium borohydride (194 mg) was added under ice-cooling to a solution of 541-fluorocyclopropyl)-2-methoxybenzaldehyde (500 mg) in methanol (10 ml). After the reaction mixture was stirred at room temperature for 2 hours, a saturated aqueous solution of sodium bicarbonate was added to the reaction mixture and extracted with ethyl acetate. The organic layer was washed with brine and dried over anhydrous magnesium sulfate. The filtrate was concentrated under reduced pressure and the residue was purified by silica gel column chromatography to obtain the title compound (400 mg).

Preparation Example 7-1

Synthesis of (5-bromo-2-chlorobenzyloxy)-tert-butylmethylsilane

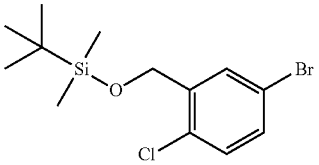 [SMILES: CC(C)(C)[Si](C)(C)OCc1cc(Br)ccc1Cl]

Synthesis of methyl 5-bromo-2-chlorobenzoate

According to the method of Preparation Example 6-1, a title compound (9.23 g) was obtained from 5-bromo-2-chlorobenzoic acid (10.0 g).

Synthesis of (5-bromo-2-chlorophenyl)methanol

A solution of methyl 5-bromo-2-chlorobenzoate (9.23 g) in THF (50 ml) was added dropwise under ice-cooling to a suspension of lithium aluminum hydride (1.42 g) in THF (100 ml). After the completion of addition, the reaction mixture was stirred at room temperature for 45 minutes. Water (1.4 ml), 5N sodium hydroxide solution (1.4 ml) and water (4.2 ml) were sequentially added under ice-cooling to the reaction mixture. The precipitate was removed through Celite and the filtrate was concentrated under reduced pressure to obtain a title compound (7.56 g).

Synthesis of (5-bromo-2-chlorobenzyloxy)-tert-butyldimethylsilane

Imidazole (5.22 g) and tert-butyldimethylsilyl chloride (8.64 g) were added to a solution of (5-bromo-2-chlorophenyl)methanol (8.47 g) in DMF (80 ml). The reaction mixture was stirred at room temperature overnight. The mixture was diluted with ethyl acetate and washed twice with water. The aqueous layer was again extracted with ethyl acetate. The combined organic layer was washed with brine and dried over anhydrous magnesium sulfate. The filtrate was concentrated under reduced pressure and the residue was purified by silica gel column chromatography to obtain the title compound (12.6 g).

The compounds of Preparation Examples 7-2 to 7-4 were obtained according to the method of Preparation Example 7-1 (Table 20).

TABLE 20

| Preparation Example No. | Structural formula |
|---|---|
| 7-2 | 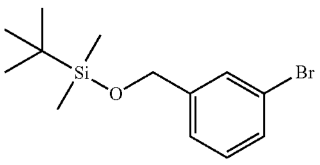 [SMILES: CC(C)(C)[Si](C)(C)OCc1cccc(Br)c1] |

TABLE 20-continued

| Preparation Example No. | Structural formula |
|---|---|
| 7-3 | 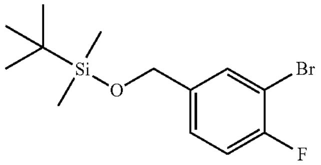 [SMILES: CC(C)(C)[Si](C)(C)OCc1ccc(F)c(Br)c1] |
| 7-4 | 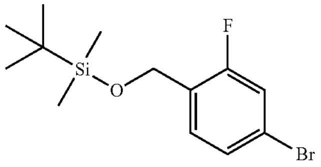 [SMILES: CC(C)(C)[Si](C)(C)OCc1ccc(Br)cc1F] |

Preparation Example 8-1

Synthesis of [(2-fluoro-5-piperidin-1-yl)phenyl]acetonitrile

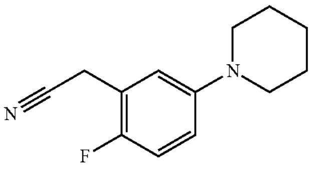 [SMILES: N#CCc1cc(N2CCCCC2)ccc1F]

Thionyl chloride (1.05 ml) was added dropwise to a solution of (2-fluoro-5-piperidin-1-yl)phenylmethanol (1.0 g) obtained in Preparation Example 6-1 in toluene (10 ml). The reaction mixture was stirred at room temperature for 8.5 hours. The reaction mixture was diluted with tert-butyl methyl ether and washed with 1N sodium hydroxide solution and saturated aqueous solution of sodium bicarbonate. The organic layer was washed with brine, dried over anhydrous sodium sulfate and then the filtrate was concentrated under reduced pressure. Potassium cyanide (623 mg) was added to a solution of the obtained residue in DMF (10 ml). After stirring at room temperature for 12 hours, tert-butyl methyl ether and water were added to the reaction mixture. The organic layer was separated, washed with water and brine, and dried over anhydrous sodium sulfate. The filtrate was concentrated under reduced pressure and the residue was purified by silica gel column chromatography to obtain the title compound (908 mg).

ESI-MS; m/z 219 [$M^{+}$+H].

The compounds of Preparation Examples 8-2 to 8-19 were obtained according to the method of Preparation Example 8-1 (Table 21).

TABLE 21
| Preparation Example No. | Structural formula |
|---|---|
| 8-2 | 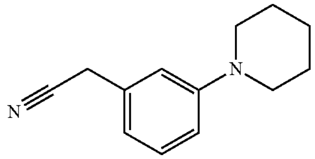 [SMILES: N#CCc1cccc(N2CCCCC2)c1] |
| 8-3 | 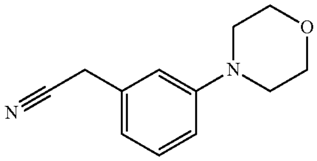 [SMILES: N#CCc1cccc(N2CCOCC2)c1] |
| 8-4 | 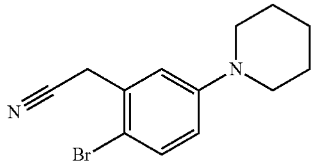 [SMILES: N#CCc1cc(N2CCCCC2)ccc1Br] |
| 8-5 | 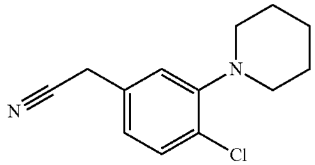 [SMILES: N#CCc1ccc(Cl)c(N2CCCCC2)c1] |
| 8-6 | 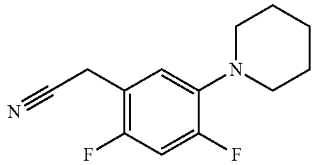 [SMILES: N#CCc1cc(N2CCCCC2)c(F)cc1F] |
| 8-7 | 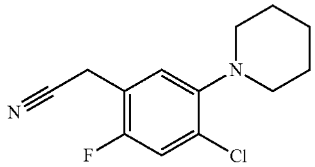 [SMILES: N#CCc1cc(N2CCCCC2)c(Cl)cc1F] |
| 8-8 | 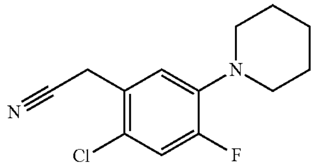 [SMILES: N#CCc1cc(N2CCCCC2)c(F)cc1Cl] |
| 8-9 | 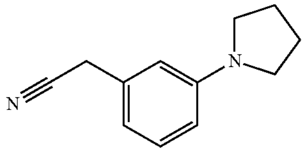 [SMILES: N#CCc1cccc(N2CCCC2)c1] |
| 8-10 | 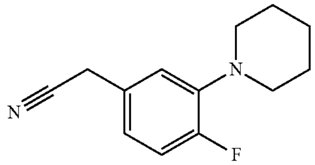 [SMILES: N#CCc1ccc(F)c(N2CCCCC2)c1] |
TABLE 21-continued
| Preparation Example No. | Structural formula |
|---|---|
| 8-11 | 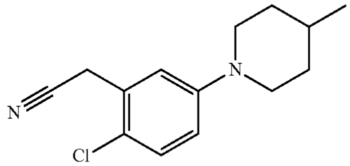 [SMILES: CC1CCN(c2ccc(Cl)c(CC#N)c2)CC1] |
| 8-12 | 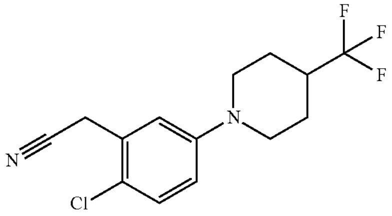 [SMILES: N#CCc1cc(N2CCC(C(F)(F)F)CC2)ccc1Cl] |
| 8-13 | 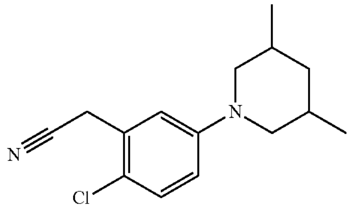 [SMILES: CC1CC(C)CN(c2ccc(Cl)c(CC#N)c2)C1] |
| 8-14 | 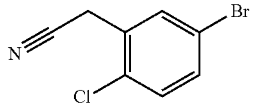 [SMILES: N#CCc1cc(Br)ccc1Cl] |
| 8-15 | 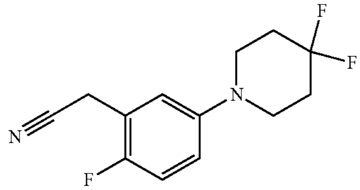 [SMILES: N#CCc1cc(N2CCC(F)(F)CC2)ccc1F] |
| 8-16 | 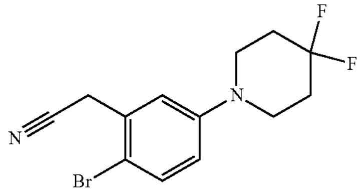 [SMILES: N#CCc1cc(N2CCC(F)(F)CC2)ccc1Br] |
| 8-17 | 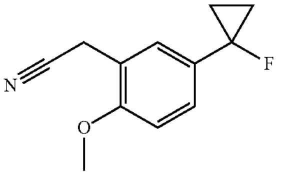 |
| 8-18 | 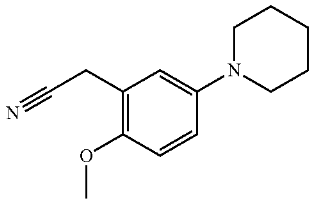 [SMILES: COc1ccc(N2CCCCC2)cc1CC#N] |

TABLE 21-continued

| Preparation Example No. | Structural formula |
| --- | --- |
| 8-19 | 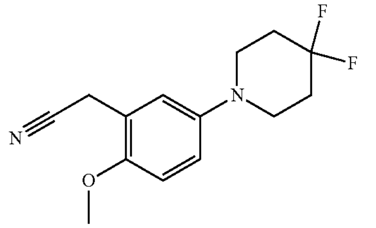 [SMILES: COc1ccc(N2CCC(F)(F)CC2)cc1CC#N] |

Preparation Example 8-20

Synthesis of (3-bromo-4-piperidin-1-yl)phenylacetonitrile

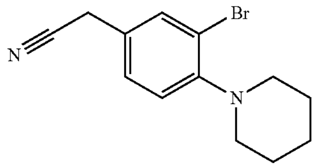 [SMILES: N#CCc1ccc(N2CCCCC2)c(Br)c1]

Synthesis of (3-bromo-4-piperidin-1-yl)benzaldehyde

Manganese dioxide (1.26 g) was added to a solution of (3-bromo-4-piperidin-1-yl)phenylmethanol (488 mg) obtained in Preparation Example 6-20 in chloroform (20 ml). The reaction mixture was heated with stirring at 90° C. for 2 hours. The reaction mixture was filtered by filter paper, then through Celite and the filtrate was concentrated under reduced pressure. The residue was purified by silica gel column chromatography to obtain the title compound (386 mg).

Synthesis of [(3-bromo-4-piperidin-1-yl)phenyl]acetonitrile

A solution of p-toluenesulfonyl isocyanide (309 ml) in 1,2-dimethoxyethane (8 ml) was added to a suspension of potassium tert-butoxide (355 mg) in 1,2-dimethoxyethane (8 ml) at −30° C. After stirring for 10 minutes, a solution of (3-bromo-4-piperidin-1-yl)benzaldehyde (386 mg) in 1,2-dimethoxyethane (8 ml) was added to the mixture. The mixture was stirred at −30° C. for 1.5 hours. Ethanol (5 nil) was added to the reaction mixture and the mixture was refluxed for 20 minutes. The mixture was cooled to room temperature, followed by addition of water and extracted with ethyl acetate. The organic layer was washed with brine and dried over anhydrous sodium sulfate. The filtrate was concentrated under reduced pressure and the residue was purified by silica gel column chromatography to obtain the title compound (255 mg).

ESI-MS; m/z 279,281 $[M^{+}+H]$.

The compounds of Preparation Examples 8-21 to 8-26 were obtained according to the method of Preparation Example 8-20 (Table 22).

TABLE 22

| Preparation Example No. | Structural formula |
| --- | --- |
| 8-21 | 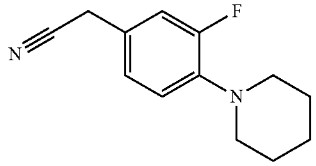 [SMILES: N#CCc1ccc(N2CCCCC2)c(F)c1] |
| 8-22 | 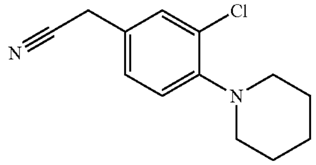 [SMILES: N#CCc1ccc(N2CCCCC2)c(Cl)c1] |
| 8-23 | 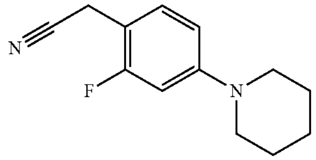 [SMILES: N#CCc1ccc(N2CCCCC2)cc1F] |
| 8-24 | 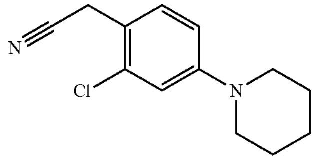 [SMILES: N#CCc1ccc(N2CCCCC2)cc1Cl] |
| 8-25 | 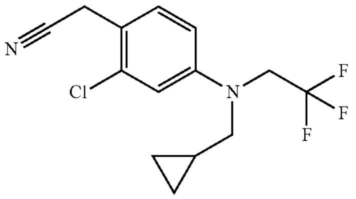 [SMILES: N#CCc1ccc(N(CC2CC2)CC(F)(F)F)cc1Cl] |
| 8-26 | 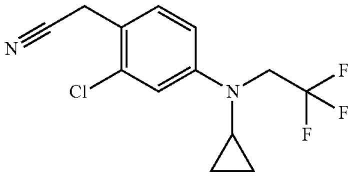 [SMILES: N#CCc1ccc(N(CC(F)(F)F)C2CC2)cc1Cl] |

Preparation Example 3-51

Synthesis of ethyl [5-chloro-2-(2-fluoro-5-piperidin-1-yl)phenyl]pentaneimidate hydrochloride

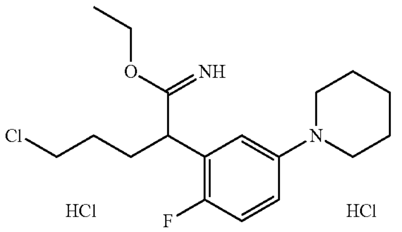 [SMILES: CCOC(=N)C(CCCCl)c1cc(N2CCCCC2)ccc1F ; Cl ; Cl]

Synthesis of ethyl [5-chloro-2-(2-fluoro-5-piperidin-1-yl)phenyl]pentaneimidate hydrochloride According to the method of Preparation Example 3-1, a title compound (1.54 g) was obtained from [(2-fluoro-5-piperidin-1-yl)phenyl]acetonitrile (908 mg) obtained in Preparation Example 8-1.

The compounds of Preparation Examples 3-52 to 3-84 were obtained according to the method of Preparation Example 3-51 (Table 23).

TABLE 23

| Preparation Example No. | Structural formula |
|---|---|
| 3-52 | 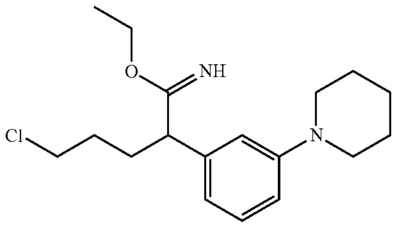 [SMILES: CCOC(=N)C(CCCCl)c1cccc(N2CCCCC2)c1] |
| 3-53 | 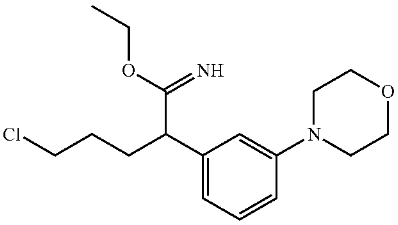 [SMILES: CCOC(=N)C(CCCCl)c1cccc(N2CCOCC2)c1] |
| 3-54 | 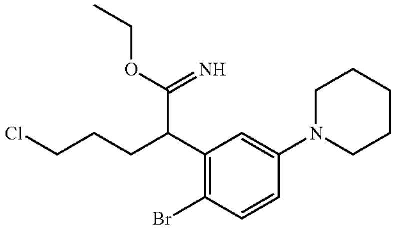 [SMILES: CCOC(=N)C(CCCCl)c1cc(N2CCCCC2)ccc1Br] |
| 3-55 | 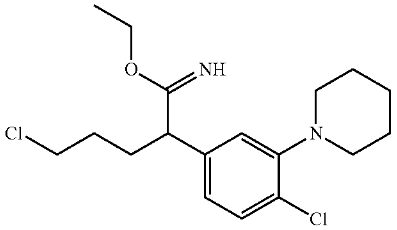 [SMILES: CCOC(=N)C(CCCCl)c1ccc(Cl)c(N2CCCCC2)c1] |
| 3-56 | 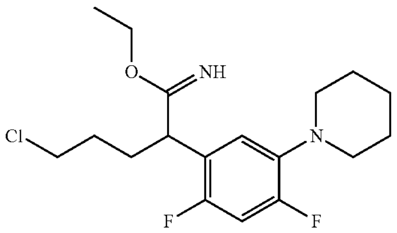 [SMILES: CCOC(=N)C(CCCCl)c1cc(N2CCCCC2)c(F)cc1F] |

TABLE 23-continued

| Preparation Example No. | Structural formula |
|---|---|
| 3-57 | 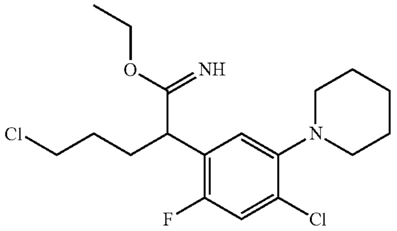 |
| 3-58 | 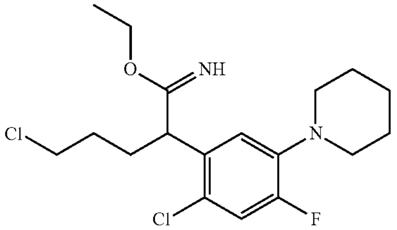 [SMILES: CCOC(=N)C(CCCCl)c1cc(N2CCCCC2)c(F)cc1Cl] |
| 3-59 | 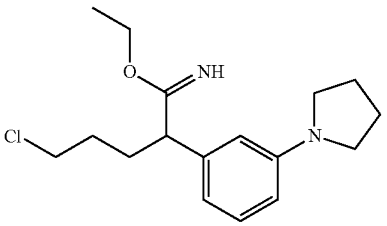 [SMILES: CCOC(=N)C(CCCCl)c1cccc(N2CCCC2)c1] |
| 3-60 | 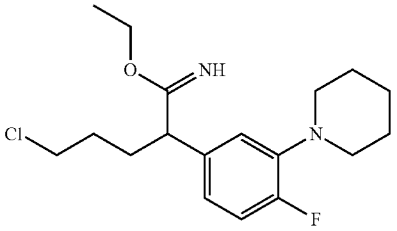 [SMILES: CCOC(=N)C(CCCCl)c1ccc(F)c(N2CCCCC2)c1] |
| 3-61 | 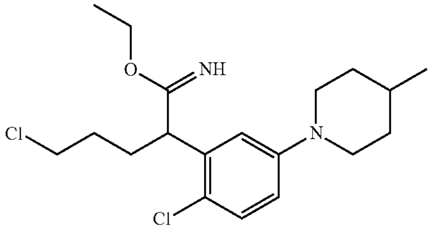 [SMILES: CCOC(=N)C(CCCCl)c1cc(N2CCC(C)CC2)ccc1Cl] |
| 3-62 | 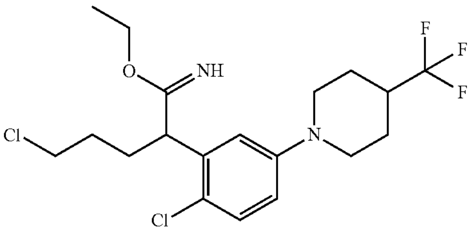 [SMILES: CCOC(=N)C(CCCCl)c1cc(N2CCC(C(F)(F)F)CC2)ccc1Cl] |

TABLE 23-continued
| Preparation Example No. | Structural formula |
|---|---|
| 3-63 | 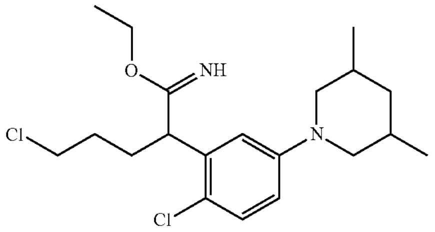 [SMILES: CCOC(=N)C(CCCCl)c1cc(N2CC(C)CC(C)C2)ccc1Cl] |
| 3-64 | 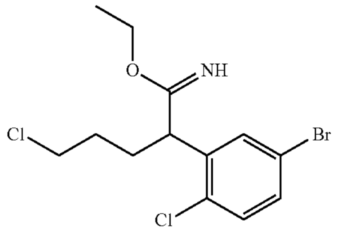 [SMILES: CCOC(=N)C(CCCCl)c1cc(Br)ccc1Cl] |
| 3-65 | 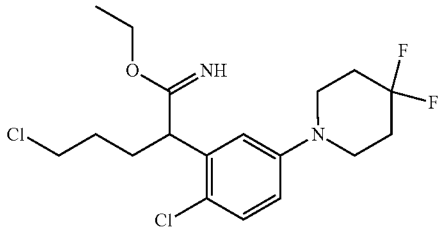 [SMILES: CCOC(=N)C(CCCCl)c1cc(N2CCC(F)(F)CC2)ccc1Cl] |
| 3-66 | 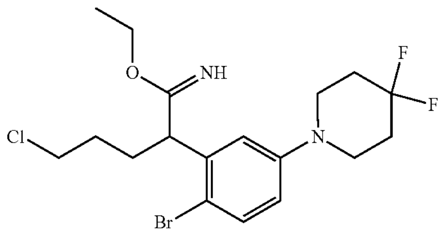 [SMILES: CCOC(=N)C(CCCCl)c1cc(N2CCC(F)(F)CC2)ccc1Br] |
| 3-67 | 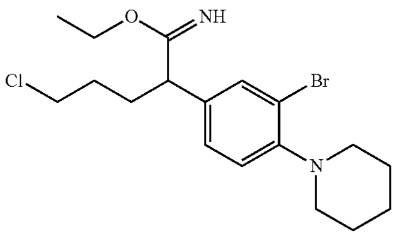 [SMILES: CCOC(=N)C(CCCCl)c1ccc(N2CCCCC2)c(Br)c1] |
| 3-68 | 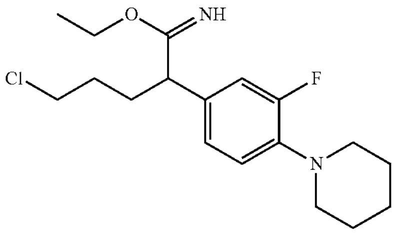 [SMILES: CCOC(=N)C(CCCCl)c1ccc(N2CCCCC2)c(F)c1] |
TABLE 23-continued
| Preparation Example No. | Structural formula |
|---|---|
| 3-69 | 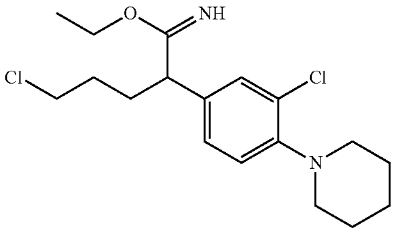 [SMILES: CCOC(=N)C(CCCCl)c1ccc(N2CCCCC2)c(Cl)c1] |
| 3-70 | 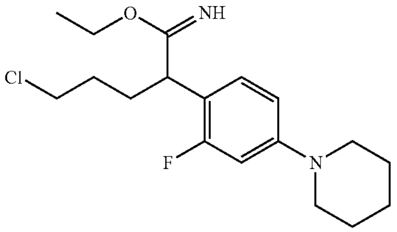 [SMILES: CCOC(=N)C(CCCCl)c1ccc(N2CCCCC2)cc1F] |
| 3-71 | 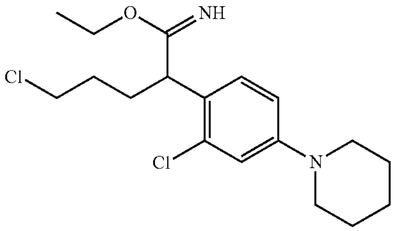 [SMILES: CCOC(=N)C(CCCCl)c1ccc(N2CCCCC2)cc1Cl] |
| 3-72 | 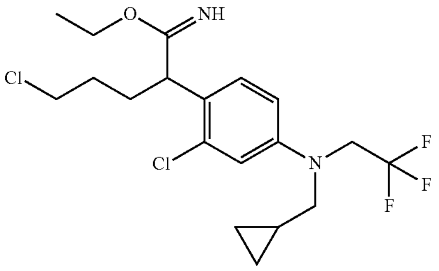 [SMILES: CCOC(=N)C(CCCCl)c1ccc(N(CC2CC2)CC(F)(F)F)cc1Cl] |
| 3-73 | 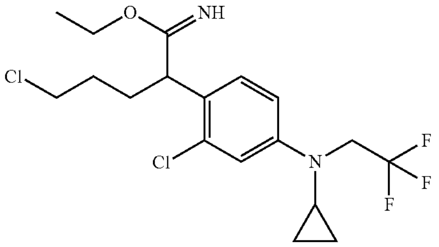 [SMILES: CCOC(=N)C(CCCCl)c1ccc(N(CC(F)(F)F)C2CC2)cc1Cl] |
| 3-74 | 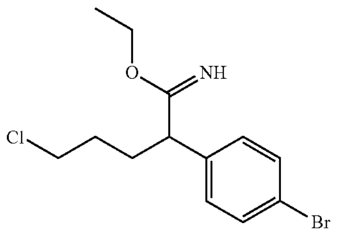 [SMILES: CCOC(=N)C(CCCCl)c1ccc(Br)cc1] |

TABLE 23-continued
| Preparation Example No. | Structural formula |
| --- | --- |
| 3-75 | 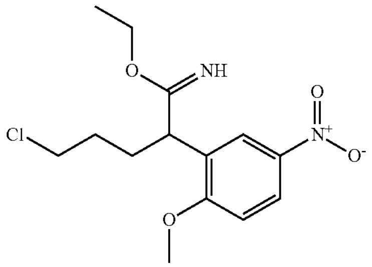 [SMILES: CCOC(=N)C(CCCCl)c1cc([N+](=O)[O-])ccc1OC] |
| 3-76 | 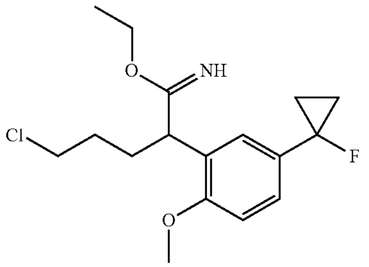 [SMILES: CCOC(=N)C(CCCCl)c1cc(C2(F)CC2)ccc1OC] |
| 3-77 | 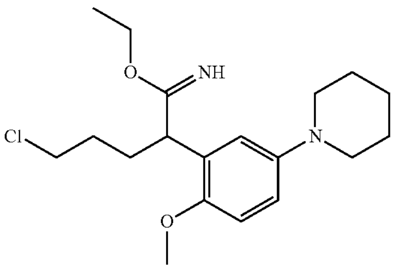 [SMILES: CCOC(=N)C(CCCCl)c1cc(N2CCCCC2)ccc1OC] |
| 3-78 | 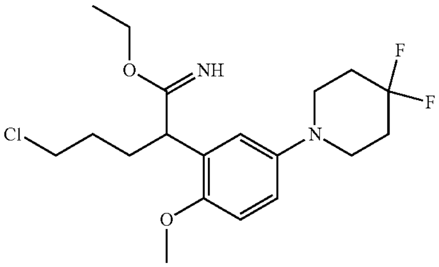 [SMILES: CCOC(=N)C(CCCCl)c1cc(N2CCC(F)(F)CC2)ccc1OC] |
| 3-79 | 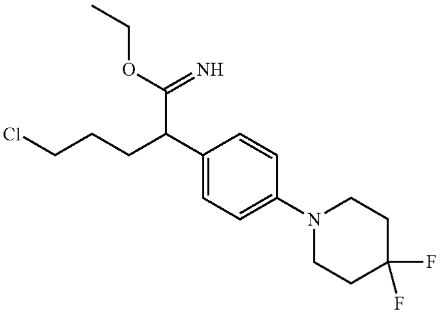 [SMILES: CCOC(=N)C(CCCCl)c1ccc(N2CCC(F)(F)CC2)cc1] |
| 3-80 | 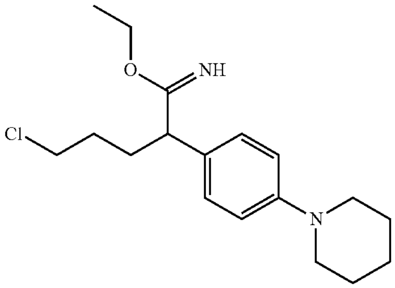 [SMILES: CCOC(=N)C(CCCCl)c1ccc(N2CCCCC2)cc1] |
| 3-81 | 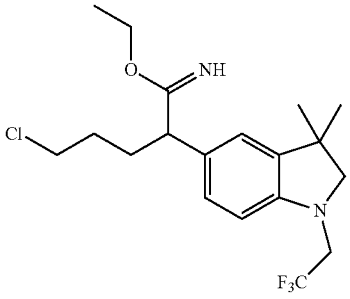 [SMILES: CCOC(=N)C(CCCCl)c1ccc2c(c1)C(C)(C)CN2CC(F)(F)F] |
| 3-82 | 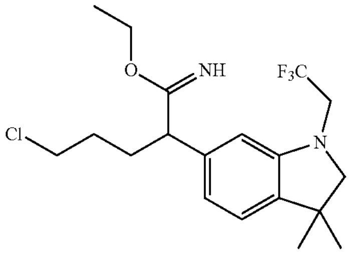 [SMILES: CCOC(=N)C(CCCCl)c1ccc2c(c1)N(CC(F)(F)F)CC2(C)C] |
| 3-83 | 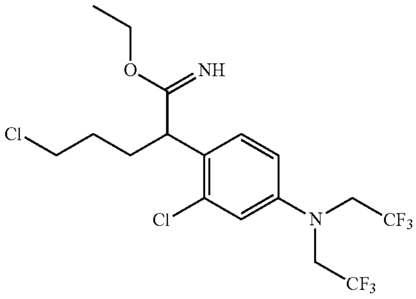 [SMILES: CCOC(=N)C(CCCCl)c1ccc(N(CC(F)(F)F)CC(F)(F)F)cc1Cl] |
| 3-84 | 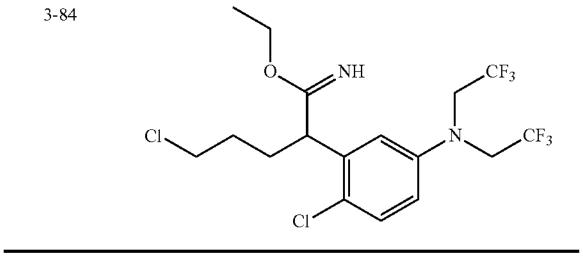 |

Preparation Example 3-85

Synthesis of ethyl 5-chloro-2-{2-chloro-5-[cyclopropylmethyl(2,2,2-trifluoroethyl)amino]phenyl}pentanimidate hydrochloride

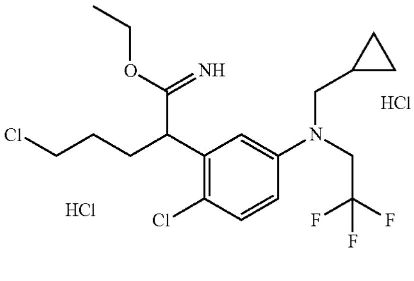 [SMILES: CCOC(=N)C(CCCCl)c1cc(N(CC2CC2)CC(F)(F)F)ccc1Cl ; Cl ; Cl]

Synthesis of ethyl 5-amino-2-chlorobenzoate

According to the method of Preparation Example 6-1, title compound (85.9 g) was obtained from 5-amino-2-chlorobenzoic acid (5 g).

ESI-MS; m/z 200 [$M^+$+H]

Syntheses of ethyl 2-chloro-5-(cyclopropylmethylamino benzoate and ethyl 5-[bis(cyclopropylmethyl)amino]-2-chlorobenzoate To the mixture of ethyl 5-amino-2-chlorobenzoate, cyclopropanecarboxaldehyde (458 μl) and acetic acid (1.43 ml) dissolved in methanol (20 ml), α-picoline borane (804 mg) was added at ice cool temperature, and was stirred under nitrogen atmosphere overnight at room temperature. After the reaction mixture was concentrated under reduced pressure, sodium hydrogencarbonate aqueous solution was added to the residue, and the mixture was extracted with ethyl acetate. The organic layer was washed with brine, dried over anhydrous sodium sulfate and concentrated under reduced pressure. The residue was purified by silica gel chromatography, and ethyl 2-chloro-5-(cyclopropylmethylamino)benzoate (881 mg) and ethyl 5-[bis(cyclopropylmethyl)amino]-2-chlorobenzoate (423 mg) were obtained.

The property value of ethyl 2-chloro-5-(cyclopropylmethylamino)benzoate is as follows.

ESI-MS; m/z 254 [$M^+$+H]

The property value of ethyl 5-[bis(cyclopropylmethyl)amino]-2-chlorobenzoate is as follows.

ESI-MS; m/z 308 [$M^+$+H]

Synthesis of ethyl 5-chloro-2-{2-chloro-5-[cyclopropylmethyl-(2,2,2-trifluoroethyl)amino]phenyl}pentanimidate hydrochloride According to the method of Preparation Example 6-23 and Preparation Example 3-51, the title compound (501 mg) was obtained from ethyl 2-chloro-5-cyclopropylmethylamino)benzoate (881 mg)

ESI-MS; m/z 425 [$M^+$+H-HCl]

Preparation Example 3-86

Synthesis of ethyl 2-{5-[bis(cyclopropylmethyl)amino]-2-chlorophenyl}-5-chloropentanimidate hydrochloride

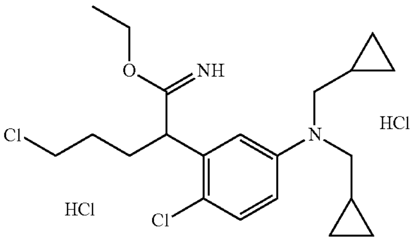 [SMILES: CCOC(=N)C(CCCCl)c1cc(N(CC2CC2)CC2CC2)ccc1Cl ; Cl ; Cl]

According to the method of Preparation Example 3-51, the title compound (578 mg) was obtained from ethyl 5-[bis(cyclopropylmethyl)amino]-2-chlorobenzoate (423 mg).

ESI-MS; m/z 397 [$M^+$+H-HCl]

Example 186-233

According to the methods of Example 42 and 43, the compounds of Example 186 to Example 233 were obtained from imidate hydrochlorides obtained in Preparation Example 3-21 to Preparation Example 3-44, and 6-methoxy-5-(4-methyl-1H-imidazol-1-yl)pyridine-2-carboxylic acid hydrazide obtained in Preparation Example 1-6. (Table 24)

TABLE 24

| Example No. | Structural formula | ESI mass |
| --- | --- | --- |
| Example 186 | 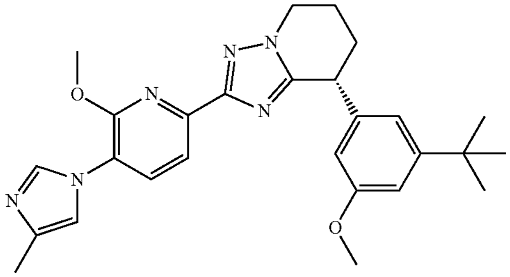 [SMILES: COc1cc([C@H]2CCCn3nc(-c4ccc(-n5cnc(C)c5)c(OC)n4)nc32)cc(C(C)(C)C)c1] | ESI-MS; m/z 473 [$M^+$ + H]. |

TABLE 24-continued
| Example No. | Structural formula | ESI mass |
| --- | --- | --- |
| Example 187 | 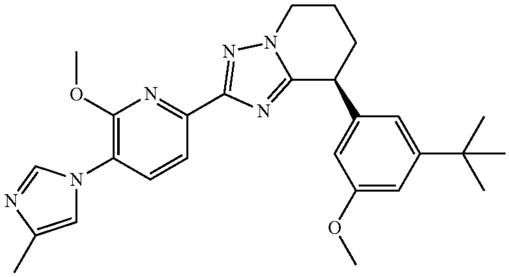 [SMILES: COc1cc([C@@H]2CCCn3nc(-c4ccc(-n5cnc(C)c5)c(OC)n4)nc32)cc(C(C)(C)C)c1] | ESI-MS; m/z 473 [$M^+$ + H]. |
| Example 188 | 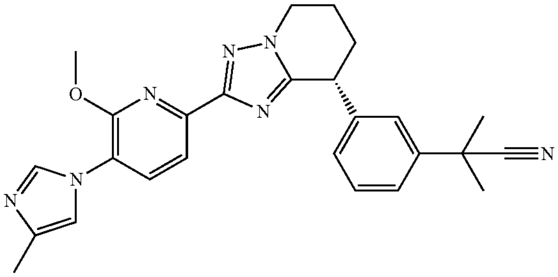 [SMILES: COc1nc(-c2nc3n(n2)CCC[C@@H]3c2cccc(C(C)(C)C#N)c2)ccc1-n1cnc(C)c1] | ESI-MS; m/z 454 [$M^+$ + H]. |
| Example 189 | 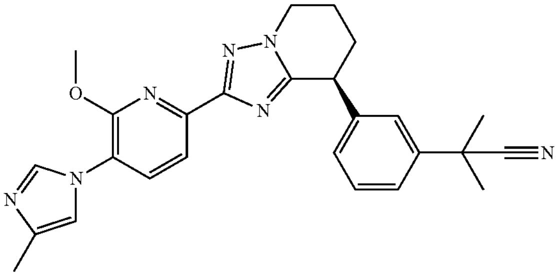 [SMILES: COc1nc(-c2nc3n(n2)CCC[C@H]3c2cccc(C(C)(C)C#N)c2)ccc1-n1cnc(C)c1] | ESI-MS; m/z 454 [$M^+$ + H]. |
| Example 190 | 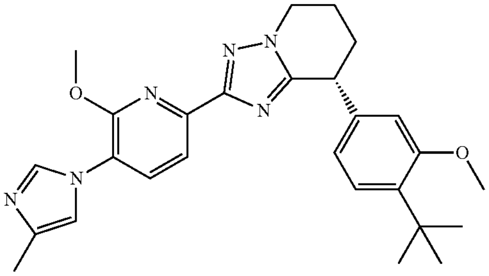 [SMILES: COc1cc([C@H]2CCCn3nc(-c4ccc(-n5cnc(C)c5)c(OC)n4)nc32)ccc1C(C)(C)C] | ESI-MS; m/z 473 [$M^+$ + H]. |
| Example 191 | 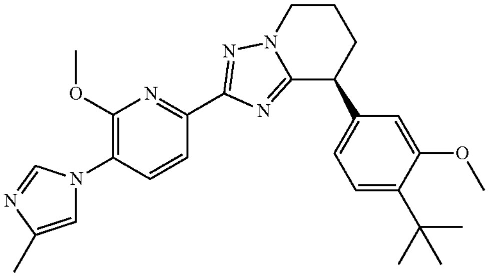 [SMILES: COc1cc([C@@H]2CCCn3nc(-c4ccc(-n5cnc(C)c5)c(OC)n4)nc32)ccc1C(C)(C)C] | ESI-MS; m/z 473 [$M^+$ + H]. |

TABLE 24-continued
| Example No. | Structural formula | ESI mass |
| --- | --- | --- |
| Example 192 | 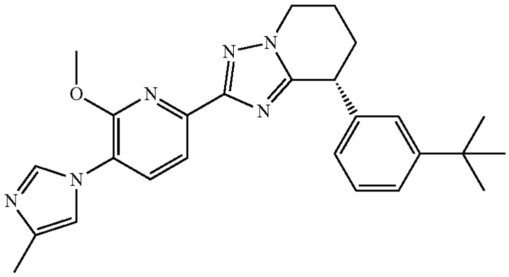 [SMILES: COc1nc(-c2nc3n(n2)CCC[C@@H]3c2cccc(C(C)(C)C)c2)ccc1-n1cnc(C)c1] | ESI-MS; m/z 443 [$M^+$ + H]. |
| Example 193 | 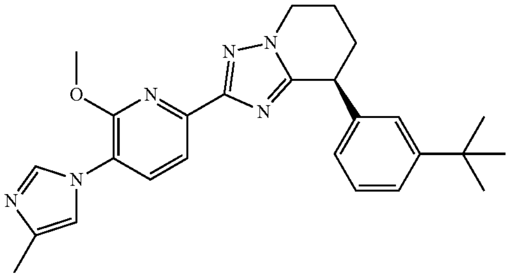 [SMILES: COc1nc(-c2nc3n(n2)CCC[C@H]3c2cccc(C(C)(C)C)c2)ccc1-n1cnc(C)c1] | ESI-MS; m/z 443 [$M^+$ + H]. |
| Example 194 | 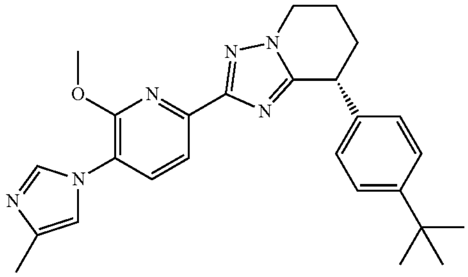 [SMILES: COc1nc(-c2nc3n(n2)CCC[C@@H]3c2ccc(C(C)(C)C)cc2)ccc1-n1cnc(C)c1] | ESI-MS; m/z 443 [$M^+$ + H]. |
| Example 195 | 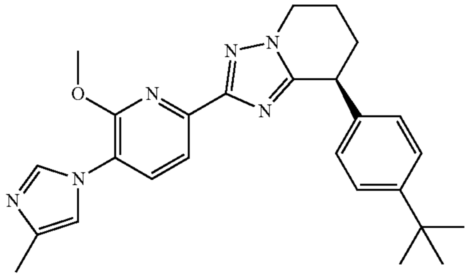 [SMILES: COc1nc(-c2nc3n(n2)CCC[C@H]3c2ccc(C(C)(C)C)cc2)ccc1-n1cnc(C)c1] | ESI-MS; m/z 443 [$M^+$ + H]. |
| Example 196 | 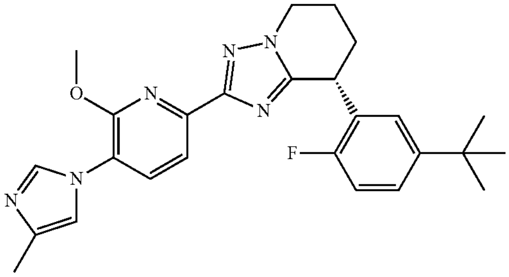 [SMILES: COc1nc(-c2nc3n(n2)CCC[C@@H]3c2cc(C(C)(C)C)ccc2F)ccc1-n1cnc(C)c1] | ESI-MS; m/z 461 [$M^+$ + H]. |

TABLE 24-continued
| Example No. | Structural formula | ESI mass |
|---|---|---|
| Example 197 | 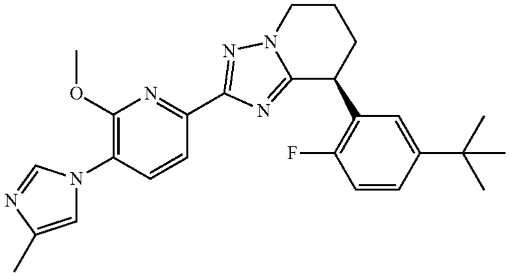 [SMILES: COc1nc(-c2nc3n(n2)CCC[C@H]3c2cc(C(C)(C)C)ccc2F)ccc1-n1cnc(C)c1] | ESI-MS; m/z 461 [$M^+$ + H]. |
| Example 198 | 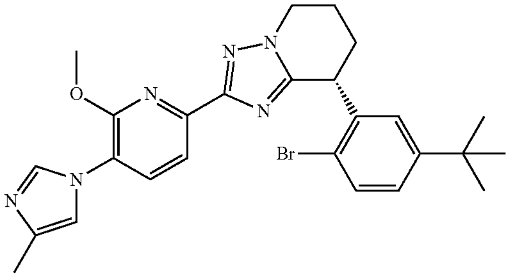 [SMILES: COc1nc(-c2nc3n(n2)CCC[C@@H]3c2cc(C(C)(C)C)ccc2Br)ccc1-n1cnc(C)c1] | ESI-MS; m/z 521 [$M^+$ + H]. |
| Example 199 | 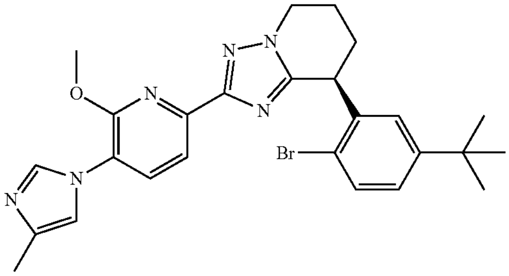 [SMILES: COc1nc(-c2nc3n(n2)CCC[C@H]3c2cc(C(C)(C)C)ccc2Br)ccc1-n1cnc(C)c1] | ESI-MS; m/z 523 [$M^+$ + H]. |
| Example 200 | 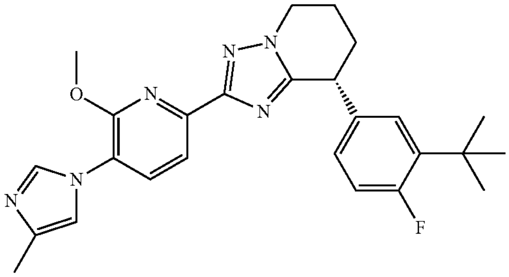 [SMILES: COc1nc(-c2nc3n(n2)CCC[C@@H]3c2ccc(F)c(C(C)(C)C)c2)ccc1-n1cnc(C)c1] | ESI-MS; m/z 461 [$M^+$ + H]. |
| Example 201 | 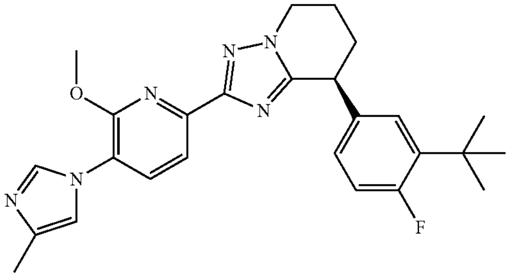 [SMILES: COc1nc(-c2nc3n(n2)CCC[C@H]3c2ccc(F)c(C(C)(C)C)c2)ccc1-n1cnc(C)c1] | ESI-MS; m/z 461 [$M^+$ + H]. |

TABLE 24-continued
| Example No. | Structural formula | ESI mass |
| --- | --- | --- |
| Example 202 | 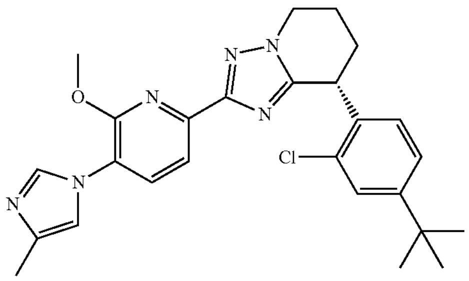 [SMILES: COc1nc(-c2nc3n(n2)CCC[C@@H]3c2ccc(C(C)(C)C)cc2Cl)ccc1-n1cnc(C)c1] | ESI-MS; m/z 477 [$M^+$ + H]. |
| Example 203 | 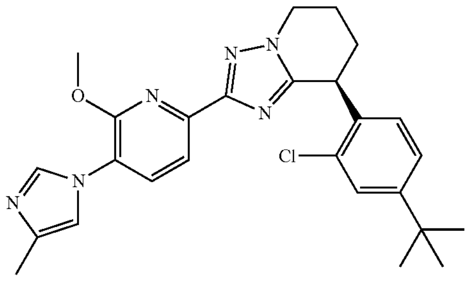 [SMILES: COc1nc(-c2nc3n(n2)CCC[C@H]3c2ccc(C(C)(C)C)cc2Cl)ccc1-n1cnc(C)c1] | ESI-MS; m/z 477 [$M^+$ + H]. |
| Example 204 | 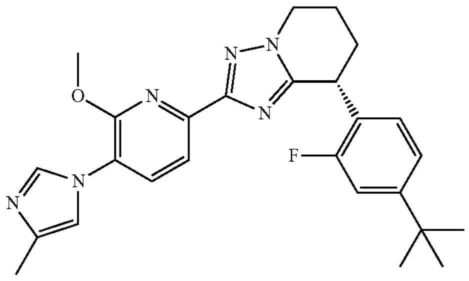 [SMILES: COc1nc(-c2nc3n(n2)CCC[C@@H]3c2ccc(C(C)(C)C)cc2F)ccc1-n1cnc(C)c1] | ESI-MS; m/z 461 [$M^+$ + H]. |
| Example 205 | 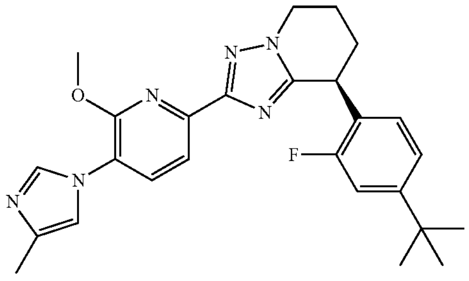 [SMILES: COc1nc(-c2nc3n(n2)CCC[C@H]3c2ccc(C(C)(C)C)cc2F)ccc1-n1cnc(C)c1] | ESI-MS; m/z 461 [$M^+$ + H]. |
| Example 206 | 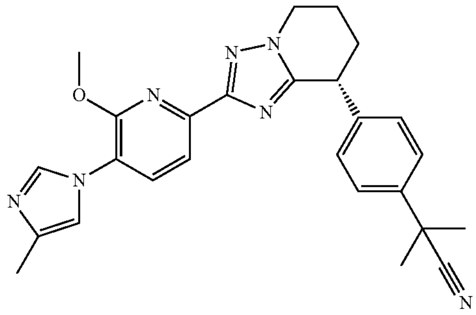 [SMILES: COc1nc(-c2nc3n(n2)CCC[C@@H]3c2ccc(C(C)(C)C#N)cc2)ccc1-n1cnc(C)c1] | ESI-MS; m/z 454 [$M^+$ + H]. |

TABLE 24-continued
| Example No. | Structural formula | ESI mass |
|---|---|---|
| Example 207 | 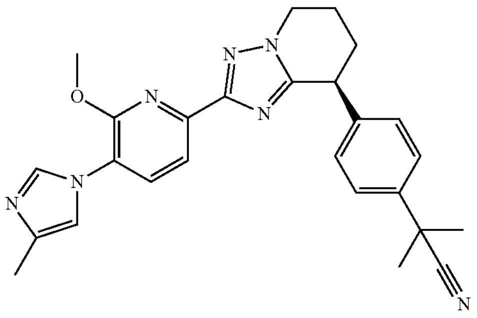 [SMILES: COc1nc(-c2nc3n(n2)CCC[C@H]3c2ccc(C(C)(C)C#N)cc2)ccc1-n1cnc(C)c1] | ESI-MS; m/z 454 [M⁺ + H]. |
| Example 208 | 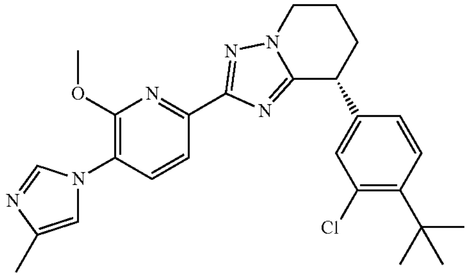 [SMILES: COc1nc(-c2nc3n(n2)CCC[C@@H]3c2ccc(C(C)(C)C)c(Cl)c2)ccc1-n1cnc(C)c1] | ESI-MS; m/z 477 [M⁺ + H]. |
| Example 209 | 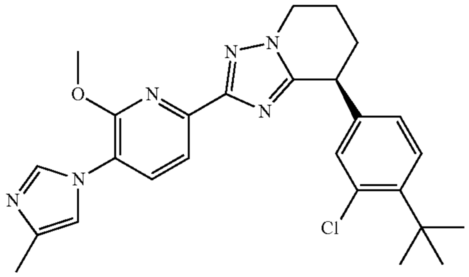 [SMILES: COc1nc(-c2nc3n(n2)CCC[C@H]3c2ccc(C(C)(C)C)c(Cl)c2)ccc1-n1cnc(C)c1] | ESI-MS; m/z 477 [M⁺ + H]. |
| Example 210 | 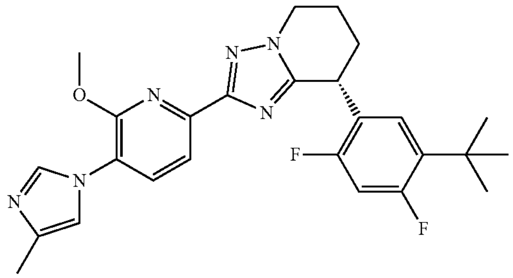 [SMILES: COc1nc(-c2nc3n(n2)CCC[C@@H]3c2cc(C(C)(C)C)c(F)cc2F)ccc1-n1cnc(C)c1] | ESI-MS; m/z 479 [M⁺ + H]. |
| Example 211 | 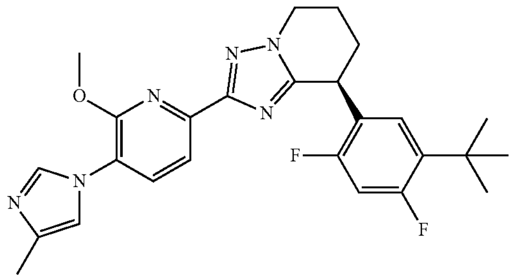 [SMILES: COc1nc(-c2nc3n(n2)CCC[C@H]3c2cc(C(C)(C)C)c(F)cc2F)ccc1-n1cnc(C)c1] | ESI-MS; m/z 479 [M⁺ + H]. |

TABLE 24-continued
| Example No. | Structural formula | ESI mass |
|---|---|---|
| Example 212 | 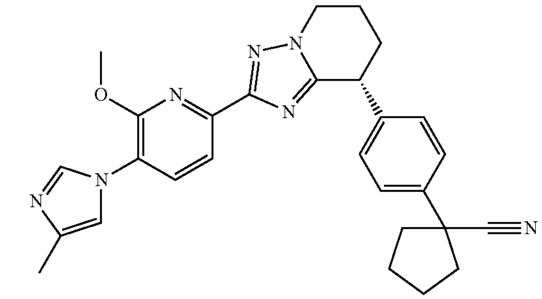 [SMILES: COc1nc(-c2nc3n(n2)CCC[C@@H]3c2ccc(C3(C#N)CCCC3)cc2)ccc1-n1cnc(C)c1] | ESI-MS; m/z 480 [$M^+$ + H]. |
| Example 213 | 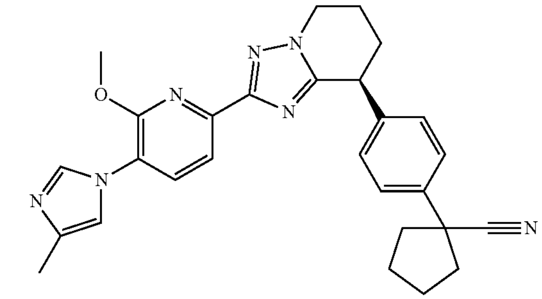 [SMILES: COc1nc(-c2nc3n(n2)CCC[C@H]3c2ccc(C3(C#N)CCCC3)cc2)ccc1-n1cnc(C)c1] | ESI-MS; m/z 480 [$M^+$ + H]. |
| Example 214 | 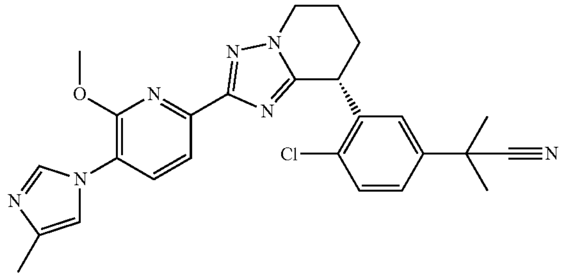 [SMILES: COc1nc(-c2nc3n(n2)CCC[C@@H]3c2cc(C(C)(C)C#N)ccc2Cl)ccc1-n1cnc(C)c1] | ESI-MS; m/z 488 [$M^+$ + H]. |
| Example 215 | 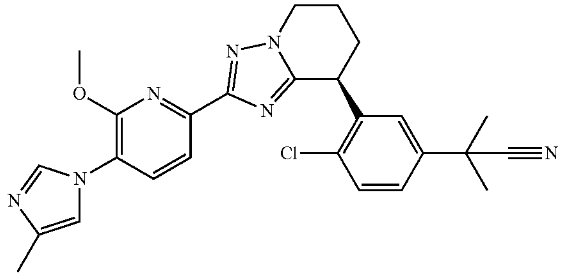 | ESI-MS; m/z 488 [$M^+$ + H]. |
| Example 216 | 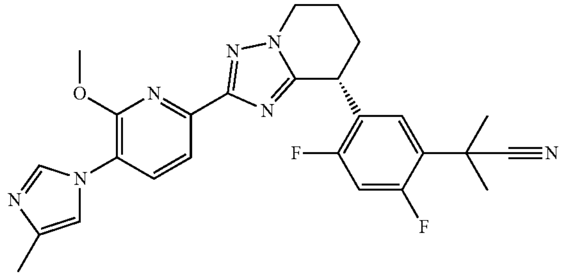 [SMILES: COc1nc(-c2nc3n(n2)CCC[C@@H]3c2cc(C(C)(C)C#N)c(F)cc2F)ccc1-n1cnc(C)c1] | ESI-MS; m/z 490 [$M^+$ + H]. |

TABLE 24-continued
| Example No. | Structural formula | ESI mass |
| --- | --- | --- |
| Example 217 | 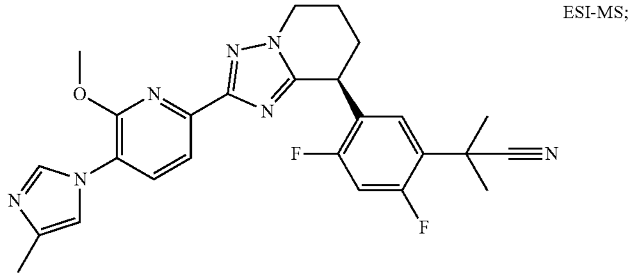 | ESI-MS; m/z 490 [M$^+$ + H]. |
| Example 218 | 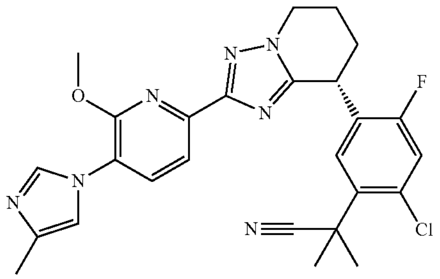 [SMILES: COc1nc(-c2nc3n(n2)CCC[C@@H]3c2cc(C(C)(C)C#N)c(Cl)cc2F)ccc1-n1cnc(C)c1] | ESI-MS; m/z 506 [M$^+$ + H]. |
| Example 219 | 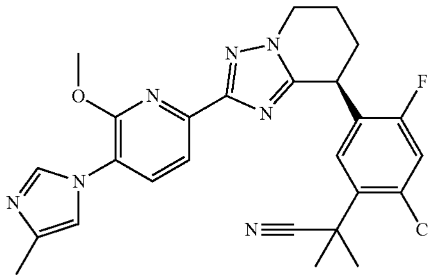 | ESI-MS; m/z 506 [M$^+$ + H]. |
| Example 220 | 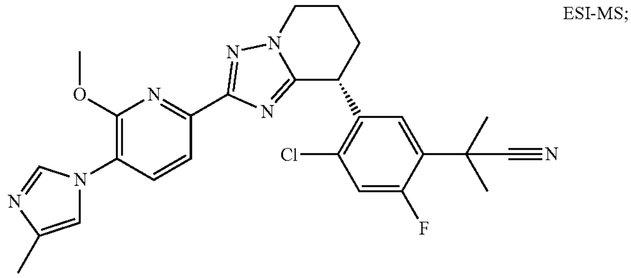 | ESI-MS; m/z 506 [M$^+$ + H]. |
| Example 221 | 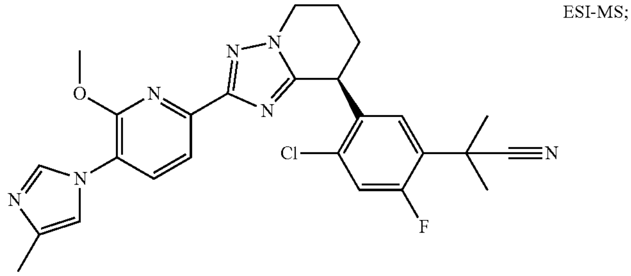 | ESI-MS; m/z 506 [M$^+$ + H]. |

TABLE 24-continued
| Example No. | Structural formula | ESI mass |
|---|---|---|
| Example 222 | 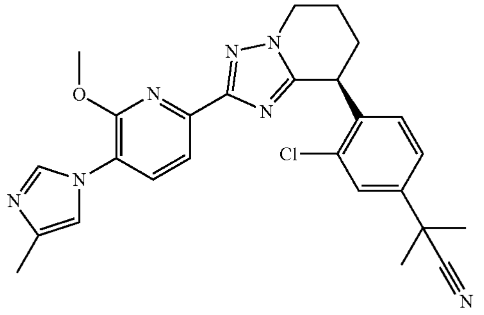 [SMILES: COc1nc(-c2nc3n(n2)CCC[C@H]3c2ccc(C(C)(C)C#N)cc2Cl)ccc1-n1cnc(C)c1] | ESI-MS; m/z 488 [M⁺ + H]. |
| Example 223 | 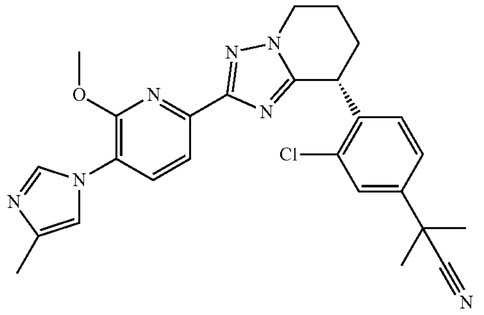 [SMILES: COc1nc(-c2nc3n(n2)CCC[C@@H]3c2ccc(C(C)(C)C#N)cc2Cl)ccc1-n1cnc(C)c1] | ESI-MS; m/z 488 [M⁺ + H]. |
| Example 224 | 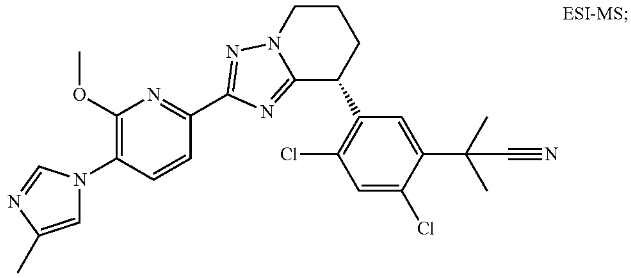 | ESI-MS; m/z 522 [M⁺ + H]. |
| Example 225 | 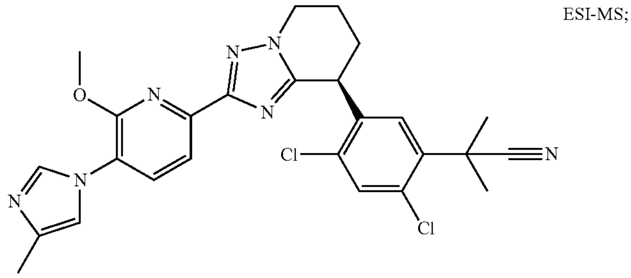 | ESI-MS; m/z 522 [M⁺ + H]. |
| Example 226 | 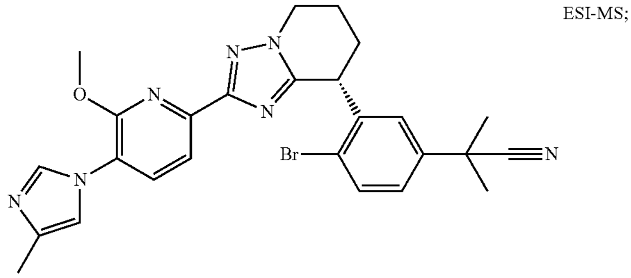 | ESI-MS; m/z 532 [M⁺ + H]. |

TABLE 24-continued
| Example No. | Structural formula | ESI mass |
|---|---|---|
| Example 227 | 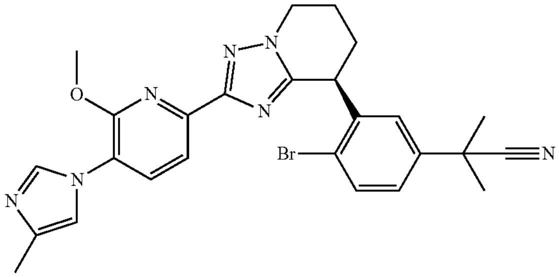 [SMILES: COc1nc(-c2nc3n(n2)CCC[C@H]3c2cc(C(C)(C)C#N)ccc2Br)ccc1-n1cnc(C)c1] | ESI-MS; m/z 534 [$M^+$ + H]. |
| Example 228 | 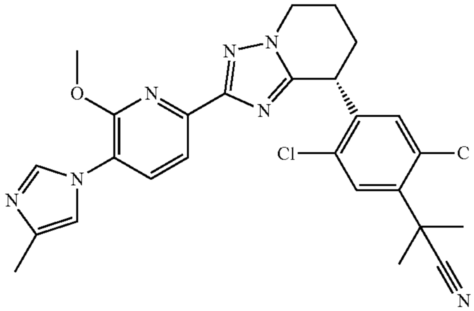 | ESI-MS; m/z 522 [$M^+$ + H]. |
| Example 229 | 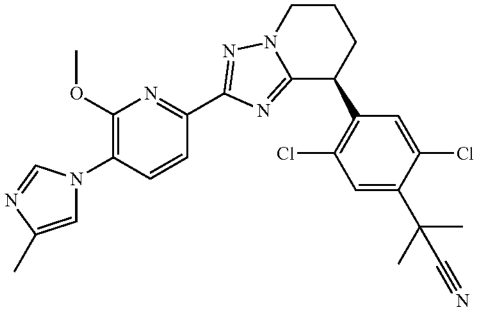 [SMILES: COc1nc(-c2nc3n(n2)CCC[C@H]3c2cc(Cl)c(C(C)(C)C#N)cc2Cl)ccc1-n1cnc(C)c1] | ESI-MS; m/z 522 [$M^+$ + H]. |
| Example 230 | 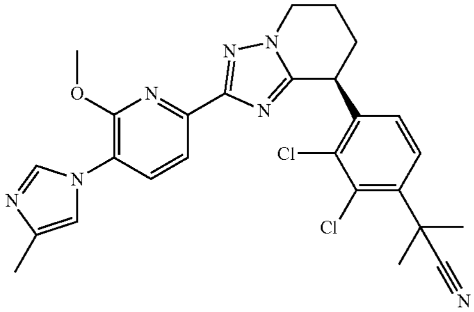 [SMILES: COc1nc(-c2nc3n(n2)CCC[C@H]3c2ccc(C(C)(C)C#N)c(Cl)c2Cl)ccc1-n1cnc(C)c1] | ESI-MS; m/z 522 [$M^+$ + H]. |
| Example 231 | 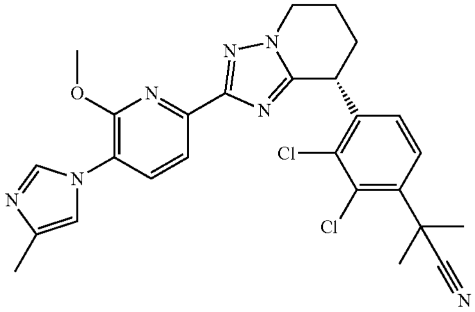 [SMILES: COc1nc(-c2nc3n(n2)CCC[C@@H]3c2ccc(C(C)(C)C#N)c(Cl)c2Cl)ccc1-n1cnc(C)c1] | ESI-MS; m/z 522 [$M^+$ + H]. |

TABLE 24-continued

| Example No. | Structural formula | ESI mass |
|---|---|---|
| Example 232 | 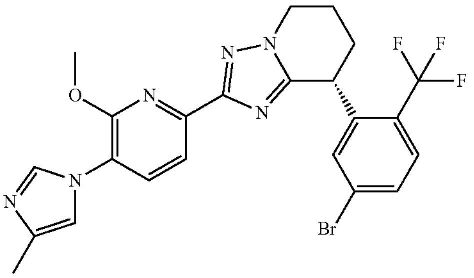 [SMILES: COc1nc(-c2nc3n(n2)CCC[C@@H]3c2cc(Br)ccc2C(F)(F)F)ccc1-n1cnc(C)c1] | ESI-MS; m/z 535 [M+ + H]. |
| Example 233 | 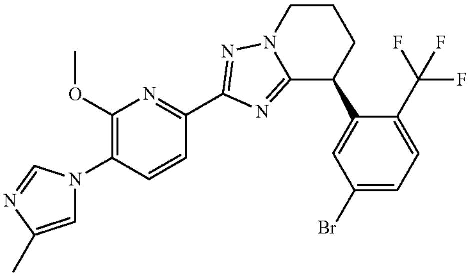 [SMILES: COc1nc(-c2nc3n(n2)CCC[C@H]3c2cc(Br)ccc2C(F)(F)F)ccc1-n1cnc(C)c1] | ESI-MS; m/z 535 [M+ + H]. |

Example 234, Example 235, Example 236 and Example 237

Syntheses of ethyl 1-(2,4-dichloro-5-{2-[6-methoxy-5-(4-methyl-1H-imidazol-1-yl)pyridine-2-yl]-5,6,7,8-tetrahydro-[1,2,4]triazolo[1,5-a]pyridine-8-}phenyl)cyclopropanecarboxylate, 1-(2,4-dichloro-5-{2-[6-methoxy-5-(4-methyl-1H-imidazol-1-yl)pyridine-2-yl]-5,6,7,8-tetrahydro-[1,2,4]triazolo[1,5-a]pyridine-8-yl}phenyl)cyclopropanecarboxylic acid amide, (+)-1-(2,4-dichloro-5-{2-[6-methoxy-5-(4-methyl-1H-imidazol-1-yl)pyridine-2-yl]-5,6,7,8-tetrahydro-[1,2,4]triazolo[1,5-a]pyridine-8-yl}phenyl)cyclopropanecarbonitrile and (−)-1-(2,4-dichloro-5-{2-[6-methoxy-5-(4-methyl-1H-imidazol-1-yl)pyridine-2-yl]-5,6,7,8-tetrahydro-[1,2,4]triazolo[1,5-a]pyridine-8-yl}phenyl)cyclopropanecarbonitrile

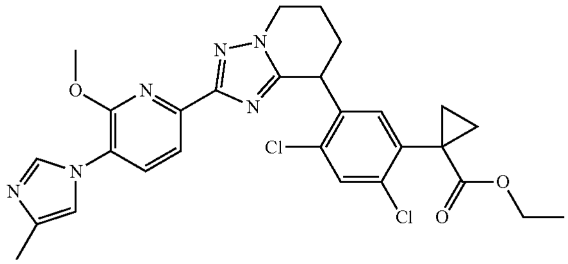

-continued

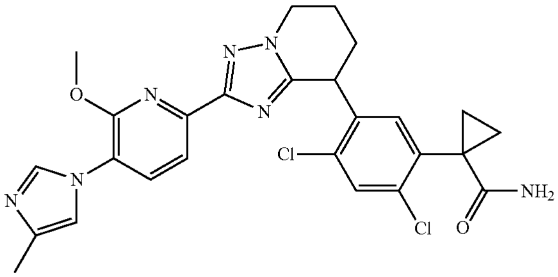

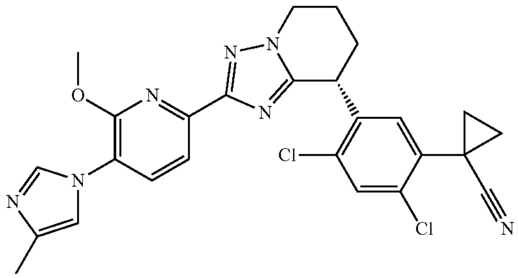

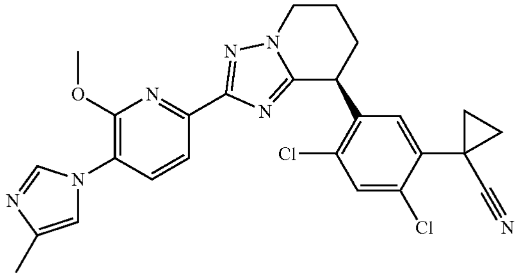

Into a ethanol (4 ml) solution of 1-[2,4-dichloro-5-(4-chloro-1-cyanobutyl)phenyl]cyclopropanecarbonitrile (113 mg) obtained in Preparation Example 3-46, hydrogen chloride gas was bubbled for 10 minutes. The reaction mixture was stirred for 2 hours at room temperature, and then was concentrated under reduced pressure. The residue was dissolved in tert-butyl methyl ether and the solution was concentrated again under reduced pressure. The resulted residue was dissolved in DMF (2 ml), and to the solution, imidazole (125 mg) and 6-methoxy-5-(4-methyl-1H-imidazol-1-yl)pyridine-2-carboxylic acid hydrazide obtained in Preparation Example 1-6 was added sequentially, the reaction mixture was stirred over night at room temperature, and then for 3.5 hours at 110° C. To the reaction mixture, after cooling, ethyl acetate, water and 1N-hydrochloric acid (0.5 ml) were added, and the organic layer was separated. The organic layer was washed with water and brine sequentially, dried over anhydrous magnesium sulfate and concentrated under reduced pressure. The residue was purified by preparative thin layer silica gel chromatography (carrier: Chromatorex™ NH; elution solvent: ethyl acetate) to obtain racemic 1-(2,4-dichloro-5-{2-[6-methoxy-5-(4-methyl-1H-imidazol-1-yl)pyridine-2-yl]-5,6,7,8-tetrahydro-[1,2,4]triazolo[1,5-a]pyridine-8-yl}phenyl)cyclopropanecarboxylic acid ethyl ester (11.7 mg). The property values of the compound are as follows.

ESI-MS; m/z 589 [$M^+$+Na]. $^1$H-NMR ($CDCl_3$) δ (ppm): 1.00-1.30 (m, 2H), 1.15 (t, J=7.2 Hz, 3H), 1.50-1.75 (m, 2H), 2.00-2.26 (m, 3H), 2.31 (s, 3H), 2.36-2.50 (m, 1H), 4.03-4.15 (m, 2H), 4.16 (s, 3H), 4.41 (t, J=6.0 Hz, 2H), 4.75 (t, J=6.0Hz, 1H), 6.86 (s, 1H), 7.01 (brs, 1H), 7.46 (s, 1H), 7.60 (d, J=8.0 Hz, 1H), 7.75 (d, J=8.0 Hz, 1H), 7.85 (brs, 1H).

And also, racemic 1-(2,4-dichloro-5-{2-[6-methoxy-5-(4-methyl-1H-imidazol-1-yl)pyridine-2-yl]-5,6,7,8-tetrahydro-[1,2,4]triazolo[1,5-a]pyridine-8-yl}phenyl)cyclopropanecarboxylic acid amide (11.9 mg) was obtained. The property values of the compound are as follows.

ESI-MS; m/z 560 [$M^+$+Na]. $^1$H-NMR ($CDCl_3$) δ (ppm): 1.01 (brs, 2H), 1.97-2.35 (m, 3H), 2.30 (s, 3H), 2.40-2.50 (m, 1H), 4.13 (s, 3H), 4.35-4.51 (m, 2H), 4.65-4.75 (m, 1H), 5.27 (brs, 1H), 5.69 (brs, 1H), 7.00 (s, 1H), 7.09 (s, 1H), 7.52 (s, 1H), 7.60 (d, J=8.0 Hz, 1H), 7.71 (d, J=8.0 Hz, 1H), 7.84 (brs, 1H).

And also, racemic 1-(2,4-dichloro-5-{2-[6-methoxy-5-(4-methyl-1H-imidazol-1-yl)pyridine-2-yl]-5,6,7,8-tetrahydro-[1,2,4]triazolo[1,5-a]pyridine-8-yl}phenyl)cyclopropanecarbonitrile (15.7 mg) was obtained. This racemic compound was purified with CHIRALCEL™ IA (Daicel Chemical Industries, Ltd.; 2 cm×25 cm; eluting solvent: 70% ethanol/hexane) to isolate the rotation (+)-optical isomer which retention time was 13 minutes (2.0 mg, >99% ee.) and the rotation (−)-optical isomer which retention time was 43 minutes (1.4 mg, >99% ee.).

The property values of the rotation (+)-optical isomer are as follows.

ESI-MS; m/z 520 [$M^+$+H]. $^1$H-NMR ($CDCl_3$) δ (ppm): 1.15-1.30 (m, 2H), 1.60-1.75 (m, 2H), 1.95-2.35 (m, 3H), 2.31 (s, 3H), 2.40-2.50 (m, 1H), 4.16 (s, 3H), 4.35-4.50 (m, 2H), 4.65-4.75 (m, 1H), 6.94 (s, 1H), 7.01 (brs, 1H), 7.53 (s, 1H), 7.60 (d, J=7.6 Hz, 1H), 7.74 (d, J=7.6 Hz, 7.86 (brs, 1H).

The property values of the rotation (−)-optical isomer are identical with (+)-isomer.

According to Example 100 and Example 101, the compounds of Example 238 to Example 251 (Table 25) were obtained from the imidate hydrochlorides obtained in Preparation Example 3-9, Preparation Example 3-25, Preparation Example 3-29, Preparation Example 3-34, Preparation Example 3-36, Preparation Example 3-44 and Preparation Example 3-45 and 6-(1-ethoxyvinyl)-2-methoxy-3-(4-methyl-1H-imidazol-1-yl)pyridine obtained in Preparation Example 1-7.

TABLE 25

| Example No. | Structural formula | ESI mass |
|---|---|---|
| Example 238 | 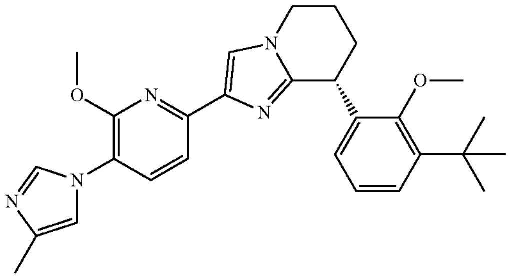 [SMILES: COc1nc(-c2cn3c(n2)[C@@H](c2cccc(C(C)(C)C)c2OC)CCC3)ccc1-n1cnc(C)c1] | ESI-MS; m/z 472 [$M^+$ + H]. |
| Example 239 | 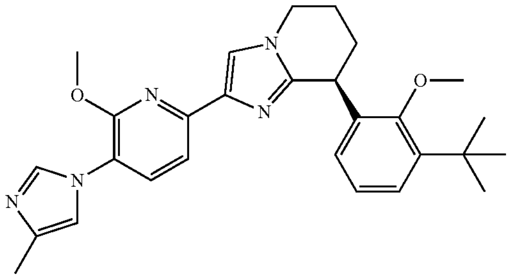 [SMILES: COc1nc(-c2cn3c(n2)[C@H](c2cccc(C(C)(C)C)c2OC)CCC3)ccc1-n1cnc(C)c1] | ESI-MS; m/z 472 [$M^+$ + H]. |

TABLE 25-continued
| Example No. | Structural formula | ESI mass |
| --- | --- | --- |
| Example 240 | 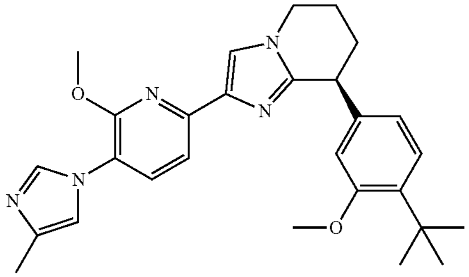 [SMILES: COc1cc([C@@H]2CCCn3cc(-c4ccc(-n5cnc(C)c5)c(OC)n4)nc32)ccc1C(C)(C)C] | ESI-MS; m/z 472 [$M^+$ + H]. |
| Example 241 | 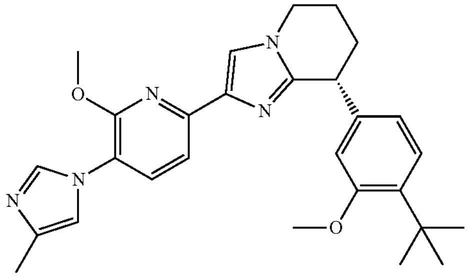 [SMILES: COc1cc([C@H]2CCCn3cc(-c4ccc(-n5cnc(C)c5)c(OC)n4)nc32)ccc1C(C)(C)C] | ESI-MS; m/z 472 [$M^+$ + H]. |
| Example 242 | 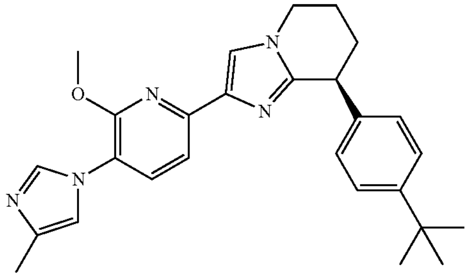 [SMILES: COc1nc(-c2cn3c(n2)[C@H](c2ccc(C(C)(C)C)cc2)CCC3)ccc1-n1cnc(C)c1] | ESI-MS; m/z 442 [$M^+$ + H]. |
| Example 243 | 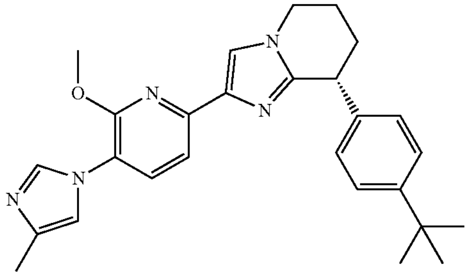 [SMILES: COc1nc(-c2cn3c(n2)[C@@H](c2ccc(C(C)(C)C)cc2)CCC3)ccc1-n1cnc(C)c1] | ESI-MS; m/z 442 [$M^+$ + H]. |
| Example 244 | 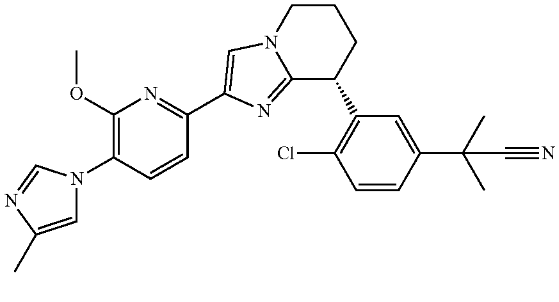 [SMILES: COc1nc(-c2cn3c(n2)[C@@H](c2cc(C(C)(C)C#N)ccc2Cl)CCC3)ccc1-n1cnc(C)c1] | ESI-MS; m/z 487 [$M^+$ + H]. |

TABLE 25-continued
| Example No. | Structural formula | ESI mass |
| --- | --- | --- |
| Example 245 | 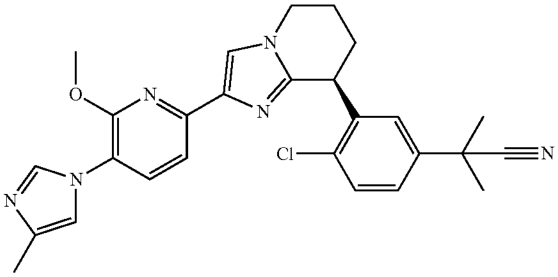 | ESI-MS; m/z 487 [M+ + H]. |
| Example 246 | 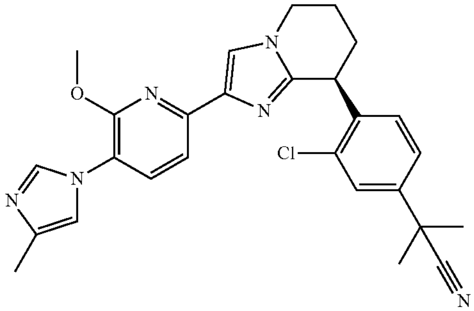 [SMILES: COc1nc(-c2cn3c(n2)[C@H](c2ccc(C(C)(C)C#N)cc2Cl)CCC3)ccc1-n1cnc(C)c1] | ESI-MS; m/z 487 [M+ + H]. |
| Example 247 | 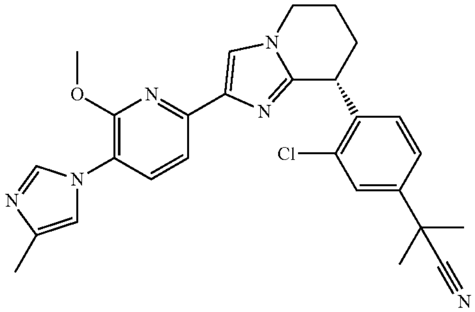 [SMILES: COc1nc(-c2cn3c(n2)[C@@H](c2ccc(C(C)(C)C#N)cc2Cl)CCC3)ccc1-n1cnc(C)c1] | ESI-MS; m/z 487 [M+ + H]. |
| Example 248 | 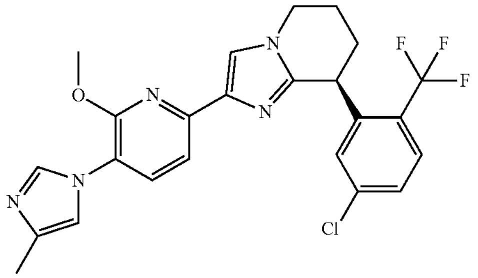 [SMILES: COc1nc(-c2cn3c(n2)[C@H](c2cc(Cl)ccc2C(F)(F)F)CCC3)ccc1-n1cnc(C)c1] | ESI-MS; m/z 488 [M+ + H]. |
| Example 249 | 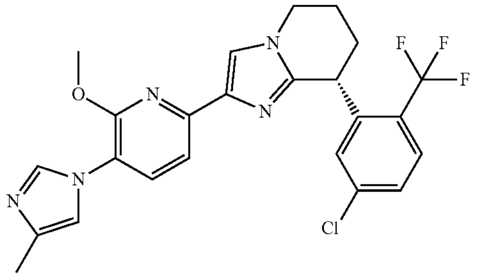 [SMILES: COc1nc(-c2cn3c(n2)[C@@H](c2cc(Cl)ccc2C(F)(F)F)CCC3)ccc1-n1cnc(C)c1] | ESI-MS; m/z 488 [M+ + H]. |

TABLE 25-continued

| Example No. | Structural formula | ESI mass |
| --- | --- | --- |
| Example 250 | 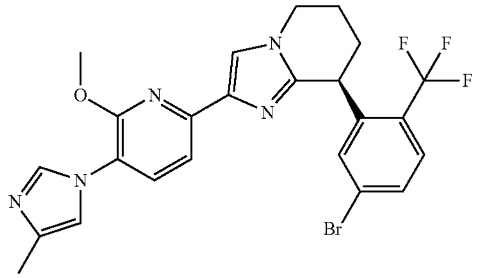 [SMILES: COc1nc(-c2cn3c(n2)[C@H](c2cc(Br)ccc2C(F)(F)F)CCC3)ccc1-n1cnc(C)c1] | ESI-MS; m/z 534 [M$^+$ + H]. |
| Example 251 | 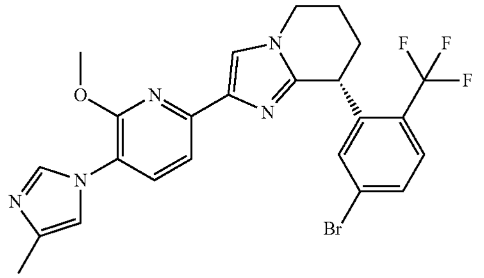 | ESI-MS; m/z 534 [M$^+$ + H]. |

According to the method of Examples 42 and 43, the compounds of Example 252 to Example 259 (Table 26) were obtained from the imidate hydrochlorides obtained in Preparation Example 3-1, Preparation Example 3-21, Preparation Example 3-25 and Preparation Example 3-29 and 3-methoxy-4-(4-methyl-1H-imidazol-1-yl)benzoic acid hydrazide obtained in Preparation Example 1-9.

TABLE 26

| Example No. | Structural formula | ESI mass |
| --- | --- | --- |
| Example 252 | 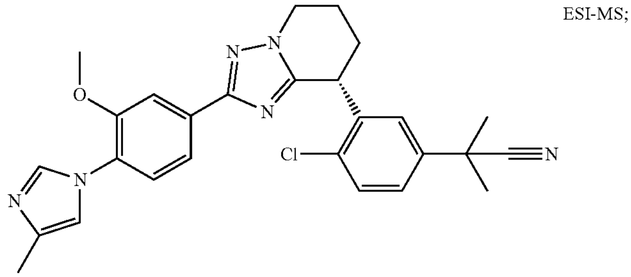 | ESI-MS; m/z 487 [M$^+$ + H]. |
| Example 253 | 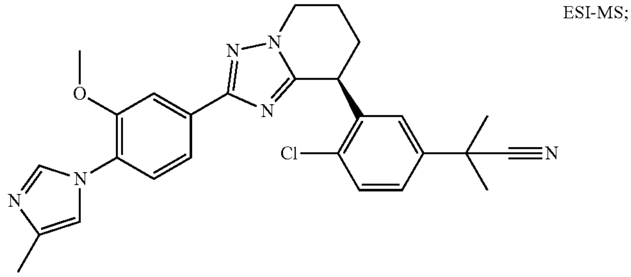 | ESI-MS; m/z 487 [M$^+$ + H]. |

TABLE 26-continued
| Example No. | Structural formula | ESI mass |
| --- | --- | --- |
| Example 254 | 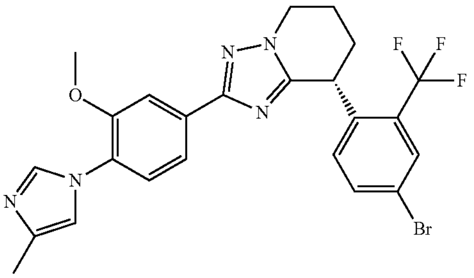 [SMILES: COc1cc(-c2nc3n(n2)CCC[C@@H]3c2ccc(Br)cc2C(F)(F)F)ccc1-n1cnc(C)c1] | ESI-MS; m/z 534 [M$^+$ + H]. |
| Example 255 | 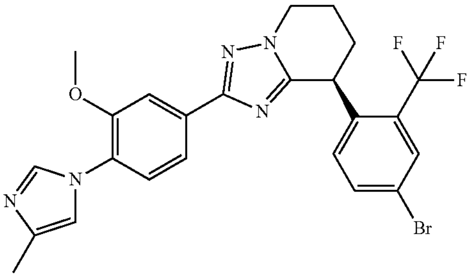 [SMILES: COc1cc(-c2nc3n(n2)CCC[C@H]3c2ccc(Br)cc2C(F)(F)F)ccc1-n1cnc(C)c1] | ESI-MS; m/z 532 [M$^+$ + H]. |
| Example 256 | 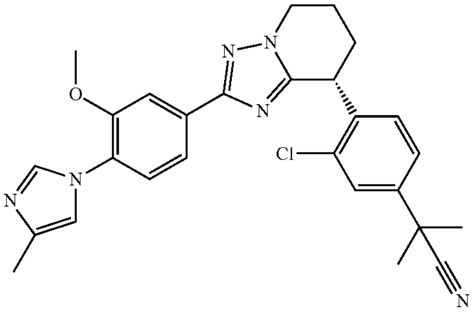 | ESI-MS; m/z 487 [M$^+$ + H]. |
| Example 257 | 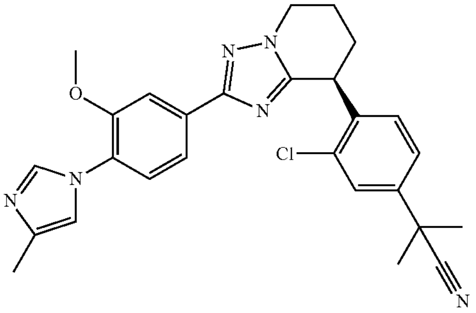 | ESI-MS; m/z 487 [M$^+$ + H]. |
| Example 258 | 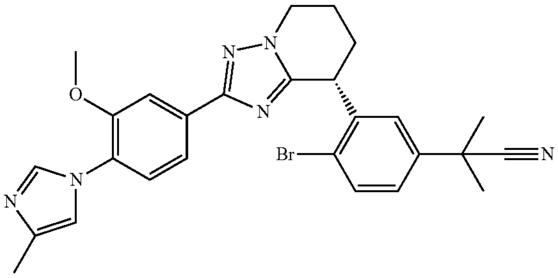 | ESI-MS; m/z 531 [M$^+$ + H]. |

TABLE 26-continued

| Example No. | Structural formula | ESI mass |
|---|---|---|
| Example 259 | 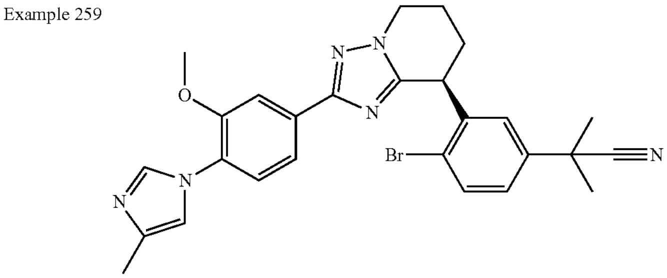 | ESI-MS; m/z 531 [$M^+$ + H]. |

Example 260 and Example 261

Syntheses of (+)-2-[6-methoxy-5-(4-methyl-1H-imidazol-1-yl)pyridin-2-yl]-8-(3-cyclopropyl-4-methoxyphenyl)5,6,7,8-tetrahydro[1,2,4]triazolo[1,5-a]pyridine and (9-2-[6-methoxy-5-(4-methyl-1H-imidazol-1-yl)pyridin-2-yl]-8-(3-cyclopropyl-4-methoxyphenyl)5,6,7,8-tetrahydro[1,2,4]triazolo[1,5-a]pyridine

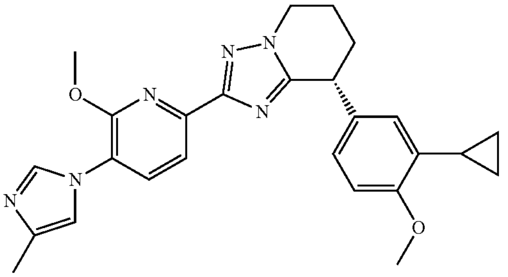

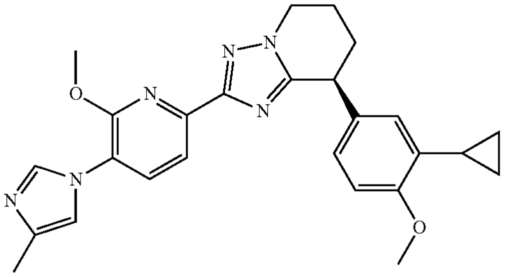

According to Example 150 and Example 151, racemic title compound (65.1 mg) was obtained starting from 2-[6-methoxy-5-(4-methyl-1H-imidazol-1-yl)pyridine-2-yl]-8-(3-bromo-4-methoxyphenyl)-5,6,7,8-tetrahydro[1,2,4]triazolo[1,5-a]pyridine. This racemic compound was purified with CHIRALCEL™ IA (Daicel Chemical Industries, Ltd.; 2 cm×25 cm; eluting solvent: 30% ethanol/hexane) to isolate the rotation (+)-optical isomer which retention time was 16 minutes (4.2 mg) and the rotation (−)-optical isomer which retention time was 28.5 minutes (3.7 mg). The property value of the title compounds is as follows.

ESI-MS; m/z 457 [$M^+$+H]

Example 262 and Example 263

Syntheses of (+)-2,6-methoxy-5-(4-methyl-1H-imidazol-1-ylpyridin-2-yl)-8-[3-(1-fluoro-1-methylethyl)phenyl]-5,6,7,8-tetrahydro[1,2,4]triazolo[1,5-a]pyridine and (−)-2-[6-methoxy-5-4-methyl-1H-imidazol-1-ylpyridin-2-yl)-8-[3-(1-fluoro-1-methylethyl)phenyl]-5,6,7,8-tetrahydro[1,2,4]triazolo[1,5-a]pyridine

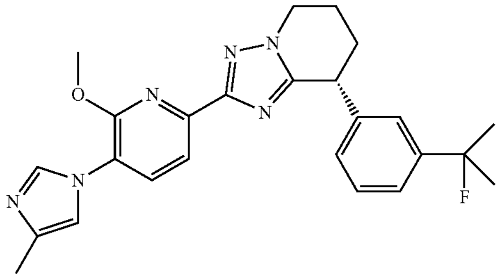

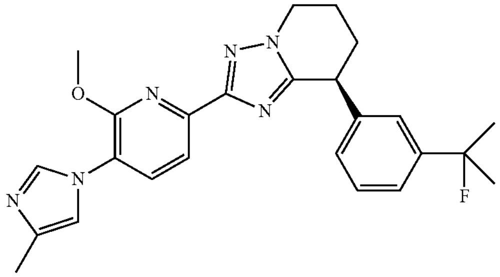

Synthesis of methyl 3-(4-chloro-1-ethoxycarbonimidoylbutyl)-benzoate

According to the method of Preparation Example 3-1, the title compound (1.47 g) was obtained from methyl 3-cyanomethyl-benzoate (999 mg). The property value of the title compounds is as follows.

ESI-MS; m/z 298 [$M^+$+H]

Synthesis of methyl 3-{2-[6-methoxy-5-(4-methyl-1H-imidazol-1-yl)pyridine-2-yl]-5,6,7,8-tetrahydro[1,2,4]triazolo[1,5-a]pyridine-8-yl}benzoate According to the method of Examples 42 and 43, title compound (1.64 g) was obtained from methyl 3-(4-chloro-1-ethoxycarbonimidoylbutyl)-benzoate hydrochloride (1.47 g)

and 6-methoxy-5-(4-methyl-1H-imidazol-1-yl)pyridine-2-carboxylic acid hydrazide (1.09 g) obtained in Preparation Example 1-6. The property value of the title compounds is as follows.

ESI-MS; m/z 445 [$M^+$+H]

Synthesis of 2-(3-{2-[6-methoxy-5-(4-methyl-1H-imidazol-1-yl)pyridin-2-yl]-5,6,7,8-tetrahydro[1,2,4]triazolo[1,5-a]pyridin-8-yl})-phenyl-propan-2-ol To the THF (19.5 ml) solution of methyl 3-{2-[6-methoxy-5-(4-methyl-1H-imidazol-1-yl)pyridine-2-yl]-5,6,7,8-tetrahydro[1,2,4]triazolo[1,5-a]pyridine-8-yl}benzoate (866 mg), methylmagnesium bromide (10.1 ml) was added at 10° C. and the reaction mixture was stirred at the same temperature. The reaction mixture was quenched by adding saturated ammonium chloride aqueous solution and extracted with ethyl acetate. This organic phase was washed with brine, dried over anhydrous magnesium sulfate and concentrated under reduced pressure. The residual oily material was purified by silica gel column chromatography (carrier: Yamazen silica gel, elution solvent: ethyl acetate/heptane=0~100% and then methanol/ethyl acetate=15%) to obtain the title compound (785 mg). The property values of the title compounds are as follows.

$^1$H-NMR ($CDCl_3$) δ (ppm): 1.59 (s, 6H), 2.06-2.16 (m, 2H), 2.16-2.27 (m, 1H), 2.30 (s, 3H), 2.34-2.44 (m, 1H), 4.16 (s, 3H), 4.32-4.47 (m, 3H), 6.94-6.98 (m, 1H), 6.99-7.01 (m, 1H), 7.3 (d, J=7.8 Hz, 1H), 7.35-7.38 (m, 2H), 7.58 (d, J=7.8 Hz, 1H), 7.78 (d, J=7.8 Hz, 1H), 7.82 (d, J=1.5 Hz, 1H).

Syntheses of (+)-2-[6-methoxy-5-(4-methyl-1H-imidazol-1-ylpyridin-2-yl)-8-[3-(1-fluoro-1-methylethyl)phenyl]-5,6,7,8-tetrahydro[1,2,4]triazolo[1,5-a]pyridine and (−)-2-[6-methoxy-5-(4-methyl-1H-imidazol-1-ylpyridin-2-yl)-8-[3-(1-fluoro-1-methylethyl)phenyl]-5,6,7,8-tetrahydro[1,2,4]triazolo[1,5-a]pyridine 2-(3-{6-methoxy-5-(4-methyl-1H-imidazol-1-yl)pyridin-2-yl}-5,6,7,8-tetrahydro[1,2,4]triazolo[1,5-a]pyridin-8-yl)-phenyl-propan-2-ol (159 mg) was dissolved in methylene chloride (3.6 ml), and to the mixture, [bis(2-methoxyethyl)amino]sulfur trifluoride (79.6 μl) was added at room temperature. After 18 hour stirring, the reaction mixture was quenched by adding saturated sodium hydrogen carbonate aqueous solution, and extracted by ethyl acetate. The organic phase was washed with saturated sodium hydrogen carbonate aqueous solution and brine sequentially, dried over anhydrous magnesium sulfate, and concentrated under reduced pressure. The residual oily material was purified by silica gel column chromatography (carrier: Yamazen silica gel, elution solvent: chloroform/methanol=25/1) to obtain the title compound (115.5 mg) as a mixture with exo-olefin compound. Subsequently, resulted material was dissolved in THF (2.7 ml), and to the mixture, 9-borabicyclo[3,3,1]nonane (644 μl) was added at room temperature, and the reaction mixture was stirred at 80° C. for 17 hours. To the reaction mixture, after cooling to 0° C., ethanol (0.9 ml), 2N-sodium hydroxide aqueous solution (0.9 ml) and hydrogen peroxide aqueous solution (0.75 ml) were added, and then the reaction mixture was stirred for 2 hours at 80° C. The reaction mixture was quenched by adding saturated sodium thiosulfate aqueous solution, and extracted with ethyl acetate. The organic layer was washed with water and brine sequentially, dried over anhydrous magnesium sulfate and concentrated under reduced pressure. The residual oily material was purified by silica gel column chromatography (carrier: Yamazen silica gel, elution solvent: ethyl acetate/heptane=0-100% and then methanol/ethyl acetate=10%) to obtain the title compound (52 mg).

The resulting racemate was separated by CHIRALPAK™ IB (2 cm×25 cm, mobile phase: 20% ethanol-hexane) to obtain the title compound with a retention time of 28 minutes and positive optical rotation (14.4 mg) and the title compound with a retention time of 54 minutes and negative optical rotation (12.4 mg).

The property values of the title optically active compound with positive optical rotation are as follows.

$^1$H-NMR ($CDCl_3$) δ (ppm): 1.64 (s, 3H), 1.69 (s, 3H), 2.04-2.16 (m, 2H), 2.20 (ddd, 0.1=8.1, 8.1, 6.3 Hz, 1H), 2.30 (s, 3H), 2.34-2.44 (m, 1H), 4.16 (s, 3H), 4.32-4.48 (m, 3H), 6.96-7.01 (m, 2H), 7.23-7.33 (m, 3H), 7.58 (d, J=7.8 Hz, 1H), 7.78 (d, J=7.8 Hz, 1H), 7.81-7.83 (m, 1H).

The property values of the title optically active compound with negative optical rotation are as follows.

$^1$H-NMR ($CDCl_3$) δ (ppm): 1.64 (s, 3H), 1.69 (s, 3H), 2.04-2.16 (m, 2H), 2.20 (ddd, J=8.1, 8.1, 6.3 Hz, 1H), 2.30 (s, 3H), 2.34-2.44 (m, 1H), 4.16 (s, 3H), 4.32-4.48 (m, 3H), 6.96-7.01 (m, 2H), 7.23-7.33 (m, 3H), 7.58 (d, J=7.8 Hz, 1H), 7.78 (d, J=7.8 Hz, 1H), 7.81-7.83 (m, 1H).

Examples 264 and 265

Synthesis of (+)-2-[6-methoxy-5-(4-methyl-1H-imidazol-1-yl)pyridin-2-yl]-8-(3-(1-methoxy-1-methylethyl)phenyl)-5,6,7,8-tetrahydro[1,2,4]triazolo[1,5-a]pyridine and (−)-2-[6-methoxy-5-(4-methyl-1H-imidazol-1-yl)pyridin-2-yl]-8-((3-(1-methoxy-1-methylethyl)phenyl)-5,6,7,8-tetrahydro[1,2,4]triazol[1,5-a]pyridine

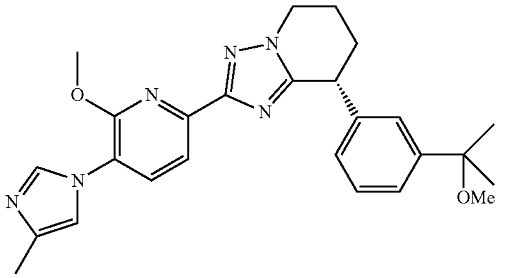

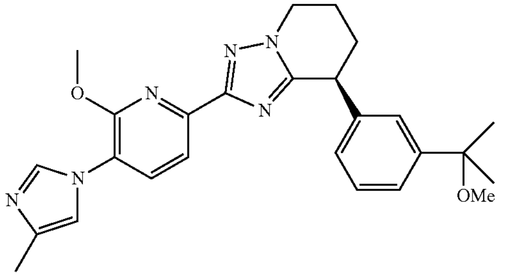

2-(3-{2-[6-Methoxy-5-(4-methyl-1H-imidazol-1-yl)pyridin-2-yl]-5,6,7,8-tetrahydro[1,2,4]triazolo[1,5-a]pyridin-8-yl}-phenyl-2-ol (60 mg) was dissolved in methanol (1.3 ml) and then DOWEX™ 50×8 (6 mg) was added at room temperature. After stirring at room temperature for 24 hours, DOWEX™ 50×8 (20 mg) was further added and the mixture was stirred for 6 hours at the same temperature. Trimethyl orthoformate (44.3 μL) was added to the reaction solution, followed by stirring for 19 hours. p-Toluenesulfonic acid mono hydrate (5.1 mg) was added thereto followed by stirring for 24 hour. Further p-Toluenesulfonic acid mono hydrate (5.1 mg) was added thereto followed by stirring for 4 days, and the reaction was quenched with a saturated potassium carbonate solution, followed by extraction with ethyl acetate. The organic layer was washed with a saturated potassium carbonate solution and dried over sodium sulfate. The solvent was removed and the resulting crude product was purified by silica gel column chromatography (carrier: Yamazen Silica gel; elution solvent: ethyl acetate:heptane=0:100→100:0, then 15% methanol-ethyl acetate) to obtain the title compound. The resulting racemate was separated by CHIRALPAK™ IB (2 cm×25 cm:mobile phase; 20% ethanol-hexane) to obtain the title compound with a retention time of 23.5 minutes and positive optical rotation (21.9 mg) and the title compound with a retention time of 47 minutes and negative optical rotation (15.1 mg).

The property values of the title optically active compound with positive optical rotation are as follows.

$^1$H-NMR ($CDCl_3$) δ(ppm): 1.50 (s, 6H), 2.04-2.16 (m, 2H), 2.16-2.27 (m, 1H), 2.30 (s, 3H), 2.34-2.44 (m, 1H), 3.07 (s, 3H), 4.16 (s, 3H), 4.32-4.48 (m, 3H), 6.94-6.98 (m, 1H), 6.99-7.01 (m, 1H), 7.24-7.27 (m, 1H), 7.29 (d, J=5.1 Hz, 1H), 7.58 (d, J=7.8 Hz, 1H), 7.77 (d, J=7.8 Hz, 1H), 7.82 (d, J=1.2 Hz, 1H).

Examples 266 and 267

Synthesis of (+)-2-[6-methoxy-5-(4-methyl-1H-imidazol-1-yl)pyridin-2-yl]-8-(2-chloro-5-(1-methoxy-1-methylethyl)phenyl)-5,6,7,8-tetrahydro [1,2,4] triazolo[1,5-a]pyridine and (−)-2-6-methoxy-5-(4-methyl-1H-imidazol-1-yl)pyridin-2-yl]-8-(2-chloro-5-(1-methoxy-1-methylethyl)phenyl)-5,6,7,8-tetrahydro[1,2,4]triazolo[1,5-a]pyridine

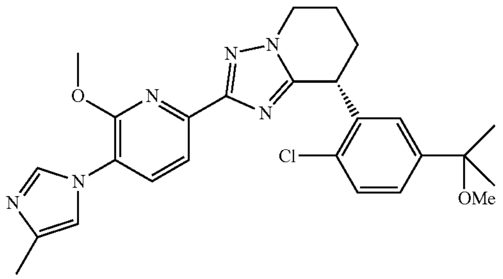

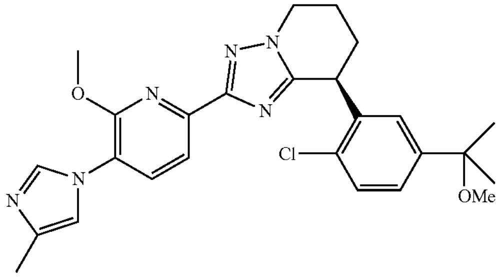

Synthesis of ethyl 4-chloro-3-(4-chloro-1-ethoxycarbonimidolylbutyl)benzoate hydrochloride

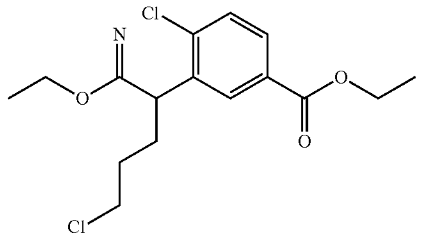 [SMILES: CCOC(=N)C(CCCCl)c1cc(C(=O)OCC)ccc1Cl]

The title compound (1.46 g) was obtained according to the method of Preparation Example 3-1 from ethyl 4-chloro-3-cyanomethylbenzoate (1.32 g). The property value of the compound is as follows.

ESI-MS; m/z 346[$M^+$+H]

Synthesis of (+)-2-[6-methoxy-5-(4-methyl-1H-imidazol-1-yl)pyridin-2-yl]-8-(2-chloro-5-(1-methoxy-1-methylethyl)phenyl)-5,6,7,8-tetrahydro[1,2,4]triazolo[1,5-a]pyridine and (−)-2-[6-methoxy-5-(4-methyl-1H-imidazol-1-yl)pyridin-2-yl]-8-(2-chloro-5-(1-methoxy-1-methylethyl)phenyl)-5,6,7,8-tetrahydro[1,2,4]triazolo[1,5-a]pyridine The racemate of the title compound (65 mg) was obtained according to the method of Examples 262 and 263 from 2-(4-chloro-3-{2-[6-methoxy-5-(4-methyl-1H-imidazol-1-yl)pyridin-2-yl]-5,6,7,8-tetrahydro[1,2,4]triazolo[1,5-a]pyridin-8-yl]-phenyl-propan-2-ol (76 mg) and ethyl 4-chloro-3-(4-chloro-1-ethoxycarbonimidolybutyl)benzoate hydrochloric acid. The resulting racemate was separated by CHIRALPAK™ IB (2 cm×25 cm, mobile phase: 20% ethanol-hexane) to obtain the title compound with a retention time of 19.5 minutes and positive optical rotation (24 mg) and the title compound with a retention time of 30 minutes and negative optical rotation (22 mg).

The property values of the title optically active compound with positive optical rotation are as follows.

$^1$H-NMR ($CDCl_3$) δ (ppm): 1.41 (s, 6H), 1.41 (s, 6H), 2.00-2.25 (m, 3H), 2.30 (s, 3H), 2.38-2.48 (m, 1H), 3.00 (s, 3H), 4.15 (s, 3H), 4.36-4.45 (m, 2H), 4.78 (dd, J=7.4, 5.9 Hz, 1H), 6.97-7.11 (m, 2H), 7.21-7.25 (m, 1H), 7.37 (d, J=8.2 Hz, 1H), 7.57 (d, J=7.8 Hz, 1H), 7.74 (d, J=7.8 Hz, 1H), 7.82 (d, J=1.2 Hz, 1H).

The property values of the title optically active compound with negative optical rotation are as follows.

$^1$H-NMR ($CDCl_3$) δ (ppm): 1.41 (s, 6H), 1.41 (s, 6H), 2.00-2.25 (m, 3H), 2.30 (s, 3H), 2.38-2.48 (m, 1H), 3.00 (s, 3H), 4.15 (s, 3H), 4.36-4.45 (m, 2H), 4.78 (dd, J=7.4, 5.9 Hz, 1H), 6.97-7.11 (m, 2H), 7.21-7.25 (m, 1H), 7.37 (d, J=8.2 Hz, 1H), 7.57 (d, J=7.8 Hz, 1H), 7.74 (d, J=7.8 Hz, 1H), 7.82 (d, J=1.2 Hz, 1H).

Examples 268 and 269

Synthesis of (+)-2-[6-methoxy-5-(4-methyl-1H-imidazol-1-yl)pyridin-2-yl]-8-(5-bromo-2-fluorophenyl)-5,6,7,8-tetrahydro[1,2,4]triazolo[1,5-a]pyridine and (−)-2-[6-methoxy-5-(4-methyl-1H-imidazol-1-yl)pyridin-2-yl]-8-(5-bromo-2-fluorophenyl)-5,6,7,8-tetrahydro[1,2,4]triazolo[1,5-a]pyridine

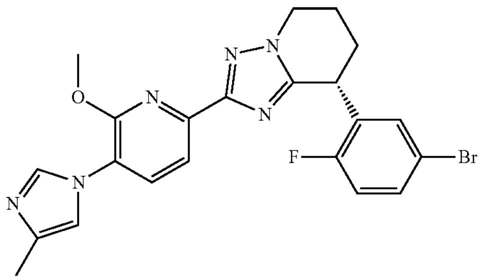

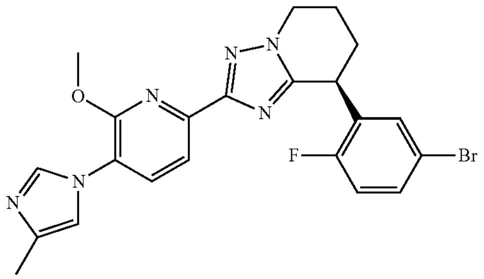

Synthesis of ethyl 2-(5-bromo-2-fluorophenyl)-5-chloropentaneimidiate

The title compound (3.1 g) was obtained according to the method of Preparation Example 3-1 from (5-bromo-2-fluorophenyl)acetonitrile. The property value of the compound is as follows.

ESI-MS; m/z 336[$M^+$+H]

Synthesis of (+)-2-[6-methoxy-5-(4-methyl-1H-imidazol-1-yl)pyridin-2-yl]-8-(5-bromo-2-fluorophenyl)-5,6,7,8-tetrahydro[1,2,4]triazolo[1,5-a]pyridine and (−)-2-[6-methoxy-5-(4-methyl-1H-imidazol-1-yl)pyridin-2-yl]-8-(5-bromo-2-fluorophenyl)-5,6,7,8-tetrahydro[1,2,4]triazolo[1,5-a]pyridine The racemate of the title compound (1.80 g) was obtained according to the method of Examples 42 and 43 from hydrazide 6-methoxy-5-(4-methyl-1H-imidazol-1-yl)pyridin-2-carboxlate (2.05 g) obtained in Preparation Example 1-6 and ethyl 2-(5-bromo-2-fluorophenyl)-5-chloropentaimidate (3.1 g).

The resulting racemate was separated by CHIRALPAK™ IB (2 cm×25 cm, mobile phase: 15% ethanol-hexane) to obtain the title compound with a retention time of 24.5 minutes and positive optical rotation (21 mg) and the title compound with a retention time of 43 minutes and negative optical rotation (22.5 mg).

The property values of the title optically active compound with positive optical rotation are as follows.

$^1$H-NMR ($CDCl_3$) δ (ppm): 2.01-2.26 (m, 3H), 2.30 (s, 3H), 2.34-2.42 (m, 1H), 4.17 (s, 3H), 4.36-4.43 (m, 2H), 4.60 (dd, J=6.6, 6.2 Hz, 1H), 6.96-7.02 (m, 2H), 7.07 (dd, J=16.6, 2.3 Hz, 1H), 7.36-7.41 (m, 1H), 7.60 (d, J=7.8 Hz, 1H), 7.77 (d, J=7.8 Hz, 1H), 7.83 (d, J=1.2 Hz, 1H).

The property values of the title optically active compound with negative optical rotation are as follows.

$^1$H-NMR ($CDCl_3$) δ (ppm): 2.01-2.26 (m, 3H), 2.30 (s, 3H), 2.34-2.42 (m, 1H), 4.17 (s, 3H), 4.36-4.43 (m, 2H), 4.60 (dd, J=6.6, 6.2 Hz, 1H), 6.96-7.02 (m, 2H), 7.07 (dd, J=16.6, 2.3 Hz, 1H), 7.36-7.41 (m, 1H), 7.60 (d, J=7.8 Hz, 1H), 7.77 (d, J=7.8 Hz, 1H), 7.83 (d, J=1.2 Hz, 1H).

Examples 270 and 271

Synthesis of (+)-8-(2-fluoro-5-piperidin-1-ylphenyl)-2-[6-methoxy-5-(4-methyl-1H-imidazol-1-yl)pyridin-2-yl]-5,6,7,8-tetrahydro[1,2,4]triazolo[1,5-a]pyridine and (−)-8-(2-fluoro-5-piperidin-1-ylphenyl)-2-[6-methoxy-5-(4-methyl-1H-imidazol-1-yl)pyridin-2-yl]-5,6,7,8-tetrahydro[1,2,4]triazolo[1,5-a]pyridine

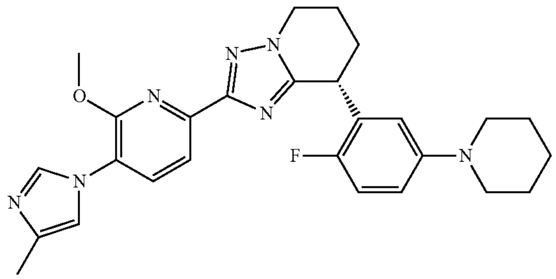

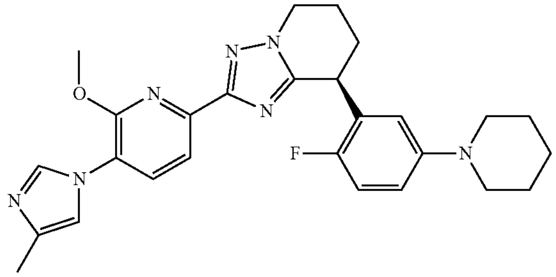

The racemate of the title compound (164 mg) was obtained according to the method of Examples 42 and 43 from 6-methoxy-5-(4-methyl-1H-imidazol-1-yl)pyridin-2-carboxylic acid hydrazide hydrochloride (200 mg) obtained in Preparation Example 1-6 and ethyl 5-chloro-2-(2-fluoro-5-piperidin-1-ylphenyl)pentaneimidate hydrochloride (350 mg) obtained in Preparation Example 3-51.

The resulting racemate was separated by CHIRALPAK™ IA (2 cm×25 cm, mobile phase: 50% ethanol-hexane) to obtain the title compound with positive optical rotation (59 mg, >99% ee) and the title compound with negative optical rotation (56 mg, >99% ee).

The property values of the title optically active compound with positive optical rotation are as follows.

ESI-MS; m/z 245 [½$M^+$+H], 488[$M^+$+H].

The property values of the title optically active compound with negative optical rotation are as follows.

ESI-MS; m/z 245 [½$M^+$+H], 488 [$M^+$+H].

Examples 272-349

Compounds of Examples 272-349 were obtained according to the method of Examples 270 and 271 shown in Tables 27-39.

TABLE 27
| Example No. | Structural formula | $^1$H-NMR or ESI mass |
| --- | --- | --- |
| Example 272 | 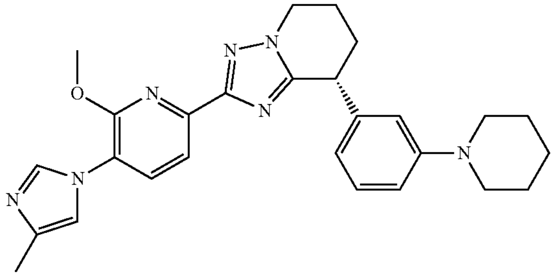 [SMILES: COc1nc(-c2nc3n(n2)CCC[C@@H]3c2cccc(N3CCCCC3)c2)ccc1-n1cnc(C)c1] | ESI-MS; m/z 236 [1/2M+ + H], 470 [M+ + H]. |
| Example 273 | 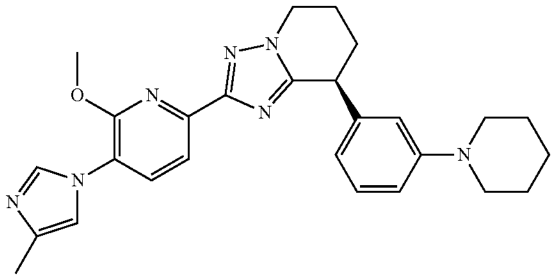 [SMILES: COc1nc(-c2nc3n(n2)CCC[C@H]3c2cccc(N3CCCCC3)c2)ccc1-n1cnc(C)c1] | ESI-MS; m/z 236 [1/2M+ + H], 470 [M+ + H]. |
| Example 274 | 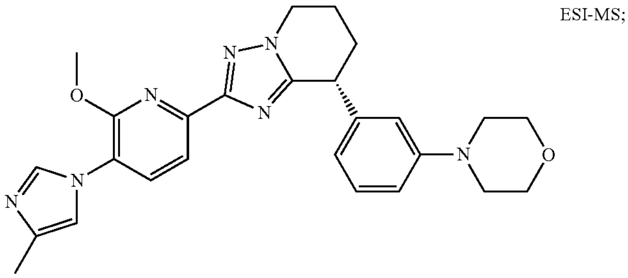 | ESI-MS; m/z 237 [1/2M+ + H], 472 [M+ + H]. |
| Example 275 | 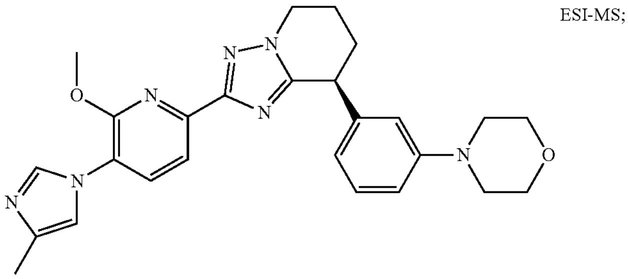 | ESI-MS; m/z 237 [1/2M+ + H], 472 [M+ + H]. |
| Example 276 | 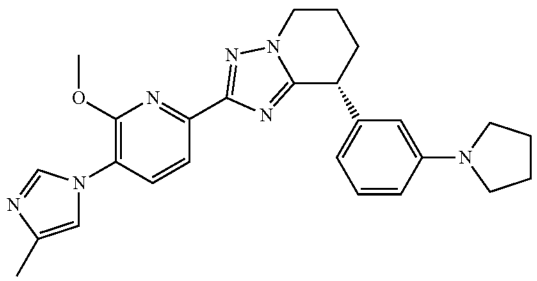 [SMILES: COc1nc(-c2nc3n(n2)CCC[C@@H]3c2cccc(N3CCCC3)c2)ccc1-n1cnc(C)c1] | ESI-MS; m/z 228 [1/2M+ + H], 456 [M+ + H]. |

TABLE 27-continued
| Example No. | Structural formula | $^1$H-NMR or ESI mass |
|---|---|---|
| Example 277 | 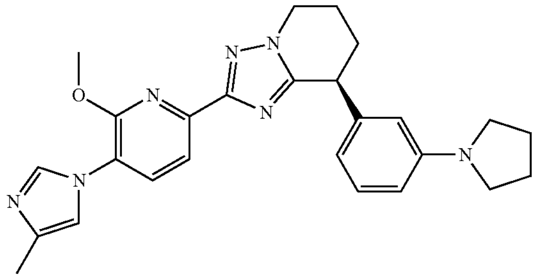 [SMILES: COc1nc(-c2nc3n(n2)CCC[C@H]3c2cccc(N3CCCC3)c2)ccc1-n1cnc(C)c1] | ESI-MS; m/z 228 [1/2M$^+$ + H], 456 [M$^+$ + H]. |
TABLE 28
| Example No. | Structural formula | $^1$H-NMR or ESI mass |
|---|---|---|
| Example 278 | 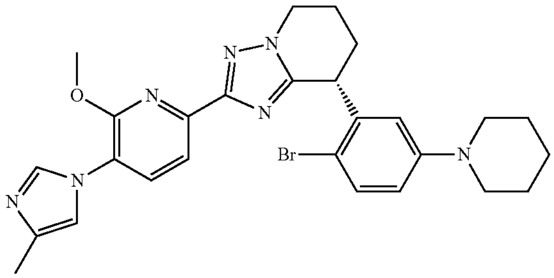 [SMILES: COc1nc(-c2nc3n(n2)CCC[C@@H]3c2cc(N3CCCCC3)ccc2Br)ccc1-n1cnc(C)c1] | ESI-MS; m/z 548, 550 [M$^+$ + H]. |
| Example 279 | 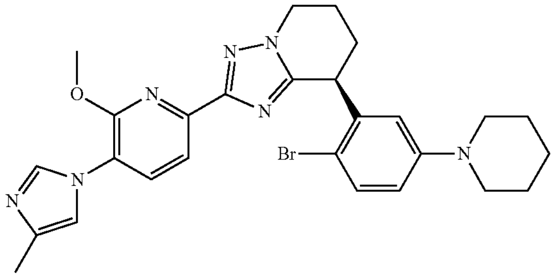 [SMILES: COc1nc(-c2nc3n(n2)CCC[C@H]3c2cc(N3CCCCC3)ccc2Br)ccc1-n1cnc(C)c1] | ESI-MS; m/z 548, 550 [M$^+$ + H]. |
| Example 280 | 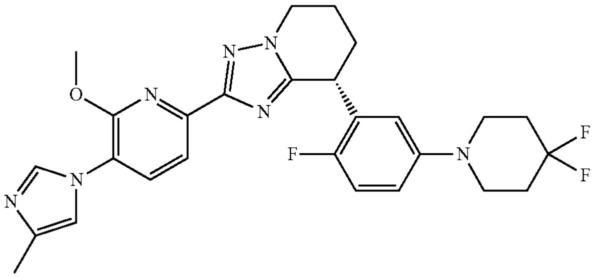 [SMILES: COc1nc(-c2nc3n(n2)CCC[C@@H]3c2cc(N3CCC(F)(F)CC3)ccc2F)ccc1-n1cnc(C)c1] | ESI-MS; m/z 263 [1/2M$^+$ + H], 524 [M$^+$ + H]. |
| Example 281 | 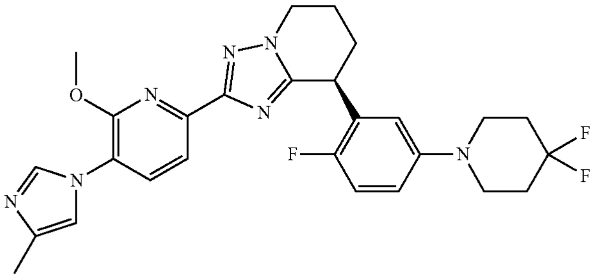 [SMILES: COc1nc(-c2nc3n(n2)CCC[C@H]3c2cc(N3CCC(F)(F)CC3)ccc2F)ccc1-n1cnc(C)c1] | ESI-MS; m/z 263 [1/2M$^+$ + H], 524 [M$^+$ + H]. |

TABLE 28-continued
| Example No. | Structural formula | $^1$H-NMR or ESI mass |
|---|---|---|
| Example 282 | 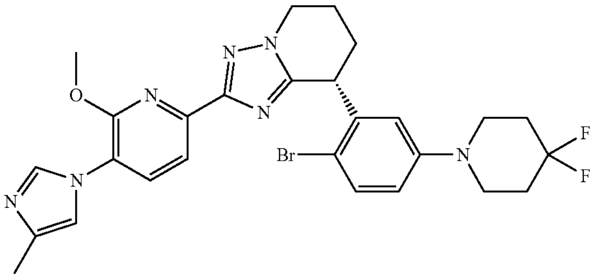 [SMILES: COc1nc(-c2nc3n(n2)CCC[C@@H]3c2cc(N3CCC(F)(F)CC3)ccc2Br)ccc1-n1cnc(C)c1] | ESI-MS; m/z 584, 586 [M$^+$ + H]. |
| Example 283 | 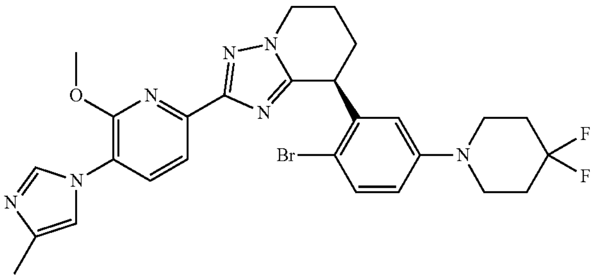 [SMILES: COc1nc(-c2nc3n(n2)CCC[C@H]3c2cc(N3CCC(F)(F)CC3)ccc2Br)ccc1-n1cnc(C)c1] | ESI-MS; m/z 584, 586 [M$^+$ + H]. |
TABLE 29
| Example No. | Structural formula | $^1$H-NMR or ESI mass |
|---|---|---|
| Example 284 | 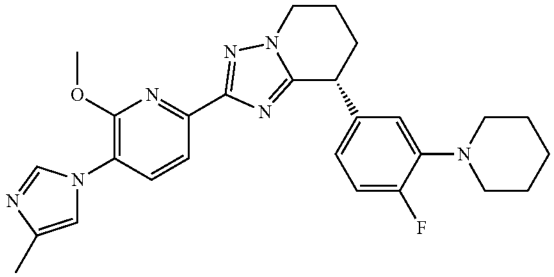 [SMILES: COc1nc(-c2nc3n(n2)CCC[C@@H]3c2ccc(F)c(N3CCCCC3)c2)ccc1-n1cnc(C)c1] | ESI-MS; m/z 245 [1/2M$^+$ + H], 488 [M$^+$ + H]. |
| Example 285 | 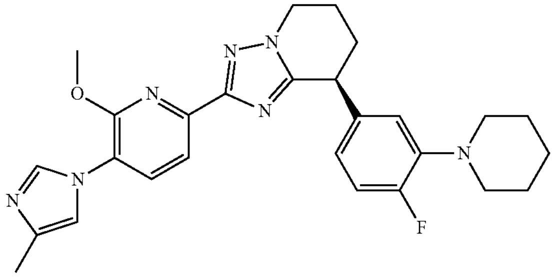 [SMILES: COc1nc(-c2nc3n(n2)CCC[C@H]3c2ccc(F)c(N3CCCCC3)c2)ccc1-n1cnc(C)c1] | ESI-MS; m/z 245 [1/2M$^+$ + H], 488 [M$^+$ + H]. |
| Example 286 | 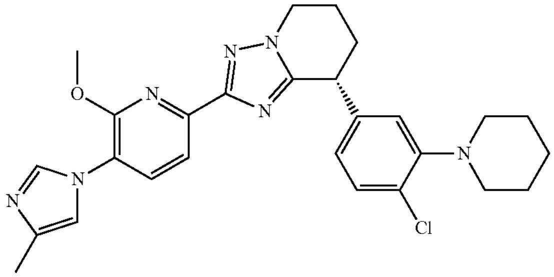 [SMILES: COc1nc(-c2nc3n(n2)CCC[C@@H]3c2ccc(Cl)c(N3CCCCC3)c2)ccc1-n1cnc(C)c1] | ESI-MS; m/z 253 [1/2M$^+$ + H], 504 [M$^+$ + H]. |

TABLE 29-continued
| Example No. | Structural formula | $^1$H-NMR or ESI mass |
|---|---|---|
| Example 287 | 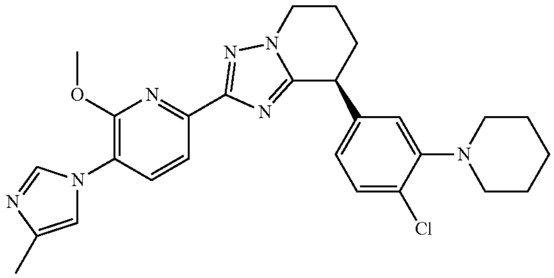 [SMILES: COc1nc(-c2nc3n(n2)CCC[C@H]3c2ccc(Cl)c(N3CCCCC3)c2)ccc1-n1cnc(C)c1] | ESI-MS; m/z 253 [1/2M$^+$ + H], 504 [M$^+$ + H]. |
| Example 288 | 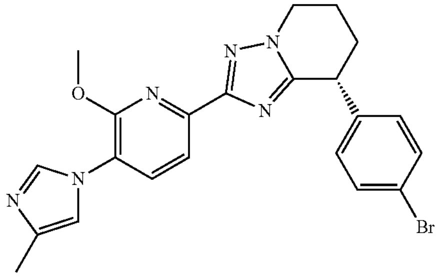 [SMILES: COc1nc(-c2nc3n(n2)CCC[C@@H]3c2ccc(Br)cc2)ccc1-n1cnc(C)c1] | ESI-MS; m/z 465, 467 [M$^+$ + H]. |
| Example 289 | 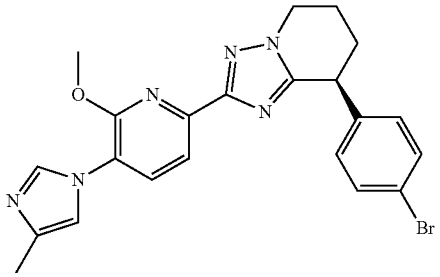 [SMILES: COc1nc(-c2nc3n(n2)CCC[C@H]3c2ccc(Br)cc2)ccc1-n1cnc(C)c1] | ESI-MS; m/z 465, 467 [M$^+$ + H]. |
TABLE 30
| Example No. | Structural formula | 1H-NMR or ESI mass |
|---|---|---|
| Example 290 | 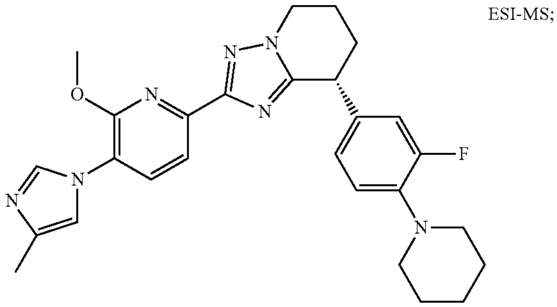 | ESI-MS; m/z 488 [M$^+$ + H]. |

TABLE 30-continued
| Example No. | Structural formula | 1H-NMR or ESI mass |
| --- | --- | --- |
| Example 291 | 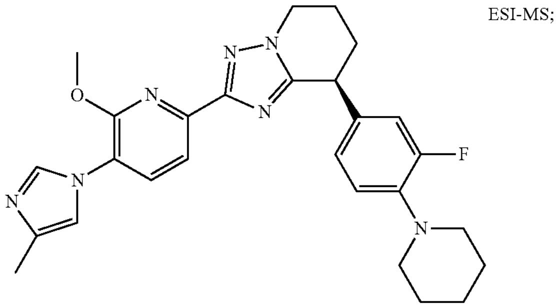 | ESI-MS; m/z 488 [M$^+$ + H]. |
| Example 292 | 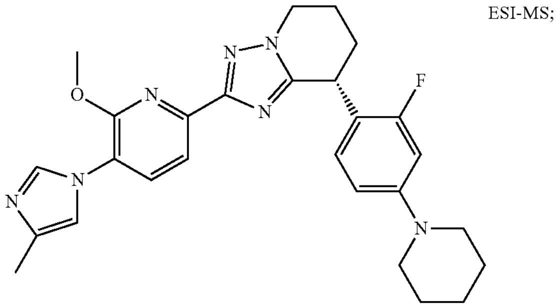 | ESI-MS; m/z 488 [M$^+$ + H]. |
| Example 293 | 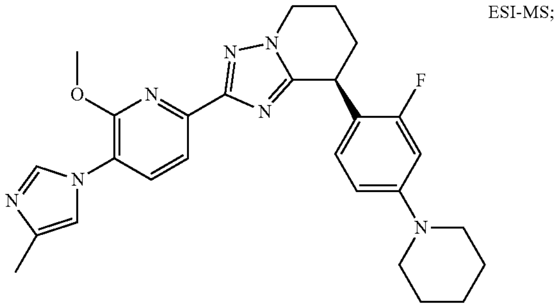 | ESI-MS; m/z 488 [M$^+$ + H]. |
| Example 294 | 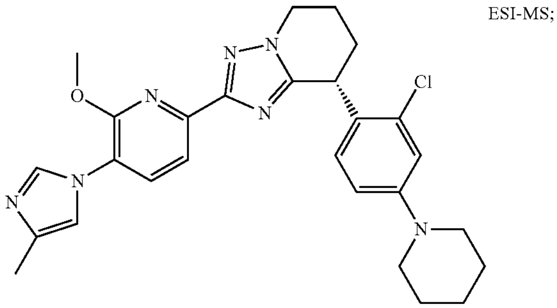 | ESI-MS; m/z 505 [M$^+$ + H]. |
| Example 295 | 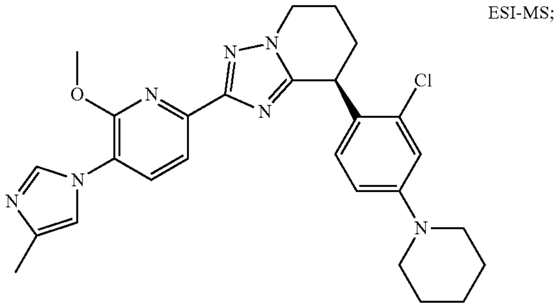 | ESI-MS; m/z 505 [M$^+$ + H]. |

TABLE 31
| Example No. | Structural formula | ¹H-NMR or ESI mass |
|---|---|---|
| Example 296 | 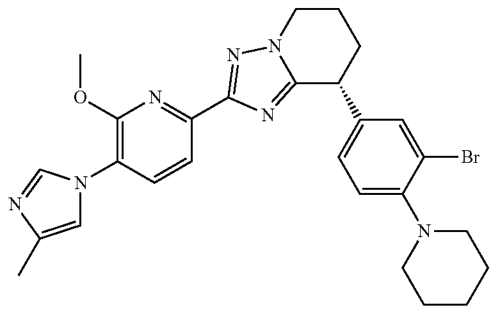 | ESI-MS; m/z 548, 550 [$M^+$ + H]. |
| Example 297 | 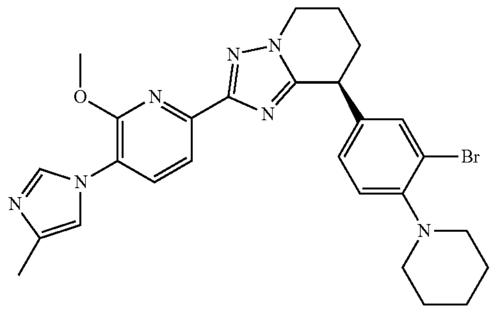 [SMILES: COc1nc(-c2nc3n(n2)CCC[C@H]3c2ccc(N3CCCCC3)c(Br)c2)ccc1-n1cnc(C)c1] | ESI-MS; m/z 548, 550 [$M^+$ + H]. |
| Example 298 | 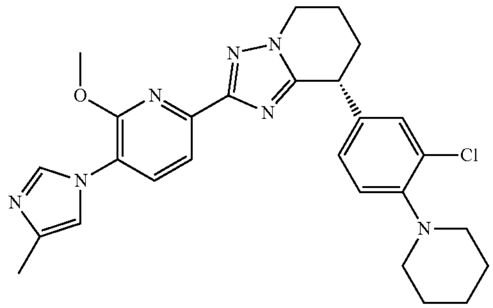 [SMILES: COc1nc(-c2nc3n(n2)CCC[C@@H]3c2ccc(N3CCCCC3)c(Cl)c2)ccc1-n1cnc(C)c1] | ESI-MS; m/z 504 [$M^+$ + H]. |
| Example 299 | 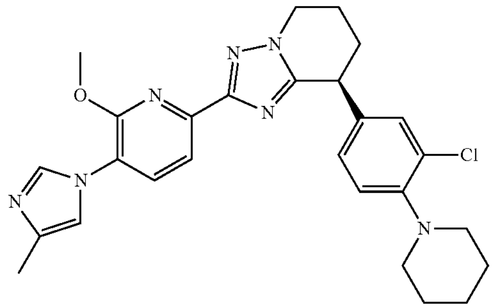 [SMILES: COc1nc(-c2nc3n(n2)CCC[C@H]3c2ccc(N3CCCCC3)c(Cl)c2)ccc1-n1cnc(C)c1] | ESI-MS; m/z 504 [$M^+$ + H]. |
| Example 300 | 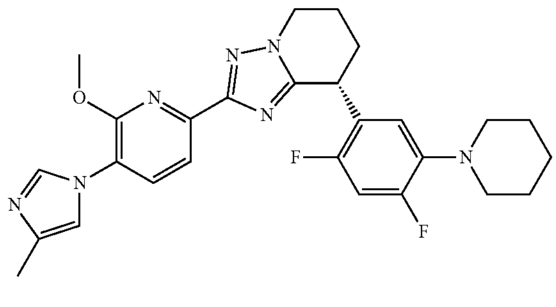 [SMILES: COc1nc(-c2nc3n(n2)CCC[C@@H]3c2cc(N3CCCCC3)c(F)cc2F)ccc1-n1cnc(C)c1] | ESI-MS; m/z 254 [1/2$M^+$ + H], 506 [$M^+$ + H]. |

TABLE 31-continued
| Example No. | Structural formula | $^1$H-NMR or ESI mass |
|---|---|---|
| Example 301 | 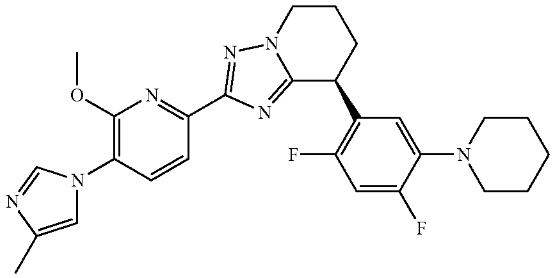 [SMILES: COc1nc(-c2nc3n(n2)CCC[C@H]3c2cc(N3CCCCC3)c(F)cc2F)ccc1-n1cnc(C)c1] | ESI-MS; m/z 254 [1/2M$^+$ + H], 506 [M$^+$ + H]. |
TABLE 32
| Example No. | Structural formula | $^1$H-NMR or ESI mass |
|---|---|---|
| Example 302 | 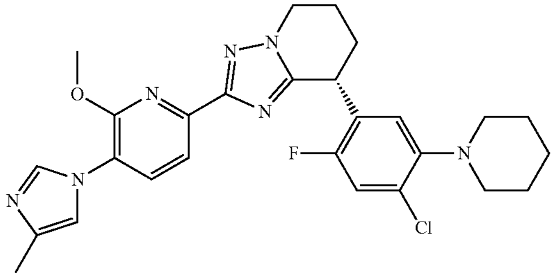 [SMILES: COc1nc(-c2nc3n(n2)CCC[C@@H]3c2cc(N3CCCCC3)c(Cl)cc2F)ccc1-n1cnc(C)c1] | ESI-MS; m/z 262 [1/2M$^+$ + H], 522 [M$^+$ + H]. |
| Example 303 | 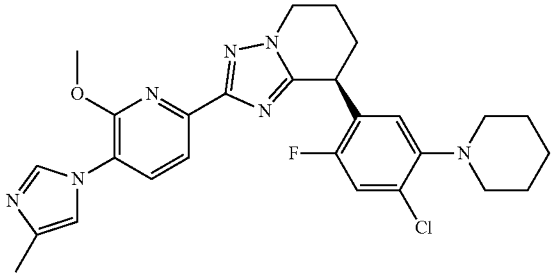 [SMILES: COc1nc(-c2nc3n(n2)CCC[C@H]3c2cc(N3CCCCC3)c(Cl)cc2F)ccc1-n1cnc(C)c1] | ESI-MS; m/z 262 [1/2M$^+$ + H], 522 [M$^+$ + H]. |
| Example 304 | 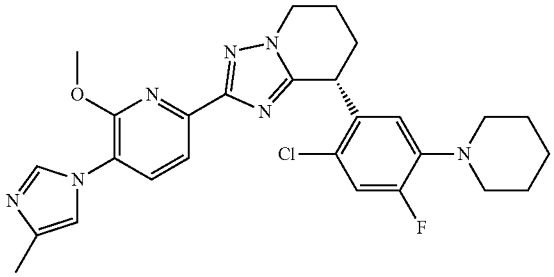 [SMILES: COc1nc(-c2nc3n(n2)CCC[C@@H]3c2cc(N3CCCCC3)c(F)cc2Cl)ccc1-n1cnc(C)c1] | ESI-MS; m/z 262 [1/2M$^+$ + H], 522 [M$^+$ + H]. |
| Example 305 | 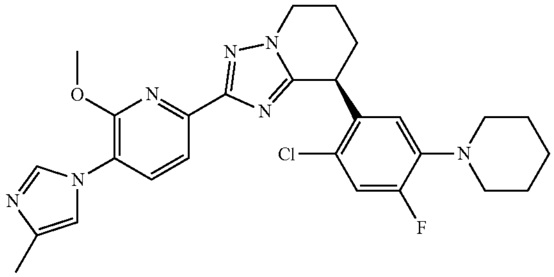 [SMILES: COc1nc(-c2nc3n(n2)CCC[C@H]3c2cc(N3CCCCC3)c(F)cc2Cl)ccc1-n1cnc(C)c1] | ESI-MS; m/z 262 [1/2M$^+$ + H], 522 [M$^+$ + H]. |

TABLE 32-continued
| Example No. | Structural formula | $^1$H-NMR or ESI mass |
|---|---|---|
| Example 306 | 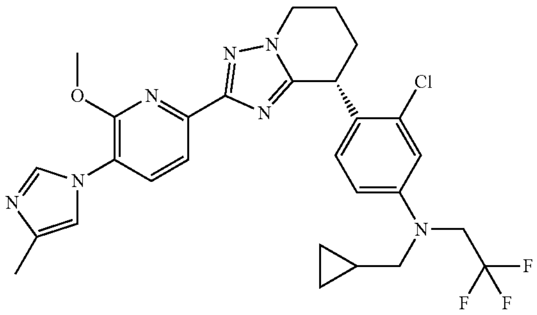 [SMILES: COc1nc(-c2nc3n(n2)CCC[C@@H]3c2ccc(N(CC3CC3)CC(F)(F)F)cc2Cl)ccc1-n1cnc(C)c1] | ESI-MS; m/z 286 [1/2M$^+$ + H], 572 [M$^+$ + H]. |
| Example 307 | 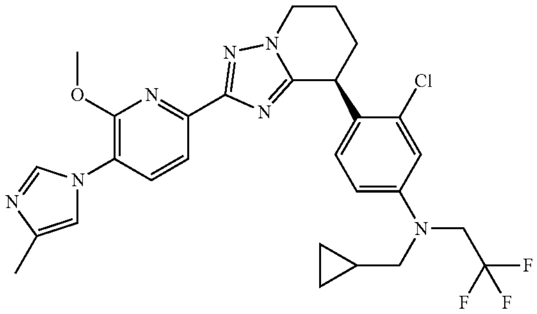 [SMILES: COc1nc(-c2nc3n(n2)CCC[C@H]3c2ccc(N(CC3CC3)CC(F)(F)F)cc2Cl)ccc1-n1cnc(C)c1] | ESI-MS; m/z 286 [1/2M$^+$ + H], 572 [M$^+$ + H]. |
TABLE 33
| Example No. | Structural formula | $^1$H-NMR or ESI mass |
|---|---|---|
| Example 308 | 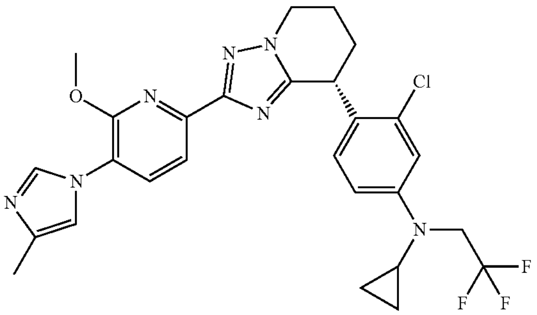 [SMILES: COc1nc(-c2nc3n(n2)CCC[C@@H]3c2ccc(N(CC(F)(F)F)C3CC3)cc2Cl)ccc1-n1cnc(C)c1] | ESI-MS; m/z 279[1/2M$^+$ + H], 558[M$^+$ + H]. |
| Example 309 | 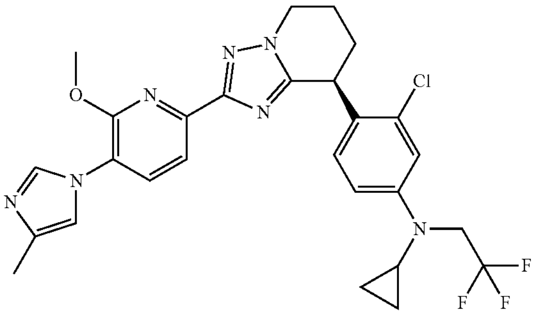 [SMILES: COc1nc(-c2nc3n(n2)CCC[C@H]3c2ccc(N(CC(F)(F)F)C3CC3)cc2Cl)ccc1-n1cnc(C)c1] | ESI-MS; m/z 279[1/2M$^+$ + H], 558[M$^+$ + H]. |

TABLE 33-continued
| Example No. | Structural formula | $^1$H-NMR or ESI mass |
|---|---|---|
| Example 310 | 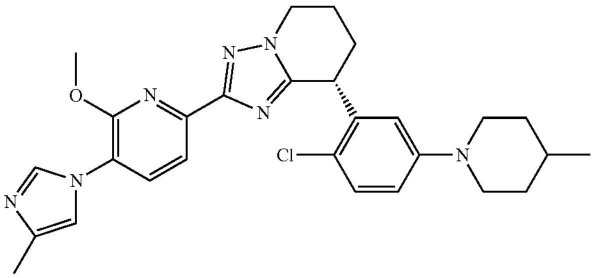 [SMILES: COc1nc(-c2nc3n(n2)CCC[C@@H]3c2cc(N3CCC(C)CC3)ccc2Cl)ccc1-n1cnc(C)c1] | ESI-MS; m/z 260[1/2M$^+$ + H], 518[M$^+$ + H]. |
| Example 311 | 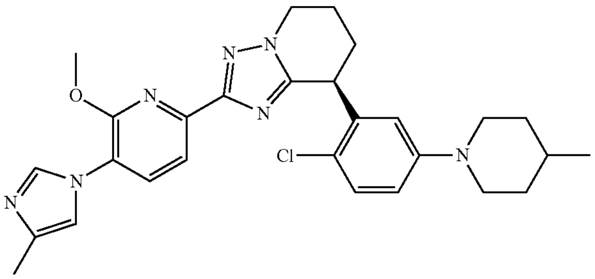 [SMILES: COc1nc(-c2nc3n(n2)CCC[C@H]3c2cc(N3CCC(C)CC3)ccc2Cl)ccc1-n1cnc(C)c1] | ESI-MS; m/z 260[1/2M$^+$ + H], 518[M$^+$ + H]. |
| Example 312 | 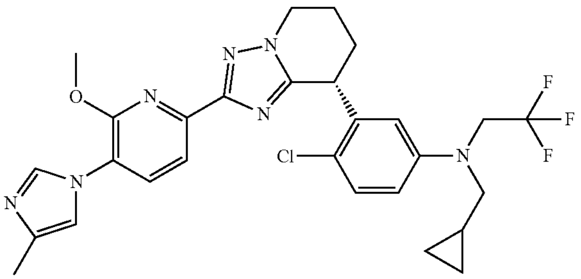 [SMILES: COc1nc(-c2nc3n(n2)CCC[C@@H]3c2cc(N(CC3CC3)CC(F)(F)F)ccc2Cl)ccc1-n1cnc(C)c1] | ESI-MS; m/z 572[M$^+$ + H]. |
| Example 313 | 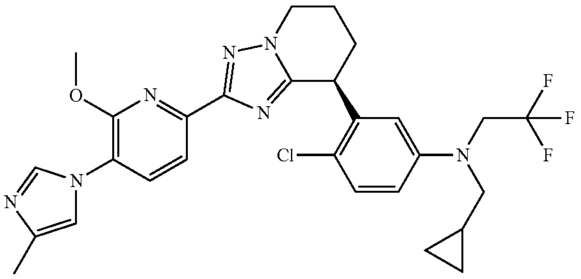 [SMILES: COc1nc(-c2nc3n(n2)CCC[C@H]3c2cc(N(CC3CC3)CC(F)(F)F)ccc2Cl)ccc1-n1cnc(C)c1] | ESI-MS; m/z 572[M$^+$ + H]. |

TABLE 34
| Example No. | Structural formula | $^1$H-NMR or ESI mass |
|---|---|---|
| Example 314 | 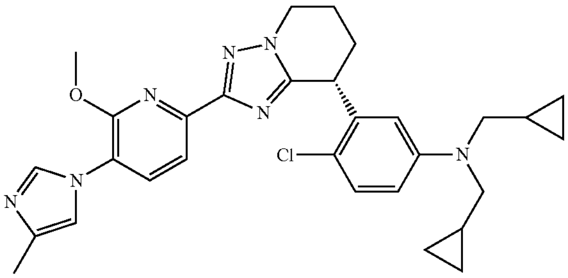 [SMILES: COc1nc(-c2nc3n(n2)CCC[C@@H]3c2cc(N(CC3CC3)CC3CC3)ccc2Cl)ccc1-n1cnc(C)c1] | ESI-MS; m/z 544[$M^+$ + H]. |
| Example 315 | 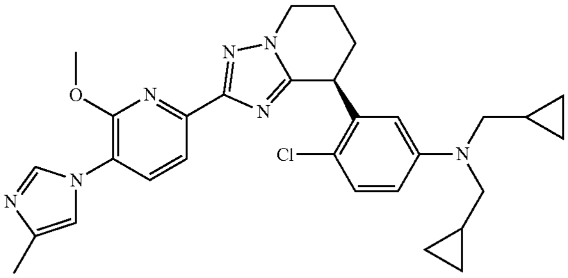 [SMILES: COc1nc(-c2nc3n(n2)CCC[C@H]3c2cc(N(CC3CC3)CC3CC3)ccc2Cl)ccc1-n1cnc(C)c1] | ESI-MS; m/z 544[$M^+$ + H]. |
| Example 316 | 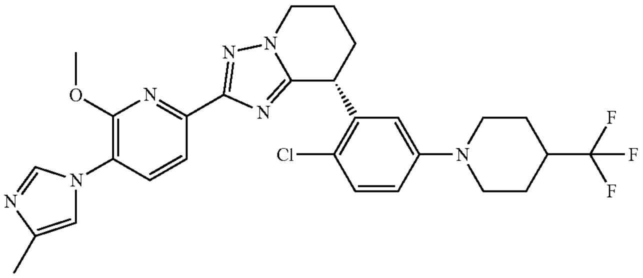 [SMILES: COc1nc(-c2nc3n(n2)CCC[C@@H]3c2cc(N3CCC(C(F)(F)F)CC3)ccc2Cl)ccc1-n1cnc(C)c1] | ESI-MS; m/z 572[$M^+$ + H]. |
| Example 317 | 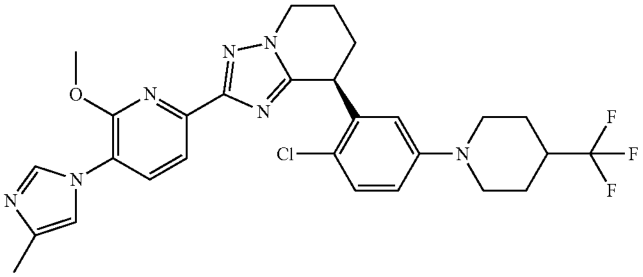 [SMILES: COc1nc(-c2nc3n(n2)CCC[C@H]3c2cc(N3CCC(C(F)(F)F)CC3)ccc2Cl)ccc1-n1cnc(C)c1] | ESI-MS; m/z 572[$M^+$ + H]. |
| Example 318 | 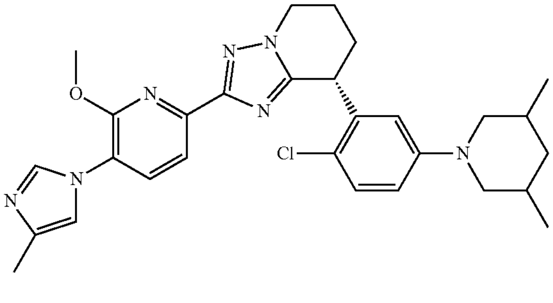 [SMILES: COc1nc(-c2nc3n(n2)CCC[C@@H]3c2cc(N3CC(C)CC(C)C3)ccc2Cl)ccc1-n1cnc(C)c1] | ESI-MS; m/z 532[$M^+$ + H]. |

TABLE 34-continued
| Example No. | Structural formula | ¹H-NMR or ESI mass |
|---|---|---|
| Example 319 | 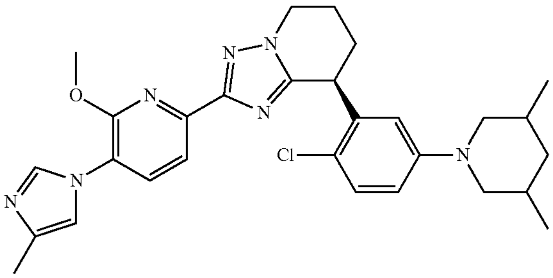 [SMILES: COc1nc(-c2nc3n(n2)CCC[C@H]3c2cc(N3CC(C)CC(C)C3)ccc2Cl)ccc1-n1cnc(C)c1] | ESI-MS; m/z 532[$M^+$ + H]. |
TABLE 35
| Example No. | Structural formula | ¹H-NMR or ESI mass |
|---|---|---|
| Example 320 | 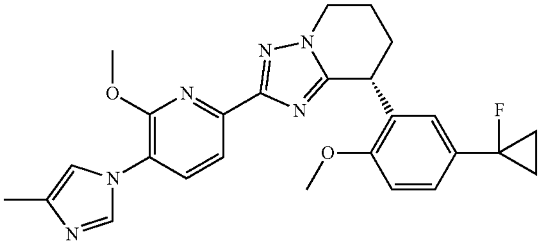 [SMILES: COc1ccc(C2(F)CC2)cc1[C@H]1CCCn2nc(-c3ccc(-n4cnc(C)c4)c(OC)n3)nc21] | ESI-MS; m/z 475[$M^+$ + H]. |
| Example 321 | 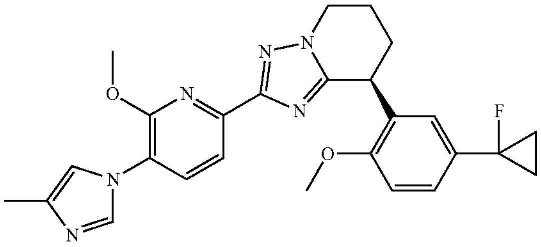 [SMILES: COc1ccc(C2(F)CC2)cc1[C@@H]1CCCn2nc(-c3ccc(-n4cnc(C)c4)c(OC)n3)nc21] | ESI-MS; m/z 475[$M^+$ + H]. |
| Example 322 | 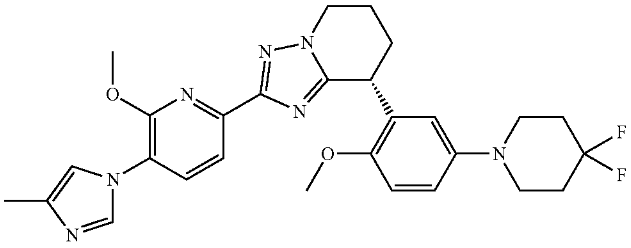 [SMILES: COc1ccc(N2CCC(F)(F)CC2)cc1[C@H]1CCCn2nc(-c3ccc(-n4cnc(C)c4)c(OC)n3)nc21] | ESI-MS; m/z 500[$M^+$ + H]. |
| Example 323 | 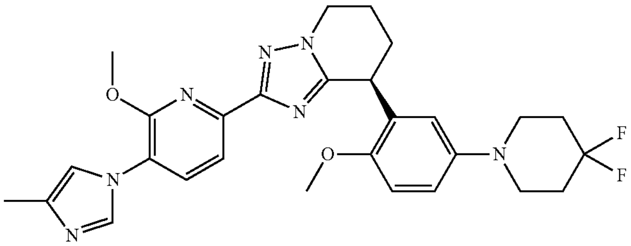 [SMILES: COc1ccc(N2CCC(F)(F)CC2)cc1[C@@H]1CCCn2nc(-c3ccc(-n4cnc(C)c4)c(OC)n3)nc21] | ESI-MS; m/z 500[$M^+$ + H]. |

TABLE 35-continued
| Example No. | Structural formula | ¹H-NMR or ESI mass |
|---|---|---|
| Example 324 | 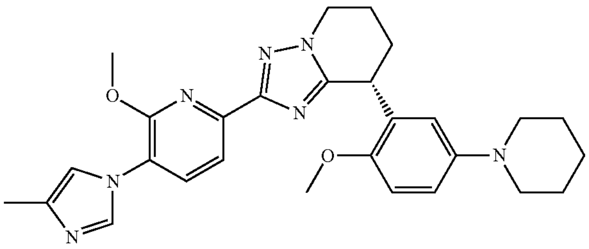 | ESI-MS; m/z 536[$M^+$ + H]. |
| Example 325 | 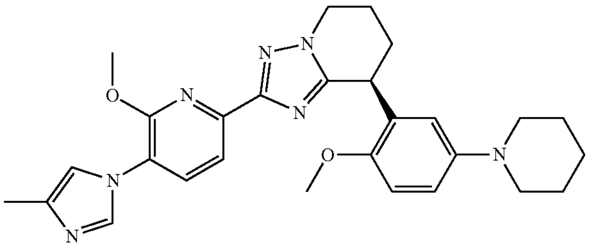 | ESI-MS; m/z 536[$M^+$ + H]. |
TABLE 36
| Example No. | Structural formula | ¹H-NMR or ESI mass |
|---|---|---|
| Example 326 | 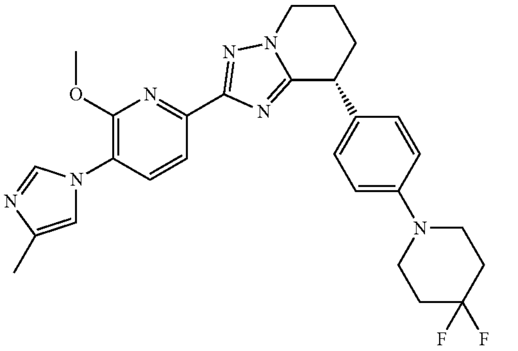 [SMILES: COc1nc(-c2nc3n(n2)CCC[C@@H]3c2ccc(N3CCC(F)(F)CC3)cc2)ccc1-n1cnc(C)c1] | ESI-MS; m/z 506[$M^+$ + H]. |
| Example 327 | 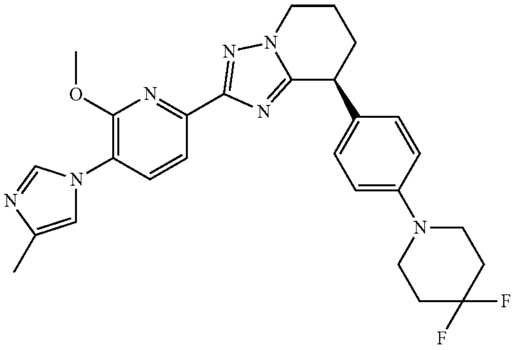 [SMILES: COc1nc(-c2nc3n(n2)CCC[C@H]3c2ccc(N3CCC(F)(F)CC3)cc2)ccc1-n1cnc(C)c1] | ESI-MS; m/z 506[$M^+$ + H]. |

TABLE 36-continued
| Example No. | Structural formula | $^1$H-NMR or ESI mass |
|---|---|---|
| Example 328 | 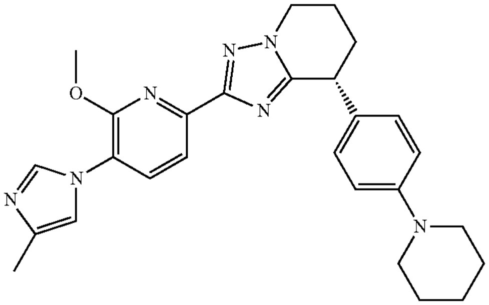 [SMILES: COc1nc(-c2nc3n(n2)CCC[C@@H]3c2ccc(N3CCCCC3)cc2)ccc1-n1cnc(C)c1] | ESI-MS; m/z 470[M$^+$ + H]. |
| Example 329 | 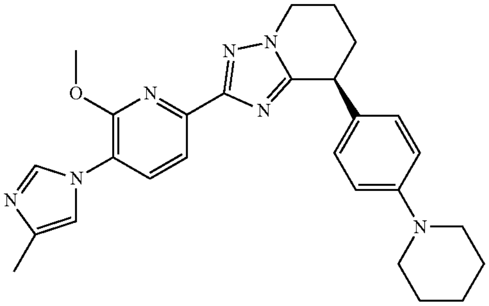 [SMILES: COc1nc(-c2nc3n(n2)CCC[C@H]3c2ccc(N3CCCCC3)cc2)ccc1-n1cnc(C)c1] | ESI-MS; m/z 470[M$^+$ + H]. |
| Example 330 | 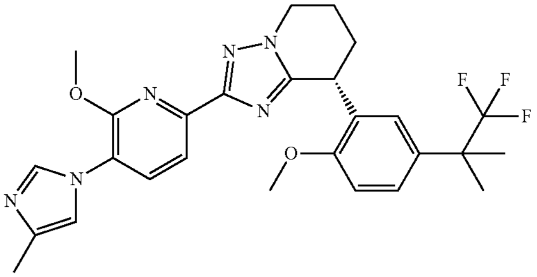 [SMILES: COc1ccc(C(C)(C)C(F)(F)F)cc1[C@H]1CCCn2nc(-c3ccc(-n4cnc(C)c4)c(OC)n3)nc21] | ESI-MS; m/z 527[M$^+$ + H]. |
| Example 331 | 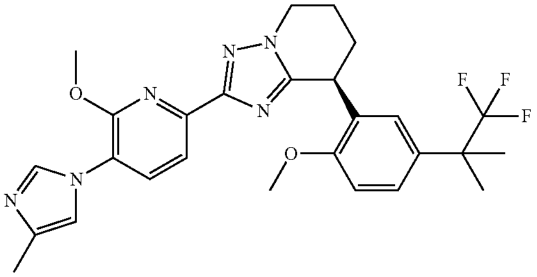 [SMILES: COc1ccc(C(C)(C)C(F)(F)F)cc1[C@@H]1CCCn2nc(-c3ccc(-n4cnc(C)c4)c(OC)n3)nc21] | ESI-MS; m/z 527[M$^+$ + H]. |

TABLE 37
| Example No. | Structural formula | $^1$H-NMR or ESI mass |
|---|---|---|
| Example 332 | 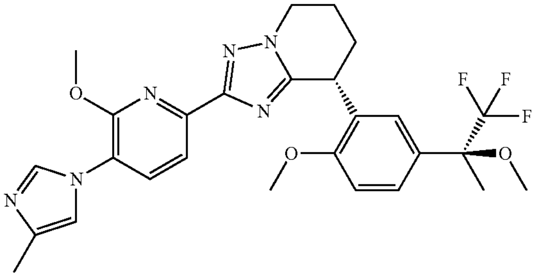 [SMILES: COc1ccc([C@](C)(OC)C(F)(F)F)cc1[C@H]1CCCn2nc(-c3ccc(-n4cnc(C)c4)c(OC)n3)nc21] | ESI-MS; m/z 543[M$^+$ + H]. |
| Example 333 | 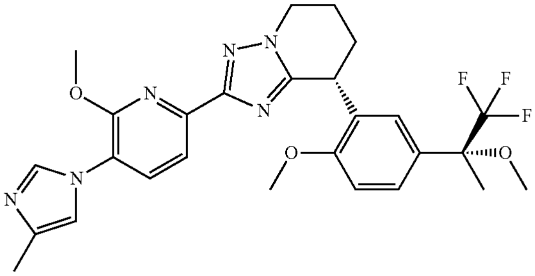 [SMILES: COc1ccc([C@@](C)(OC)C(F)(F)F)cc1[C@H]1CCCn2nc(-c3ccc(-n4cnc(C)c4)c(OC)n3)nc21] | ESI-MS; m/z 543[M$^+$ + H]. |
| Example 334 | 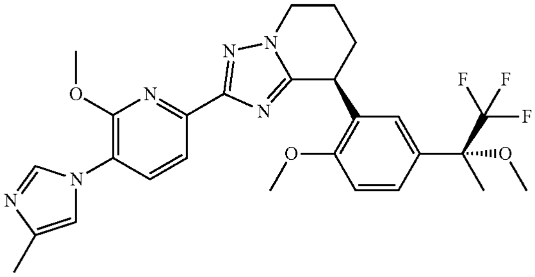 [SMILES: COc1ccc([C@@](C)(OC)C(F)(F)F)cc1[C@@H]1CCCn2nc(-c3ccc(-n4cnc(C)c4)c(OC)n3)nc21] | ESI-MS; m/z 543[M$^+$ + H]. |
| Example 335 | 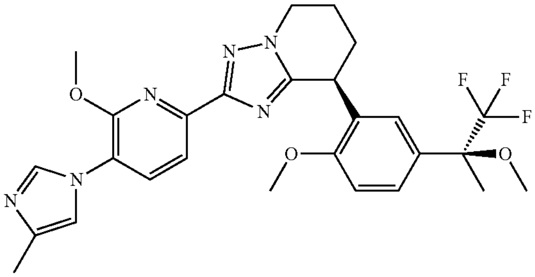 [SMILES: COc1ccc([C@](C)(OC)C(F)(F)F)cc1[C@@H]1CCCn2nc(-c3ccc(-n4cnc(C)c4)c(OC)n3)nc21] | ESI-MS; m/z 543[M$^+$ + H]. |
| Example 336 | 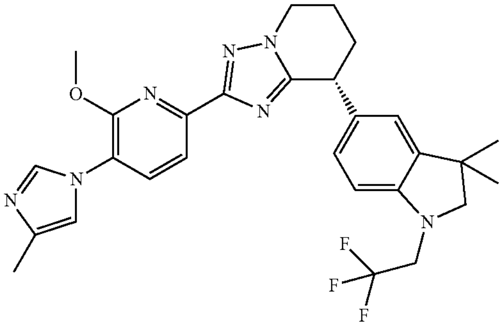 [SMILES: COc1nc(-c2nc3n(n2)CCC[C@@H]3c2ccc3c(c2)C(C)(C)CN3CC(F)(F)F)ccc1-n1cnc(C)c1] | ESI-MS; m/z 538[M$^+$ + H]. |

TABLE 37-continued
| Example No. | Structural formula | $^1$H-NMR or ESI mass |
|---|---|---|
| Example 337 | 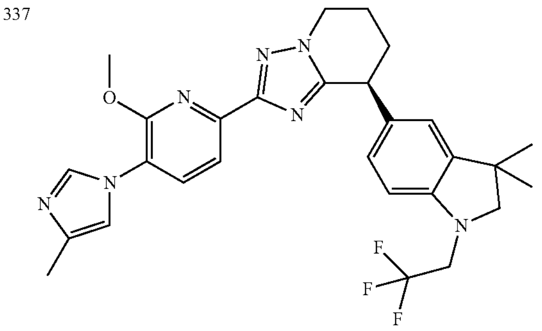 | ESI-MS; m/z 538[M$^+$ + H]. |
TABLE 38
| Example No. | Structural formula | $^1$H-NMR or ESI mass |
|---|---|---|
| Example 338 | 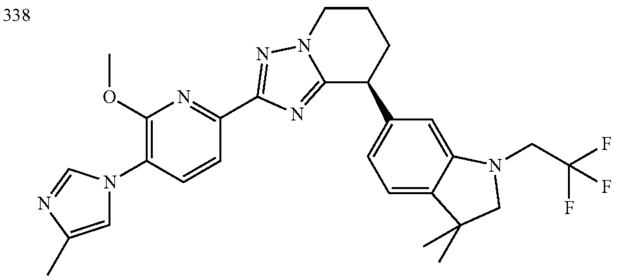 | ESI-MS; m/z 538[M$^+$ + H]. |
| Example 339 | 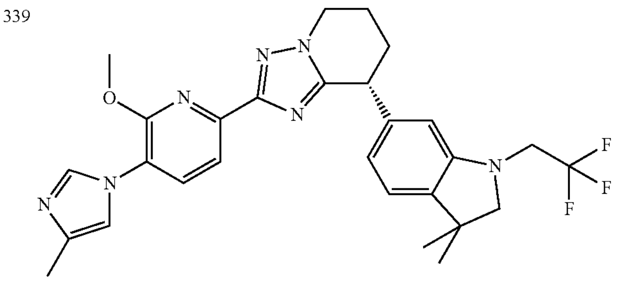 | ESI-MS; m/z 538[M$^+$ + H]. |
| Example 340 | 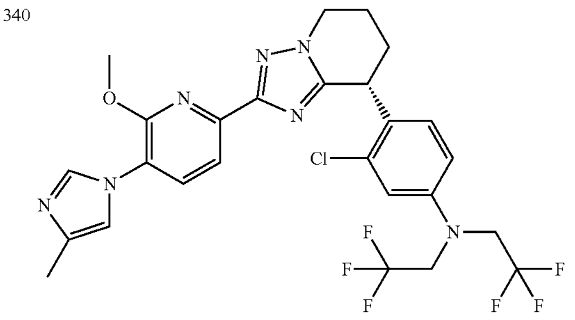 | ESI-MS; m/z 600[M$^+$ + H]. |

TABLE 38-continued
| Example No. | Structural formula | $^1$H-NMR or ESI mass |
|---|---|---|
| Example 341 | 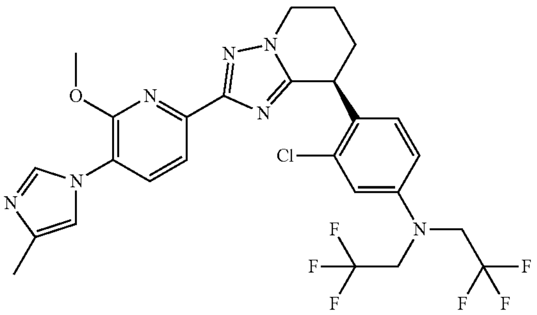 [SMILES: COc1nc(-c2nc3n(n2)CCC[C@H]3c2ccc(N(CC(F)(F)F)CC(F)(F)F)cc2Cl)ccc1-n1cnc(C)c1] | ESI-MS; m/z 600[$M^+$ + H]. |
| Example 342 | 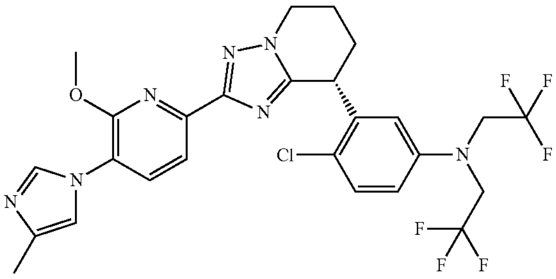 [SMILES: COc1nc(-c2nc3n(n2)CCC[C@@H]3c2cc(N(CC(F)(F)F)CC(F)(F)F)ccc2Cl)ccc1-n1cnc(C)c1] | ESI-MS; m/z 600[$M^+$ + H]. |
| Example 343 | 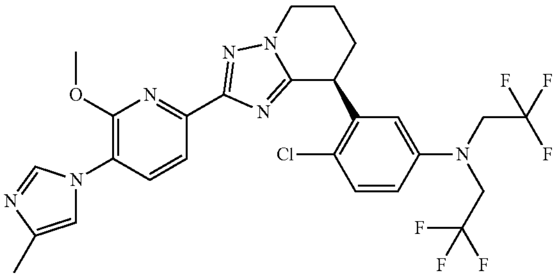 [SMILES: COc1nc(-c2nc3n(n2)CCC[C@H]3c2cc(N(CC(F)(F)F)CC(F)(F)F)ccc2Cl)ccc1-n1cnc(C)c1] | ESI-MS; m/z 600[$M^+$ + H]. |
TABLE 39
| Example No. | Structural formula | $^1$H-NMR or ESI mass |
|---|---|---|
| Example 344 | 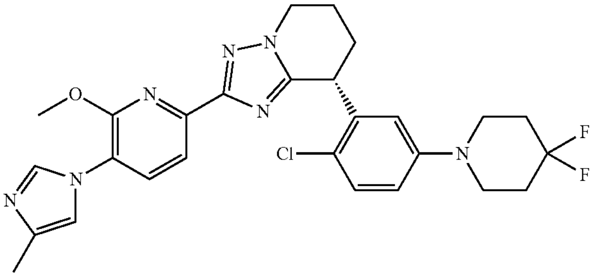 [SMILES: COc1nc(-c2nc3n(n2)CCC[C@@H]3c2cc(N3CCC(F)(F)CC3)ccc2Cl)ccc1-n1cnc(C)c1] | ESI-MS; m/z 540[$M^+$ + H]. |

TABLE 39-continued
| Example No. | Structural formula | $^1$H-NMR or ESI mass |
|---|---|---|
| Example 345 | 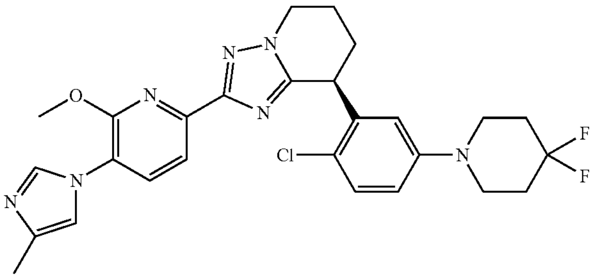 [SMILES: COc1nc(-c2nc3n(n2)CCC[C@H]3c2cc(N3CCC(F)(F)CC3)ccc2Cl)ccc1-n1cnc(C)c1] | ESI-MS; m/z 540[$M^+$ + H]. |
| Example 346 | 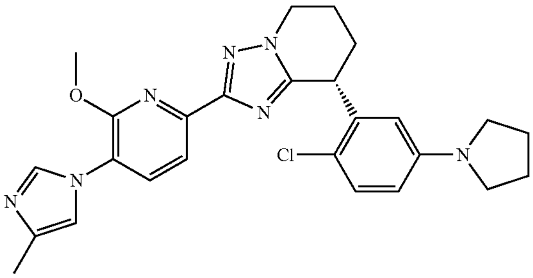 [SMILES: COc1nc(-c2nc3n(n2)CCC[C@@H]3c2cc(N3CCCC3)ccc2Cl)ccc1-n1cnc(C)c1] | ESI-MS; m/z 490[$M^+$ + H]. |
| Example 347 | 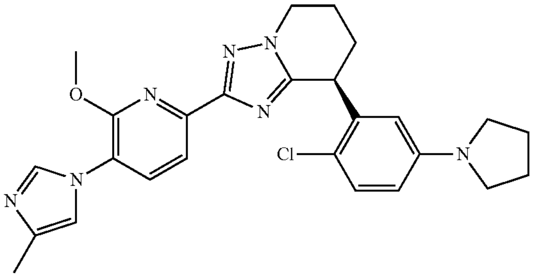 [SMILES: COc1nc(-c2nc3n(n2)CCC[C@H]3c2cc(N3CCCC3)ccc2Cl)ccc1-n1cnc(C)c1] | ESI-MS; m/z 490[$M^+$ + H]. |
| Example 348 | 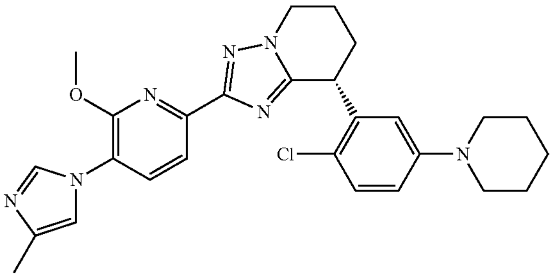 | ESI-MS; m/z 504[$M^+$ + H]. |
| Example 349 | 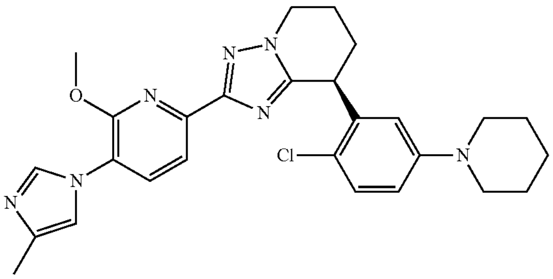 [SMILES: COc1nc(-c2nc3n(n2)CCC[C@H]3c2cc(N3CCCCC3)ccc2Cl)ccc1-n1cnc(C)c1] | ESI-MS; m/z 504[$M^+$ + H]. |

Examples 350 and 351

Syntheses of (+)-8-(2-chloro-5-pyridin-3-yl)phenyl)-2-[6-methoxy-5-(4-methyl-1H-imidazol-1-yl)pyridin-2-yl]-5,6,7,8-tetrahydro[1,2,4]triazolo[1,5-a]pyridine and (−)-8-(2-chloro-5-pyridin-3-yl)phenyl)-2,6-methoxy-5-(4-methyl-1H-imidazol-1-yl)pyridin-2-yl]-5,6,7,8-tetrahydro[1,2,4]triazolo[1,5-a]pyridine

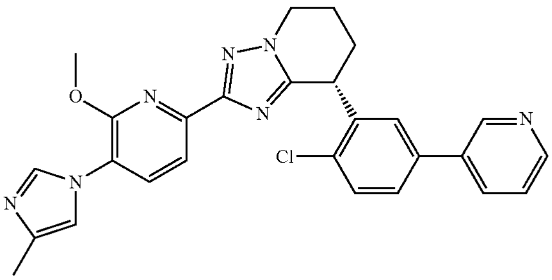

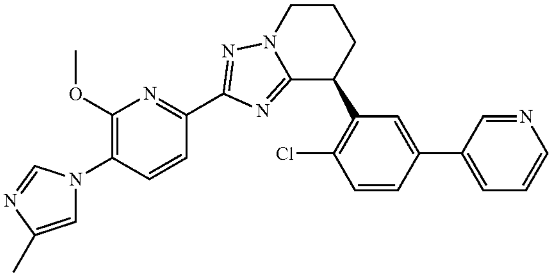

8-(5-bromo-2-fluorophenyl)-2-[6-methoxy-5-(4-methyl-1H-imidazol-1-yl)pyridin-2-yl]-5,6,7,8-tetrahydro[1,2,4]triazolo[1,5-a]pyridine The racemate of the title compound (3.22 g) was obtained according to the method of Examples 42 and 43 from 6-methoxy-5-(4-methyl-1H-imidazol-1-yl)pyridin 2-carboxylic acid hydrazide hydrochloride (2.48 g) obtained in Preparation Example 1-6 and ethyl 2-(5-bromo-2-chlorophenyl)-5-chloropentaneimidiate hydrochloride (3.9 g) obtained in Preparation Example 3-64.

ESI-MS; m/z 501[$M^+$+H].

Synthesis of (+)-8-(2-chloro-5-pyridin-3-yl)phenyl)-2-[6-methoxy-5-(4-methyl-1H-imidazol-1-yl)pyridin-2-yl]-5,6,7,8-tetrahydro[1,2,4]triazolo[1,5-a]pyridine and (−)-8-2-chloro-5-pyridin-3-yl)phenyl]-2-[6-methoxy-5-(4-methyl-1H-imidazol-1-yl)pyridin-2-yl]-5,6,7,8-tetrahydro[1,2,4]triazolo[1,5-a]pyridine The racemate of the title compound (181 mg) was obtained according to the method of Examples 1 and 2 from 8-(5-bromo-2-chlorophenyl)-2-[6-methoxy-5-(4-methyl-1H-imidazol-1-yl)pyridin-2-yl]-5,6,7,8-tetrahydro[1,2,4]triazolo[1,5-a]pyridine (200 mg) and 3-tributylstannylpyridine (221 mg).

The resulting racemate was separated by CHIRALPAK™ IB (2 cm×25 cm, mobile phase: 50% ethanol-hexane) to obtain the title compound with positive optical rotation (80 mg, >99% ee) and the title compound with negative optical rotation (78 mg, >99% ee).

The property values of the title optically active compound with positive optical rotation are as follows.

ESI-MS; m/z 250 [½$M^+$+H], 498[$M^+$+H].

The property values of the title optically active compound with negative optical rotation are as follows.

ESI-MS; m/z 250 [½$M^+$+H], 498[$M^+$+H].

Examples 352-359

Compounds of Examples 352-359 were obtained according to the method of Examples 350 and 351 shown in Table 40.

TABLE 40

| Example No. | Structural formula | $^1$H-NMR or ESI mass |
|---|---|---|
| Example 352 | 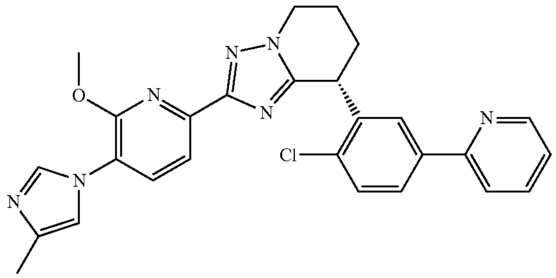 [SMILES: COc1nc(-c2nc3n(n2)CCC[C@@H]3c2cc(-c3ccccn3)ccc2Cl)ccc1-n1cnc(C)c1] | ESI-MS; m/z 250[1/2$M^+$ + H], 498[$M^+$ + H]. |
| Example 353 | 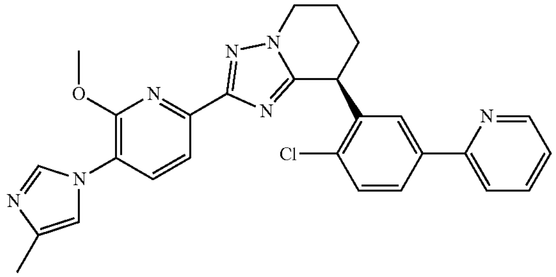 [SMILES: COc1nc(-c2nc3n(n2)CCC[C@H]3c2cc(-c3ccccn3)ccc2Cl)ccc1-n1cnc(C)c1] | ESI-MS; m/z 250[1/2$M^+$ + H], 498[$M^+$ + H]. |

TABLE 40-continued
| Example No. | Structural formula | $^1$H-NMR or ESI mass |
|---|---|---|
| Example 354 | 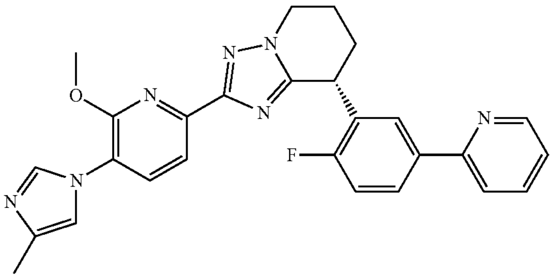 [SMILES: COc1nc(-c2nc3n(n2)CCC[C@@H]3c2cc(-c3ccccn3)ccc2F)ccc1-n1cnc(C)c1] | ESI-MS; m/z 242[1/2M$^+$ + H], 482[M$^+$ + H]. |
| Example 355 | 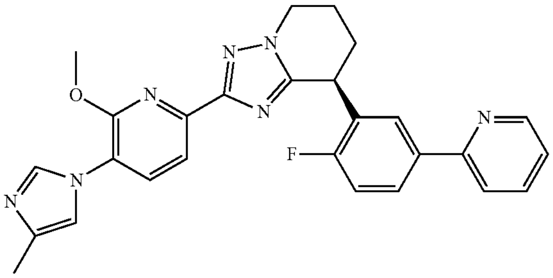 [SMILES: COc1nc(-c2nc3n(n2)CCC[C@H]3c2cc(-c3ccccn3)ccc2F)ccc1-n1cnc(C)c1] | ESI-MS; m/z 242[1/2M$^+$ + H], 482[M$^+$ + H]. |
| Example 356 | 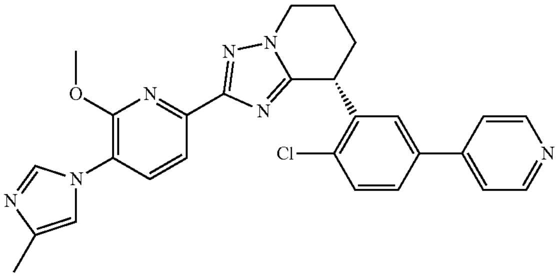 [SMILES: COc1nc(-c2nc3n(n2)CCC[C@@H]3c2cc(-c3ccncc3)ccc2Cl)ccc1-n1cnc(C)c1] | ESI-MS; m/z 250[1/2M$^+$ + H], 498[M$^+$ + H]. |
| Example 357 | 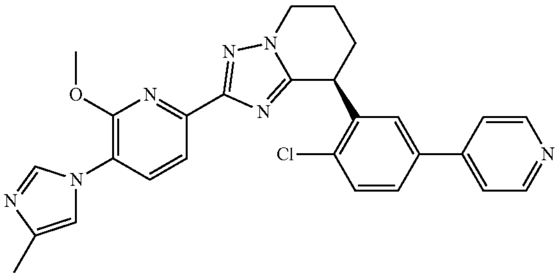 [SMILES: COc1nc(-c2nc3n(n2)CCC[C@H]3c2cc(-c3ccncc3)ccc2Cl)ccc1-n1cnc(C)c1] | ESI-MS; m/z 250[1/2M$^+$ + H], 498[M$^+$ + H]. |
| Example 358 | 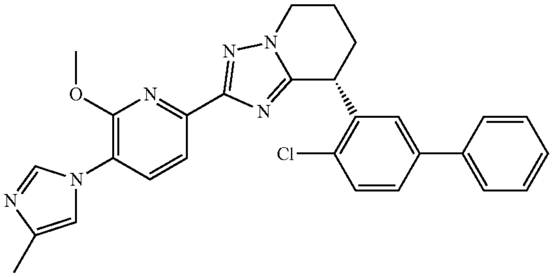 [SMILES: COc1nc(-c2nc3n(n2)CCC[C@@H]3c2cc(-c3ccccc3)ccc2Cl)ccc1-n1cnc(C)c1] | ESI-MS; m/z 249[1/2M$^+$ + H], 497[M$^+$ + H]. |

TABLE 40-continued

| Example No. | Structural formula | $^1$H-NMR or ESI mass |
|---|---|---|
| Example 359 | 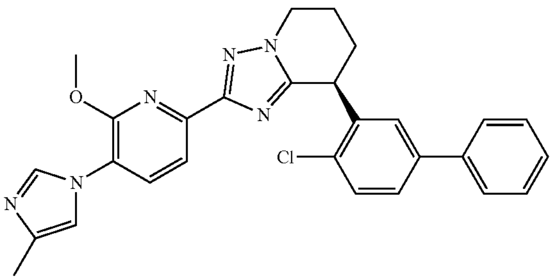 [SMILES: COc1nc(-c2nc3n(n2)CCC[C@H]3c2cc(-c3ccccc3)ccc2Cl)ccc1-n1cnc(C)c1] | ESI-MS; m/z 249[1/2M$^+$ + H], 497[M$^+$ + H]. |

Example 360-361

Syntheses of (+)-8-[2-chloro-5-5-trifluoromethylpyridine-2-yl)phenyl]-2-6-methoxy-5-4-methyl-1H-imidazol-1-yl)pyridine-2-yl]-5,6,7,8-tetrahydro[1,2,4]triazolo [1,5-a]pyridine and (−)-8-[2-chloro-5-5-trifluoromethylpyridine-2-yl)phenyl]-2-[6-methoxy-5-(4-methyl-1H-imidazol-1-yl)pyridine-2-yl]-5,6,7,8-tetrahydro[1,2,4]triazolo[1,5-a]pyridine

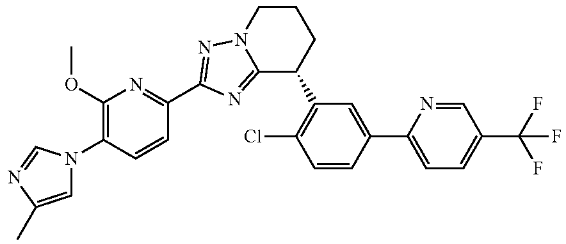

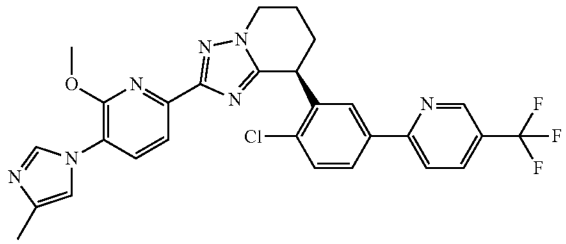

Synthesis of 8-(2-chloro-5-tributylstannylphenyl)-2,6-methoxy-5-(4-methyl-1H-imidazol-1-yl)pyridine-2-yl]-5,6,7,8-tetrahydro [1,2,4]triazolo[1,5-a]pyridine To a solution of 8-(5-bromo-2-chlorophenyl)-2-[6-methoxy-5-(4-methyl-1H-imidazole-1-yl) pyridine-2-yl]-5,6,7,8-tetrahydro [1,2,4]triazolo[1,5-a]pyridine (500 mg) obtained in Examples 350 and 351 and hexa-n-butylditin (633 μl) in N-methyl-2-pyrrolidine (10 ml) was added tetrakis(triphenylphosphine) palladium (57.8 mg), and the mixture was stirred at 120° C. for 7 hr under a nitrogen atmosphere. After cooling the reaction mixture, ethyl acetate was added and the mixture was washed with water. The obtained organic layer was washed with brine and dried over anhydrous sodium sulfate. After filtration of the drying agent, the organic layer was concentrated under reduced pressure. The residue was purified by NH silica gel column chromatography to obtain the title compound. (507 mg)

Syntheses of (+)-8-[2-chloro-5-(5-trifluoromethylpyridine-2-yl)phenyl]-2-[6-methoxy-5-(4-methyl-1H-imidazol-1-yl)pyridine-2-yl]-5,6,7,8-tetrahydro [1,2,4]triazolo[1,5-a]pyridine and (−)-8-[2-chloro-5-(5-trifluoromethylpyridine-2-yl)phenyl]-2-[6-methoxy-5-(4-methyl-1H-imidazole-1-yl)pyridine-2-yl]-5,6,7,8-tetrahydro[1,2,4]triazolo[1,5-a]pyridine The racemate (253 mg) of the title compound was obtained according to the methods of Examples 1 and 2 from 8-(2-chloro-5-tri-n-butylstannylphenyl)-2-[6-methoxy-5-(4-methyl-1H-imidazol-1-yl)pyridine-2-yl]-5,6,7,8-tetrahydro [1,2,4]triazolo[1,5-a]pyridine (507 mg) and 2-bromo-5-(trifluoromethyl)pyridine (242 mg). The obtained racemate was separated by CHIRALPAK™ IB (2 cm×25 cm: elution solvent; hexane:ethanol=5:5, Daicel Co., Ltd.) to obtain the title optically active compound with positive optical rotation (83 mg, >99% ee) and the title optically active compound with negative optical rotation (84 mg, >99% ee).

The property values of the title compound with positive optical rotation were as follows;

ESI-MS; m/z 284 [½M$^+$+H], 566[M$^+$+H].

The property values of the title compound with negative optical rotation were as follows;

ESI-MS; m/z 284 [½M$^+$+H],566 [M$^+$+H].

The compounds of Examples 362-363 were obtained according to the method of Examples 360-361 (Table 29).

TABLE 29
| Example No. | Structural formula | $^1$H-NMR or ESI mass |
|---|---|---|
| Example 362 | 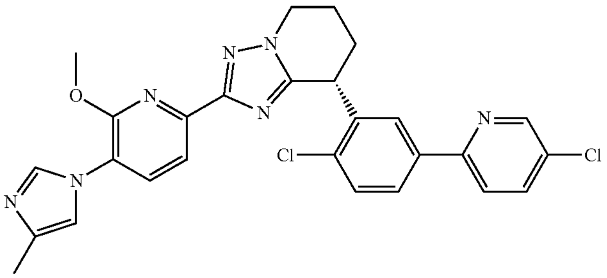 [SMILES: COc1nc(-c2nc3n(n2)CCC[C@@H]3c2cc(-c3ccc(Cl)cn3)ccc2Cl)ccc1-n1cnc(C)c1] | ESI-MS; m/z 267[1/2M$^+$ + H], 532[M$^+$ + H]. |
| Example 363 | 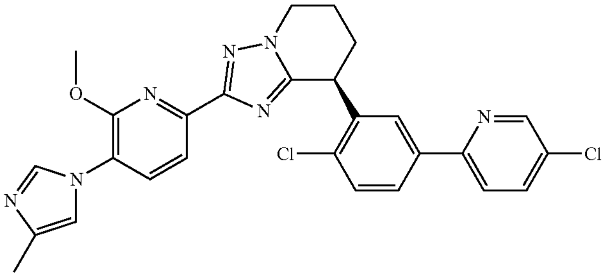 [SMILES: COc1nc(-c2nc3n(n2)CCC[C@H]3c2cc(-c3ccc(Cl)cn3)ccc2Cl)ccc1-n1cnc(C)c1] | ESI-MS; m/z 267[1/2M$^+$ + H], 532[M$^+$ + H]. |
The compounds in Examples 364-371 were obtained by the same synthetic methods as in Examples 100-101 (Table 30).
TABLE 30
| Example No. | Structural formula | $^1$H-NMR or ESI mass |
|---|---|---|
| Example 364 | 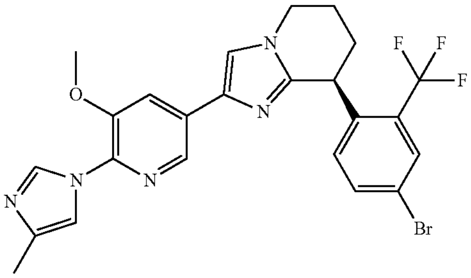 | ESI-MS; m/z 532, 534[M$^+$ + H]. |
| Example 365 | 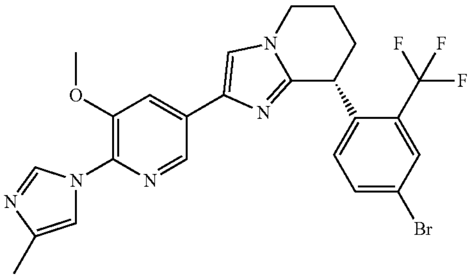 [SMILES: COc1cc(-c2cn3c(n2)[C@@H](c2ccc(Br)cc2C(F)(F)F)CCC3)cnc1-n1cnc(C)c1] | ESI-MS; m/z 532, 534[M$^+$ + H]. |

TABLE 30-continued
| Example No. | Structural formula | $^1$H-NMR or ESI mass |
|---|---|---|
| Example 366 | 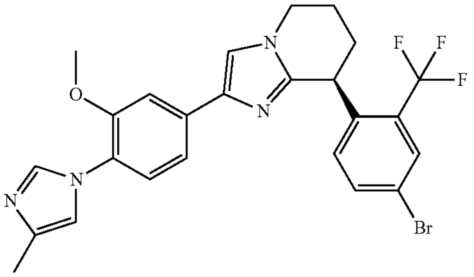 [SMILES: COc1cc(-c2cn3c(n2)[C@H](c2ccc(Br)cc2C(F)(F)F)CCC3)ccc1-n1cnc(C)c1] | ESI-MS; m/z 531, 533[M$^+$ + H]. |
| Example 367 | 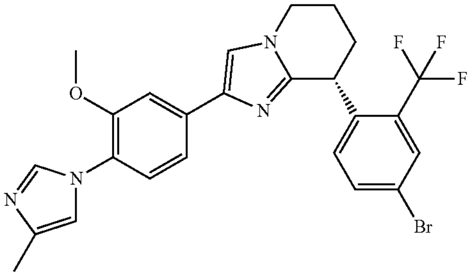 [SMILES: COc1cc(-c2cn3c(n2)[C@@H](c2ccc(Br)cc2C(F)(F)F)CCC3)ccc1-n1cnc(C)c1] | ESI-MS; m/z 531, 533[M$^+$ + H]. |
| Example 368 | 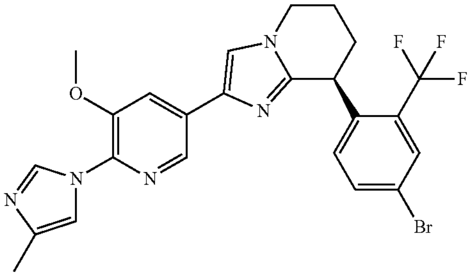 | ESI-MS; m/z 518, 520[M$^+$ + H]. |
| Example 369 | 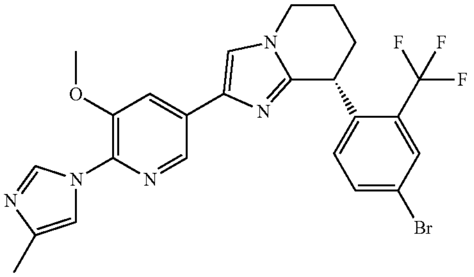 | ESI-MS; m/z 518, 520[M$^+$ + H]. |
| Example 370 | 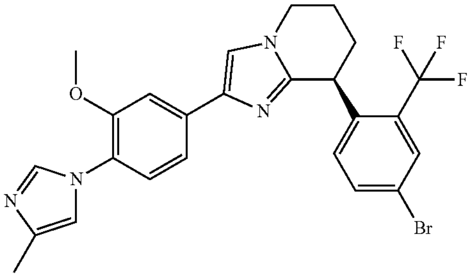 [SMILES: COc1cc(-c2cn3c(n2)[C@H](c2ccc(Br)cc2C(F)(F)F)CCC3)ccc1-n1cnc(C)c1] | ESI-MS; m/z 532, 534[M$^+$ + H]. |

TABLE 30-continued

| Example No. Structural formula | | $^1$H-NMR or ESI mass |
|---|---|---|
| Example 371 | 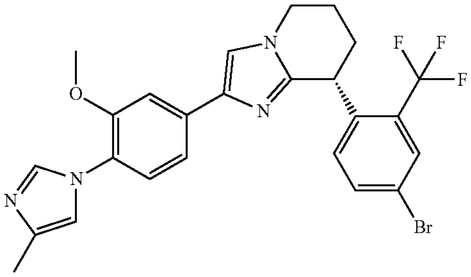 [SMILES: COc1cc(-c2cn3c(n2)[C@@H](c2ccc(Br)cc2C(F)(F)F)CCC3)ccc1-n1cnc(C)c1] | ESI-MS; m/z 532, 534[M$^+$ + H]. |

Example 372-373

Syntheses of (+)-2-[6-methoxy-5-(4-methyl-1H-imidazol-1-yl)pyridine-2-yl]-8-(5-piperidine-1-yl-thiophene-2-171)-5,6,7,8-tetrahydro triazolo[1,5-a]pyridine and (−)-2-[6-methoxy-5-(4-methyl-1H-imidazol-1-yl)pyridine-2-yl]-8-(5-piperidine-1-yl-thiophene-2-yl)-5,6,7,8-tetrahydro[1,2,4]triazolo[1,5-a]pyridine

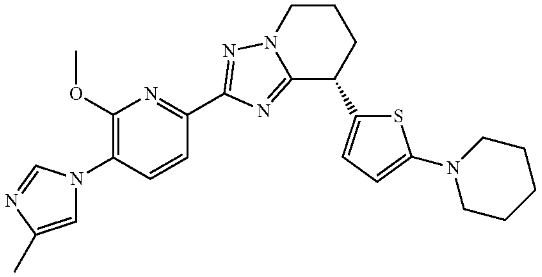

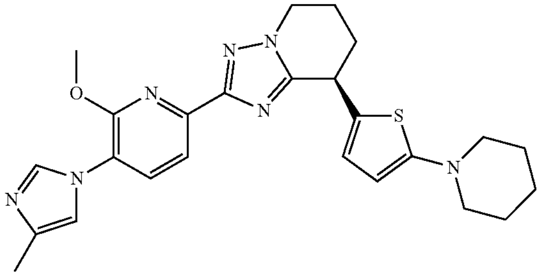

To a solution of 8-(5-bromothiophene-2-yl)-2-[6-methoxy-5-(4-methyl-1H-imidazol-1-yl)pyridine-2-yl]-5,6,7,8-tetrahydro[1,2,4]triazolo[1,5-a]pyridine (43.8 mg) obtained in Examples 82 and 83 and piperidine (9.49 mg) in dioxane (2.0 ml), bis(dibenzylideneacetone) palladium (2.67 mg), 4,5-bis(diphenylphosphino)-9,9-dimethylxanthene (5.38 mg), and sodium tert-butoxide (35.7 mg) were added and stirred at 120° C. for 3 hr under a nitrogen atmosphere. After cooling, the reaction mixture was filtrated with NH silica gel pad, and the filtrate was concentrated under reduced pressure. The residue was purified by NH silica gel chromatography to obtain the racemate of the title compound. (12.8 mg) The racemate was separated by CHIRALPAK™ IB (2 cm×25 cm: elution solvent; hexane:ethanol=8:2, Daicel Co., Ltd.) to obtain the title optically active compound with positive optical rotation (1.2 mg, >99% ee) and the title optically active compound with negative optical rotation (1.3 mg, >99% ee).

The property value of the title compound with positive optical rotation is as follows;

ESI-MS; m/z 476 [M$^+$+H].

The property value of the title compound with negative optical rotation is as follows;

ESI-MS; m/z 476 [M$^+$+H].

The compounds of Examples 374 to 383 were obtained by the same methods as in Examples 372-373 (Table 31).

TABLE 31

| Example No. Structural formula | | $^1$H-NMR or ESI mass |
|---|---|---|
| Example 374 | 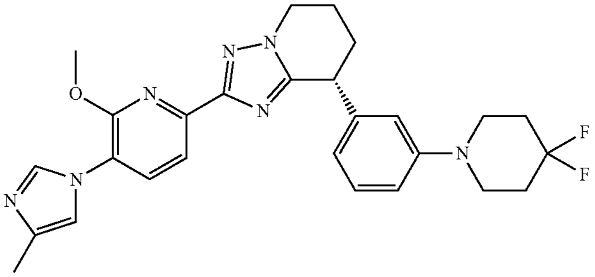 [SMILES: COc1nc(-c2nc3n(n2)CCC[C@@H]3c2cccc(N3CCC(F)(F)CC3)c2)ccc1-n1cnc(C)c1] | ESI-MS; m/z 506[M$^+$ + H]. |

TABLE 31-continued
| Example No. | Structural formula | $^1$H-NMR or ESI mass |
|---|---|---|
| Example 375 | 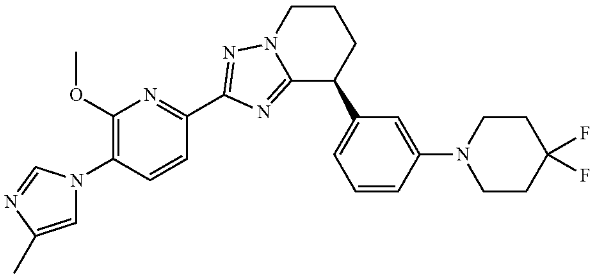 [SMILES: COc1nc(-c2nc3n(n2)CCC[C@H]3c2cccc(N3CCC(F)(F)CC3)c2)ccc1-n1cnc(C)c1] | ESI-MS; m/z 506[$M^+$ + H]. |
| Example 376 | 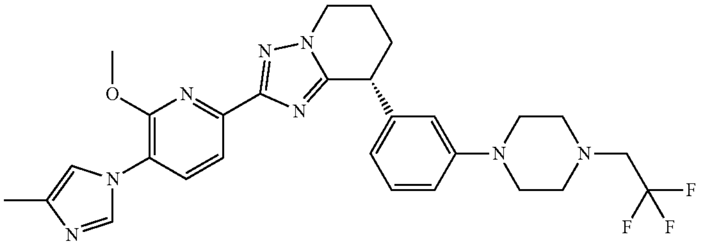 [SMILES: COc1nc(-c2nc3n(n2)CCC[C@@H]3c2cccc(N3CCN(CC(F)(F)F)CC3)c2)ccc1-n1cnc(C)c1] | ESI-MS; m/z 553[$M^+$ + H]. |
| Example 377 | 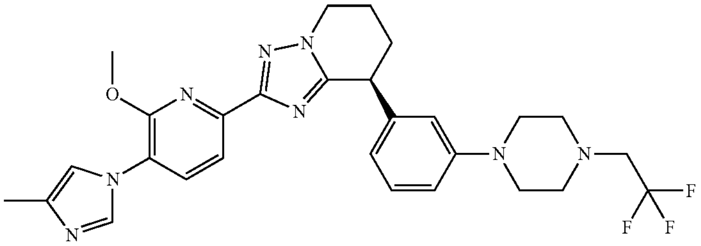 [SMILES: COc1nc(-c2nc3n(n2)CCC[C@H]3c2cccc(N3CCN(CC(F)(F)F)CC3)c2)ccc1-n1cnc(C)c1] | ESI-MS; m/z 553[$M^+$ + H]. |
TABLE 32
| Example No. | Structural formula | $^1$H-NMR or ESI mass |
|---|---|---|
| Example 378 | 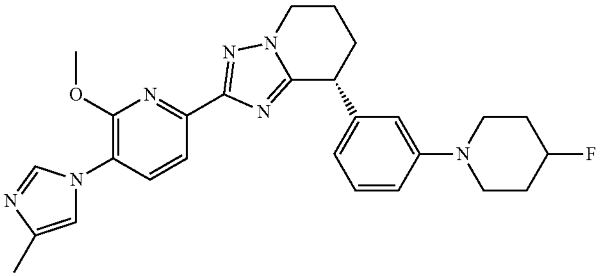 [SMILES: COc1nc(-c2nc3n(n2)CCC[C@@H]3c2cccc(N3CCC(F)CC3)c2)ccc1-n1cnc(C)c1] | ESI-MS; m/z 488[$M^+$ + H]. |
| Example 379 | 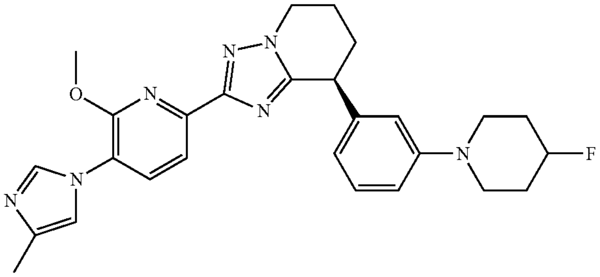 [SMILES: COc1nc(-c2nc3n(n2)CCC[C@H]3c2cccc(N3CCC(F)CC3)c2)ccc1-n1cnc(C)c1] | ESI-MS; m/z 488[$M^+$ + H]. |

TABLE 32-continued
| Example No. | Structural formula | $^1$H-NMR or ESI mass |
|---|---|---|
| Example 380 | 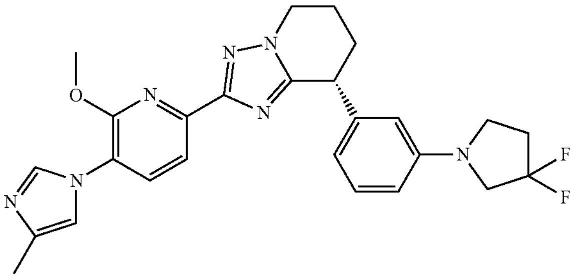 [SMILES: COc1nc(-c2nc3n(n2)CCC[C@@H]3c2cccc(N3CCC(F)(F)C3)c2)ccc1-n1cnc(C)c1] | ESI-MS; m/z 492[$M^+$ + H]. |
| Example 381 | 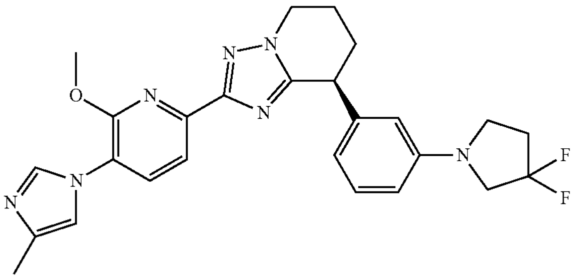 [SMILES: COc1nc(-c2nc3n(n2)CCC[C@H]3c2cccc(N3CCC(F)(F)C3)c2)ccc1-n1cnc(C)c1] | ESI-MS; m/z 492[$M^+$ + H]. |
| Example 382 | 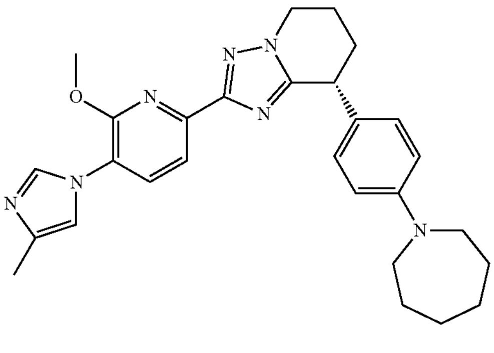 [SMILES: COc1nc(-c2nc3n(n2)CCC[C@@H]3c2ccc(N3CCCCCC3)cc2)ccc1-n1cnc(C)c1] | ESI-MS; m/z 484[M+ + H]. |
| Example 383 | 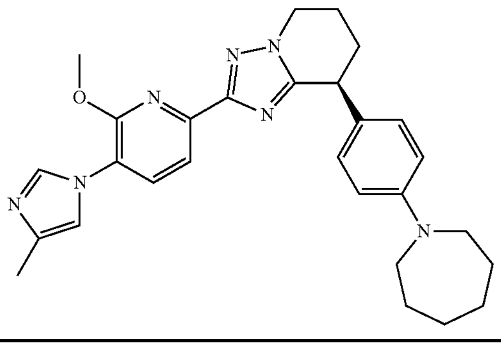 | ESI-MS; m/z 484[M+ + H]. |

The compounds in Examples 384-385 were obtained by the same synthetic methods as in Examples 150-151 (Table 33).

TABLE 33

| Example No. | Structural formula | $^1$H-NMR or ESI mass |
|---|---|---|
| Example 384 | 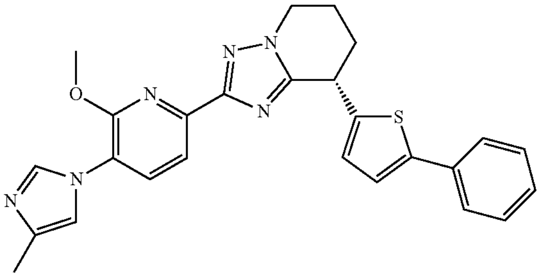 [SMILES: COc1nc(-c2nc3n(n2)CCC[C@@H]3c2ccc(-c3ccccc3)s2)ccc1-n1cnc(C)c1] | ESI-MS; m/z 469[M$^+$ + H]. |
| Example 385 | 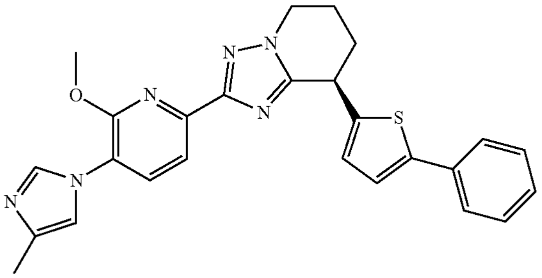 [SMILES: COc1nc(-c2nc3n(n2)CCC[C@H]3c2ccc(-c3ccccc3)s2)ccc1-n1cnc(C)c1] | ESI-MS; m/z 469[M$^+$ + H]. |

Examples 386-387

Syntheses of (−)-2-{2-[6-methoxy-5-(4-methyl-1H-imidazol-1-yl)pyridine-2-yl]-5,6,7,8-tetrahydro[1,2,4]triazolo[1,5-a]pyridine-8-yl}-4-piperidine-1-yl benzonitrile and (+)-2-{2-[6-methoxy-5-(4-methyl-1H-imidazol-1-yl)pyridine-2-yl]-5,6,7,8-tetrahydro[1,2,4]triazolo[1,5-a]pyridine-8-yl]-4-piperidine-1-yl benzonitrile

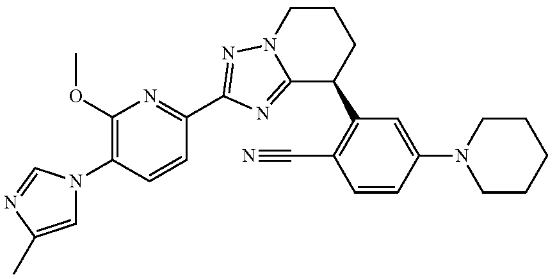

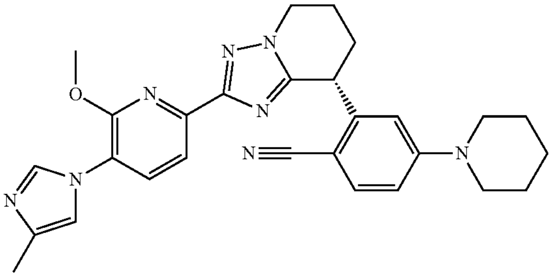

To a solution of 8-(2 bromo-5-piperidine-1-yl phenyl)-2-[6-methoxy-5-(4-methyl-1H-imidazole-1-yl)pyridine-2-yl]-5,6,7,8-tetrahydro[1,2,4]triazolo[1,5-a]pyridine (29 mg) obtained in Examples 278 and 279 and zinc cyanide (13 mg) in N-methyl-2-pyrrolidinone (3 ml) was added tetrakis(triphenylphosphine) palladium (6 mg), and the reaction mixture was stirred at 130° C. for 1 hr in a microwave reactor. Then water was added and the reaction mixture was extracted with ethyl acetate. The extract was washed with brine and dried over anhydrous sodium sulfate. After filtration of the drying agent, the filtrate was concentrated under reduced pressure. The residue was purified by NH silica gel column chromatography to obtain a racemate of the title compound. (20 mg) The racemate was separated by CHIRALPAK™ IB (2 cm×25 cm: elution solvent; hexane:ethanol=4:6, Daicel Co., Ltd.).

The title optically active compound with negative optical rotation (6 mg, >99% ee) and the title optically active compound with positive optical rotation (7 mg, >99% ee) were obtained.

The property values of the title compound with negative optical rotation is as follows;

ESI-MS; m/z 248 [½M$^+$+H], 495 [M$^+$+H]

The property values of the title compound with positive optical rotation is as follows;

ESI-MS; m/z 248 [½M$^+$+H], 495 [M$^+$+H].

Compounds in Examples 388-389 were obtained by the same synthetic methods as in Examples 386-387 (Table 34).

TABLE 34

| Example No. | Structural formula | $^1$H-NMR or ESI mass |
| --- | --- | --- |
| Example 388 | 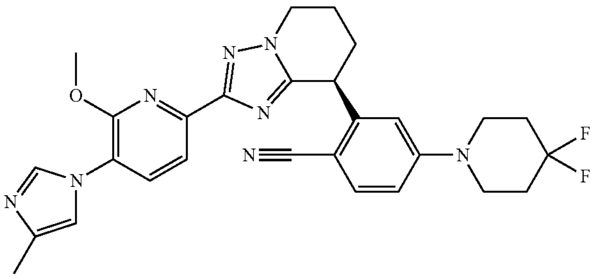 [SMILES: COc1nc(-c2nc3n(n2)CCC[C@H]3c2cc(N3CCC(F)(F)CC3)ccc2C#N)ccc1-n1cnc(C)c1] | ESI-MS; m/z 531[M$^+$ + H]. |
| Example 389 | 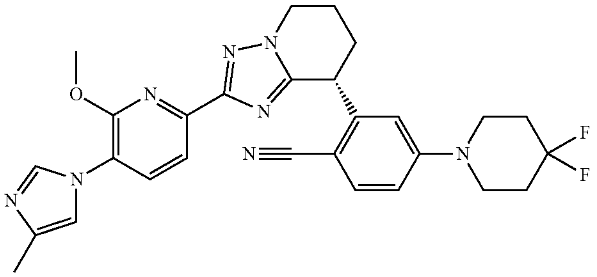 [SMILES: COc1nc(-c2nc3n(n2)CCC[C@@H]3c2cc(N3CCC(F)(F)CC3)ccc2C#N)ccc1-n1cnc(C)c1] | ESI-MS; m/z 531[M$^+$ + H]. |

Examples 390-391

Syntheses of (+)-2-[6-methoxy-5-(4-methyl-1H-imidazol-1-yl)pyridin-2-yl]-8-(4-trimethylsilanphenyl)-5,6,7,8-tetrahydro[1,2,4]triazolo[1,5-a]pyridine and (−)-2-[6-methoxy-5-4-methyl-1H-imidazol-1-yl)pyridin-2-yl]-8-4-trimethylsilanphenyl)-5,6,7,8-tetrahydro[1,2,4]triazolo[1,5-a]pyridine

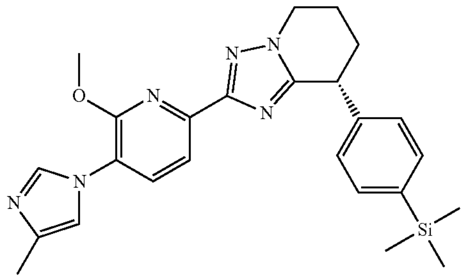

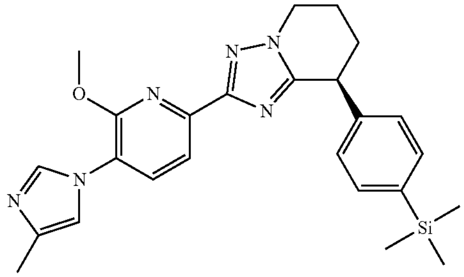

A suspension of 844-bromophenyl]-2-[6-methoxy-5-(4-methyl-1H-imidazole-1-yl)pyridine-2-yl]-5,6,7,8-tetrahydro[1,2,4]triazolo[1,5-a]pyridine (40 mg) obtained in Examples 288 and 289, tris(dibenzylideneacetone)dipalladium (1.6 mg), 2-(di-tert-butylphosphino)biphenyl (2.6 mg) and potassium fluoride (25 mg) in 1,3-dimethyl-3,4,5,6-tetrahydro-2(1H)-pyrimidinone (3 ml) was stirred at room temperature for 5 min. Tetramethyldisilane (21 μl) and water (28 μl) were added to the reaction mixture and it was stirred at 150° C. for 1 hr in a microwave reactant. Water was added to the reaction mixture and the mixture was extracted with ethyl acetate. The extract was washed with brine and dried over anhydrous sodium sulfate. After filtration of the drying agent, the filtrate was concentrated under reduced pressure. The residue was purified by NH silica gel column chromatography to obtain a racemate of the title compound. (22 mg) The crude racemate was separated by CHIRALPAK™ IA (2 cm×25 cm: elution solvent; hexane:ethanol=6:4, Daicel Co., Ltd.). The title optically active compound with positive optical rotation (1.7 mg, >99% ee) and the title optically active compound with negative optical rotation (1 mg, >99% ee) were obtained.

The property values of the title compound with positive optical rotation is as follows;

ESI-MS; m/z 459[M$^+$+H].

The property values of the title compound with negative optical rotation is as follows;

ESI-MS; m/z 459[M$^+$+H].

Examples 392-393

Syntheses of (+)-1-(3-{2-[6-methoxy-5-(4-methyl-1H-imidazol-1-yl) pyridine-2-yl]-5,6-dihydro-8H-[1,2,4]triazolo[1,5-c][1,4]oxazin-8-yl}phenyl)pyrrolidin-2-one and (−)-1-(3-{2-[6-methoxy-5-4-methyl-1H-imidazol-1-yl)pyridine-2-yl]-5,6-dihydro-8H-[1,2,4]triazolo[1,5-c][1,4]oxazin-8-yl}phenyl) pyrrolidin-2-one

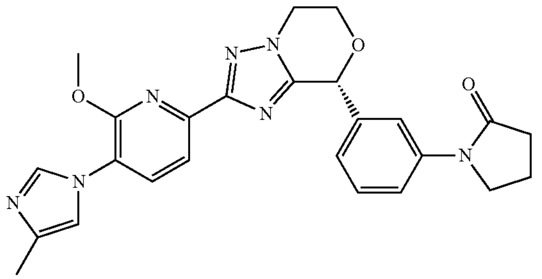

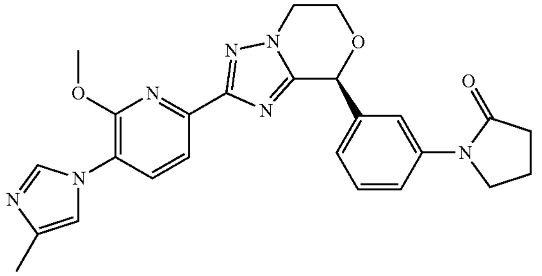

Syntheses of 3-{2-[6-methoxy-5-(4-methyl-1H-imidazol-1-yl)pyridin-2-yl]-5,6-dihydro-8H-[1,2,4]triazolo[1,5-c][1,4]oxazin-8-yl}phenylamine A suspension of 2-[6-methoxy-5-(4-methyl-1H-imidazol-1-yl)pyridin-2-yl]-8-(3-nitrophenyl)-5,6-dihydro-8H-[1,2,4]triazolo[1,5-c][1,4]oxazine (703 mg) obtained in Examples 66 and 67, iron powder (362 mg) and ammonium chloride (693 mg) in the mixture of ethanol (25 ml) and water (5 ml) was stirred at 90° C. for 5.3 hr and then at room temperature overnight. Insoluble product was removed by filtration with Celite, and the effluent was concentrated under reduced pressure. A saturated sodium bicarbonate aqueous solution was added to the residue and it was extracted with ethyl acetate. The extract was washed with brine and dried over anhydrous magnesium sulfate. After filtration of the drying agent, the organic layer was concentrated under reduced pressure to obtain the title compound. (403 mg)

Syntheses of (+)-1-(3-{2-[6-methoxy-5-(4-methyl-1H-imidazol-1-yl)pyridin-2-yl]-5,6-dihydro-8H-[1,2,4]triazolo[1,5-c][1,4]oxazin-8-yl}phenyl)pyrrolidin-2-one and (−)-1-(3-{2-[6-methoxy-5-(4-methyl-5,6-dihydro-8H-[1,2,4]triazolo[1,5-c][1,4]oxazin-8-yl}phenyl)pyrrolidin-2-one To a solution of 3-{2-[6-methoxy-5-(4-methyl-1H-imidazol-1-yl)pyridin-2-yl]-5,6-dihydro-8H-[1,2,4]triazolo[1,5-c][1,4]oxazin-8-yl}phenylamine (49 mg) and triethylamine (67.6 µl) in dichloromethane (4.3 ml) was added 4-chlorobutyrylchloride (15.2 µl). The reaction mixture was stirred at room temperature for 1 hr. A saturated sodium bicarbonate aqueous solution was added to the reaction mixture and it was extracted with chloroform. The extract was concentrated under reduced pressure, and the obtained residue was dissolved into THF (5 ml). Potassium-tert-butoxide (13.6 mg) was added to the solution and the reaction mixture was stirred at room temperature for 3.5 hr. After an addition of saturated sodium bicarbonate aqueous solution, the reaction mixture was extracted with ethyl acetate. The extract was washed with brine and dried over anhydrous magnesium sulfate. After filtration of the drying agent, the filtrate was concentrated under reduced pressure to obtain the crude racemate of the title compound. The racemate was separated by CHIRALPAK™ IB (2 cm×25 cm: elution solvent; hexane:ethanol=5:5, Daicel Co., Ltd.). The title optically active compound with positive optical rotation (6.6 mg) and the title optically active compound with negative optical rotation (6 mg) were obtained.

The property values of the title compound with positive optical rotation is as follows;

ESI-MS; m/z 472[$M^+$+H].

The property values of the title compound with negative optical rotation is as follows;

ESI-MS; m/z 472[$M^+$+H].

Examples 394-395

Syntheses of N-(+)-(3-{2-[6-methoxy-5-(4-methyl-1H-imidazol-1-yl)pyridin-2-yl]-5,6-dihydro-8H-[1,2,4]triazolo[1,5-c][1,4]oxazin-8-yl}phenyl)cyclohexanecarboxamide and N-(−) -(3-{2-[6-methoxy-5-(4-methyl-1H-imidazol-1-yl) pyridin-2-yl]-5,6-dihydro-8H-[1,2,4]triazolo[1,5-c][1,4]oxazin-8-yl}phenyl) cyclohexanecarboxamide

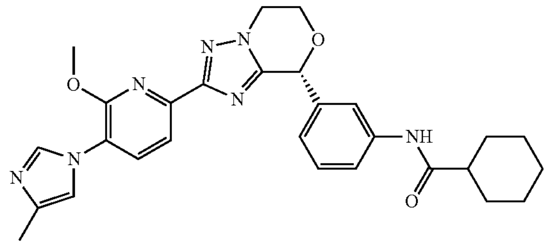

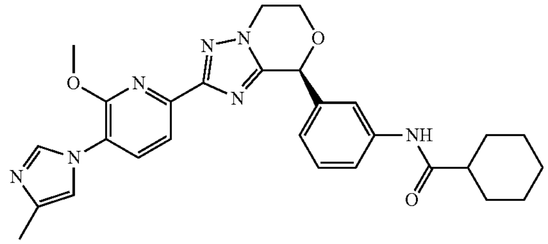

To a solution of 3-{2-[6-methoxy-5-(4-methyl-1H-imidazol-1-yl)pyridin-2-yl]-5,6-dihydro-8H-[1,2,4]triazolo[1,5-c][1,4]oxazin-8-yl}phenylamine (40 mg) obtained in Examples 392 and 393 and triethylamine (41.4 µl) in dichloromethane (3 ml) was added cyclohexanecarbonylchloride (16.1 µl). The reaction mixture was stirred at room temperature for 4 days. A saturated sodium bicarbonate aqueous solution was added to the reaction mixture and it was extracted with chloroform. The extract was concentrated under reduced pressure and the residue was purified by NH silica gel column chromatography to obtain a crude racemate of the title compound. (35 mg) The crude racemate was separated by CHIRALPAK™ IA (2 cm×25 cm: elution solvent; hexane:ethanol=6.5:3.5, Daicel Co., Ltd.). The title optically active compound with positive optical rotation (17 mg) and the title optically active compound with negative optical rotation (12 mg) were obtained.

The property values of the title compound with positive optical rotation is as follows;

ESI-MS; m/z 514 [$M^+$+H].

The property values of the title compound with negative optical rotation is as follows;

ESI-MS; m/z 514 [$M^+$+H].

Compounds in Examples 396-397 were obtained by the same synthetic methods as in Examples 394-395 (Table 35).

-continued

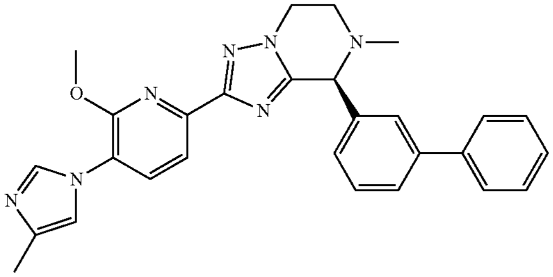

TABLE 35

| Example No. | Structural formula | $^1$H-NMR or ESI mass |
|---|---|---|
| Example 396 | 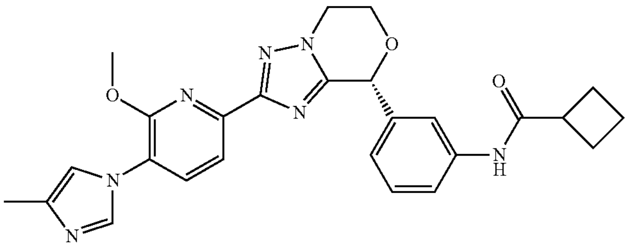 [SMILES: COc1nc(-c2nc3n(n2)CCO[C@@H]3c2cccc(NC(=O)C3CCC3)c2)ccc1-n1cnc(C)c1] | ESI-MS; m/z 486[$M^+$ + H]. |
| Example 397 | 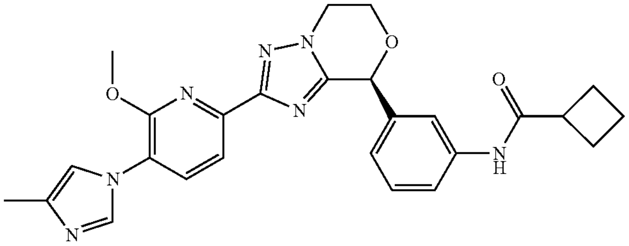 [SMILES: COc1nc(-c2nc3n(n2)CCO[C@H]3c2cccc(NC(=O)C3CCC3)c2)ccc1-n1cnc(C)c1] | ESI-MS; m/z 486[$M^+$ + H]. |

Examples 398-399

Syntheses of (+)-8-biphenyl-3-yl-2-[6-methoxy-5-(4-methyl-1H-imidazol-1-yl)pyridin-2-yl]-7-methyl-5,6,7,8-tetrahydro[1,2,4]triazolo[1,5-a]pyrazine and (−)-8-biphenyl-3-yl-2-[6-methoxy-5-(4-methyl-1H-imidazol-1-yl)pyridin-2-yl]-7-methyl-5,6,7,8-tetrahydro[1,2,4]triazolo[1,5-a]pyrazine

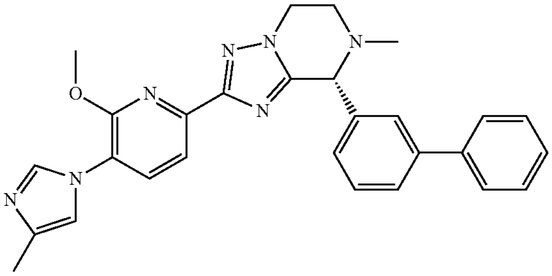

Synthesis of 7-benzyl-8-biphenyl-3-yl-2-[6-methoxy-5-4-methyl-1H-imidazol-1-yl)pyridin-2-yl]-5,6,7,8-tetrahydro[1,2,4]triazolo[1,5-a]pyrazine To a solution of 7-benzyl-8-(3-bromophenyl)-2-[6-methoxy-5-(4-methyl-1H-imidazol-1-yl)pyridine-2-yl]-5,6,7,8-tetrahydro[1,2,4]triazolo[1,5-a]pyrazine (400 mg) obtained in Example 84 and 85 in toluene (18 ml) and methanol (4 ml) was added 2M sodium carbonate aqueous solution (395 μl), phenylboronic acid (219 mg), and tetrakis(triphenylphosphine) palladium (83.1 mg). The mixture was stirred at 120° C. for 7 hr. Water was added to the reaction mixture and it was extracted with ethyl acetate. The extract was washed with brine and dried over anhydrous magnesium sulfate. After filtration of the drying agent, the filtrate was concentrated under reduced pressure to obtain the title compound. (541 mg)

Synthesis of 8-biphenyl-3-yl-2-[6-methoxy-5-(4-methyl-1H-imidazol-1-yl)pyridin-2-yl]-5,6,7,8-tetrahydro[1,2,4]triazolo[1,5-a]pyrazine To a solution of 7-benzyl-8-biphenyl-3-yl-2-[6-methoxy-5-(4-methyl-1H-imidazol-1-yl)pyridin-2-yl]-5,6,7,8-tetrahydro[1,2,4]triazolo[1,5-a]pyrazine (541 mg) and acetic acid (1.32 ml) in methanol (52 ml) was added 20% palladium hydroxide (743 mg) and the reaction mixture was stirred at room temperature in a hydrogen atmosphere for 4 days. After the reaction atmosphere was replaced with nitrogen, ethyl acetate was added to the reaction mixture. The catalyst was removed by filtration by Celite. The filtrate was concentrated under reduced pressure and the residue was purified by NH silica gel column chromatography to obtain the title compound (45 mg) and the raw material. (291 mg)

Syntheses of (+)-8-biphenyl-3-yl-2-[6-methoxy-5-(4-methyl-1H-imidazol-1-yl) pyridin-2-yl]-7-methyl-5,6,7,8-tetrahydro[1,2,4]triazolo[1,5-a]pyrazine and (−)-8-biphenyl-3-yl-2-[6-methoxy-5-(4-methyl-1H-imidazol-1-yl)pyridin-2-yl]-7-methyl-5,6,7,8-tetrahydro[1,2,4]triazolo[1,5-a]pyrazine A mixture of 8-biphenyl-3-yl-2-[6-methoxy-5(4-methyl-1H-imidazol-1-yl)pyridin-2-yl]-5,6,7,8-tetrahydro[1,2,4]triazolo[1,5-a]pyrazine (45 mg), formaldehyde (37% solution) (2 ml) and formic acid (2 ml) was refluxed for 3 hr. The reaction mixture was chilled on ice and neutralized with saturated sodium bicarbonate aqueous solution, then extracted with ethyl acetate. The extract was washed with brine and dried over anhydrous magnesium sulfate. After filtration of the drying agent, the filtrate was concentrated under reduced pressure. The residue was purified by NH silica gel column chromatography to obtain a crude racemate of the title compound. (41 mg) The obtained crude racemate was separated by CHIRALPAK IA (2 cm×25 cm, Daicel Co., Ltd.). The title optically active compound with positive optical rotation (17 mg) and the title optically active compound with negative optical rotation (14 mg) were obtained.

The property values of the title compound with positive optical rotation is as follows;

ESI-MS; m/z 478[$M^+$+H].

The property values of the title compound with negative optical rotation is as follows;

ESI-MS; m/z 478[$M^+$+H].

Test Example 1

Quantification of Aβ Peptide in Culture of Neurons from Rat Fetus Brain

The present inventors performed the following tests in order to exhibit utility of the compound of the general formula (I) according to the present invention.

(1) Rat Primary Neuronal Culture

Primary neuronal cultures were prepared from the cerebral cortex of embryonic day 18 Wistar rats (Charles River Japan, Yokohama, Japan). Specifically, the embryos were aseptically removed from pregnant rats under ether anesthesia. The brain was isolated from the embryo and immersed in an ice-cold L-15 medium (Invitrogen Corp. Cat #11415-064, Carlsbad, Calif., USA, or SIGMA L1518, for example). The cerebral cortex was collected from the isolated brain under a stereoscopic microscope. The cerebral cortex fragments collected were enzymatically treated in an enzyme solution containing 0.25% trypsin (Invitrogen Corp. Cat #15050-065, Carlsbad, Calif., USA) and 0.01% DNase (Sigma D5025, St. Louis, Mo., USA) at 37° C. for 30 minutes to disperse the cells. Here, the enzymatic reaction was stopped by adding inactivated horse serum to the solution. The enzymatically treated solution was centrifuged at 1,500 rpm for five minutes to remove the supernatant 5 to 10 ml of a medium was added to the resulting cell mass. Neurobasal medium (Invitrogen Corp. Cat #21103-049, Carlsbad, Calif., USA) supplemented with 2% B27 supplement (Invitrogen Corp. Cat #17504-044, Carlsbad, Calif., USA), 25 μM 2-mercaptoethanol (2-ME, WAKO Cat #139-06861, Osaka, Japan), 0.5 mM L-glutamine (Invitrogen Corp. Cat #25030-081, Carlsbad, Calif., USA), and Antibiotics-Antimycotics (Invitrogen Corp. Cat #15240-062, Carlsbad, Calif., USA) was used as the medium (Neurobasal/B27/2-ME). However, the above Neurobasal medium not supplemented with 2-ME (Neurobasal/B27) was used for the assay. The cells were redispersed by mild pipetting of the cell mass to which the medium was added. The cell dispersion was filtered through a 40-μm nylon mesh (Cell Strainer, Cat #35-2340, Becton Dickinson Labware, Franklin Lakes, N.J., USA) to remove the remaining cell mass, and thus a neuronal cell suspension was obtained. The neuronal cell suspension was diluted with the medium and then plated in a volume of 100 μl/well at an initial cell density of $5\times10^5$ cells/$cm^2$ in a 96-well polystyrene culture plate pre-coated with poly-L or D-lysine (Falcon Cat #35-3075, Becton Dickinson Labware, Franklin Lakes, N.J., USA coated with poly-L-lysine using the method shown below, or BIOCOAT™ cell environments Poly-D-lysine cell ware 96-well plate, Cat #35-6461, Becton Dickinson Labware, Franklin Lakes, N.J., USA). Poly-L-lysine coating was carried out as follows. 100 μg/ml of a poly-L-lysine (SIGMA P2636, St. Louis, Mo., USA) solution was aseptically prepared with a 0.15 M borate buffer (pH 8.5). 100 μg/well of the solution was added to the 96-well polystyrene culture plate and incubated at room temperature for one or more hours or at 4° C. overnight or longer. Thereafter, the coated 96-well polystyrene culture plate was washed with sterile water four or more times, and then dried or rinsed with sterile PBS or medium, and used for cell plating. The plated cells were cultured in the culture plate at 37° C. in 5% $CO_2$-95% air for one day. Then, the total amount of the medium was replaced with a fresh Neurobasal/B27/2-ME medium, and then the cells were cultured for further three days.

Addition of Compounds

The drug was added to the culture plate on Day 4 of culture as follows. The total amount of the medium was removed from the wells, and 180 μl/well of Neurobasal medium not containing 2-ME and containing 2% B-27 (Neurobasal/B27) was added thereto. A solution of the test compound in dimethyl sulfoxide (hereinafter abbreviated as DMSO) was diluted with Neurobasal/B27 to a concentration 10-fold higher than the final concentration. 20 μl/well of the dilution was added to and sufficiently mixed with the medium. The final DMSO concentration was 1% or less. Only DMSO was added to the control group.

Sampling

The cells were cultured for three days after addition of the compound, and the total amount of the medium was collected. The resulting medium was used as an ELISA sample.

Evaluation of Cell Survival

Cell survival was evaluated by an MTT assay according to the following procedure. After collecting the medium, 100 Owen of a pre-warmed medium was added to the wells. Further, 8 μl/well of a solution of 8 mg/ml of MIT (SIGMA M2128, St. Louis, Mo., USA) in D-PBS(−) (Dulbecco's phosphate buffered Saline, SIGMA D8537, St. Louis, Mo., USA) was added to the wells. The 96-well polystyrene culture plate was incubated in an incubator at 37° C. in 5% $CO_2$-95% air for 20 minutes. 100 μl/well of an MTT lysis buffer was added thereto, and MTT formazan crystals were sufficiently dissolved in the buffer in the incubator at 37° C. in 5% $CO_2$-95% air. Then, the absorbance at 550 nm in each well was measured. The MTT lysis buffer was prepared as follows. 100 g of SDS (sodium dodecyl sulfate (sodium lauryl sulfate), WAKO 191-07145, Osaka, Japan) was dissolved in a mixed solution of 250 mL of N,N-dimethylformamide (WAKO 045-02916, Osaka, Japan) with 250 mL of distilled water. 350 μl each of concentrated hydrochloric acid and acetic acid were further added to the solution to allow the solution to have a final pH of about 4.7.

Upon measurement, wells having no cells plated and containing only the medium and MTT solution were set as background (bkg). The measured values were respectively applied to the following formula including subtracting bkg values from them. Thus, the proportion against the control group (group not treated with the drug, CTRL) (% of CTRL) was calculated to compare and evaluate cell survival activities.

% of CTRL=((A550_sample−A550_bkg)/(A550_CTRL−bkg))×100 (A550_sample: absorbance at 550 nm of sample well, A550_bkg: absorbance at 550 nm of background well, A550STRL: absorbance at 550 nm of control group well)

Aβ ELISA

For Aβ ELISA, Human/Rat β Amyloid (42) ELISA Kit Wako (#290-62601) from Wako Pure Chemical Industries, Ltd. or Human Amyloid beta (1-42) Assay Kit (#277H) from ML Co., Ltd. was used. Aβ ELISA was carried out according to the protocols recommended by the manufacturers (methods described in the attached documents). However, the Aβ calibration curve was created using beta-amyloid peptide 1-42, rat (Calbiochem, #171596 [$A\beta_{42}$]).

(2) The measurement results are shown in Table 10 as percentage to the Aβ concentration in the medium of the control group (% of CTRL).

TABLE 10

| Test Compound | Aβ42 Production reducing action $IC_{50}$ (nM) |
|---|---|
| Example 2 | 10 |
| Example 42 | 52 |
| Example 59 | 7 |
| Example 100 | 9 |
| Example 102 | 55 |
| Example 104 | 91 |
| Example 108 | 18 |
| Example 187 | 11 |
| Example 191 | 7 |
| Example 193 | 13 |
| Example 197 | 13 |
| Example 199 | 6 |
| Example 211 | 15 |
| Example 225 | 28 |
| Example 239 | 12 |
| Example 240 | 5 |
| Example 242 | 9 |
| Example 245 | 16 |
| Example 246 | 55 |
| Example 250 | 13 |
| Example 267 | 29 |
| Example 279 | 8 |
| Example 287 | 22 |
| Example 295 | 33 |
| Example 307 | 13 |
| Example 309 | 14 |
| Example 311 | 12 |
| Example 313 | 6 |
| Example 315 | 4 |
| Example 317 | 15 |
| Example 319 | 10 |
| Example 331 | 12 |
| Example 337 | 13 |
| Example 347 | 30 |
| Example 359 | 16 |
| Example 361 | 13 |
| Example 383 | 21 |

As is clear from the results of Table 10, the compound of the present invention was proved to have an Aβ42 production reducing effect.

Accordingly, the compound of the general formula (I) or pharmacologically acceptable salt thereof according to the present invention have an Aβ42 production reducing effect. Thus, the present invention can particularly provide a therapeutic agent for a neurodegenerative disease caused by Aβ such as Alzheimer's disease or Down's syndrome.

INDUSTRIAL APPLICABILITY

The compound of the general formula (I) according to the present invention has an Aβ production reducing effect, and thus is particularly useful as a therapeutic agent for a neurodegenerative disease caused by Aβ such as Alzheimer's disease or Down's syndrome.

The invention claimed is:

1. A compound represented by the formula [I]:

[I]

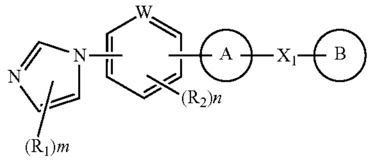

or a pharmacologically acceptable salt or ester thereof, wherein $R_1$ and $R_2$ are the same or different and each represent a substituent selected from the following Substituent Group a1;

m represents an integer of 0 to 3;

n represents an integer of 0 to 2;

W represents a nitrogen atom;

Ring A represents a five-membered aromatic heterocyclic group fused with a 5- to 14-membered non-aromatic ring group, which contains two or more nitrogen atoms and may have 1 to 3 substituents selected from the following Substituent Group b1 (wherein the 5- to 14-membered non-aromatic ring group may have a crosslinked structure);

$X_1$ represents i) a single bond, ii) a C1-6 alkylene group, iii) a vinylene group which may have 1 to 2 C1-6 alkyl groups or iv)-$X_2$—(wherein $X_2$ represents —$NR_3$—, —$NR_3C(O)$—, —$C(O)NR_3$—, —O—, —S—, —S(O)— or —$S(O)_2$— and $R_3$ represents a hydrogen atom, a C1-6 alkyl group, a C3-6 cycloalkyl group, a C2-6 alkanoyl group or a C1-6 alkylsulfonyl group); and Ring B represents a monocyclic or fused cyclic aromatic ring group selected from the formulas [2] to [3]:

2

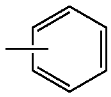

,

3

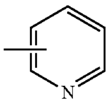

each of which may have 1 to 3 substituents selected from the following Substituent Group c1

[Substituent Group a1: a C1-6 alkyl group, a C3-8 cycloalkyl group, a C2-6 alkenyl group, a C1-6 alkoxy group, a C2-6 alkenyloxy group, a C3-8 cycloalkyloxy group, an amino group (wherein the amino group may have one C2-6 alkanoyl group or C1-6 alkylsulfonyl group or 1 to 2 C1-6 alkyl groups or C3-8 cycloalkyl groups), a cyano group, a formyl group, a halogen atom, a hydroxyl group and a nitro group;

Substituent Group b1: a C1-6 alkyl group (wherein the alkyl group may be substituted with 1 to 3 halogen atoms), a C2-6 alkenyl group, a C3-8 cycloalkyl group, a C6-14 aryl group, a C6-14 aryl-C1-6 alkyl group, a C1-6 alkoxy group, a C2-6 alkenyloxy group, a C3-8 cycloalkyloxy group, a C2-6 alkanoyl group, a C4-9 cycloalkylcarbonyl group, a C7-15 aroyl group, a C1-6 alkylsulfonyl group, a C2-6 alkenylsulfonyl group, a C3-8 cycloalkylsulfonyl group, a C6-14 arylsulfonyl group, a C1-6 alkylthio group, a C2-6 alkenylthio group, a C3-8 cycloalkylthio group, an aminosulfonyl group (wherein the aminosulfonyl group may have 1 to 2 C1-6 alkyl groups, C2-6 alkenyl groups or C3-8 cycloalkyl groups), an amino group (wherein the amino group may have one C2-6 alkanoyl group, C1-6 alkylsulfonyl group or C3-8 cycloalkylsulfonyl group or 1 to 2 C1-6 alkyl groups or C3-8 cycloalkyl groups), a cyano group, a formyl group, a halogen atom, a hydroxyl group, a nitro group, an oxo group, a 1-pyrrolidinyl group, a 1-piperidinyl group, a 1-homopiperidinyl group, an indolin-1-yl group, a 1,2,3,4-tetrahydroquinolin-1-yl group and a 4-morpholinyl group;

Substituent Group c1: i) an amino group (wherein the amino group may have one C2-6 alkanoyl group, C1-6 alkylsulfonyl group or C3-8 cycloalkylsulfonyl group or 1 to 2 C1-6 alkyl groups or C3-8 cycloalkyl groups), ii) a cyano group, iii) a halogen atom, iv) a hydroxyl group and v) v-i) a C1-6 alkyl group, v-ii) a C2-6 alkenyl group, v-IIi) a C2-6 alkynyl group, v-iv) a C1-6 alkoxy group, v-v) a C1-6 alkylaminocarbonyl group, v-vi) a C1-6 alkylaminosulfonyl group, v-vii) a C1-6 alkylsulfonyl group, v-viii) a C1-6 alkylthio group, v-ix) a C2-6 alkanoyl group, v-x) a phenyl group, v-xi) a pyridyl group, v-xii) a pyridazinyl group, v-xiii) a pyrimidinyl group, v-xiv) a 1-pyrrolidinyl group, v-xv) a 1-piperidinyl group, v-xvi) a 1-homopiperidinyl group and v-xvii) a 4-morpholinyl group, each of which may have 1 to 3 substituents selected from the group consisting of a C1-6 alkyl group and a halogen atom].

2. The compound or pharmacologically acceptable salt or ester thereof according to claim 1, wherein Ring A is any one ring selected from the group consisting of the formulas [20] to [32]:

20

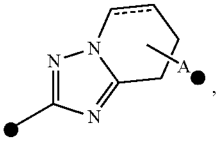

21

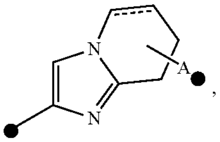

-continued

22

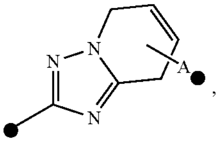

23

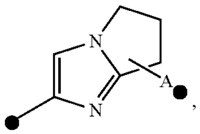

24

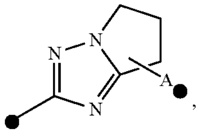

25

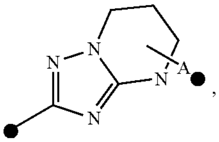

26

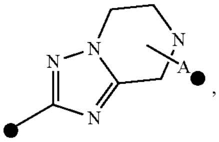

27

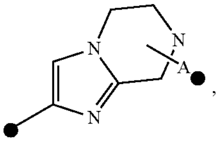

28

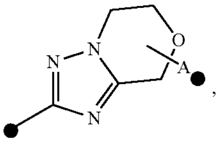

29

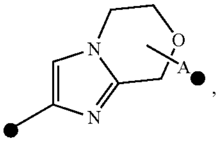

30

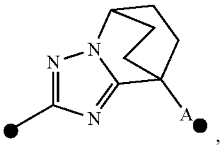

31

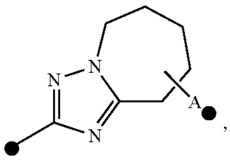

-continued

32

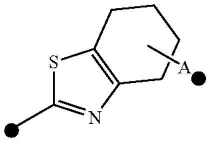

each of which may have 1 to 3 substituents selected from Substituent Group b1, wherein • represents a bonding site to the formula [33]:

33

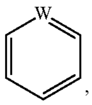,

A • represents a bonding site to $X_1$, and represents a single bond or a double bond.

3. The compound or pharmacologically acceptable salt or ester thereof according to claim 2, wherein Ring A is any one ring selected from the group consisting of the formulas [20], [21], [23], [24] and [26] to [29]:

20

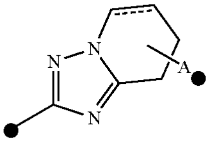,

21

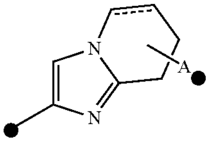,

23

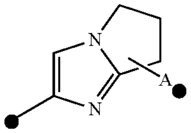,

24

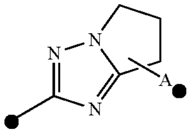,

26

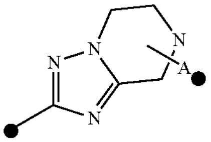,

27

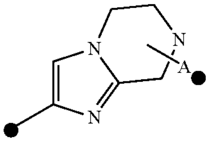,

-continued

28

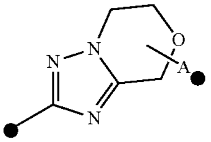,

29

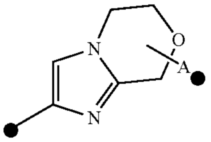.

4. The compound or pharmacologically acceptable salt or ester thereof according to claim 2, wherein Ring A is any one ring selected from the group consisting of the formulas [20-1], [21-1], [23-1], [24-1] and [26-1] to [29-1]:

20-1

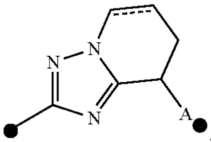, 21-1

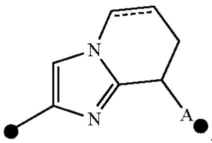, 23-1

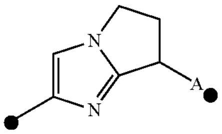, 24-1

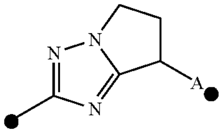, 26-1

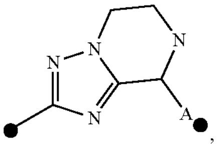, 27-1

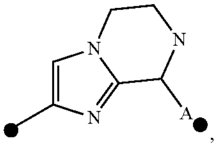, 28-1

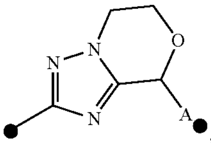,

-continued 29-1

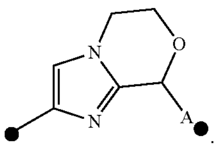

5. The compound or pharmacologically acceptable salt or ester thereof according to claim 1, wherein Ring B is a phenyl group, or a pyridyl group.

6. The compound or pharmacologically acceptable salt or ester thereof according to claim 1, wherein $X_1$ is i) a single bond or ii) a C1-6 alkylene group.

7. The compound or pharmacologically acceptable salt or ester thereof according to claim 1, wherein $R_1$ is a C1-6 alkyl group or a halogen atom and m is 1 to 2.

8. The compound or pharmacologically acceptable salt or ester thereof according to claim 1, wherein $R_2$ is a C1-6 alkoxy group and n is 1.

9. The compound or pharmacologically acceptable salt or ester thereof according to claim 1, wherein the substituent for Ring A is selected from the group consisting of:

a C1-6 alkyl group (wherein the alkyl group may be substituted with 1 to 3 halogen atoms), a C3-8 cycloalkyl group, a C6-14 aryl group, a C6-14 aryl-C1-6 alkyl group, a C1-6 alkoxy group, a C3-8 cycloalkyloxy group, a C2-6 alkanoyl group, a C7-15 aroyl group, a C1-6 alkylsulfonyl group, a C3-8 cycloalkylsulfonyl group, a C6-14 arylsulfonyl group, a cyano group, a formyl group, a halogen atom, a hydroxyl group and an oxo group.

10. The compound or pharmacologically acceptable salt or ester thereof according to claim 1, wherein the substituent for Ring B is selected from the group consisting of:

i) an amino group (wherein the amino group may have one C2-6 alkanoyl group, C1-6 alkylsulfonyl group or C3-8 cycloalkylsulfonyl group or 1 to 2 C1-6 alkyl groups or C3-8 cycloalkyl groups), ii) a cyano group, iii) a halogen atom, iv) a hydroxyl group and v) v)-i) a C1-6 alkyl group, v)-ii) a C1-6 alkoxy group, v)-iii) a C1-6 alkylthio group and v)-iv) a phenyl group, each of which may have 1 to 3 substituents selected from the group consisting of a C1-6 alkyl group and a halogen atom.

11. A compound having the following formula [A-1]:

A-1

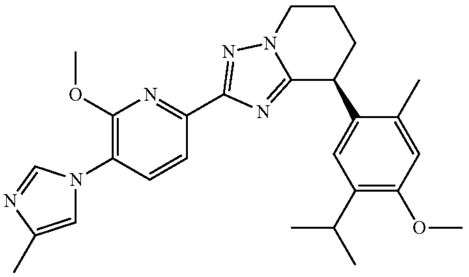

or a pharmacologically acceptable salt thereof.

12. A compound, which is

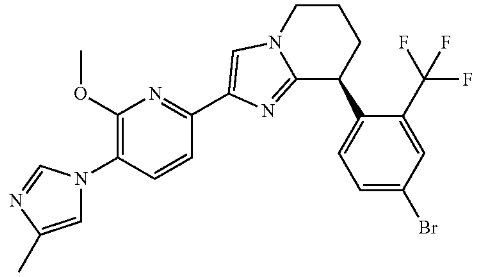

or a pharmaceutically acceptable salt thereof.

13. The compound according to claim 1, which is

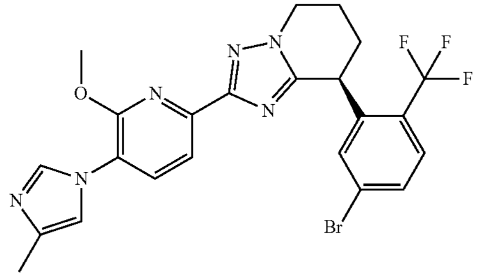 [SMILES: COc1nc(-c2nc3n(n2)CCC[C@H]3c2cc(Br)ccc2C(F)(F)F)ccc1-n1cnc(C)c1]

or a pharmaceutically acceptable salt thereof.

14. A compound, which is

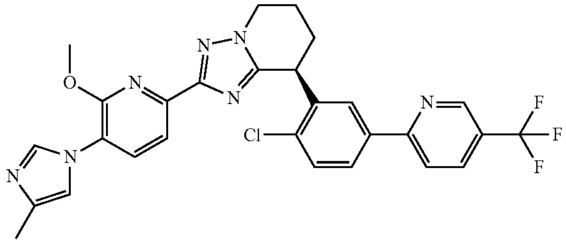 [SMILES: COc1nc(-c2nc3n(n2)CCC[C@H]3c2cc(-c3ccc(C(F)(F)F)cn3)ccc2Cl)ccc1-n1cnc(C)c1]

or a pharmaceutically acceptable salt thereof.

15. A compound having the following formula [A-2]:

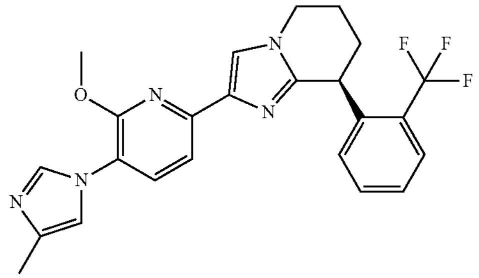 [SMILES: COc1nc(-c2cn3c(n2)[C@H](c2ccccc2C(F)(F)F)CCC3)ccc1-n1cnc(C)c1]

or a pharmaceutically acceptable salt thereof.

16. A compound having the following formula [A-3]:

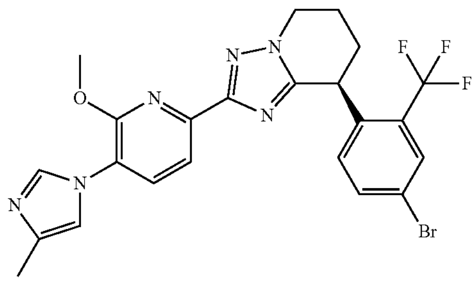

or a pharmaceutically acceptable salt thereof.

17. A compound having the following formula [A-5]:

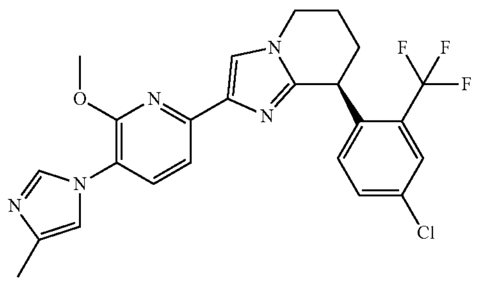 [SMILES: COc1nc(-c2cn3c(n2)[C@H](c2ccc(Cl)cc2C(F)(F)F)CCC3)ccc1-n1cnc(C)c1]

or a pharmaceutically acceptable salt thereof.

18. A compound having the following formula [A-6]:

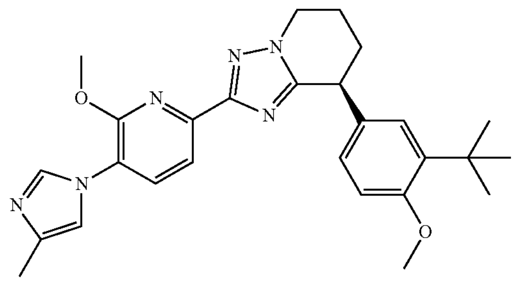

or a pharmaceutically acceptable salt thereof.

19. A compound having the following formula [A-7]:

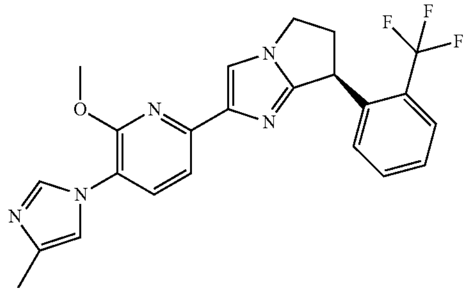 [SMILES: COc1nc(-c2cn3c(n2)[C@H](c2ccccc2C(F)(F)F)CC3)ccc1-n1cnc(C)c1]

or a pharmaceutically acceptable salt thereof.

20. A medicine comprising the compound or pharmacologically acceptable salt or ester thereof according to any one of claims 1 to 6, 7 to 11, 12-14 and 15-19 as an active ingredient.

* * * * *